United States Patent [19]
Hartzell

[11] Patent Number: 4,762,550
[45] Date of Patent: Aug. 9, 1988

[54] HERBICIDAL PYRAZOLESULFONAMIDES

[75] Inventor: Stephen L. Hartzell, Wilmington, Del.

[73] Assignee: E. I. Du Pont de Nemours and Company, Wilmington, Del.

[21] Appl. No.: 85,026

[22] Filed: Aug. 13, 1987

Related U.S. Application Data

[60] Division of Ser. No. 760,713, Aug. 1, 1985, Pat. No. 4,705,558, which is a continuation-in-part of Ser. No. 662,789, Oct. 19, 1984, abandoned, which is a continuation-in-part of Ser. No. 651,082, Sep. 17, 1984, abandoned.

[51] Int. Cl.$^4$ .................. C07D 401/14; A01N 43/40; A01N 43/56

[52] U.S. Cl. .......................... 71/94; 71/90; 71/92; 71/93; 546/279; 546/275; 546/276; 546/277; 546/278; 546/256; 544/2; 544/3; 544/7; 544/8; 544/10; 544/54; 544/55; 544/58.5; 544/63; 544/66; 544/67; 544/68; 544/96; 544/131; 544/180; 544/212; 544/216; 544/217; 544/218; 544/219; 544/182; 544/238; 544/310; 544/316; 544/317; 544/320; 544/321; 544/324; 544/327; 544/328; 544/331; 544/333

[58] Field of Search ............... 71/92, 93, 90, 94; 546/279, 275, 276, 277, 278, 256; 544/2, 3, 7, 10, 54, 55, 58.5, 180, 212, 216, 217, 218, 219, 182, 238, 310, 316, 317, 320, 321, 324, 327, 328, 331, 333, 63, 66, 67, 68, 96, 131, 8

[56] References Cited

U.S. PATENT DOCUMENTS

| | | | |
|---|---|---|---|
| 4,434,790 | 3/1984 | Olesen | 128/200.14 |
| 4,460,401 | 7/1984 | Sauers | 71/92 |
| 4,465,505 | 8/1984 | Wolf | 71/92 |
| 4,494,980 | 1/1985 | Shapiro | 71/92 |
| 4,511,392 | 4/1985 | Rorer | 71/90 |
| 4,534,790 | 8/1985 | Wolf | 71/93 |
| 4,592,775 | 6/1986 | Sauers | 71/90 |
| 4,602,940 | 7/1986 | Wolf | 71/92 |
| 4,609,397 | 9/1986 | Wexler | 71/92 |
| 4,666,501 | 5/1987 | Hay et al. | 71/90 |
| 4,699,647 | 10/1987 | Rorer | 71/90 |

FOREIGN PATENT DOCUMENTS

| | | |
|---|---|---|
| 87780 | 9/1983 | European Pat. Off. |
| 95925 | 12/1983 | European Pat. Off. |
| 83/3850 | 11/1983 | South Africa |

Primary Examiner—John M. Ford

[57] ABSTRACT

This invention relates to novel pyrazolesulfonamides, agricultural compositions thereof and the methods of their use as general and/or selective herbicides and/or plant growth regulants.

21 Claims, No Drawings

HERBICIDAL PYRAZOLESULFONAMIDES

RELATED APPLICATION

This is a division of U.S. application Ser. No. 760,713, filed Aug. 1, 1985, now U.S. Pat. No. 4,705,558, which is a continuation-in-part of U.S. application Ser. No. 662,789, filed Oct. 19, 1984, now abandoned, which is a continuation-in-part of U.S. application Ser. No. 651,082, filed Sept. 17, 1984, now abandoned.

BACKGROUND OF THE INVENTION

This invention relates to herbicidally active pyrazolesulfonamides having certain heterocycles attached, agriculturally suitable compositions thereof and the method of their use as herbicides and/or plant growth regulants.

In the most common situation, the control of undesired vegetation is desired to permit the growth of useful crops such as cotton, rice, corn, wheat and soybeans, to name a few. Unchecked weed growth in such useful crops can cause significant losses, reducing profit to the farmer and increasing costs to the consumer. In other situations, herbicides are desired which will control all plant growth. Examples of areas in which complete control of all vegetation is desired are areas around fuel storage tanks, ammunition depots and industrial storage areas. There are many products commercially available for these purposes, but the search continues for products which are more effective, less costly and environmentally safe.

European Patent Application (EP-A) No. 95,925 (published Dec. 7, 1983) discloses herbicidal pyrazolesulfonamides in which the group adjacent to the sulfonamide moiety may be selected from H, $C_1$-$C_3$ alkyl, F, Cl, Br, $NO_2$, $OR_{16}$, $CO_2R_{23}$, $S(O)_nR_{24}$ or $SO_2NR_{19}R_{20}$.

EP-A No. 87,780 (published Sept. 7, 1983) claims pyrazolesulfonamides of general formula

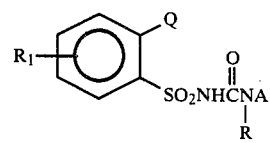

wherein
A is H, $C_1$-$C_8$ alkyl or optionally substituted phenyl;
B and C are independently H, halogen, $NO_2$, $C_1$-$C_8$ alkyl, $CO_2R$, etc.; and
D is H or $C_1$-$C_8$ alkyl.

South African Patent Application No. 83/3850 published Nov. 28, 1983, discloses herbicidal compounds of general formula

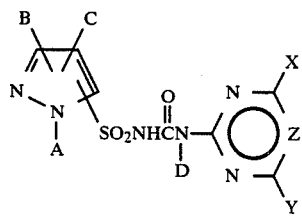

wherein
$R_1$ is H or $C_1$-$C_3$ alkyl; and
Q is an unsubstituted or substituted five-membered heterocyclic radical which is bound by way of a carbon atom and which contains 2 or 3 identical or different heteroatoms.

Unexamined Japanese Patent Application No. 9,013,778 published Jan. 24, 1984 describes herbicidal pyrazolesulfonamides with halo, alkyl and alkoxycarbonyl substituents.

EP-A No. 83,975 (published July 20, 1983) and EP-A No. 85,476 (published Aug. 10, 1983) disclose herbicidal benzenesulfonamides of general formula

wherein Q is one of a variety of 5- and 6-membered saturated or unsaturated heterocyclic rings.

SUMMARY OF THE INVENTION

This invention relates to novel compounds of Formula I, suitable agricultural compositions containing them and their method of use as general and/or selective preemergence and/or postemergence herbicides and/or plant growth regulants.

$$LSO_2NHCN-A \quad\text{I}$$
(with W above C, R below N)

wherein
L is

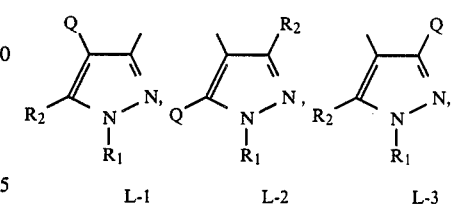

L-1    L-2    L-3

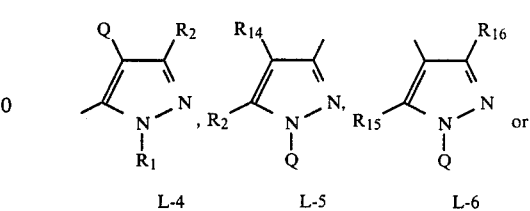

L-4    L-5    L-6

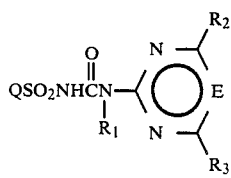

L-7

Q is selected from a saturated 5- and 6-membered ring containing one S or O heteroatom, and an unsaturated 5- or 6-membered ring containing 1-3 heteroatoms selected from one S, one O, 1-3 N and combinations thereof and Q may optionally be substituted by one or more groups selected from $C_1$-$C_4$ alkyl, $C_1$-$C_4$ haloalkyl, mercapto, benzylthio, halogen, $C_1$-$C_4$ alkoxy, $C_1$-$C_6$ alkylthio, $C_3$-$C_4$ alkenyl, $C_3$-$C_4$ alkenylthio, $C_3$-$C_4$ alkynylthio, $C_3$-$C_4$ haloalkenylthio, $C_3$-$C_4$ alkenyloxy, $C_1$-$C_2$ haloalkoxy, $C_1$-$C_2$ haloalkylthio, $C_2$-$C_4$ cyanoalkylthio, $C_3$-$C_6$ alkoxycarbonylalkylthio, $C_2$-$C_5$ alkoxyalkylthio or $C_3$-$C_5$ acetylalkylthio;

W is O or S;

R is H or $CH_3$;

$R_1$ is H, $C_1$-$C_3$ alkyl, $C_1$-$C_3$ haloalkyl or phenyl optionally substituted by Cl, $NO_2$, $CH_3$ or $OCH_3$;

$R_2$ is H, Cl or $CH_3$;

$R_{14}$ is H, $C_1$-$C_4$ alkyl, F, Cl, Br, $NO_2$, $C_1$-$C_3$ haloalkylthio, $C_3$-$C_4$ alkenyl, $C_3$-$C_4$ alkynyl, $CO_2R_{17}$, $C_1$-$C_3$ alkylthio, $C_1$-$C_3$ alkylsulfinyl, $C_1$-$C_3$ alkylsulfonyl or $SO_2NR^{I}R^{II}$;

$R_{15}$ and $R_{16}$ are independently H, $C_1$-$C_4$ alkyl, $C_2$-$C_4$ alkoxyalkyl, $C_1$-$C_3$ haloalkylthio, $C_1$-$C_3$ haloalkoxy, $C_1$-$C_3$ alkoxy, $C_1$-$C_3$ alkylthio, $C_1$-$C_3$ alkylsulfonyl, F, Cl, Br, $CO_2R_{17}$ or $SO_2NR^{I}R^{II}$;

$R^{I}$ and $R^{II}$ are independently $C_1$-$C_3$ alkyl;

$R_{17}$ is $C_1$-$C_3$ alkyl, $CH_2CH{=}CH_2$, $CH_2C{\equiv}CH$, $CH_2CH_2Cl$ or $CH_2CH_2OCH_3$;

A is

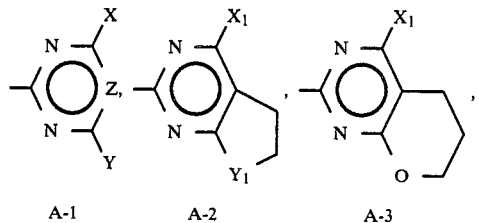

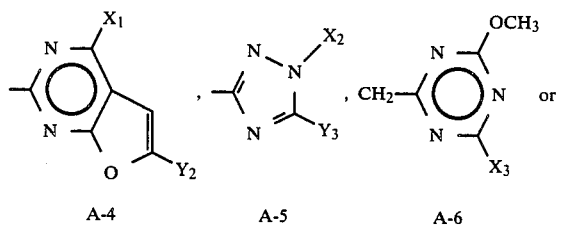

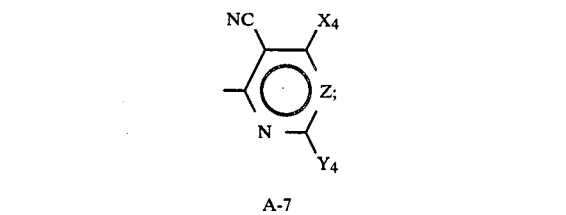

X is H, $C_1$-$C_4$ alkyl, $C_1$-$C_4$ alkoxy, $C_1$-$C_4$ haloalkoxy, $C_1$-$C_4$ haloalkyl, $C_1$-$C_4$ haloalkylthio, $C_1$-$C_4$ alkylthio, halogen, $C_2$-$C_5$ alkoxyalkyl, $C_2$-$C_5$ alkoxyalkoxy, amino, $C_1$-$C_3$ alkylamino or di($C_1$-$C_3$ alkyl)amino;

Y is H, $C_1$-$C_4$ alkyl, $C_1$-$C_4$ alkoxy, $C_1$-$C_4$ haloalkoxy, $C_1$-$C_4$ haloalkylthio, $C_1$-$C_4$ alkylthio, $C_2$-$C_5$ alkoxyalkyl, $C_2$-$C_5$ alkoxyalkoxy, amino, $C_1$-$C_3$ alkylamino, di($C_1$-$C_3$ alkyl)amino, $C_3$-$C_4$ alkenyloxy, $C_3$-$C_4$ alkynyloxy, $C_2$-$C_5$ alkylthioalkyl, $C_2$-$C_5$ alkylsulfinylalkyl, $C_2$-$C_5$ alkylsulfonylalkyl, $C_1$-$C_4$ haloalkyl, $C_3$-$C_5$ cycloalkyl, $C_2$-$C_4$ alkynyl, $C(O)R_3$,

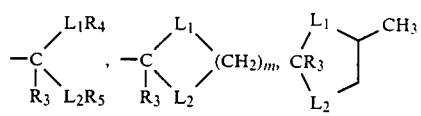

or $N(OCH_3)CH_3$;

m is 2 or 3;

$L_1$ and $L_2$ are independently O or S;

$R_3$ is H or $CH_3$;

$R_4$ and $R_5$ are independently $C_1$-$C_2$ alkyl;

Z is CH or N;

$Y_1$ is O or $CH_2$;

$X_1$ is $CH_3$, $OCH_3$, $OC_2H_5$ or $OCF_2H$;

$Y_2$ is H or $CH_3$;

$X_2$ is $CH_3$, $C_2H_5$ or $CH_2CF_3$;

$Y_3$ is $OCH_3$, $OC_2H_5$, $SCH_3$, $SC_2H_5$, $OCF_2H$, $SCF_2H$, $CH_3$ or $C_2H_5$;

$X_3$ is $CH_3$ or $OCH_3$;

$X_4$ is $CH_3$, $OCH_3$, $OC_2H_5$, $CH_2OCH_3$ or Cl; and $Y_4$ is $CH_3$, $OCH_3$ or $OC_2H_5$;

and their agriculturally suitable salts; provided that
 (1) when X is Cl, Br, F or I, then Z is CH and Y is $OCH_3$, $OC_2H_5$, $N(OCH_3)CH_3$, $NHCH_3$, $N(CH_3)_2$, $NH_2$ or $OCF_2H$;
 (2) when X or Y is $OCF_2H$, then Z is CH;
 (3) when W is S, then R is H, A is A-1, and Y is $CH_3$, $OCH_3$, $OC_2H_5$, $CH_2OCH_3$, $C_2H_5$, $CF_3$, $SCH_3$, $OCH_2CH{=}CH_2$, $OCH_2C{\equiv}CH$, $OCH_2CH_2OCH_3$, $CH(OCH_3)_2$ or

(4) when the total number of carbon atoms of X and Y is greater than four, then the total amount of carbon atoms of Q and $R_2$, $R_{14}$, $R_{15}$ or $R_{16}$ is less than or equal to ten; and
 (5) when L is L-5, L-6 or L-7, then Q must be bonded to the pyrazole ring nitrogen through a carbon atom.

In the above definitions, the term "alkyl", used either alone or in compound words such as "alkylthio" or "haloalkyl", denotes straight chain or branched alkyl, e.g. methyl, ethyl, n-propyl, isopropyl or the different butyl, pentyl and hexyl isomers.

Alkoxy is meant to include isomers, e.g., methoxy, ethoxy, n-propoxy, isopropoxy and the different butoxy isomers.

Alkenyl means straight chain or branched alkenes, e.g. 1-propenyl, 2-propenyl, 3-propenyl and the different butenyl isomers.

Alkynyl means straight chain or branched alkynes, e.g. ethynyl, 1-propynyl, 2-propynyl and the different butynyl isomers.

Alkoxycarbonyl means methoxycarbonyl or ethoxycarbonyl.

Alkylsulfonyl means methylsulfonyl, ethylsulfonyl and the different propylsulfonyl isomers.

Alkylthio, alkylsulfinyl, alkylamino, etc. are defined in an analogous manner.

Cycloalkyl means, e.g. cyclopropyl, cyclobutyl and cyclopentyl.

The term "halogen", either alone or in compound words such as "haloalkyl", denotes fluorine, chlorine, bromine or iodine.

The total number of carbon atoms in a substituent group is indicated by the $C_i$–$C_j$ prefix where i and j are numbers from 1 to 6. For example, $C_2$–$C_5$ alkoxyalkylthio is meant to include $SCH_2OCH_3$ through $SCH_2OC_4H_9$ or $SCH_2CH_2CH_2CH_2OCH_3$ and the various structural isomers embraced therein. The term $C_2$–$C_4$ cyanoalkylthio denotes $SCH_2CN$, $SCH_2CH_2CN$, $SCH(CH_3)CN$, $SCH_2CH_2CH_2CN$ and the various $C_4$ isomers. The term $C_3$–$C_5$ acetylalkylthio means $SCH_2C(O)CH_3$ through $SCH_2CH_2CH_2C(O)CH_3$ and the various structural isomers embraced therein.

Preferred for reasons of increased ease of synthesis and/or greater herbicidal efficacy are (1) Compounds of Formula I where
Q is

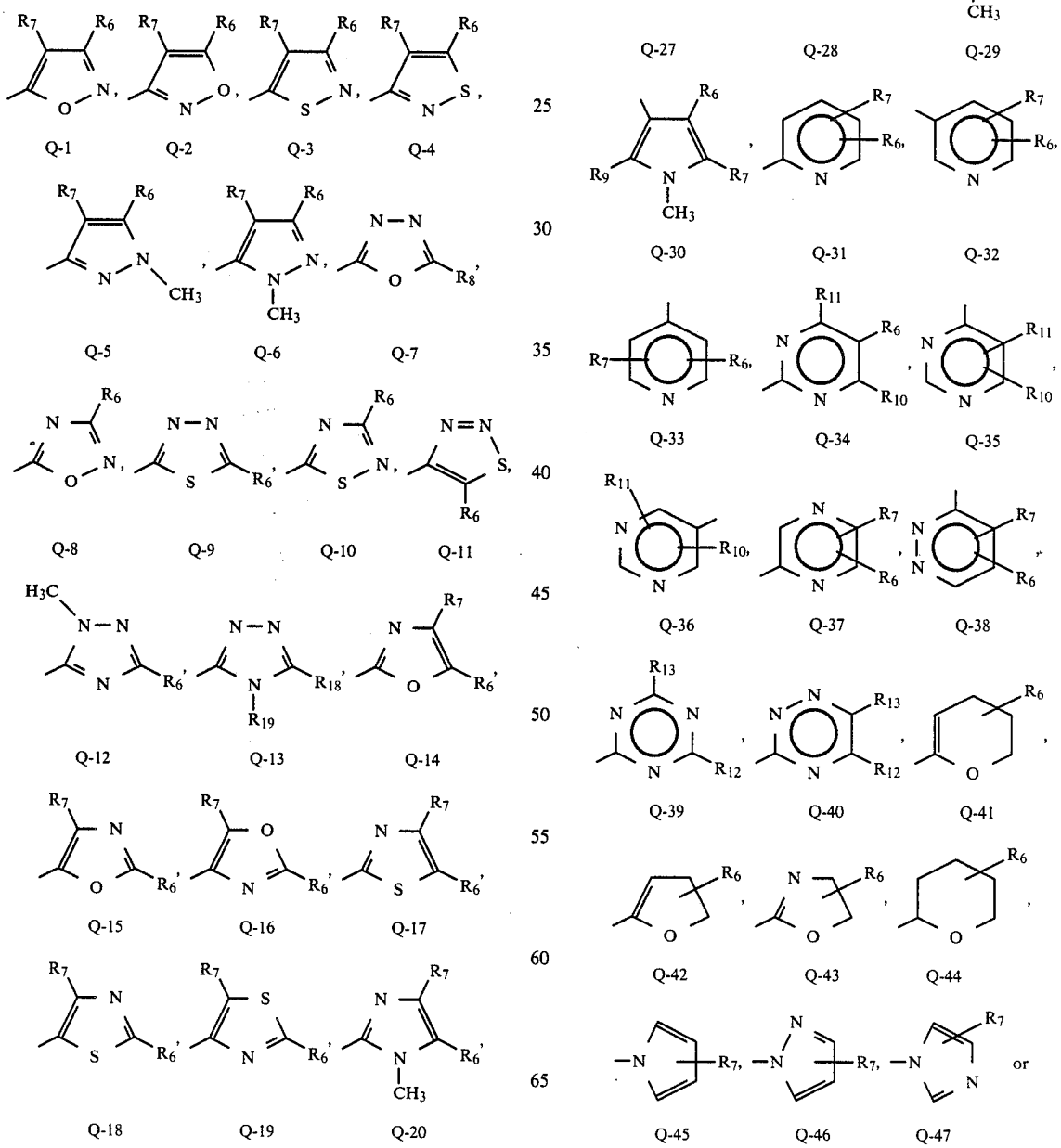

-continued

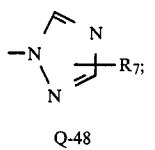
Q-48

$R_6$ and $R_9$ are independently H or $CH_3$;
$R_7$ is H, $CH_3$ or Cl;
$R_8$ is H, SH, $CH_3$, $CH_2CH_3$, $S(C_1-C_4\ alkyl)$, $S(C_3-C_4\ alkenyl)$ optionally substituted with 1 or 2 halogen atoms, $S(C_3-C_4\ alkynyl)$, $OCH_3$, $OCH_2CH_3$, $SCF_2H$, $CF_3$, or $S(C_1-C_3\ alkyl)$ substituted with CN, $CO_2R_4$, $OR_4$ or $C(O)CH_3$;
$R_{10}$ and $R_{11}$ are independently H, $CH_3$ or $OCH_3$;
$R_{12}$ and $R_{13}$ are independently $CH_3$ or $OCH_3$;
$R_{18}$ is H, $C_1-C_3$ alkyl or $C_1-C_3$ alkylthio; and
$R_{19}$ is $C_1-C_3$ alkyl or $CH_2CH=CH_2$;
provided that when L is L-5, L-6 or L-7, then Q is not Q-25, Q-26, Q-27, Q-28, Q-41, Q-42, Q-43 or Q-44;

(2) Compounds of Preferred 1 where R is H and W is O;

(3) Compounds of Preferred 2 where $R_1$ is $C_1-C_3$ alkyl, Y is $CH_3$, $OCH_3$, $CH_2OCH_3$, $NHCH_3$, $CH_2CH_3$, $C\equiv CH$, $C\equiv CCH_3$, $CH(OCH_3)_2$, $CH(CH_3)_2$ or cyclopropyl, $R_8$ is H, SH, $CH_3$, $SCH_3$ or $OCH_3$, $R_{14}$ is H, $CH_3$, $C_2H_5$, $CO_2CH_3$, $CO_2C_2H_5$, F, Cl Br, $SO_2CH_3$, $SO_2C_2H_5$, $OCF_2H$ or $SO_2N(CH_3)_2$, and $R_{15}$ and $R_{16}$ are independently H, $CH_3$, $C_2H_5$, $CO_2CH_3$, $CO_2C_2H_5$, F, Cl, Br, $SO_2CH_3$, $SO_2C_2H_5$, $OCF_2H$, or $SO_2N(CH_3)_2$;

(4) Compounds of Preferred 3 where X is $CH_3$, $OCH_3$, $OC_2H_5$, Cl, Br or $OCF_2H$;

(5) Compounds of Preferred 4 where A is A-1, L is L-1 and Q is Q-1;
(6) Compounds of Preferred 4 where A is A-1, L is L-1 and Q is Q-2;
(7) Compounds of Preferred 4 where A is A-1, L is L-1 and Q is Q-3;
(8) Compounds of Preferred 4 where A is A-1, L is L-1 and Q is Q-4;
(9) Compounds of Preferred 4 where A is A-1, L is L-1 and Q is Q-5;
(10) Compounds of Preferred 4 where A is A-1, L is L-1 and Q is Q-6;
(11) Compounds of Preferred 4 where A is A-1, L is L-1 and Q is Q-7;
(12) Compounds of Preferred 4 where A is A-1, L is L-1 and Q is Q-8;
(13) Compounds of Preferred 4 where A is A-1, L is L-1 and Q is Q-9;
(14) Compounds of Preferred 4 where A is A-1, L is L-1 and Q is Q-10;
(15) Compounds of Preferred 4 where A is A-1, L is L-1 and Q is Q-11;
(16) Compounds of Preferred 4 where A is A-1, L is L-1 and Q is Q-12;
(17) Compounds of Preferred 4 where A is A-1, L is L-1 and Q is Q-13;
(18) Compounds of Preferred 4 where A is A-1, L is L-1 and Q is Q-14;
(19) Compounds of Preferred 4 where A is A-1, L is L-1 and Q is Q-15;
(20) Compounds of Preferred 4 where A is A-1, L is L-1 and Q is Q-16;
(21) Compounds of Preferred 4 where A is A1, L is L-1 and Q is Q-17;
(22) Compounds of Preferred 4 where A is A-1, L is L-1 and Q is Q-18;
(23) Compounds of Preferred 4 where A is A-1, L is L-1 and Q is Q-19;
(24) Compounds of Preferred 4 where A is A-1, L is L-1 and Q is Q-20;
(25) Compounds of Preferred 4 where A is A-1, L is L-1 and Q is Q-21;
(26) Compounds of Preferred 4 where A is A-1, L is L-1 and Q is Q-22;
(27) Compounds of Preferred 4 where A is A-1, L is L-1 and Q is Q-23;
(28) Compounds of Preferred 4 where A is A-1, L is L-1 and Q is Q-24;
(29) Compounds of Preferred 4 where A is A-1, L is L-1 and Q is Q-25;
(30) Compounds of Preferred 4 where A is A-1, L is L-1 and Q is Q-26;
(31) Compounds of Preferred 4 where A is A-1, L is L-1 and Q is Q-27;
(32) Compounds of Preferred 4 where A is A-1, L is L-1 and Q is Q-28;
(33) Compounds of Preferred 4 where A-1, L is L-1 and Q is Q-29;
(34) Compounds of Preferred 4 where A is A-1, L is L-1 and Q is Q-30;
(35) Compounds of Preferred 4 where A is A-1, L is L-1 and Q is Q-31;
(36) Compounds of Preferred 4 where A is A-1, L is L-1 and Q is Q-32;
(37) Compounds of Preferred 4 where A is A-1, L is L-1 and Q is Q-33;
(38) Compounds of Preferred 4 where A is A-1, L is L-1 and Q is Q-34;
(39) Compounds of Preferred 4 where A is A-1, L is L-1 and Q is Q-35;
(40) Compounds of Preferred 4 where A is A-1, L is L-1 and Q is Q-36;
(41) Compounds of Preferred 4 where A is A-1, L is L-1 and Q is Q-37;
(42) Compounds of Preferred 4 where A is A-1, L is L-1 and Q is Q-38;
(43) Compounds of Preferred 4 where A is A-1, L is L-1 and Q is Q-39;
(44) Compounds of Preferred 4 where A is A-1, L is L-1 and Q is Q-40;
(45) Compounds of Preferred 4 where A is A-1, L is L-1 and Q is Q-41;
(46) Compounds of Preferred 4 where A is A-1, L is L-1 and Q is Q-42;
(47) Compounds of Preferred 4 where A is A-1, L is L-1 and Q is Q-43;
(48) Compounds of Preferred 4 where A is A-1, L is L-1 and Q is Q-44;
(49) Compounds of Preferred 4 where A is A-1, L is L-1 and Q is Q-45;
(50) Compounds of Preferred 4 where A is A-1, L is L-1 and Q is Q-46;
(51) Compounds of Preferred 4 where A is A-1, L is L-1 and Q is Q-47;
(52) Compounds of Preferred 4 where A is A-1, L is L-1 and Q is Q-48;
(53) Compounds of Preferred 4 where A is A-1, L is L-2 and Q is Q-1;
(54) Compounds of Preferred 4 where A is A-1, L is L-2 and Q is Q-2;
(55) Compounds of Preferred 4 where A is A-1, L is L-2 and Q is Q-3;

(56) Compounds of Preferred 4 where A is A-1, L is L-2 and Q is Q-4;
(57) Compounds of Preferred 4 where A is A-1, L is L-2 and Q is Q-5;
(58) Compounds of Preferred 4 where A is A-1, L is L-2 and Q is Q-6;
(59) Compounds of Preferred 4 where A is A-1, L is L-2 and Q is Q-7;
(60) Compounds of Preferred 4 where A is A-1, L is L-2 and Q is Q-8;
(61) Compounds of Preferred 4 where A is A-1, L is L-2 and Q is Q-9;
(62) Compounds of Preferred 4 where A is A-1, L is L-2 and Q is Q-10;
(63) Compounds of Preferred 4 where A is A-1, L is L-2 and Q is Q-11;
(64) Compounds of Preferred 4 where A is A-1, L is L-2 and Q is Q-12;
(65) Compounds of Preferred 4 where A is A-1, L is L-2 and Q is Q-13;
(66) Compounds of Preferred 4 where A is A-1, L is L-2 and Q is Q-14;
(67) Compounds of Preferred 4 where A is A-1, L is L-2 and Q is Q-15;
(68) Compounds of Preferred 4 where A is A-1, L is L-2 and Q is Q-16;
(69) Compounds of Preferred 4 where A is A-1, L is L-2 and Q is Q-17;
(70) Compounds of Preferred 4 where A is A-1, L is L-2 and Q is Q-18;
(71) Compounds of Preferred 4 where A is A-1, L is L-2 and Q is Q-19;
(72) Compounds of Preferred 4 where A is A-1, L is L-2 and Q is Q-20;
(73) Compounds of Preferred 4 where A is A-1, L is L-2 and Q is Q-21;
(74) Compounds of Preferred 4 where A is A-1, L is L-2 and Q is Q-22;
(75) Compounds of Preferred 4 where A is A-1, L is L-2 and Q is Q-23;
(76) Compounds of Preferred 4 where A is A-1, L is L-2 and Q is Q-24;
(77) Compounds of Preferred 4 where A is A-1, L is L-2 and Q is Q-25;
(78) Compounds of Preferred 4 where A is A-1, L is L-2 and Q is Q-26;
(79) Compounds of Preferred 4 where A is A-1, L is L-2 and Q is Q-27;
(80) Compounds of Preferred 4 where A is A-1, L is L-2 and Q is Q-28;
(81) Compounds of Preferred 4 where A is A-1, L is L-2 and Q is Q-29;
(82) Compounds of Preferred 4 where A is A-1, L is L-2 and Q is Q-30;
(83) Compounds of Preferred 4 where A is A-1, L is L-2 and Q is Q-31;
(84) Compounds of Preferred 4 where A is A-1, L is L-2 and Q is Q-32;
(85) Compounds of Preferred 4 where A is A-1, L is L-2 and Q is Q-33;
(86) Compounds of Preferred 4 where A is A-1, L is L-2 and Q is Q-34;
(87) Compounds of Preferred 4 where A is A-1, L is L-2 and Q is Q-35;
(88) Compounds of Preferred 4 where A is A-1, L is L-2 and Q is Q-36;
(89) Compounds of Preferred 4 where A is A-1, L is L-2 and Q is Q-37;
(90) Compounds of Preferred 4 where A is A-1, L is L-2 and Q is Q-38;
(91) Compounds of Preferred 4 where A is A-1, L is L-2 and Q is Q-39;
(92) Compounds of Preferred 4 where A is A-1, L is L-2 and Q is Q-40;
(93) Compounds of Preferred 4 where A is A-1, L is L-2 and Q is Q-41;
(94) Compounds of Preferred 4 where A is A-1, L is L-2 and Q is Q-42;
(95) Compounds of Preferred 4 where A is A-1, L is L-2 and Q is Q-43;
(96) Compounds of Preferred 4 where A is A-1, L is L-2 and Q is Q-44;
(97) Compounds of Preferred 4 where A is A-1, L is L-2 and Q is Q-45;
(98) Compounds of Preferred 4 where A is A-1, L is L-2 and Q is Q-46;
(99) Compounds of Preferred 4 where A is A-1, L is L-2 and Q is Q-47;
(100) Compounds of Preferred 4 where A is A-1, L is L-2 and Q is Q-48;
(101) Compounds of Preferred 4 where A is A-1, L is L-3 and Q is Q-1;
(102) Compounds of Preferred 4 where A is A-1, L is L-3 and Q is Q-2;
(103) Compounds of Preferred 4 where A is A-1, L is L-3 and Q is Q-3;
(104) Compounds of Preferred 4 where A is A-1, L is L-3 and Q is Q-4;
(105) Compounds of Preferred 4 where A is A-1, L is L-3 and Q is Q-5;
(106) Compounds of Preferred 4 where A is A-1, L is L-3 and Q is Q-6;
(107) Compounds of Preferred 4 where A is A-1, L is L-3 and Q is Q-7;
(108) Compounds of Preferred 4 where A is A-1, L is L-3 and Q is Q-8;
(109) Compounds of Preferred 4 where A is A-1, L is L-3 and Q is Q-9;
(110) Compounds of Preferred 4 where A is A-1, L is L-3 and Q is Q-10;
(111) Compounds of Preferred 4 where A is A-1, L is L-3 and Q is Q-11;
(112) Compounds of Preferred 4 where A is A-1, L is L-3 and Q is Q-12;
(113) Compounds of Preferred 4 where A is A-1, L is L-3 and Q is Q-13;
(114) Compounds of Preferred 4 where A is A-1, L is L-3 and Q is Q-14;
(115) Compounds of Preferred 4 where A is A-1, L is L-3 and Q is Q-15;
(116) Compounds of Preferred 4 where A is A-1, L is L-3 and Q is Q-16;
(117) Compounds of Preferred 4 where A is A-1, L is L-3 and Q is Q-17;
(118) Compounds of Preferred 4 where A is A-1, L is L-3 and Q is Q-18;
(119) Compounds of Preferred 4 where A is A-1, L is L-3 and Q is Q-19;
(120) Compounds of Preferred 4 where A is A-1, L is L-3 and Q is Q-20;
(121) Compounds of Preferred 4 where A is A-1, L is L-3 and Q is Q-21;
(122) Compounds of Preferred 4 where A is A-1, L is L-3 and Q is Q-22;
(123) Compounds of Preferred 4 where A is A-1, L is L-3 and Q is Q-23;

(124) Compounds of Preferred 4 where A is A-1, L is L-3 and Q is Q-24;
(125) Compounds of Preferred 4 where A is A-1, L is L-3 and Q is Q-25;
(126) Compounds of Preferred 4 where A is A-1, L is L-3 and Q is Q-26;
(127) Compounds of Preferred 4 where A is A-1, L is L-3 and Q is Q-27;
(128) Compounds of Preferred 4 where A is A-1, L is L-3 and Q is Q-28;
(129) Compounds of Preferred 4 where A is A-1, L is L-3 and Q is Q-29;
(130) Compounds of Preferred 4 where A is A-1, L is L-3 and Q is Q-30;
(131) Compounds of Preferred 4 where A is A-1, L is L-3 and Q is Q-31;
(132) Compounds of Preferred 4 where A is A-1, L is L-3 and Q is Q-32;
(133) Compounds of Preferred 4 where A is A-1, L is L-3 and Q is Q-33;
(134) Compounds of Preferred 4 where A is A-1, L is L-3 and Q is Q-34;
(135) Compounds of Preferred 4 where A is A-1, L is L-3 and Q is Q-35;
(136) Compounds of Preferred 4 where A is A-1, L is L-3 and Q is Q-36;
(137) Compounds of Preferred 4 where A is A-1, L is L-3 and Q is Q-37;
(138) Compounds of Preferred 4 where A is A-1, L is L-3 and Q is Q-38;
(139) Compounds of Preferred 4 where A is A-1, L is L-3 and Q is Q-39;
(140) Compounds of Preferred 4 where A is A-1, L is L-3 and Q is Q-40;
(141) Compounds of Preferred 4 where A is A-1, L is L-3 and Q is Q-41;
(142) Compounds of Preferred 4 where A is A-1, L is L-3 and Q is Q-42;
(143) Compounds of Preferred 4 where A is A-1, L is L-3 and Q is Q-43;
(144) Compounds of Preferred 4 where A is A-1, L is L-3 and Q is Q-44;
(145) Compounds of Preferred 4 where A is A-1, L is L-3 and Q is Q-45;
(146) Compounds of Preferred 4 where A is A-1, L is L-3 and Q is Q-46;
(147) Compounds of Preferred 4 where A is A-1, L is L-3 and Q is Q-47;
(148) Compounds of Preferred 4 where A is A-1, L is L-3 and Q is Q-48;
(149) Compounds of Preferred 4 where A is A-1, L is L-4 and Q is Q-1;
(150) Compounds of Preferred 4 where A is A-1, L is L-4 and Q is Q-2;
(151) Compounds of Preferred 4 where A is A-1, L is L-4 and Q is Q-3;
(152) Compounds of Preferred 4 where A is A-1, L is L-4 and Q is Q-4;
(153) Compounds of Preferred 4 where A is A-1, L is L-4 and Q is Q-5;
(154) Compounds of Preferred 4 where A is A-1, L is L-4 and Q is Q-6;
(155) Compounds of Preferred 4 where A is A-1, L is L-4 and Q is Q-7;
(156) Compounds of Preferred 4 where A is A-1, L is L-4 and Q is Q-8;
(157) Compounds of Preferred 4 where A is A-1, L is L-4 and Q is Q-9;
(158) Compounds of Preferred 4 where A is A-1, L is L-4 and Q is Q-10;
(159) Compounds of Preferred 4 where A is A-1, L is L-4 and Q is Q-11;
(160) Compounds of Preferred 4 where A is A-1, L is L-4 and Q is Q-12;
(161) Compounds of Preferred 4 where A is A-1, L is L-4 and Q is Q-13;
(162) Compounds of Preferred 4 where A is A-1, L is L-4 and Q is Q-14;
(163) Compounds of Preferred 4 where A is A-1, L is L-4 and Q is Q-15;
(164) Compounds of Preferred 4 where A is A-1, L is L-4 and Q is Q-16;
(165) Compounds of Preferred 4 where A is A-1, L is L-4 and Q is Q-17;
(166) Compounds of Preferred 4 where A is A-1, L is L-4 and Q is Q-18;
(167) Compounds of Preferred 4 where A is A-1, L is L-4 and Q is Q-19;
(168) Compounds of Preferred 4 where A is A-1, L is L-4 and Q is Q-20;
(169) Compounds of Preferred 4 where A is A-1, L is L-4 and Q is Q-21;
(170) Compounds of Preferred 4 where A is A-1, L is L-4 and Q is Q-22;
(171) Compounds of Preferred 4 where A is A-1, L is L-4 and Q is Q-23;
(172) Compounds of Preferred 4 where A is A-1, L is L-4 and Q is Q-24;
(173) Compounds of Preferred 4 where A is A-1, L is L-4 and Q is Q-25;
(174) Compounds of Preferred 4 where A is A-1, L is L-4 and Q is Q-26;
(175) Compounds of Preferred 4 where A is A-1, L is L-4 and Q is Q-27;
(176) Compounds of Preferred 4 where A is A-1, L is L-4 and Q is Q-28;
(177) Compounds of Preferred 4 where A is A-1, L is L-4 and Q is Q-29;
(178) Compounds of Preferred 4 where A is A-1, L is L-4 and Q is Q-30;
(179) Compounds of Preferred 4 where A is A-1, L is L-4 and Q is Q-31;
(180) Compounds of Preferred 4 where A is A-1, L is L-4 and Q is Q-32;
(181) Compounds of Preferred 4 where A is A-1, L is L-4 and Q is Q-33;
(182) Compounds of Preferred 4 where A is A-1, L is L-4 and Q is Q-34;
(183) Compounds of Preferred 4 where A is A-1, L is L-4 and Q is Q-35;
(184) Compounds of Preferred 4 where A is A-1, L is L-4 and Q is Q-36;
(185) Compounds of Preferred 4 where A is A-1, L is L-4 and Q is Q-37;
(186) Compounds of Preferred 4 where A is A-1, L is L-4 and Q is Q-38;
(187) Compounds of Preferred 4 where A is A-1, L is L-4 and Q is Q-39;
(188) Compounds of Preferred 4 where A is A-1, L is L-4 and Q is Q-40;
(189) Compounds of Preferred 4 where A is A-1, L is L-4 and Q is Q-41;
(190) Compounds of Preferred 4 where A is A-1, L is L-4 and Q is Q-42;
(191) Compounds of Preferred 4 where A is A-1, L is L-4 and q is Q-43;

(192) Compounds of Preferred 4 where A is A-1, L is L-4 and Q is Q-44;
(193) Compounds of Preferred 4 where A is A-1, L is L-4 and Q is Q-45;
(194) Compounds of Preferred 4 where A is A-1, L is L-4 and Q is Q-46;
(195) Compounds of Preferred 4 where A is A-1, L is L-4 and Q is Q-47;
(196) Compounds of Preferred 4 where A is A-1, L is L-4 and Q is Q-48;
(197) Compounds of Preferred 4 where A is A-1, L is L-5 and Q is Q-1;
(198) Compounds of Preferred 4 where A is A-1, L is L-5 and Q is Q-2;
(199) Compounds of Preferred 4 where A is A-1, L is L-5 and Q is Q-3;
(200) Compounds of Preferred 4 where A is A-1, L is L-5 and Q is Q-4;
(201) Compounds of Preferred 4 where A is A-1, L is L-5 and Q is Q-5;
(202) Compounds of Preferred 4 where A is A-1, L is L-5 and Q is Q-6;
(203) Compounds of Preferred 4 where A is A-1, L is L-5 and Q is Q-7;
(204) Compounds of Preferred 4 where A is A-1, L is L-5 and Q is Q-8;
(205) Compounds of Preferred 4 where A is A-1, L is L-5 and Q is Q-9;
(206) Compounds of Preferred 4 where A is A-1, L is L-5 and Q is Q-10;
(207) Compounds of Preferred 4 where A is A-1, L is L-5 and Q is Q-11;
(208) Compounds of Preferred 4 where A is A-1, L is L-5 and Q is Q-12;
(209) Compounds of Preferred 4 where A is A-1, L is L-5 and Q is Q-13;
(210) Compounds of Preferred 4 where A is A-1, L is L-5 and Q is Q-14;
(211) Compounds of Preferred 4 where A is A-1, L is L-5 and Q is Q-15;
(212) Compounds of Preferred 4 where A is A-1, L is L-5 and Q is Q-16;
(213) Compounds of Preferred 4 where A is A-1, L is L-5 and Q is Q-17;
(214) Compounds of Preferred 4 where A is A-1, L is L-5 and Q is Q-18;
(215) Compounds of Preferred 4 where A is A-1, L is L-5 and Q is Q-19;
(216) Compounds of Preferred 4 where A is A-1, L is L-5 and Q is Q-20;
(217) Compounds of Preferred 4 where A is A-1, L is L-5 and Q is Q-21;
(218) Compounds of Preferred 4 where A is A-1, L is L-5 and Q is Q-22;
(219) Compounds of Preferred 4 where A is A-1, L is L-5 and Q is Q-23;
(220) Compounds of Preferred 4 where A is A-1, L is L-5 and Q is Q-24;
(221) Compounds of Preferred 4 where A is A-1, L is L-5 and Q is Q-29;
(222) Compounds of Preferred 4 where A is A-1, L is L-5 and Q is Q-30;
(223) Compounds of Preferred 4 where A is A-1, L is L-5 and Q is Q-31;
(224) Compounds of Preferred 4 where A is A-1, L is L-5 and Q is Q-32;
(225) Compounds of Preferred 4 where A is A-1, L is L-5 and Q is Q-33;
(226) Compounds of Preferred 4 where A is A-1, L is L-5 and Q is Q-34;
(227) Compounds of Preferred 4 where A is A-1, L is L-5 and Q is Q-35;
(228) Compounds of Preferred 4 where A is A-1, L is L-5 and Q is Q-36;
(229) Compounds of Preferred 4 where A is A-1, L is L-5 and Q is Q-37;
(230) Compounds of Preferred 4 where A is A-1, L is L-5 and Q is Q-38;
(231) Compounds of Preferred 4 where A is A-1, L is L-5 and Q is Q-39;
(232) Compounds of Preferred 4 where A is A-1, L is L-5 and Q is Q-40;
(233) Compounds of Preferred 4 where A is A-1, L is L-6 and Q is Q-1;
(234) Compounds of Preferred 4 where A is A-1, L is L-6 and Q is Q-2;
(235) Compounds of Preferred 4 where A is A-1, L is L-6 and Q is Q-3;
(236) Compounds of Preferred 4 where A is A-1, L is L-6 and Q is Q-4;
(237) Compounds of Preferred 4 where A is A-1, L is L-6 and Q is Q-5;
(238) Compounds of Preferred 4 where A is A-1, L is L-6 and Q is Q-6;
(239) Compounds of Preferred 4 where A is A-1, L is L-6 and Q is Q-7;
(240) Compounds of Preferred 4 where A is A-1, L is L-6 and Q is Q-8;
(241) Compounds of Preferred 4 where A is A-1, L is L-6 and Q is Q-9;
(242) Compounds of Preferred 4 where A is A-1, L is L-6 and Q is Q-10;
(243) Compounds of Preferred 4 where A is A-1, L is L-6 and Q is Q-11;
(244) Compounds of Preferred 4 where A is A-1, L is L-6 and Q is Q-12;
(245) Compounds of Preferred 4 where A is A-1, L is L-6 and Q is Q-13;
(246) Compounds of Preferred 4 where A is A-1, L is L-6 and Q is Q-14;
(247) Compounds of Preferred 4 where A is A-1, L is L-6 and Q is Q-15;
(248) Compounds of Preferred 4 where A is A-1, L is L-6 and Q is Q-16;
(249) Compounds of Preferred 4 where A is A-1, L is L-6 and Q is Q-17;
(250) Compounds of Preferred 4 where A is A-1, L is L-6 and Q is Q-18;
(251) Compounds of Preferred 4 where A is A-1, L is L-6 and Q is Q-19;
(252) Compounds of Preferred 4 where A is A-1, L is L-6 and Q is Q-20;
(253) Compounds of Preferred 4 where A is A-1, L is L-6 and Q is Q-21;
(254) Compounds of Preferred 4 where A is A-1, L is L-6 and Q is Q-22;
(255) Compounds of Preferred 4 where A is A-1, L is L-6 and Q is Q-23;
(256) Compounds of Preferred 4 where A is A-1, L is L-6 and Q is Q-24;
(257) Compounds of Preferred 4 where A is A-1, L is L-6 and Q is Q-29;
(258) Compounds of Preferred 4 where A is A-1, L is L-6 and Q is Q-30;
(259) Compounds of Preferred 4 where A is A-1, L is L-6 and Q is Q-31;

(260) Compounds of Preferred 4 where A is A-1, L is L-6 and Q is Q-32;
(261) Compounds of Preferred 4 where A is A-1, L is L-6 and Q is Q-33;
(262) Compounds of Preferred 4 where A is A-1, L is L-6 and Q is Q-34;
(263) Compounds of Preferred 4 where A is A-1, L is L-6 and Q is Q-35;
(264) Compounds of Preferred 4 where A is A-1, L is L-6 and Q is Q-36;
(265) Compounds of Preferred 4 where A is A-1, L is L-6 and Q is Q-37;
(266) Compounds of Preferred 4 where A is A-1, L is L-6 and Q is Q-38;
(267) Compounds of Preferred 4 where A is A-1, L is L-6 and Q is Q-39;
(268) Compounds of Preferred 4 where A is A-1, L is L-6 and Q is Q-40;
(269) Compounds of Preferred 4 where A is A-1, L is L-7 and Q is Q-1;
(270) Compounds of Preferred 4 where A is A-1, L is L-7 and Q is Q-2;
(271) Compounds of Preferred 4 where A is A-1, L is L-7 and Q is Q-3;
(272) Compounds of Preferred 4 where A is A-1, L is L-7 and Q is Q-4;
(273) Compounds of Preferred 4 where A is A-1, L is L-7 and Q is Q-5;
(274) Compounds of Preferred 4 where A is A-1, L is L-7 and Q is Q-6;
(275) Compounds of Preferred 4 where A is A-1, L is L-7 and Q is Q-7;
(276) Compounds of Preferred 4 where A is A-1, L is L-7 and Q is Q-8;
(277) Compounds of Preferred 4 where A is A-1, L is L-7 and Q is Q-9;
(278) Compounds of Preferred 4 where A is A-1, L is L-7 and Q is Q-10;
(279) Compounds of Preferred 4 where A is A-1, L is L-7 and Q is Q-11;
(280) Compounds of Preferred 4 where A is A-1, L is L-7 and Q is Q-12;
(281) Compounds of Preferred 4 where A is A-1, L is L-7 and Q is Q-13;
(282) Compounds of Preferred 4 where A is A-1, L is L-7 and Q is Q-14;
(283) Compounds of Preferred 4 where A is A-1, L is L-7 and Q is Q-15;
(284) Compounds of Preferred 4 where A is A-1, L is L-7 and Q is Q-16;
(285) Compounds of Preferred 4 where A is A-1, L is L-7 and Q is Q-17;
(286) Compounds of Preferred 4 where A is A-1, L is L-7 and Q is Q-18;
(287) Compounds of Preferred 4 where A is A-1, L is L-7 and Q is Q-19;
(288) Compounds of Preferred 4 where A is A-1, L is L-7 and Q is Q-20;
(289) Compounds of Preferred 4 where A is A-1, L is L-7 and Q is Q-21;
(290) Compounds of Preferred 4 where A is A-1, L is L-7 and Q is Q-22;
(291) Compounds of Preferred 4 where A is A-1, L is L-7 and Q is Q-23;
(292) Compounds of Preferred 4 where A is A-1, L is L-7 and Q is Q-24;
(293) Compounds of Preferred 4 where A is A-1, L is L-7 and Q is Q-29;
(294) Compounds of Preferred 4 where A is A-1, L is L-7 and Q is Q-30;
(295) Compounds of Preferred 4 where A is A-1, L is L-7 and Q is Q-31;
(296) Compounds of Preferred 4 where A is A-1, L is L-7 and Q is Q-32;
(297) Compounds of Preferred 4 where A is A-1, L is L-7 and Q is Q-33;
(298) Compounds of Preferred 4 where A is A-1, L is L-7 and Q is Q-34;
(299) Compounds of Preferred 4 where A is A-1, L is L-7 and Q is Q-35;
(300) Compounds of Preferred 4 where A is A-1, L is L-7 and Q is Q-36;
(301) Compounds of Preferred 4 where A is A-1, L is L-7 and Q is Q-37;
(302) Compounds of Preferred 4 where A is A-1, L is L-7 and Q is Q-38;
(303) Compounds of Preferred 4 where A is A-1, L is L-7 and Q is Q-39;
(304) Compounds of Preferred 4 where A is A-1, L is L-7 and Q is Q-40;

Specifically preferred compounds of this invention for reasons of greatest ease of synthesis and/or greatest herbicidal efficacy are:

N-[(4,6-dimethoxypyrimidin-2-yl)aminocarbonyl]-1,5-dimethyl-3-[5-(methylthio)-1,3,4-oxadiazol-2-yl]-1H-pyrazole-4-sulfonamide m.p. 201°–203.5° C.;

N-[(4-methoxy-6-methyl-1,3,5-triazin-2-yl)aminocarbonyl]-1,5-dimethyl-3-[5-(methylthio)-1,3,4-oxadiazol-2-yl]-1H-pyrazole-4-sulfonamide, m.p. 205°–206.5° C.;

N-[(4-chloro-6-methoxypyrimidin-2-yl)aminocarbonyl]-1,3-dimethyl-5-[5-(2-propenylthio)-1,3,4-oxadiazol-2-yl]-1H-pyrazole-4-sulfonamide, m.p. 183°–185° C.;

N-[(4,6-dimethoxypyrimidin-2-yl)aminocarbonyl]-4-(5-mercapto-1,3,4-oxadiazol-2-yl)-1,5-dimethyl-1H-pyrazole-3-sulfonamide, m.p. 202°–204° C.; and 3-[[(4,6-dimethoxypyrimidin-2-yl)aminocarbonyl]aminosulfonyl]-1-(2-pyridinyl)-1H-pyrazole-4-carboxylic acid, methyl ester, m.p. 183°–188° C.

DETAILED DESCRIPTION OF THE INVENTION

Synthesis

The compounds of Formula I can be prepared by one or more of the methods described below in Equations 1, 2, 3 and 4.

As shown in Equation 1 below, the compounds of Formula I, where W is O, can be prepared by treating sulfonamides of Formula 2 with the methyl ester of a pyrimidine or triazinecarbamic acid of Formula 3 in the presence of an equimolar quantity of trimethylaluminum.

Equation 1

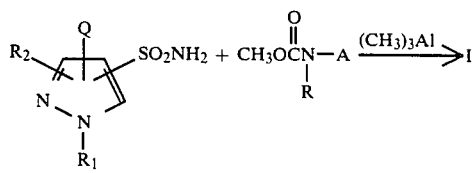

2          3 wherein A, $R_1$, Q, and $R_2$ are as previously defined, and R is H.

The reaction of Equation 1 is best carried out at temperatures between 23° to 83° C. in an inert solvent such as methylene chloride or 1,2-dichloroethane for 12 to 96 hours under an inert atmosphere. The product can be isolated by the addition of an aqueous acetic acid solution followed by extraction of the product into methylene chloride or direct filtration of a product of low solubility. The product can ordinarily be purified by trituration with solvents such as n-butyl chloride, ethyl acetate or diethyl ether or by chromatography procedures. The methyl carbamates, 3, can be conveniently prepared by treatment of the corresponding heterocyclic amines of Formula 6 with dimethyl carbonate or methyl chloroformate in the presence of a base such as sodium hydride or pyridine.

Further details of this reaction and the preparation of the carbamates of Formula 3 can be found in EP-A No. 83,975 (published July 20, 1983).

Alternatively, compounds of Formula I, where W is O, can be prepared by the reaction of sulfonamides of Formula 2 with the phenyl ester of the appropriate carbamic acid, 4, in the presence of an equimolar quantity of a tertiary amine base such as 1,8-diazabicyclo[5.4.0]-undec-7-ene (DBU).

Equation 2

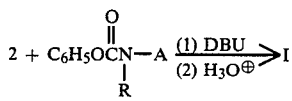

4 wherein $R_2$, A, $R_1$ and Q are as previously defined, and R is H.

The reaction of Equation 2 is best carried out at 20° to 30° C. in an inert solvent such as dioxane or acetonitrile. Aqueous acid work-up affords the desired products, according to the teachings of EP-A No. 70,804 (published Jan. 26, 1983) and South African Patent Application Nos. 825,042 and 830,441. The phenyl carbamates, 4, can be prepared by treating the corresponding heterocyclic amines of Formula 6 with diphenyl carbonate or phenyl chloroformate in the presence of a base such as sodium hydride or pyridine.

Also, many compounds of Formula I can be prepared by reacting an appropriate sulfonyl isocyanate or sulfonyl isothiocyanate, 5, with the appropriately substituted aminoheterocycle, 6, as shown in Equation 3 below.

Equation 3

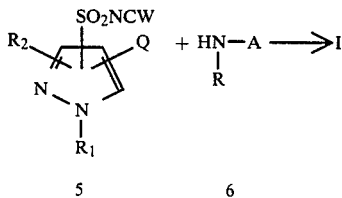

wherein $R_2$, A, R, $R_1$ and W are as previously defined except $R_1$ is other than H.

The reaction is best performed in an inert solvent such as methylene chloride, tetrahydrofuran, acetonitrile or toluene at 23° to 100° C. for 1 to 24 hours. In cases where the products are insoluble in the reaction solvent, they may be isolated by simple filtration. When the products are soluble, they may be isolated by evaporation of the solvent and trituration of the residue with an appropriate solvent such as 1-chlorobutane, diethyl ether, methanol or ethyl acetate and filtration. The products may be further purified by column chromatography procedures.

Sulfonyl isocyanates of Formula 5 above where W=O may be prepared, although often times in low yields, from corresponding sulfonamides of Formula 2 by methods analogous to those described in U.S. Pat. No. 4,238,621 and EP-A No. 83,975 (published July 20, 1983). By a preferred method, sulfonamides are reacted with phosgene, in the presence of n-butyl isocyanate and a tertiary amine catalyst, at reflux in an inert solvent such as xylenes. A preferred catalyst is 1,4-diazabicyclo[2.2.2]octane (DABCO). Alternatively, isocyanates, 5, may be prepared by (1) reacting sulfonamides, 2, with n-butyl isocyanate and a base such as potassium carbonate at reflux in an inert solvent such as 2-butanone to form a n-butyl sulfonylurea; and (2) reacting this compound with phosgene and DABCO catalyst at reflux in xylenes solvent.

Sulfonyl isothiocyanates can be prepared by treatment of sulfonamides with carbon disulfide and potassium hydroxide followed by reaction of the dipotassium salt with phosgene according to the teaching of K. Hartke, *Arch. Pharm.*, 299, 174 (1966).

Some of the compounds of Formula I also can be prepared as shown in Equation 4.

Equation 4

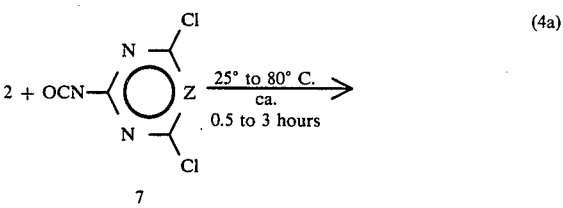

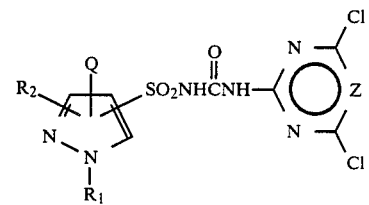

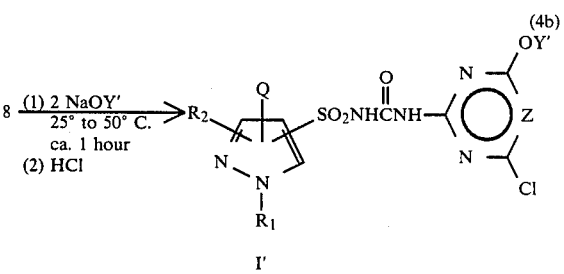

-continued

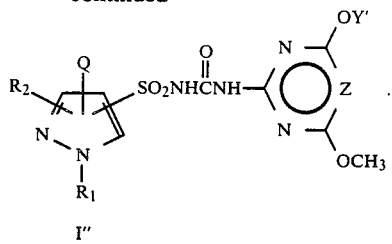

I'' wherein

Y' is $CH_3$, $C_2H_5$, $CH_2CH_2F$, $CH_2CHF_2$ or $CH_2CF_3$; and $R_1$, $R_2$ and Q are as previously defined except $R_1$ is other than H.

The reaction series is performed according to the procedures disclosed in EPO Publication No. 80,140 and the requisite heterocyclic isocyanates of Formula 7 can be prepared according to methods described in Swiss No. 579,062, U.S. Pat. No. 3,919,228, U.S. Pat. No. 3,732,223 and U. von Gizycki, *Angew Chem. Ind. Ed. Engl.* 1976, 10, 402 and 403.

Many sulfonamides of Formula 2a where Q is Q-1 to Q-24 or Q-29 to Q-40, can be prepared by the sequence of reactions shown below in Equation 5.

Equation 5

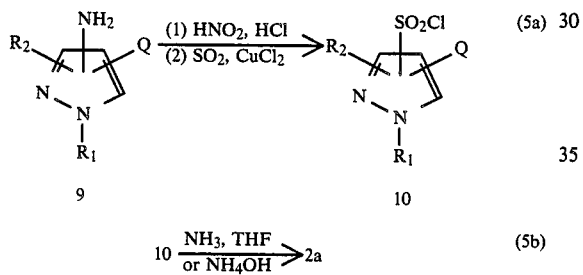

wherein $R_1$ and $R_2$ are as previously defined except $R_1$ is other than H;

Q is Q-1 to Q-24 or Q-29 to Q-40; and

L is $L_1$ to $L_4$.

The reactions of Equation 5(a,b) can be run by methods anlogous to those described in EP-A Nos. 83,975 and 85,476 (published July 20, 1983 and Aug. 10, 1983, respectively). The reaction of Equation 5a is accomplished by treating a solution of amine 9 in a mixture of concentrated hydrochloric acid and glacial acetic acid with a solution of sodium nitrite in water at $-5°$ C. to $5°$ C. After stirring for 10–30 minutes at about $0°$ C. to insure complete diazotization, the solution is added to a mixture of an excess of sulfur dioxide and a catalytic amount of copper(I) chloride or copper(II) chloride in glacial acetic acid at about $10°$ C. The temperature is kept at about $10°$ C. for ¼ to 1 hour, and then raised to $20°$ C. to $30°$ C. and held at that temperature for 2 to about 24 hours. This solution is then poured into a large excess of icewater. The sulfonyl chloride 10 can be isolated by filtration or by extraction into a solvent such as ethyl ether, methylene chloride or preferably, 1-chlorobutane, followed by evaporation of the solvent.

The amination described in Equation 5b is conveniently carried out by treating a solution of the sulfonyl chloride 10 with at least two mole equivalents of anhydrous ammonia or aqueous ammonium hydroxide in an inert solvent such as tetrahydrofuran. Sulfonamides 2a are isolated by filtration, washing with water to remove the by-product ammonium chloride, and concentration of the organic solution. The sulfonamides may be further purified by recrystallization or chromatographic procedures.

Certain sulfonamides of Formula 2b, where Q is Q-7 to Q-13, can be prepared by analogy with the methods described in EP-A No. 83,975, and references cited therein, as shown in Equation 6. By carrying out the appropriate reactions taught in EP-A No. 83,975 or simple modifications thereof, those skilled in the art can prepare N-t-butyl protected pyrazolesulfonamides of Formula 12, where Q is Q-7 to Q-13.

Equation 6

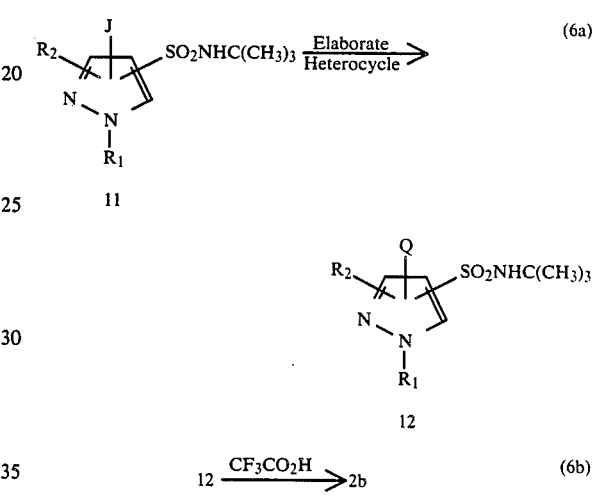

wherein

L is L-1 to L-4;

$R_1$ and $R_2$ are as previously defined except $R_1$ is other than H;

Q is Q-7 to Q-13; and

J are appropriate functional groups taught in EP-A No. 83,975 and reference cited therein, to prepare Q groups Q-7 to Q-13.

In certain instances removal of the t-butyl protecting group may be concomitant with the heterocycle elaboration step, however most cases require treatment with trifluoroacetic acid or with an acidic catalyst in an alcoholic solvent. The sulfonamides of Formula 11 can be prepared by the procedures taught in EP-A Nos. 95,925 and 87,780 or simple modifications thereof, which should be obvious to one skilled in the art.

Sulfonamides of formula 2c containing a pyridinyl, pyrimidinyl, pyrazinyl, pyridazinyl, or triazinyl group (Q is Q-31 to Q-40) may be prepared by the sequence of reactions outlined in Equation 7.

Equation 7

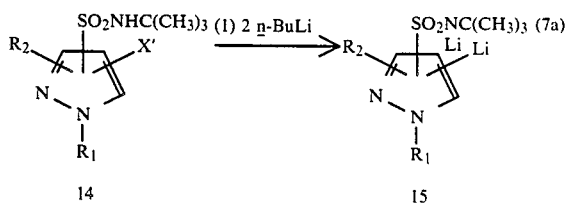

-continued

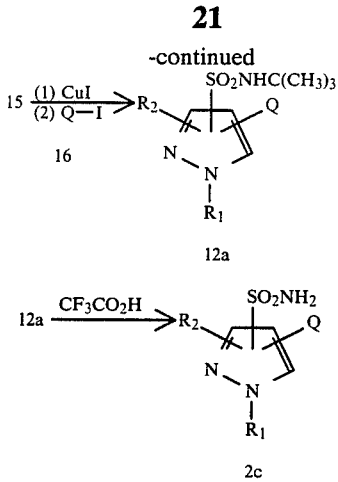

wherein
L is L-1, L-2 and L-4;
X' is Br in the 4-position and H in the 5-position;
Q is Q-31 to Q-40;
R$_1$ is as previously defined with the exception that R$_1$ does not represent H; and
R$_2$ is as defined previously.

The compounds of Formula 2c are prepared by analogy with the teachings of EP-A No. 85,476 (published Aug. 10, 1983).

Equations 7(a,b)

An N-t-butyl sulfonamide of Formula 14 is dissolved in an ethereal solvent, such as tetrahydrofuran, and two equivalents of n-butyllithium in hexane are added at about −70° C. After 1-5 hours at about −70° C., the compound of Formula 15 is formed. This is not isolated, but one equivalent of copper(I) iodide is added at about −70° C., followed by 1-1.5 equivalents of an appropriately substituted heteroaromatic iodide of Formula 16. The reaction mixture is heated at 0° to 70° C. for 1-3 days, concentrated and poured onto aqueous ammonia. Compounds of Formula 12a are isolated by filtration if solids or by extraction with methylene chloride and concentration if oils. The compounds, 12a, may be further purified by recrystallization or chromatography procedures.

The compounds of Formula 16 above may be prepared according to methods known in the art, such as those reviewed in "The Chemistry of Heterocyclic Compounds", a series published by Interscience Publ., New York and London, the teachings of which are incorporated herein by reference. The iodopyridines are described in Vol. 14 of the above series, pp. 407–488. Iodopyrimidines are described by D. J. Brown and S. F. Mason in Vol. 16 of the above series. The preparation of iodopyrazines is taught by A. Hirshberg and P. E. Spoerri, *J. Org. Chem.*, 26, 1907 (1981) and iodopyridazines are described by D. L. Aldons and R. N. Castle in Vol. 28 of the Interscience series, pp. 240–241. The iodo-1,3,5-triazines are described by E. M. Smolin and L. Rapoport, in Vol. 13 of the above series, and a method for preparing iodo-1,2,4-triazines is taught by A. Rykowski and H. C. van der Plas, in *J. Org. Chem.*, 45, 881 (1980).

Equation 7(c)

This reaction is conducted by heating a compound of Formula 12a with 2-10 equivalents of trifluoroacetic acid with or without an inert solvent at 30°-70° C. for 1-3 days. The product, 2c, may be isolated as a trifluoroacetate by evaporation of solvent and excess acid and trituration with ether. The free base may be obtained by neutralization of the salt with aqueous base, extraction into an organic solvent, and concentration of the organic extracts. Products 2c may be further purified by recrystallization or chromatographic procedures. The sulfonamides of Formula 14 may be prepared by procedures taught in EP-A Nos. 95,925 and 87,780 or simple modifications thereof.

Some sulfonamides containing a tetrahydrofuranyl, or tetrahydropyranyl, dihydrofuranyl or dihydropyranyl group can be prepared by analogy with the teachings of EP-A No. 84,476 as illustrated in Equations 8 and 9.

Equation 8

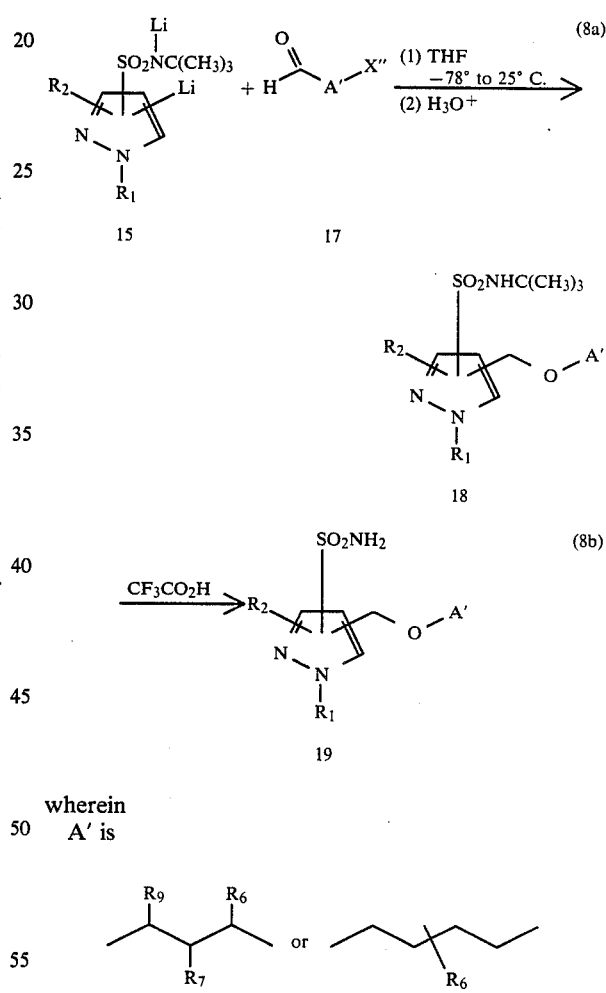

wherein
A' is

R$_1$ is as previously defined with the exception that R$_1$ does not represent H;
X" is Br or Cl; and
L is L-1, L-2 or L-4.

Equations 8(a,b)

Reaction of the dilithiosulfonamides 15 with haloaldehydes of formula 17 in an inert solvent such as THF at temperatures of −78° C. to 25° C. affords pyrazolalkoxides which undergo intramolecular cyclization to the cyclic ethers 18. These in turn may be deprotected to afford the corresponding sulfonamides by the procedure of Equation 7c.

Sulfonamides of Formula 22 which contain a dihydrofuran or dihydropyran group (Q-41,42), can be prepared by the method shown in Equation 9.

Equation 9

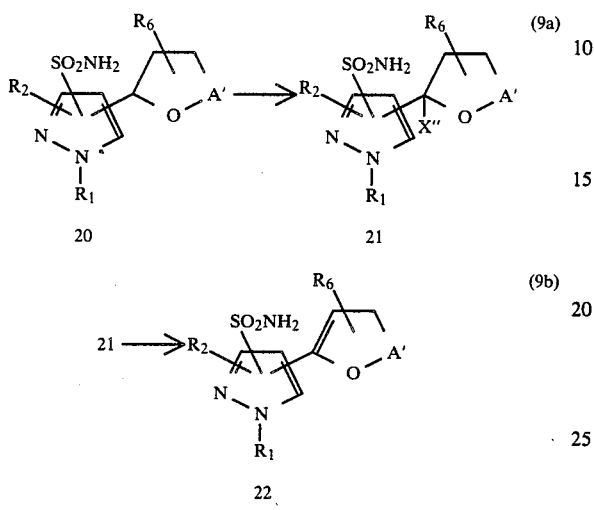

wherein
A' is $CH_2$ or $CH_2CH_2$;
X" is Br or Cl;
L is L-1 to L-4; and
$R_1$ and $R_2$ are as previously defined.

Equation (9a)

In this reaction a sulfonamide of Formula 20 is treated with one equivalent of N-chlorosuccinimide or N-bromosuccinimide of 0°-60° C. in a solvent such as carbon tetrachloride or chloroform for 2-24 hours. The by-product succinimide is removed by filtration and the solution carried directly on to the next step.

Equation (9b)

The sulfonamides of Formula 21 are dehydrohalogenated in carbon tetrachloride or chloroform solution by treatment with at least one equivalent of an appropriate base such as triethylamine, DABCO, pyridine, sodium methoxide or anhydrous potassium carbonate at 0°-60° C. for 1-6 hours. The products are isolated by washing the organic solution with water, drying and stripping off the solvent. The sulfonamides of Formula 22 can be obtained in pure form by recrystallization or column chromatography.

Certain sulfonamides of Formula 2 are preferably prepared from the appropriately substituted benzylthiosulfonamides of Formula 23, as shown in Equation 10.

Equation 10

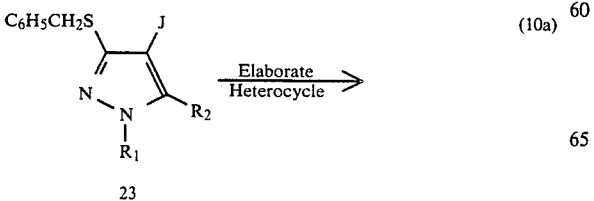

-continued

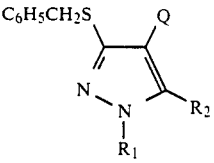

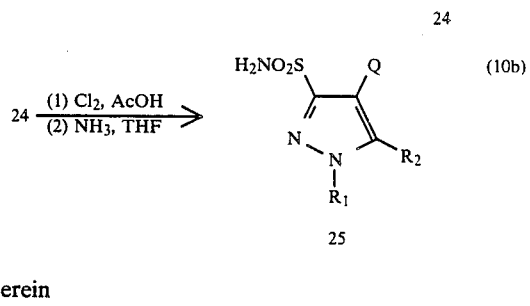

wherein
J are the appropriate functional groups taught in EP-A 83,975 and references cited therein, to prepare Q groups Q-1 to Q-20;
Q is Q-1 to Q-20;
$R_1$ and $R_2$ are as previously defined; and
$R_8$ is H or alkyl.

Equations 10(a,b)

In this sequence of reactions an appropriately functionalized thiopyrazole of the Formula 23 is elaborated, via the methods taught in EP-A No. 83,975, to the corresponding heteroaromatic substituted thiopyrazides of the Formula 24 (Q-1 to Q-20) and Q-43. Mild oxidative chlorination of 24 leads to an intermediate sulfonyl chloride which is converted to the sulfonamide of Formula 25 by treatment with ammonia in THF solution at temperatures of −35° C. to 25° C. The thiopyrazoles of Formula 23 can be prepared by the procedures described by T. Liljefors and J. Sandstrom *Acta Chemica Scandinavica*, 1970, 24, 3109 or simple modifications thereof.

Additional sulfonamides of the Formula 29 may conveniently be prepared by the metallation procedure outlined in Equation 11. For a general review of metallation reactions, see H. W. Gschwend and H. R. Rodriquez, *Org. Reactions* 1979, 26, 1.

Equation 11

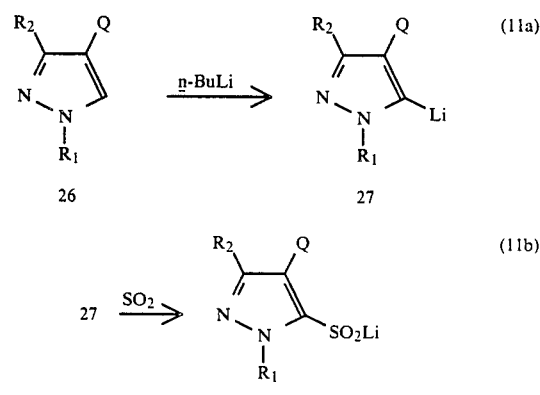

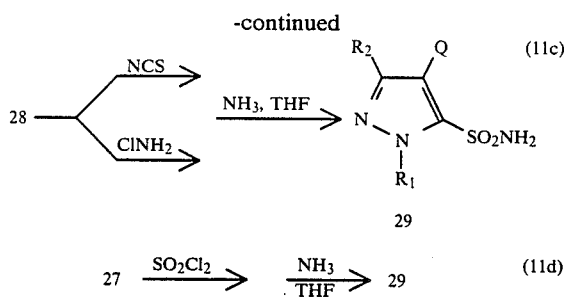

(11c)

$$27 \xrightarrow{SO_2Cl_2} \xrightarrow[THF]{NH_3} 29 \quad (11d)$$

wherein $R_1$ is as defined except other than H, $R_2$ is as previously defined; and Q is Q-1 to Q-4, Q-14 to Q-20, and Q-43.

Equations (11a,b)

In this sequence of reactions a heteroaromatic substituted pyrazole of Formula 26 is treated with one equivalent of n-butyllithium of −70° to 25° C. in an ethereal solvent, such as tetrahydrofuran. After 1–5 hours the compounds of the Formula 27 are formed. The lithium salts are then immediately treated with at least one equivalent of sulfur dioxide of 0° C. to −50° C. After warming to 25° C., the lithium sulfinates of Formula 28 are filtered off, and carried on directly to the next reaction.

Equation (11c)

The lithium sulfinates of Formula 28 may be converted to the sulfonamides 29 by treatment at 0° C. with chloramine in ether and then warming to 35° C. and stirring for 2–24 hours. The product sulfonamides are isolated by extraction into a solvent such as ethyl acetate followed by evaporation of the solvent. The sulfonamides are purified by recrystallization or column chromatography. For details of this procedure, see: G. H. Coleman and C. R. Hauser *J. Am. Chem. Soc.* 1928, 50, 1193. Sulfinate salts of Formula 28 also may be converted to the sulfonamides 29 in a two step process: chlorination with N-chlorosuccinimide affords an intermediate sulfonyl chloride, as described by J. F. Sculley and E. V. Brown *J. Org. Chem.* 1954, 19, 894, W. E. Trull, and E. Wellisch *J. Am. Chem. Soc.* 1952, 74, 5177 and Y. K. Yuriev and N. K. Sadavaya *J. Gen. Chem. USSR* 1964, 34, 1814 and treatment of the sulfonyl chloride with ammonia in an ethereal solvent such as THF. The pyrazoles of Formula 26 are prepared from the appropriately functionalized pyrazoles utilizing the methods taught in EP-A No. 83,975 or simple modifications thereof.

The anion 27 is generated as described for Reaction 11a. The tetrahydrofuran solution is cooled to −78° C. and immediately treated with at least one equivalent of sulfuryl chloride at −78° C. The reaction is warmed to 0° C. and treated with a saturated solution of ammonium chloride. The organic solution is separated and aminated as described under Reaction 11c. Alternatively, the crude sulfonyl chloride solution can be treated with ammonium carbonate and the crude sulfonamide 29 isolated directly.

Additionally, some lithiopyrazoles containing a pyrazole, furan, thiophene or pyrrole substituent can be prepared by the reaction shown in Equation 12.

Equation 12

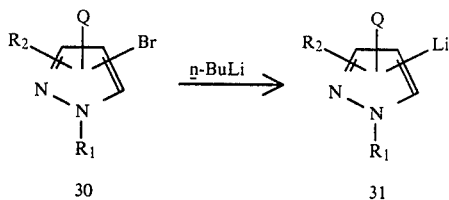

wherein

L=L-2, L-3 or L-4;

Q=5, 6, 21–24, 29, 30;

$R_1$ is as defined except not H; and $R_2$ is as previously defined.

The lithio compounds of Formula 31 are prepared from the bromo compounds of Formula 30 by treatment with one equivalent of n-butyllithium of −70° C. to 25° C. in either ether or tetrahydrofuran. The details of this type of lithiation procedure are described by R. Hüttel and M. E. Schön *Justus Liebigs Ann. Chemie* 1959, 625, 55. Lithio compounds of Formula 31 may be converted to the corresponding sulfonamides by the same sequence of reactions outlined in Equations 11(b and c).

The bromo compounds of Formula 30 can be prepared by methods known in the art, some of which are reviewed by A. P. Dunlop and F. N. Peters "The Furans", Reinhold, New York, 1953, P. Bosshard and C. H. Eugster *Adv. Heterocyclic Chem.* 1966, 7, 377 for furans; A. R. Jones and G. P. Bear in "The Chemistry of Pyrroles" Academic Press. New York, 1977 for pyrroles; S. Gronowitz *Adv. Heterocyclic Chemistry* 1963, 1, 1 for the thiophenes; K. Schofield, M. R. Grimmett and B. R. T. Keene "The Azoles" Cambridge University Press, Cambridge, 1976, and R. Fusco in "The Chemistry of Heterocyclic Compounds", Interscience Publishers, New York, 1967, part 1 the pyrazoles, for the pyrazoles.

Some of the sulfonamides of Formula 2 containing a pyridinyl, pyrimidinyl, pyrazinyl, pyridazinyl, triazinyl group (Q-31 to Q-40), thiazoyl group (Q-17 to Q-19), or a thienyl group (Q-23 and Q-24) can be prepared as outlined in Equation 13.

Equation 13

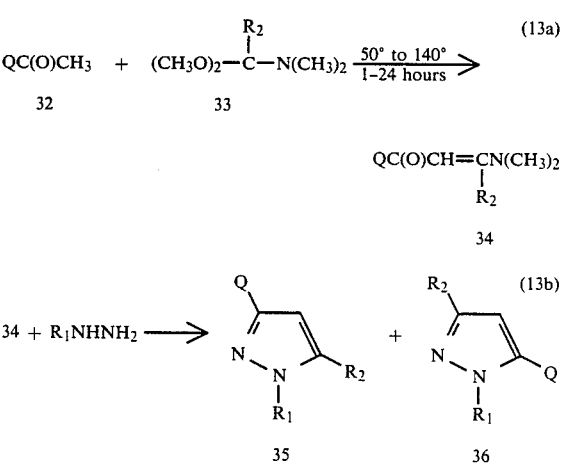

-continued $$35 + 36 \xrightarrow{Br_2}$$

(13c)

[Structure 37: pyrazole with Q, Br substituents, N-N-R₁, R₂]
37

+ [Structure 38: pyrazole with R₂, Br substituents, N-N-R₁, Q]
38 wherein
R₁ and R₂ are as defined previously;
Z₁, Z₂ and Z₃, are independently CH or N; and
Q is Q-31 to Q-40.

The reaction of Equation 13a is run at 50° C. to 140° C. for 1 to 24 hours in a solvent such as ethanol, toluene, dimethylformamide or an excess dimethylalkanamide dimethyl acetal. The product can be isolated by evaporation of the solvent. For more details refer to similar procedures described in Technical Information Bulletin "DMF Acetals", Aldrich Chemical, December 1973 and Y. Lin and S. A. Lang *J. Org. Chem.* 1980, 45, 4837.

The reaction of Equation 13b is run in an inert solvent such as ethanol at 25° to 100° C. for 1 to 48 hours. The isomeric products are isolated by addition of water and extraction with ethyl acetate or methylene chloride. Pyrazoles 35 and 36 may be separated by high pressure liquid chromatography by one skilled in the art, or carried on to the next reaction as a mixture. For more details of this reaction refer to Y. Lin and S. A. Lang, *J. Heterocycl. Chem.* 1977, 14, 345.

The reaction of Equation 13c is run in chloroform with an excess of bromine at reflux for 2 to 8 hours. The products are isolated by neutralization, extraction into a solvent such as methylene chloride, and removal of the solvent by evaporation. Pyrazoles 37 and 38 may be separated at this stage by chromatography or carried on to the next reaction. Details of this procedure are available from R. Hüttel, H. Wagner, P. Jochun, *Justus Liebigs Ann. Chemie* 1953, 593, 13.

The bromopyrazoles of Formulae 37 and 38 are converted to their corresponding sulfonamides by the procedures of Equations 12 and 11(b,c).

The aminopyrazoles of Formula 9 can be prepared by reduction of the corresponding nitropyrazoles of Formula 39 as illustrated in Equation 14.

Equation 14

[Structure 39: nitropyrazole with NO₂, R₂, Q substituents, N-N-R₁] $\xrightarrow{H_2}$ 9

39 wherein
Q is Q-1 to Q-24, and Q-43;
R₂ is as defined;
R₁ is as defined other than NO₂ on a phenyl ring; and
L is L-1 to L-4.

The reduction reaction of Equation 14 can be run by methods known in the literature by those skilled in the art. For details see, EP-A Nos. 83,975 and 84,476. For an extensive compilation of methods see, R. Schofield, M. R. Grimmett, and B. R. T. Keene "The Azoles", Cambridge University Press, Cambridge, 1976, pp. 233.

The nitropyrazoles of Formula 39 are important intermediates for the preparation of many of the compounds of this invention. They can be prepared by those skilled in the art by the application of appropriate methods selected from a variety of known literature procedures.

For example, nitropyrazoles of Formula 39a can be prepared by one skilled in the art from the appropriately functionalized nitropyrazoles of Formula 40 by analogy with the teachings of EP-A No. 83,975 and references cites therein as illustrated in Equation 15.

Equation 15

[Structure 40: pyrazole with NO₂, R₂, J substituents, N-N-R₁] $\xrightarrow{\text{Elaborate Heterocycle}}$ [Structure 39a: pyrazole with NO₂, R₂, Q substituents, N-N-R₁]

40                                    39a wherein
Q is Q-1 to Q-20, and Q-43;
R₁ and R₂ are as defined; and
J are the appropriate functional groups taught in EP-A No. 83,975 and references cited therein to prepare Q groups Q-1 to Q-20 and Q-43.

The nitropyrazoles of Formula 40 can be prepared by one skilled in the art utilizing a variety of literature procedures. For leading references see, R. Fusco in "Pyrazoles, Pyrazolines, Pyrazolidines, Indazoles and Condensed Rings", The Chemistry of Heterocyclic Compounds Series, Interscience Publishers, New York, N.Y. 1967, pp. 1–137; K. Schofield, M. R. Grimmett, and B. R. F. Keene, "The Azoles", Cambridge University, S. Balian, K. C. Van Erk, *Tetrahedron Lett.* 1970, 479 and references cited therein.

Additionally, nitropyrazoles of Formula 39b containing a furan thiophene or pyrrole group (Q is Q-21 to Q-24, Q-29) can be prepared by analogy with the teachings in EP-A 85,476 and references cited therein, as illustrated Equation 16a.

Equation 16a

[Structure 41: pyrazole with NO₂, R₂, Br(I) substituents, N-N-R₁] $\xrightarrow{\text{Q—Cu}}_{42}$ [Structure 39b: pyrazole with NO₂, R₂, Q substituents, N-N-R₁]

41                                    39b wherein
R₁ is as defined except is not H;
R₂ is as defined;
Q is Q-21 to Q-24, and Q-29; and
L is L-1 to L-4.

Thus, a furyl-, thienyl-, or pyrrolycopper compound of Formula 42 is reacted with a bromo- or iodonitropyrazole of the Formula 41 in a solvent such as pyridine or quinoline at 0° C. to 60° C. for 1–3 days. The product 39b is isolated by addition of an acid such as acetic acid and water, extraction with methylene chloride, and removal of the solvent by evaporation. The compounds may be purified by chromatography. The copper compounds of formula 42 are prepared by reacting the corresponding lithium reagent with cuprous iodide or cuprous bromide in an inert solvent such as ethyl ether. The detailed procedures for analogous types of reactions are described by: M. Nilsson and C. Ullenius, *Acta Chem. Scand.* 1970, 24, 2379: C. Ullenius, *Acta Chem. Scand* 1972, 26, 3383.

Equation 16b

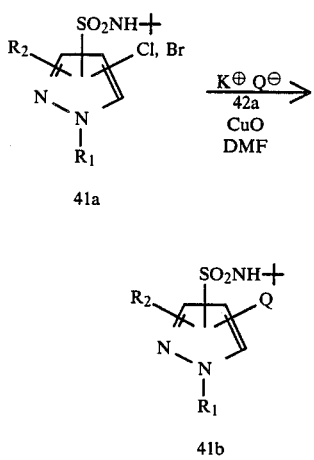

wherein $R_1$ and $R_2$ are as previously defined;

Q is Q-45, Q-46, Q-47, or Q-48;

L is L-1 to L-4.

Reaction 16b is carried out essentially as Reaction 16a except the solvent is N,N-dimethylformamide. The intermediate 41b is isolated by removal of the solvent in vacuo, treating the residue with an acid such as acetic acid and water, extraction with ethyl acetate, and removal of the solvent by evaporation. The compounds may be purified by chromatography. The potassium compounds of formula 42a are prepared by reacting the heterocycle Q with potassium hydride in N,N-dimethylformamide. The product 41c is obtained by stirring the intermediate 41b in trifluoroacetic acid for one or more days.

Equation 16c

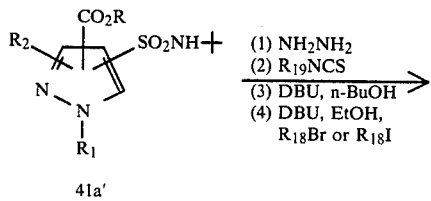

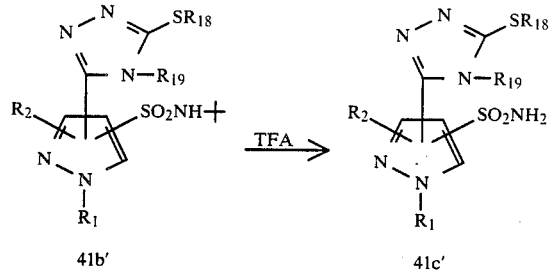

wherein

R is $CH_3$, $C_2H_5$;

$R_1$, $R_{18}$, and $R_{19}$ are as previously defined;

L is L-1 to L-4.

Compounds of formula 41c' are obtained by the procedures disclosed by Y. Kurasawa, K. Suzuki, S. Nakamura, K. Moriyama, and A. Takeda, *Heterocycles*, 22, 695 (1984).

As shown in Equation 17 below, sulfonamides of the Formula 2e containing a tetrahydrofuran or tetrahydrothiophene group (Q is Q-25 to Q-28) may be prepared by catalytic reduction of the corresponding furan or thiophene groups of sulfonamides of Formula 2d (Q' is Q-21 to Q-24).

Equation 17

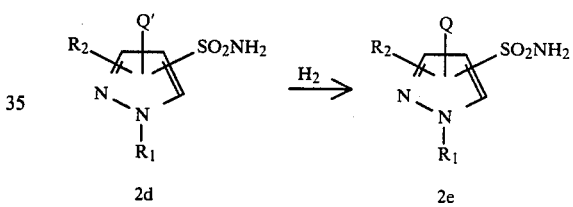

wherein

Q' is Q-21 to Q-24;

Q is Q-25 to Q-28; and $R_1$ and $R_2$ are as defined previously.

Selective reductions of the type shown in Equation 17 are well known in the literature. The choice of catalyst, solvent, pressure and temperature for the reduction of furans has been reviewed by S. Sevandesh in "The Furans", by A. P. Dunlop and F. N. Peters, Reinhold Publishing Corporation, New York, N.Y. 1953, pp. 674–713 and by P. N. Rylander in "Catalytic Hydrogenation in Organic Synthesis", Academic Press, 1979, pp. 227–234. The reduction of thiophenes is reviewed by H. D. Hartough in "Thiophene and its Derivatives", The Chemistry of Heterocyclic Compound series, Interscience Publishers Inc., New York, N.Y. 1952, pp. 167–169.

The procedures of Equations 7, 8, 11, 12, 16a, 16b, and 16c require that substituents for $R_1$ be those which are compatible with the reaction conditions. Suitable protecting groups can be employed as required. Protection of the pyrazole nitrogen as their tetrahydropyranyl, methoxyethoxymethyl, or t-butyl ethers and subsequent deprotection and nitrogen functionalization is taught in EP-A 95,925. Analogous procedures as outlined in Equation 18 provides additional routes to pyrazole sulfonamides of the Formula 2f.

Equation 18

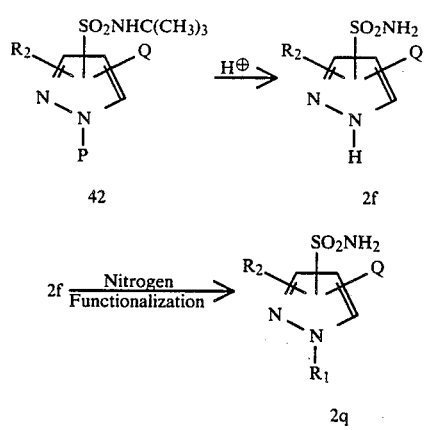

wherein
P is protective groups as above;
Q and $R_2$ are defined previously; and
L is L-1 to L-4.

Sulfonamides of Formula L-5 (compound 47) where Q, $R_2$, $R_6$ through $R_{13}$ and $R_{14}$ are as previously defined may be prepared as outlined below in Equations 19, 19a, 19b and 20.

Equation 19

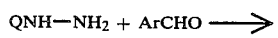

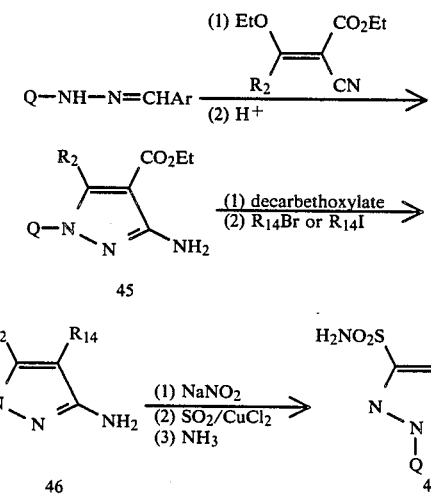

Alternately, compounds of Formula 47 may be prepared from amine 45 via the route outlined below in Equation 19a.

Equation 19a

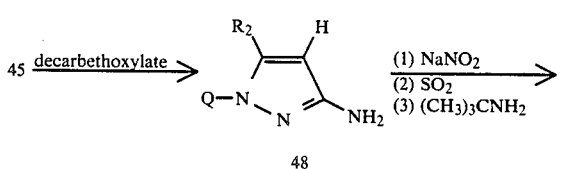

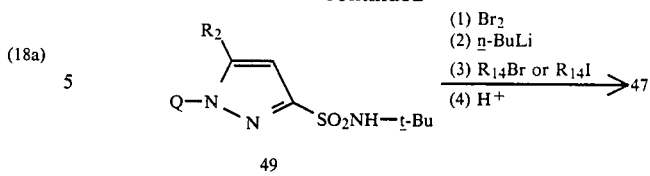

The reactions described in Equation 19 and 19a are well known in the literature; for leading references see R. Fusco in "Pyrazoles, Pyrazolines, Pyrazolidines, Indazoles and Condensed Rings", The Chemistry of Heterocyclic Compounds Series, Interscience Publishers, New York, N.Y. 1967, pp. 1–137.

Sulfonamides of structure 47 may be prepared from dithioketene acetals such as 45c as depicted in Equation 19b ($R_2 \neq Cl$).

Equation 19b

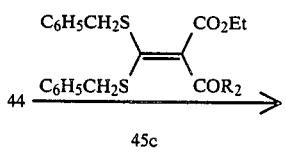

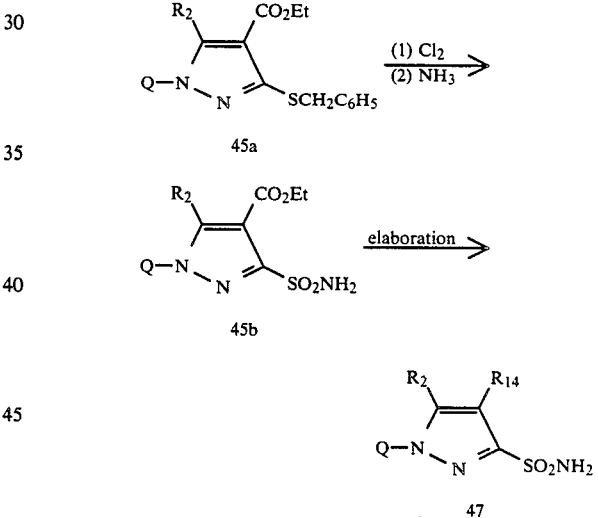

Hydrazine 44 can be reacted with intermediates 45c, which are well known in the literature and may be prepared by one skilled in the art. For leading references see Sandström and Wennerbeck. *Acta Chem. Scand.*, 24, 1191 (1970) and Gompper and Töpfl, *Chem. Ber.*, 95, 2861 (1962) and references cited therein. It is obvious to one skilled in the art that intermediates 45a and 45b can be manipulated using procedures described in Equations 19 and 19a to provide many additional elaborated pyrazoles, 47.

Equation 20

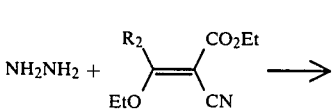

-continued

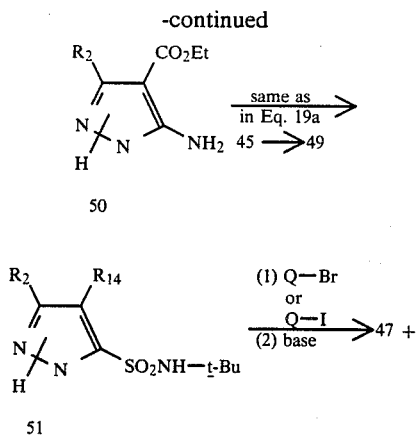

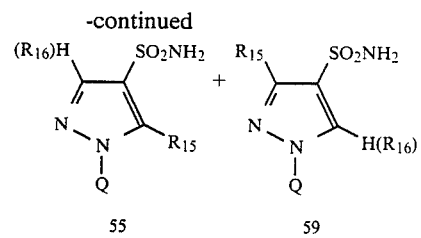

Alternatively, 50 can be N-protected, elaborated to a protected 51 then deprotected to afford 52. This sequence affords both isomers 47 and 52 (L-7).

Sulfonamides of Formula L-6 (compounds 55 and 59) where Q, $R_1$ through $R_{13}$, $R_{15}$ and $R_{16}$ are as previously defined may be prepared as outlined in Equations 21, 22a, 22b, 23a, and 23b.

Equation 21

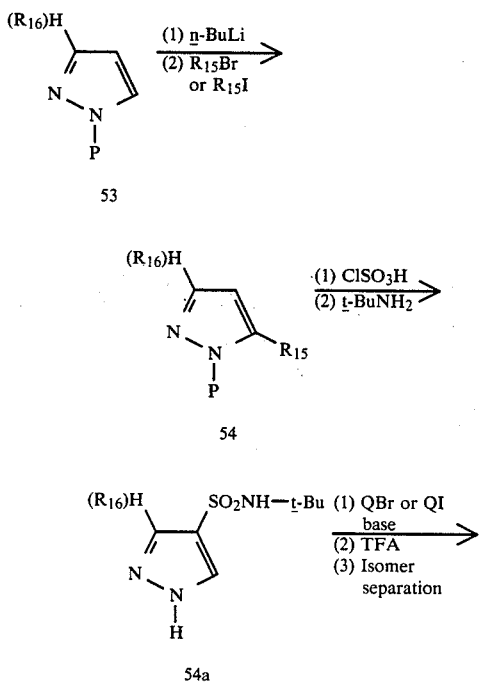

The procedures of Equation 21 require that substituents be compatible with the reaction conditions. Thus, $R_{16}$ is initially other than Br, $CO_2R_{17}$, or halogenated side chain and P is an acid sensitive protecting group such as $CH(OR)_2$. Equations 11a–11d discuss the metallation of pyrazoles and their sequential reaction with electrophiles. Chlorosulfonation and N-alkylation reactions are well known in the literature. For examples of these reactions, see R. Cremlyn, F. Swinbourne, and K-M. Yung, *J. Het. Chem.*, 18, 997 (1981) and I. Finar and G. Lord, *J. Chem. Soc.*, 3314 (1957).

Equation 22

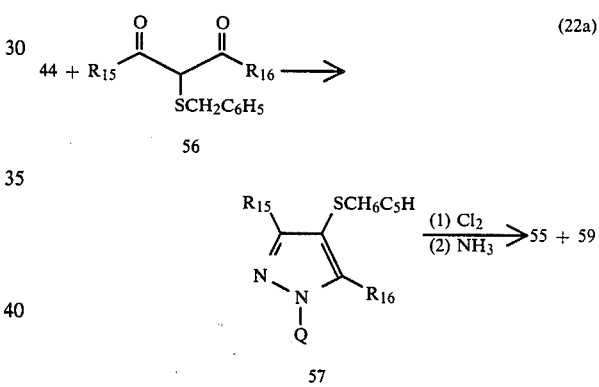

where $R_{15}$ and $R_{16}$ are alkyl, alkoxycarbonyl or alkoxyalkyl.

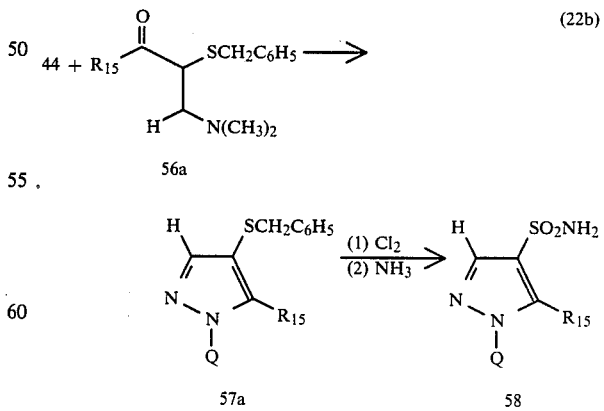

where $R_{15}$ is alkyl, alkoxycarbonyl or alkoxyalkyl.

Compounds such as 56 and 56a in Equations 22a and 22b may be prepared by one skilled in the art.

Equation 23

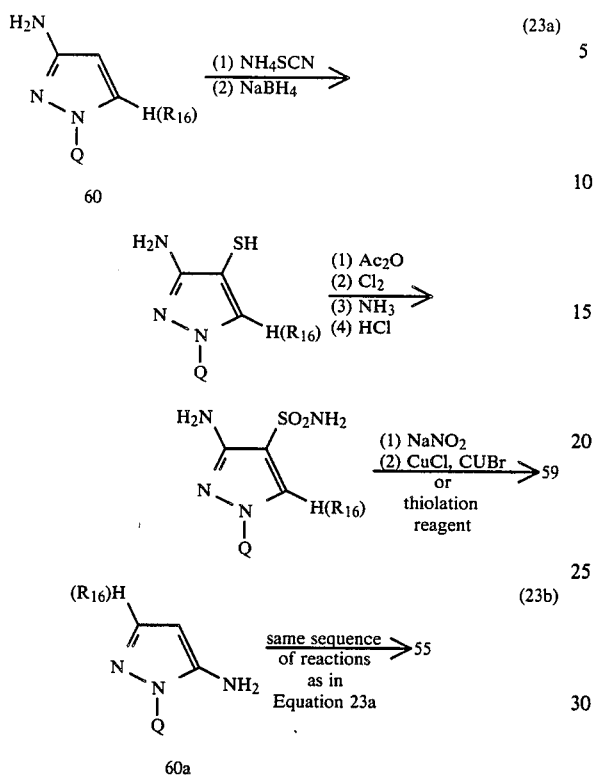

where $R_{15}$ is Cl, Br or SH.

Compounds such as 60 and 60a are well known in the art and may be prepared by one skilled in the art. It should be obvious to one skilled in the art that compounds 55 and 59 can be further elaborated providing additional derivatives of $R_{15}$ and $R_{16}$. Information pertaining to the thiolation of 60 and 60a to the thiols may be found in P. Giori et al., *Il Farmaco*, Ed. Sc., 38 274 (1983) R. Olsen and H. Snyder, *J. Org. Chem.*, 30, 184 (1965).

Sulfonamides of Formula L-7 (compound 52) where Q, $R_2$, $R_6$ through $R_{13}$ and $R_{14}$ are as previously defined may be prepared as outlined in Equations 20, 24a, 24b, and 25.

Equation 24

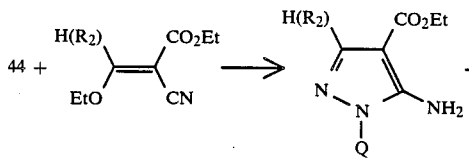

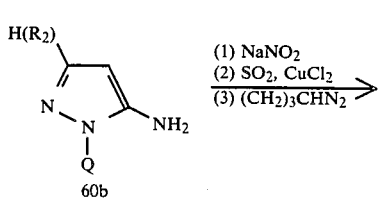

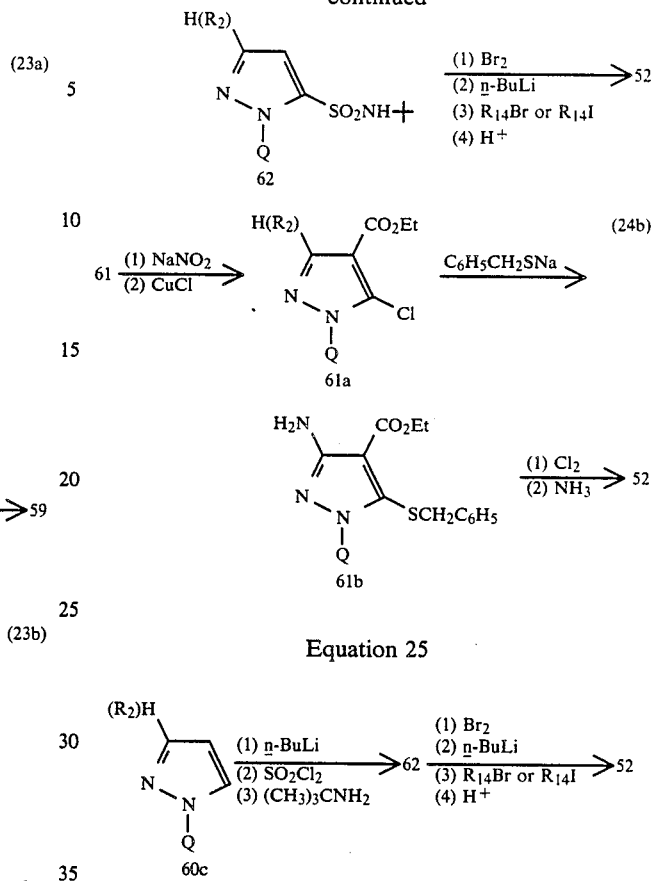

Equation 25

For further details concerning the elaboration of pyrazoles to substituted sulfonamidopyrazoles as outlined above in Equations 18 through 25, see the previous examples taught in Equations 5, 7c, 10b, 11, 12, 13b, 13c, and 14 and the references cited within. In addition EP-A-95,925 teaches the synthesis of N-substituted pyrazolesulfonamides.

The prerequisite starting material 44 in Equations 19, 19b, 22a, 22b and 24a may be prepared in a number of ways. For example, alkylation of a protected hydrazine 63 with a substituted heterocycle 64, followed by hydrolysis leads to compounds such as 44. This reaction is outlined in Equation 26.

Equation 26

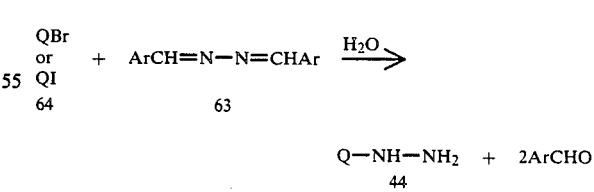

Further details pertaining to this type of transformation may be found in *Organic Synthesis, Coll. Vol.* 2, 208 (1943); ibid. 395 (1943) and *Organic Reactions*, 4, 378 (1948).

Alternatively, compounds of Formula 44 may be prepared from the reaction of a suitable ketone with hydrazine as shown in Equation 27. This methodology would be particularly suited to values of Q where Q is a saturated heterocycle such as Q-25 through Q-28 or partially saturated such as Q-41 through Q-44.

Equation 27

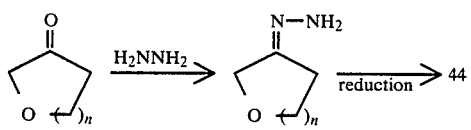

For a review of the Wolf Kishner reaction see Todd, *Organic Reactions*, 4, 378 (1948).

The prerequisite starting material 60c in Equation 25 may be prepared in several ways. For example alkylation of pyrazole with the properly functionalized heterocycle QBr or QI would yield 60c directly, as shown in Equation 28.

Equation 28

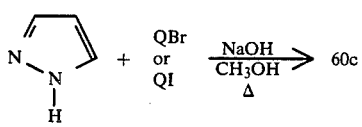

N-Alkylation of pyrazoles is well known to those skilled in the art. Alternatively, pyrazole may be coupled with halogenated heterocycles utilizing a modification of the Ullmann reaction as shown in Equations 29a and 29b. Reaction 29b would allow for the introduction of the N-heterocycle to the preconstructed pyrazolesulfonamide.

Equation 29

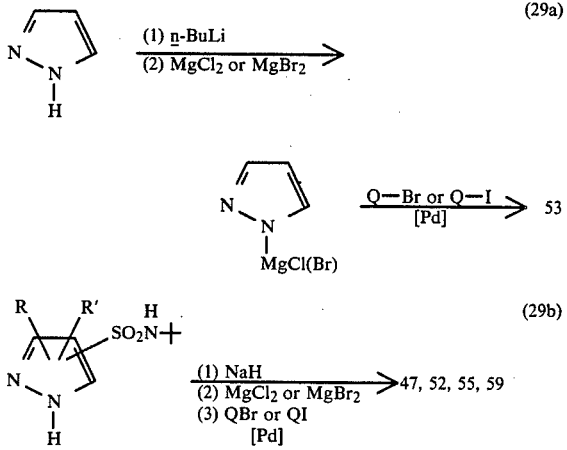

For further details of Pd or Cu catalyzed couplings see S. Gronowitz, and S. Lilgefors, *Chemica Scripta*, 13, 157–161 (1978–1979) and A. Minato, K. Tamo, T. Hayashi, K. Suzuki and M. Kumada; *Tetrahedron Letters*, Vol. 22, 5319 (1981).

An alternate synthesis of compounds such as 44 or 60c utilizes the heterocyclic amines such as 65. Diazotization of 65 followed by reduction affords 44 directly as shown in Equation 30a. Hydrazine 44 may then be converted to 60c via condensation with 1,1,3,3-tetraethoxypropane ($R_2=H$).

Equation 30a

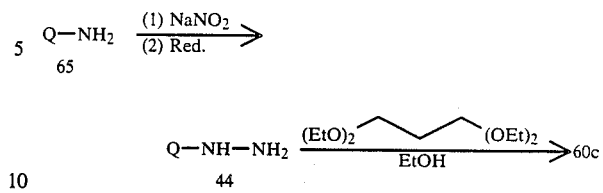

For further details see Jones, *J. Am. Chem. Soc.*, 71, 3994 (1949) and S. R. Sandler, W. Karo; "Organic Functional Group Preparations", 2nd ed., p. 452–453, Academic Press, Inc., New York 1983.

Heterocyclic hydrazines may also be prepared by nucleophilic displacement of active halogens from 66 as shown in Equation 30b. Hydrazine 44 may then be converted to 61 as illustrated in Equation 24a.

Equation 30b

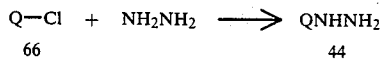

Compounds such as 44 are well known in the literature and may be prepared by one skilled in the art. For examples of this general displacement reaction see P. Nelson and K. Potts, *J. Org. Chem.*, 27, 3243 (1962).

The heterocyclic amines of Formula 6 in Equation 3 can be prepared by methods known in the literature or simple modifications thereof, by those skilled in the art. For instance, EP-A No. 84,224 (published July 27, 1983) and W. Braker et al, *J. Am. Chem. Soc.* 1947, 69, 3072 describe methods for preparing aminopyrimidines and triazines substituted by acetal groups. Also, South African Patent Application Nos. 82/5045 and 82/5671 describe methods for preparing aminopyrimidines and triazines substituted by haloalkyl or haloalkylthio groups such as $OCH_2CH_2F$, $OCH_2CF_3$, $SCF_2H$, or $OCF_2H$ among other groups. South African Patent Application No. 83/7434 (published Oct. 5, 1983) describes methods for the synthesis of cyclopropylpyrimidines and triazines substituted by such groups as alkyl, haloalkyl, alkoxy, haloalkoxy, alkylamino, dialkylamino, or alkoxy alkyl.

Also, the 5,6-dihydrofuro[2.3-d]pyrimidin-2-amines, the cyclopenta[d]pyrimidin-2-amines 6 where A is A-2 and the 6,7-dihydro-5H-pyrano[2.3-d]pyrimidin-2-amines 6 where A is A-3 can be prepared as described in EP-A No. 15,683. Also, the furo[2.3-d]pyrimidin-2-amines 6 where A is A-4 are described in EP-A No. 46,677.

Compounds of Formula 6, where A is A-5, can be prepared by methods taught in U.S. Pat. No. 4,421,550.

Compounds of Formula 6, where A is A-6, can be prepared by methods taught in European Patent Application No. 94,260 (published Nov. 16, 1983).

Compounds of Formula 6, where A is A-7, can be prepared by methods taught in European Patent Application No. 125,864 (published Nov. 21, 1984).

In addition, general methods for preparing aminopyrimidines and triazines have been reviewed in the following publications:

"The Chemistry of Heterocyclic Compounds", a series published by Interscience Publishers, Inc., New York and London;

"Pyrimidines", Vol. 16 of the same series by D. J. Brown;

"s-Triazines and Derivatives", Vol. 13 of the same series by E. M. Smolin and L. Rappoport; and F. C. Schaefer, U.S. Pat. No. 3,154,547 and K. R. Huffman and F. C. Schaefer, *J. Org. Chem.*, 28, 1812 (1963), which describe the synthesis of triazines.

Agriculturally suitable salts of compounds of Formula I are also useful herbicides and can be prepared in a number of ways known to the art. For example, metal salts can be made by contacting compounds of Formula I with a solution of an alkali or alkaline earth metal salt having a sufficiently basic anion (e.g., hydroxide, alkoxide or carbonate). Quaternary amine salts can be made by similar techniques.

Salts of compounds of Formula I can also be prepared by exchange of one cation for another. Cationic exchange can be effected by direct contact of an aqueous solution of a salt of a compound of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of a compound of Formula I (e.g., an alkali metal or quaternary amine salt) through a column packed with a cation exchange resin containing the cation to be exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I with a suitable acid, e.g., p-toluenesulfonic acid, trichloroacetic acid or the like.

The preparation of the compounds of this invention is illustrated by the following specific examples.

EXAMPLE 1

1,5-Dimethyl-4-sulfonamido-3-pyrazolecarboxylic Acid Hydrazide

To a solution of 27 g of methyl 1,5-dimethyl-4-sulfonamido-3-pyrazolecarboxylate in 250 mL of ethanol at room temperature was added 29 g of hydrazine monohydrate. The solution was heated to reflux for 2 hours and then cooled to room temperature. The product crystallizes from solution upon standing, to afford 25.6 g of the title compound; m.p. 211°–213° C.

EXAMPLE 2

1,5-Dimethyl-3-(2-mercapto-1,3,4-oxadiazol-5-yl)-4-pyrazolesulfonamide

To a suspension of 5.0 g of 1,5-dimethyl-4-sulfonamido-3-pyrazole hydrazide in 50 mL of ethanol was added a solution of 1.4 g of potassium hydroxide in 10 mL of water in one portion. The solution was stirred for an additional 15 minutes at room temperature and then 2.1 g of carbon disulfide was added dropwise. The solution was heated to reflux for 19 hours and then concentrated in vacuo. The solid residue wasd dissolved in 100 mL of water, the solution acidified with concentrated hydrochloric acid and the solids collected and air dried to provide 4.7 g of the title compounds; m.p. 243°–245° C.

EXAMPLE 3

1,5-Dimethyl-3-(2-methylthio-1,3,4-oxadiazol-5-yl)-4-pyrazolesulfonamide

To a solution of 1.1 g of 85% potassium hydroxide in 50 mL of methanol at room temperature was added 4.0 g of 1,5-dimethyl-3-(2-mercapto-1,3,4-oxadiaz-5-yl)pyrazolesulfonamide in one portion. The solution was stirred an additional 10 minutes and then 2.67 g of iodomethane was added dropwise. The solution was sitrred for 1 hour at room temperature and 1 hour at reflux. The reaction mixture was concentrated in vacuo and the solid obtained washed with 100 mL of water, and then air dried to afford 3.3 g of the title compound; m.p. 156°–157.5° C.

EXAMPLE 4

Ethyl 5-amino-1-(2-pyridinyl)-1H-pyrazole-4-carboxylate

Ethyl(ethoxymethylene)cyanoacetate, 19.5 g, was added in one portion into a solution of 2-hydrazinopyridine, 12.5 g, in 100 mL of absolute ethanol. The reaction was then heated at reflux for 2½ hours and cooled. The solid which formed was collected by filtration and washed with absolute ethanol. After air-drying, the product weighed 22.6 g and melted at 92°–93° C.

EXAMPLE 5

Ethyl 5-chloro-1-(2-pyridinyl)-1H-pyrazole-4-carboxylate

The product from Example 4, 21.6 g, was dissolved in 100 mL of concentrated hydrochloric acid at 0° C. To this resulting clear solution was added a solution of sodium nitrite, 7.3 g, in 10 mL of water at 0° C. during 15 minutes. The resulting suspension was stirred an additional 30 minutes then added portionwise during 10 minutes to a solution of cuprous chloride, 9.3 g, in 100 mL concentrated hydrochloric acid. The reaction was very exothermic and accompanied by rapid nitrogen evolution. The suspension was then heated on the steambath until a test for diazonium salts was negative. The contents of the flask were cooled and the pH of the suspension adjusted to 8 with ammonium hydroxide and finally diluted with 100 mL of water. The solid were removed from the reaction by filtration through Celite ® and the aqueous filtrate was washed with 200 mL of methylene chloride. After separating and drying the organic solution with anhydrous sodium sulfate, 17.4 g of a light brown oil was isolated after removal of the solvent by evaporation. The crude oil was flash chromatographed in Kieselgel 60, 230–400 mesh, using 1-1 hexanes/ethyl acetate as the eluent. 14.2 g of the title compound was obtained melting at 52°–53° C.

EXAMPLE 6

Methyl 5-(phenylmethylthio)-1-(2-pyridinyl)-1H-pyrazole-4-carboxylate and Ethyl 5-(phenylmethylthio)-1-(2-pyridinyl)-1H-pyrazole-4-carboxylate Sodium metal, 1.4 g, was dissolved in 50 mL of methanol. After all the metal had dissolved, the solvent was removed in vacuo, and the white powder dissolved in 65 mL DMF. Benzylmercaptan, 7.35 g, was added in one portion and stirred for 30 minutes. The compound from Example 5 was added portionwise during 5 minutes accompanied by a strong exotherm. After stirring the reaction for 30 minutes, the solvent was removed in vacuo, and the residue poured into ice-water. The sticky mass was disolved in methylene chloride followed with an aqueous wash of the organic solution. After removal of the solvent, the material was flash chromatographed on Kieselgel 60 using 5-1 hexanes/ethyl acetate as the eluent. 13 g of the mixed esters was isolated melting at 78°–80.5° C.

EXAMPLE 7

Methyl 3-(aminosulfonyl)-1-(2-pyridinyl)-1H-pyrazole-4-carboxylate and Ethyl 3-(aminosulfonyl)-1-(2-pyridinyl)-1H-pyrazole-4-carboxylate The mixture, 12 g, obtained from Example 6 was dissolved in 100 mL of glacial acetic acid and 1.75 mL of water. The solution was cooled to 10° C. and 13.1 g of chlorine was added dropwise. The resulting suspension was allowed to stir at ambient temperature for 2 hours. The reaction was poured into ice-water, and the aqueous solution washed two times with ether. The organic solution was dried with anhydrous sodium sulfate and concentrated to afford a white solid. The solid was added portionwise to a solution of 2.2 mL of ammonia and 100 mL of THF causing an exotherm. The reaction was diluted with water until all solids dissolved. The organic layer was removed and dried with anhydrous sodium sulfate. Evaporation of the solvent provided 3.0 g of yellow oil which was flash chromatographed on Kieselgel 60 using 3-1 hexanes/ethyl acetate as eluent.

100 mg of the ethyl ester of the title compound was isolated.

NMR (CDCl$_3$/TMS): δ8.57–7.30 (m, 5H, pyridine ring and pyrazole 3-H); 6.50 (b, 1.3H, NH protons); 4.37 (q, 2H, OCH$_2$); 1.40 (t, 3H, CH$_3$ of ethyl ester).

350 mg of the methyl ester of the title compound was isolated melting at 139°–141° C.

NMR (CDCl$_3$, DMSO-d$_6$/TMS): δ8.63–7.30 (m, 7H, pyridine ring, pyrazole 3-H and NH$_2$; δ3.90 (s, 3H, ester OCH$_3$).

EXAMPLE 8

Methyl [[(4,6-dimethoxypyrimidin-2-yl)aminocarbonyl]aminosulfonyl]-1-(2-pyridinyl)-1H-pyrazole-4-carboxylate 280 mg of Methyl 3-(aminosulfonyl)-1-(2-pyridinyl)-1H-pyrazole-4-carboxylate and phenyl(4,6-dimethoxy-2-pyrimidinyl)carbamate were dissolved in 10 mL of acetonitrile. 1,8-Diazabicyclo[5.4.0]undec-7-ene, 0.15 mL, was added, and the reaction was stirred one hour. The solution was diluted with 30 mL of ice-water and made acidic with concentrated hydrochloric acid. The solid that separated was collected to afford 260 mg of the title compound melting 183°–188° C.

Using the procedures of Examples 1–8, the techniques described in Equations 1–30 or simple modifications thereof, the following compounds of Tables I–XXIV can be prepared by those skilled in the art.

GENERAL FORMULAE FOR TABLES

W = O unless indicated by *, then W = S

TABLE I

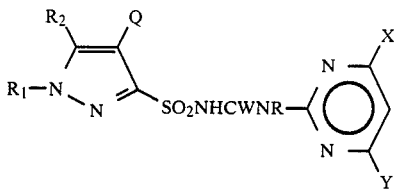

TABLE II

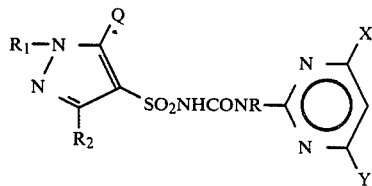

TABLE III

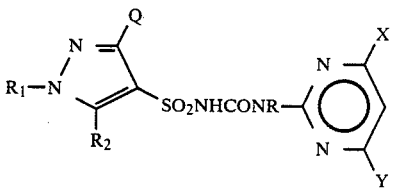

TABLE IV

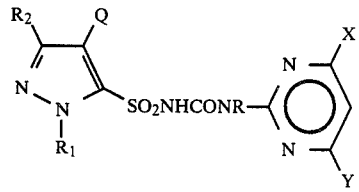

TABLE V

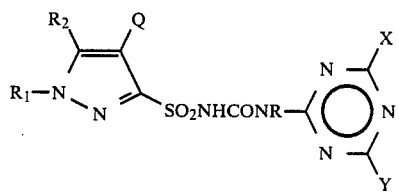

TABLE VI

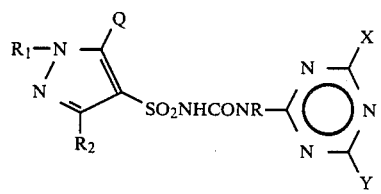

TABLE VII

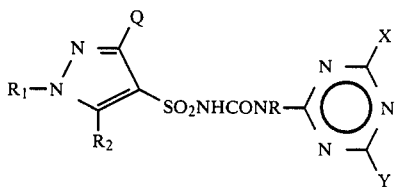

TABLE VIII

-continued
GENERAL FORMULAE FOR TABLES
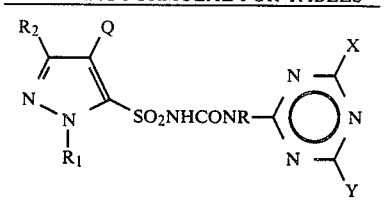
TABLE IX
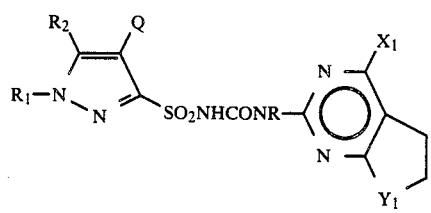
TABLE X
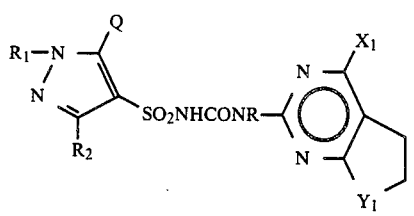
TABLE XI
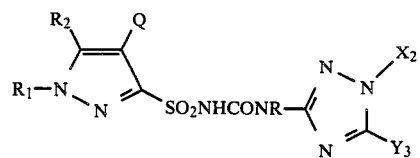
TABLE XII
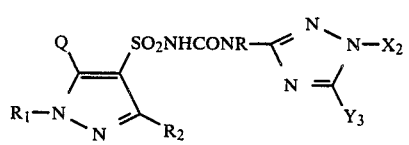
TABLE XIII
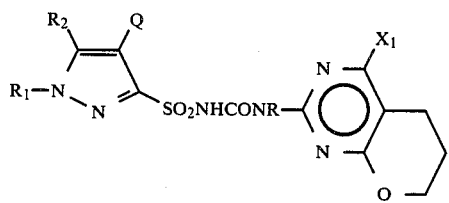
TABLE XIV
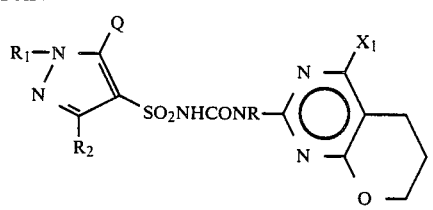
TABLE XV
-continued
GENERAL FORMULAE FOR TABLES
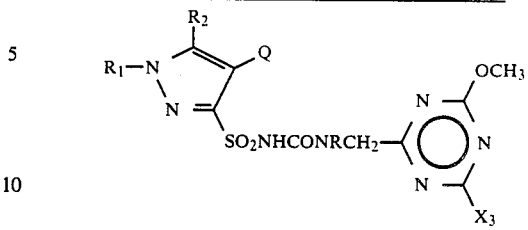
TABLE XVI
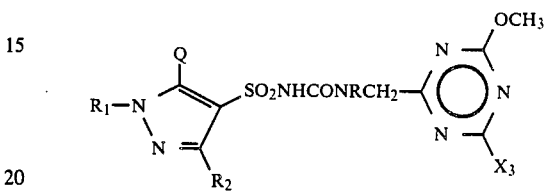
TABLE XVII
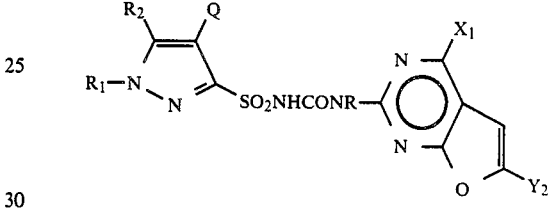
TABLE XVIII
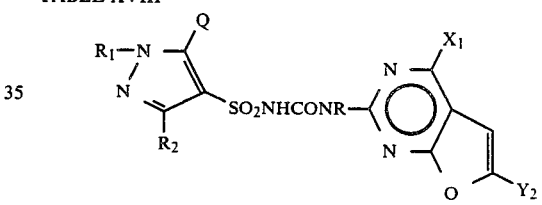
TABLE XIX
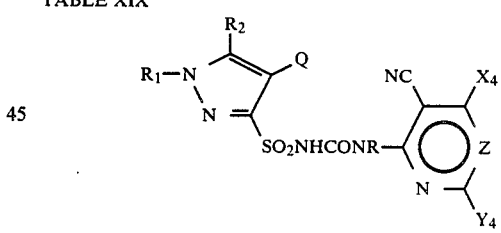
TABLE XX
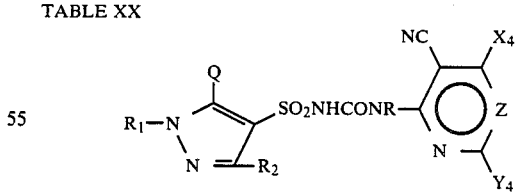
TABLE XXI
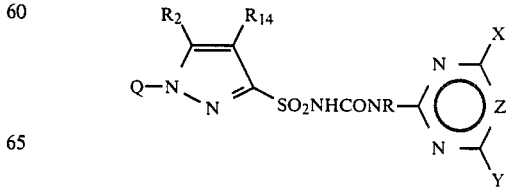
TABLE XXII

-continued
GENERAL FORMULAE FOR TABLES

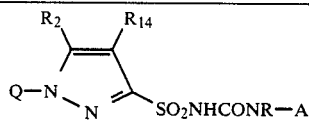

TABLE XXIII

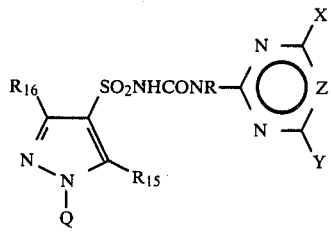

TABLE XXIV

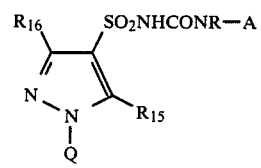

TABLE XXV

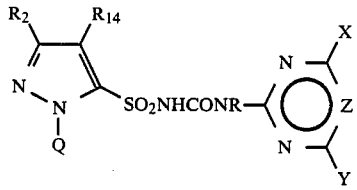

-continued
GENERAL FORMULAE FOR TABLES
TABLE XXVI

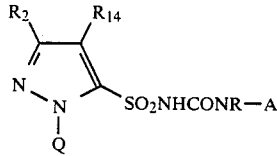

TABLE XXVII

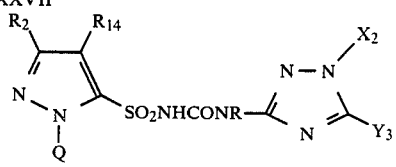

TABLE XXVIII

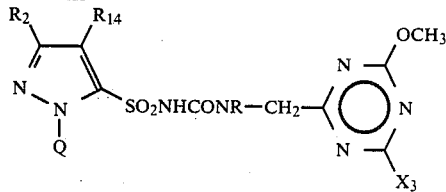

TABLE XXIX

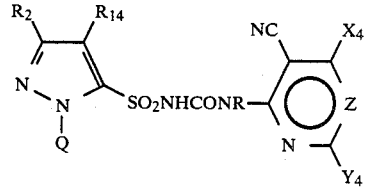

TABLE I

General Formula I

| Q | | R | $R_1$ | $R_2$ | X | Y | m.p. °C. |
|---|---|---|---|---|---|---|---|
| Q-1 | ($R_6$ = H, $R_7$ = H) | H | $CH_3$ | H | $CH_3$ | $CH_3$ | |
| Q-1 | ($R_6$ = H, $R_7$ = H) | H | $CH_3$ | H | $CH_3$ | $OCH_3$ | * |
| Q-1 | ($R_6$ = H, $R_7$ = H) | H | $CH_3$ | H | $OCH_3$ | $OCH_3$ | |
| Q-1 | ($R_6$ = H, $R_7$ = H) | H | $CH_3$ | Cl | $OCH_3$ | $CH_3$ | |
| Q-1 | ($R_6$ = H, $R_7$ = $CH_3$) | H | $CH_3$ | H | $OCH_3$ | $OCH_3$ | |
| Q-1 | ($R_6$ = H, $R_7$ = H) | $CH_3$ | $CH_3$ | H | $OCH_3$ | $CH_3$ | |
| Q-1 | ($R_6$ = H, $R_7$ = H) | H | $CH_2CH_3$ | H | $OCH_3$ | $OCH_3$ | |
| Q-1 | ($R_6$ = $CH_3$, $R_7$ = H) | H | $Ch_3$ | H | $OCH_3$ | $OCH_3$ | |
| Q-2 | ($R_6$ = H, $R_7$ = H) | H | $CH_3$ | H | $CH_3$ | $CH_3$ | |
| Q-2 | ($R_6$ = H, $R_7$ = H) | H | $CH_3$ | H | $OCH_3$ | $CH_3$ | |
| Q-2 | ($R_6$ = H, $R_7$ = H) | H | $CH_3$ | H | $OCH_3$ | $OCH_3$ | |
| Q-2 | ($R_6$ = H, $R_7$ = H) | H | $CH_3$ | Cl | $OCH_3$ | $OCH_3$ | |
| Q-2 | ($R_6$ = H, $R_7$ = H) | H | $CH_2CH_3$ | H | $OCH_3$ | $CH_3$ | |
| Q-2 | ($R_6$ = H, $R_7$ = H) | $CH_3$ | $CH_3$ | H | $OCH_3$ | $OCH_3$ | |
| Q-2 | ($R_6$ = H, $R_7$ = H) | H | $C_6H_5$ | H | $CH_3$ | $OCH_3$ | |
| Q-2 | ($R_6$ = H, $R_7$ = $CH_3$) | H | $CH_3$ | H | $OCH_3$ | $OCH_3$ | |
| Q-2 | ($R_6$ = $CH_3$, $R_7$ = H) | H | $CH_3$ | H | $OCH_3$ | $OCH_3$ | |
| Q-3 | ($R_6$ = H, $R_7$ = H) | H | $CH_3$ | H | $CH_3$ | $CH_3$ | |
| Q-3 | ($R_6$ = H, $R_7$ = H) | H | $CH_3$ | H | $OCH_3$ | $CH_3$ | |
| Q-3 | ($R_6$ = H, $R_7$ = H) | H | $CH_2CF_3$ | H | $OCH_3$ | $OCH_3$ | |
| Q-3 | ($R_6$ = H, $R_7$ = H) | $CH_3$ | $CH_3$ | H | $OCH_3$ | $OCH_3$ | |
| Q-3 | ($R_6$ = H, $R_7$ = H) | H | $CH_2CH_3$ | H | $OCH_3$ | $CH_3$ | |
| Q-3 | ($R_6$ = H, $R_7$ = $CH_3$) | H | $CH_3$ | H | $OCH_3$ | $OCH_3$ | |
| Q-4 | ($R_6$ = H, $R_7$ = H) | H | $CH_3$ | H | $OCH_3$ | $CH_3$ | |
| Q-4 | ($R_6$ = H, $R_7$ = H) | H | $CH_3$ | H | $CH_3$ | $CH_3$ | |
| Q-4 | ($R_6$ = H, $R_7$ = H) | H | $CH_3$ | H | $OCH_3$ | $OCH_3$ | |
| Q-5 | ($R_6$ = H, $R_7$ = H) | H | $CH_3$ | H | $OCH_3$ | $CH_3$ | * |
| Q-5 | ($R_6$ = H, $R_7$ = H) | H | $CH_3$ | H | $CH_3$ | $CH_3$ | |
| Q-5 | ($R_6$ = H, $R_7$ = H) | H | $CH_3$ | H | $OCH_3$ | $OCH_3$ | |
| Q-5 | ($R_6$ = H, $R_7$ = H) | H | $C_6H_5$ | H | $OCH_3$ | $OCH_3$ | |
| Q-6 | ($R_6$ = H, $R_7$ = H) | H | $CH_3$ | H | $CH_3$ | $CH_3$ | |
| Q-6 | ($R_6$ = H, $R_7$ = H) | H | $CH_3$ | H | $OCH_3$ | $OCH_3$ | |
| Q-6 | ($R_6$ = H, $R_7$ = H) | H | $CH_3$ | H | $OCH_3$ | $CH_3$ | |
| Q-6 | ($R_6$ = H, $R_7$ = H) | $CH_3$ | $CH_3$ | H | $OCH_3$ | $CH_3$ | |
| Q-6 | ($R_6$ = H, $R_7$ = H) | H | $C_6H_5$ | H | $OCH_3$ | $OCH_3$ | |
| Q-7 | ($R_8$ = $SCH_3$) | H | $CH_3$ | H | $CH_3$ | $CH_3$ | |

TABLE I-continued

General Formula I

| Q | | R | R₁ | R₂ | X | Y | m.p. °C. |
|---|---|---|---|---|---|---|---|
| Q-7 | (R₈ = SCH₃) | H | CH₃ | H | CH₃ | OCH₃ | |
| Q-7 | (R₈ = SCH₃) | H | CH₃ | H | OCH₃ | OCH₃ | |
| Q-7 | (R₈ = SCH₃) | H | CH₃ | Cl | OCH₃ | OCH₃ | |
| Q-7 | (R₈ = SCH₃) | H | C₂H₅ | H | OCH₃ | CH₃ | |
| Q-7 | (R₈ = SCH₃) | H | C₆H₅ | H | OCH₃ | OCH₃ | |
| Q-7 | (R₈ = SCH₃) | H | CH₃ | H | Cl | OCH₃ | |
| Q-7 | (R₈ = SCH₃) | H | H | H | OCH₃ | OCH₃ | |
| Q-7 | (R₈ = SCH₃) | CH₃ | CH₃ | H | OCH₃ | OCH₃ | |
| Q-7 | (R₈ = SCH₃) | H | C₃H₇ | H | OCH₃ | OCH₃ | |
| Q-7 | (R₈ = SC₂H₅) | H | CH₃ | H | OCH₃ | CH₃ | |
| Q-7 | (R₈ = SC₂H₅) | H | CH₃ | H | CH₃ | CH₃ | |
| Q-7 | (R₈ = SC₂H₅) | H | CH₃ | H | OCH₃ | OCH₃ | |
| Q-7 | (R₈ = SC₂H₅) | H | C₃H₇ | H | OCH₃ | OCH₃ | |
| Q-7 | (R₈ = SC₂H₅) | CH₃ | CH₃ | CH₃ | OCH₃ | OCH₃ | |
| Q-7 | (R₈ = SC₂H₅) | H | CH₃ | CH₃ | OCH₃ | CH₃ | |
| Q-7 | (R₈ = CH₃) | H | CH₃ | H | CH₃ | CH₃ | * |
| Q-7 | (R₈ = CH₃) | H | CH₃ | H | OCH₃ | OCH₃ | |
| Q-7 | (R₈ = CH₃) | H | CH₃ | H | OCH₃ | CH₃ | |
| Q-7 | (R₈ = CH₃) | H | CH₃ | H | Cl | OCH₃ | |
| Q-7 | (R₈ = CH₃) | H | CH₃ | CH₃ | OCH₃ | CH₃ | |
| Q-7 | (R₈ = CH₃) | H | C₆H₅ | H | OCH₃ | OCH₃ | |
| Q-7 | (R₈ = C₂H₅) | H | CH₃ | H | CH₃ | OCH₃ | |
| Q-7 | (R₈ = C₂H₅) | H | CH₃ | H | CH₃ | CH₃ | |
| Q-7 | (R₈ = C₂H₅) | H | CH₃ | H | OCH₃ | OCH₃ | |
| Q-7 | (R₈ = OCH₃) | H | CH₃ | H | CH₃ | OCH₃ | |
| Q-7 | (R₈ = OCH₃) | H | CH₃ | H | CH₃ | CH₃ | |
| Q-7 | (R₈ = OCH₃) | H | CH₃ | H | OCH₃ | OCH₃ | |
| Q-7 | (R₈ = OCH₃) | H | CH₃ | H | Cl | OCH₃ | |
| Q-7 | (R₈ = OCH₃) | H | CH₃ | CH₃ | OCH₃ | OCH₃ | |
| Q-7 | (R₈ = OC₂H₅) | H | CH₃ | H | OCH₃ | OCH₃ | |
| Q-7 | (R₈ = OC₂H₅) | H | CH₃ | H | CH₃ | CH₃ | |
| Q-7 | (R₈ = OC₂H₅) | H | CH₃ | H | OCH₃ | CH₃ | |
| Q-7 | (R₈ = H) | H | CH₂CF₃ | H | OCH₃ | CH₃ | |
| Q-7 | (R₈ = H) | H | CH₃ | H | CH₃ | CH₃ | |
| Q-7 | (R₈ = H) | H | CH₃ | H | OCH₃ | OCH₃ | |
| Q-7 | (R₈ = H) | H | C₃H₇ | H | OCH₃ | OCH₃ | |
| Q-7 | (R₈ = H) | H | C₆H₅ | H | OCH₃ | CH₃ | |
| Q-7 | (R₈ = H) | H | CH₃ | CH₃ | OCH₃ | OCH₃ | |
| Q-7 | (R₈ = SCF₂H) | H | CH₃ | H | Cl | OCH₃ | |
| Q-7 | (R₈ = SCF₂H) | H | CH₃ | H | CH₃ | CH₃ | |
| Q-7 | (R₈ = SCF₂H) | H | CH₃ | H | OCH₃ | OCH₃ | |
| Q-7 | (R₈ = SCF₂H) | H | CH₃ | H | OCH₃ | CH₃ | |
| Q-7 | (R₈ = SCF₂H) | H | CH₃ | Cl | OCH₃ | OCH₃ | |
| Q-7 | (R₈ = SCF₂H) | H | CH₃ | CH₃ | OCH₃ | OCH₃ | |
| Q-8 | (R₆ = H) | H | CH₃ | H | CH₃ | CH₃ | |
| Q-8 | (R₆ = H) | H | CH₃ | H | OCH₃ | CH₃ | |
| Q-8 | (R₆ = H) | H | CH₃ | H | OCH₃ | OCH₃ | |
| Q-8 | (R₆ = H) | H | CH₃ | Cl | OCH₃ | OCH₃ | |
| Q-8 | (R₆ = H) | H | CH₃ | CH₃ | OCH₃ | OCH₃ | |
| Q-8 | (R₆ = H) | H | CH₃ | H | Cl | OCH₃ | |
| Q-8 | (R₆ = CH₃) | H | CH₃ | H | Cl | OCH₃ | |
| Q-8 | (R₆ = CH₃) | H | CH₃ | H | CH₃ | CH₃ | |
| Q-8 | (R₆ = CH₃) | H | CH₃ | H | OCH₃ | OCH₃ | |
| Q-8 | (R₆ = CH₃) | H | CH₃ | H | OCH₃ | CH₃ | |
| Q-8 | (R₆ = CH₃) | H | C₃H₇ | H | OCH₃ | OCH₃ | |
| Q-8 | (R₆ = CH₃) | H | CH₃ | CH₃ | OCH₃ | OCH₃ | |
| Q-9 | (R₆ = CH₃) | H | CH₃ | H | OCH₃ | CH₃ | |
| Q-9 | (R₆ = CH₃) | H | CH₃ | H | CH₃ | CH₃ | |
| Q-9 | (R₆ = CH₃) | H | CH₃ | H | OCH₃ | OCH₃ | |
| Q-9 | (R₆ = H) | H | CH₃ | CH₃ | OCH₃ | OCH₃ | |
| Q-9 | (R₆ = H) | H | CH₃ | Cl | OCH₃ | OCH₃ | |
| Q-9 | (R₆ = H) | H | C₃H₇ | H | OCH₃ | OCH₃ | |
| Q-10 | (R₆ = CH₃) | H | CH₃ | H | OCH₃ | OCH₃ | |
| Q-10 | (R₆ = CH₃) | H | CH₃ | H | OCH₃ | OCH₃ | |
| Q-10 | (R₆ = CH₃) | H | CH₃ | H | Cl | OCH₃ | |
| Q-10 | (R₆ = H) | H | CH₃ | H | Cl | OCH₃ | |
| Q-10 | (R₆ = H) | H | CH₃ | H | OCH₃ | OCH₃ | |
| Q-10 | (R₆ = H) | H | CH₃ | CH₃ | OCH₃ | OCH₃ | |
| Q-11 | (R₆ = CH₃) | H | CH₃ | H | OCH₃ | CH₃ | |
| Q-11 | (R₆ = CH₃) | H | CH₃ | H | OCH₃ | OCH₃ | |
| Q-11 | (R₆ = CH₃) | H | CH₃ | H | Cl | OCH₃ | |
| Q-11 | (R₆ = CH₃) | H | CH₃ | CH₃ | OCH₃ | OCH₃ | |
| Q-11 | (R₆ = CH₃) | H | CH₃ | Cl | OCH₃ | OCH₃ | |
| Q-11 | (R₆ = CH₃) | H | CH₃ | H | CH₃ | CH₃ | |
| Q-12 | (R₆ = CH₃) | H | CH₃ | H | OCH₃ | OCH₃ | |
| Q-12 | (R₆ = CH₃) | H | CH₃ | H | CH₃ | OCH₃ | |
| Q-12 | (R₆ = CH₃) | H | CH₃ | H | Cl | OCH₃ | |
| Q-12 | (R₆ = H) | H | CH₃ | H | Cl | OCH₃ | |
| Q-12 | (R₆ = H) | H | CH₃ | H | OCH₃ | OCH₃ | |
| Q-12 | (R₆ = H) | H | CH₃ | H | OCH₃ | CH₃ | * |

TABLE I-continued

General Formula I

| Q | | R | $R_1$ | $R_2$ | X | Y | m.p. °C. |
|---|---|---|---|---|---|---|---|
| Q-13 | ($R_6$ = $CH_3$) | H | $CH_3$ | H | $OCH_3$ | $OCH_3$ | |
| Q-13 | ($R_6$ = $CH_3$) | H | $CH_3$ | H | Cl | $OCH_3$ | |
| Q-13 | ($R_6$ = $CH_3$) | H | $CH_3$ | $CH_3$ | $OCH_3$ | $OCH_3$ | |
| Q-13 | ($R_6$ = $CH_3$) | H | $CH_3$ | Cl | $OCH_3$ | $OCH_3$ | |
| Q-14 | ($R_6$ = H, $R_7$ = H) | H | $CH_3$ | H | $OCH_3$ | $OCH_3$ | |
| Q-14 | ($R_6$ = H, $R_7$ = H) | H | $CH_3$ | H | $CH_3$ | $CH_3$ | |
| Q-14 | ($R_6$ = H, $R_7$ = H) | H | $CH_3$ | H | $OCH_3$ | $CH_3$ | |
| Q-14 | ($R_6$ = H, $R_7$ = H) | H | $CH_3$ | H | Cl | $OCH_3$ | |
| Q-14 | ($R_6$ = H, $R_7$ = H) | H | $CH_3$ | $CH_3$ | $OCH_3$ | $OCH_3$ | |
| Q-14 | ($R_6$ = H, $R_7$ = H) | H | $CH_3$ | Cl | $OCH_3$ | $OCH_3$ | |
| Q-14 | ($R_6$ = H, $R_7$ = H) | H | $C_3H_7$ | H | $OCH_3$ | $OCH_3$ | |
| Q-14 | ($R_6$ = H, $R_7$ = H) | H | $C_6H_5$ | H | $OCH_3$ | $OCH_3$ | |
| Q-15 | ($R_6$ = H, $R_7$ = $CH_3$) | H | $CH_3$ | H | $OCH_3$ | $OCH_3$ | |
| Q-15 | ($R_6$ = H, $R_7$ = $CH_3$) | H | $CH_3$ | H | Cl | $OCH_3$ | |
| Q-15 | ($R_6$ = H, $R_7$ = $CH_3$) | H | $CH_3$ | H | $CH_3$ | $CH_3$ | |
| Q-16 | ($R_6$ = $CH_3$, $R_7$ = H) | H | $CH_3$ | H | $OCH_3$ | $OCH_3$ | |
| Q-16 | ($R_6$ = $CH_3$, $R_7$ = H) | H | $CH_3$ | H | $OCH_3$ | $CH_3$ | |
| Q-16 | ($R_6$ = $CH_3$, $R_7$ = H) | H | $CH_3$ | H | $CH_3$ | $CH_3$ | |
| Q-16 | ($R_6$ = $CH_3$, $R_7$ = H) | H | $CH_3$ | H | Cl | $OCH_3$ | |
| Q-17 | ($R_6$ = $CH_3$, $R_7$ = $CH_3$) | H | $CH_3$ | H | $OCH_3$ | $OCH_3$ | |
| Q-17 | ($R_6$ = $CH_3$, $R_7$ = $CH_3$) | H | $CH_3$ | H | Cl | $OCH_3$ | |
| Q-17 | ($R_6$ = $CH_3$, $R_7$ = $CH_3$) | H | $CH_3$ | H | $OCH_3$ | $CH_3$ | |
| Q-18 | ($R_6$ = H, $R_7$ = $CH_3$) | H | $CH_3$ | H | $OCH_3$ | $OCH_3$ | |
| Q-18 | ($R_6$ = H, $R_7$ = $CH_3$) | H | $CH_3$ | H | $CH_3$ | $OCH_3$ | |
| Q-18 | ($R_6$ = H, $R_7$ = $CH_3$) | H | $CH_3$ | H | Cl | $OCH_3$ | |
| Q-19 | ($R_6$ = H, $R_7$ = $CH_3$) | H | $CH_3$ | H | $OCH_3$ | $CH_3$ | |
| Q-19 | ($R_6$ = H, $R_7$ = $CH_3$) | H | $CH_3$ | H | $OCH_3$ | $OCH_3$ | |
| Q-19 | ($R_6$ = H, $R_7$ = $CH_3$) | H | $CH_3$ | H | Cl | $OCH_3$ | |
| Q-20 | ($R_6$ = $CH_3$, $R_7$ = $CH_3$) | H | $CH_3$ | H | $OCH_3$ | $OCH_3$ | |
| Q-20 | ($R_6$ = $CH_3$, $R_7$ = $CH_3$) | H | $CH_3$ | H | $CH_3$ | $CH_3$ | |
| Q-20 | ($R_6$ = $CH_3$, $R_7$ = $CH_3$) | H | $CH_3$ | $CH_3$ | $OCH_3$ | $OCH_3$ | |
| Q-21 | ($R_6$ = $R_7$ = $R_9$ = H) | H | $CH_3$ | H | $OCH_3$ | $CH_3$ | |
| Q-21 | ($R_6$ = $R_7$ = $R_9$ = H) | H | $CH_3$ | H | $OCH_3$ | $OCH_3$ | |
| Q-21 | ($R_6$ = $R_7$ = $R_9$ = H) | H | $CH_3$ | H | Cl | $OCH_3$ | |
| Q-21 | ($R_6$ = $R_9$ = H, $R_7$ = $CH_3$) | H | $CH_3$ | H | $OCH_3$ | $OCH_3$ | |
| Q-21 | ($R_6$ = $R_9$ = H, $R_7$ = $CH_3$) | H | $CH_3$ | $CH_3$ | $OCH_3$ | $OCH_3$ | |
| Q-21 | ($R_6$ = $R_7$ = $R_9$ = H) | H | $CH_3$ | $CH_3$ | $OCH_3$ | $CH_3$ | |
| Q-22 | ($R_6$ = $R_7$ = $R_9$ = H) | H | $CH_3$ | H | $OCH_3$ | $CH_3$ | |
| Q-22 | ($R_6$ = $R_7$ = $R_9$ = H) | H | $CH_3$ | H | $OCH_3$ | $OCH_3$ | |
| Q-22 | ($R_6$ = $R_7$ = $R_9$ = H) | H | $CH_3$ | H | Cl | $OCH_3$ | |
| Q-23 | ($R_6$ = $R_7$ = $R_9$ = H) | H | $CH_3$ | H | $OCH_3$ | $OCH_3$ | |
| Q-23 | ($R_6$ = $R_7$ = $R_9$ = H) | H | $CH_3$ | H | Cl | $OCH_3$ | |
| Q-24 | ($R_6$ = $R_7$ = $R_9$ = H) | H | $CH_3$ | H | $OCH_3$ | $OCH_3$ | |
| Q-24 | ($R_6$ = $R_7$ = $R_9$ = H) | H | $CH_3$ | H | Cl | $OCH_3$ | |
| Q-25 | ($R_6$ = $R_7$ = $R_9$ = H) | H | $CH_3$ | H | $OCH_3$ | $OCH_3$ | |
| Q-25 | ($R_6$ = $R_7$ = $R_9$ = H) | H | $CH_3$ | H | Cl | $OCH_3$ | |
| Q-25 | ($R_6$ = $R_7$ = $R_9$ = H) | H | $CH_3$ | H | $OCH_3$ | $OCH_3$ | |
| Q-26 | ($R_6$ = $R_7$ = $R_9$ = H) | H | $CH_3$ | H | $OCH_3$ | $CH_3$ | |
| Q-26 | ($R_6$ = $R_7$ = $R_9$ = H) | H | $CH_3$ | H | $OCH_3$ | $OCH_3$ | |
| Q-26 | ($R_6$ = $R_7$ = $R_9$ = H) | H | $CH_3$ | H | Cl | $OCH_3$ | |
| Q-27 | ($R_6$ = $R_7$ = $R_9$ = H) | H | $CH_3$ | H | $OCH_3$ | $OCH_3$ | |
| Q-27 | ($R_6$ = $R_7$ = $R_9$ = H) | H | $CH_3$ | H | Cl | $OCH_3$ | |
| Q-28 | ($R_6$ = $R_7$ = $R_9$ = H) | H | $CH_3$ | H | $OCH_3$ | $OCH_3$ | |
| Q-28 | ($R_6$ = $R_7$ = $R_9$ = H) | H | $CH_3$ | H | Cl | $OCH_3$ | |
| Q-29 | ($R_6$ = $R_7$ = $R_9$ = H) | H | $CH_3$ | H | $OCH_3$ | $OCH_3$ | |
| Q-29 | ($R_6$ = $R_7$ = $R_9$ = H) | H | $CH_3$ | H | Cl | $OCH_3$ | |
| Q-31 | ($R_6$, $R_7$ = H) | H | $CH_3$ | H | $OCH_3$ | $OCH_3$ | |
| Q-31 | ($R_6$, $R_7$ = H) | H | CH | H | Cl | $OCH_3$ | |
| Q-31 | ($R_6$, $R_7$ = H) | H | $CH_3$ | $CH_3$ | $OCH_3$ | $OCH_3$ | |
| Q-32 | ($R_6$, $R_7$ = H) | H | $CH_3$ | H | $OCH_3$ | $OCH_3$ | |
| Q-32 | ($R_6$, $R_7$ = H) | H | $CH_3$ | H | Cl | $OCH_3$ | |
| Q-32 | ($R_6$, $R_7$ = H) | H | $CH_3$ | $CH_3$ | $OCH_3$ | $OCH_3$ | * |
| Q-33 | ($R_6$, $R_7$ = H) | H | $CH_3$ | H | $OCH_3$ | $OCH_3$ | |
| Q-33 | ($R_6$, $R_7$ = H) | H | $CH_3$ | H | Cl | $OCH_3$ | |
| Q-33 | ($R_6$, $R_7$ = H) | H | $CH_3$ | $CH_3$ | $OCH_3$ | $OCH_3$ | |
| Q-34 | ($R_6$, $R_{10}$, $R_{11}$ = H) | H | $CH_3$ | H | $OCH_3$ | $OCH_3$ | |
| Q-34 | ($R_6$, $R_{10}$, $R_{11}$ = H) | H | $CH_3$ | H | $OCH_3$ | $CH_3$ | |
| Q-34 | ($R_6$, $R_{10}$, $R_{11}$ = H) | H | $CH_3$ | H | Cl | $OCH_3$ | |
| Q-34 | ($R_6$ = H, $R_{10}$, $R_{11}$ = $OCH_3$) | H | $CH_3$ | H | $OCH_3$ | $OCH_3$ | |
| Q-34 | ($R_6$ = H, $R_{10}$, $R_{11}$ = $CH_3$) | H | $CH_3$ | H | $OCH_3$ | $OCH_3$ | |
| Q-34 | ($R_6$ = H, $R_{10}$, $R_{11}$ = $OCH_3$) | H | CH | H | Cl | $OCH_3$ | |
| Q-35 | ($R_{10}$, $R_{11}$ = H) | H | $CH_3$ | H | $OCH_3$ | $OCH_3$ | |
| Q-35 | ($R_{10}$, $R_{11}$ = H) | H | $CH_3$ | H | $OCH_3$ | $CH_3$ | |
| Q-36 | ($R_{10}$, $R_{11}$ = H) | H | $CH_3$ | H | $OCH_3$ | $CH_3$ | |
| Q-36 | ($R_{10}$, $R_{11}$ = H) | H | $CH_3$ | H | $OCH_3$ | $OCH_3$ | |
| Q-37 | ($R_6$, $R_7$ = H) | H | $CH_3$ | H | $OCH_3$ | $CH_3$ | |
| Q-37 | ($R_6$, $R_7$ = H) | H | $CH_3$ | H | $OCH_3$ | $OCH_3$ | |
| Q-38 | ($R_6$, $R_7$ = H) | H | $CH_3$ | H | $CH_3$ | $OCH_3$ | |
| Q-38 | ($R_6$, $R_7$ = H) | H | $CH_3$ | H | $OCH_3$ | $OCH_3$ | |
| Q-39 | ($R_{12}$, $R_{13}$ = $CH_3$) | H | $CH_3$ | H | $OCH_3$ | $OCH_3$ | |

TABLE I-continued

General Formula I

| Q | | R | $R_1$ | $R_2$ | X | Y | m.p. °C. |
|---|---|---|---|---|---|---|---|
| Q-39 | ($R_{12}$, $R_{13}$ = $OCH_3$) | H | $CH_3$ | H | $OCH_3$ | $OCH_3$ | |
| Q-39 | ($R_{12}$ = $CH_3$, $R_{13}$ = $OCH_3$) | H | $CH_3$ | H | $OCH_3$ | $OCH_3$ | |
| Q-40 | ($R_{12}$, $R_{13}$ = $OCH_3$) | H | $CH_3$ | H | $OCH_3$ | $OCH_3$ | |
| Q-40 | ($R_{12}$, $R_{13}$ = $CH_3$) | H | $CH_3$ | H | $OCH_3$ | $OCH_3$ | |
| Q-40 | ($R_{12}$, $R_{13}$ = $OCH_3$) | H | $CH_3$ | $CH_3$ | $OCH_3$ | $OCH_3$ | |
| Q-41 | ($R_6$ = H) | H | $CH_3$ | H | $OCH_3$ | $OCH_3$ | |
| Q-41 | ($R_6$ = H) | H | $CH_3$ | H | $CH_3$ | $OCH_3$ | |
| Q-42 | ($R_6$ = H) | H | $CH_3$ | H | $OCH_3$ | $OCH_3$ | |
| Q-42 | ($R_6$ = H) | H | $CH_3$ | H | $CH_3$ | $OCH_3$ | |
| Q-43 | ($R_6$ = $CH_3$) | H | $CH_3$ | H | $OCH_3$ | $OCH_3$ | |
| Q-43 | ($R_6$ = H) | H | $CH_3$ | H | $CH_3$ | $OCH_3$ | |
| Q-43 | ($R_6$ = H) | H | $CH_3$ | H | $OCH_3$ | $OCH_3$ | |
| Q-44 | ($R_6$ = H) | H | $CH_3$ | H | $OCH_3$ | $OCH_3$ | |
| Q-44 | ($R_6$ = H) | H | $CH_3$ | H | $CH_3$ | $OCH_3$ | |
| Q-44 | ($R_6$ = H) | H | $CH_3$ | $CH_3$ | $OCH_3$ | $OCH_3$ | |
| Q-1 | ($R_6$, $R_7$ = H) | H | $CH_3$ | H | $OC_2H_5$ | $CH_3$ | |
| Q-1 | ($R_6$, $R_7$ = H) | H | $CH_3$ | H | F | $OCH_3$ | |
| Q-7 | ($R_8$ = $CH_3$) | H | $CH_3$ | H | $OCF_2H$ | $OCH_3$ | |
| Q-7 | ($R_8$ = $CH_3$) | H | $CH_3$ | H | $OCH_2CH_2F$ | $CH_3$ | |
| Q-7 | ($R_8$ = $SCH_3$) | H | $CH_3$ | H | $OC_2H_5$ | $N(OCH_3)CH_3$ | |
| Q-8 | ($R_6$ = H) | H | $CH_3$ | H | $OCH_3$ | $CH_2OCH_3$ | |
| Q-8 | ($R_6$ = H) | H | $CH_3$ | H | Cl | $OC_2H_5$ | |
| Q-8 | ($R_6$ = H) | H | $CH_3$ | H | $CH_3$ | $OCH_2C\equiv CH$ | |
| Q-8 | ($R_6$ = $CH_3$) | H | $CH_3$ | H | $CH_3$ | $OCH_2CH_2OCH_3$ | |
| Q-7 | ($R_8$ = $SCH_3$) | H | $CH_3$ | $CH_3$ | $OCH_3$ | $CH_2OCH_3$ | |
| Q-1 | ($R_6$, $R_7$ = H) | H | $CH_3$ | H | Br | $OCH_3$ | |
| Q-1 | ($R_6$, $R_7$ = H) | H | $CH_3$ | H | I | $OCH_3$ | |
| Q-2 | ($R_6$, $R_7$ = H) | H | $CH_3$ | H | $CH_2F$ | $CH_3$ | |
| Q-2 | ($R_6$, $R_7$ = H) | H | $CH_3$ | H | $OCH_2CHF_2$ | $CH_3$ | |
| Q-2 | ($R_6$, $R_7$ = H) | H | $CH_3$ | H | $CH_3$ | $OCH_2CH=CH_2$ | |
| Q-1 | ($R_6$, $R_7$ = H) | H | $CH_3$ | H | $OCH_3$ | $CH_2SCH_3$ | |
| Q-1 | ($R_6$, $R_7$ = H) | H | $CH_3$ | H | $OCH_3$ | $SCH_3$ | |
| Q-7 | ($R_8$ = $SCH_3$) | H | $CH_3$ | $CH_3$ | $CH_3$ | $CH(OCH_3)_2$ | |
| Q-7 | ($R_8$ = $SCH_3$) | H | $CH_3$ | $CH_3$ | $OCH_3$ | $N(CH_3)_2$ | |
| Q-7 | ($R_8$ = $SCH_3$) | H | $CH_3$ | $CH_3$ | $CH_3$ | $CF_3$ | |
| Q-7 | ($R_8$ = $SCH_3$) | H | $CH_3$ | $CH_3$ | $OCH_3$ | $CH(OCH_3)_2$ | |
| Q-7 | ($R_8$ = $SCH_3$) | H | $CH_3$ | $CH_3$ | $CH_3$ | $CH_2OCH_3$ | |
| Q-7 | ($R_8$ = $SCH_3$) | H | $CH_3$ | H | $CH_2F$ | $OCH_3$ | |
| Q-7 | ($R_8$ = $SCH_3$) | H | $CH_3$ | H | $OCH_2CF_3$ | $CH_3$ | |
| Q-1 | ($R_6$, $R_7$ = H) | H | $CH_3$ | H | Cl | $NHCH_3$ | |
| Q-1 | ($R_6$, $R_7$ = H) | H | $CH_3$ | H | $OC_2H_5$ | $N(OCH_3)CH_3$ | |
| Q-14 | ($R_6$, $R_7$ = H) | H | $CH_3$ | H | $CH_3$ | $N(CH_3)_2$ | |
| Q-14 | ($R_6$, $R_7$ = H) | H | $CH_3$ | H | $OCH_3$ | $C_2H_5$ | |
| Q-14 | ($R_6$, $R_7$ = H) | H | $CH_3$ | H | $CF_3$ | $CF_3$ | |
| Q-14 | ($R_6$, $R_7$ = H) | H | $CH_3$ | H | $CH_3$ | $SCH_3$ | |
| Q-21 | ($R_6$, $R_7$, $R_9$ = H) | H | $CH_3$ | H | $OCH_3$ | $OCH_2CH=CH_2$ | |
| Q-3 | ($R_6$, $R_7$ = H) | H | $CH_3$ | H | $CH_3$ | $OCH_2C\equiv CH$ | |
| Q-3 | ($R_6$, $R_7$ = H) | H | $CH_3$ | H | $OCH_3$ | $CH_2OC_2H_5$ | |
| Q-33 | ($R_6$, $R_7$ = H) | H | $CH_3$ | H | $CH_3$ | $OCH_2CH_2OCH_3$ | |
| Q-33 | ($R_6$, $R_7$ = H) | H | $CH_3$ | H | $CH_3$ | $CH_2SCH_3$ | |
| Q-14 | ($R_6$, $R_7$ = H) | H | $CH_3$ | H | $CH_3$ | CHO | |
| Q-14 | ($R_6$, $R_7$ = H) | H | $CH_3$ | H | $CH_3$ | $\overset{O}{\underset{\|}{C}}CH_3$ | |
| Q-8 | ($R_6$ = $CH_3$) | H | $CH_3$ | H | $OCH_3$ | $CH(OCH_3)_2$ | |
| Q-8 | ($R_6$ = $CH_3$) | H | $CH_3$ | H | $OCH_3$ | $CH(OC_2H_5)_2$ | |
| Q-8 | ($R_6$ = $CH_3$) | H | $CH_3$ | H | $OCH_3$ | $CH(SCH_3)_2$ | |
| Q-14 | ($R_6$, $R_7$ = H) | H | $CH_3$ | H | $OCH_3$ | $C(CH_3)(OCH_3)_2$ | |
| Q-43 | ($R_6$ = H) | H | $CH_3$ | H | $OCH_3$ | 1,3-dioxolan-2-yl | |
| Q-43 | ($R_6$ = H) | H | $CH_3$ | H | $CH_3$ | 1,3-dioxolan-2-yl | |
| Q-15 | ($R_6$ = H, $R_7$ = $CH_3$) | H | $CH_3$ | H | $OCH_3$ | 1,3-dithiolan-2-yl | |
| Q-15 | ($R_6$ = H, $R_7$ = $CH_3$) | H | $CH_3$ | H | $OCH_3$ | 1,3-oxathiolan-2-yl | |
| Q-14 | ($R_6$, $R_7$ = H) | H | $CH_3$ | H | $OCH_3$ | 2-methyl-1,3-dioxolan-2-yl | |
| Q-14 | ($R_6$, $R_7$ = H) | H | $CH_3$ | H | $OCH_3$ | 4-methyl-1,3-dioxolan-2-yl | |
| Q-3 | ($R_6$, $R_7$ = H) | H | $CH_3$ | H | $OCH_3$ | 5-methyl-1,3-oxathiolan-2-yl | |
| Q-2 | ($R_6$, $R_7$ = H) | H | $CH_3$ | H | $OCH_3$ | 4-methyl-1,3-dithiolan-2-yl | |
| Q-2 | ($R_6$, $R_7$ = H) | H | $CH_3$ | H | $OCH_3$ | 2,4-dimethyl-1,3-dioxolan-2-yl | |
| Q-7 | ($R_8$ = $CH_3$) | H | $CH_3$ | H | $CH_3$ | $SCF_2H$ | |
| Q-7 | ($R_8$ = $CH_3$) | H | $CH_3$ | H | Cl | $OCF_2H$ | |
| Q-7 | ($R_8$ = $CH_3$) | H | $CH_3$ | H | $OCH_3$ | isopropyl | |
| Q-7 | ($R_8$ = $CH_3$) | H | $CH_3$ | H | $OCH_3$ | cyclopropyl | |
| Q-7 | ($R_8$ = $SCH_3$) | H | $CH_3$ | $CH_3$ | $CH_3$ | $CH_3$ | 185–186 |
| Q-7 | ($R_8$ = $SCH_3$) | H | $CH_3$ | $CH_3$ | $CH_3$ | $OCH_3$ | 179–181 |

TABLE I-continued

General Formula I

| Q | | R | $R_1$ | $R_2$ | X | Y | m.p. °C. |
|---|---|---|---|---|---|---|---|
| Q-7 | ($R_8$ = $SCH_3$) | H | $CH_3$ | $CH_3$ | $OCH_3$ | $OCH_3$ | 216–217 |
| Q-7 | ($R_8$ = $SCH_3$) | H | $CH_3$ | $CH_3$ | Cl | $OCH_3$ | 195–196 |
| Q-7 | ($R_8$ = $SCH_2-CH=CH_2$) | H | $CH_3$ | $CH_3$ | $CH_3$ | $OCH_3$ | 169–170 |
| Q-7 | ($R_8$ = $SCH_2-CH=CH_2$) | H | $CH_3$ | $CH_3$ | $CH_3$ | $CH_3$ | 212–213 |
| Q-7 | ($R_8$ = $SCH_2-CH=CH_2$) | H | $CH_3$ | $CH_3$ | $OCH_3$ | $OCH_3$ | 189–190 |
| Q-7 | ($R_8$ = $SCH_2-CH=CH_2$) | H | $CH_3$ | $CH_3$ | Cl | $OCH_3$ | 192–193 |
| Q-7 | ($R_8$ = $SCH_2CH_3$) | H | $CH_3$ | $CH_3$ | $OCH_3$ | $OCH_3$ | |
| Q-7 | ($R_8$ = $SCH_2CH_3$) | H | $CH_3$ | $CH_3$ | $CH_3$ | $CH_3$ | |
| Q-7 | ($R_8$ = $SCH_2CH_3$) | H | $CH_3$ | $CH_3$ | Cl | $OCH_3$ | |
| Q-7 | ($R_8$ = $SCH_2CO_2CH_3$) | H | $CH_3$ | $CH_3$ | $CH_3$ | $CH_3$ | |
| Q-7 | ($R_8$ = $SCH_2CO_2CH_3$) | H | $CH_3$ | $CH_3$ | $OCH_3$ | $CH_3$ | |
| Q-7 | ($R_8$ = $SCH_2CO_2CH_3$) | H | $CH_3$ | $CH_3$ | $OCH_3$ | $OCH_3$ | |
| Q-7 | ($R_8$ = $SCH_2CO_2CH_3$) | H | $CH_3$ | $CH_3$ | Cl | $OCH_3$ | |
| Q-7 | ($R_8$ = $SCH_3$) | H | $CH_3$ | $CH_3$ | $OCH_3$ | i-$C_3H_7$ | |
| Q-7 | ($R_8$ = $SCH_3$) | H | $CH_3$ | $CH_3$ | $CH_3$ | i-$C_3H_7$ | |
| Q-7 | ($R_8$ = SH) | H | $CH_3$ | $CH_3$ | $OCH_3$ | $OCH_3$ | 202–204 |
| Q-45 | ($R_7$ = H) | H | $CH_3$ | H | $OCH_3$ | $OCH_3$ | |
| Q-45 | ($R_7$ = H) | H | $C_6H_5$ | H | $CH_3$ | $OCH_3$ | |
| Q-46 | ($R_7$ = H) | H | $CH_3$ | H | $OCH_3$ | $OCH_3$ | |
| Q-46 | ($R_7$ = H) | H | $CH_3$ | $CH_3$ | $CH_3$ | $OCH_3$ | |
| Q-47 | ($R_7$ = H) | H | $CH_3$ | H | $OCH_3$ | $OCH_3$ | |
| Q-47 | ($R_7$ = H) | H | $CH_3$ | H | Cl | $OCH_3$ | |
| Q-48 | ($R_7$ = H) | H | $C_6H_5$ | H | $OCH_3$ | $OCH_3$ | |
| Q-48 | ($R_7$ = H) | H | $CH_3$ | H | $CH_3$ | $OCH_3$ | |

TABLE II

General Formula II

| Q | | R | $R_1$ | $R_2$ | X | Y | m.p. °C. |
|---|---|---|---|---|---|---|---|
| Q-1 | ($R_6$ = H, $R_7$ = H) | H | $CH_3$ | H | $CH_3$ | $CH_3$ | |
| Q-1 | ($R_6$ = H, $R_7$ = H) | H | $CH_3$ | H | $CH_3$ | $OCH_3$ | |
| Q-1 | ($R_6$ = H, $R_7$ = H) | H | $CH_3$ | H | $OCH_3$ | $OCH_3$ | |
| Q-1 | ($R_6$ = H, $R_7$ = H) | H | $CH_3$ | Cl | $OCH_3$ | $CH_3$ | |
| Q-1 | ($R_6$ = H, $R_7$ = $CH_3$) | H | $CH_3$ | H | $OCH_3$ | $OCH_3$ | |
| Q-1 | ($R_6$ = H, $R_7$ = H) | $CH_3$ | $CH_3$ | H | $OCH_3$ | $CH_3$ | |
| Q-1 | ($R_6$ = H, $R_7$ = H) | H | $CH_2CH_3$ | H | $OCH_3$ | $OCH_3$ | |
| Q-1 | ($R_6$ = $CH_3$, $R_7$ = H) | H | $CH_3$ | H | $OCH_3$ | $OCH_3$ | |
| Q-2 | ($R_6$ = H, $R_7$ = H) | H | $CH_3$ | H | $CH_3$ | $CH_3$ | |
| Q-2 | ($R_6$ = H, $R_7$ = H) | H | $CH_3$ | H | $OCH_3$ | $CH_3$ | |
| Q-2 | ($R_6$ = H, $R_7$ = H) | H | $CH_3$ | H | $OCH_3$ | $OCH_3$ | |
| Q-2 | ($R_6$ = H, $R_7$ = H) | H | $CH_3$ | Cl | $OCH_3$ | $OCH_3$ | |
| Q-2 | ($R_6$ = H, $R_7$ = H) | H | $CH_2CH_3$ | H | $OCH_3$ | $CH_3$ | |
| Q-2 | ($R_6$ = H, $R_7$ = H) | $CH_3$ | $CH_3$ | H | $OCH_3$ | $OCH_3$ | |
| Q-2 | ($R_6$ = H, $R_7$ = H) | H | $C_6H_5$ | H | $CH_3$ | $CH_3$ | |
| Q-2 | ($R_6$ = H, $R_7$ = $CH_3$) | H | $CH_3$ | H | $OCH_3$ | $OCH_3$ | |
| Q-2 | ($R_6$ = $CH_3$, $R_7$ = H) | H | $CH_3$ | H | $OCH_3$ | $OCH_3$ | |
| Q-3 | ($R_6$ = H, $R_7$ = H) | H | $CH_3$ | H | $CH_3$ | $CH_3$ | |
| Q-3 | ($R_6$ = H, $R_7$ = H) | H | $CH_3$ | H | $OCH_3$ | $CH_3$ | |
| Q-3 | ($R_6$ = H, $R_7$ = H) | H | $CH_3$ | H | $OCH_3$ | $OCH_3$ | |
| Q-3 | ($R_6$ = H, $R_7$ = H) | $CH_3$ | $CH_3$ | H | $OCH_3$ | $OCH_3$ | |
| Q-3 | ($R_6$ = H, $R_7$ = H) | H | $CH_2CH_3$ | H | $OCH_3$ | $CH_3$ | |
| Q-3 | ($R_6$ = H, $R_7$ = $CH_3$) | H | $CH_3$ | H | $OCH_3$ | $OCH_3$ | |
| Q-4 | ($R_6$ = H, $R_7$ = H) | H | $CH_3$ | H | $OCH_3$ | $CH_3$ | |
| Q-4 | ($R_6$ = H, $R_7$ = H) | H | $CH_3$ | H | $CH_3$ | $CH_3$ | |
| Q-4 | ($R_6$ = H, $R_7$ = H) | H | $CH_3$ | H | $OCH_3$ | $OCH_3$ | |
| Q-5 | ($R_6$ = H, $R_7$ = H) | H | $CH_3$ | H | $OCH_3$ | $CH_3$ | |
| Q-5 | ($R_6$ = H, $R_7$ = H) | H | $CH_3$ | H | $CH_3$ | $CH_3$ | |
| Q-5 | ($R_6$ = H, $R_7$ = H) | H | $C_6H_5$ | H | $OCH_3$ | $OCH_3$ | |
| Q-6 | ($R_6$ = H, $R_7$ = H) | H | $CH_3$ | H | $CH_3$ | $CH_3$ | |
| Q-6 | ($R_6$ = H, $R_7$ = H) | H | $CH_3$ | H | $OCH_3$ | $CH_3$ | |
| Q-6 | ($R_6$ = H, $R_7$ = H) | H | $CH_3$ | H | $OCH_3$ | $OCH_3$ | |
| Q-6 | ($R_6$ = H, $R_7$ = H) | $CH_3$ | $CH_3$ | H | $OCH_3$ | $CH_3$ | |
| Q-6 | ($R_6$ = H, $R_7$ = H) | H | $C_6H_5$ | H | $OCH_3$ | $OCH_3$ | |
| Q-7 | ($R_8$ = $SCH_3$) | H | $CH_3$ | H | $CH_3$ | $CH_3$ | |
| Q-7 | ($R_8$ = $SCH_3$) | H | $CH_3$ | H | $CH_3$ | $OCH_3$ | |
| Q-7 | ($R_8$ = $SCH_3$) | H | $CH_3$ | H | $OCH_3$ | $OCH_3$ | |
| Q-7 | ($R_8$ = $SCH_3$) | H | $CH_3$ | Cl | $OCH_3$ | $OCH_3$ | |
| Q-7 | ($R_8$ = $SCH_3$) | H | $C_2H_5$ | H | $OCH_3$ | $CH_3$ | |
| Q-7 | ($R_8$ = $SCH_3$) | H | $C_6H_5$ | H | $OCH_3$ | $OCH_3$ | |
| Q-7 | ($R_8$ = $SCH_3$) | H | $CH_3$ | H | Cl | $OCH_3$ | |
| Q-7 | ($R_8$ = $SCH_3$) | H | H | H | $OCH_3$ | $OCH_3$ | |
| Q-7 | ($R_8$ = $SCH_3$) | $CH_3$ | $CH_3$ | H | $OCH_3$ | $OCH_3$ | |
| Q-7 | ($R_8$ = $SCH_3$) | H | $C_3H_7$ | H | $OCH_3$ | $OCH_3$ | |
| Q-7 | ($R_8$ = $SC_2H_5$) | H | $CH_3$ | H | $OCH_3$ | $CH_3$ | |
| Q-7 | ($R_8$ = $SC_2H_5$) | H | $CH_3$ | H | $CH_3$ | $CH_3$ | |
| Q-7 | ($R_8$ = $SC_2H_5$) | H | $CH_3$ | H | $OCH_3$ | $OCH_3$ | |
| Q-7 | ($R_8$ = $SC_2H_5$) | H | $C_3H_7$ | H | $OCH_3$ | $OCH_3$ | |

TABLE II-continued

| | Q | R | R₁ | R₂ | X | Y | m.p. °C. |
|---|---|---|---|---|---|---|---|
| Q-7 | (R₈ = SC₂H₅) | CH₃ | CH₃ | CH₃ | OCH₃ | OCH₃ | |
| Q-7 | (R₈ = SC₂H₅) | H | CH₃ | CH₃ | OCH₃ | CH₃ | |
| Q-7 | (R₈ = CH₃) | H | CH₃ | H | CH₃ | CH₃ | |
| Q-7 | (R₈ = CH₃) | H | CH₃ | H | OCH₃ | OCH₃ | |
| Q-7 | (R₈ = CH₃) | H | CH₃ | H | OCH₃ | CH₃ | |
| Q-7 | (R₈ = CH₃) | H | CH₃ | H | Cl | OCH₃ | |
| Q-7 | (R₈ = CH₃) | H | CH₃ | CH₃ | OCH₃ | CH₃ | |
| Q-7 | (R₈ = CH₃) | H | C₆H₅ | H | OCH₃ | OCH₃ | |
| Q-7 | (R₈ = C₂H₅) | H | CH₃ | H | CH₃ | OCH₃ | |
| Q-7 | (R₈ = C₂H₅) | H | CH₃ | H | CH₃ | CH₃ | |
| Q-7 | (R₈ = C₂H₅) | H | CH₃ | H | OCH₃ | OCH₃ | |
| Q-7 | (R₈ = OCH₃) | H | CH₃ | H | CH₃ | OCH₃ | |
| Q-7 | (R₈ = OCH₃) | H | CH₃ | H | CH₃ | CH₃ | |
| Q-7 | (R₈ = OCH₃) | H | CH₃ | H | OCH₃ | OCH₃ | |
| Q-7 | (R₈ = OCH₃) | H | CH₃ | H | Cl | OCH₃ | |
| Q-7 | (R₈ = OCH₃) | H | CH₃ | CH₃ | OCH₃ | OCH₃ | |
| Q-7 | (R₈ = OC₂H₅) | H | CH₃ | H | OCH₃ | OCH₃ | |
| Q-7 | (R₈ = OC₂H₅) | H | CH₃ | H | CH₃ | CH₃ | |
| Q-7 | (R₈ = OC₂H₅) | H | CH₃ | H | OCH₃ | CH₃ | |
| Q-7 | (R₈ = H) | H | CH₃ | H | OCH₃ | CH₃ | |
| Q-7 | (R₈ = H) | H | CH₃ | H | CH₃ | CH₃ | |
| Q-7 | (R₈ = H) | H | CH₃ | H | OCH₃ | OCH₃ | |
| Q-7 | (R₈ = H) | H | C₃H₇ | H | OCH₃ | OCH₃ | |
| Q-7 | (R₈ = H) | H | C₆H₅ | H | OCH₃ | CH₃ | |
| Q-7 | (R₈ = H) | H | CH₃ | CH₃ | OCH₃ | OCH₃ | |
| Q-7 | (R₈ = SCF₂H) | H | CH₃ | H | Cl | OCH₃ | |
| Q-7 | (R₈ = SCF₂H) | H | CH₃ | H | CH₃ | CH₃ | |
| Q-7 | (R₈ = SCF₂H) | H | CH₃ | H | OCH₃ | OCH₃ | |
| Q-7 | (R₈ = SCF₂H) | H | CH₃ | H | OCH₃ | CH₃ | |
| Q-7 | (R₈ = SCF₂H) | H | CH₃ | Cl | OCH₃ | OCH₃ | |
| Q-7 | (R₈ = SCF₂H) | H | CH₃ | CH₃ | OCH₃ | OCH₃ | |
| Q-8 | (R₆ = H) | H | CH₃ | H | CH₃ | CH₃ | |
| Q-8 | (R₆ = H) | H | CH₃ | H | OCH₃ | CH₃ | |
| Q-8 | (R₆ = H) | H | CH₃ | H | OCH₃ | OCH₃ | |
| Q-8 | (R₆ = H) | H | CH₃ | Cl | OCH₃ | OCH₃ | |
| Q-8 | (R₆ = H) | H | CH₃ | CH₃ | OCH₃ | OCH₃ | |
| Q-8 | (R₆ = H) | H | CH₃ | H | Cl | OCH₃ | |
| Q-8 | (R₆ = CH₃) | H | CH₃ | H | Cl | OCH₃ | |
| Q-8 | (R₆ = CH₃) | H | CH₃ | H | CH₃ | CH₃ | |
| Q-8 | (R₆ = CH₃) | H | CH₃ | H | OCH₃ | OCH₃ | |
| Q-8 | (R₆ = CH₃) | H | CH₃ | H | OCH₃ | CH₃ | |
| Q-8 | (R₆ = CH₃) | H | C₃H₇ | H | OCH₃ | OCH₃ | |
| Q-8 | (R₆ = CH₃) | H | CH₃ | CH₃ | OCH₃ | OCH₃ | |
| Q-9 | (R₆ = CH₃) | H | CH₃ | H | OCH₃ | CH₃ | |
| Q-9 | (R₆ = CH₃) | H | CH₃ | H | CH₃ | CH₃ | |
| Q-9 | (R₆ = CH₃) | H | CH₃ | H | OCH₃ | OCH₃ | |
| Q-9 | (R₆ = CH₃) | H | CH₃ | CH₃ | OCH₃ | OCH₃ | |
| Q-9 | (R₆ = H) | H | CH₃ | Cl | OCH₃ | OCH₃ | |
| Q-9 | (R₆ = H) | H | C₃H₇ | H | OCH₃ | OCH₃ | |
| Q-10 | (R₆ = CH₃) | H | CH₃ | H | OCH₃ | OCH₃ | |
| Q-10 | (R₆ = CH₃) | H | CH₃ | H | OCH₃ | OCH₃ | |
| Q-10 | (R₆ = CH₃) | H | CH₃ | H | Cl | OCH₃ | |
| Q-10 | (R₆ = H) | H | CH₃ | H | Cl | OCH₃ | |
| Q-10 | (R₆ = H) | H | CH₃ | H | OCH₃ | OCH₃ | |
| Q-10 | (R₆ = H) | H | CH₃ | CH₃ | OCH₃ | OCH₃ | |
| Q-11 | (R₆ = CH₃) | H | CH₃ | H | OCH₃ | CH₃ | |
| Q-11 | (R₆ = CH₃) | H | CH₃ | H | OCH₃ | OCH₃ | |
| Q-11 | (R₆ = CH₃) | H | CH₃ | H | Cl | OCH₃ | |
| Q-11 | (R₆ = CH₃) | H | CH₃ | CH₃ | OCH₃ | OCH₃ | |
| Q-11 | (R₆ = CH₃) | H | CH₃ | Cl | OCH₃ | OCH₃ | |
| Q-11 | (R₆ = CH₃) | H | CH₃ | H | CH₃ | CH₃ | |
| Q-12 | (R₆ = CH₃) | H | CH₃ | H | OCH₃ | OCH₃ | |
| Q-12 | (R₆ = CH₃) | H | CH₃ | H | CH₃ | OCH₃ | |
| Q-12 | (R₆ = CH₃) | H | CH₃ | H | Cl | OCH₃ | |
| Q-12 | (R₆ = H) | H | CH₃ | H | Cl | OCH₃ | |
| Q-12 | (R₆ = H) | H | CH₃ | H | OCH₃ | OCH₃ | |
| Q-12 | (R₆ = H) | H | CH₃ | H | OCH₃ | CH₃ | |
| Q-13 | (R₆ = CH₃) | H | CH₃ | H | OCH₃ | OCH₃ | |
| Q-13 | (R₆ = CH₃) | H | CH₃ | H | Cl | OCH₃ | |
| Q-13 | (R₆ = CH₃) | H | CH₃ | CH₃ | OCH₃ | OCH₃ | |
| Q-13 | (R₆ = CH₃) | H | CH₃ | Cl | OCH₃ | OCH₃ | |
| Q-14 | (R₆ = H, R₇ = H) | H | CH₃ | H | OCH₃ | OCH₃ | |
| Q-14 | (R₆ = H, R₇ = H) | H | CH₃ | H | CH₃ | CH₃ | |
| Q-14 | (R₆ = H, R₇ = H) | H | CH₃ | H | OCH₃ | CH₃ | |
| Q-14 | (R₆ = H, R₇ = H) | H | CH₃ | H | Cl | OCH₃ | |
| Q-14 | (R₆ = H, R₇ = H) | H | CH₃ | CH₃ | OCH₃ | OCH₃ | |
| Q-14 | (R₆ = H, R₇ = H) | H | CH₃ | Cl | OCH₃ | OCH₃ | |
| Q-14 | (R₆ = H, R₇ = H) | H | C₃H₇ | H | OCH₃ | OCH₃ | |
| Q-14 | (R₆ = H, R₇ = H) | H | C₆H₅ | H | OCH₃ | OCH₃ | |
| Q-15 | (R₆ = H, R₇ = CH₃) | H | CH₃ | H | OCH₃ | OCH₃ | |

TABLE II-continued

General Formula II

| Q | | R | R₁ | R₂ | X | Y | m.p. °C. |
|---|---|---|---|---|---|---|---|
| Q-15 | (R₆ = H, R₇ = CH₃) | H | CH₃ | H | Cl | OCH₃ | |
| Q-15 | (R₆ = H, R₇ = CH₃) | H | CH₃ | H | CH₃ | OCH₃ | |
| Q-16 | (R₆ = CH₃, R₇ = H) | H | CH₃ | H | OCH₃ | OCH₃ | |
| Q-16 | (R₆ = CH₃, R₇ = H) | H | CH₃ | H | OCH₃ | CH₃ | |
| Q-16 | (R₆ = CH₃, R₇ = H) | H | CH₃ | H | CH₃ | CH₃ | |
| Q-16 | (R₆ = CH₃, R₇ = H) | H | CH₃ | H | Cl | OCH₃ | |
| Q-17 | (R₆ = R₇ = H) | H | CH₃ | H | OCH₃ | OCH₃ | 204–205 |
| Q-17 | (R₆ = R₇ = H) | H | CH₃ | H | Cl | OCH₃ | 180–181 |
| Q-17 | (R₆ = R₇ = H) | H | CH₃ | H | OCH₃ | CH₃ | 183–184 |
| Q-18 | (R₆ = CH₃, R₇ = CH₃) | H | CH₃ | H | OCH₃ | OCH₃ | 228–229 |
| Q-18 | (R₆ = CH₃, R₇ = CH₃) | H | CH₃ | H | CH₃ | OCH₃ | 211–214 |
| Q-18 | (R₆ = CH₃, R₇ = CH₃) | H | CH₃ | H | Cl | OCH₃ | 208–221 |
| Q-19 | (R₆ = H, R₇ = CH₃) | H | CH₃ | H | OCH₃ | CH₃ | |
| Q-19 | (R₆ = H, R₇ = CH₃) | H | CH₃ | H | OCH₃ | OCH₃ | |
| Q-19 | (R₆ = H, R₇ = CH₃) | H | CH₃ | H | Cl | OCH₃ | |
| Q-20 | (R₆ = CH₃, R₇ = CH₃) | H | CH₃ | H | OCH₃ | OCH₃ | |
| Q-20 | (R₆ = CH₃, R₇ = CH₃) | H | CH₃ | H | CH₃ | OCH₃ | |
| Q-20 | (R₆ = CH₃, R₇ = CH₃) | H | CH₃ | OCH₃ | OCH₃ | OCH₃ | |
| Q-21 | (R₆ = R₇ = R₉ = H) | H | CH₃ | H | OCH₃ | CH₃ | |
| Q-21 | (R₆ = R₇ = R₉ = H) | H | CH₃ | H | OCH₃ | OCH₃ | |
| Q-21 | (R₆ = R₇ = R₉ = H) | H | CH₃ | H | Cl | OCH₃ | |
| Q-21 | (R₆ = R₉ = H, R₇ = CH₃) | H | CH₃ | H | OCH₃ | OCH₃ | |
| Q-21 | (R₆ = R₉ = H, R₇ = CH₃) | H | CH₃ | CH₃ | OCH₃ | OCH₃ | |
| Q-21 | (R₆ = R₇ = R₉ = H) | H | CH₃ | CH₃ | OCH₃ | CH₃ | |
| Q-22 | (R₆ = R₇ = R₉ = H) | H | CH₃ | H | OCH₃ | CH₃ | |
| Q-22 | (R₆ = R₇ = R₉ = H) | H | CH₃ | H | OCH₃ | OCH₃ | |
| Q-22 | (R₆ = R₇ = R₉ = H) | H | CH₃ | H | Cl | OCH₃ | |
| Q-23 | (R₆ = R₇ = R₉ = H) | H | CH₃ | H | OCH₃ | OCH₃ | |
| Q-23 | (R₆ = R₇ = R₉ = H) | H | CH₃ | H | Cl | OCH₃ | |
| Q-24 | (R₆ = R₇ = R₉ = H) | H | CH₃ | H | OCH₃ | OCH₃ | |
| Q-24 | (R₆ = R₇ = R₉ = H) | H | CH₃ | H | Cl | OCH₃ | |
| Q-25 | (R₆ = R₇ = R₉ = H) | H | CH₃ | H | OCH₃ | OCH₃ | |
| Q-25 | (R₆ = R₇ = R₉ = H) | H | CH₃ | H | Cl | OCH₃ | |
| Q-25 | (R₆ = R₇ = R₉ = H) | H | CH₃ | H | OCH₃ | OCH₃ | |
| Q-26 | (R₆ = R₇ = R₉ = H) | H | CH₃ | H | OCH₃ | CH₃ | |
| Q-26 | (R₆ = R₇ = R₉ = H) | H | CH₃ | H | OCH₃ | OCH₃ | |
| Q-26 | (R₆ = R₇ = R₉ = H) | H | CH₃ | H | Cl | OCH₃ | |
| Q-27 | (R₆ = R₇ = R₉ = H) | H | CH₃ | H | OCH₃ | OCH₃ | |
| Q-27 | (R₆ = R₇ = R₉ = H) | H | CH₃ | H | Cl | OCH₃ | |
| Q-28 | (R₆ = R₇ = R₉ = H) | H | CH₃ | H | OCH₃ | OCH₃ | |
| Q-28 | (R₆ = R₇ = R₉ = H) | H | CH₃ | H | Cl | OCH₃ | |
| Q-29 | (R₆ = R₇ = R₉ = H) | H | CH₃ | H | OCH₃ | OCH₃ | |
| Q-29 | (R₆ = R₇ = R₉ = H) | H | CH₃ | H | Cl | OCH₃ | |
| Q-31 | (R₆, R₇ = H) | H | CH₃ | H | CH₃ | OCH₃ | 145–149 |
| Q-31 | (R₆, R₇ = H) | H | CH | H | Cl | OCH₃ | |
| Q-31 | (R₆, R₇ = H) | H | CH₃ | H | OCH₃ | OCH₃ | 167–171 |
| Q-32 | (R₆, R₇ = H) | H | CH₃ | H | OCH₃ | OCH₃ | 209–212 |
| Q-32 | (R₆, R₇ = H) | H | CH₃ | H | OCH₃ | CH₃ | 233–234 |
| Q-32 | (R₆, R₇ = H) | H | CH₃ | H | CH₃ | CH₃ | 219–221 |
| Q-32 | (R₆, R₇ = H) | H | CH₃ | H | CH₃ | CH₃ | 233–234 |
| Q-32 | (R₆, R₇ = H) | H | CH₃ | H | CH₃ | OCH₃ | 219–221 |
| Q-33 | (R₆, R₇ = H) | H | CH₃ | H | OCH₃ | OCH₃ | 188–194 |
| Q-33 | (R₆, R₇ = H) | H | CH₃ | H | OCH₃ | CH₃ | 150–153 |
| Q-33 | (R₆, R₇ = H) | H | CH₃ | CH₃ | CH₃ | OCH₃ | 190–203 |
| Q-33 | (R₆, R₇ = H) | H | CH₃ | H | CH₃ | CH₃ | 150–153 |
| Q-33 | (R₆, R₇ = H) | H | CH₃ | H | CH₃ | OCH₃ | 199–202 |
| Q-34 | (R₆, R₁₀, R₁₁ = H) | H | CH₃ | H | OCH₃ | OCH₃ | |
| Q-34 | (R₆, R₁₀, R₁₁ = H) | H | CH₃ | H | OCH₃ | CH₃ | |
| Q-34 | (R₆, R₁₀, R₁₁ = H) | H | CH₃ | H | Cl | OCH₃ | |
| Q-34 | (R₆ = H, R₁₀, R₁₁ = OCH₃) | H | CH₃ | H | OCH₃ | OCH₃ | |
| Q-34 | (R₆ = H, R₁₀, R₁₁ = CH₃) | H | CH₃ | H | OCH₃ | OCH₃ | |
| Q-34 | (R₆ = H, R₁₀, R₁₁ = OCH₃) | H | CH | H | Cl | OCH₃ | |
| Q-35 | (R₁₀, R₁₁ = H) | H | CH₃ | H | OCH₃ | OCH₃ | |
| Q-35 | (R₁₀, R₁₁ = H) | H | CH₃ | H | OCH₃ | CH₃ | |
| Q-36 | (R₁₀, R₁₁ = H) | H | CH₃ | H | OCH₃ | CH₃ | |
| Q-36 | (R₁₀, R₁₁ = H) | H | CH₃ | H | OCH₃ | OCH₃ | |
| Q-37 | (R₆, R₇ = H) | H | CH₃ | H | OCH₃ | CH₃ | |
| Q-37 | (R₆, R₇ = H) | H | CH₃ | H | OCH₃ | OCH₃ | 211–213 |
| Q-38 | (R₆, R₇ = H) | H | CH₃ | H | CH₃ | OCH₃ | |
| Q-38 | (R₆, R₇ = H) | H | CH₃ | H | OCH₃ | OCH₃ | |
| Q-39 | (R₁₂, R₁₃ = CH₃) | H | CH₃ | H | OCH₃ | OCH₃ | |
| Q-39 | (R₁₂, R₁₃ = OCH₃) | H | CH₃ | H | OCH₃ | OCH₃ | |
| Q-39 | (R₁₂ = CH₃, R₁₃ = OCH₃) | H | CH₃ | H | OCH₃ | OCH₃ | |
| Q-40 | (R₁₂, R₁₃ = OCH₃) | H | CH₃ | H | OCH₃ | OCH₃ | |
| Q-40 | (R₁₂, R₁₃ = CH₃) | H | CH₃ | H | OCH₃ | OCH₃ | |
| Q-40 | (R₁₂, R₁₃ = OCH₃) | H | CH₃ | CH₃ | OCH₃ | OCH₃ | |
| Q-41 | (R₆ = H) | H | CH₃ | H | OCH₃ | OCH₃ | |
| Q-41 | (R₆ = H) | H | CH₃ | H | CH₃ | OCH₃ | |
| Q-42 | (R₆ = H) | H | CH₃ | H | OCH₃ | OCH₃ | |
| Q-42 | (R₆ = H) | H | CH₃ | H | CH₃ | OCH₃ | |

TABLE II-continued

General Formula II

| Q | | R | $R_1$ | $R_2$ | X | Y | m.p. °C. |
|---|---|---|---|---|---|---|---|
| Q-43 | ($R_6$ = $CH_3$) | H | $CH_3$ | H | $OCH_3$ | $OCH_3$ | |
| Q-43 | ($R_6$ = H) | H | $CH_3$ | H | $CH_3$ | $OCH_3$ | |
| Q-43 | ($R_6$ = H) | H | $CH_3$ | H | $OCH_3$ | $OCH_3$ | |
| Q-44 | ($R_6$ = H) | H | $CH_3$ | H | $OCH_3$ | $OCH_3$ | |
| Q-44 | ($R_6$ = H) | H | $CH_3$ | H | $CH_3$ | $OCH_3$ | |
| Q-44 | ($R_6$ = H) | H | $CH_3$ | $CH_3$ | $OCH_3$ | $OCH_3$ | |
| Q-1 | ($R_6$, $R_7$ = H) | H | $CH_3$ | H | $OC_2H_5$ | $CH_3$ | |
| Q-1 | ($R_6$, $R_7$ = H) | H | $CH_3$ | H | F | $OCH_3$ | |
| Q-7 | ($R_8$ = $CH_3$) | H | $CH_3$ | H | $OCF_2H$ | $OCH_3$ | |
| Q-7 | ($R_8$ = $CH_3$) | H | $CH_3$ | H | $OCH_2CH_2F$ | $CH_3$ | |
| Q-7 | ($R_8$ = $SCH_3$) | H | $CH_3$ | H | $OC_2H_5$ | $N(OCH_3)CH_3$ | |
| Q-8 | ($R_6$ = H) | H | $CH_3$ | H | $OCH_3$ | $CH_2OCH_3$ | |
| Q-8 | ($R_6$ = H) | H | $CH_3$ | H | Cl | $OC_2H_5$ | |
| Q-8 | ($R_6$ = H) | H | $CH_3$ | H | $CH_3$ | $OCH_2C \equiv CH$ | |
| Q-8 | ($R_6$ = $CH_3$) | H | $CH_3$ | H | $CH_3$ | $OCH_2CH_2OCH_3$ | |
| Q-7 | ($R_8$ = $SCH_3$) | H | $CH_3$ | $CH_3$ | $OCH_3$ | $CH_2OCH_3$ | |
| Q-1 | ($R_6$, $R_7$ = H) | H | $CH_3$ | H | Br | $OCH_3$ | |
| Q-1 | ($R_6$, $R_7$ = H) | H | $CH_3$ | H | I | $OCH_3$ | |
| Q-2 | ($R_6$, $R_7$ = H) | H | $CH_3$ | H | $CH_2F$ | $CH_3$ | |
| Q-2 | ($R_6$, $R_7$ = H) | H | $CH_3$ | H | $OCH_2CHF_2$ | $CH_3$ | |
| Q-2 | ($R_6$, $R_7$ = H) | H | $CH_3$ | H | $CH_3$ | $OCH_2CH=CH_2$ | |
| Q-1 | ($R_6$, $R_7$ = H) | H | $CH_3$ | H | $OCH_3$ | $CH_2SCH_3$ | |
| Q-1 | ($R_6$, $R_7$ = H) | H | $CH_3$ | H | $OCH_3$ | $SCH_3$ | |
| Q-7 | ($R_8$ = $SCH_3$) | H | $CH_3$ | $CH_3$ | $CH_3$ | $CH(OCH_3)_2$ | |
| Q-7 | ($R_8$ = $SCH_3$) | H | $CH_3$ | $CH_3$ | $OCH_3$ | $N(CH_3)_2$ | |
| Q-7 | ($R_8$ = $SCH_3$) | H | $CH_3$ | $CH_3$ | $CH_3$ | $CF_3$ | |
| Q-7 | ($R_8$ = $SCH_3$) | H | $CH_3$ | $CH_3$ | $OCH_3$ | $CH(OCH_3)_2$ | |
| Q-7 | ($R_8$ = $SCH_3$) | H | $CH_3$ | $CH_3$ | $CH_3$ | $CH_2OCH_3$ | |
| Q-7 | ($R_8$ = $SCH_3$) | H | $CH_3$ | H | $CH_2F$ | $OCH_3$ | |
| Q-7 | ($R_8$ = $SCH_3$) | H | $CH_3$ | H | $OCH_2CF_3$ | $CH_3$ | |
| Q-1 | ($R_6$, $R_7$ = H) | H | $CH_3$ | H | Cl | $NHCH_3$ | |
| Q-1 | ($R_6$, $R_7$ = H) | H | $CH_3$ | H | $OC_2H_5$ | $N(OCH_3)CH_3$ | |
| Q-14 | ($R_6$, $R_7$ = H) | H | $CH_3$ | H | $CH_3$ | $N(CH_3)_2$ | |
| Q-14 | ($R_6$, $R_7$ = H) | H | $CH_3$ | H | $OCH_3$ | $C_2H_5$ | |
| Q-14 | ($R_6$, $R_7$ = H) | H | $CH_3$ | H | $CF_3$ | $CF_3$ | |
| Q-14 | ($R_6$, $R_7$ = H) | H | $CH_3$ | H | $CH_3$ | $SCH_3$ | |
| Q-21 | ($R_6$, $R_7$, $R_9$ = H) | H | $CH_3$ | H | $OCH_3$ | $OCH_2CH=CH_2$ | |
| Q-3 | ($R_6$, $R_7$ = H) | H | $CH_3$ | H | $CH_3$ | $OCH_2C \equiv CH$ | |
| Q-3 | ($R_6$, $R_7$ = H) | H | $CH_3$ | H | $OCH_3$ | $CH_2OC_2H_5$ | |
| Q-33 | ($R_6$, $R_7$ = H) | H | $CH_3$ | H | $CH_3$ | $OCH_2CH_2OCH_3$ | |
| Q-33 | ($R_6$, $R_7$ = H) | H | $CH_3$ | H | $CH_3$ | $CH_2SCH_3$ | |
| Q-14 | ($R_6$, $R_7$ = H) | H | $CH_3$ | H | $CH_3$ | CHO | |
| Q-14 | ($R_6$, $R_7$ = H) | H | $CH_3$ | H | $CH_3$ | $\overset{O}{\underset{\parallel}{C}}CH_3$ | |
| Q-8 | ($R_6$ = $CH_3$) | H | $CH_3$ | H | $OCH_3$ | $CH(OCH_3)_2$ | |
| Q-8 | ($R_6$ = $CH_3$) | H | $CH_3$ | H | $OCH_3$ | $CH(OC_2H_5)_2$ | |
| Q-8 | ($R_6$ = $CH_3$) | H | $CH_3$ | H | $OCH_3$ | $CH(SCH_3)_2$ | |
| Q-14 | ($R_6$, $R_7$ = H) | H | $CH_3$ | H | $OCH_3$ | $C(CH_3)(OCH_3)_2$ | |
| Q-43 | ($R_6$ = H) | H | $CH_3$ | H | $OCH_3$ | 1,3-dioxolan-2-yl | |
| Q-43 | ($R_6$ = H) | H | $CH_3$ | H | $CH_3$ | 1,3-dioxolan-2-yl | |
| Q-15 | ($R_6$ = H, $R_7$ = $CH_3$) | H | $CH_3$ | H | $OCH_3$ | 1,3-dithiolan-2-yl | |
| Q-15 | ($R_6$ = H, $R_7$ = $CH_3$) | H | $CH_3$ | H | $OCH_3$ | 1,3-oxathioaln-2-yl | |
| Q-14 | ($R_6$, $R_7$ = H) | H | $CH_3$ | H | $OCH_3$ | 2-methyl-1,3-dioxolan-2-yl | |
| Q-14 | ($R_6$, $R_7$ = H) | H | $CH_3$ | H | $OCH_3$ | 4-methyl-1,3-dioxolan-2-yl | |
| Q-3 | ($R_6$, $R_7$ = H) | H | $CH_3$ | H | $OCH_3$ | 5-methyl-1,3-oxathiolan-2-yl | |
| Q-2 | ($R_6$, $R_7$ = H) | H | $CH_3$ | H | $OCH_3$ | 4-methyl-1,3-dithiolan-2-yl | |
| Q-2 | ($R_6$, $R_7$ = H) | H | $CH_3$ | H | $OCH_3$ | 2,4-dimethyl-1,3-dioxolan-2-yl | |
| Q-7 | ($R_8$ = $CH_3$) | H | $CH_3$ | H | $CH_3$ | $SCF_2H$ | |
| Q-7 | ($R_8$ = $CH_3$) | H | $CH_3$ | H | Cl | $OCF_2H$ | |
| Q-7 | ($R_8$ = $CH_3$) | H | $CH_3$ | H | $OCH_3$ | cyclopropyl | |
| Q-7 | ($R_8$ = $CH_3$) | H | $CH_3$ | H | $OCH_3$ | isopropyl | |
| Q-7 | ($R_8$ = $SCH_3$) | H | $CH_3$ | $CH_3$ | $CH_3$ | $CH_3$ | 184–185 |
| Q-7 | ($R_8$ = $SCH_3$) | H | $CH_3$ | $CH_3$ | $CH_3$ | $OCH_3$ | 178–180 |
| Q-7 | ($R_8$ = $SCH_3$) | H | $CH_3$ | $CH_3$ | $OCH_3$ | $OCH_3$ | 195–197 |
| Q-7 | ($R_8$ = $SCH_3$) | H | $CH_3$ | $CH_3$ | Cl | $OCH_3$ | 176–178 |
| Q-7 | ($R_8$ = $SCH_2-CH=CH_2$) | H | $CH_3$ | $CH_3$ | $CH_3$ | $OCH_3$ | 184–186 |
| Q-7 | ($R_8$ = $SCH_2-CH=CH_2$) | H | $CH_3$ | $CH_3$ | $CH_3$ | $CH_3$ | 210–211 |
| Q-7 | ($R_8$ = $SCH_2-CH=CH_2$) | H | $CH_3$ | $CH_3$ | $OCH_3$ | $OCH_3$ | 140–141 |
| Q-7 | ($R_8$ = $SCH_2-CH=CH_2$) | H | $CH_3$ | $CH_3$ | Cl | $OCH_3$ | 183–185 |
| Q-7 | ($R_8$ = $SCH_2CH_3$) | H | $CH_3$ | $CH_3$ | $OCH_3$ | $OCH_3$ | |
| Q-7 | ($R_8$ = $SCH_2CH_3$) | H | $CH_3$ | $CH_3$ | $CH_3$ | $CH_3$ | |
| Q-7 | ($R_8$ = $SCH_2CH_3$) | H | $CH_3$ | $CH_3$ | Cl | $OCH_3$ | |

TABLE II-continued

General Formula II

| Q | | R | $R_1$ | $R_2$ | X | Y | m.p. °C. |
|---|---|---|---|---|---|---|---|
| Q-7 | ($R_8$ = SCH$_2$CO$_2$CH$_3$) | H | CH$_3$ | CH$_3$ | CH$_3$ | CH$_3$ | |
| Q-7 | ($R_8$ = SCH$_2$CO$_2$CH$_3$) | H | CH$_3$ | CH$_3$ | OCH$_3$ | CH$_3$ | 171–173 |
| Q-7 | ($R_8$ = SCH$_2$CO$_2$CH$_3$) | H | CH$_3$ | CH$_3$ | OCH$_3$ | OCH$_3$ | 163–164 |
| Q-7 | ($R_8$ = SCH$_2$CO$_2$CH$_3$) | H | CH$_3$ | CH$_3$ | Cl | OCH$_3$ | 188–189 |
| Q-7 | ($R_8$ = SCH$_3$) | H | CH$_3$ | CH$_3$ | OCH$_3$ | i-C$_3$H$_7$ | |
| Q-7 | ($R_8$ = SCH$_3$) | H | CH$_3$ | CH$_3$ | CH$_3$ | i-C$_3$H$_7$ | |
| Q-7 | ($R_8$ = S—CH$_2$COCH$_3$) | H | CH$_3$ | CH$_3$ | CH$_3$ | CH$_3$ | |
| Q-7 | ($R_8$ = S—CH$_2$COCH$_3$) | H | CH$_3$ | CH$_3$ | CH$_3$ | OCH$_3$ | 184–186 |
| Q-7 | ($R_8$ = S—CH$_2$COCH$_3$) | H | CH$_3$ | CH$_3$ | OCH$_3$ | OCH$_3$ | 183–186 |
| Q-7 | ($R_8$ = S—CH$_2$CO$_2$CH$_3$) | H | CH$_3$ | CH$_3$ | Cl | OCH$_3$ | 183–185 |
| Q-7 | ($R_8$ = S—CH(CH$_3$)$_2$) | H | CH$_3$ | CH$_3$ | CH$_3$ | CH$_3$ | |
| Q-7 | ($R_8$ = S—CH(CH$_3$)$_2$) | H | CH$_3$ | CH$_3$ | CH$_3$ | OCH$_3$ | 187–188 |
| Q-7 | ($R_8$ = S—CH(CH$_3$)$_2$) | H | CH$_3$ | CH$_3$ | OCH$_3$ | OCH$_3$ | 169–170 |
| Q-7 | ($R_8$ = S—CH(CH$_3$)$_2$) | H | CH$_3$ | CH$_3$ | Cl | OCH$_3$ | |
| Q-7 | ($R_8$ = S—CH$_2$CCl=CH$_2$) | H | CH$_3$ | CH$_3$ | CH$_3$ | CH$_3$ | |
| Q-7 | ($R_8$ = S—CH$_2$—C(Cl)=CH$_2$) | H | CH$_3$ | CH$_3$ | CH$_3$ | OCH$_3$ | 181–183 |
| Q-7 | ($R_8$ = S—CH$_2$—C(Cl)=CH$_2$) | H | CH$_3$ | CH$_3$ | OCH$_3$ | OCH$_3$ | 171–173 |
| Q-7 | ($R_8$ = S—CH$_2$—C(Cl)=CH$_2$) | H | CH$_3$ | CH$_3$ | Cl | OCH$_3$ | |
| Q-7 | ($R_8$ = SCH$_2$CN) | H | CH$_3$ | CH$_3$ | CH$_3$ | CH$_3$ | |
| Q-7 | ($R_8$ = SCH$_2$CN) | H | CH$_3$ | CH$_3$ | CH$_3$ | OCH$_3$ | 163–165 |
| Q-7 | ($R_8$ = SCH$_2$CN) | H | CH$_3$ | CH$_3$ | OCH$_3$ | OCH$_3$ | 183–185 |
| Q-7 | ($R_8$ = SCH$_2$CN) | H | CH$_3$ | CH$_3$ | Cl | OCH$_3$ | 188–189 |
| Q-7 | ($R_8$ = SC$_6$H$_{13}$) | H | CH$_3$ | CH$_3$ | CH$_3$ | CH$_3$ | |
| Q-7 | ($R_8$ = SC$_6$H$_{13}$) | H | CH$_3$ | CH$_3$ | CH$_3$ | OCH$_3$ | 173–175 |
| Q-7 | ($R_8$ = SC$_6$H$_{13}$) | H | CH$_3$ | CH$_3$ | OCH$_3$ | OCH$_3$ | 155–156 |
| Q-7 | ($R_8$ = SC$_6$H$_{13}$) | H | CH$_3$ | CH$_3$ | Cl | OCH$_3$ | 169–170 |
| Q-7 | ($R_8$ = SH) | H | CH$_3$ | CH$_3$ | CH$_3$ | CH$_3$ | |
| Q-7 | ($R_8$ = SH) | H | CH$_3$ | CH$_3$ | CH$_3$ | OCH$_3$ | |
| Q-7 | ($R_8$ = SH) | H | CH$_3$ | CH$_3$ | OCH$_3$ | OCH$_3$ | |
| Q-7 | ($R_8$ = SH) | H | CH$_3$ | CH$_3$ | Cl | OCH$_3$ | |
| Q-17 | ($R_6$ = $R_7$ = H) | H | CH$_3$ | H | CH$_3$ | CH$_3$ | 214–215 |
| Q-18 | ($R_6$ = $R_7$ = CH$_3$) | H | CH$_3$ | H | CH$_3$ | CH$_3$ | 125–126 |
| Q-32 | ($R_6$ = $R_7$ = H) | H | CH$_3$ | CH$_3$ | CH$_3$ | OCH$_3$ | 202–203 |
| Q-32 | ($R_6$ = $R_7$ = H) | H | CH$_3$ | CH$_3$ | OCH$_3$ | OCH$_3$ | 203–204 |
| Q-33 | ($R_6$ = $R_7$ = H) | H | CH$_3$ | CH$_3$ | OCH$_3$ | OCH$_3$ | 202–204 |
| Q-33 | ($R_6$ = $R_7$ = H) | H | CH$_3$ | CH$_3$ | Cl | OCH$_3$ | 158.5–164 |
| Q-45 | ($R_7$ = H) | H | CH$_3$ | H | OCH$_3$ | OCH$_3$ | |
| Q-45 | ($R_7$ = H) | H | C$_6$H$_5$ | H | CH$_3$ | OCH$_3$ | |
| Q-46 | ($R_7$ = H) | H | CH$_3$ | H | OCH$_3$ | OCH$_3$ | |
| Q-46 | ($R_7$ = H) | H | CH$_3$ | CH$_3$ | CH$_3$ | OCH$_3$ | |
| Q-47 | ($R_7$ = H) | H | CH$_3$ | H | OCH$_3$ | OCH$_3$ | |
| Q-47 | ($R_7$ = H) | H | CH$_3$ | H | Cl | OCH$_3$ | |
| Q-48 | ($R_7$ = H) | H | C$_6$H$_5$ | H | OCH$_3$ | OCH$_3$ | |
| Q-48 | ($R_7$ = H) | H | CH$_3$ | H | CH$_3$ | OCH$_3$ | |
| Q-45 | ($R_7$ = H) | H | CH$_3$ | CH$_3$ | CH$_3$ | CH$_3$ | 203–205 |
| Q-45 | ($R_7$ = H) | H | CH$_3$ | CH$_3$ | CH$_3$ | OCH$_3$ | 208–209 |
| Q-45 | ($R_7$ = H) | H | CH$_3$ | CH$_3$ | OCH$_3$ | OCH$_3$ | 223–225 |
| Q-45 | ($R_7$ = H) | H | CH$_3$ | CH$_3$ | Cl | OCH$_3$ | 204–205 |
| Q-46 | ($R_7$ = H) | H | CH$_3$ | CH$_3$ | CH$_3$ | CH$_3$ | 208–209.5 |
| Q-46 | ($R_7$ = H) | H | CH$_3$ | CH$_3$ | CH$_3$ | OCH$_3$ | 193–195 |
| Q-46 | ($R_7$ = H) | H | CH$_3$ | CH$_3$ | OCH$_3$ | OCH$_3$ | 214–215 |
| Q-46 | ($R_7$ = H) | H | CH$_3$ | CH$_3$ | Cl | OCH$_3$ | 194–195 |
| Q-47 | ($R_7$ = H) | H | CH$_3$ | CH$_3$ | CH$_3$ | CH$_3$ | 202–205 |
| Q-47 | ($R_7$ = H) | H | CH$_3$ | CH$_3$ | CH$_3$ | OCH$_3$ | 223–225 |
| Q-47 | ($R_7$ = H) | H | CH$_3$ | CH$_3$ | OCH$_3$ | OCH$_3$ | 209–211.5 |
| Q-47 | ($R_7$ = H) | H | CH$_3$ | CH$_3$ | Cl | OCH$_3$ | 207–210 |
| Q-48 | ($R_7$ = H) | H | CH$_3$ | CH$_3$ | CH$_3$ | CH$_3$ | 233–234 |
| Q-48 | ($R_7$ = H) | H | CH$_3$ | CH$_3$ | CH$_3$ | OCH$_3$ | 200–202 |
| Q-48 | ($R_7$ = H) | H | CH$_3$ | CH$_3$ | OCH$_3$ | OCH$_3$ | 209–211.5 |
| Q-48 | ($R_7$ = H) | H | CH$_3$ | CH$_3$ | Cl | OCH$_3$ | 223–224 |
| Q-15 | ($R_6$, $R_7$ = H) | H | CH$_3$ | CH$_3$ | CH$_3$ | CH$_3$ | 222–223 |
| Q-15 | ($R_6$, $R_7$ = H) | H | CH$_3$ | CH$_3$ | CH$_3$ | OCH$_3$ | 211–213 |
| Q-15 | ($R_6$, $R_7$ = H) | H | CH$_3$ | CH$_3$ | OCH$_3$ | OCH$_3$ | 206–208 |
| Q-15 | ($R_6$, $R_7$ = H) | H | CH$_3$ | CH$_3$ | Cl | OCH$_3$ | 241–242 |

TABLE III

| Q | | R | $R_1$ | $R_2$ | X | Y | m.p. °C. |
|---|---|---|---|---|---|---|---|
| | | \multicolumn{5}{c}{General Formula III} | |
| Q-1 | ($R_6$ = H, $R_7$ = H) | H | $CH_3$ | H | $CH_3$ | $CH_3$ | |
| Q-1 | ($R_6$ = H, $R_7$ = H) | H | $CH_3$ | H | $CH_3$ | $OCH_3$ | |
| Q-1 | ($R_6$ = H, $R_7$ = H) | H | $CH_3$ | H | $OCH_3$ | $OCH_3$ | |
| Q-1 | ($R_6$ = H, $R_7$ = H) | H | $CH_3$ | Cl | $OCH_3$ | $CH_3$ | |
| Q-1 | ($R_6$ = H, $R_7$ = $CH_3$) | H | $CH_3$ | H | $OCH_3$ | $OCH_3$ | |
| Q-1 | ($R_6$ = H, $R_7$ = H) | $CH_3$ | $CH_3$ | H | $OCH_3$ | $CH_3$ | |
| Q-1 | ($R_6$ = H, $R_7$ = H) | H | $CH_2CH_3$ | H | $OCH_3$ | $OCH_3$ | |
| Q-1 | ($R_6$ = $CH_3$, $R_7$ = H) | H | $CH_3$ | H | $OCH_3$ | $OCH_3$ | |
| Q-2 | ($R_6$ = H, $R_7$ = H) | H | $CH_3$ | H | $CH_3$ | $CH_3$ | |
| Q-2 | ($R_6$ = H, $R_7$ = H) | H | $CH_3$ | H | $OCH_3$ | $CH_3$ | |
| Q-2 | ($R_6$ = H, $R_7$ = H) | H | $CH_3$ | H | $OCH_3$ | $OCH_3$ | |
| Q-2 | ($R_6$ = H, $R_7$ = H) | H | $CH_3$ | Cl | $OCH_3$ | $OCH_3$ | |
| Q-2 | ($R_6$ = H, $R_7$ = H) | H | $CH_2CH_3$ | H | $OCH_3$ | $CH_3$ | |
| Q-2 | ($R_6$ = H, $R_7$ = H) | $CH_3$ | $CH_3$ | H | $OCH_3$ | $OCH_3$ | |
| Q-2 | ($R_6$ = H, $R_7$ = H) | H | $C_6H_5$ | H | $CH_3$ | $OCH_3$ | |
| Q-2 | ($R_6$ = H, $R_7$ = $CH_3$) | H | $CH_3$ | H | $OCH_3$ | $OCH_3$ | |
| Q-2 | ($R_6$ = $CH_3$, $R_7$ = H) | H | $CH_3$ | H | $OCH_3$ | $OCH_3$ | |
| Q-3 | ($R_6$ = H, $R_7$ = H) | H | $CH_3$ | H | $CH_3$ | $CH_3$ | |
| Q-3 | ($R_6$ = H, $R_7$ = H) | H | $CH_3$ | H | $OCH_3$ | $CH_3$ | |
| Q-3 | ($R_6$ = H, $R_7$ = H) | H | $CH_3$ | H | $OCH_3$ | $OCH_3$ | |
| Q-3 | ($R_6$ = H, $R_7$ = H) | $CH_3$ | $CH_3$ | H | $OCH_3$ | $OCH_3$ | |
| Q-3 | ($R_6$ = H, $R_7$ = H) | H | $CH_2CH_3$ | H | $OCH_3$ | $OCH_3$ | |
| Q-3 | ($R_6$ = H, $R_7$ = $CH_3$) | H | $CH_3$ | H | $OCH_3$ | $OCH_3$ | |
| Q-4 | ($R_6$ = H, $R_7$ = H) | H | $CH_3$ | H | $OCH_3$ | $CH_3$ | |
| Q-4 | ($R_6$ = H, $R_7$ = H) | H | $CH_3$ | H | $CH_3$ | $CH_3$ | |
| Q-4 | ($R_6$ = H, $R_7$ = H) | H | $CH_3$ | H | $OCH_3$ | $OCH_3$ | |
| Q-5 | ($R_6$ = H, $R_7$ = H) | H | $CH_3$ | H | $OCH_3$ | $CH_3$ | |
| Q-5 | ($R_6$ = H, $R_7$ = H) | H | $CH_3$ | H | $CH_3$ | $CH_3$ | |
| Q-5 | ($R_6$ = H, $R_7$ = H) | H | $CH_3$ | H | $OCH_3$ | $OCH_3$ | |
| Q-5 | ($R_6$ = H, $R_7$ = H) | H | $C_6H_5$ | H | $OCH_3$ | $OCH_3$ | |
| Q-6 | ($R_6$ = H, $R_7$ = H) | H | $CH_3$ | H | $CH_3$ | $CH_3$ | |
| Q-6 | ($R_6$ = H, $R_7$ = H) | H | $CH_3$ | H | $OCH_3$ | $CH_3$ | |
| Q-6 | ($R_6$ = H, $R_7$ = H) | H | $CH_3$ | H | $OCH_3$ | $OCH_3$ | |
| Q-6 | ($R_6$ = H, $R_7$ = H) | $CH_3$ | $CH_3$ | H | $OCH_3$ | $CH_3$ | |
| Q-6 | ($R_6$ = H, $R_7$ = H) | H | $C_6H_3$ | H | $OCH_3$ | $OCH_3$ | |
| Q-7 | ($R_8$ = $SCH_3$) | H | $CH_3$ | H | $CH_3$ | $CH_3$ | |
| Q-7 | ($R_8$ = $SCH_3$) | H | $CH_3$ | H | $CH_3$ | $OCH_3$ | |
| Q-7 | ($R_8$ = $SCH_3$) | H | $CH_3$ | H | $OCH_3$ | $OCH_3$ | |
| Q-7 | ($R_8$ = $SCH_3$) | H | $CH_3$ | Cl | $OCH_3$ | $OCH_3$ | |
| Q-7 | ($R_8$ = $SCH_3$) | H | $C_2H_5$ | H | $OCH_3$ | $CH_3$ | |
| Q-7 | ($R_8$ = $SCH_3$) | H | $C_6H_5$ | H | $OCH_3$ | $OCH_3$ | |
| Q-7 | ($R_8$ = $SCH_3$) | H | $CH_3$ | H | Cl | $OCH_3$ | |
| Q-7 | ($R_8$ = $SCH_3$) | H | H | H | $OCH_3$ | $OCH_3$ | |
| Q-7 | ($R_8$ = $SCH_3$) | $CH_3$ | $CH_3$ | H | $OCH_3$ | $OCH_3$ | |
| Q-7 | ($R_8$ = $SCH_3$) | H | $C_3H_7$ | H | $OCH_3$ | $OCH_3$ | |
| Q-7 | ($R_8$ = $SC_2H_5$) | H | $CH_3$ | H | $OCH_3$ | $CH_3$ | |
| Q-7 | ($R_8$ = $SC_2H_5$) | H | $CH_3$ | H | $CH_3$ | $CH_3$ | |
| Q-7 | ($R_8$ = $SC_2H_5$) | H | $CH_3$ | H | $OCH_3$ | $OCH_3$ | |
| Q-7 | ($R_8$ = $SC_2H_5$) | H | $C_3H_7$ | H | $OCH_3$ | $OCH_3$ | |
| Q-7 | ($R_8$ = $SC_2H_5$) | $CH_3$ | $CH_3$ | $CH_3$ | $OCH_3$ | $OCH_3$ | |
| Q-7 | ($R_8$ = $SC_2H_5$) | H | $CH_3$ | $CH_3$ | $OCH_3$ | $CH_3$ | |
| Q-7 | ($R_8$ = $CH_3$) | H | $CH_3$ | H | $CH_3$ | $CH_3$ | |
| Q-7 | ($R_8$ = $CH_3$) | H | $CH_3$ | H | $OCH_3$ | $OCH_3$ | |
| Q-7 | ($R_8$ = $CH_3$) | H | $CH_3$ | H | $OCH_3$ | $CH_3$ | |
| Q-7 | ($R_8$ = $CH_3$) | H | $CH_3$ | H | Cl | $OCH_3$ | |
| Q-7 | ($R_8$ = $CH_3$) | H | $CH_3$ | $CH_3$ | $OCH_3$ | $CH_3$ | |
| Q-7 | ($R_8$ = $CH_3$) | H | $C_6H_5$ | H | $OCH_3$ | $OCH_3$ | |
| Q-7 | ($R_8$ = $C_2H_5$) | H | $CH_3$ | H | $CH_3$ | $OCH_3$ | |
| Q-7 | ($R_8$ = $CH_2H_5$) | H | $CH_3$ | H | $CH_3$ | $CH_3$ | |
| Q-7 | ($R_8$ = $C_2H_5$) | H | $CH_3$ | H | $OCH_3$ | $OCH_3$ | |
| Q-7 | ($R_8$ = $OCH_3$) | H | $CH_3$ | H | $CH_3$ | $OCH_3$ | |
| Q-7 | ($R_8$ = $OCH_3$) | H | $CH_3$ | H | $CH_3$ | $CH_3$ | |
| Q-7 | ($R_8$ = $OCH_3$) | H | $CH_3$ | H | $OCH_3$ | $OCH_3$ | |
| Q-7 | ($R_8$ = $OCH_3$) | H | $CH_3$ | H | Cl | $OCH_3$ | |
| Q-7 | ($R_8$ = $OCH_3$) | H | $CH_3$ | $CH_3$ | $OCH_3$ | $OCH_3$ | |
| Q-7 | ($R_8$ = $OC_2H_5$) | H | $CH_3$ | H | $OCH_3$ | $OCH_3$ | |
| Q-7 | ($R_8$ = $OC_2H_5$) | H | $CH_3$ | H | $CH_3$ | $CH_3$ | |
| Q-7 | ($R_8$ = $OC_2H_5$) | H | $CH_3$ | H | $OCH_3$ | $CH_3$ | |
| Q-7 | ($R_8$ = H) | H | $CH_3$ | H | $OCH_3$ | $CH_3$ | |
| Q-7 | ($R_8$ = H) | H | $CH_3$ | H | $CH_3$ | $CH_3$ | |
| Q-7 | ($R_8$ = H) | H | $CH_3$ | H | $OCH_3$ | $OCH_3$ | |
| Q-7 | ($R_8$ = H) | H | $C_3H_7$ | H | $OCH_3$ | $OCH_3$ | |
| Q-7 | ($R_8$ = H) | H | $C_6H_5$ | H | $OCH_3$ | $CH_3$ | |
| Q-7 | ($R_8$ = H) | H | $CH_3$ | $CH_3$ | $OCH_3$ | $OCH_3$ | |
| Q-7 | ($R_8$ = $SCF_2H$) | H | $CH_3$ | H | Cl | $OCH_3$ | |
| Q-7 | ($R_8$ = $SCF_2H$) | H | $CH_3$ | H | $CH_3$ | $CH_3$ | |
| Q-7 | ($R_8$ = $SCF_2H$) | H | $CH_3$ | H | $OCH_3$ | $OCH_3$ | |
| Q-7 | ($R_8$ = $SCF_2H$) | H | $CH_3$ | H | $OCH_3$ | $CH_3$ | |
| Q-7 | ($R_8$ = $SCF_2H$) | H | $CH_3$ | Cl | $OCH_3$ | $OCH_3$ | |
| Q-7 | ($R_8$ = $SCF_2H$) | H | $CH_3$ | $CH_3$ | $OCH_3$ | $OCH_3$ | |

TABLE III-continued

| Q | | General Formula III R | $R_1$ | $R_2$ | X | Y | m.p. °C. |
|---|---|---|---|---|---|---|---|
| Q-8 | ($R_6$ = H) | H | $CH_3$ | H | $CH_3$ | $CH_3$ | |
| Q-8 | ($R_6$ = H) | H | $CH_3$ | H | $OCH_3$ | $CH_3$ | |
| Q-8 | ($R_6$ = H) | H | $CH_3$ | H | $OCH_3$ | $OCH_3$ | |
| Q-8 | ($R_6$ = H) | H | $CH_3$ | Cl | $OCH_3$ | $OCH_3$ | |
| Q-8 | ($R_6$ = H) | H | $CH_3$ | $CH_3$ | $OCH_3$ | $OCH_3$ | |
| Q-8 | ($R_6$ = H) | H | $CH_3$ | H | Cl | $OCH_3$ | |
| Q-8 | ($R_6$ = $CH_3$) | H | $CH_3$ | H | Cl | $OCH_3$ | |
| Q-8 | ($R_6$ = $CH_3$) | H | $CH_3$ | H | $CH_3$ | $CH_3$ | |
| Q-8 | ($R_6$ = $CH_3$) | H | $CH_3$ | H | $OCH_3$ | $OCH_3$ | |
| Q-8 | ($R_6$ = $CH_3$) | H | $CH_3$ | H | $OCH_3$ | $CH_3$ | |
| Q-8 | ($R_6$ = $CH_3$) | H | $C_3H_7$ | H | $OCH_3$ | $OCH_3$ | |
| Q-8 | ($R_6$ = $CH_3$) | H | $CH_3$ | $CH_3$ | $OCH_3$ | $OCH_3$ | |
| Q-9 | ($R_6$ = $CH_3$) | H | $CH_3$ | H | $OCH_3$ | $CH_3$ | |
| Q-9 | ($R_6$ = $CH_3$) | H | $CH_3$ | H | $CH_3$ | $CH_3$ | |
| Q-9 | ($R_6$ = $CH_3$) | H | $CH_3$ | H | $OCH_3$ | $OCH_3$ | |
| Q-9 | ($R_6$ = H) | H | $CH_3$ | $CH_3$ | $OCH_3$ | $OCH_3$ | |
| Q-9 | ($R_6$ = H) | H | $CH_3$ | Cl | $OCH_3$ | $OCH_3$ | |
| Q-9 | ($R_6$ = H) | H | $C_3H_7$ | H | $OCH_3$ | $OCH_3$ | |
| Q-10 | ($R_6$ = $CH_3$) | H | $CH_3$ | H | $OCH_3$ | $OCH_3$ | |
| Q-10 | ($R_6$ = $CH_3$) | H | $CH_3$ | H | $OCH_3$ | $OCH_3$ | |
| Q-10 | ($R_6$ = $CH_3$) | H | $CH_3$ | H | Cl | $OCH_3$ | |
| Q-10 | ($R_6$ = H) | H | $CH_3$ | H | Cl | $OCH_3$ | |
| Q-10 | ($R_6$ = H) | H | $CH_3$ | H | $OCH_3$ | $OCH_3$ | |
| Q-10 | ($R_6$ = H) | H | $CH_3$ | $CH_3$ | $OCH_3$ | $OCH_3$ | |
| Q-11 | ($R_6$ = $CH_3$) | H | $CH_3$ | H | $OCH_3$ | $CH_3$ | |
| Q-11 | ($R_6$ = $CH_3$) | H | $CH_3$ | H | $OCH_3$ | $OCH_3$ | |
| Q-11 | ($R_6$ = $CH_3$) | H | $CH_3$ | H | Cl | $OCH_3$ | |
| Q-11 | ($R_6$ = $CH_3$) | H | $CH_3$ | $CH_3$ | $OCH_3$ | $OCH_3$ | |
| Q-11 | ($R_6$ = $CH_3$) | H | $CH_3$ | Cl | $OCH_3$ | $OCH_3$ | |
| Q-11 | ($R_6$ = $CH_3$) | H | $CH_3$ | H | $CH_3$ | $CH_3$ | |
| Q-12 | ($R_6$ = $CH_3$) | H | $CH_3$ | H | $OCH_3$ | $OCH_3$ | |
| Q-12 | ($R_6$ = $CH_3$) | H | $CH_3$ | H | $CH_3$ | $CH_3$ | |
| Q-12 | ($R_6$ = $CH_3$) | H | $CH_3$ | H | Cl | $OCH_3$ | |
| Q-12 | ($R_6$ = H) | H | $CH_3$ | H | Cl | $OCH_3$ | |
| Q-12 | ($R_6$ = H) | H | $CH_3$ | H | $OCH_3$ | $OCH_3$ | |
| Q-12 | ($R_6$ = H) | H | $CH_3$ | H | $OCH_3$ | $CH_3$ | |
| Q-13 | ($R_6$ = $CH_3$) | H | $CH_3$ | H | $OCH_3$ | $OCH_3$ | |
| Q-13 | ($R_6$ = $CH_3$) | H | $CH_3$ | H | Cl | $OCH_3$ | |
| Q-13 | ($R_6$ = $CH_3$) | H | $CH_3$ | $CH_3$ | $OCH_3$ | $OCH_3$ | |
| Q-13 | ($R_6$ = $CH_3$) | H | $CH_3$ | Cl | $OCH_3$ | $OCH_3$ | |
| Q-14 | ($R_6$ = H, $R_7$ = H) | H | $CH_3$ | H | $OCH_3$ | $OCH_3$ | |
| Q-14 | ($R_6$ = H, $R_7$ = H) | H | $CH_3$ | H | $CH_3$ | $CH_3$ | |
| Q-14 | ($R_6$ = H, $R_7$ = H) | H | $CH_3$ | H | $OCH_3$ | $CH_3$ | |
| Q-14 | ($R_6$ = H, $R_7$ = H) | H | $CH_3$ | H | Cl | $OCH_3$ | |
| Q-14 | ($R_6$ = H, $R_7$ = H) | H | $CH_3$ | $CH_3$ | $OCH_3$ | $OCH_3$ | |
| Q-14 | ($R_6$ = H, $R_7$ = H) | H | $CH_3$ | Cl | $OCH_3$ | $OCH_3$ | |
| Q-14 | ($R_6$ = H, $R_7$ = H) | H | $C_3H_7$ | H | $OCH_3$ | $OCH_3$ | |
| Q-14 | ($R_6$ = H, $R_7$ = H) | H | $C_6H_5$ | H | $OCH_3$ | $OCH_3$ | |
| Q-15 | ($R_6$ = H, $R_7$ = $CH_3$) | H | $CH_3$ | H | $OCH_3$ | $OCH_3$ | |
| Q-15 | ($R_6$ = H, $R_7$ = $CH_3$) | H | $CH_3$ | H | Cl | $OCH_3$ | |
| Q-15 | ($R_6$ = H, $R_7$ = $CH_3$) | H | $CH_3$ | H | $CH_3$ | $CH_3$ | |
| Q-16 | ($R_6$ = $CH_3$, $R_7$ = H) | H | $CH_3$ | H | $OCH_3$ | $OCH_3$ | |
| Q-16 | ($R_6$ = $CH_3$, $R_7$ = H) | H | $CH_3$ | H | $OCH_3$ | $CH_3$ | |
| Q-16 | ($R_6$ = $CH_3$, $R_7$ = H) | H | $CH_3$ | H | $CH_3$ | $CH_3$ | |
| Q-16 | ($R_6$ = $CH_3$, $R_7$ = H) | H | $CH_3$ | H | Cl | $OCH_3$ | |
| Q-17 | ($R_6$ = , $R_7$ = H) | H | $CH_3$ | H | $OCH_3$ | $OCH_3$ | 232–234 |
| Q-17 | ($R_6$ = $CH_3$, $R_7$ = $CH_3$) | H | $CH_3$ | H | Cl | $OCH_3$ | |
| Q-17 | ($R_6$ = $CH_3$, $R_7$ = $CH_3$) | H | $CH_3$ | H | $OCH_3$ | $CH_3$ | |
| Q-18 | ($R_6$ = H, $R_7$ = $CH_3$) | H | $CH_3$ | H | $OCH_3$ | $OCH_3$ | |
| Q-18 | ($R_6$ = H, $R_7$ = $CH_3$) | H | $CH_3$ | H | $CH_3$ | $CH_3$ | |
| Q-18 | ($R_6$ = H, $R_7$ = $CH_3$) | H | $CH_3$ | H | Cl | $OCH_3$ | |
| Q-19 | ($R_6$ = H, $R_7$ = $CH_3$) | H | $CH_3$ | H | $OCH_3$ | $OCH_3$ | |
| Q-19 | ($R_6$ = H, $R_7$ = $CH_3$) | H | $CH_3$ | H | $OCH_3$ | $OCH_3$ | |
| Q-19 | ($R_6$ = H, $R_7$ = $CH_3$) | H | $CH_3$ | H | Cl | $OCH_3$ | |
| Q-20 | ($R_6$ = H, $R_7$ = $CH_3$) | H | $CH_3$ | H | $OCH_3$ | $OCH_3$ | |
| Q-20 | ($R_6$ = H, $R_7$ = $CH_3$) | H | $CH_3$ | H | $CH_3$ | $OCH_3$ | |
| Q-20 | ($R_6$ = H, $R_7$ = $CH_3$) | H | $CH_3$ | $CH_3$ | $OCH_3$ | $OCH_3$ | |
| Q-21 | ($R_6$ = $R_7$ = $R_9$ = H) | H | $CH_3$ | H | $OCH_3$ | $CH_3$ | |
| Q-21 | ($R_6$ = $R_7$ = $R_9$ = H) | H | $CH_3$ | H | $OCH_3$ | $OCH_3$ | |
| Q-21 | ($R_6$ = $R_7$ = $R_9$ = H) | H | $CH_3$ | H | Cl | $OCH_3$ | |
| Q-21 | ($R_6$ = $R_9$ = H, $R_7$ = $CH_3$) | H | $CH_3$ | H | $OCH_3$ | $OCH_3$ | |
| Q-21 | ($R_6$ = $R_9$ = H, $R_7$ = $CH_3$) | H | $CH_3$ | $CH_3$ | $OCH_3$ | $OCH_3$ | |
| Q-21 | ($R_6$ = $R_7$ = $R_9$ = H) | H | $CH_3$ | $CH_3$ | $OCH_3$ | $CH_3$ | |
| Q-22 | ($R_6$ = $R_7$ = $R_9$ = H) | H | $CH_3$ | H | $OCH_3$ | $CH_3$ | |
| Q-22 | ($R_6$ = $R_7$ = $R_9$ = H) | H | $CH_3$ | H | $OCH_3$ | $OCH_3$ | |
| Q-22 | ($R_6$ = $R_7$ = $R_9$ = H) | H | $CH_3$ | H | Cl | $OCH_3$ | |
| Q-23 | ($R_6$ = $R_7$ = $R_9$ = H) | H | $CH_3$ | H | $OCH_3$ | $OCH_3$ | |
| Q-23 | ($R_6$ = $R_7$ = $R_9$ = H) | H | $CH_3$ | H | Cl | $OCH_3$ | |
| Q-24 | ($R_6$ = $R_7$ = $R_9$ = H) | H | $CH_3$ | H | $OCH_3$ | $OCH_3$ | |
| Q-24 | ($R_6$ = $R_7$ = $R_9$ = H) | H | $CH_3$ | H | Cl | $OCH_3$ | |

TABLE III-continued

| Q | | R | $R_1$ | $R_2$ | X | Y | m.p. °C. |
|---|---|---|---|---|---|---|---|
| | | \multicolumn{5}{c}{General Formula III} | |
| Q-25 | ($R_6 = R_7 = R_9 = H$) | H | $CH_3$ | H | $OCH_3$ | $OCH_3$ | |
| Q-25 | ($R_6 = R_7 = R_9 = H$) | H | $CH_3$ | H | Cl | $OCH_3$ | |
| Q-25 | ($R_6 = R_7 = R_9 = H$) | H | $CH_3$ | H | $OCH_3$ | $OCH_3$ | |
| Q-26 | ($R_6 = R_7 = R_9 = H$) | H | $CH_3$ | H | $OCH_3$ | $CH_3$ | |
| Q-26 | ($R_6 = R_7 = R_9 = H$) | H | $CH_3$ | H | $OCH_3$ | $OCH_3$ | |
| Q-26 | ($R_6 = R_7 = R_9 = H$) | H | $CH_3$ | H | Cl | $OCH_3$ | |
| Q-27 | ($R_6 = R_7 = R_9 = H$) | H | $CH_3$ | H | $OCH_3$ | $OCH_3$ | |
| Q-27 | ($R_6 = R_7 = R_9 = H$) | H | $CH_3$ | H | Cl | $OCH_3$ | |
| Q-28 | ($R_6 = R_7 = R_9 = H$) | H | $CH_3$ | H | $OCH_3$ | $OCH_3$ | |
| Q-28 | ($R_6 = R_7 = R_9 = H$) | H | $CH_3$ | H | Cl | $OCH_3$ | |
| Q-29 | ($R_6 = R_7 = R_9 = H$) | H | $CH_3$ | H | $OCH_3$ | $OCH_3$ | |
| Q-29 | ($R_6 = R_7 = R_9 = H$) | H | $CH_3$ | H | Cl | $OCH_3$ | |
| Q-31 | ($R_6, R_7 = H$) | H | $CH_3$ | H | $OCH_3$ | $OCH_3$ | |
| Q-31 | ($R_6, R_7 = H$) | H | $CH_3$ | H | Cl | $OCH_3$ | |
| Q-31 | ($R_6, R_7 = H$) | H | $CH_3$ | $CH_3$ | $OCH_3$ | $OCH_3$ | |
| Q-32 | ($R_6, R_7 = H$) | H | $CH_3$ | H | $OCH_3$ | $OCH_3$ | |
| Q-32 | ($R_6, R_7 = H$) | H | $CH_3$ | H | Cl | $OCH_3$ | |
| Q-32 | ($R_6, R_7 = H$) | H | $CH_3$ | $CH_3$ | $OCH_3$ | $OCH_3$ | |
| Q-33 | ($R_6, R_7 = H$) | H | $CH_3$ | H | $OCH_3$ | $OCH_3$ | |
| Q-33 | ($R_6, R_7 = H$) | H | $CH_3$ | H | Cl | $OCH_3$ | |
| Q-33 | ($R_6, R_7 = H$) | H | $CH_3$ | $CH_3$ | $OCH_3$ | $OCH_3$ | |
| Q-34 | ($R_6, R_{10}, R_{11} = H$) | H | $CH_3$ | H | $OCH_3$ | $OCH_3$ | |
| Q-34 | ($R_6, R_{10}, R_{11} = H$) | H | $CH_3$ | H | $OCH_3$ | $CH_3$ | |
| Q-34 | ($R_6, R_{10}, R_{11} = H$) | H | $CH_3$ | H | Cl | $OCH_3$ | |
| Q-34 | ($R_6 = H, R_{10}, R_{11} = OCH_3$) | H | $CH_3$ | H | $OCH_3$ | $OCH_3$ | |
| Q-34 | ($R_6 = H, R_{10}, R_{11} = CH_3$) | H | $CH_3$ | H | $OCH_3$ | $OCH_3$ | |
| Q-34 | ($R_6 = H, R_{10}, R_{11} = OCH_3$) | H | $CH_3$ | H | Cl | $OCH_3$ | |
| Q-35 | ($R_{10}, R_{11} = H$) | H | $CH_3$ | H | $OCH_3$ | $OCH_3$ | |
| Q-35 | ($R_{10}, R_{11} = H$) | H | $CH_3$ | H | $OCH_3$ | $CH_3$ | |
| Q-36 | ($R_{10}, R_{11} = H$) | H | $CH_3$ | H | $OCH_3$ | $CH_3$ | |
| Q-36 | ($R_{10}, R_{11} = H$) | H | $CH_3$ | H | $OCH_3$ | $OCH_3$ | |
| Q-37 | ($R_6, R_7 = H$) | H | $CH_3$ | H | $OCH_3$ | $CH_3$ | |
| Q-37 | ($R_6, R_7 = H$) | H | $CH_3$ | H | $OCH_3$ | $OCH_3$ | |
| Q-38 | ($R_6, R_7 = H$) | H | $CH_3$ | H | $CH_3$ | $OCH_3$ | |
| Q-38 | ($R_6, R_7 = H$) | H | $CH_3$ | H | $OCH_3$ | $OCH_3$ | |
| Q-39 | ($R_{12}, R_{13} = CH_3$) | H | $CH_3$ | H | $OCH_3$ | $OCH_3$ | |
| Q-39 | ($R_{12}, R_{13} = OCH_3$) | H | $CH_3$ | H | $OCH_3$ | $OCH_3$ | |
| Q-39 | ($R_{12} = CH_3, R_{13} = OCH_3$) | H | $CH_3$ | H | $OCH_3$ | $OCH_3$ | |
| Q-40 | ($R_{12}, R_{13} = OCH_3$) | H | $CH_3$ | H | $OCH_3$ | $OCH_3$ | |
| Q-40 | ($R_{12}, R_{13} = CH_3$) | H | $CH_3$ | H | $OCH_3$ | $OCH_3$ | |
| Q-40 | ($R_{12}, R_{13} = OCH_3$) | H | $CH_3$ | $CH_3$ | $OCH_3$ | $OCH_3$ | |
| Q-41 | ($R_6 = H$) | H | $CH_3$ | H | $OCH_3$ | $OCH_3$ | |
| Q-41 | ($R_6 = H$) | H | $CH_3$ | H | $CH_3$ | $OCH_3$ | |
| Q-42 | ($R_6 = H$) | H | $CH_3$ | H | $OCH_3$ | $OCH_3$ | |
| Q-42 | ($R_6 = H$) | H | $CH_3$ | H | $CH_3$ | $OCH_3$ | |
| Q-43 | ($R_6 = CH_3$) | H | $CH_3$ | H | $OCH_3$ | $OCH_3$ | |
| Q-43 | ($R_6 = H$) | H | $CH_3$ | H | $CH_3$ | $OCH_3$ | |
| Q-43 | ($R_6 = H$) | H | $CH_3$ | H | $OCH_3$ | $OCH_3$ | |
| Q-44 | ($R_6 = H$) | H | $CH_3$ | H | $OCH_3$ | $OCH_3$ | |
| Q-44 | ($R_6 = H$) | H | $CH_3$ | H | $CH_3$ | $OCH_3$ | |
| Q-44 | ($R_6 = H$) | H | $CH_3$ | $CH_3$ | $OCH_3$ | $OCH_3$ | |
| Q-1 | ($R_6, R_7 = H$) | H | $CH_3$ | H | $OC_2H_5$ | $CH_3$ | |
| Q-1 | ($R_6, R_7 = H$) | H | $CH_3$ | H | F | $OCH_3$ | |
| Q-7 | ($R_8 = CH_3$) | H | $CH_3$ | H | $OCF_2H$ | $OCH_3$ | |
| Q-7 | ($R_8 = CH_3$) | H | $CH_3$ | H | $OCH_2CH_2F$ | $CH_3$ | |
| Q-7 | ($R_8 = SCH_3$) | H | $CH_3$ | H | $OC_2H_5$ | $N(OCH_3)CH_3$ | |
| Q-8 | ($R_6 = H$) | H | $CH_3$ | H | $OCH_3$ | $CH_2OCH_3$ | |
| Q-8 | ($R_6 = H$) | H | $CH_3$ | H | Cl | $OC_2H_5$ | |
| Q-8 | ($R_6 = H$) | H | $CH_3$ | H | $CH_3$ | $OCH_2C{\equiv}CH$ | |
| Q-8 | ($R_6 = CH_3$) | H | $CH_3$ | H | $CH_3$ | $OCH_2CH_2OCH_3$ | |
| Q-7 | ($R_8 = SCH_3$) | H | $CH_3$ | $CH_3$ | $OCH_3$ | $CH_2OCH_3$ | |
| Q-1 | ($R_6, R_7 = H$) | H | $CH_3$ | H | Br | $OCH_3$ | |
| Q-1 | ($R_6, R_7 = H$) | H | $CH_3$ | H | I | $OCH_3$ | |
| Q-2 | ($R_6, R_7 = H$) | H | $CH_3$ | H | $CH_2F$ | $CH_3$ | |
| Q-2 | ($R_6, R_7 = H$) | H | $CH_3$ | H | $OCH_2CHF_2$ | $CH_3$ | |
| Q-2 | ($R_6, R_7 = H$) | H | $CH_3$ | H | $CH_3$ | $OCH_2CH{=}CH_2$ | |
| Q-1 | ($R_6, R_7 = H$) | H | $CH_3$ | H | $OCH_3$ | $CH_2SCH_3$ | |
| Q-1 | ($R_6, R_7 = H$) | H | $CH_3$ | H | $OCH_3$ | $SCH_3$ | |
| Q-7 | ($R_8 = SCH_3$) | H | $CH_3$ | $CH_3$ | $CH_3$ | $CH(OCH_3)_2$ | |
| Q-7 | ($R_8 = SCH_3$) | H | $CH_3$ | $CH_3$ | $OCH_3$ | $N(CH_3)_2$ | |
| Q-7 | ($R_8 = SCH_3$) | H | $CH_3$ | $CH_3$ | $CH_3$ | $CF_3$ | |
| Q-7 | ($R_8 = SCH_3$) | H | $CH_3$ | $CH_3$ | $OCH_3$ | $CH(OCH_3)_2$ | |
| Q-7 | ($R_8 = SCH_3$) | H | $CH_3$ | $CH_3$ | $CH_3$ | $CH_2OCH_3$ | |
| Q-7 | ($R_8 = SCH_3$) | H | $CH_3$ | H | $CH_2F$ | $OCH_3$ | |
| Q-7 | ($R_8 = SCH_3$) | H | $CH_3$ | H | $OCH_2CF_3$ | $CH_3$ | |
| Q-1 | ($R_6, R_7 = H$) | H | $CH_3$ | H | Cl | $NHCH_3$ | |
| Q-1 | ($R_6, R_7 = H$) | H | $CH_3$ | H | $OC_2H_5$ | $N(OCH_3)CH_3$ | |
| Q-14 | ($R_6, R_7 = H$) | H | $CH_3$ | H | $CH_3$ | $N(CH_3)_2$ | |
| Q-14 | ($R_6, R_7 = H$) | H | $CH_3$ | H | $OCH_3$ | $C_2H_5$ | |
| Q-14 | ($R_6, R_7 = H$) | H | $CH_3$ | H | $CF_3$ | $CF_3$ | |

TABLE III-continued

| Q | | General Formula III R | $R_1$ | $R_2$ | X | Y | m.p. °C. |
|---|---|---|---|---|---|---|---|
| Q-14 | ($R_6, R_7 =$ H) | H | $CH_3$ | H | $CH_3$ | $SCH_3$ | |
| Q-21 | ($R_6, R_7, R_9 =$ H) | H | $CH_3$ | H | $OCH_3$ | $OCH_2CH=CH_2$ | |
| Q-3 | ($R_6, R_7 =$ H) | H | $CH_3$ | H | $CH_3$ | $OCH_2C\equiv CH$ | |
| Q-3 | ($R_6, R_7 =$ H) | H | $CH_3$ | H | $OCH_3$ | $CH_2OC_2H_5$ | |
| Q-33 | ($R_6, R_7 =$ H) | H | $CH_3$ | H | $CH_3$ | $OCH_2CH_2OCH_3$ | |
| Q-33 | ($R_6, R_7 =$ H) | H | $CH_3$ | H | $CH_3$ | $CH_2SCH_3$ | |
| Q-14 | ($R_6, R_7 =$ H) | H | $CH_3$ | H | $CH_3$ | CHO | |
| Q-14 | ($R_6, R_7 =$ H) | H | $CH_3$ | H | $CH_3$ | $\overset{O}{\underset{\|}{C}}CH_3$ | |
| Q-8 | ($R_6 = CH_3$) | H | $CH_3$ | H | $OCH_3$ | $CH(OCH_3)_2$ | |
| Q-8 | ($R_6 = CH_3$) | H | $CH_3$ | H | $OCH_3$ | $CH(OC_2H_5)_2$ | |
| Q-8 | ($R_6 = CH_3$) | H | $CH_3$ | H | $OCH_3$ | $CH(SCH_3)_2$ | |
| Q-14 | ($R_6, R_7 =$ H) | H | $CH_3$ | H | $OCH_3$ | $C(CH_3)(OCH_3)_2$ | |
| Q-43 | ($R_6 =$ H) | H | $CH_3$ | H | $OCH_3$ | 1,3-dioxo-lan-2-yl | |
| Q-43 | ($R_6 =$ H) | H | $CH_3$ | H | $CH_3$ | 1,3-dioxo-lan-2-yl | |
| Q-15 | ($R_6 =$ H, $R_7 = CH_3$) | H | $CH_3$ | H | $OCH_3$ | 1,3-dithio-lan-2-yl | |
| Q-15 | ($R_6 =$ H, $R_7 = CH_3$) | H | $CH_3$ | H | $OCH_3$ | 1,3-oxathlio-lan-2-yl | |
| Q-14 | ($R_6, R_7 =$ H) | H | $CH_3$ | H | $OCH_3$ | 2-methyl-1,3-dioxolan-2-yl | |
| Q-14 | ($R_6, R_7 =$ H) | H | $CH_3$ | H | $OCH_3$ | 4-methyl-1,3-dioxolan-2-yl | |
| Q-3 | ($R_6, R_7 =$ H) | H | $CH_3$ | H | $OCH_3$ | 5-methyl-1,3-oxathiolan-2-yl | |
| Q-2 | ($R_6, R_7 =$ H) | H | $CH_3$ | H | $OCH_3$ | 4-methyl-1,3-dithiolan-2-yl | |
| Q-2 | ($R_6, R_7 =$ H) | H | $CH_3$ | H | 2,4-dimethyl-1,3-dioxolan-2-yl | | |
| Q-7 | ($R_8 = CH_3$) | H | $CH_3$ | H | $CH_3$ | $SCF_2H$ | |
| Q-7 | ($R_8 = CH_3$) | H | $CH_3$ | H | Cl | $OCF_2H$ | |
| Q-7 | ($R_8 = CH_3$) | H | $CH_3$ | H | $OCH_3$ | cyclopropyl | |
| Q-7 | ($R_8 = CH_3$) | H | $CH_3$ | H | $OCH_3$ | isopropyl | |
| Q-7 | ($R_8 = SCH_3$) | H | $CH_3$ | $CH_3$ | $CH_3$ | $CH_3$ | 195–197 |
| Q-7 | ($R_8 = SCH_3$) | H | $CH_3$ | $CH_3$ | $CH_3$ | $OCH_3$ | 205–206.5 |
| Q-7 | ($R_8 = SCH_3$) | H | $CH_3$ | $CH_3$ | $OCH_3$ | $OCH_3$ | 201–203.5 |
| Q-7 | ($R_8 = SCH_3$) | H | $CH_3$ | $CH_3$ | Cl | $OCH_3$ | 188.5–190 |
| Q-7 | ($R_8 = SCH_2-CH=CH_2$) | H | $CH_3$ | $CH_3$ | $OCH_3$ | $OCH_3$ | 183–185 |
| Q-7 | ($R_8 = SCH_2-CH=CH_2$) | H | $CH_3$ | $CH_3$ | $CH_3$ | $CH_3$ | 194–197 |
| Q-7 | ($R_8 = SCH_2-CH=CH_2$) | H | $CH_3$ | $CH_3$ | $OCH_3$ | $OCH_3$ | 169–172 |
| Q-7 | ($R_8 = SCH_2-CH=CH_2$) | H | $CH_3$ | $CH_3$ | Cl | $OCH_3$ | 186–190 |
| Q-7 | ($R_8 = SCH_2CH_3$) | H | $CH_3$ | $CH_3$ *OCH₃* | $OCH_3$ | | |
| Q-7 | ($R_8 = SCH_2CH_3$) | H | $CH_3$ | $CH_3$ *CH₃* | $CH_3$ | | |
| Q-7 | ($R_8 = SCH_2CH_3$) | H | $CH_3$ | $CH_3$ | Cl | $OCH_3$ | |
| Q-7 | ($R_8 = SCH_2O_2CH_3$) | H | $CH_3$ | $CH_3$ | $CH_3$ | $CH_3$ | |
| Q-7 | ($R_8 = SCH_2CO_2CH_3$) | H | $CH_3$ | $CH_3$ *OCH₃* | | | |
| Q-7 | ($R_8 = SCH_2CO_2CH_3$) | H | $CH_3$ | $CH_3$ | $OCH_3$ | $OCH_3$ | |
| Q-7 | ($R_8 = SCH_2CO_2CH_3$) | H | $CH_3$ | $CH_3$ | Cl | $OCH_3$ | |
| Q-7 | ($R_8 = SCH_3$) | H | $CH_3$ | $CH_3$ | $OCH_3$ | i-$C_3H_7$ | |
| Q-7 | ($R_8 = SCH_3$) | H | $CH_3$ | $CH_3$ | $CH_3$ | i-$C_3H_7$ | |
| Q-13 | ($R_{18} = SCH_3, R_{19} = CH_3$) | H | $CH_3$ | $CH_3$ | $CH_3$ | $CH_3$ | 243–245 |
| Q-13 | ($R_{18} = SCH_3, R_{19} = CH_3$) | H | $CH_3$ | $CH_3$ | $CH_3$ | $OCH_3$ | 228–230 |
| Q-13 | ($R_{18} = SCH_3, R_{19} = CH_3$) | H | $CH_3$ | $CH_3$ | $OCH_3$ | $OCH_3$ | 212–214 |
| Q-13 | ($R_{18} = SCH_3, R_{19} = CH_3$) | H | $CH_3$ | $CH_3$ | Cl | $OCH_3$ | 213–214 |
| Q-13 | ($R_{18} = SCH_3, R_{19} = CH_2CH=CH_2$) | H | $CH_3$ | $CH_3$ | $CH_3$ | $CH_3$ | 212–214 |
| Q-13 | ($R_{18} = SCH_3, R_{19} = CH_2CH=CH_2$) | H | $CH_3$ | $CH_3$ | $CH_3$ | $OCH_3$ | 215–216 |
| Q-13 | ($R_{18} = SCH_3, R_{19} = CH_2CH=CH_2$) | H | $CH_3$ | $CH_3$ | $OCH_3$ | $OCH_3$ | 201–202 |
| Q-13 | ($R_{18} = SCH_3, R_{19} = CH_2CH=CH_2$) | H | $CH_3$ | $CH_3$ | Cl | $OCH_3$ | 219–220 |
| Q-13 | ($R_{18} = SCH_2CH=CH_2, R_{19} = CH_3$) | H | $CH_3$ | $CH_3$ | $CH_3$ | $CH_3$ | 199–201 |
| Q-13 | ($R_{18} = SCH_2CH=CH_2, R_{19} = CH_3$) | H | $CH_3$ | $CH_3$ | $CH_3$ | $OCH_3$ | 202–203 |
| Q-13 | ($R_{18} = SCH_2CH=CH_2, R_{19} = CH_3$) | H | $CH_3$ | $CH_3$ | $OCH_3$ | $OCH_3$ | 204–205 |
| Q-13 | ($R_{18} = SCH_2CH=CH_2, R_{19} = CH_3$) | H | $CH_3$ | $CH_3$ | Cl | $OCH_3$ | 205–206 |
| Q-13 | ($R_{18} = SCH_2CH=CH_2, R_{19} = CH_2CH=CH_2$) | H | $CH_3$ | $CH_3$ | $CH_3$ | $CH_3$ | 215–216 |
| Q-13 | ($R_{18} = SCH_2CH=CH_2, R_{19} = CH_2CH=CH_2$) | H | $CH_3$ | $CH_3$ | $CH_3$ | $OCH_3$ | 201–203 |
| Q-13 | ($R_{18} = SCH_2CH=CH_2, R_{19} = CH_2CH=CH_2$) | H | $CH_3$ | $CH_3$ | $OCH_3$ | $OCH_3$ | 193–194 |
| Q-13 | ($R_{18} = SCH_2CH=CH_2, R_{19} = CH_2CH=CH_2$) | H | $CH_3$ | $CH_3$ | Cl | $OCH_3$ | 209–210 |
| Q-45 | ($R_7 =$ H) | H | $CH_3$ | H | $OCH_3$ | $OCH_3$ | |
| Q-45 | ($R_7 =$ H) | H | $C_6H_5$ | H | $CH_3$ | $OCH_3$ | |
| Q-46 | ($R_7 =$ H) | H | $CH_3$ | H | $OCH_3$ | $OCH_3$ | |
| Q-46 | ($R_7 =$ H) | H | $CH_3$ | $CH_3$ | $CH_3$ | $OCH_3$ | |
| Q-47 | ($R_7 =$ H) | H | $CH_3$ | H | $OCH_3$ | $OCH_3$ | |

TABLE III-continued

| Q | | R | R$_1$ | R$_2$ | X | Y | m.p. °C. |
|---|---|---|---|---|---|---|---|
| Q-47 | (R$_7$ = H) | H | CH$_3$ | H | Cl | OCH$_3$ | |
| Q-48 | (R$_7$ = H) | H | C$_6$H$_5$ | H | OCH$_3$ | OCH$_3$ | |
| Q-48 | (R$_7$ = H) | H CH$_3$ | H | | CH$_3$ | OCH$_3$ | |

TABLE IV

General Formula IV

| Q | | R | R$_1$ | R$_2$ | X | Y | m.p.,°C. |
|---|---|---|---|---|---|---|---|
| Q-1 | (R$_6$ = H, R$_7$ = H) | H | CH$_3$ | H | CH$_3$ | CH$_3$ | |
| Q-1 | (R$_6$ = H, R$_7$ = H) | H | CH$_3$ | H | CH$_3$ | OCH$_3$ | |
| Q-1 | (R$_6$ = H, R$_7$ = H) | H | CH$_3$ | H | OCH$_3$ | OCH$_3$ | |
| Q-1 | (R$_6$ = H, R$_7$ = H) | H | CH$_3$ | Cl | OCH$_3$ | CH$_3$ | |
| Q-1 | (R$_6$ = H, R$_7$ = CH$_3$) | H | CH$_3$ | H | OCH$_3$ | OCH$_3$ | |
| Q-1 | (R$_6$ = H, R$_7$ = H) | CH$_3$ | CH$_3$ | H | OCH$_3$ | CH$_3$ | |
| Q-1 | (R$_6$ = H, R$_7$ = H) | H | CH$_2$CH$_3$ | H | OCH$_3$ | OCH$_3$ | |
| Q-1 | (R$_6$ = CH$_3$, R$_7$ = H) | H | CH$_3$ | H | OCH$_3$ | OCH$_3$ | |
| Q-2 | (R$_6$ = H, R$_7$ = H) | H | CH$_3$ | H | CH$_3$ | CH$_3$ | |
| Q-2 | (R$_6$ = H, R$_7$ = H) | H | CH$_3$ | H | OCH$_3$ | CH$_3$ | |
| Q-2 | (R$_6$ = H, R$_7$ = H) | H | CH$_3$ | H | OCH$_3$ | OCH$_3$ | |
| Q-2 | (R$_6$ = H, R$_7$ = H) | H | CH$_3$ | Cl | OCH$_3$ | OCH$_3$ | |
| Q-2 | (R$_6$ = H, R$_7$ = H) | H | CH$_2$CH$_3$ | H | OCH$_3$ | CH$_3$ | |
| Q-2 | (R$_6$ = H, R$_7$ = H) | CH$_3$ | CH$_3$ | H | OCH$_3$ | OCH$_3$ | |
| Q-2 | (R$_6$ = H, R$_7$ = H) | H | C$_6$H$_5$ | H | CH$_3$ | OCH$_3$ | |
| Q-2 | (R$_6$ = H, R$_7$ = CH$_3$) | H | CH$_3$ | H | OCH$_3$ | OCH$_3$ | |
| Q-2 | (R$_6$ = CH$_3$, R$_7$ = H) | H | CH$_3$ | H | OCH$_3$ | OCH$_3$ | |
| Q-3 | (R$_6$ = H, R$_7$ = H) | H | CH$_3$ | H | CH$_3$ | CH$_3$ | |
| Q-3 | (R$_6$ = H, R$_7$ = H) | H | CH$_3$ | H | OCH$_3$ | CH$_3$ | |
| Q-3 | (R$_6$ = H, R$_7$ = H) | H | CH$_3$ | H | OCH$_3$ | OCH$_3$ | |
| Q-3 | (R$_6$ = H, R$_7$ = H) | CH$_3$ | CH$_3$ | H | OCH$_3$ | OCH$_3$ | |
| Q-3 | (R$_6$ = H, R$_7$ = H) | H | CH$_2$CH$_3$ | H | OCH$_3$ | CH$_3$ | |
| Q-3 | (R$_6$ = H, R$_7$ = CH$_3$) | H | CH$_3$ | H | OCH$_3$ | OCH$_3$ | |
| Q-4 | (R$_6$ = H, R$_7$ = H) | H | CH$_3$ | H | OCH$_3$ | CH$_3$ | |
| Q-4 | (R$_6$ = H, R$_7$ = H) | H | CH$_3$ | H | CH$_3$ | CH$_3$ | |
| Q-4 | (R$_6$ = H, R$_7$ = H) | H | CH$_3$ | H | OCH$_3$ | OCH$_3$ | |
| Q-5 | (R$_6$ = H, R$_7$ = H) | H | CH$_3$ | H | OCH$_3$ | CH$_3$ | |
| Q-5 | (R$_6$ = H, R$_7$ = H) | H | CH$_3$ | H | CH$_3$ | CH$_3$ | |
| Q-5 | (R$_6$ = H, R$_7$ = H) | H | CH$_3$ | H | OCH$_3$ | OCH$_3$ | |
| Q-5 | (R$_6$ = H, R$_7$ = H) | H | C$_6$H$_5$ | H | OCH$_3$ | OCH$_3$ | |
| Q-6 | (R$_6$ = H, R$_7$ = H) | H | CH$_3$ | H | CH$_3$ | CH$_3$ | |
| Q-6 | (R$_6$ = H, R$_7$ = H) | H | CH$_3$ | H | OCH$_3$ | CH$_3$ | |
| Q-6 | (R$_6$ = H, R$_7$ = H) | H | CH$_3$ | H | OCH$_3$ | OCH$_3$ | |
| Q-6 | (R$_6$ = H, R$_7$ = H) | CH$_3$ | CH$_3$ | H | OCH$_3$ | CH$_3$ | |
| Q-6 | (R$_6$ = H, R$_7$ = H) | H | C$_6$H$_5$ | H | OCH$_3$ | OCH$_3$ | |
| Q-7 | (R$_8$ = SCH$_3$) | H | CH$_3$ | H | CH$_3$ | CH$_3$ | 181–182 |
| Q-7 | (R$_8$ = SCH$_3$) | H | CH$_3$ | H | CH$_3$ | OCH$_3$ | 161–163.5 |
| Q-7 | (R$_8$ = SCH$_3$) | H | CH$_3$ | H | OCH$_3$ | OCH$_3$ | 189–191 |
| Q-7 | (R$_8$ = SCH$_3$) | H | CH$_3$ | Cl | OCH$_3$ | OCH$_3$ | |
| Q-7 | (R$_8$ = SCH$_3$) | H | C$_2$H$_5$ | H | OCH$_3$ | CH$_3$ | |
| Q-7 | (R$_8$ = SCH$_3$) | H | C$_6$H$_5$ | H | OCH$_3$ | OCH$_3$ | |
| Q-7 | (R$_8$ = SCH$_3$) | H | CH$_3$ | H | Cl | OCH$_3$ | 171–173 |
| Q-7 | (R$_8$ = SCH$_3$) | H | H | H | OCH$_3$ | OCH$_3$ | |
| Q-7 | (R$_8$ = SCH$_3$) | CH$_3$ | CH$_3$ | H | OCH$_3$ | OCH$_3$ | |
| Q-7 | (R$_8$ = SCH$_3$) | H | C$_3$H$_7$ | H | OCH$_3$ | OCH$_3$ | |
| Q-7 | (R$_8$ = SC$_2$H$_5$) | H | CH$_3$ | H | OCH$_3$ | CH$_3$ | |
| Q-7 | (R$_8$ = SC$_2$H$_5$) | H | CH$_3$ | H | CH$_3$ | CH$_3$ | |
| Q-7 | (R$_8$ = SC$_2$H$_5$) | H | CH$_3$ | H | OCH$_3$ | OCH$_3$ | |
| Q-7 | (R$_8$ = SC$_2$H$_5$) | H | C$_3$H$_7$ | H | OCH$_3$ | OCH$_3$ | |
| Q-7 | (R$_8$ = SC$_2$H$_5$) | CH$_3$ | CH$_3$ | CH$_3$ | OCH$_3$ | OCH$_3$ | |
| Q-7 | (R$_8$ = SC$_2$H$_5$) | H | CH$_3$ | CH$_3$ | OCH$_3$ | CH$_3$ | |
| Q-7 | (R$_8$ = CH$_3$) | H | CH$_3$ | H | CH$_3$ | CH$_3$ | |
| Q-7 | (R$_8$ = CH$_3$) | H | CH$_3$ | H | OCH$_3$ | OCH$_3$ | |
| Q-7 | (R$_8$ = CH$_3$) | H | CH$_3$ | H | OCH$_3$ | CH$_3$ | |
| Q-7 | (R$_8$ = CH$_3$) | H | CH$_3$ | H | Cl | OCH$_3$ | |
| Q-7 | (R$_8$ = CH$_3$) | H | CH$_3$ | CH$_3$ | OCH$_3$ | CH$_3$ | |
| Q-7 | (R$_8$ = CH$_3$) | H | C$_6$H$_5$ | H | OCH$_3$ | OCH$_3$ | |
| Q-7 | (R$_8$ = C$_2$H$_5$) | H | CH$_3$ | H | CH$_3$ | CH$_3$ | |
| Q-7 | (R$_8$ = C$_2$H$_5$) | H | CH$_3$ | H | CH$_3$ | CH$_3$ | |
| Q-7 | (R$_8$ = C$_2$H$_5$) | H | CH$_3$ | H | OCH$_3$ | OCH$_3$ | |
| Q-7 | (R$_8$ = OCH$_3$) | H | CH$_3$ | H | CH$_3$ | CH$_3$ | |
| Q-7 | (R$_8$ = OCH$_3$) | H | CH$_3$ | H | CH$_3$ | CH$_3$ | |
| Q-7 | (R$_8$ = OCH$_3$) | H | CH$_3$ | H | OCH$_3$ | OCH$_3$ | |
| Q-7 | (R$_8$ = OCH$_3$) | H | CH$_3$ | H | Cl | OCH$_3$ | |
| Q-7 | (R$_8$ = OCH$_3$) | H | CH$_3$ | CH$_3$ | OCH$_3$ | OCH$_3$ | |
| Q-7 | (R$_8$ = OC$_2$H$_5$) | H | CH$_3$ | H | OCH$_3$ | OCH$_3$ | |
| Q-7 | (R$_8$ = OC$_2$H$_5$) | H | CH$_3$ | H | CH$_3$ | CH$_3$ | |
| Q-7 | (R$_8$ = OC$_2$H$_5$) | H | CH$_3$ | H | OCH$_3$ | CH$_3$ | |
| Q-7 | (R$_8$ = H) | H | CH$_3$ | H | OCH$_3$ | CH$_3$ | |
| Q-7 | (R$_8$ = H) | H | CH$_3$ | H | CH$_3$ | CH$_3$ | |

TABLE IV-continued

General Formula IV

| Q | | R | R$_1$ | R$_2$ | X | Y | m.p. °C. |
|---|---|---|---|---|---|---|---|
| Q-7 | (R$_8$ = H) | H | CH$_3$ | H | OCH$_3$ | OCH$_3$ | |
| Q-7 | (R$_8$ = H) | H | C$_3$H$_7$ | H | OCH$_3$ | OCH$_3$ | |
| Q-7 | (R$_8$ = H) | H | C$_6$H$_5$ | H | OCH$_3$ | CH$_3$ | |
| Q-7 | (R$_8$ = H) | H | CH$_3$ | CH$_3$ | OCH$_3$ | OCH$_3$ | |
| Q-7 | (R$_8$ = SCF$_2$H) | H | CH$_3$ | H | Cl | OCH$_3$ | |
| Q-7 | (R$_8$ = SCF$_2$H) | H | CH$_3$ | H | CH$_3$ | CH$_3$ | |
| Q-7 | (R$_8$ = SCF$_2$H) | H | CH$_3$ | H | OCH$_3$ | OCH$_3$ | |
| Q-7 | (R$_8$ = SCF$_2$H) | H | CH$_3$ | H | OCH$_3$ | CH$_3$ | |
| Q-7 | (R$_8$ = SCF$_2$H) | H | CH$_3$ | Cl | OCH$_3$ | OCH$_3$ | |
| Q-7 | (R$_8$ = SCF$_2$H) | H | CH$_3$ | CH$_3$ | OCH$_3$ | OCH$_3$ | |
| Q-8 | (R$_6$ = H) | H | CH$_3$ | H | CH$_3$ | CH$_3$ | |
| Q-8 | (R$_6$ = H) | H | CH$_3$ | H | OCH$_3$ | CH$_3$ | |
| Q-8 | (R$_6$ = H) | H | CH$_3$ | H | OCH$_3$ | OCH$_3$ | |
| Q-8 | (R$_6$ = H) | H | CH$_3$ | Cl | OCH$_3$ | OCH$_3$ | |
| Q-8 | (R$_6$ = H) | H | CH$_3$ | CH$_3$ | OCH$_3$ | OCH$_3$ | |
| Q-8 | (R$_6$ = H) | H | CH$_3$ | H | Cl | OCH$_3$ | |
| Q-8 | (R$_6$ = CH$_3$) | H | CH$_3$ | H | Cl | OCH$_3$ | |
| Q-8 | (R$_6$ = CH$_3$) | H | CH$_3$ | H | CH$_3$ | CH$_3$ | |
| Q-8 | (R$_6$ = CH$_3$) | H | CH$_3$ | H | OCH$_3$ | OCH$_3$ | |
| Q-8 | (R$_6$ = CH$_3$) | H | CH$_3$ | H | OCH$_3$ | CH$_3$ | |
| Q-8 | (R$_6$ = CH$_3$) | H | C$_3$H$_7$ | H | OCH$_3$ | OCH$_3$ | |
| Q-8 | (R$_6$ = CH$_3$) H | CH$_3$ | CH$_3$ | OCH$_3$ | OCH$_3$ | | |
| Q-9 | (R$_6$ = CH$_3$) | H | CH$_3$ | H | OCH$_3$ | CH$_3$ | |
| Q-9 | (R$_6$ = CH$_3$) | H | CH$_3$ | H | CH$_3$ | CH$_3$ | |
| Q-9 | (R$_6$ = CH$_3$) | H | CH$_3$ | H | OCH$_3$ | OCH$_3$ | |
| Q-9 | (R$_6$ = H) | H | CH$_3$ | CH$_3$ | OCH$_3$ | OCH$_3$ | |
| Q-9 | (R$_6$ = H) | H | CH$_3$ | Cl | OCH$_3$ | OCH$_3$ | |
| Q-9 | (R$_6$ = H) | H | C$_3$H$_7$ | H | OCH$_3$ | OCH$_3$ | |
| Q-10 | (R$_6$ = CH$_3$) | H | CH$_3$ | H | OCH$_3$ | OCH$_3$ | |
| Q-10 | (R$_6$ = CH$_3$) | H | CH$_3$ | H | OCH$_3$ | OCH$_3$ | |
| Q-10 | (R$_6$ = CH$_3$) | H | CH$_3$ | H | Cl | OCH$_3$ | |
| Q-10 | (R$_6$ = H) | H | CH$_3$ | H | Cl | OCH$_3$ | |
| Q-10 | (R$_6$ = H) | H | CH$_3$ | H | OCH$_3$ | OCH$_3$ | |
| Q-10 | (R$_6$ = H) | H | CH$_3$ | CH$_3$ | OCH$_3$ | OCH$_3$ | |
| Q-11 | (R$_6$ = CH$_3$) | H | CH$_3$ | H | OCH$_3$ | CH$_3$ | |
| Q-11 | (R$_6$ = CH$_3$) | H | CH$_3$ | H | OCH$_3$ | OCH$_3$ | |
| Q-11 | (R$_6$ = CH$_3$) | H | CH$_3$ | H | Cl | OCH$_3$ | |
| Q-11 | (R$_6$ = CH$_3$) | H | CH$_3$ | CH$_3$ | OCH$_3$ | OCH$_3$ | |
| Q-11 | (R$_6$ = CH$_3$) | H | CH$_3$ | Cl | OCH$_3$ | OCH$_3$ | |
| Q-11 | (R$_6$ = CH$_3$) | H | CH$_3$ | H | CH$_3$ | CH$_3$ | |
| Q-12 | (R$_6$ = CH$_3$) | H | CH$_3$ | H | OCH$_3$ | OCH$_3$ | |
| Q-12 | (R$_6$ = CH$_3$) | H | CH$_3$ | H | CH$_3$ | OCH$_3$ | |
| Q-12 | (R$_6$ = H) | H | CH$_3$ | H | Cl | OCH$_3$ | |
| Q-12 | (R$_6$ = H) | H | CH$_3$ | H | OCH$_3$ | OCH$_3$ | |
| Q-12 | (R$_6$ = H) | H | CH$_3$ | H | OCH$_3$ | CH$_3$ | |
| Q-13 | (R$_6$ = CH$_3$) | H | CH$_3$ | H | OCH$_3$ | OCH$_3$ | |
| Q-13 | (R$_6$ = CH$_3$) | H | CH$_3$ | H | Cl | OCH$_3$ | |
| Q-13 | (R$_6$ = CH$_3$) | H | CH$_3$ | CH$_3$ | OCH$_3$ | OCH$_3$ | |
| Q-13 | (R$_6$ = CH$_3$) | H | CH$_3$ | Cl | OCH$_3$ | OCH$_3$ | |
| Q-14 | (R$_6$ = H, R$_7$ = H) | H | CH$_3$ | H | OCH$_3$ | OCH$_3$ | |
| Q-14 | (R$_6$ = H, R$_7$ = H) | H | CH$_3$ | H | CH$_3$ | CH$_3$ | |
| Q-14 | (R$_6$ = H, R$_7$ = H) | H | CH$_3$ | H | OCH$_3$ | CH$_3$ | |
| Q-14 | (R$_6$ = H, R$_7$ = H) | H | CH$_3$ | H | Cl | OCH$_3$ | |
| Q-14 | (R$_6$ = H, R$_7$ = H) | H | CH$_3$ | CH$_3$ | OCH$_3$ | OCH$_3$ | |
| Q-14 | (R$_6$ = H, R$_7$ = H) | H | CH$_3$ | Cl | OCH$_3$ | OCH$_3$ | |
| Q-14 | (R$_6$ = H, R$_7$ = H) | H | C$_3$H$_7$ | H | OCH$_3$ | OCH$_3$ | |
| Q-14 | (R$_6$ = H, R$_7$ = H) | H | C$_6$H$_5$ | H | OCH$_3$ | OCH$_3$ | |
| Q-15 | (R$_6$ = H, R$_7$ = CH$_3$) | H | CH$_3$ | H | OCH$_3$ | OCH$_3$ | |
| Q-15 | (R$_6$ = H, R$_7$ = CH$_3$) | H | CH$_3$ | H | Cl | OCH$_3$ | |
| Q-15 | (R$_6$ = H, R$_7$ = CH$_3$) | H | CH$_3$ | H | CH$_3$ | OCH$_3$ | |
| Q-16 | (R$_6$ = CH$_3$, R$_7$ = H) | H | CH$_3$ | H | OCH$_3$ | OCH$_3$ | |
| Q-16 | (R$_6$ = CH$_3$, R$_7$ = H) | H | CH$_3$ | H | OCH$_3$ | CH$_3$ | |
| Q-16 | (R$_6$ = CH$_3$, R$_7$ = H) | H | CH$_3$ | H | CH$_3$ | CH$_3$ | |
| Q-16 | (R$_6$ = CH$_3$, R$_7$ = H) | H | CH$_3$ | H | Cl | OCH$_3$ | |
| Q-17 | (R$_6$ = CH$_3$, R$_7$ = CH$_3$) | H | CH$_3$ | H | OCH$_3$ | OCH$_3$ | |
| Q-17 | (R$_6$ = CH$_3$, R$_7$ = CH$_3$) | H | CH$_3$ | H | Cl | OCH$_3$ | |
| Q-17 | (R$_6$ = CH$_3$, R$_7$ = CH$_3$) | H | CH$_3$ | H | OCH$_3$ | CH$_3$ | |
| Q-18 | (R$_6$ = H, R$_7$ = CH$_3$) | H | CH$_3$ | H | OCH$_3$ | OCH$_3$ | |
| Q-18 | (R$_6$ = H, R$_7$ = CH$_3$) | H | CH$_3$ | H | CH$_3$ | OCH$_3$ | |
| Q-18 | (R$_6$ = H, R$_7$ = CH$_3$) | H | CH$_3$ | H | Cl | OCH$_3$ | |
| Q-19 | (R$_6$ = H, R$_7$ = CH$_3$) | H | CH$_3$ | H | OCH$_3$ | CH$_3$ | |
| Q-19 | (R$_6$ = H, R$_7$ = CH$_3$) | H | CH$_3$ | H | OCH$_3$ | OCH$_3$ | |
| Q-19 | (R$_6$ = H, R$_7$ = CH$_3$) | H | CH$_3$ | H | Cl | OCH$_3$ | |
| Q-20 | (R$_6$ = CH$_3$, R$_7$ = CH$_3$) | H | CH$_3$ | H | OCH$_3$ | OCH$_3$ | |
| Q-20 | (R$_6$ = CH$_3$, R$_7$ = CH$_3$) | H | CH$_3$ | H | CH$_3$ | OCH$_3$ | |
| Q-20 | (R$_6$ = CH$_3$, R$_7$ = CH$_3$) | H | CH$_3$ | CH$_3$ | OCH$_3$ | OCH$_3$ | |
| Q-21 | (R$_6$ = R$_7$ = R$_9$ = H) | H | CH$_3$ | H | OCH$_3$ | CH$_3$ | |
| Q-21 | (R$_6$ = R$_7$ = R$_9$ = H) | H | CH$_3$ | H | OCH$_3$ | OCH$_3$ | |
| Q-21 | (R$_6$ = R$_7$ = R$_9$ = H) | H | CH$_3$ | H | Cl | OCH$_3$ | |

TABLE IV-continued

General Formula IV

| Q | | R | $R_1$ | $R_2$ | X | Y | m.p. °C. |
|---|---|---|---|---|---|---|---|
| Q-21 | ($R_6 = R_9 = H, R_7 = CH_3$) | H | $CH_3$ | H | $OCH_3$ | $OCH_3$ | |
| Q-21 | ($R_6 = R_9 = H, R_7 = CH_3$) | H | $CH_3$ | $CH_3$ | $OCH_3$ | $OCH_3$ | |
| Q-21 | ($R_6 = R_7 = R_9 = H$) | H | $CH_3$ | $CH_3$ | $OCH_3$ | $CH_3$ | |
| Q-22 | ($R_6 = R_7 = R_9 = H$) | H | $CH_3$ | H | $OCH_3$ | $CH_3$ | |
| Q-22 | ($R_6 = R_7 = R_9 = H$) | H | $CH_3$ | H | $OCH_3$ | $OCH_3$ | |
| Q-22 | ($R_6 = R_7 = R_9 = H$) | H | $CH_3$ | H | Cl | $OCH_3$ | |
| Q-23 | ($R_6 = R_7 = R_9 = H$) | H | $CH_3$ | H | $OCH_3$ | $OCH_3$ | |
| Q-23 | ($R_6 = R_7 = R_9 = H$) | H | $CH_3$ | H | Cl | $OCH_3$ | |
| Q-24 | ($R_6 = R_7 = R_9 = H$) | H | $CH_3$ | H | $OCH_3$ | $OCH_3$ | |
| Q-24 | ($R_6 = R_7 = R_9 = H$) | H | $CH_3$ | H | Cl | $OCH_3$ | |
| Q-25 | ($R_6 = R_7 = R_9 = H$) | H | $CH_3$ | H | $OCH_3$ | $OCH_3$ | |
| Q-25 | ($R_6 = R_7 = R_9 = H$) | H | $CH_3$ | H | Cl | $OCH_3$ | |
| Q-25 | ($R_6 = R_7 = R_9 = H$) | H | $CH_3$ | H | $OCH_3$ | $OCH_3$ | |
| Q-26 | ($R_6 = R_7 = R_9 = H$) | H | $CH_3$ | H | $OCH_3$ | $CH_3$ | |
| Q-26 | ($R_6 = R_7 = R_9 = H$) | H | $CH_3$ | H | $OCH_3$ | $OCH_3$ | |
| Q-26 | ($R_6 = R_7 = R_9 = H$) | H | $CH_3$ | H | Cl | $OCH_3$ | |
| Q-27 | ($R_6 = R_7 = R_9 = H$) | H | $CH_3$ | H | $OCH_3$ | $OCH_3$ | |
| Q-27 | ($R_6 = R_7 = R_9 = H$) | H | $CH_3$ | H | Cl | $OCH_3$ | |
| Q-28 | ($R_6 = R_7 = R_9 = H$) | H | $CH_3$ | H | $OCH_3$ | $OCH_3$ | |
| Q-28 | ($R_6 = R_7 = R_9 = H$) | H | $CH_3$ | H | Cl | $OCH_3$ | |
| Q-29 | ($R_6 = R_7 = R_9 = H$) | H | $CH_3$ | H | $OCH_3$ | $OCH_3$ | |
| Q-29 | ($R_6 = R_7 = R_9 = H$) | H | $CH_3$ | H | Cl | $OCH_3$ | |
| Q-31 | ($R_6, R_7 = H$) | H | $CH_3$ | H | $OCH_3$ | $OCH_3$ | |
| Q-31 | ($R_6, R_7 = H$) | H | CH | H | Cl | $OCH_3$ | |
| Q-31 | ($R_6, R_7 = H$) | H | $CH_3$ | $CH_3$ | $OCH_3$ | $OCH_3$ | |
| Q-32 | ($R_6, R_7 = H$) | H | $CH_3$ | H | $OCH_3$ | $OCH_3$ | |
| Q-32 | ($R_6, R_7 = H$) | H | $CH_3$ | H | Cl | $OCH_3$ | |
| Q-32 | ($R_6, R_7 = H$) | H | $CH_3$ | $CH_3$ | $OCH_3$ | $OCH_3$ | |
| Q-33 | ($R_6, R_7 = H$) | H | $CH_3$ | H | $OCH_3$ | $OCH_3$ | |
| Q-33 | ($R_6, R_7 = H$) | H | $CH_3$ | H | Cl | $OCH_3$ | |
| Q-33 | ($R_6, R_7 = H$) | H | $CH_3$ | $CH_3$ | $OCH_3$ | $OCH_3$ | |
| Q-34 | ($R_6, R_{10}, R_{11} = H$) | H | $CH_3$ | H | $OCH_3$ | $OCH_3$ | |
| Q-34 | ($R_6, R_{10}, R_{11} = H$) | H | $CH_3$ | H | $OCH_3$ | $CH_3$ | |
| Q-34 | ($R_6, R_{10}, R_{11} = H$) | H | $CH_3$ | H | Cl | $OCH_3$ | |
| Q-34 | ($R_6 = H, R_{10}, R_{11} = OCH_3$) | H | $CH_3$ | H | $OCH_3$ | $OCH_3$ | |
| Q-34 | ($R_6 = H, R_{10}, R_{11} = OCH_3$) | H | $CH_3$ | H | $OCH_3$ | $OCH_3$ | |
| Q-34 | ($R_6 = H, R_{10}, R_{11} = OCH_3$) | H | $CH_3$ | H | Cl | $OCH_3$ | |
| Q-35 | ($R_{10}, R_{11} = H$) | H | $CH_3$ | H | $OCH_3$ | $OCH_3$ | |
| Q-35 | ($R_{10}, R_{11} = H$) | H | $CH_3$ | H | $OCH_3$ | $CH_3$ | |
| Q-36 | ($R_{10}, R_{11} = H$) H | $CH_3$ | H | $OCH_3$ | $CH_3$ | | |
| Q-36 | ($R_{10}, R_{11} = H$) | H | $CH_3$ | H | $OCH_3$ | $OCH_3$ | |
| Q-37 | ($R_6, R_7 = H$) | H | $CH_3$ | H | $OCH_3$ | $CH_3$ | |
| Q-37 | ($R_6, R_7 = H$) | H | $CH_3$ | H | $OCH_3$ | $OCH_3$ | |
| Q-38 | ($R_6, R_7 = H$) | H | $CH_3$ | H | $CH_3$ | $OCH_3$ | |
| Q-38 | ($R_6, R_7 = H$) | H | $CH_3$ | H | $OCH_3$ | $OCH_3$ | |
| Q-39 | ($R_{12}, R_{13} = CH_3$) | H | $CH_3$ | H | $OCH_3$ | $OCH_3$ | |
| Q-39 | ($R_{12}, R_{13} = OCH_3$) | H | $CH_3$ | H | $OCH_3$ | $OCH_3$ | |
| Q-39 | ($R_{12} = CH_3, R_{13} = OCH_3$) | H | $CH_3$ | H | $OCH_3$ | $OCH_3$ | |
| Q-40 | ($R_{12}, R_{13} = OCH_3$) | H | $CH_3$ | H | $OCH_3$ | $OCH_3$ | |
| Q-40 | ($R_{12}, R_{13} = CH_3$) | H | $CH_3$ | H | $OCH_3$ | $OCH_3$ | |
| Q-40 | ($R_{12}, R_{13} = OCH_3$) | H | $CH_3$ | $CH_3$ | $OCH_3$ | $OCH_3$ | |
| Q-41 | ($R_6 = H$) | H | $CH_3$ | H | $OCH_3$ | $OCH_3$ | |
| Q-41 | ($R_6 = H$) | H | $CH_3$ | H | $CH_3$ | $OCH_3$ | |
| Q-42 | ($R_6 = H$) | H | $CH_3$ | H | $OCH_3$ | $OCH_3$ | |
| Q-42 | ($R_6 = H$) | H | $CH_3$ | H | $CH_3$ | $OCH_3$ | |
| Q-43 | ($R_6 = CH_3$) | H | $CH_3$ | H | $OCH_3$ | $OCH_3$ | |
| Q-43 | ($R_6 = H$) | H | $CH_3$ | H | $CH_3$ | $OCH_3$ | |
| Q-43 | ($R_6 = H$) | H | $CH_3$ | H | $OCH_3$ | $OCH_3$ | |
| Q-44 | ($R_6 = H$) | H | $CH_3$ | H | $OCH_3$ | $OCH_3$ | |
| Q-44 | ($R_6 = H$) | H | $CH_3$ | H | $CH_3$ | $OCH_3$ | |
| Q-44 | ($R_6 = H$) | H | $CH_3$ | $CH_3$ | $OCH_3$ | $OCH_3$ | |
| Q-1 | ($R_6, R_7 = H$) | H | $CH_3$ | H | $OC_2H_5$ | $CH_3$ | |
| Q-1 | ($R_6, R_7 = H$) | H | $CH_3$ | H | F | $OCH_3$ | |
| Q-7 | ($R_8 = CH_3$) | H | $CH_3$ | H | $OCF_2H$ | $OCH_3$ | |
| Q-7 | ($R_8 = CH_3$) | H | $CH_3$ | H | $OCH_2CH_2F$ | $CH_3$ | |
| Q-7 | ($R_8 = SCH_3$) | H | $CH_3$ | H | $OC_2H_5$ | $N(OCH_3)CH_3$ | |
| Q-8 | ($R_6 = H$) | H | $CH_3$ | H | $OCH_3$ | $CH_2OCH_3$ | |
| Q-8 | ($R_6 = H$) | H | $CH_3$ | H | Cl | $OC_2H_5$ | |
| Q-8 | ($R_6 = H$) | H | $CH_3$ | H | $CH_3$ | $OCH_2C\equiv CH$ | |
| Q-8 | ($R_6 = CH_3$) | H | $CH_3$ | H | $CH_3$ | $OCH_2CH_2OCH_3$ | |
| Q-7 | ($R_8 = SCH_3$) | H | $CH_3$ | $CH_3$ | $OCH_3$ | $CH_2OCH_3$ | |
| Q-1 | ($R_6, R_7 = H$) | H | $CH_3$ | H | Br | $OCH_3$ | |
| Q-1 | ($R_6, R_7 = H$) | H | $CH_3$ | H | I | $OCH_3$ | |
| Q-2 | ($R_6, R_7 = H$) | H | $CH_3$ | H | $CH_2F$ | $CH_3$ | |
| Q-2 | ($R_6, R_7 = H$) | H | $CH_3$ | H | $OCH_2CHF_2$ | $CH_3$ | |
| Q-2 | ($R_6, R_7 = H$) | H | $CH_3$ | H | $CH_3$ | $OCH_2CH=CH_2$ | |
| Q-1 | ($R_6, R_7 = H$) | H | $CH_3$ | H | $OCH_3$ | $CH_2SCH_3$ | |
| Q-1 | ($R_6, R_7 = H$) | H | $CH_3$ | H | $OCH_3$ | $SCH_3$ | |
| Q-7 | ($R_8 = SCH_3$) | H | $CH_3$ | $CH_3$ | $CH_3$ | $CH(OCH_3)_2$ | |
| Q-7 | ($R_8 = SCH_3$) | H | $CH_3$ | $CH_3$ | $OCH_3$ | $N(CH_3)_2$ | |

TABLE IV-continued

| Q | | R | $R_1$ | $R_2$ | X | Y | m.p. °C. |
|---|---|---|---|---|---|---|---|
| Q-7 | ($R_8$ = $SCH_3$) | H | $CH_3$ | $CH_3$ | $CH_3$ | $CF_3$ | |
| Q-7 | ($R_8$ = $SCH_3$) | H | $CH_3$ | $CH_3$ | $OCH_3$ | $CH(OCH_3)_2$ | |
| Q-7 | ($R_8$ = $SCH_3$) | H | $CH_3$ | $CH_3$ | $CH_3$ | $CH_2OCH_3$ | |
| Q-7 | ($R_8$ = $SCH_3$) | H | $CH_3$ | H | $CH_2F$ | $OCH_3$ | |
| Q-7 | ($R_8$ = $SCH_3$) | H | $CH_3$ | H | $OCH_2CF_3$ | $CH_3$ | |
| Q-1 | ($R_6, R_7$ = H) | H | $CH_3$ | H | Cl | $NHCH_3$ | |
| Q-1 | ($R_6, R_7$ = H) | H | $CH_3$ | H | $OC_2H_5$ | $N(OCH_3)CH_3$ | |
| Q-14 | ($R_6, R_7$ = H) | H | $CH_3$ | H | $CH_3$ | $N(CH_3)_2$ | |
| Q-14 | ($R_6, R_7$ = H) | H | $CH_3$ | H | $OCH_3$ | $C_2H_5$ | |
| Q-14 | ($R_6, R_7$ = H) | H | $CH_3$ | H | $CF_3$ | $CF_3$ | |
| Q-14 | ($R_6, R_7$ = H) | H | $CH_3$ | H | $CH_3$ | $SCH_3$ | |
| Q-21 | ($R_6, R_7, R_9$ = H) | H | $CH_3$ | H | $OCH_3$ | $OCH_2CH=CH_2$ | |
| Q-3 | ($R_6, R_7$ = H) | H | $CH_3$ | H | $CH_3$ | $OCH_2C\equiv CH$ | |
| Q-3 | ($R_6, R_7$ = H) | H | $CH_3$ | H | $OCH_3$ | $CH_2OC_2H_5$ | |
| Q-33 | ($R_6, R_7$ = H) | H | $CH_3$ | H | $CH_3$ | $OCH_2CH_2OCH_3$ | |
| Q-33 | ($R_6, R_7$ = H) | H | $CH_3$ | H | $CH_3$ | $CH_2SCH_3$ | |
| Q-14 | ($R_6, R_7$ = H) | H | $CH_3$ | H | $CH_3$ | CHO | |
| Q-14 | ($R_6, R_7$ = H) | H | $CH_3$ | H | $CH_3$ | $\overset{O}{\underset{\|}{C}}CH_3$ | |
| Q-8 | ($R_6$ = $CH_3$) | H | $CH_3$ | H | $OCH_3$ | $CH(OCH_3)_2$ | |
| Q-8 | ($R_6$ = $CH_3$) | H | $CH_3$ | H | $OCH_3$ | $CH(OC_2H_5)_2$ | |
| Q-8 | ($R_6$ = $CH_3$) | H | $CH_3$ | H | $OCH_3$ | $CH(SCH_3)_2$ | |
| Q-14 | ($R_6, R_7$ = H) | H | $CH_3$ | H | $OCH_3$ | $C(CH_3)(OCH_3)_2$ | |
| Q-43 | ($R_6$ = H) | H | $CH_3$ | H | $OCH_3$ | 1,3-dioxolan-2-yl | |
| Q-43 | ($R_6$ = H) | H | $CH_3$ | H | $CH_3$ | 1,3-dioxolan-2-yl | |
| Q-15 | ($R_6$ = H, $R_7$ = $CH_3$) | H | $CH_3$ | H | $OCH_3$ | 1,3-dithiolan-2-yl | |
| Q-15 | ($R_6$ = H, $R_7$ = $CH_3$) | H | $CH_3$ | H | $OCH_3$ | 1,3-oxathiolan-2-yl | |
| Q-14 | ($R_6, R_7$ = H) | H | $CH_3$ | H | $OCH_3$ | 2-methyl-1,3-dioxolan-2-yl | |
| Q-14 | ($R_6, R_7$ = H) | H | $CH_3$ | H | $OCH_3$ | 4-methyl-1,3-dioxolan-2-yl | |
| Q-3 | ($R_6, R_7$ = H) | H | $CH_3$ | H | $OCH_3$ | 5-methyl-1,3-oxathiolan-2-yl | |
| Q-2 | ($R_6, R_7$ = H) | H | $CH_3$ | H | $OCH_3$ | 4-methyl-1,3-dithiolan-2-yl | |
| Q-2 | ($R_6, R_7$ = H) | H | $CH_3$ | H | $OCH_3$ | 2,4 dimethyl-1,3-dioxolan-2-yl | |
| Q-7 | ($R_8$ = $CH_3$) | H | $CH_3$ | H | $CH_3$ | $SCF_2H$ | |
| Q-7 | ($R_8$ = $CH_3$) | H | $CH_3$ | H | Cl | $OCF_2H$ | |
| Q-7 | ($R_8$ = $CH_3$) | H | $CH_3$ | H | $OCH_3$ | cyclopropyl | |
| Q-7 | ($R_8$ = $CH_3$) | H | $CH_3$ | H | $OCH_3$ | isopropyl | |
| Q-7 | ($R_8$ = $SCH_3$) | H | $CH_3$ | $CH_3$ | $CH_3$ | $CH_3$ | |
| Q-7 | ($R_8$ = $SCH_3$) | H | $CH_3$ | $CH_3$ | $CH_3$ | $OCH_3$ | |
| Q-7 | ($R_8$ = $SCH_3$) | H | $CH_3$ | $CH_3$ | $OCH_3$ | $OCH_3$ | |
| Q-7 | ($R_8$ = $SCH_3$) | H | $CH_3$ | $CH_3$ | Cl | $OCH_3$ | |
| Q-7 | ($R_8$ = $SCH_2-CH=CH_2$) | H | $CH_3$ | $CH_3$ | $CH_3$ | $OCH_3$ | |
| Q-7 | ($R_8$ = $SCH_2-CH=CH_2$) | H | $CH_3$ | $CH_3$ | $CH_3$ | $CH_3$ | |
| Q-7 | ($R_8$ = $SCH_2-CH=CH_2$) | H | $CH_3$ | $CH_3$ | $OCH_3$ | $OCH_3$ | |
| Q-7 | ($R_8$ = $SCH_2-CH=CH_2$) | H | $CH_3$ | $CH_3$ | Cl | $OCH_3$ | |
| Q-7 | ($R_8$ = $SCH_2CH_3$) | H | $CH_3$ | $CH_3$ | $OCH_3$ | $OCH_3$ | |
| Q-7 | ($R_8$ = $SCH_2CH_3$) | H | $CH_3$ | $CH_3$ | $CH_3$ | $CH_3$ | |
| Q-7 | ($R_8$ = $SCH_2CH_3$) | H | $CH_3$ | $CH_3$ | Cl | $OCH_3$ | |
| Q-7 | ($R_8$ = $SCH_2CO_2CH_3$) | H | $CH_3$ | $CH_3$ | $CH_3$ | $CH_3$ | |
| Q-7 | ($R_8$ = $SCH_2CO_2CH_3$) | H | $CH_3$ | $CH_3$ | $OCH_3$ | $CH_3$ | |
| Q-7 | ($R_8$ = $SCH_2CO_2CH_3$) | H | $CH_3$ | $CH_3$ | $OCH_3$ | $OCH_3$ | |
| Q-7 | ($R_8$ = $SCH_2CO_2CH_3$) | H | $CH_3$ | $CH_3$ | Cl | $OCH_3$ | |
| Q-7 | ($R_8$ = $SCH_3$) | H | $CH_3$ | $CH_3$ | $OCH_3$ | $i$-$C_3H_7$ | |
| Q-7 | ($R_8$ = $SCH_3$) | H | $CH_3$ | $CH_3$ | $CH_3$ | $i$-$C_3H_7$ | |
| Q-13 | ($R_8$ = $S-CH_2-C_6H_5$) | H | $CH_3$ | H | $CH_3$ | $CH_{33}$ | 187–188 |
| Q-13 | ($R_8$ = $S-CH_2-C_6H_5$) | H | $CH_3$ | H | $CH_3$ | $OCH_3$ | 180–182 |
| Q-13 | ($R_8$ = $S-CH_2-C_6H_5$) | H | $CH_3$ | H | $OCH_3$ | $OCH_3$ | 176–178 |
| Q-13 | ($R_8$ = $S-CH_2-C_6H_5$) | H | $CH_3$ | H | Cl | $OCH_3$ | 201–203 |
| Q-13 | ($R_8$ = SH) | H | $CH_3$ | H | $CH_3$ | $CH_3$ | |
| Q-13 | ($R_8$ = SH) | H | $CH_3$ | H | $CH_3$ | $OCH_3$ | |
| Q-13 | ($R_8$ = SH) | H | $CH_3$ | H | $OCH_3$ | $OCH_3$ | >250 |
| Q-13 | ($R_8$ = SH) | H | $CH_3$ | H | Cl | $OCH_3$ | |
| Q-48 | ($R_7$ = H) | H | $CH_3$ | H | $CH_3$ | $CH_3$ | |
| Q-48 | ($R_7$ = H) | H | $CH_3$ | H | $CH_3$ | $OCH_3$ | 192–195 |
| Q-48 | ($R_7$ = H) | H | $CH_3$ | H | $OCH_3$ | $OCH_3$ | 195–196 |
| Q-48 | ($R_7$ = H) | H | $CH_3$ | H | Cl | $OCH_3$ | |
| Q-45 | ($R_7$ = H) | H | $CH_3$ | H | $OCH_3$ | $OCH_3$ | |
| Q-45 | ($R_7$ = H) | H | $C_6H_5$ | H | $CH_3$ | $OCH_3$ | |
| Q-46 | ($R_7$ = H) | H | $CH_3$ | H | $OCH_3$ | $OCH_3$ | |

TABLE IV-continued

| Q | | R | $R_1$ | $R_2$ | X | Y | m.p. °C. |
|---|---|---|---|---|---|---|---|
| | | | General Formula IV | | | | |
| Q-46 | ($R_7$ = H) | H | $CH_3$ | $CH_3$ | $CH_3$ | $OCH_3$ | |
| Q-47 | ($R_7$ = H) | H | $CH_3$ | H | $OCH_3$ | $OCH_3$ | |
| Q-47 | ($R_7$ = H) | H | $CH_3$ | H | Cl | $OCH_3$ | |
| Q-48 | ($R_7$ = H) | H | $C_6H_5$ | H | $OCH_3$ | $OCH_3$ | |
| Q-48 | ($R_7$ = H) | H | $CH_3$ | H | $CH_3$ | $OCH_3$ | |

TABLE V

| Q | | R | $R_1$ | $R_2$ | X | Y | m.p. °C. |
|---|---|---|---|---|---|---|---|
| | | | General Formula V | | | | |
| Q-1 | ($R_6, R_7$ = H) | H | $CH_3$ | H | $OCH_3$ | $OCH_3$ | |
| Q-1 | ($R_6, R_7$ = H) | H | $CH_3$ | H | $OCH_3$ | $CH_3$ | |
| Q-1 | ($R_6, R_7$ = H) | H | $CH_3$ | $CH_3$ | $OCH_3$ | $CH_3$ | |
| Q-1 | ($R_6, R_7$ = H) | H | $C_3H_7$ | H | $OCH_3$ | $CH_3$ | |
| Q-1 | ($R_6, R_7$ = H) | H | $C_6H_5$ | H | $OCH_3$ | $OCH_3$ | |
| Q-1 | ($R_6, R_7$ = $CH_3$) | H | $CH_3$ | H | $OCH_3$ | $OCH_3$ | |
| Q-2 | ($R_6, R_7$ = H) | H | $CH_3$ | H | $OCH_3$ | $OCH_3$ | |
| Q-2 | ($R_6, R_7$ = H) | H | $CH_3$ | H | $CH_3$ | $OCH_3$ | |
| Q-2 | ($R_6, R_7$ = H) | H | $CH_3$ | $CH_3$ | $OCH_3$ | $OCH_3$ | |
| Q-2 | ($R_6, R_7$ = H) | H | $C_3H_7$ | H | $OCH_3$ | $OCH_3$ | |
| Q-2 | ($R_6$ = $CH_3$, $R_7$ = H) | H | $CH_3$ | H | $OCH_3$ | $OCH_3$ | |
| Q-2 | ($R_6$ = H, $R_7$ = $CH_3$) | H | $CH_3$ | H | $OCH_3$ | $CH_3$ | |
| Q-2 | ($R_6, R_7$ = H) | H | $C_6H_5$ | H | $OCH_3$ | $OCH_3$ | |
| Q-3 | ($R_6, R_7$ = H) | H | $CH_3$ | H | $OCH_3$ | $CH_3$ | |
| Q-3 | ($R_6, R_7$ = H) | H | $CH_3$ | H | $OCH_3$ | $OCH_3$ | |
| Q-3 | ($R_6, R_7$ = H) | H | $CH_3$ | $CH_3$ | $OCH_3$ | $OCH_3$ | |
| Q-3 | ($R_6, R_7$ = H) | H | $C_3H_7$ | H | $CH_3$ | $OCH_3$ | |
| Q-4 | ($R_6, R_7$ = H) | H | $CH_3$ | H | $OCH_3$ | $CH_3$ | |
| Q-4 | ($R_6, R_7$ = H) | H | $CH_3$ | H | $OCH_3$ | $OCH_3$ | |
| Q-4 | ($R_6, R_7$ = H) | H | $CH_3$ | $CH_3$ | $CH_3$ | $OCH_3$ | |
| Q-5 | ($R_6, R_7$ = H) | H | $CH_3$ | H | $CH_3$ | $OCH_3$ | |
| Q-5 | ($R_6, R_7$ = H) | H | $CH_3$ | H | $OCH_3$ | $OCH_3$ | |
| Q-6 | ($R_6, R_7$ = H) | H | $CH_3$ | H | $CH_3$ | $OCH_3$ | |
| Q-6 | ($R_6, R_7$ = H) | H | $CH_3$ | H | $OCH_3$ | $OCH_3$ | |
| Q-7 | ($R_8$ = H) | H | $CH_3$ | H | $OCH_3$ | $CH_3$ | |
| Q-7 | ($R_8$ = H) | H | $CH_3$ | H | $OCH_3$ | $OCH_3$ | |
| Q-7 | ($R_8$ = H) | H | $CH_3$ | $CH_3$ | $OCH_3$ | $OCH_3$ | |
| Q-7 | ($R_8$ = H) | H | $C_3H_7$ | H | $CH_3$ | $OCH_3$ | |
| Q-7 | ($R_8$ = H) | H | $C_6H_5$ | H | $CH_3$ | $OCH_3$ | |
| Q-7 | ($R_8$ = $CH_3$) | H | $CH_3$ | H | $OCH_3$ | $OCH_3$ | |
| Q-7 | ($R_8$ = $CH_3$) | H | $CH_3$ | H | $CH_3$ | $OCH_3$ | |
| Q-7 | ($R_8$ = $CH_3$) | H | $CH_3$ | $CH_3$ | $OCH_3$ | $OCH_3$ | |
| Q-7 | ($R_8$ = $CH_3$) | H | $C_3H_7$ | H | $OCH_3$ | $CH_3$ | |
| Q-7 | ($R_8$ = $CH_3$) | H | $C_6H_5$ | H | $OCH_3$ | $CH_3$ | |
| Q-7 | ($R_8$ = $SCH_3$) | H | $CH_3$ | H | $OCH_3$ | $OCH_3$ | |
| Q-7 | ($R_8$ = $SCH_3$) | H | $CH_3$ | H | $OCH_3$ | $CH_3$ | |
| Q-7 | ($R_8$ = $SCH_3$) | H | $CH_3$ | $CH_3$ | $OCH_3$ | $CH_3$ | 192–193 |
| Q-7 | ($R_8$ = $SCH_3$) | H | $C_3H_7$ | H | $OCH_3$ | $CH_3$ | |
| Q-7 | ($R_8$ = $OCH_3$) | H | $CH_3$ | H | $OCH_3$ | $OCH_3$ | |
| Q-7 | ($R_8$ = $OCH_3$) | H | $CH_3$ | H | $CH_3$ | $OCH_3$ | |
| Q-7 | ($R_8$ = $OCH_3$) | H | $CH_3$ | $CH_3$ | $OCH_3$ | $CH_3$ | |
| Q-7 | ($R_8$ = $OCH_3$) | H | $C_3H_7$ | H | $OCH_3$ | $CH_3$ | |
| Q-8 | ($R_6$ = H) | H | $CH_3$ | H | $OCH_3$ | $CH_3$ | |
| Q-8 | ($R_6$ = H) | H | $CH_3$ | H | $OCH_3$ | $OCH_3$ | |
| Q-8 | ($R_6$ = H) | H | $CH_3$ | $CH_3$ | $OCH_3$ | $CH_3$ | |
| Q-8 | ($R_6$ = $CH_3$) | H | $CH_3$ | $CH_3$ | $OCH_3$ | $CH_3$ | |
| Q-8 | ($R_6$ = $CH_3$) | H | $CH_3$ | H | $OCH_3$ | $OCH_3$ | |
| Q-8 | ($R_6$ = $CH_3$) | H | $CH_3$ | H | $CH_3$ | $OCH_3$ | |
| Q-9 | ($R_6$ = $CH_3$) | H | $CH_3$ | H | $OCH_3$ | $OCH_3$ | |
| Q-9 | ($R_6$ = $CH_3$) | H | $CH_3$ | H | $CH_3$ | $OCH_3$ | |
| Q-9 | ($R_6$ = $CH_3$) | H | $CH_3$ | $CH_3$ | $OCH_3$ | $OCH_3$ | |
| Q-10 | ($R_6$ = H) | H | $CH_3$ | H | $OCH_3$ | $CH_3$ | |
| Q-10 | ($R_6$ = H) | H | $CH_3$ | H | $OCH_3$ | $OCH_3$ | |
| Q-10 | ($R_6$ = $CH_3$) | H | $CH_3$ | H | $OCH_3$ | $OCH_3$ | |
| Q-10 | ($R_6$ = $CH_3$) | H | $CH_3$ | H | $CH_3$ | $OCH_3$ | |
| Q-11 | ($R_6$ = $CH_3$) | H | $CH_3$ | H | $OCH_3$ | $OCH_3$ | |
| Q-11 | ($R_6$ = $CH_3$) | H | $CH_3$ | H | $CH_3$ | $OCH_3$ | |
| Q-11 | ($R_6$ = $CH_3$) | H | $CH_3$ | $CH_3$ | $OCH_3$ | $OCH_3$ | |
| Q-12 | ($R_6$ = $CH_3$) | H | $CH_3$ | H | $OCH_3$ | $OCH_3$ | |
| Q-12 | ($R_6$ = $CH_3$) | H | $CH_3$ | H | $OCH_3$ | $CH_3$ | |
| Q-13 | ($R_6$ = $CH_3$) | H | $CH_3$ | H | $OCH_3$ | $OCH_3$ | |
| Q-13 | ($R_6$ = $CH_3$) | H | $CH_3$ | H | $OCH_3$ | $CH_3$ | |
| Q-14 | ($R_6, R_7$ = H) | H | $CH_3$ | H | $OCH_3$ | $OCH_3$ | |
| Q-14 | ($R_6, R_7$ = H) | H | $CH_3$ | H | $OCH_3$ | $CH_3$ | |
| Q-14 | ($R_6, R_7$ = H) | H | $CH_3$ | $CH_3$ | $OCH_3$ | $OCH_3$ | |
| Q-14 | ($R_6, R_7$ = H) | H | $CH_3$ | Cl | $CH_3$ | $OCH_3$ | |
| Q-15 | ($R_6$ = H, $R_7$ = $CH_3$) | H | $CH_3$ | H | $OCH_3$ | $OCH_3$ | |
| Q-15 | ($R_6$ = H, $R_7$ = $CH_3$) | H | $CH_3$ | H | $CH_3$ | $CH_3$ | |

TABLE V-continued

General Formula V

| Q | | R | $R_1$ | $R_2$ | X | Y | m.p. °C. |
|---|---|---|---|---|---|---|---|
| Q-16 | ($R_6$ = $CH_3$, $R_7$ = H) | H | $CH_3$ | H | $OCH_3$ | $OCH_3$ | |
| Q-16 | ($R_6$ = $CH_3$, $R_7$ = H) | H | $CH_3$ | H | $CH_3$ | $OCH_3$ | |
| Q-16 | ($R_6$ = $CH_3$, $R_7$ = H) | H | $CH_3$ | $CH_3$ | $OCH_3$ | $OCH_3$ | |
| Q-17 | ($R_6$, $R_7$ = $CH_3$) | H | $CH_3$ | H | $OCH_3$ | $OCH_3$ | |
| Q-17 | ($R_6$, $R_7$ = $CH_3$) | H | $CH_3$ | H | $CH_3$ | $OCH_3$ | |
| Q-18 | ($R_6$ = H, $R_7$ = $CH_3$) | H | $CH_3$ | H | $CH_3$ | $OCH_3$ | |
| Q-18 | ($R_6$ = H, $R_7$ = $CH_3$) | H | $C_3H_7$ | H | $OCH_3$ | $CH_3$ | |
| Q-19 | ($R_6$ = H, $R_7$ = $CH_3$) | H | $CH_3$ | H | $OCH_3$ | $CH_3$ | |
| Q-19 | ($R_6$ = H, $R_7$ = $CH_3$) | H | $CH_3$ | $CH_3$ | $CH_3$ | $OCH_3$ | |
| Q-20 | ($R_6$, $R_7$ = $CH_3$) | H | $CH_3$ | H | $OCH_3$ | $CH_3$ | |
| Q-20 | ($R_6$, $R_7$ = $CH_3$) | H | $CH_3$ | H | $OCH_3$ | $OCH_3$ | |
| Q-20 | ($R_6$, $R_7$ = $CH_3$) | H | $C_3H_7$ | H | $OCH_3$ | $CH_3$ | |
| Q-21 | ($R_6$, $R_7$, $R_9$ = H) | H | $CH_3$ | H | $OCH_3$ | $OCH_3$ | |
| Q-21 | ($R_6$, $R_7$, $R_9$ = H) | H | $CH_3$ | H | $CH_3$ | $OCH_3$ | |
| Q-21 | ($R_6$, $R_7$, $R_9$ = H) | H | $CH_3$ | $CH_3$ | $OCH_3$ | $OCH_3$ | |
| Q-22 | ($R_6$, $R_7$, $R_9$ = H) | H | $CH_3$ | H | $OCH_3$ | $OCH_3$ | |
| Q-22 | ($R_6$, $R_7$, $R_9$ = H) | H | $CH_3$ | H | $CH_3$ | $OCH_3$ | |
| Q-23 | ($R_6$, $R_7$, $R_9$ = H) | H | $CH_3$ | H | $CH_3$ | $OCH_3$ | |
| Q-23 | ($R_6$, $R_7$, $R_9$ = H) | H | $CH_3$ | H | $OCH_3$ | $OCH_3$ | |
| Q-24 | ($R_6$, $R_7$, $R_9$ = H) | H | $CH_3$ | H | $OCH_3$ | $OCH_3$ | |
| Q-24 | ($R_6$, $R_7$, $R_9$ = H) | H | $CH_3$ | H | $CH_3$ | $OCH_3$ | |
| Q-25 | ($R_6$, $R_7$, $R_9$ = H) | H | $CH_3$ | H | $OCH_3$ | $OCH_3$ | |
| Q-25 | ($R_6$, $R_7$, $R_9$ = H) | H | $CH_3$ | H | $OCH_3$ | $CH_3$ | |
| Q-25 | ($R_6$, $R_7$, $R_9$ = H) | H | $C_3H_7$ | H | $CH_3$ | $OCH_3$ | |
| Q-26 | ($R_6$, $R_7$, $R_9$ = H) | H | $CH_3$ | H | $CH_3$ | $OCH_3$ | |
| Q-27 | ($R_6$, $R_7$, $R_9$ = H) | H | $CH_3$ | H | $CH_3$ | $OCH_3$ | |
| Q-28 | ($R_6$, $R_7$, $R_9$ = H) | H | $CH_3$ | H | $CH_3$ | $OCH_3$ | |
| Q-29 | ($R_6$, $R_7$, $R_9$ = H) | H | $CH_3$ | H | $OCH_3$ | $OCH_3$ | |
| Q-29 | ($R_6$, $R_7$, $R_9$ = H) | H | $CH_3$ | $CH_3$ | $CH_3$ | $OCH_3$ | |
| Q-31 | ($R_6$, $R_7$ = H) | H | $CH_3$ | H | $OCH_3$ | $CH_3$ | |
| Q-31 | ($R_6$, $R_7$ = H) | H | $CH_3$ | H | $OCH_3$ | $OCH_3$ | |
| Q-32 | ($R_6$, $R_7$ = H) | H | $CH_3$ | H | $OCH_3$ | $OCH_3$ | |
| Q-32 | ($R_6$, $R_7$ = H) | H | $CH_3$ | H | $CH_3$ | $OCH_3$ | |
| Q-33 | ($R_6$, $R_7$ = H) | H | $CH_3$ | H | $OCH_3$ | $OCH_3$ | |
| Q-33 | ($R_6$, $R_7$ = H) | H | $CH_3$ | H | $CH_3$ | $OCH_3$ | |
| Q-34 | ($R_6$, $R_{10}$, $R_{11}$ = H) | H | $CH_3$ | H | $OCH_3$ | $CH_3$ | |
| Q-34 | ($R_6$, $R_{10}$, $R_{11}$ = H) | H | $CH_3$ | H | $OCH_3$ | $OCH_3$ | |
| Q-34 | ($R_6$ = H, $R_{10}$, $R_{11}$ = $CH_3$) | H | $CH_3$ | H | $OCH_3$ | $CH_3$ | |
| Q-34 | ($R_6$ = H, $R_{10}$, $R_{11}$ = $OCH_3$) | H | $CH_3$ | H | $OCH_3$ | $CH_3$ | |
| Q-34 | ($R_6$ = H, $R_{10}$, $R_{11}$ = $OCH_3$) | H | $CH_3$ | H | $OCH_3$ | $OCH_3$ | |
| Q-34 | ($R_6$ = H, $R_{10}$, $R_{11}$ = $OCH_3$) | H | $CH_3$ | $CH_3$ | $OCH_3$ | $CH_3$ | |
| Q-35 | ($R_{10}$, $R_{11}$ = H) | H | $CH_3$ | H | $OCH_3$ | $CH_3$ | |
| Q-35 | ($R_{10}$, $R_{11}$ = H) | H | $CH_3$ | $CH_3$ | $OCH_3$ | $OCH_3$ | |
| Q-36 | ($R_{10}$, $R_{11}$ = H) | H | $CH_3$ | H | $OCH_3$ | $CH_3$ | |
| Q-36 | ($R_{10}$, $R_{11}$ = H) | H | $CH_3$ | H | $OCH_3$ | $OCH_3$ | |
| Q-37 | ($R_6$, $R_7$ = H) | H | $CH_3$ | H | $OCH_3$ | $CH_3$ | |
| Q-37 | ($R_6$, $R_7$ = H) | H | $CH_3$ | H | $OCH_3$ | $OCH_3$ | |
| Q-38 | ($R_6$, $R_7$ = H) | H | $CH_3$ | H | $OCH_3$ | $CH_3$ | |
| Q-38 | ($R_6$, $R_7$ = H) | H | $CH_3$ | H | $OCH_3$ | $OCH_3$ | |
| Q-39 | ($R_{12}$, $R_{13}$ = $CH_3$) | H | $CH_3$ | H | $OCH_3$ | $CH_3$ | |
| Q-39 | ($R_{12}$, $R_{13}$ = $OCH_3$) | H | $CH_3$ | H | $OCH_3$ | $CH_3$ | |
| Q-39 | ($R_{12}$ = $CH_3$, $R_{13}$ = $OCH_3$) | H | $CH_3$ | H | $OCH_3$ | $CH_3$ | |
| Q-40 | ($R_{12}$, $R_{13}$ = $CH_3$) | H | $CH_3$ | H | $OCH_3$ | $CH_3$ | |
| Q-40 | ($R_{12}$, $R_{13}$ = $OCH_3$) | H | $CH_3$ | H | $OCH_3$ | $CH_3$ | |
| Q-41 | ($R_6$ = H) | H | $CH_3$ | H | $OCH_3$ | $OCH_3$ | |
| Q-41 | ($R_6$ = H) | H | $CH_3$ | H | $CH_3$ | $OCH_3$ | |
| Q-42 | ($R_6$ = H) | H | $CH_3$ | H | $CH_3$ | $OCH_3$ | |
| Q-42 | ($R_6$ = H) | H | $CH_3$ | H | $OCH_3$ | $OCH_3$ | |
| Q-43 | ($R_6$ = H) | H | $CH_3$ | H | $OCH_3$ | $CH_3$ | |
| Q-43 | ($R_6$ = H) | H | $CH_3$ | H | $OCH_3$ | $OCH_3$ | |
| Q-43 | ($R_6$ = $CH_3$) | H | $CH_3$ | H | $OCH_3$ | $CH_3$ | |
| Q-44 | ($R_6$ = H) | H | $CH_3$ | H | $OCH_3$ | $OCH_3$ | |
| Q-44 | ($R_6$ = H) | H | $CH_3$ | H | $CH_3$ | $OCH_3$ | |
| Q-7 | ($R_8$ = $CH_3$) | H | $CH_3$ | $CH_3$ | $OCH_3$ | $CH_2OCH_3$ | |
| Q-7 | ($R_8$ = $CH_3$) | H | $CH_3$ | $CH_3$ | $OCH_3$ | $OCH_2CF_3$ | |
| Q-7 | ($R_8$ = $CH_3$) | H | $CH_3$ | $CH_3$ | $OC_2H_5$ | $NHCH_3$ | |
| Q-7 | ($R_8$ = $CH_3$) | H | $CH_3$ | $CH_3$ | $OCH_2CF_3$ | $NHCH_3$ | |
| Q-1 | ($R_6$, $R_7$ = H) | H | $CH_3$ | $CH_3$ | $CH_3$ | $OCH_2C\equiv CH_3$ | |
| Q-7 | ($R_8$ = $CH_3$) | H | $CH_3$ | $CH_3$ | $OCH_3$ | $N(CH_3)_2$ | |
| Q-7 | ($R_8$ = $CH_3$) | H | $CH_3$ | $CH_3$ | $CH_3$ | $CH_2OCH_3$ | |
| Q-34 | ($R_6$ = H, $R_{10}$, $R_{11}$ = $CH_3$) | H | $CH_3$ | H | $CH_3$ | $OCH_2CH_2OCH_3$ | |
| Q-34 | ($R_6$ = H, $R_{10}$, $R_{11}$ = $OCH_3$) | $CH_3$ | H | $CH_3$ | $OCH_2CF_3$ | | |
| Q-14 | ($R_6$, $R_7$ = H) | H | $CH_3$ | H | $OCH_3$ | cyclopropyl | |
| Q-14 | ($R_6$, $R_7$ = H) | H | $CH_3$ | H | $OCH_3$ | $C(CH_3)(OCH_3)_2$ | |

TABLE V-continued

General Formula V

| Q | | R | $R_1$ | $R_2$ | X | Y | m.p. °C. |
|---|---|---|---|---|---|---|---|
| Q-1 | ($R_6$, $R_7$ = H) | H | $CH_3$ | H | $OCH_3$ | $OCH_2CF_3$ | |
| Q-15 | ($R_6$ = H, $R_7$ = $CH_3$) | H | $CH_3$ | H | $OCH_3$ | $OCH_2CH=CH_2$ | |
| Q-15 | ($R_6$ = H, $R_7$ = $CH_3$) | H | $CH_3$ | H | $OCH_3$ | $SCH_3$ | |
| Q-43 | ($R_6$ = $CH_3$) | H | $CH_3$ | H | $OCH_3$ | $N(CH_3)_2$ | |
| Q-43 | ($R_6$ = $CH_3$) | H | $CH_3$ | H | $OCH_3$ | $C_2H_5$ | |
| Q-43 | ($R_6$ = $CH_3$) | H | $CH_3$ | H | $OCH_3$ | isopropyl | |
| Q-7 | ($R_8$ = $SCH_3$) | H | $CH_3$ | $CH_3$ | $OCH_3$ | $OCH_3$ | 202–203 |
| Q-7 | (R = $SCH_2CH_3$) | H | $CH_3$ | $CH_3$ | $OCH_3$ | $CH_3$ | |
| Q-7 | (R = $SCH_2CH_3$) | H | $CH_3$ | $CH_3$ | $OCH_3$ | $OCH_3$ | |
| Q-7 | (R = $SCH_2CH_3$) | H | $CH_3$ | $CH_3$ | $CH_3$ | $CH_3$ | |
| Q-7 | ($R_8$ = $SCH_2CO_2CH_3$) | H | $CH_3$ | $CH_3$ | $OCH_3$ | $OCH_3$ | |
| Q-7 | ($R_8$ = $SCH_2CO_2CH_3$) | H | $CH_3$ | $CH_3$ | $CH_3$ | $OCH_3$ | |
| Q-7 | ($R_8$ = $SCH_2CO_2CH_3$) | H | $CH_3$ | $CH_3$ | $CH_3$ | $CH_3$ | |
| Q-7 | ($R_8$ = $SCH_2$—CH=$CH_2$) | H | $CH_3$ | $CH_3$ | $CH_3$ | $OCH_3$ | 188–189 |
| Q-7 | ($R_8$ = $SCH_2$—CH=$CH_2$) | H | $CH_3$ | $CH_3$ | $OCH_3$ | $OCH_3$ | 167–168 |
| Q-7 | ($R_8$ = $SCH_2$—CH=$CH_2$) | H | $CH_3$ | $CH_3$ | $CH_3$ | $CH_3$ | |
| Q-7 | ($R_8$ = $SCH_3$) | H | $CH_3$ | $CH_3$ | $CH_3$ | $CH_3$ | |
| Q-7 | ($R_8$ = $SCH_3$) | H | $CH_3$ | $CH_3$ | $OCH_3$ | i—$C_3H_7$ | |
| Q-7 | ($R_8$ = $SCH_3$) | H | $CH_3$ | $CH_3$ | $CH_3$ | i—$C_3H_7$ | |
| Q-45 | ($R_7$ = H) | H | $CH_3$ | H | $OCH_3$ | $OCH_3$ | |
| Q-45 | ($R_7$ = H) | H | $C_6H_5$ | H | $CH_3$ | $OCH_3$ | |
| Q-46 | ($R_7$ = H) | H | $CH_3$ | H | $OCH_3$ | $OCH_3$ | |
| Q-46 | ($R_7$ = H) | H | $CH_3$ | $CH_3$ | $CH_3$ | $OCH_3$ | |
| Q-47 | ($R_7$ = H) | H | $CH_3$ | H | $OCH_3$ | $OCH_3$ | |
| Q-48 | ($R_7$ = H) | H | $C_6H_5$ | H | $OCH_3$ | $OCH_3$ | |
| Q-48 | ($R_7$ = H) | H | $CH_3$ | H | $CH_3$ | $OCH_3$ | |

TABLE VI

General Formula VI

| Q | | R | $R_1$ | $R_2$ | X | Y | m.p. °C. |
|---|---|---|---|---|---|---|---|
| Q-1 | ($R_6$, $R_7$ = H) | H | $CH_3$ | H | $OCH_3$ | $OCH_3$ | |
| Q-1 | ($R_6$, $R_7$ = H) | H | $CH_3$ | H | $OCH_3$ | $CH_3$ | |
| Q-1 | ($R_6$, $R_7$ = H) | H | $CH_3$ | $CH_3$ | $OCH_3$ | $CH_3$ | |
| Q-1 | ($R_6$, $R_7$ = H) | H | $C_3H_7$ | H | $OCH_3$ | $CH_3$ | |
| Q-1 | ($R_6$, $R_7$ = H) | H | $C_6H_5$ | H | $OCH_3$ | $OCH_3$ | |
| Q-1 | ($R_6$, $R_7$ = $CH_3$) | H | $CH_3$ | H | $OCH_3$ | $OCH_3$ | |
| Q-2 | ($R_6$, $R_7$ = H) | H | $CH_3$ | H | $OCH_3$ | $OCH_3$ | |
| Q-2 | ($R_6$, $R_7$ = H) | H | $CH_3$ | H | $CH_3$ | $OCH_3$ | |
| Q-2 | ($R_6$, $R_7$ = H) | H | $CH_3$ | $CH_3$ | $OCH_3$ | $OCH_3$ | |
| Q-2 | ($R_6$, $R_7$ = H) | H | $C_3H_7$ | H | $OCH_3$ | $OCH_3$ | |
| Q-2 | ($R_6$ = $CH_3$, $R_7$ = H) | H | $CH_3$ | H | $OCH_3$ | $OCH_3$ | |
| Q-2 | ($R_6$ = H, $R_7$ = $CH_3$) | H | $CH_3$ | H | $OCH_3$ | $CH_3$ | |
| Q-2 | ($R_6$, $R_7$ = H) | H | $C_6H_5$ | H | $OCH_3$ | $OCH_3$ | |
| Q-3 | ($R_6$, $R_7$ = H) | H | $CH_3$ | H | $OCH_3$ | $CH_3$ | |
| Q-3 | ($R_6$, $R_7$ = H) | H | $CH_3$ | H | $OCH_3$ | $OCH_3$ | |
| Q-3 | ($R_6$, $R_7$ = H) | H | $CH_3$ | $CH_3$ | $OCH_3$ | $OCH_3$ | |
| Q-3 | ($R_6$, $R_7$ = H) | H | $C_3H_7$ | H | $CH_3$ | $OCH_3$ | |
| Q-4 | ($R_6$, $R_7$ = H) | H | $CH_3$ | H | $OCH_3$ | $CH_3$ | |
| Q-4 | ($R_6$, $R_7$ = H) | H | $CH_3$ | H | $OCH_3$ | $OCH_3$ | |
| Q-4 | ($R_6$, $R_7$ = H) | H | $CH_3$ | $CH_3$ | $CH_3$ | $OCH_3$ | |
| Q-5 | ($R_6$, $R_7$ = H) | H | $CH_3$ | H | $CH_3$ | $OCH_3$ | |
| Q-5 | ($R_6$, $R_7$ = H) | H | $CH_3$ | H | $OCH_3$ | $OCH_3$ | |
| Q-6 | ($R_6$, $R_7$ = H) | H | $CH_3$ | H | $CH_3$ | $OCH_3$ | |
| Q-6 | ($R_6$, $R_7$ = H) | H | $CH_3$ | H | $OCH_3$ | $OCH_3$ | |
| Q-7 | ($R_8$ = H) | H | $CH_3$ | H | $OCH_3$ | $CH_3$ | |
| Q-7 | ($R_8$ = H) | H | $CH_3$ | H | $OCH_3$ | $OCH_3$ | |
| Q-7 | ($R_8$ = H) | H | $CH_3$ | $CH_3$ | $OCH_3$ | $OCH_3$ | |
| Q-7 | ($R_8$ = H) | H | $C_3H_7$ | H | $CH_3$ | $OCH_3$ | |
| Q-7 | ($R_8$ = H) | H | $C_6H_5$ | H | $CH_3$ | $OCH_3$ | |
| Q-7 | ($R_8$ = $CH_3$) | H | $CH_3$ | H | $OCH_3$ | $OCH_3$ | |
| Q-7 | ($R_8$ = $SCH_3$) | H | $CH_3$ | $CH_3$ | $OCH_3$ | $OCH_3$ | 186–188 |
| Q-7 | ($R_8$ = $CH_3$) | H | $CH_3$ | H | $CH_3$ | $OCH_3$ | |
| Q-7 | ($R_8$ = $CH_3$) | H | $CH_3$ | $CH_3$ | $OCH_3$ | $OCH_3$ | |
| Q-7 | ($R_8$ = $CH_3$) | H | $C_3H_7$ | H | $OCH_3$ | $CH_3$ | |
| Q-7 | ($R_8$ = $CH_3$) | H | $C_6H_5$ | H | $OCH_3$ | $CH_3$ | |
| Q-7 | ($R_8$ = $SCH_3$) | H | $CH_3$ | H | $OCH_3$ | $OCH_3$ | |
| Q-7 | ($R_8$ = $SCH_3$) | H | $CH_3$ | H | $OCH_3$ | $CH_3$ | |
| Q-7 | ($R_8$ = $SCH_3$) | H | $CH_3$ | $CH_3$ | $OCH_3$ | $CH_3$ | 182.5–184 |
| Q-7 | ($R_8$ = $SCH_3$) | H | $C_3H_7$ | H | $OCH_3$ | $CH_3$ | |
| Q-7 | ($R_8$ = $OCH_3$) | H | $CH_3$ | H | $OCH_3$ | $OCH_3$ | |
| Q-7 | ($R_8$ = $OCH_3$) | H | $CH_3$ | H | $OCH_3$ | $CH_3$ | |
| Q-7 | ($R_8$ = $OCH_3$) | H | $CH_3$ | $CH_3$ | $OCH_3$ | $CH_3$ | |
| Q-7 | ($R_8$ = $OCH_3$) | H | $C_3H_7$ | H | $OCH_3$ | $CH_3$ | |
| Q-8 | ($R_6$ = H) | H | $CH_3$ | H | $OCH_3$ | $CH_3$ | |
| Q-8 | ($R_6$ = H) | H | $CH_3$ | H | $OCH_3$ | $OCH_3$ | |
| Q-8 | ($R_6$ = H) | H | $CH_3$ | $CH_3$ | $OCH_3$ | $CH_3$ | |
| Q-8 | ($R_6$ = $CH_3$) | H | $CH_3$ | $CH_3$ | $OCH_3$ | $CH_3$ | |

TABLE VI-continued

| | | General Formula VI | | | | | |
|---|---|---|---|---|---|---|---|
| Q | | R | $R_1$ | $R_2$ | X | Y | m.p. °C. |
| Q-8 | ($R_6$ = $CH_3$) | H | $CH_3$ | H | $OCH_3$ | $OCH_3$ | |
| Q-8 | ($R_6$ = $CH_3$) | H | $CH_3$ | H | $CH_3$ | $OCH_3$ | |
| Q-9 | ($R_6$ = $CH_3$) | H | $CH_3$ | H | $OCH_3$ | $OCH_3$ | |
| Q-9 | ($R_6$ = $CH_3$) | H | $CH_3$ | H | $CH_3$ | $OCH_3$ | |
| Q-9 | ($R_6$ = $CH_3$) | H | $CH_3$ | $CH_3$ | $OCH_3$ | $OCH_3$ | |
| Q-10 | ($R_6$ = H) | H | $CH_3$ | H | $OCH_3$ | $CH_3$ | |
| Q-10 | ($R_6$ = H) | H | $CH_3$ | H | $OCH_3$ | $OCH_3$ | |
| Q-10 | ($R_6$ = $CH_3$) | H | $CH_3$ | H | $OCH_3$ | $OCH_3$ | |
| Q-10 | ($R_6$ = $CH_3$) | H | $CH_3$ | H | $CH_3$ | $OCH_3$ | |
| Q-11 | ($R_6$ = $CH_3$) | H | $CH_3$ | H | $OCH_3$ | $OCH_3$ | |
| Q-11 | ($R_6$ = $CH_3$) | H | $CH_3$ | H | $CH_3$ | $OCH_3$ | |
| Q-11 | ($R_6$ = $CH_3$) | H | $CH_3$ | $CH_3$ | $OCH_3$ | $OCH_3$ | |
| Q-12 | ($R_6$ = $CH_3$) | H | $CH_3$ | H | $OCH_3$ | $OCH_3$ | |
| Q-12 | ($R_6$ = $CH_3$) | H | $CH_3$ | H | $OCH_3$ | $CH_3$ | |
| Q-13 | ($R_6$ = $CH_3$) | H | $CH_3$ | H | $OCH_3$ | $OCH_3$ | |
| Q-13 | ($R_6$ = $CH_3$) | H | $CH_3$ | H | $OCH_3$ | $CH_3$ | |
| Q-14 | ($R_6$, $R_7$ = H) | H | $CH_3$ | H | $OCH_3$ | $OCH_3$ | |
| Q-14 | ($R_6$, $R_7$ = H) | H | $CH_3$ | H | $OCH_3$ | $CH_3$ | |
| Q-14 | ($R_6$, $R_7$ = H) | H | $CH_3$ | $CH_3$ | $OCH_3$ | $OCH_3$ | |
| Q-14 | ($R_6$, $R_7$ = H) | H | $CH_3$ | Cl | $CH_3$ | $OCH_3$ | |
| Q-15 | ($R_6$ = H, $R_7$ = $CH_3$) | H | $CH_3$ | H | $OCH_3$ | $OCH_3$ | |
| Q-15 | ($R_6$ = H, $R_7$ = $CH_3$) | H | $CH_3$ | H | $CH_3$ | $CH_3$ | |
| Q-16 | ($R_6$ = $CH_3$, $R_7$ = H) | H | $CH_3$ | H | $OCH_3$ | $OCH_3$ | |
| Q-16 | ($R_6$ = $CH_3$, $R_7$ = H) | H | $CH_3$ | H | $CH_3$ | $OCH_3$ | |
| Q-16 | ($R_6$ = $CH_3$, $R_7$ = H) | H | $CH_3$ | $CH_3$ | $OCH_3$ | $OCH_3$ | |
| Q-17 | ($R_6$, $R_7$ = H) | H | $CH_3$ | H | $OCH_3$ | $OCH_3$ | 190–192 |
| Q-17 | ($R_6$, $R_7$ = H) | H | $CH_3$ | H | $CH_3$ | $OCH_3$ | 193–195 |
| Q-18 | ($R_6$ = $CH_3$, $R_7$ = $CH_3$) | H | $CH_3$ | H | $CH_3$ | $OCH_3$ | 161–165 |
| Q-18 | ($R_6$ = $CH_3$, $R_7$ = $CH_3$) | H | $CH_3$ | H | $OCH_3$ | $OCH_3$ | 181–187 |
| Q-19 | ($R_6$ = H, $R_7$ = $CH_3$) | H | $CH_3$ | H | $OCH_3$ | $CH_3$ | |
| Q-19 | ($R_6$ = H, $R_7$ = $CH_3$) | H | $CH_3$ | $CH_3$ | $CH_3$ | $OCH_3$ | |
| Q-20 | ($R_6$, $R_7$ = $CH_3$) | H | $CH_3$ | H | $OCH_3$ | $CH_3$ | |
| Q-20 | ($R_6$, $R_7$ = $CH_3$) | H | $CH_3$ | H | $OCH_3$ | $OCH_3$ | |
| Q-20 | ($R_6$, $R_7$ = $CH_3$) | H | $C_3H_7$ | H | $OCH_3$ | $CH_3$ | |
| Q-21 | ($R_6$, $R_7$, $R_9$ = H) | H | $CH_3$ | H | $OCH_3$ | $OCH_3$ | |
| Q-21 | ($R_6$, $R_7$, $R_9$ = H) | H | $CH_3$ | H | $CH_3$ | $OCH_3$ | |
| Q-21 | ($R_6$, $R_7$, $R_9$ = H) | H | $CH_3$ | $CH_3$ | $OCH_3$ | $OCH_3$ | |
| Q-22 | ($R_6$, $R_7$, $R_9$ = H) | H | $CH_3$ | H | $OCH_3$ | $OCH_3$ | |
| Q-22 | ($R_6$, $R_7$, $R_9$ = H) | H | $CH_3$ | H | $CH_3$ | $OCH_3$ | |
| Q-23 | ($R_6$, $R_7$, $R_9$ = H) | H | $CH_3$ | H | $CH_3$ | $OCH_3$ | |
| Q-23 | ($R_6$, $R_7$, $R_9$ = H) | H | $CH_3$ | H | $OCH_3$ | $OCH_3$ | |
| Q-24 | ($R_6$, $R_7$, $R_9$ = H) | H | $CH_3$ | H | $OCH_3$ | $OCH_3$ | |
| Q-24 | ($R_6$, $R_7$, $R_9$ = H) | H | $CH_3$ | H | $CH_3$ | $OCH_3$ | |
| Q-25 | ($R_6$, $R_7$, $R_9$ = H) | H | $CH_3$ | H | $OCH_3$ | $OCH_3$ | |
| Q-25 | ($R_6$, $R_7$, $R_9$ = H) | H | $CH_3$ | H | $OCH_3$ | $CH_3$ | |
| Q-25 | ($R_6$, $R_7$, $R_9$ = H) | H | $C_3H_7$ | H | $CH_3$ | $OCH_3$ | |
| Q-26 | ($R_6$, $R_7$, $R_9$ = H) | H | $CH_3$ | H | $CH_3$ | $OCH_3$ | |
| Q-27 | ($R_6$, $R_7$, $R_9$ = H) | H | $CH_3$ | H | $CH_3$ | $OCH_3$ | |
| Q-28 | ($R_6$, $R_7$, $R_9$ = H) | H | $CH_3$ | H | $CH_3$ | $OCH_3$ | |
| Q-29 | ($R_6$, $R_7$, $R_9$ = H) | H | $CH_3$ | H | $OCH_3$ | $OCH_3$ | |
| Q-29 | ($R_6$, $R_7$, $R_9$ = H) | H | $CH_3$ | $CH_3$ | $CH_3$ | $OCH_3$ | |
| Q-31 | ($R_6$, $R_7$ = H) | H | $CH_3$ | H | $OCH_3$ | $CH_3$ | 183–186 |
| Q-31 | ($R_6$, $R_7$ = H) | H | $CH_3$ | H | $OCH_3$ | $OCH_3$ | 167–171 |
| Q-32 | ($R_6$, $R_7$ = H) | H | $CH_3$ | H | $OCH_3$ | $OCH_3$ | 130–134 |
| Q-32 | ($R_6$, $R_7$ = H) | H | $CH_3$ | H | $CH_3$ | $OCH_3$ | 183–186 |
| Q-32 | ($R_6$, $R_7$ = H) | H | $CH_3$ | H | $CH_3$ | $CH_3$ | 186–191 |
| Q-33 | ($R_6$, $R_7$ = H) | H | $CH_3$ | H | $OCH_3$ | $OCH_3$ | 145–150 |
| Q-33 | ($R_6$, $R_7$ = H) | H | $CH_3$ | H | $OCH_3$ | $OCH_3$ | 191–196 |
| Q-33 | ($R_6$, $R_7$ = H) | H | $CH_3$ | H | $CH_3$ | $CH_3$ | 200–201 |
| Q-34 | ($R_6$, $R_{10}$, $R_{11}$ = H) | H | $CH_3$ | H | $OCH_3$ | $CH_3$ | |
| Q-34 | ($R_6$, $R_{10}$, $R_{11}$ = H) | H | $CH_3$ | H | $OCH_3$ | $OCH_3$ | |
| Q-34 | ($R_6$ = H, $R_{10}$, $R_{11}$ = $CH_3$) | H | $CH_3$ | H | $OCH_3$ | $CH_3$ | |
| Q-34 | ($R_6$ = H, $R_{10}$, $R_{11}$ = $OCH_3$) | H | $CH_3$ | H | $OCH_3$ | $CH_3$ | |
| Q-34 | ($R_6$ = H, $R_{10}$, $R_{11}$ = $OCH_3$) | H | $CH_3$ | H | $OCH_3$ | $OCH_3$ | |
| Q-34 | ($R_6$ = H, $R_{10}$, $R_{11}$ = $OCH_3$) | H | $CH_3$ | $CH_3$ | $OCH_3$ | $CH_3$ | |
| Q-35 | ($R_{10}$, $R_{11}$ = H) | H | $CH_3$ | H | $OCH_3$ | $CH_3$ | |
| Q-35 | ($R_{10}$, $R_{11}$ = H) | H | $CH_3$ | $CH_3$ | $OCH_3$ | $OCH_3$ | |
| Q-36 | ($R_{10}$, $R_{11}$ = H) | H | $CH_3$ | H | $OCH_3$ | $CH_3$ | |
| Q-36 | ($R_{10}$, $R_{11}$ = H) | H | $CH_3$ | H | $OCH_3$ | $OCH_3$ | |
| Q-37 | ($R_6$, $R_7$ = H) | H | $CH_3$ | H | $OCH_3$ | $CH_3$ | |
| Q-37 | ($R_6$, $R_7$ = H) | H | $CH_3$ | H | $OCH_3$ | $OCH_3$ | |
| Q-38 | ($R_6$, $R_7$ = H) | H | $CH_3$ | H | $OCH_3$ | $CH_3$ | |
| Q-38 | ($R_6$, $R_7$ = H) | H | $CH_3$ | H | $OCH_3$ | $OCH_3$ | |
| Q-39 | ($R_{12}$, $R_{13}$ = $CH_3$) | H | $CH_3$ | H | $OCH_3$ | $CH_3$ | |
| Q-39 | ($R_{12}$, $R_{13}$ = $OCH_3$) | H | $CH_3$ | H | $OCH_3$ | $CH_3$ | |
| Q-39 | ($R_{12}$ = $CH_3$, $R_{13}$ = $OCH_3$) | H | $CH_3$ | H | $OCH_3$ | $CH_3$ | |
| Q-40 | ($R_{12}$, $R_{13}$ = $CH_3$) | H | $CH_3$ | H | $OCH_3$ | $CH_3$ | |
| Q-40 | ($R_{12}$, $R_{13}$ = $OCH_3$) | H | $CH_3$ | H | $OCH_3$ | $CH_3$ | |
| Q-41 | ($R_6$ = H) | H | $CH_3$ | H | $OCH_3$ | $OCH_3$ | |
| Q-41 | ($R_6$ = H) | H | $CH_3$ | H | $CH_3$ | $OCH_3$ | |

TABLE VI-continued

General Formula VI

| Q | | R | $R_1$ | $R_2$ | X | Y | m.p. °C. |
|---|---|---|---|---|---|---|---|
| Q-42 | ($R_6$ = H) | H | $CH_3$ | H | $CH_3$ | $OCH_3$ | |
| Q-42 | ($R_6$ = H) | H | $CH_3$ | H | $OCH_3$ | $OCH_3$ | |
| Q-43 | ($R_6$ = H) | H | $CH_3$ | H | $OCH_3$ | $CH_3$ | |
| Q-43 | ($R_6$ = H) | H | $CH_3$ | H | $OCH_3$ | $OCH_3$ | |
| Q-43 | ($R_6$ = $CH_3$) | H | $CH_3$ | H | $OCH_3$ | $CH_3$ | |
| Q-44 | ($R_6$ = H) | H | $CH_3$ | H | $OCH_3$ | $OCH_3$ | |
| Q-44 | ($R_6$ = H) | H | $CH_3$ | H | $CH_3$ | $OCH_3$ | |
| Q-7 | ($R_8$ = $CH_3$) | H | $CH_3$ | $CH_3$ | $OCH_3$ | $CH_2OCH_3$ | |
| Q-7 | ($R_8$ = $CH_3$) | H | $CH_3$ | $CH_3$ | $OCH_3$ | $OCH_2CF_3$ | |
| Q-7 | ($R_8$ = $CH_3$) | H | $CH_3$ | $CH_3$ | $OC_2H_5$ | $NHCH_3$ | |
| Q-7 | ($R_8$ = $CH_3$) | H | $CH_3$ | $CH_3$ | $OCH_2CF_3$ | $NHCH_3$ | |
| Q-1 | ($R_6$, $R_7$ = H) | H | $CH_3$ | $CH_3$ | $CH_3$ | $OCH_2C\equiv CH$ | |
| Q-7 | ($R_8$ = $CH_3$) | H | $CH_3$ | $CH_3$ | $OCH_3$ | $N(CH_3)_2$ | |
| Q-7 | ($R_8$ = $CH_3$) | H | $CH_3$ | $CH_3$ | $CH_3$ | $CH_2OCH_3$ | |
| Q-34 | ($R_6$ = H, $R_{10}$, $R_{11}$ = $CH_3$) | H | $CH_3$ | H | $CH_3$ | $OCH_2CH_2OCH_3$ | |
| Q-34 | ($R_6$ = H, $R_{10}$, $R_{11}$ = $OCH_3$) | H | $CH_3$ | H | $CH_3$ | $OCH_2CF_3$ | |
| Q-14 | ($R_6$, $R_7$ = H) | H | $CH_3$ | H | $OCH_3$ | cyclopropyl | |
| Q-14 | ($R_6$, $R_7$ = H) | H | $CH_3$ | H | $OCH_3$ | $C(CH_3)(OCH_3)_2$ | |
| Q-1 | ($R_6$, $R_7$ = H) | H | $CH_3$ | H | $OCH_3$ | $OCH_2CF_3$ | |
| Q-15 | ($R_6$ = H, $R_7$ = $CH_3$) | H | $CH_3$ | H | $OCH_3$ | $OCH_2CH=CH_2$ | |
| Q-15 | ($R_6$ = H, $R_7$ = $CH_3$) | H | $CH_3$ | H | $OCH_3$ | $SCH_3$ | |
| Q-43 | ($R_6$ = $CH_3$) | H | $CH_3$ | H | $OCH_3$ | $N(CH_3)_2$ | |
| Q-43 | ($R_6$ = $CH_3$) | H | $CH_3$ | H | $OCH_3$ | $C_2H_5$ | |
| Q-43 | ($R_6$ = $CH_3$) | H | $CH_3$ | H | $OCH_3$ | isopropyl | |
| Q-7 | (R = $SCH_2CH_3$) | H | $CH_3$ | $CH_3$ | $OCH_3$ | $CH_3$ | |
| Q-7 | (R = $SCH_2CH_3$) | H | $CH_3$ | $CH_3$ | $OCH_3$ | $OCH_3$ | |
| Q-7 | (R = $SCH_2CH_3$) | H | $CH_3$ | $CH_3$ | $CH_3$ | $CH_3$ | |
| Q-7 | ($R_8$ = $SCH_2CO_2CH_3$) | H | $CH_3$ | $CH_3$ | $OCH_3$ | $OCH_3$ | 162–164 |
| Q-7 | ($R_8$ = $SCH_2CO_2CH_3$) | H | $CH_3$ | $CH_3$ | $OCH_3$ | $CH_3$ | 176–177 |
| Q-7 | ($R_8$ = $SCH_2CO_2CH_3$) | H | $CH_3$ | $CH_3$ | $CH_3$ | $CH_3$ | |
| Q-7 | ($R_8$ = $SCH_2-CH=CH_2$) | H | $CH_3$ | $CH_3$ | $CH_3$ | $OCH_3$ | 161–163 |
| Q-7 | ($R_8$ = $SCH_2-CH=CH_2$) | H | $CH_3$ | $CH_3$ | $OCH_3$ | $OCH_3$ | 153–155 |
| Q-7 | ($R_8$ = $SCH_2-CH=CH_2$) | H | $CH_3$ | $CH_3$ | $CH_3$ | $CH_3$ | 180–182 |
| Q-7 | ($R_8$ = $SCH_3$) | H | $CH_3$ | $CH_3$ | $CH_3$ | $CH_3$ | 179–180 |
| Q-7 | ($R_8$ = $SCH_3$) | H | $CH_3$ | $CH_3$ | $OCH_3$ | i-$C_3H_7$ | |
| Q-7 | ($R_8$ = $SCH_3$) | H | $CH_3$ | $CH_3$ | $CH_3$ | i-$C_3H_7$ | |
| Q-7 | ($R_8$ = $SCH_2COCH_3$) | H | $CH_3$ | $CH_3$ | $CH_3$ | $CH_3$ | |
| Q-7 | ($R_8$ = $SCH_2COCH_3$) | H | $CH_3$ | $CH_3$ | $CH_3$ | $OCH_3$ | 209–210 |
| Q-7 | ($R_8$ = $SCH_2COCH_3$) | H | $CH_3$ | $CH_3$ | $OCH_3$ | $OCH_3$ | 203–204 |
| Q-7 | ($R_8$ = S—CH($CH_3$)$_2$) | H | $CH_3$ | $CH_3$ | $CH_3$ | $CH_3$ | |
| Q-7 | ($R_8$ = S—CH($CH_3$)$_2$) | H | $CH_3$ | $CH_3$ | $CH_3$ | $OCH_3$ | 164–166 |
| Q-7 | ($R_8$ = S—CH($CH_3$)$_2$) | H | $CH_3$ | $CH_3$ | $OCH_3$ | $OCH_3$ | 150–152 |
| Q-7 | ($R_8$ = S—$CH_2$—$\underset{\underset{Cl}{\mid}}{C}$=$CH_2$) | H | $CH_3$ | $CH_3$ | $CH_3$ | $CH_3$ | |
| Q-7 | ($R_8$ = S—$CH_2$—$\underset{\underset{Cl}{\mid}}{C}$=$CH_2$) | H | $CH_3$ | $CH_3$ | $OCH_3$ | $CH_3$ | 193–194 |
| Q-7 | ($R_8$ = S—$CH_2$—$\underset{\underset{Cl}{\mid}}{C}$=$CH_2$) | H | $CH_3$ | $CH_3$ | $OCH_3$ | $OCH_3$ | 176–179 |
| Q-7 | ($R_8$ = $SCH_2CN$) | H | $CH_3$ | $CH_3$ | $CH_3$ | $CH_3$ | |
| Q-7 | ($R_8$ = $SCH_2CN$) | H | $CH_3$ | $CH_3$ | $CH_3$ | $OCH_3$ | 209–210 |
| Q-7 | ($R_8$ = $SCH_2CN$) | H | $CH_3$ | $CH_3$ | $OCH_3$ | $OCH_3$ | 180–182 |
| Q-7 | ($R_8$ = $SC_6H_{13}$) | H | $CH_3$ | $CH_3$ | $CH_3$ | $CH_3$ | |
| Q-7 | ($R_8$ = $SC_6H_{13}$) | H | $CH_3$ | $CH_3$ | $CH_3$ | $OCH_3$ | 108–110 |
| Q-7 | ($R_8$ = $SC_6H_{13}$) | H | $CH_3$ | $CH_3$ | $OCH_3$ | $OCH_3$ | 107–109 |
| Q-7 | ($R_8$ = SH) | H | $CH_3$ | $CH_3$ | $CH_3$ | $CH_3$ | |
| Q-7 | ($R_8$ = SH) | H | $CH_3$ | $CH_3$ | $CH_3$ | $OCH_3$ | |
| Q-7 | ($R_8$ = SH) | H | $CH_3$ | $CH_3$ | $OCH_3$ | $OCH_3$ | |
| Q-32 | ($R_6$ = $R_7$ = H) | H | $CH_3$ | $CH_3$ | $CH_3$ | $OCH_3$ | 170–172 |
| Q-32 | ($R_6$ = $R_7$ = H) | H | $CH_3$ | $CH_3$ | $OCH_3$ | $OCH_3$ | 198–200 |
| Q-33 | ($R_6$ = $R_7$ = H) | H | $CH_3$ | $CH_3$ | $OCH_3$ | $OCH_3$ | 163–165 |
| Q-45 | ($R_7$ = H) | H | $CH_3$ | H | $OCH_3$ | $OCH_3$ | |
| Q-45 | ($R_7$ = H) | H | $C_6H_5$ | H | $CH_3$ | $OCH_3$ | |
| Q-46 | ($R_7$ = H) | H | $CH_3$ | H | $OCH_3$ | $OCH_3$ | |
| Q-46 | ($R_7$ = H) | H | $CH_3$ | H | $CH_3$ | $OCH_3$ | |
| Q-47 | ($R_7$ = H) | H | $CH_3$ | H | $OCH_3$ | $OCH_3$ | |
| Q-48 | ($R_7$ = H) | H | $C_6H_5$ | H | $OCH_3$ | $OCH_3$ | |
| Q-48 | ($R_7$ = H) | H | $CH_3$ | H | $CH_3$ | $OCH_3$ | |
| Q-45 | ($R_7$ = H) | H | $CH_3$ | $CH_3$ | $CH_3$ | $OCH_3$ | 194–196 |
| Q-45 | ($R_7$ = H) | H | $CH_3$ | $CH_3$ | $OCH_3$ | $OCH_3$ | 189–191 |
| Q-46 | ($R_7$ = H) | H | $CH_3$ | $CH_3$ | $CH_3$ | $OCH_3$ | 176–181 |
| Q-46 | ($R_7$ = H) | H | $CH_3$ | $CH_3$ | $OCH_3$ | $OCH_3$ | 186–188 |
| Q-47 | ($R_7$ = H) | H | $CH_3$ | $CH_3$ | $OCH_3$ | $OCH_3$ | 203–205 |
| Q-48 | ($R_7$ = H) | H | $CH_3$ | $CH_3$ | $CH_3$ | $OCH_3$ | 196–198 |

TABLE VI-continued

| Q | | General Formula VI | | | | | m.p. °C. |
|---|---|---|---|---|---|---|---|
| | | R | $R_1$ | $R_2$ | X | Y | |
| Q-48 | ($R_7$ = H) | H | $CH_3$ | $CH_3$ | $OCH_3$ | $OCH_3$ | 226–228 |
| Q-15 | ($R_6, R_7$ = H) | H | $CH_3$ | H | $CH_3$ | $OCH_3$ | 178–180 |
| Q-15 | ($R_6, R_7$ = H) | H[a] | $CH_3$ | H | $OCH_3$ | $OCH_3$ | 192–194 |

TABLE VII

General Formula VII

| Q | | R | $R_1$ | $R_2$ | X | Y | m.p. °C. |
|---|---|---|---|---|---|---|---|
| Q-1 | ($R_6, R_7$ = H) | H | $CH_3$ | H | $OCH_3$ | $OCH_3$ | |
| Q-1 | ($R_6, R_7$ = H) | H | $CH_3$ | H | $OCH_3$ | $CH_3$ | |
| Q-1 | ($R_6, R_7$ = H) | H | $CH_3$ | $CH_3$ | $OCH_3$ | $CH_3$ | |
| Q-1 | ($R_6, R_7$ = H) | H | $C_3H_7$ | H | $OCH_3$ | $CH_3$ | |
| Q-1 | ($R_6, R_7$ = H) | H | $C_6H_5$ | H | $OCH_3$ | $OCH_3$ | |
| Q-1 | ($R_6, R_7$ = $CH_3$) | H | $CH_3$ | H | $OCH_3$ | $OCH_3$ | |
| Q-2 | ($R_6, R_7$ = H) | H | $CH_3$ | H | $OCH_3$ | $OCH_3$ | |
| Q-2 | ($R_6, R_7$ = H) | H | $CH_3$ | H | $CH_3$ | $OCH_3$ | |
| Q-2 | ($R_6, R_7$ = H) | H | $CH_3$ | $CH_3$ | $OCH_3$[b] | $OCH_3$ | |
| Q-2 | ($R_6, R_7$ = H) | H | $C_3H_7$ | H | $OCH_3$ | $OCH_3$ | |
| Q-2 | ($R_6$ = $CH_3$, $R_7$ = H) | H | $CH_3$ | H | $OCH_3$ | $OCH_3$ | |
| Q-2 | ($R_6$ = H, $R_7$ = $CH_3$) | H | $CH_3$ | H | $OCH_3$ | $CH_3$ | |
| Q-2 | ($R_6, R_7$ = H) | H | $C_6H_5$ | H | $OCH_3$ | $OCH_3$ | |
| Q-3 | ($R_6, R_7$ = H) | H | $CH_3$ | H | $OCH_3$ | $CH_3$ | |
| Q-3 | ($R_6, R_7$ = H) | H | $CH_3$ | H | $OCH_3$ | $OCH_3$ | |
| Q-3 | ($R_6, R_7$ = H) | H | $CH_3$ | $CH_3$ | $OCH_3$ | $OCH_3$ | |
| Q-3 | ($R_6, R_7$ = H) | H | $C_3H_7$ | H | $CH_3$ | $OCH_3$ | |
| Q-4 | ($R_6, R_7$ = H) | H | $CH_3$ | H | $OCH_3$ | $CH_3$ | |
| Q-4 | ($R_6, R_7$ = H) | H | $CH_3$ | H | $OCH_3$ | $OCH_3$ | |
| Q-4 | ($R_6, R_7$ = H) | H | $CH_3$ | $CH_3$ | $CH_3$ | $OCH_3$ | |
| Q-5 | ($R_6, R_7$ = H) | H | $CH_3$ | H | $CH_3$ | $OCH_3$ | |
| Q-5 | ($R_6, R_7$ = H) | H | $CH_3$ | H | $OCH_3$ | $OCH_3$ | |
| Q-6 | ($R_6, R_7$ = H) | H | $CH_3$ | H | $CH_3$ | $OCH_3$ | |
| Q-6 | ($R_6, R_7$ = H) | H | $CH_3$ | H | $OCH_3$ | $OCH_3$ | |
| Q-7 | ($R_8$ = H) | H | $CH_3$ | H | $OCH_3$ | $CH_3$ | |
| Q-7 | ($R_8$ = H) | H | $CH_3$ | H | $OCH_3$ | $OCH_3$ | |
| Q-7 | ($R_8$ = H) | H | $CH_3$ | $CH_3$ | $OCH_3$ | $OCH_3$ | |
| Q-7 | ($R_8$ = H) | H | $C_3H_7$ | H | $CH_3$ | $OCH_3$ | |
| Q-7 | ($R_8$ = H) | H | $C_6H_5$ | H | $CH_3$ | $OCH_3$ | |
| Q-7 | ($R_8$ = $CH_3$) | H | $CH_3$ | H | $OCH_3$ | $OCH_3$ | |
| Q-7 | ($R_8$ = $CH_3$) | H | $CH_3$ | H | $CH_3$ | $OCH_3$ | |
| Q-7 | ($R_8$ = $CH_3$) | H | $CH_3$ | $CH_3$ | $OCH_3$ | $OCH_3$ | |
| Q-7 | ($R_8$ = $CH_3$) | H | $C_3H_7$ | H | $OCH_3$ | $CH_3$ | |
| Q-7 | ($R_8$ = $CH_3$) | H | $C_6H_5$ | H | $OCH_3$ | $CH_3$ | |
| Q-7 | ($R_8$ = $SCH_3$) | H | $CH_3$ | H | $OCH_3$ | $OCH_3$ | |
| Q-7 | ($R_8$ = $SCH_3$) | H | $CH_3$ | H | $OCH_3$ | $CH_3$ | |
| Q-7 | ($R_8$ = $SCH_3$) | H | $CH_3$ | $CH_3$ | $OCH_3$ | $CH_3$ | 182–183.5 |
| Q-7 | ($R_8$ = $SCH_3$) | H | $C_3H_7$ | H | $OCH_3$ | $CH_3$ | |
| Q-7 | ($R_8$ = $OCH_3$) | H | $CH_3$ | H | $OCH_3$ | $OCH_3$ | |
| Q-7 | ($R_8$ = $OCH_3$) | H | $CH_3$ | H | $CH_3$ | $OCH_3$ | |
| Q-7 | ($R_8$ = $OCH_3$) | H | $CH_3$ | $CH_3$ | $OCH_3$ | $CH_3$ | |
| Q-7 | ($R_8$ = $OCH_3$) | H | $C_3H_7$ | H | $OCH_3$ | $CH_3$ | |
| Q-8 | ($R_6$ = H) | H | $CH_3$ | H | $OCH_3$ | $CH_3$ | |
| Q-8 | ($R_6$ = H) | H | $CH_3$ | H | $OCH_3$ | $OCH_3$ | |
| Q-8 | ($R_6$ = H) | H | $CH_3$ | $CH_3$ | $OCH_3$ | $CH_3$ | |
| Q-8 | ($R_6$ = $CH_3$) | H | $CH_3$ | $CH_3$ | $OCH_3$ | $CH_3$ | |
| Q-8 | ($R_6$ = $CH_3$) | H | $CH_3$ | H | $OCH_3$ | $OCH_3$ | |
| Q-8 | ($R_6$ = $CH_3$) | H | $CH_3$ | H | $CH_3$ | $OCH_3$ | |
| Q-8 | ($R_6$ = $CH_3$) | H | $CH_3$ | H | $OCH_3$ | $OCH_3$ | |
| Q-9 | ($R_6$ = $CH_3$) | H | $CH_3$ | H | $CH_3$ | $OCH_3$ | |
| Q-9 | ($R_6$ = $CH_3$) | H | $CH_3$ | $CH_3$ | $OCH_3$ | $OCH_3$ | |
| Q-10 | ($R_6$ = H) | H | $CH_3$ | H | $OCH_3$ | $CH_3$ | |
| Q-10 | ($R_6$ = H) | H | $CH_3$ | H | $OCH_3$ | $OCH_3$ | |
| Q-10 | ($R_6$ = $CH_3$) | H | $CH_3$ | H | $OCH_3$ | $OCH_3$ | |
| Q-10 | ($R_6$ = $CH_3$) | H | $CH_3$ | H | $CH_3$ | $OCH_3$ | |
| Q-11 | ($R_6$ = $CH_3$) | H | $CH_3$ | H | $OCH_3$ | $OCH_3$ | |
| Q-11 | ($R_6$ = $CH_3$) | H | $CH_3$ | H | $CH_3$ | $OCH_3$ | |
| Q-11 | ($R_6$ = $CH_3$) | H | $CH_3$ | $CH_3$ | $OCH_3$ | $OCH_3$ | |
| Q-12 | ($R_6$ = $CH_3$) | H | $CH_3$ | H | $OCH_3$ | $OCH_3$ | |
| Q-12 | ($R_6$ = $CH_3$) | H | $CH_3$ | H | $OCH_3$ | $CH_3$ | |
| Q-13 | ($R_6$ = $CH_3$) | H | $CH_3$ | H | $OCH_3$ | $OCH_3$ | |
| Q-13 | ($R_6$ = $CH_3$) | H | $CH_3$ | H | $OCH_3$ | $CH_3$ | |
| Q-14 | ($R_6, R_7$ = H) | H | $CH_3$ | H | $OCH_3$ | $OCH_3$ | |
| Q-14 | ($R_6, R_7$ = H) | H | $CH_3$ | H | $OCH_3$ | $CH_3$ | |
| Q-14 | ($R_6, R_7$ = H) | H | $CH_3$ | $CH_3$ | $OCH_3$ | $OCH_3$ | |
| Q-14 | ($R_6, R_7$ = H) | H | $CH_3$ | Cl | $CH_3$ | $OCH_3$ | |
| Q-15 | ($R_6$ = H, $R_7$ = $CH_3$) | H | $CH_3$ | H | $OCH_3$ | $OCH_3$ | |
| Q-15 | ($R_6$ = H, $R_7$ = $CH_3$) | H | $CH_3$ | H | $CH_3$ | $CH_3$ | |
| Q-16 | ($R_6$ = $CH_3$, $R_7$ = H) | H | $CH_3$ | H | $OCH_3$ | $OCH_3$ | |
| Q-16 | ($R_6$ = $CH_3$, $R_7$ = H) | H | $CH_3$ | H | $CH_3$ | $OCH_3$ | |

TABLE VII-continued

General Formula VII

| Q | | R | $R_1$ | $R_2$ | X | Y | m.p. °C. |
|---|---|---|---|---|---|---|---|
| Q-16 | ($R_6$ = $CH_3$, $R_7$ = H) | H | $CH_3$ | $CH_3$ | $OCH_3$ | $OCH_3$ | |
| Q-17 | ($R_6$, $R_7$ = $CH_3$) | H | $CH_3$ | H | $OCH_3$ | $OCH_3$ | |
| Q-17 | ($R_6$, $R_7$ = H) | H | $CH_3$ | H | $OCH_3$ | $OCH_3$ | 208–210 |
| Q-18 | ($R_6$ = H, $R_7$ = $CH_3$) | H | $CH_3$ | H | $CH_3$ | $OCH_3$ | |
| Q-18 | ($R_6$ = H, $R_7$ = $CH_3$) | H | $C_3H_7$ | H | $OCH_3$ | $CH_3$ | |
| Q-19 | ($R_6$ = H, $R_7$ = $CH_3$) | H | $CH_3$ | H | $OCH_3$ | $CH_3$ | |
| Q-19 | ($R_6$ = H, $R_7$ = $CH_3$) | H | $CH_3$ | $CH_3$ | $CH_3$ | $OCH_3$ | |
| Q-20 | ($R_6$, $R_7$ = $CH_3$) | H | $CH_3$ | H | $OCH_3$ | $CH_3$ | |
| Q-20 | ($R_6$, $R_7$ = $CH_3$) | H | $CH_3$ | H | $OCH_3$ | $OCH_3$ | |
| Q-20 | ($R_6$, $R_7$ = $CH_3$) | H | $C_3H_7$ | H | $OCH_3$ | $CH_3$ | |
| Q-21 | ($R_6$, $R_7$, $R_9$ = H) | H | $CH_3$ | H | $OCH_3$ | $OCH_3$ | |
| Q-21 | ($R_6$, $R_7$, $R_9$ = H) | H | $CH_3$ | H | $CH_3$ | $OCH_3$ | |
| Q-21 | ($R_6$, $R_7$, $R_9$ = H) | H | $CH_3$ | $CH_3$ | $OCH_3$ | $OCH_3$ | |
| Q-22 | ($R_6$, $R_7$, $R_9$ = H) | H | $CH_3$ | H | $OCH_3$ | $OCH_3$ | |
| Q-22 | ($R_6$, $R_7$, $R_9$ = H) | H | $CH_3$ | H | $CH_3$ | $OCH_3$ | |
| Q-23 | ($R_6$, $R_7$, $R_9$ = H) | H | $CH_3$ | H | $CH_3$ | $OCH_3$ | |
| Q-23 | ($R_6$, $R_7$, $R_9$ = H) | H | $CH_3$ | H | $OCH_3$ | $OCH_3$ | |
| Q-24 | ($R_6$, $R_7$, $R_9$ = H) | H | $CH_3$ | H | $OCH_3$ | $OCH_3$ | |
| Q-24 | ($R_6$, $R_7$, $R_9$ = H) | H | $CH_3$ | H | $CH_3$ | $OCH_3$ | |
| Q-25 | ($R_6$, $R_7$, $R_9$ = H) | H | $CH_3$ | H | $OCH_3$ | $OCH_3$ | |
| Q-25 | ($R_6$, $R_7$, $R_9$ = H) | H | $CH_3$ | H | $OCH_3$ | $CH_3$ | |
| Q-25 | ($R_6$, $R_7$, $R_9$ = H) | H | $C_3H_7$ | H | $CH_3$ | $OCH_3$ | |
| Q-26 | ($R_6$, $R_7$, $R_9$ = H) | H | $CH_3$ | H | $CH_3$ | $OCH_3$ | |
| Q-27 | ($R_6$, $R_7$, $R_9$ = H) | H | $CH_3$ | H | $CH_3$ | $OCH_3$ | |
| Q-28 | ($R_6$, $R_7$, $R_9$ = H) | H | $CH_3$ | H | $CH_3$ | $OCH_3$ | |
| Q-29 | ($R_6$, $R_7$, $R_9$ = H) | H | $CH_3$ | H | $OCH_3$ | $OCH_3$ | |
| Q-29 | ($R_6$, $R_7$, $R_9$ = H) | H | $CH_3$ | $CH_3$ | $CH_3$ | $OCH_3$ | |
| Q-31 | ($R_6$, $R_7$ = H) | H | $CH_3$ | H | $OCH_3$ | $CH_3$ | |
| Q-31 | ($R_6$, $R_7$ = H) | H | $CH_3$ | H | $OCH_3$ | $OCH_3$ | |
| Q-32 | ($R_6$, $R_7$ = H) | H | $CH_3$ | H | $OCH_3$ | $OCH_3$ | |
| Q-32 | ($R_6$, $R_7$ = H) | H | $CH_3$ | H | $CH_3$ | $OCH_3$ | |
| Q-33 | ($R_6$, $R_7$ = H) | H | $CH_3$ | H | $OCH_3$ | $OCH_3$ | |
| Q-33 | ($R_6$, $R_7$ = H) | H | $CH_3$ | H | $CH_3$ | $OCH_3$ | |
| Q-34 | ($R_6$, $R_{10}$, $R_{11}$ = H) | H | $CH_3$ | H | $OCH_3$ | $CH_3$ | |
| Q-34 | ($R_6$, $R_{10}$, $R_{11}$ = H) | H | $CH_3$ | H | $OCH_3$ | $OCH_3$ | |
| Q-34 | ($R_6$ = H, $R_{10}$, $R_{11}$ = $CH_3$) | H | $CH_3$ | H | $OCH_3$ | $CH_3$ | |
| Q-34 | ($R_6$ = H, $R_{10}$, $R_{11}$ = $OCH_3$) | H | $CH_3$ | H | $OCH_3$ | $CH_3$ | |
| Q-34 | ($R_6$ = H, $R_{10}$, $R_{11}$ = $OCH_3$) | H | $CH_3$ | H | $OCH_3$ | $OCH_3$ | |
| Q-34 | ($R_6$ = H, $R_{10}$, $R_{11}$ = $OCH_3$) | H | $CH_3$ | $CH_3$ | $OCH_3$ | $OCH_3$ | |
| Q-35 | ($R_{10}$, $R_{11}$ = H) | H | $CH_3$ | H | $OCH_3$ | $CH_3$ | |
| Q-35 | ($R_{10}$, $R_{11}$ = H) | H | $CH_3$ | $CH_3$ | $OCH_3$ | $OCH_3$ | |
| Q-36 | ($R_{10}$, $R_{11}$ = H) | H | $CH_3$ | H | $OCH_3$ | $CH_3$ | |
| Q-36 | ($R_{10}$, $R_{11}$ = H) | H | $CH_3$ | H | $OCH_3$ | $OCH_3$ | |
| Q-37 | ($R_6$, $R_7$ = H) | H | $CH_3$ | H | $OCH_3$ | $CH_3$ | |
| Q-37 | ($R_6$, $R_7$ = H) | H | $CH_3$ | H | $OCH_3$ | $OCH_3$ | |
| Q-38 | ($R_6$, $R_7$ = H) | H | $CH_3$ | H | $OCH_3$ | $CH_3$ | |
| Q-38 | ($R_6$, $R_7$ = H) | H | $CH_3$ | H | $OCH_3$ | $OCH_3$ | |
| Q-39 | ($R_{12}$, $R_{13}$ = $CH_3$) | H | $CH_3$ | H | $OCH_3$ | $CH_3$ | |
| Q-39 | ($R_{12}$, $R_{13}$ = $OCH_3$) | H | $CH_3$ | H | $OCH_3$ | $CH_3$ | |
| Q-39 | ($R_{12}$ = $CH_3$, $R_{13}$ = $OCH_3$) | H | $CH_3$ | H | $OCH_3$ | $CH_3$ | |
| Q-40 | ($R_{12}$, $R_{13}$ = $CH_3$) | H | $CH_3$ | H | $OCH_3$ | $CH_3$ | |
| Q-40 | ($R_{12}$, $R_{13}$ = $OCH_3$) | H | $CH_3$ | H | $OCH_3$ | $CH_3$ | |
| Q-41 | ($R_6$ = H) | H | $CH_3$ | H | $OCH_3$ | $OCH_3$ | |
| Q-41 | ($R_6$ = H) | H | $CH_3$ | H | $CH_3$ | $OCH_3$ | |
| Q-42 | ($R_6$ = H) | H | $CH_3$ | H | $CH_3$ | $OCH_3$ | |
| Q-42 | ($R_6$ = H) | H | $CH_3$ | H | $OCH_3$ | $OCH_3$ | |
| Q-43 | ($R_6$ = H) | H | $CH_3$ | H | $OCH_3$ | $CH_3$ | |
| Q-43 | ($R_6$ = H) | H | $CH_3$ | H | $OCH_3$ | $OCH_3$ | |
| Q-43 | ($R_6$ = $CH_3$) | H | $CH_3$ | H | $OCH_3$ | $CH_3$ | |
| Q-44 | ($R_6$ = H) | H | $CH_3$ | H | $OCH_3$ | $OCH_3$ | |
| Q-44 | ($R_6$ = H) | H | $CH_3$ | H | $CH_3$ | $OCH_3$ | |
| Q-7 | ($R_8$ = $CH_3$) | H | $CH_3$ | $CH_3$ | $OCH_3$ | $CH_2OCH_3$ | |
| Q-7 | ($R_8$ = $CH_3$) | H | $CH_3$ | $CH_3$ | $OCH_3$ | $OCH_2CF_3$ | |
| Q-7 | ($R_8$ = $CH_3$) | H | $CH_3$ | $CH_3$ | $OC_2H_5$ | $NHCH_3$ | |
| Q-7 | ($R_8$ = $CH_3$) | H | $CH_3$ | $CH_3$ | $OCH_2CF_3$ | $NHCH_3$ | |
| Q-1 | ($R_6$, $R_7$ = H) | H | $CH_3$ | $CH_3$ | $CH_3$ | $OCH_2C\equiv CH$ | |
| Q-7 | ($R_8$ = $CH_3$) | H | $CH_3$ | $CH_3$ | $OCH_3$ | $N(CH_3)_2$ | |
| Q-7 | ($R_8$ = $CH_3$). | H | $CH_3$ | $CH_3$ | $CH_3$ | $CH_2OCH_3$ | |
| Q-34 | ($R_6$ = H, $R_{10}$, $R_{11}$ = $CH_3$) | H | $CH_3$ | H | $CH_3$ | $OCH_2CH_2OCH_3$ | |
| Q-34 | ($R_6$ = H, $R_{10}$, $R_{11}$ = $OCH_3$) | H | $CH_3$ | H | $CH_3$ | $OCH_2CF_3$ | |
| Q-14 | ($R_6$, $R_7$ = H) | H | $CH_3$ | H | $OCH_3$ | cyclopropyl | |
| Q-14 | ($R_6$, $R_7$ = H) | H | $CH_3$ | H | $OCH_3$ | $C(CH_3)(OCH_3)_2$ | |
| Q-1 | ($R_6$, $R_7$ = H) | H | $CH_3$ | H | $OCH_3$ | $OCH_2CF_3$ | |
| Q-15 | ($R_6$ = H, $R_7$ = $CH_3$) | H | $CH_3$ | H | $OCH_3$ | $OCH_2CH=CH_2$ | |
| Q-15 | ($R_6$ = H, $R_7$ = $CH_3$) | H | $CH_3$ | H | $OCH_3$ | $SCH_3$ | |
| Q-43 | ($R_6$ = $CH_3$) | H | $CH_3$ | H | $OCH_3$ | $N(CH_3)_2$ | |
| Q-43 | ($R_6$ = $CH_3$) | H | $CH_3$ | H | $OCH_3$ | $C_2H_5$ | |
| Q-43 | ($R_6$ = $CH_3$) | H | $CH_3$ | H | $OCH_3$ | $CH_2CH_2CH_3$ | |
| Q-43 | ($R_6$ = $CH_3$) | H | $CH_3$ | H | $OCH_3$ | $CH(CH_3)_2$ | |
| Q-7 | ($R_8$ = $SCH_3$) | H | $CH_3$ | $CH_3$ | $OCH_3$ | $OCH_3$ | 163–165 |

TABLE VII-continued

General Formula VII

| Q | | R | $R_1$ | $R_2$ | X | Y | m.p. °C. |
|---|---|---|---|---|---|---|---|
| Q-7 | (R = $SCH_2CH_3$) | H | $CH_3$ | $CH_3$ | $OCH_3$ | $CH_3$ | |
| Q-7 | (R = $SCH_2CH_3$) | H | $CH_3$ | $CH_3$ | $OCH_3$ | $OCH_3$ | |
| Q-7 | (R = $SCH_2CH_3$) | H | $CH_3$ | $CH_3$ | $CH_3$ | $CH_3$ | |
| Q-7 | ($R_8$ = $SCH_2CO_2CH_3$) | H | $CH_3$ | $CH_3$ | $OCH_3$ | $OCH_3$ | |
| Q-7 | ($R_8$ = $SCH_2CO_2CH_3$) | H | $CH_3$ | $CH_3$ | $CH_3$ | $OCH_3$ | |
| Q-7 | ($R_8$ = $SCH_2CO_2CH_3$) | H | $CH_3$ | $CH_3$ | $CH_3$ | $CH_3$ | |
| Q-7 | ($R_8$ = $SCH_2-CH=CH_2$) | H | $CH_3$ | $CH_3$ | $CH_3$ | $OCH_3$ | 198-200 |
| Q-7 | ($R_8$ = $SCH_2-CH=CH_2$) | H | $CH_3$ | $CH_3$ | $OCH_3$ | $OCH_3$ | 187-190 |
| Q-7 | ($R_8$ = $SCH_2-CH=CH_2$) | H | $CH_3$ | $CH_3$ | $CH_3$ | $CH_3$ | 197-199 |
| Q-7 | ($R_8$ = $SCH_3$) | H | $CH_3$ | $CH_3$ | $CH_3$ | $CH_3$ | 175.5-177 |
| Q-7 | ($R_8$ = $SCH_3$) | H | $CH_3$ | $CH_3$ | $OCH_3$ | $i-C_3H_7$ | |
| Q-7 | ($R_8$ = $SCH_3$) | H | $CH_3$ | $CH_3$ | $CH_3$ | $i-C_3H_7$ | |
| Q-13 | ($R_{18}$ = $SCH_3$, $R_{19}$ = $CH_3$) | H | $CH_3$ | $CH_3$ | $CH_3$ | $CH_3$ | |
| Q-13 | ($R_{18}$ = $SCH_3$, $R_{19}$ = $CH_3$) | H | $CH_3$ | $CH_3$ | $CH_3$ | $OCH_3$ | 225-227 |
| Q-13 | ($R_{18}$ = $SCH_3$, $R_{19}$ = $CH_3$) | H | $CH_3$ | $CH_3$ | $OCH_3$ | $OCH_3$ | 220-222 |
| Q-13 | ($R_{18}$ = $SCH_3$, $R_{19}$ = $CH_2CH=CH_2$) | H | $CH_3$ | $CH_3$ | $OCH_3$ | $CH_3$ | 194-195 |
| Q-13 | ($R_{18}$ = $SCH_3$, $R_{19}$ = $CH_2CH=CH_2$) | H | $CH_3$ | $CH_3$ | $OCH_3$ | $OCH_3$ | 196-197 |
| Q-13 | ($R_{18}$ = $SCH_2CH=CH_2$, $R_{19}$ = $CH_3$) | H | $CH_3$ | $CH_3$ | $OCH_3$ | $CH_3$ | 184-185 |
| Q-13 | ($R_{18}$ = $SCH_2CH=CH_2$, $R_{19}$ = $CH_3$) | H | $CH_3$ | $CH_3$ | $OCH_3$ | $OCH_3$ | 189-190 |
| Q-13 | ($R_{18}$ = $S-CH_2CH=CH_2$, $R_{19}$ = $CH_2CH=CH_2$) | H | $CH_3$ | $CH_3$ | $OCH_3$ | $CH_3$ | 199-200 |
| Q-13 | ($R_{18}$ = $S-CH_2CH=CH_2$, $R_{19}$ = $CH_2CH=CH_2$) | H | $CH_3$ | $CH_3$ | $OCH_3$ | $OCH_3$ | 195-196 |
| Q-45 | ($R_7$ = H) | H | $CH_3$ | H | $OCH_3$ | $OCH_3$ | |
| Q-45 | ($R_7$ = H) | H | $C_6H_5$ | H | $CH_3$ | $OCH_3$ | |
| Q-46 | ($R_7$ = H) | H | $CH_3$ | H | $OCH_3$ | $OCH_3$ | |
| Q-46 | ($R_7$ = H) | H | $CH_3$ | $CH_3$ | $OCH_3$ | $CH_3$ | |
| Q-47 | ($R_7$ = H) | H | $CH_3$ | H | $OCH_3$ | $OCH_3$ | |
| Q-48 | ($R_7$ = H) | H | $C_6H_5$ | H | $OCH_3$ | $OCH_3$ | |
| Q-48 | ($R_7$ = H) | H | $CH_3$ | H | $CH_3$ | $OCH_3$ | |

TABLE VIII

General Formula VIII

| Q | | R | $R_1$ | $R_2$ | X | Y | m.p.°C. |
|---|---|---|---|---|---|---|---|
| Q-1 | ($R_6$, $R_7$ = H) | H | $CH_3$ | H | $OCH_3$ | $OCH_3$ | |
| Q-1 | ($R_6$, $R_7$ = H) | H | $CH_3$ | H | $OCH_3$ | $CH_3$ | |
| Q-1 | ($R_6$, $R_7$ = H) | H | $CH_3$ | $CH_3$ | $OCH_3$ | $CH_3$ | |
| Q-1 | ($R_6$, $R_7$ = H) | H | $C_3H_7$ | H | $OCH_3$ | $CH_3$ | |
| Q-1 | ($R_6$, $R_7$ = H) | H | $C_6H_5$ | H | $OCH_3$ | $OCH_3$ | |
| Q-1 | ($R_6$, $R_7$ = $CH_3$) | H | $CH_3$ | H | $OCH_3$ | $OCH_3$ | |
| Q-2 | ($R_6$, $R_7$ = H) | H | $CH_3$ | H | $OCH_3$ | $OCH_3$ | |
| Q-2 | ($R_6$, $R_7$ = H) | H | $CH_3$ | H | $CH_3$ | $OCH_3$ | |
| Q-2 | ($R_6$, $R_7$ = H) | H | $CH_3$ | $CH_3$ | $OCH_3$ | $OCH_3$ | |
| Q-2 | ($R_6$, $R_7$ = H) | H | $C_3H_7$ | H | $OCH_3$ | $OCH_3$ | |
| Q-2 | ($R_6$ = $CH_3$, $R_7$ = H) | H | $CH_3$ | H | $OCH_3$ | $OCH_3$ | |
| Q-2 | ($R_6$ = H, $R_7$ = $CH_3$) | H | $CH_3$ | H | $OCH_3$ | $CH_3$ | |
| Q-2 | ($R_6$, $R_7$ = H) | H | $C_6H_5$ | H | $OCH_3$ | $OCH_3$ | |
| Q-3 | ($R_6$, $R_7$ = H) | H | $CH_3$ | H | $OCH_3$ | $CH_3$ | |
| Q-3 | ($R_6$, $R_7$ = H) | H | $CH_3$ | H | $OCH_3$ | $OCH_3$ | |
| Q-3 | ($R_6$, $R_7$ = H) | H | $CH_3$ | $CH_3$ | $OCH_3$ | $OCH_3$ | |
| Q-3 | ($R_6$, $R_7$ = H) | H | $C_3H_7$ | H | $CH_3$ | $OCH_3$ | |
| Q-4 | ($R_6$, $R_7$ = H) | H | $CH_3$ | H | $OCH_3$ | $CH_3$ | |
| Q-4 | ($R_6$, $R_7$ = H) | H | $CH_3$ | H | $OCH_3$ | $OCH_3$ | |
| Q-4 | ($R_6$, $R_7$ = H) | H | $CH_3$ | $CH_3$ | $CH_3$ | $OCH_3$ | |
| Q-5 | ($R_6$, $R_7$ = H) | H | $CH_3$ | H | $CH_3$ | $OCH_3$ | |
| Q-5 | ($R_6$, $R_7$ = H) | H | $CH_3$ | H | $OCH_3$ | $OCH_3$ | |
| Q-6 | ($R_6$, $R_7$ = H) | H | $CH_3$ | H | $CH_3$ | $OCH_3$ | |
| Q-6 | ($R_6$, $R_7$ = H) | H | $CH_3$ | H | $OCH_3$ | $OCH_3$ | |
| Q-7 | ($R_8$ = H) | H | $CH_3$ | H | $OCH_3$ | $CH_3$ | |
| Q-7 | ($R_8$ = H) | H | $CH_3$ | H | $OCH_3$ | $OCH_3$ | |
| Q-7 | ($R_8$ = H) | H | $CH_3$ | $CH_3$ | $OCH_3$ | $OCH_3$ | |
| Q-7 | ($R_8$ = H) | H | $C_3H_7$ | H | $CH_3$ | $OCH_3$ | |
| Q-7 | ($R_8$ = H) | H | $C_6H_5$ | H | $CH_3$ | $OCH_3$ | |
| Q-7 | ($R_8$ = $CH_3$) | H | $CH_3$ | H | $OCH_3$ | $OCH_3$ | |
| Q-7 | ($R_8$ = $CH_3$) | H | $CH_3$ | H | $OCH_3$ | $CH_3$ | |
| Q-7 | ($R_8$ = $CH_3$) | H | $CH_3$ | $CH_3$ | $OCH_3$ | $OCH_3$ | |
| Q-7 | ($R_8$ = $CH_3$) | H | $C_3H_7$ | H | $OCH_3$ | $CH_3$ | |
| Q-7 | ($R_8$ = $CH_3$) | H | $C_6H_5$ | H | $OCH_3$ | $CH_3$ | |
| Q-7 | ($R_8$ = $SCH_3$) | H | $CH_3$ | H | $OCH_3$ | $OCH_3$ | 174-176 |
| Q-7 | ($R_8$ = $SCH_3$) | H | $CH_3$ | H | $OCH_3$ | $CH_3$ | 140-142 |
| Q-7 | ($R_8$ = $SCH_3$) | H | $CH_3$ | $CH_3$ | $OCH_3$ | $CH_3$ | |
| Q-7 | ($R_8$ = $SCH_3$) | H | $C_3H_7$ | H | $OCH_3$ | $CH_3$ | |
| Q-7 | ($R_8$ = $OCH_3$) | H | $CH_3$ | H | $OCH_3$ | $OCH_3$ | |
| Q-7 | ($R_8$ = $OCH_3$) | H | $CH_3$ | H | $CH_3$ | $OCH_3$ | |
| Q-7 | ($R_8$ = $OCH_3$) | H | $CH_3$ | $CH_3$ | $OCH_3$ | $CH_3$ | |
| Q-7 | ($R_8$ = $OCH_3$) | H | $C_3H_7$ | H | $OCH_3$ | $CH_3$ | |
| Q-8 | ($R_6$ = H) | H | $CH_3$ | H | $CH_3$ | $OCH_3$ | |
| Q-8 | ($R_6$ = H) | H | $CH_3$ | H | $OCH_3$ | $OCH_3$ | |
| Q-8 | ($R_6$ = H) | H | $CH_3$ | $CH_3$ | $OCH_3$ | $CH_3$ | |

TABLE VIII-continued

General Formula VIII

| Q | | R | R₁ | R₂ | X | Y | m.p.°C. |
|---|---|---|---|---|---|---|---|
| Q-8 | (R₆ = CH₃) | H | CH₃ | CH₃ | OCH₃ | CH₃ | |
| Q-8 | (R₆ = CH₃) | H | CH₃ | H | OCH₃ | OCH₃ | |
| Q-8 | (R₆ = CH₃) | H | CH₃ | H | CH₃ | OCH₃ | |
| Q-9 | (R₆ = CH₃) | H | CH₃ | H | OCH₃ | OCH₃ | |
| Q-9 | (R₆ = CH₃) | H | CH₃ | H | CH₃ | OCH₃ | |
| Q-9 | (R₆ = CH₃) | H | CH₃ | CH₃ | OCH₃ | OCH₃ | |
| Q-10 | (R₆ = H) | H | CH₃ | H | OCH₃ | CH₃ | |
| Q-10 | (R₆ = H) | H | CH₃ | H | OCH₃ | OCH₃ | |
| Q-10 | (R₆ = CH₃) | H | CH₃ | H | OCH₃ | OCH₃ | |
| Q-10 | (R₆ = CH₃) | H | CH₃ | H | CH₃ | OCH₃ | |
| Q-11 | (R₆ = CH₃) | H | CH₃ | H | OCH₃ | OCH₃ | |
| Q-11 | (R₆ = CH₃) | H | CH₃ | H | CH₃ | OCH₃ | |
| Q-11 | (R₆ = CH₃) | H | CH₃ | CH₃ | OCH₃ | OCH₃ | |
| Q-12 | (R₆ = CH₃) | H | CH₃ | H | OCH₃ | OCH₃ | |
| Q-12 | (R₆ = CH₃) | H | CH₃ | H | OCH₃ | CH₃ | |
| Q-13 | (R₆ = CH₃) | H | CH₃ | H | OCH₃ | OCH₃ | |
| Q-13 | (R₆ = CH₃) | H | CH₃ | H | OCH₃ | CH₃ | |
| Q-14 | (R₆, R₇ = H) | H | CH₃ | H | OCH₃ | OCH₃ | |
| Q-14 | (R₆, R₇ = H) | H | CH₃ | H | OCH₃ | CH₃ | |
| Q-14 | (R₆, R₇ = H) | H | CH₃ | CH₃ | OCH₃ | OCH₃ | |
| Q-14 | (R₆, R₇ = H) | H | CH₃ | Cl | CH₃ | OCH₃ | |
| Q-15 | (R₆ = H, R₇ = CH₃) | H | CH₃ | H | OCH₃ | OCH₃ | |
| Q-15 | (R₆ = H, R₇ = CH₃) | H | CH₃ | H | CH₃ | CH₃ | |
| Q-16 | (R₆ = CH₃, R₇ = H) | H | CH₃ | H | OCH₃ | OCH₃ | |
| Q-16 | (R₆ = CH₃, R₇ = H) | H | CH₃ | H | CH₃ | OCH₃ | |
| Q-16 | (R₆ = CH₃, R₇ = H) | H | CH₃ | CH₃ | OCH₃ | OCH₃ | |
| Q-17 | (R₆, R₇ = CH₃) | H | CH₃ | H | OCH₃ | OCH₃ | |
| Q-17 | (R₆, R₇ = CH₃) | H | CH₃ | H | CH₃ | OCH₃ | |
| Q-18 | (R₆ = H, R₇ = CH₃) | H | CH₃ | H | CH₃ | OCH₃ | |
| Q-18 | (R₆ = H, R₇ = CH₃) | H | C₃H₇ | H | OCH₃ | CH₃ | |
| Q-19 | (R₆ = H, R₇ = CH₃) | H | CH₃ | H | OCH₃ | CH₃ | |
| Q-19 | (R₆ = H, R₇ = CH₃) | H | CH₃ | CH₃ | CH₃ | OCH₃ | |
| Q-20 | (R₆, R₇ = CH₃) | H | CH₃ | H | OCH₃ | CH₃ | |
| Q-20 | (R₆, R₇ = CH₃) | H | CH₃ | H | OCH₃ | OCH₃ | |
| Q-20 | (R₆, R₇ = CH₃) | H | C₃H₇ | H | OCH₃ | CH₃ | |
| Q-21 | (R₆, R₇, R₉ = H) | H | CH₃ | H | OCH₃ | OCH₃ | |
| Q-21 | (R₆, R₇, R₉ = H) | H | CH₃ | H | CH₃ | OCH₃ | |
| Q-21 | (R₆, R₇, R₉ = H) | H | CH₃ | CH₃ | OCH₃ | OCH₃ | |
| Q-22 | (R₆, R₇, R₉ = H) | H | CH₃ | H | OCH₃ | OCH₃ | |
| Q-22 | (R₆, R₇, R₉ = H) | H | CH₃ | H | CH₃ | OCH₃ | |
| Q-23 | (R₆, R₇, R₉ = H) | H | CH₃ | H | CH₃ | OCH₃ | |
| Q-23 | (R₆, R₇, R₉ = H) | H | CH₃ | H | OCH₃ | OCH₃ | |
| Q-24 | (R₆, R₇, R₉ = H) | H | CH₃ | H | OCH₃ | OCH₃ | |
| Q-24 | (R₆, R₇, R₉ = H) | H | CH₃ | H | CH₃ | OCH₃ | |
| Q-25 | (R₆, R₇, R₉ = H) | H | CH₃ | H | OCH₃ | OCH₃ | |
| Q-25 | (R₆, R₇, R₉ = H) | H | CH₃ | H | OCH₃ | CH₃ | |
| Q-25 | (R₆, R₇, R₉ = H) | H | C₃H₇ | H | CH₃ | OCH₃ | |
| Q-26 | (R₆, R₇, R₉ = H) | H | CH₃ | H | CH₃ | OCH₃ | |
| Q-27 | (R₆, R₇, R₉ = H) | H | CH₃ | H | CH₃ | OCH₃ | |
| Q-28 | (R₆, R₇, R₉ = H) | H | CH₃ | H | CH₃ | OCH₃ | |
| Q-29 | (R₆, R₇, R₉ = H) | H | CH₃ | H | OCH₃ | OCH₃ | |
| Q-29 | (R₆, R₇, R₉ = H) | H | CH₃ | CH₃ | CH₃ | OCH₃ | |
| Q-31 | (R₆, R₇ = H) | H | CH₃ | H | OCH₃ | CH₃ | |
| Q-31 | (R₆, R₇ = H) | H | CH₃ | H | OCH₃ | OCH₃ | |
| Q-32 | (R₆, R₇ = H) | H | CH₃ | H | OCH₃ | OCH₃ | |
| Q-32 | (R₆, R₇ = H) | H | CH₃ | H | CH₃ | OCH₃ | |
| Q-33 | (R₆, R₇ = H) | H | CH₃ | H | OCH₃ | OCH₃ | |
| Q-33 | (R₆, R₇ = H) | H | CH₃ | H | CH₃ | OCH₃ | |
| Q-34 | (R₆, R₁₀, R₁₁ = H) | H | CH₃ | H | OCH₃ | CH₃ | |
| Q-34 | (R₆, R₁₀, R₁₁ = H) | H | CH₃ | H | OCH₃ | OCH₃ | |
| Q-34 | (R₆ = H, R₁₀, R₁₁ = CH₃) | H | CH₃ | H | OCH₃ | CH₃ | |
| Q-34 | (R₆ = H, R₁₀, R₁₁ = OCH₃) | H | CH₃ | H | CH₃ | CH₃ | |
| Q-34 | (R₆ = H, R₁₀, R₁₁ = OCH₃) | H | CH₃ | H | OCH₃ | OCH₃ | |
| Q-34 | (R₆ = H, R₁₀, R₁₁ = OCH₃) | H | CH₃ | CH₃ | OCH₃ | CH₃ | |
| Q-35 | (R₁₀, R₁₁ = H) | H | CH₃ | H | OCH₃ | CH₃ | |
| Q-35 | (R₁₀, R₁₁ = H) | H | CH₃ | CH₃ | OCH₃ | OCH₃ | |
| Q-36 | (R₁₀, R₁₁ = H) | H | CH₃ | H | OCH₃ | CH₃ | |
| Q-36 | (R₁₀, R₁₁ = H) | H | CH₃ | H | OCH₃ | OCH₃ | |
| Q-37 | (R₆, R₇ = H) | H | CH₃ | H | OCH₃ | CH₃ | |
| Q-37 | (R₆, R₇ = H) | H | CH₃ | H | OCH₃ | OCH₃ | |
| Q-38 | (R₆, R₇ = H) | H | CH₃ | H | OCH₃ | CH₃ | |
| Q-38 | (R₆, R₇ = H) | H | CH₃ | H | OCH₃ | OCH₃ | |
| Q-39 | (R₁₂, R₁₃ = CH₃) | H | CH₃ | H | OCH₃ | CH₃ | |
| Q-39 | (R₁₂, R₁₃ = OCH₃) | H | CH₃ | H | OCH₃ | CH₃ | |
| Q-39 | (R₁₂ = CH₃, R₁₃ = OCH₃) | H | CH₃ | H | OCH₃ | CH₃ | |
| Q-40 | (R₁₂, R₁₃ = CH₃) | H | CH₃ | H | OCH₃ | CH₃ | |
| Q-40 | (R₁₂, R₁₃ = OCH₃) | H | CH₃ | H | OCH₃ | CH₃ | |
| Q-41 | (R₆ = H) | H | CH₃ | H | OCH₃ | OCH₃ | |
| Q-41 | (R₆ = H) | H | CH₃ | H | CH₃ | OCH₃ | |
| Q-42 | (R₆ = H) | H | CH₃ | H | CH₃ | OCH₃ | |

TABLE VIII-continued

General Formula VIII

| Q | | R | $R_1$ | $R_2$ | X | Y | m.p. °C. |
|---|---|---|---|---|---|---|---|
| Q-42 | ($R_6$ = H) | H | $CH_3$ | H | $OCH_3$ | $OCH_3$ | |
| Q-43 | ($R_6$ = H) | H | $CH_3$ | H | $OCH_3$ | $CH_3$ | |
| Q-43 | ($R_6$ = H) | H | $CH_3$ | H | $OCH_3$ | $OCH_3$ | |
| Q-43 | ($R_6$ = $CH_3$) | H | $CH_3$ | H | $OCH_3$ | $CH_3$ | |
| Q-44 | ($R_6$ = H) | H | $CH_3$ | H | $OCH_3$ | $OCH_3$ | |
| Q-44 | ($R_6$ = H) | H | $CH_3$ | H | $CH_3$ | $OCH_3$ | |
| Q-7 | ($R_8$ = $CH_3$) | H | $CH_3$ | $CH_3$ | $OCH_3$ | $CH_2OCH_3$ | |
| Q-7 | ($R_8$ = $CH_3$) | H | $CH_3$ | $CH_3$ | $OCH_3$ | $OCH_2CF_3$ | |
| Q-7 | ($R_8$ = $CH_3$) | H | $CH_3$ | $CH_3$ | $OC_2H_5$ | $NHCH_3$ | |
| Q-7 | ($R_8$ = $CH_3$) | H | $CH_3$ | $CH_3$ | $OCH_2CF_3$ | $NHCH_3$ | |
| Q-1 | ($R_6$, $R_7$ = H) | H | $CH_3$ | $CH_3$ | $CH_3$ | $OCH_2C\equiv CH$ | |
| Q-7 | ($R_8$ = $CH_3$) | H | $CH_3$ | $CH_3$ | $OCH_3$ | $N(CH_3)_2$ | |
| Q-7 | ($R_8$ = $CH_3$) | H | $CH_3$ | $CH_3$ | $CH_3$ | $CH_2OCH_3$ | |
| Q-34 | ($R_6$ = H, $R_{10}$, $R_{11}$ = $CH_3$) | H | $CH_3$ | H | $CH_3$ | $OCH_2CH_2OCH_3$ | |
| Q-34 | ($R_6$ = H, $R_{10}$, $R_{11}$ = $OCH_3$) | H | $CH_3$ | H | $CH_3$ | $OCH_2CF_3$ | |
| Q-14 | ($R_6$, $R_7$ = H) | H | $CH_3$ | H | $OCH_3$ | cyclopropyl | |
| Q-14 | ($R_6$, $R_7$ = H) | H | $CH_3$ | H | $OCH_3$ | $C(CH_3)(OCH_3)_2$ | |
| Q-1 | ($R_6$, $R_7$ = H) | H | $CH_3$ | H | $OCH_3$ | $OCH_2CF_3$ | |
| Q-15 | ($R_6$ = H, $R_7$ = $CH_3$) | H | $CH_3$ | H | $OCH_3$ | $OCH_2CH=CH_2$ | |
| Q-15 | ($R_6$ = H, $R_7$ = $CH_3$) | H | $CH_3$ | H | $OCH_3$ | $SCH_3$ | |
| Q-43 | ($R_6$ = $CH_3$) | H | $CH_3$ | H | $OCH_3$ | $N(CH_3)_2$ | |
| Q-43 | ($R_6$ = $CH_3$) | H | $CH_3$ | H | $OCH_3$ | $C_2H_5$ | |
| Q-7 | ($R_8$ = $SCH_3$) | H | $CH_3$ | $CH_3$ | $OCH_3$ | $OCH_3$ | |
| Q-7 | (R = $SCH_2CH_3$) | H | $CH_3$ | $CH_3$ | $OCH_3$ | $CH_3$ | |
| Q-7 | (R = $SCH_2CH_3$) | H | $CH_3$ | $CH_3$ | $OCH_3$ | $OCH_3$ | |
| Q-7 | (R = $SCH_2CH_3$) | H | $CH_3$ | $CH_3$ | $CH_3$ | $CH_3$ | |
| Q-7 | ($R_8$ = $SCH_2CO_2CH_3$) | H | $CH_3$ | $CH_3$ | $OCH_3$ | $OCH_3$ | |
| Q-7 | ($R_8$ = $SCH_2CO_2CH_3$) | H | $CH_3$ | $CH_3$ | $CH_3$ | $OCH_3$ | |
| Q-7 | ($R_8$ = $SCH_2CO_2CH_3$) | H | $CH_3$ | $CH_3$ | $CH_3$ | $CH_3$ | |
| Q-7 | ($R_8$ = $SCH_2-CH=CH_2$) | H | $CH_3$ | $CH_3$ | $CH_3$ | $OCH_3$ | |
| Q-7 | ($R_8$ = $SCH_2-CH=CH_2$) | H | $CH_3$ | $CH_3$ | $OCH_3$ | $OCH_3$ | |
| Q-7 | ($R_8$ = $SCH_2-CH=CH_2$) | H | $CH_3$ | $CH_3$ | $CH_3$ | $CH_3$ | |
| Q-7 | ($R_8$ = $SCH_3$) | H | $CH_3$ | $CH_3$ | $CH_3$ | $CH_3$ | |
| Q-7 | ($R_8$ = $SCH_3$) | H | $CH_3$ | $CH_3$ | $OCH_3$ | $i-C_3H_7$ | |
| Q-7 | ($R_8$ = $SCH_3$) | H | $CH_3$ | $CH_3$ | $CH_3$ | $i-C_3H_7$ | |
| Q-7 | ($R_8$ = $SCH_2(C_6H_5)$) | H | $CH_3$ | H | $OCH_3$ | $CH_3$ | 169–170 |
| Q-7 | ($R_8$ = $SCH_2(C_6H_5)$) | H | $CH_3$ | H | $OCH_3$ | $OCH_3$ | 194–196 |
| Q-45 | ($R_7$ = H) | H | $CH_3$ | H | $OCH_3$ | $OCH_3$ | |
| Q-45 | ($R_7$ = H) | H | $C_6H_5$ | H | $CH_3$ | $OCH_3$ | |
| Q-46 | ($R_7$ = H) | H | $CH_3$ | H | $OCH_3$ | $OCH_3$ | |
| Q-46 | ($R_7$ = H) | H | $CH_3$ | $CH_3$ | $CH_3$ | $OCH_3$ | |
| Q-47 | ($R_7$ = H) | H | $CH_3$ | H | $OCH_3$ | $OCH_3$ | |
| Q-48 | ($R_7$ = H) | H | $C_6H_5$ | H | $OCH_3$ | $OCH_3$ | |
| Q-48 | ($R_7$ = H) | H | $CH_3$ | H | $CH_3$ | $OCH_3$ | |

TABLE IX

General Formula IX

| Q | | R | $R_1$ | $R_2$ | $X_1$ | $Y_1$ | m.p. °C. |
|---|---|---|---|---|---|---|---|
| Q-1 | ($R_6$, $R_7$ = H) | H | $CH_3$ | H | $CH_3$ | O | |
| Q-1 | ($R_6$, $R_7$ = H) | H | $CH_3$ | H | $CH_3$ | $CH_2$ | |
| Q-2 | ($R_6$, $R_7$ = H) | H | $CH_3$ | H | $CH_3$ | O | |
| Q-2 | ($R_6$, $R_7$ = H) | H | $CH_3$ | H | $CH_3$ | $CH_2$ | |
| Q-3 | ($R_6$, $R_7$ = H) | H | $CH_3$ | H | $CH_3$ | O | |
| Q-4 | ($R_6$, $R_7$ = H) | H | $CH_3$ | H | $CH_3$ | O | |
| Q-7 | ($R_8$ = $CH_3$) | H | $CH_3$ | H | $OCH_3$ | O | |
| Q-7 | ($R_8$ = H) | H | $CH_3$ | H | $CH_3$ | $CH_2$ | |
| Q-7 | ($R_8$ = $SCH_3$) | H | $CH_3$ | $CH_3$ | $OCH_3$ | O | |
| Q-7 | ($R_8$ = $SCH_3$) | H | $CH_3$ | H | $OCF_2H$ | O | |
| Q-7 | ($R_8$ = $CH_3$) | H | $CH_3$ | $CH_3$ | $OCF_2H$ | O | |
| Q-7 | ($R_8$ = $CH_3$) | H | $CH_3$ | H | $OCH_3$ | $CH_2$ | |
| Q-7 | ($R_8$ = H) | H | $CH_3$ | $CH_3$ | $CH_3$ | O | |
| Q-7 | ($R_8$ = H) | H | $CH_3$ | H | $OC_2H_5$ | O | |
| Q-8 | ($R_6$ = H) | H | $CH_3$ | H | $CH_3$ | O | |
| Q-8 | ($R_6$ = H) | H | $CH_3$ | $CH_3$ | $CH_3$ | O | |
| Q-8 | ($R_6$ = $CH_3$) | H | $CH_3$ | H | $CH_3$ | O | |
| Q-8 | ($R_6$ = $CH_3$) | H | $CH_3$ | $CH_3$ | $CH_3$ | O | |
| Q-9 | ($R_6$ = $CH_3$) | H | $CH_3$ | H | $CH_3$ | O | |
| Q-9 | ($R_6$ = $CH_3$) | H | $CH_3$ | $CH_3$ | $CH_3$ | O | |
| Q-14 | ($R_6$, $R_7$ = H) | H | $CH_3$ | H | $CH_3$ | O | |
| Q-14 | ($R_6$, $R_7$ = H) | H | $CH_3$ | $CH_3$ | $CH_3$ | O | |
| Q-15 | ($R_6$ = H, $R_7$ = $CH_3$) | H | $CH_3$ | H | $CH_3$ | O | |
| Q-15 | ($R_6$ = H, $R_7$ = $CH_3$) | H | $CH_3$ | $CH_3$ | $CH_3$ | O | |
| Q-16 | ($R_6$ = $CH_3$, $R_7$ = H) | H | $CH_3$ | H | $CH_3$ | O | |
| Q-16 | ($R_6$ = $CH_3$, $R_7$ = H) | H | $CH_3$ | $CH_3$ | $CH_3$ | O | |
| Q-34 | ($R_6$ = H, $R_{10}$, $R_{11}$ = $OCH_3$) | H | $CH_3$ | H | $CH_3$ | 0 | |
| Q-34 | ($R_6$ = H, $R_{10}$, $R_{11}$ = $CH_3$) | H | $CH_3$ | $CH_3$ | $CH_3$ | O | |

TABLE IX-continued

General Formula IX

| Q | | R | $R_1$ | $R_2$ | $X_1$ | $Y_1$ | m.p. °C. |
|---|---|---|---|---|---|---|---|
| Q-43 | ($R_6$ = H) | H | $CH_3$ | H | $CH_3$ | O | |
| Q-43 | ($R_6$ = $CH_3$) | H | $CH_3$ | $CH_3$ | $CH_3$ | O | |

TABLE X

General Formula X

| Q | | R | $R_1$ | $R_2$ | $X_1$ | $Y_1$ | m.p. °C. |
|---|---|---|---|---|---|---|---|
| Q-1 | ($R_6$, $R_7$ = H) | H | $CH_3$ | H | $CH_3$ | O | |
| Q-1 | ($R_6$, $R_7$ = H) | H | $CH_3$ | H | $CH_3$ | $CH_2$ | |
| Q-2 | ($R_6$, $R_7$ = H) | H | $CH_3$ | H | $CH_3$ | O | |
| Q-2 | ($R_6$, $R_7$ = H) | H | $CH_3$ | H | $CH_3$ | $CH_2$ | |
| Q-3 | ($R_6$, $R_7$ = H) | H | $CH_3$ | H | $CH_3$ | O | |
| Q-4 | ($R_6$, $R_7$ = H) | H | $CH_3$ | H | $CH_3$ | O | |
| Q-7 | ($R_8$ = $CH_3$) | H | $CH_3$ | H | $OCH_3$ | O | |
| Q-7 | ($R_8$ = H) | H | $CH_3$ | H | $CH_3$ | $CH_2$ | |
| Q-7 | ($R_8$ = $SCH_3$) | H | $CH_3$ | $CH_3$ | $OCH_3$ | O | |
| Q-7 | ($R_8$ = $SCH_3$) | H | $CH_3$ | H | $OCF_2H$ | O | |
| Q-7 | ($R_8$ = $CH_3$) | H | $CH_3$ | $CH_3$ | $OCF_2H$ | O | |
| Q-7 | ($R_8$ = $CH_3$) | H | $CH_3$ | H | $OCH_3$ | $CH_2$ | |
| Q-7 | ($R_8$ = H) | H | $CH_3$ | $CH_3$ | $CH_3$ | O | |
| Q-7 | ($R_8$ = H) | H | $CH_3$ | H | $OC_2H_5$ | O | |
| Q-8 | ($R_6$ = H) | H | $CH_3$ | H | $CH_3$ | O | |
| Q-8 | ($R_6$ = H) | H | $CH_3$ | $CH_3$ | $CH_3$ | O | |
| Q-8 | ($R_6$ = $CH_3$) | H | $CH_3$ | H | $CH_3$ | O | |
| Q-8 | ($R_6$ = $CH_3$) | H | $CH_3$ | $CH_3$ | $CH_3$ | O | |
| Q-9 | ($R_6$ = $CH_3$) | H | $CH_3$ | H | $CH_3$ | O | |
| Q-9 | ($R_6$ = $CH_3$) | H | $CH_3$ | $CH_3$ | $CH_3$ | O | |
| Q-14 | ($R_6$, $R_7$ = H) | H | $CH_3$ | H | $CH_3$ | O | |
| Q-14 | ($R_6$, $R_7$ = H) | H | $CH_3$ | $CH_3$ | $CH_3$ | O | |
| Q-15 | ($R_6$ = H, $R_7$ = $CH_3$) | H | $CH_3$ | H | $CH_3$ | O | |
| Q-15 | ($R_6$ = H, $R_7$ = $CH_3$) | H | $CH_3$ | $CH_3$ | $CH_3$ | O | |
| Q-16 | ($R_6$ = $CH_3$, $R_7$ = H) | H | $CH_3$ | H | $CH_3$ | O | |
| Q-16 | ($R_6$ = $CH_3$, $R_7$ = H) | H | $CH_3$ | $CH_3$ | $CH_3$ | O | |
| Q-34 | ($R_6$ = H, $R_{10}$, $R_{11}$ = $OCH_3$) | H | $CH_3$ | H | $CH_3$ | O | |
| Q-34 | ($R_6$ = H, $R_{10}$, $R_{11}$ = $CH_3$) | H | $CH_3$ | $CH_3$ | $CH_3$ | O | |
| Q-43 | ($R_6$ = H) | H | $CH_3$ | H | $CH_3$ | O | |
| Q-43 | ($R_6$ = H) | H | $CH_3$ | $CH_3$ | $CH_3$ | O | |

TABLE XI

General Formula XI

| Q | | R | $R_1$ | $R_2$ | $X_2$ | $Y_3$ | m.p. °C. |
|---|---|---|---|---|---|---|---|
| Q-1 | ($R_6$, $R_7$ = H) | H | $CH_3$ | H | $CH_3$ | $OCH_3$ | |
| Q-1 | ($R_6$, $R_7$ = H) | H | $CH_3$ | H | $CH_3$ | $OC_2H_5$ | |
| Q-2 | ($R_6$, $R_7$ = H) | H | $CH_3$ | H | $CH_3$ | $SCH_3$ | |
| Q-2 | ($R_6$, $R_7$ = H) | H | $CH_3$ | H | $CH_3$ | $SC_2H_5$ | |
| Q-3 | ($R_6$, $R_7$ = H) | H | $CH_3$ | H | $CH_3$ | $OCF_2H$ | |
| Q-4 | ($R_6$, $R_7$ = H) | H | $CH_3$ | H | $CH_3$ | $SCF_2H$ | |
| Q-7 | ($R_8$ = $CH_3$) | H | $CH_3$ | H | $CH_2CH_3$ | $C_2H_5$ | |
| Q-7 | ($R_8$ = H) | H | $CH_3$ | H | $CH_3$ | $CH_3$ | |
| Q-7 | ($R_8$ = $SCH_3$) | H | $CH_3$ | $CH_3$ | $CH_3$ | $CH_3$ | |
| Q-7 | ($R_8$ = $SCH_3$) | H | $CH_3$ | H | $CH_2CF_3$ | $CH_3$ | |
| Q-7 | ($R_8$ = $CH_3$) | H | $CH_3$ | $CH_3$ | $CH_2CF_3$ | $CH_3$ | |
| Q-7 | ($R_8$ = $CH_3$) | H | $CH_3$ | H | $CH_3$ | $CH_3$ | |
| Q-7 | ($R_8$ = H) | H | $CH_3$ | $CH_3$ | $CH_3$ | $CH_3$ | |
| Q-7 | ($R_8$ = H) | H | $CH_3$ | H | $C_2H_5$ | $CH_3$ | |
| Q-8 | ($R_6$ = H) | H | $CH_3$ | H | $CH_3$ | $CH_3$ | |
| Q-8 | ($R_6$ = H) | H | $CH_3$ | $CH_3$ | $CH_3$ | $CH_3$ | |
| Q-8 | ($R_6$ = $CH_3$) | H | $CH_3$ | H | $CH_3$ | $CH_3$ | |
| Q-8 | ($R_6$ = $CH_3$) | H | $CH_3$ | $CH_3$ | $CH_3$ | $CH_3$ | |
| Q-9 | ($R_6$ = $CH_3$) | H | $CH_3$ | H | $CH_3$ | $CH_3$ | |
| Q-9 | ($R_6$ = $CH_3$) | H | $CH_3$ | $CH_3$ | $CH_3$ | $CH_3$ | |
| Q-14 | ($R_6$, $R_7$ = H) | H | $CH_3$ | H | $CH_3$ | $CH_3$ | |
| Q-14 | ($R_6$, $R_7$ = H) | H | $CH_3$ | $CH_3$ | $CH_3$ | $CH_3$ | |
| Q-15 | ($R_6$ = H, $R_7$ = $CH_3$) | H | $CH_3$ | H | $CH_3$ | $CH_3$ | |
| Q-15 | ($R_6$ = H, $R_7$ = $CH_3$) | H | $CH_3$ | $CH_3$ | $CH_3$ | $CH_3$ | |
| Q-16 | ($R_6$ = $CH_3$, $R_7$ = H) | H | $CH_3$ | H | $CH_3$ | $CH_3$ | |
| Q-16 | ($R_6$ = $CH_3$, $R_7$ = H) | H | $CH_3$ | $CH_3$ | $CH_3$ | $CH_3$ | |
| Q-34 | ($R_6$ = H, $R_{10}$, $R_{11}$ = $OCH_3$) | H | $CH_3$ | H | $CH_3$ | $CH_3$ | |
| Q-34 | ($R_6$ = H, $R_{10}$, $R_{11}$ = $CH_3$) | H | $CH_3$ | $CH_3$ | $CH_3$ | $CH_3$ | |
| Q-43 | ($R_6$ = H) | H | $CH_3$ | H | $CH_3$ | $CH_3$ | |

TABLE XI-continued

General Formula XI

| Q | | R | $R_1$ | $R_2$ | $X_2$ | $Y_3$ | m.p. °C. |
|---|---|---|---|---|---|---|---|
| Q-43 | ($R_6$ = $CH_3$) | H | $CH_3$ | $CH_3$ | $CH_3$ | $CH_3$ | |

TABLE XII

Genral Formula XII

| Q | | R | $R_1$ | $R_2$ | $X_2$ | $Y_3$ | m.p. °C. |
|---|---|---|---|---|---|---|---|
| Q-1 | ($R_6$, $R_7$ = H) | H | $CH_3$ | H | $CH_3$ | $OCH_3$ | |
| Q-1 | ($R_6$, $R_7$ = H) | H | $CH_3$ | H | $CH_3$ | $OC_2H_5$ | |
| Q-2 | ($R_6$, $R_7$ = H) | H | $CH_3$ | H | $CH_3$ | $SCH_3$ | |
| Q-2 | ($R_6$, $R_7$ = H) | H | $CH_3$ | H | $CH_3$ | $SC_2H_5$ | |
| Q-3 | ($R_6$, $R_7$ = H) | H | $CH_3$ | H | $CH_3$ | $OCF_2H$ | |
| Q-4 | ($R_6$, $R_7$ = H) | H | $CH_3$ | H | $CH_3$ | $SCF_2H$ | |
| Q-7 | ($R_8$ = $CH_3$) | H | $CH_3$ | H | $CH_3$ | $C_2H_5$ | |
| Q-7 | ($R_8$ = H) | H | $CH_3$ | H | $CH_3$ | $CH_3$ | |
| Q-7 | ($R_8$ = $SCH_3$) | H | $CH_3$ | $CH_3$ | $OCH_3$ | $CH_3$ | |
| Q-7 | ($R_8$ = $SCH_3$) | H | $CH_3$ | H | $CH_2CF_3$ | $CH_3$ | |
| Q-7 | ($R_8$ = $CH_3$) | H | $CH_3$ | $CH_3$ | $CH_2CF_3$ | $CH_3$ | |
| Q-7 | ($R_8$ = $CH_3$) | H | $CH_3$ | H | $CH_3$ | $CH_3$ | |
| Q-7 | ($R_8$ = H) | H | $CH_3$ | $CH_3$ | $CH_3$ | $CH_3$ | |
| Q-7 | ($R_8$ = H) | H | $CH_3$ | H | $C_2H_5$ | $CH_3$ | |
| Q-8 | ($R_6$ = H) | H | $CH_3$ | H | $CH_3$ | $CH_3$ | |
| Q-8 | ($R_6$ = H) | H | $CH_3$ | $CH_3$ | $CH_3$ | $CH_3$ | |
| Q-8 | ($R_6$ = $CH_3$) | H | $CH_3$ | H | $CH_3$ | $CH_3$ | |
| Q-8 | ($R_6$ = $CH_3$) | H | $CH_3$ | $CH_3$ | $CH_3$ | $CH_3$ | |
| Q-9 | ($R_6$ = $CH_3$) | H | $CH_3$ | H | $CH_3$ | $CH_3$ | |
| Q-9 | ($R_6$ = $CH_3$) | H | $CH_3$ | $CH_3$ | $CH_3$ | $CH_3$ | |
| Q-14 | ($R_6$, $R_7$ = H) | H | $CH_3$ | H | $CH_3$ | $CH_3$ | |
| Q-14 | ($R_6$, $R_7$ = H) | H | $CH_3$ | $CH_3$ | $CH_3$ | $CH_3$ | |
| Q-15 | ($R_6$ = H, $R_7$ = $CH_3$) | H | $CH_3$ | H | $CH_3$ | $CH_3$ | |
| Q-15 | ($R_6$ = H, $R_7$ = $CH_3$) | H | $CH_3$ | $CH_3$ | $CH_3$ | $CH_3$ | |
| Q-16 | ($R_6$ = $CH_3$, $R_7$ = H) | H | $CH_3$ | H | $CH_3$ | $CH_3$ | |
| Q-16 | ($R_6$ = $CH_3$, $R_7$ = H) | H | $CH_3$ | $CH_3$ | $CH_3$ | $CH_3$ | |
| Q-34 | ($R_6$ = H, $R_{10}$, $R_{11}$ = $OCH_3$) | H | $CH_3$ | H | $CH_3$ | $CH_3$ | |
| Q-34 | ($R_6$ = H, $R_{10}$, $R_{11}$ = $CH_3$) | H | $CH_3$ | $CH_3$ | $CH_3$ | $CH_3$ | |
| Q-43 | ($R_6$ = H) | H | $CH_3$ | H | $CH_3$ | $CH_3$ | |
| Q-43 | ($R_6$ = H) | H | $CH_3$ | $CH_3$ | $CH_3$ | $CH_3$ | |

TABLE XIII

GENERAL FORMULA XIII

| Q | | R | $R_1$ | $R_2$ | $X_1$ | m.p. °C. |
|---|---|---|---|---|---|---|
| Q-1 | ($R_6$, $R_7$ = H) | H | $CH_3$ | H | $CH_3$ | |
| Q-1 | ($R_6$, $R_7$ = H) | H | $CH_3$ | H | $OCH_3$ | |
| Q-2 | ($R_6$, $R_7$ = H) | H | $CH_3$ | H | $CH_3$ | |
| Q-2 | ($R_6$, $R_7$ = H) | H | $CH_3$ | H | $OCH_3$ | |
| Q-3 | ($R_6$, $R_7$ = H) | H | $CH_3$ | H | $OCH_3$ | |
| Q-4 | ($R_6$, $R_7$ = H) | H | $CH_3$ | H | $OCH_3$ | |
| Q-7 | ($R_8$ = H) | H | $CH_3$ | H | $OCH_3$ | |
| Q-7 | ($R_8$ = $CH_3$) | H | $CH_3$ | H | $CH_3$ | |
| Q-7 | ($R_8$ = $CH_3$) | H | $CH_3$ | $CH_3$ | $OCH_3$ | |
| Q-7 | ($R_8$ = $SCH_3$) | H | $CH_3$ | H | $CH_3$ | |
| Q-7 | ($R_8$ = $SCH_3$) | H | $CH_3$ | $CH_3$ | $OCH_3$ | |
| Q-8 | ($R_6$ = $CH_3$) | H | $CH_3$ | H | $CH_3$ | |
| Q-8 | ($R_6$ = $CH_3$) | H | $CH_3$ | $CH_3$ | $OCH_3$ | |
| Q-9 | ($R_6$ = $CH_3$) | H | $CH_3$ | H | $OCH_3$ | |
| Q-9 | ($R_6$ = $CH_3$) | H | $CH_3$ | $CH_3$ | $CH_3$ | |
| Q-14 | ($R_6$, $R_7$ = H) | H | $CH_3$ | H | $CH_3$ | |
| Q-14 | ($R_6$, $R_7$ = H) | H | $CH_3$ | $CH_3$ | $OCH_3$ | |
| Q-16 | ($R_6$ = $CH_3$, $R_7$ = H) | H | $CH_3$ | H | $CH_3$ | |
| Q-16 | ($R_6$ = $CH_3$, $R_7$ = H) | H | $CH_3$ | $CH_3$ | $OCH_3$ | |
| Q-34 | ($R_6$ = H, $R_{10}$, $R_{11}$ = $CH_3$) | H | $CH_3$ | H | $CH_3$ | |
| Q-34 | ($R_6$ = H, $R_{10}$, $R_{11}$ = $OCH_3$) | H | $CH_3$ | $CH_3$ | $OCH_3$ | |
| Q-43 | ($R_6$ = $CH_3$) | H | $CH_3$ | H | $CH_3$ | |
| Q-43 | ($R_6$ = H) | H | $CH_3$ | $CH_3$ | $OCH_3$ | |

TABLE XIV

General Formula XIV

| Q | | R | $R_1$ | $R_2$ | $X_1$ | m.p. °C. |
|---|---|---|---|---|---|---|
| Q-1 | ($R_6$, $R_7$ = H) | H | $CH_3$ | H | $CH_3$ | |
| Q-1 | ($R_6$, $R_7$ = H) | H | $CH_3$ | H | $OCH_3$ | |
| Q-2 | ($R_6$, $R_7$ = H) | H | $CH_3$ | H | $CH_3$ | |

TABLE XIV-continued

General Formula XIV

| Q | | R | $R_1$ | $R_2$ | $X_1$ | m.p. °C. |
|---|---|---|---|---|---|---|
| Q-2 | ($R_6$, $R_7$ = H) | H | $CH_3$ | H | $OCH_3$ | |
| Q-3 | ($R_6$, $R_7$ = H) | H | $CH_3$ | H | $OCH_3$ | |
| Q-4 | ($R_6$, $R_7$ = H) | H | $CH_3$ | H | $OCH_3$ | |
| Q-7 | ($R_8$ = H) | H | $CH_3$ | H | $OCH_3$ | |
| Q-7 | ($R_8$ = $CH_3$) | H | $CH_3$ | H | $CH_3$ | |
| Q-7 | ($R_8$ = $CH_3$) | H | $CH_3$ | $CH_3$ | $OCH_3$ | |
| Q-7 | ($R_8$ = $SCH_3$) | H | $CH_3$ | H | $CH_3$ | |
| Q-7 | ($R_8$ = $SCH_3$) | H | $CH_3$ | $CH_3$ | $OCH_3$ | |
| Q-8 | ($R_6$ = $CH_3$) | H | $CH_3$ | H | $CH_3$ | |
| Q-8 | ($R_6$ = $CH_3$) | H | $CH_3$ | $CH_3$ | $OCH_3$ | |
| Q-9 | ($R_6$ = $CH_3$) | H | $CH_3$ | H | $OCH_3$ | |
| Q-9 | ($R_6$ = $CH_3$) | H | $CH_3$ | $CH_3$ | $CH_3$ | |
| Q-14 | ($R_6$, $R_7$ = H) | H | $CH_3$ | H | $CH_3$ | |
| Q-14 | ($R_6$, $R_7$ = H) | H | $CH_3$ | $CH_3$ | $OCH_3$ | |
| Q-16 | ($R_6$ = $CH_3$, $R_7$ = H) | H | $CH_3$ | H | $CH_3$ | |
| Q-16 | ($R_6$ = $CH_3$, $R_7$ = H) | H | $CH_3$ | $CH_3$ | $OCH_3$ | |
| Q-34 | ($R_6$ = H, $R_{10}$, $R_{11}$ = $CH_3$) | H | $CH_3$ | H | $CH_3$ | |
| Q-34 | ($R_6$ = H, $R_{10}$, $R_{11}$ = $OCH_3$) | H | $CH_3$ | $CH_3$ | $OCH_3$ | |
| Q-43 | ($R_6$ = $CH_3$) | H | $CH_3$ | H | $CH_3$ | |
| Q-43 | ($R_6$ = H) | H | $CH_3$ | $CH_3$ | $OCH_3$ | |

TABLE XV

General Formula XV

| Q | | R | $R_1$ | $R_2$ | $X_3$ | m.p. °C. |
|---|---|---|---|---|---|---|
| Q-1 | ($R_6$, $R_7$ = H) | H | $CH_3$ | H | $CH_3$ | |
| Q-1 | ($R_6$, $R_7$ = H) | H | $CH_3$ | H | $OCH_3$ | |
| Q-2 | ($R_6$, $R_7$ = H) | H | $CH_3$ | H | $CH_3$ | |
| Q-2 | ($R_6$, $R_7$ = H) | H | $CH_3$ | H | $OCH_3$ | |
| Q-3 | ($R_6$, $R_7$ = H) | H | $CH_3$ | H | $OCH_3$ | |
| Q-4 | ($R_6$, $R_7$ = H) | H | $CH_3$ | H | $OCH_3$ | |
| Q-7 | ($R_8$ = H) | H | $CH_3$ | H | $OCH_3$ | |
| Q-7 | ($R_8$ = $CH_3$) | H | $CH_3$ | H | $CH_3$ | |
| Q-7 | ($R_8$ = $CH_3$) | H | $CH_3$ | $CH_3$ | $OCH_3$ | |
| Q-7 | ($R_8$ = $SCH_3$) | H | $CH_3$ | H | $CH_3$ | |
| Q-7 | ($R_8$ = $SCH_3$) | H | $CH_3$ | $CH_3$ | $OCH_3$ | |
| Q-8 | ($R_6$ = $CH_3$) | H | $CH_3$ | H | $CH_3$ | |
| Q-8 | ($R_6$ = $CH_3$) | H | $CH_3$ | $CH_3$ | $OCH_3$ | |
| Q-9 | ($R_6$ = $CH_3$) | H | $CH_3$ | H | $OCH_3$ | |
| Q-9 | ($R_6$ = $CH_3$) | H | $CH_3$ | $CH_3$ | $CH_3$ | |
| Q-14 | ($R_6$, $R_7$ = H) | H | $CH_3$ | H | $CH_3$ | |
| Q-14 | ($R_6$, $R_7$ = H) | H | $CH_3$ | $CH_3$ | $OCH_3$ | |
| Q-16 | ($R_6$ = $CH_3$, $R_7$ = H) | H | $CH_3$ | H | $CH_3$ | |
| Q-16 | ($R_6$ = $CH_3$, $R_7$ = H) | H | $CH_3$ | $CH_3$ | $OCH_3$ | |
| Q-34 | ($R_6$ = H, $R_{10}$, $R_{11}$ = $CH_3$) | H | $CH_3$ | H | $CH_3$ | |
| Q-34 | ($R_6$ = H, $R_{10}$, $R_{11}$ = $OCH_3$) | H | $CH_3$ | $CH_3$ | $OCH_3$ | |
| Q-43 | ($R_6$ = $CH_3$) | H | $CH_3$ | H | $CH_3$ | |
| Q-43 | ($R_6$ = H) | H | $CH_3$ | $CH_3$ | $OCH_3$ | |

TABLE XVI

General Formula XVI

| Q | | R | $R_1$ | $R_2$ | $X_3$ | m.p. °C. |
|---|---|---|---|---|---|---|
| Q-1 | ($R_6$, $R_7$ = H) | H | $CH_3$ | H | $CH_3$ | |
| Q-1 | ($R_6$, $R_7$ = H) | H | $CH_3$ | H | $OCH_3$ | |
| Q-2 | ($R_6$, $R_7$ = H) | H | $CH_3$ | H | $CH_3$ | |
| Q-2 | ($R_6$, $R_7$ = H) | H | $CH_3$ | H | $OCH_3$ | |
| Q-3 | ($R_6$, $R_7$ = H) | H | $CH_3$ | H | $OCH_3$ | |
| Q-4 | ($R_6$, $R_7$ = H) | H | $CH_3$ | H | $OCH_3$ | |
| Q-7 | ($R_8$ = H) | H | $CH_3$ | H | $OCH_3$ | |
| Q-7 | ($R_8$ = $CH_3$) | H | $CH_3$ | H | $CH_3$ | |
| Q-7 | ($R_8$ = $CH_3$) | H | $CH_3$ | $CH_3$ | $OCH_3$ | |
| Q-7 | ($R_8$ = $SCH_3$) | H | $CH_3$ | H | $CH_3$ | |
| Q-7 | ($R_8$ = $SCH_3$) | H | $CH_3$ | $CH_3$ | $OCH_3$ | |
| Q-8 | ($R_6$ = $CH_3$) | H | $CH_3$ | H | $CH_3$ | |
| Q-8 | ($R_6$ = $CH_3$) | H | $CH_3$ | $CH_3$ | $OCH_3$ | |
| Q-9 | ($R_6$ = $CH_3$) | H | $CH_3$ | H | $OCH_3$ | |
| Q-9 | ($R_6$ = $CH_3$) | H | $CH_3$ | $CH_3$ | $CH_3$ | |
| Q-14 | ($R_6$, $R_7$ = H) | H | $CH_3$ | H | $CH_3$ | |
| Q-14 | ($R_6$, $R_7$ = H) | H | $CH_3$ | $CH_3$ | $OCH_3$ | |
| Q-16 | ($R_6$ = $CH_3$, $R_7$ = H) | H | $CH_3$ | H | $CH_3$ | |
| Q-16 | ($R_6$ = $CH_3$, $R_7$ = H) | H | $CH_3$ | $CH_3$ | $OCH_3$ | |
| Q-34 | ($R_6$ = H, $R_{10}$, $R_{11}$ = $CH_3$) | H | $CH_3$ | H | $CH_3$ | |
| Q-34 | ($R_6$ = H, $R_{10}$, $R_{11}$ = $CH_3$) | H | $CH_3$ | $CH_3$ | $OCH_3$ | |
| Q-43 | ($R_6$ = $CH_3$) | H | $CH_3$ | H | $CH_3$ | |

TABLE XVI-continued

General Formula XVI

| Q | | R | $R_1$ | $R_2$ | $X_3$ | m.p. °C. |
|---|---|---|---|---|---|---|
| Q-43 | ($R_6$ = H) | H | $CH_3$ | $CH_3$ | $OCH_3$ | |

TABLE XVII

General Formula XVII

| Q | | R | $R_1$ | $R_2$ | $X_1$ | $Y_2$ | m.p. °C. |
|---|---|---|---|---|---|---|---|
| Q-1 | ($R_6, R_7$ = H) | H | $CH_3$ | H | $CH_3$ | $CH_3$ | |
| Q-1 | ($R_6, R_7$ = H) | H | $CH_3$ | $CH_3$ | $CH_3$ | H | |
| Q-2 | ($R_6, R_7$ = H) | H | $CH_3$ | H | $CH_3$ | $CH_3$ | |
| Q-2 | ($R_6, R_7$ = H) | H | $CH_3$ | H | $OCH_3$ | $CH_3$ | |
| Q-3 | ($R_6, R_7$ = H) | H | $CH_3$ | H | $OCH_3$ | $CH_3$ | |
| Q-4 | ($R_6, R_7$ = H) | H | $CH_3$ | H | $CH_3$ | $CH_3$ | |
| Q-7 | ($R_8$ = H) | H | $CH_3$ | H | $OCH_3$ | $CH_3$ | |
| Q-7 | ($R_8$ = H) | $CH_3$ | H | $CH_3$ | H | | |
| Q-7 | ($R_8$ = $CH_3$) | H | $CH_3$ | H | $OCH_3$ | $CH_3$ | |
| Q-7 | ($R_8$ = $CH_3$) | H | $CH_3$ | H | $CH_3$ | $CH_3$ | |
| Q-7 | ($R_8$ = $SCH_3$) | H | $CH_3$ | $CH_3$ | $CH_3$ | $CH_3$ | |
| Q-7 | ($R_8$ = $SCH_3$) | H | $CH_3$ | $CH_3$ | $OCH_3$ | $CH_3$ | |
| Q-8 | ($R_6$ = H) | H | $CH_3$ | H | $OCH_3$ | $CH_3$ | |
| Q-8 | ($R_6$ = H) | H | $CH_3$ | H | $CH_3$ | H | |
| Q-8 | ($R_6$ = $CH_3$) | H | $CH_3$ | H | $OCH_3$ | $CH_3$ | |
| Q-8 | ($R_6$ = $CH_3$) | H | $CH_3$ | H | $CH_3$ | H | |
| Q-9 | ($R_6$ = $CH_3$) | H | $CH_3$ | H | $OCH_3$ | $CH_3$ | |
| Q-14 | ($R_6, R_7$ = H) | H | $CH_3$ | H | $OCH_3$ | $CH_3$ | |
| Q-14 | ($R_6, R_7$ = H) | H | $CH_3$ | H | $CH_3$ | $CH_3$ | |
| Q-15 | ($R_6$ = H, $R_7$ = $CH_3$) | H | $CH_3$ | H | $OCH_3$ | $CH_3$ | |
| Q-16 | ($R_6$ = $CH_3$, $R_7$ = H) | H | $CH_3$ | H | $CH_3$ | $CH_3$ | |
| Q-34 | ($R_6$ = H, $R_{10}, R_{11}$ = $OCH_3$) | H | $CH_3$ | H | $OCH_3$ | $CH_3$ | |
| Q-43 | ($R_6$ = H) | H | $CH_3$ | H | $OCH_3$ | $CH_3$ | |

TABLE XVIII

General Formula XVIII

| Q | | R | $R_1$ | $R_2$ | $X_1$ | $Y_2$ | m.p. °C. |
|---|---|---|---|---|---|---|---|
| Q-1 | ($R_6, R_7$ = H) | H | $CH_3$ | H | $CH_3$ | $CH_3$ | |
| Q-1 | ($R_6, R_7$ = H) | H | $CH_3$ | $CH_3$ | $CH_3$ | H | |
| Q-2 | ($R_6, R_7$ = H) | H | $CH_3$ | H | $CH_3$ | $CH_3$ | |
| Q-2 | ($R_6, R_7$ = H) | H | $CH_3$ | H | $OCH_3$ | $CH_3$ | |
| Q-3 | ($R_6, R_7$ = H) | H | $CH_3$ | H | $OCH_3$ | $CH_3$ | |
| Q-4 | ($R_6, R_7$ = H) | H | $CH_3$ | H | $CH_3$ | $CH_3$ | |
| Q-7 | ($R_8$ = H) | H | $CH_3$ | H | $OCH_3$ | $CH_3$ | |
| Q-7 | ($R_8$ = H) | H | $CH_3$ | H | $CH_3$ | H | |
| Q-7 | ($R_8$ = $CH_3$) | H | $CH_3$ | H | $OCH_3$ | $CH_3$ | |
| Q-7 | ($R_8$ = $CH_3$) | H | $CH_3$ | H | $CH_3$ | $CH_3$ | |
| Q-7 | ($R_8$ = $SCH_3$) | H | $CH_3$ | $CH_3$ | $CH_3$ | $CH_3$ | |
| Q-7 | ($R_8$ = $SCH_3$) | H | $CH_3$ | $CH_3$ | $OCH_3$ | $CH_3$ | |
| Q-8 | ($R_6$ = H) | H | $CH_3$ | H | $OCH_3$ | $CH_3$ | |
| Q-8 | ($R_6$ = H) | H | $CH_3$ | H | $CH_3$ | H | |
| Q-8 | ($R_6$ = $CH_3$) | H | $CH_3$ | H | $OCH_3$ | $CH_3$ | |
| Q-8 | ($R_6$ = $CH_3$) | H | $CH_3$ | H | $CH_3$ | H | |
| Q-9 | ($R_6$ = $CH_3$) | H | $CH_3$ | H | $OCH_3$ | $CH_3$ | |
| Q-14 | ($R_6, R_7$ = H) | H | $CH_3$ | H | $OCH_3$ | $CH_3$ | |
| Q-14 | ($R_6, R_7$ = H) | H | $CH_3$ | H | $CH_3$ | $CH_3$ | |
| Q-15 | ($R_6$ = H, $R_7$ = $CH_3$) | H | $CH_3$ | H | $OCH_3$ | $CH_3$ | |
| Q-16 | ($R_6$ = $CH_3$, $R_7$ = H) | H | $CH_3$ | H | $CH_3$ | $CH_3$ | |
| Q-34 | ($R_6$ = H, $R_{10}, R_{11}$ = $OCH_3$) | H | $CH_3$ | H | $OCH_3$ | $CH_3$ | |
| Q-43 | ($R_6$ = H) | H | $CH_3$ | H | $OCH_3$ | $CH_3$ | |

TABLE XIX

General Formula XIX

| Q | | R | $R_1$ | $R_2$ | Z | $X_4$ | $Y_4$ | m.p. °C. |
|---|---|---|---|---|---|---|---|---|
| Q-1 | ($R_6, R_7$ = H) | H | $CH_3$ | H | CH | $CH_3$ | Cl | |
| Q-1 | ($R_6, R_7$ = H) | H | $CH_3$ | $CH_3$ | CH | Cl | $OCH_3$ | |
| Q-2 | ($R_6, R_7$ = H) | H | $CH_3$ | H | CH | $CH_3$ | $OC_2H_5$ | |
| Q-2 | ($R_6, R_7$ = H) | H | $CH_3$ | H | CH | $OCH_3$ | $CH_3$ | |
| Q-3 | ($R_6, R_7$ = H) | H | $CH_3$ | H | CH | $OCH_2CH_3$ | $CH_3$ | |
| Q-4 | ($R_6, R_7$ = H) | H | $CH_3$ | H | N | $CH_3$ | $CH_3$ | |
| Q-7 | ($R_8$ = H) | H | $CH_3$ | H | CH | $OCH_3$ | $CH_3$ | |
| Q-7 | ($R_8$ = H) | H | $CH_3$ | H | N | $CH_3$ | $CH_3$ | |

TABLE XIX-continued

General Formula XIX

| Q | | R | $R_1$ | $R_2$ | Z | $X_4$ | $Y_4$ | m.p. °C. |
|---|---|---|---|---|---|---|---|---|
| Q-7 | ($R_8$ = $CH_3$) | H | $CH_3$ | H | CH | $OCH_3$ | $CH_3$ | |
| Q-7 | ($R_8$ = $CH_3$) | H | $CH_3$ | H | CH | $CH_3$ | $CH_3$ | |
| Q-7 | ($R_8$ = $SCH_3$) | H | $CH_3$ | $CH_3$ | CH | $CH_3$ | $CH_3$ | |
| Q-7 | ($R_8$ = $SCH_3$) | H | $CH_3$ | $CH_3$ | CH | $OCH_3$ | $CH_3$ | |
| Q-8 | ($R_6$ = H) | H | $CH_3$ | H | CH | $OCH_3$ $CH_3$ | | |
| Q-8 | ($R_6$ = H) | H | $CH_3$ | H | N | $CH_3$ | $CH_3$ | |
| Q-8 | ($R_6$ = $CH_3$) | H | $CH_3$ | H | CH | $OCH_3$ | $CH_3$ | |
| Q-8 | ($R_6$ = $CH_3$) | H | $CH_3$ | H | N | $CH_3$ | $CH_3$ | |
| Q-9 | ($R_6$ = $CH_3$) | H | $CH_3$ | | CH | $OCH_3$ | $CH_3$ | |
| Q-14 | ($R_6$, $R_7$ = H) | H | $CH_3$ | H | N | $OCH_3$ | $CH_3$ | |
| Q-14 | ($R_6$, $R_7$ = H) | H | $CH_3$ | H | CH | $CH_3$ | $CH_3$ | |
| Q-15 | ($R_6$ = H, $R_7$ = $CH_3$) | H | $CH_3$ | H | CH | $OCH_3$ | $CH_3$ | |
| Q-16 | ($R_6$ = $CH_3$, $R_7$ = H) | H | $CH_3$ | H | CH | $CH_3$ | $CH_3$ | |
| Q-34 | ($R_6$ = H, $R_{10}$, $R_{11}$ = $OCH_3$) | H | $CH_3$ | H | CH | $OCH_3$ | $CH_3$ | |
| Q-43 | ($R_6$ = H) | H | $CH_3$ | H | CH | $CH_2OCH_3$ | $CH_3$ | |

TABLE XX

General Formula XX

| Q | | R | $R_1$ | $R_2$ | Z | $X_4$ | $Y_4$ | m.p. °C. |
|---|---|---|---|---|---|---|---|---|
| Q-1 | ($R_6$, $R_7$ = H) | H | $CH_3$ | H | CH | $CH_3$ | Cl | |
| Q-1 | ($R_6$, $R_7$ = H) | H | $CH_3$ | $CH_3$ | CH | Cl | $OCH_3$ | |
| Q-2 | ($R_6$, $R_7$ = H) | H | $CH_3$ | H | CH | $CH_3$ | $OC_2H_5$ | |
| Q-2 | ($R_6$, $R_7$ = H) | H | $CH_3$ | H | CH | $OCH_2CH_3$ | $CH_3$ | |
| Q-3 | ($R_6$, $R_7$ = H) | H | $CH_3$ | H | CH | $OCH_3$ | $CH_3$ | |
| Q-4 | ($R_6$, $R_7$ = H) | H | $CH_3$ | H | N | $CH_3$ | $CH_3$ | |
| Q-7 | ($R_8$ = H) | H | $CH_3$ | H | CH | $OCH_3$ | $CH_3$ | |
| Q-7 | ($R_8$ = H) | H | $CH_3$ | H | N | $CH_3$ | $CH_3$ | |
| Q-7 | ($R_8$ = $CH_3$) | H | $CH_3$ | H | CH | $OCH_3$ | $CH_3$ | |
| Q-7 | ($R_8$ = $CH_3$) | H | $CH_3$ | H | CH | $CH_3$ | $CH_3$ | |
| Q-7 | ($R_8$ = $SCH_3$) | H | $CH_3$ | $CH_3$ | CH | $CH_3$ | $CH_3$ | |
| Q-7 | ($R_8$ = $SCH_3$) | H | $CH_3$ | $CH_3$ | CH | $OCH_3$ | $CH_3$ | |
| Q-8 | ($R_6$ = H) | H | $CH_3$ | H | CH | $OCH_3$ $CH_3$ | | |
| Q-8 | ($R_6$ = H) | H | $CH_3$ | H | N | $CH_3$ | $CH_3$ | |
| Q-8 | ($R_6$ = $CH_3$) | H | $CH_3$ | H | CH | $OCH_3$ | $CH_3$ | |
| Q-8 | ($R_6$ = $CH_3$) | H | $CH_3$ | H | CH | $CH_3$ | $CH_3$ | |
| Q-9 | ($R_6$ = $CH_3$) | H | $CH_3$ | H | CH | $OCH_3$ | $CH_3$ | |
| Q-14 | ($R_6$, $R_7$ = H) | H | $CH_3$ | H | N | $OCH_3$ | $CH_3$ | |
| Q-14 | ($R_6$, $R_7$ = H) | H | $CH_3$ | H | CH | $CH_3$ | $CH_3$ | |
| Q-15 | ($R_6$ = H, $R_7$ = $CH_3$) | H | $CH_3$ | H | CH | $OCH_3$ | $CH_3$ | |
| Q-16 | ($R_6$ = $CH_3$, $R_7$ = H) | H | $CH_3$ | H | CH | $CH_3$ | $CH_3$ | |
| Q-34 | ($R_6$ = H, $R_{10}$, $R_{11}$ = $OCH_3$) | H | $CH_3$ | H | CH | $OCH_3$ | $CH_3$ | |
| Q-43 | ($R_6$ = H) | H | $CH_3$ | H | CH | $CH_2OCH_3$ | $CH_3$ | |

TABLE XXI

General Formula XXI

| Q | R | $R_2$ | $R_{14}$ | $R_6$ | $R_7$ | X | Y | Z | m.p. °C. |
|---|---|---|---|---|---|---|---|---|---|
| Q-1 | H | H | H | H | H | $CH_3$ | $OCH_3$ | CH | |
| Q-1 | H | H | $CH_3$ | H | H | $CH_3$ | $CH_3$ | N | |
| Q-1 | H | H | $CH_2CH_2CH_3$ | H | H | $OCH_3$ | $OCH_3$ | N | |
| Q-1 | H | H | F | H | H | $OCH_3$ | $OCH_3$ | CH | |
| Q-1 | H | H | Cl | H | H | $OCH_3$ | $OCH_3$ | CH | |
| Q-1 | H | H | Cl | H | H | $OCH_3$ | $CH_3$ | N | |
| Q-1 | H | H | Br | H | H | $CH_3$ | $OCH_3$ | CH | |
| Q-1 | H | H | $NO_2$ | H | H | Cl | $OCH_3$ | CH | |
| Q-1 | H | H | $SCH_2CH_2F$ | H | H | $OCH_3$ | $OCH_3$ | CH | |
| Q-1 | H | H | $CH_2-CH=CH_2$ | H | H | $OCH_3$ | $CH_3$ | CH | |
| Q-1 | H | H | $CH_2-C\equiv CH$ | H | H | $CH_3$ | $CH_3$ | CH | |
| Q-1 | H | H | $CO_2CH_3$ | H | H | $CH_3$ | $OCH_3$ | N | |
| Q-1 | H | H | $CO_2CH_3$ | H | H | $OCH_3$ | $OCH_3$ | CH | |
| Q-1 | H | H | $CO_2CH_3$ | H | H | $CH_3$ | $OCH_3$ | CH | |
| Q-1 | H | H | $CO_2CH_2CH_3$ | H | H | $CH_3$ | $CH_3$ | CH | |
| Q-1 | H | H | $CO_2CH_2CH_2CH_3$ | H | H | $OCH_3$ | $OCH_3$ | CH | |
| Q-1 | H | H | $SCH_3$ | H | H | $CH_3$ | $CH_3$ | N | |
| Q-1 | H | H | $SOCH_3$ | H | H | $CH_3$ | $CH_3$ | CH | |
| Q-1 | H | H | $SO_2CH_3$ | H | H | $OCH_3$ | $OCH_3$ | CH | |
| Q-1 | H | H | $SO_2CH_2CH_3$ | H | H | $OCH_3$ | $OCH_3$ | N | |
| Q-1 | H | H | $SO_2N(CH_3)_2$ | H | H | $CH_3$ | $OCH_3$ | CH | |
| Q-1 | H | H | $SO_2N(CH_2CH_3)_2$ | H | H | $OCH_3$ | $OCH_3$ | CH | |
| Q-1 | $CH_3$ | H | $CO_2CH_3$ | H | H | $OCH_3$ | $OCH_3$ | CH | |
| Q-1 | H | H | Br | H | $CH_3$ | $OCH_3$ | $OCH_3$ | CH | |
| Q-1 | H | $CH_3$ | Cl | H | H | $OCH_3$ | $OCH_3$ | N | |
| Q-2 | H | H | H | H | H | $CH_3$ | $OCH_3$ | CH | |

TABLE XXI-continued

General Formula XXI

| | | | | | | | | |
|---|---|---|---|---|---|---|---|---|
| Q-2 | H | H | CH$_2$CH$_3$ | H | H | OCH$_3$ | OCH$_3$ | CH |
| Q-2 | H | H | F | H | H | CH$_3$ | CH$_3$ | CH |
| Q-2 | H | H | Cl | H | H | OCH$_3$ | OCH$_3$ | CH |
| Q-2 | H | H | Br | H | H | OCH$_3$ | CH$_3$ | CH |
| Q-2 | H | H | NO$_2$ | H | H | OCH$_3$ | OCH$_3$ | CH |
| Q-2 | H | H | SCH$_2$F | H | H | CH$_3$ | OCH$_3$ | CH |
| Q-2 | H | H | SCH$_2$F | H | H | OCH$_3$ | OCH$_3$ | CH |
| Q-2 | H | H | CH$_2$—CH=CH$_2$ | H | H | Cl | OCH$_3$ | CH |
| Q-2 | H | H | CH$_2$—C≡CH | H | H | OCH$_3$ | OCH$_3$ | CH |
| Q-2 | H | H | CO$_2$CH$_3$ | H | H | OCH$_3$ | OCH$_3$ | CH |
| Q-2 | H | H | CO$_2$CH$_3$ | H | H | OCH$_3$ | CH$_3$ | CH |
| Q-2 | H | H | CO$_2$CH$_3$ | H | H | CH$_3$ | CH$_3$ | N |
| Q-2 | H | H | CO$_2$CH$_2$CH$_3$ | H | H | OCH$_3$ | OCH$_3$ | CH |
| Q-2 | H | H | SCH$_3$ | H | H | CH$_3$ | OCH$_3$ | CH |
| Q-2 | H | H | SOCH$_3$ | H | H | CH$_3$ | CH$_3$ | CH |
| Q-2 | H | H | SO$_2$CH$_3$ | H | H | OCH$_3$ | OCH$_3$ | CH |
| Q-2 | H | H | SO$_2$N(CH$_3$)$_2$ | H | H | OCH$_3$ | CH$_3$ | CH |
| Q-2 | H | H | SO$_2$N(CH$_3$)$_2$ | H | H | OCH$_3$ | CH$_3$ | N |
| Q-2 | H | H | SO$_2$N(CH$_2$CH$_3$)$_2$ | H | H | OCH$_3$ | OCH$_3$ | CH |
| Q-2 | CH$_3$ | H | Cl | H | H | CH$_3$ | CH$_3$ | CH |
| Q-2 | H | CH$_3$ | Br | H | H | OCH$_3$ | OCH$_3$ | N |
| Q-2 | H | Cl | CO$_2$CH$_3$ | H | H | CH$_3$ | OCH$_3$ | CH |
| Q-3 | H | H | H | H | H | CH$_3$ | OCH$_3$ | CH |
| Q-3 | H | H | CH$_3$ | H | H | CH$_3$ | CH$_3$ | N |
| Q-3 | H | H | CH$_2$CH$_2$CH$_3$ | H | H | OCH$_3$ | OCH$_3$ | N |
| Q-3 | H | H | F | H | H | OCH$_3$ | OCH$_3$ | CH |
| Q-3 | H | H | Cl | H | H | OCH$_3$ | OCH$_3$ | CH |
| Q-3 | H | H | Cl | H | H | OCH$_3$ | CH$_3$ | N |
| Q-3 | H | H | Br | H | H | CH$_3$ | OCH$_3$ | CH |
| Q-3 | H | H | NO$_2$ | H | H | Cl | OCH$_3$ | CH |
| Q-3 | H | H | SCH$_2$CH$_2$F | H | H | OCH$_3$ | OCH$_3$ | CH |
| Q-3 | H | H | CH$_2$—CH=CH$_2$ | H | H | OCH$_3$ | CH$_3$ | CH |
| Q-3 | H | H | CH$_2$—C≡CH | H | H | CH$_3$ | CH$_3$ | CH |
| Q-3 | H | H | CO$_2$CH$_3$ | H | H | CH$_3$ | OCH$_3$ | N |
| Q-3 | H | H | CO$_2$CH$_3$ | H | H | OCH$_3$ | OCH$_3$ | CH |
| Q-3 | H | H | CO$_2$CH$_3$ | H | H | CH$_3$ | OCH$_3$ | CH |
| Q-3 | H | H | CO$_2$CH$_2$CH$_3$ | H | H | CH$_3$ | CH$_3$ | CH |
| Q-3 | H | H | CO$_2$CH$_2$CH$_2$CH$_3$ | H | H | OCH$_3$ | OCH$_3$ | CH |
| Q-3 | H | H | SCH$_3$ | H | H | CH$_3$ | CH$_3$ | N |
| Q-3 | H | H | SOCH$_3$ | H | H | CH$_3$ | CH$_3$ | CH |
| Q-3 | H | H | SO$_2$CH$_3$ | H | H | OCH$_3$ | OCH$_3$ | CH |
| Q-3 | H | H | SO$_2$CH$_2$CH$_3$ | H | H | OCH$_3$ | OCH$_3$ | N |
| Q-3 | H | H | SO$_2$N(CH$_3$)$_2$ | H | H | CH$_3$ | OCH$_3$ | CH |
| Q-3 | H | H | SO$_2$N(CH$_2$CH$_3$)$_2$ | H | H | OCH$_3$ | OCH$_3$ | CH |
| Q-3 | CH$_3$ | H | CO$_2$CH$_3$ | H | H | OCH$_3$ | OCH$_3$ | CH |
| Q-3 | H | H | Br | H | CH$_3$ | OCH$_3$ | OCH$_3$ | CH |
| Q-3 | H | CH$_3$ | Cl | H | H | OCH$_3$ | OCH$_3$ | N |
| Q-4 | H | H | H | H | H | CH$_3$ | OCH$_3$ | CH |
| Q-4 | H | H | CH$_2$CH$_3$ | H | H | OCH$_3$ | OCH$_3$ | CH |
| Q-4 | H | H | F | H | H | CH$_3$ | CH$_3$ | CH |
| Q-4 | H | H | Cl | H | H | OCH$_3$ | OCH$_3$ | CH |
| Q-4 | H | H | Br | H | H | OCH$_3$ | CH$_3$ | CH |
| Q-4 | H | H | NO$_2$ | H | H | OCH$_3$ | OCH$_3$ | CH |
| Q-4 | H | H | SCH$_2$F | H | H | CH$_3$ | OCH$_3$ | CH |
| Q-4 | H | H | SCH$_2$F | H | H | OCH$_3$ | OCH$_3$ | CH |
| Q-4 | H | H | CH$_2$—CH=CH$_2$ | H | H | Cl | OCH$_3$ | CH |
| Q-4 | H | H | CH$_2$—C≡CH | H | H | OCH$_3$ | OCH$_3$ | CH |
| Q-4 | H | H | CO$_2$CH$_3$ | H | H | OCH$_3$ | OCH$_3$ | CH |
| Q-4 | H | H | CO$_2$CH$_3$ | H | H | OCH$_3$ | CH$_3$ | CH |
| Q-4 | H | H | CO$_2$CH$_3$ | H | H | CH$_3$ | CH$_3$ | N |
| Q-4 | H | H | CO$_2$CH$_2$CH$_3$ | H | H | OCH$_3$ | OCH$_3$ | CH |
| Q-4 | H | H | SCH$_3$ | H | H | CH$_3$ | OCH$_3$ | CH |
| Q-4 | H | H | SOCH$_3$ | H | H | CH$_3$ | CH$_3$ | CH |
| Q-4 | H | H | SO$_2$CH$_3$ | H | H | OCH$_3$ | OCH$_3$ | CH |
| Q-4 | H | H | SO$_2$N(CH$_3$)$_2$ | H | H | OCH$_3$ | CH$_3$ | CH |
| Q-4 | H | H | SO$_2$N(CH$_3$)$_2$ | H | H | OCH$_3$ | CH$_3$ | N |
| Q-4 | H | H | SO$_2$N(CH$_2$CH$_3$)$_2$ | H | H | OCH$_3$ | OCH$_3$ | CH |
| Q-4 | CH$_3$ | H | Cl | H | H | CH$_3$ | CH$_3$ | CH |
| Q-4 | H | CH$_3$ | Br | H | H | OCH$_3$ | OCH$_3$ | N |
| Q-4 | H | Cl | CO$_2$CH$_3$ | H | H | CH$_3$ | OCH$_3$ | CH |
| Q-5 | H | H | H | H | H | CH$_3$ | OCH$_3$ | CH |
| Q-5 | H | H | CH$_3$ | H | H | CH$_3$ | CH$_3$ | N |
| Q-5 | H | H | CH$_2$CH$_2$CH$_3$ | H | H | OCH$_3$ | OCH$_3$ | N |
| Q-5 | H | H | F | H | H | OCH$_3$ | OCH$_3$ | CH |
| Q-5 | H | H | Cl | H | H | OCH$_3$ | OCH$_3$ | CH |
| Q-5 | H | H | Cl | H | H | OCH$_3$ | CH$_3$ | N |
| Q-5 | H | H | Br | H | H | CH$_3$ | OCH$_3$ | CH |
| Q-5 | H | H | NO$_2$ | H | H | Cl | OCH$_3$ | CH |
| Q-5 | H | H | SCH$_2$CH$_2$F | H | H | OCH$_3$ | OCH$_3$ | CH |
| Q-5 | H | H | CH$_2$—CH=CH$_2$ | H | H | OCH$_3$ | CH$_3$ | CH |
| Q-5 | H | H | CH$_2$—C≡CH | H | H | CH$_3$ | CH$_3$ | CH |

TABLE XXI-continued
General Formula XXI

| Q | R | R$_2$ | R$_{14}$ | R$_8$ | R$_6$ | X | Y | Z | m.p. °C. |
|---|---|---|---|---|---|---|---|---|---|
| Q-5 | H | H | CO$_2$CH$_3$ | H | H | CH$_3$ | OCH$_3$ | N | |
| Q-5 | H | H | CO$_2$CH$_3$ | H | H | OCH$_3$ | OCH$_3$ | CH | |
| Q-5 | H | H | CO$_2$CH$_3$ | H | H | CH$_3$ | OCH$_3$ | CH | |
| Q-5 | H | H | CO$_2$CH$_2$CH$_3$ | H | H | CH$_3$ | CH$_3$ | CH | |
| Q-5 | H | H | CO$_2$CH$_2$CH$_2$CH$_3$ | H | H | OCH$_3$ | OCH$_3$ | CH | |
| Q-5 | H | H | SCH$_3$ | H | H | CH$_3$ | CH$_3$ | N | |
| Q-5 | H | H | SOCH$_3$ | H | H | CH$_3$ | CH$_3$ | CH | |
| Q-5 | H | H | SO$_2$CH$_3$ | H | H | OCH$_3$ | OCH$_3$ | CH | |
| Q-5 | H | H | SO$_2$CH$_2$CH$_3$ | H | H | OCH$_3$ | OCH$_3$ | N | |
| Q-5 | H | H | SO$_2$N(CH$_3$)$_2$ | H | H | CH$_3$ | OCH$_3$ | CH | |
| Q-5 | H | H | SO$_2$N(CH$_2$CH$_3$)$_2$ | H | H | OCH$_3$ | OCH$_3$ | CH | |
| Q-5 | CH$_3$ | H | CO$_2$CH$_3$ | H | H | OCH$_3$ | OCH$_3$ | CH | |
| Q-5 | H | H | Br | H | CH$_3$ | OCH$_3$ | OCH$_3$ | CH | |
| Q-5 | H | CH$_3$ | Cl | H | H | OCH$_3$ | OCH$_3$ | N | |
| Q-6 | H | H | H | H | H | CH$_3$ | OCH$_3$ | CH | |
| Q-6 | H | H | CH$_2$CH$_3$ | H | H | OCH$_3$ | OCH$_3$ | CH | |
| Q-6 | H | H | F | H | H | CH$_3$ | CH$_3$ | CH | |
| Q-6 | H | H | Cl | H | H | OCH$_3$ | OCH$_3$ | CH | |
| Q-6 | H | H | Br | H | H | OCH$_3$ | CH$_3$ | CH | |
| Q-6 | H | H | NO$_2$ | H | H | OCH$_3$ | OCH$_3$ | CH | |
| Q-6 | H | H | SCH$_2$F | H | H | CH$_3$ | OCH$_3$ | CH | |
| Q-6 | H | H | SCH$_2$F | H | H | OCH$_3$ | OCH$_3$ | CH | |
| Q-6 | H | H | CH$_2$—CH=CH$_2$ | H | H | Cl | OCH$_3$ | CH | |
| Q-6 | H | H | CH$_2$—C≡CH | H | H | OCH$_3$ | OCH$_3$ | CH | |
| Q-6 | H | H | CO$_2$CH$_3$ | H | H | OCH$_3$ | OCH$_3$ | CH | |
| Q-6 | H | H | CO$_2$CH$_3$ | H | H | OCH$_3$ | CH$_3$ | CH | |
| Q-6 | H | H | CO$_2$CH$_3$ | H | H | CH$_3$ | CH$_3$ | N | |
| Q-6 | H | H | CO$_2$CH$_2$CH$_3$ | H | H | OCH$_3$ | OCH$_3$ | CH | |
| Q-6 | H | H | SCH$_3$ | H | H | CH$_3$ | OCH$_3$ | CH | |
| Q-6 | H | H | SOCH$_3$ | H | H | CH$_3$ | CH$_3$ | CH | |
| Q-6 | H | H | SO$_2$CH$_3$ | H | H | OCH$_3$ | OCH$_3$ | CH | |
| Q-6 | H | H | SO$_2$N(CH$_3$)$_2$ | H | H | OCH$_3$ | CH$_3$ | CH | |
| Q-6 | H | H | SO$_2$N(CH$_3$)$_2$ | H | H | OCH$_3$ | CH$_3$ | N | |
| Q-6 | H | H | SO$_2$N(CH$_2$CH$_3$)$_2$ | H | H | OCH$_3$ | OCH$_3$ | CH | |
| Q-6 | CH$_3$ | H | Cl | H | H | CH$_3$ | CH$_3$ | CH | |
| Q-6 | H | CH$_3$ | Br | H | H | OCH$_3$ | OCH$_3$ | N | |
| Q-6 | H | Cl | CO$_2$CH$_3$ | H | H | CH$_3$ | OCH$_3$ | CH | |

| Q | R | R$_2$ | R$_{14}$ | R$_8$ | R$_6$ | X | Y | Z | m.p. °C. |
|---|---|---|---|---|---|---|---|---|---|
| Q-7 | H | H | H | H | — | CH$_3$ | OCH$_3$ | CH | |
| Q-7 | H | H | CH$_3$ | H | — | CH$_3$ | CH$_3$ | N | |
| Q-7 | H | H | CH$_2$CH$_2$CH$_3$ | H | — | OCH$_3$ | OCH$_3$ | N | |
| Q-7 | H | H | F | H | — | OCH$_3$ | OCH$_3$ | CH | |
| Q-7 | H | H | Cl | H | — | OCH$_3$ | OCH$_3$ | CH | |
| Q-7 | H | H | Cl | H | — | OCH$_3$ | CH$_3$ | N | |
| Q-7 | H | H | Br | H | — | CH$_3$ | OCH$_3$ | CH | |
| Q-7 | H | H | NO$_2$ | H | — | Cl | OCH$_3$ | CH | |
| Q-7 | H | H | SCH$_2$CH$_2$F | H | — | OCH$_3$ | OCH$_3$ | CH | |
| Q-7 | H | H | CH$_2$—CH=CH$_2$ | H | — | OCH$_3$ | CH$_3$ | CH | |
| Q-7 | H | H | CH$_2$—C≡CH | H | — | CH$_3$ | CH$_3$ | CH | |
| Q-7 | H | H | CO$_2$CH$_3$ | H | — | CH$_3$ | OCH$_3$ | N | |
| Q-7 | H | H | CO$_2$CH$_3$ | H | — | OCH$_3$ | OCH$_3$ | CH | |
| Q-7 | H | H | CO$_2$CH$_3$ | H | — | CH$_3$ | OCH$_3$ | CH | |
| Q-7 | H | H | CO$_2$CH$_2$CH$_3$ | H | — | CH$_3$ | CH$_3$ | CH | |
| Q-7 | H | H | CO$_2$CH$_2$CH$_2$CH$_3$ | H | — | OCH$_3$ | OCH$_3$ | CH | |
| Q-7 | H | H | SCH$_3$ | H | — | CH$_3$ | CH$_3$ | N | |
| Q-7 | H | H | SOCH$_3$ | H | — | CH$_3$ | CH$_3$ | CH | |
| Q-7 | H | H | SO$_2$CH$_3$ | H | — | OCH$_3$ | OCH$_3$ | CH | |
| Q-7 | H | H | SO$_2$CH$_2$CH$_3$ | H | — | OCH$_3$ | OCH$_3$ | N | |
| Q-7 | H | H | SO$_2$N(CH$_3$)$_2$ | H | — | CH$_3$ | OCH$_3$ | CH | |
| Q-7 | H | H | SO$_2$N(CH$_2$CH$_3$)$_2$ | H | — | OCH$_3$ | OCH$_3$ | CH | |
| Q-7 | CH$_3$ | H | CO$_2$CH$_3$ | H | — | OCH$_3$ | OCH$_3$ | CH | |
| Q-7 | H | H | Br | H | — | OCH$_3$ | OCH$_3$ | CH | |
| Q-7 | H | CH$_3$ | Cl | H | — | OCH$_3$ | OCH$_3$ | N | |
| Q-8 | H | H | H | — | H | CH$_3$ | OCH$_3$ | CH | |
| Q-8 | H | H | CH$_2$CH$_3$ | — | H | OCH$_3$ | OCH$_3$ | CH | |
| Q-8 | H | H | F | — | H | CH$_3$ | CH$_3$ | CH | |
| Q-8 | H | H | Cl | — | H | OCH$_3$ | OCH$_3$ | CH | |
| Q-8 | H | H | Br | — | H | OCH$_3$ | CH$_3$ | CH | |
| Q-8 | H | H | NO$_2$ | — | H | OCH$_3$ | OCH$_3$ | CH | |
| Q-8 | H | H | SCH$_2$F | — | H | CH$_3$ | OCH$_3$ | CH | |
| Q-8 | H | H | SCH$_2$F | — | H | OCH$_3$ | OCH$_3$ | CH | |
| Q-8 | H | H | CH$_2$—CH=CH$_2$ | — | H | Cl | OCH$_3$ | CH | |
| Q-8 | H | H | CH$_2$—C≡CH | — | H | OCH$_3$ | OCH$_3$ | CH | |
| Q-8 | H | H | CO$_2$CH$_3$ | — | H | OCH$_3$ | OCH$_3$ | CH | |
| Q-8 | H | H | CO$_2$CH$_3$ | — | H | OCH$_3$ | CH$_3$ | CH | |
| Q-8 | H | H | CO$_2$CH$_3$ | — | H | CH$_3$ | CH$_3$ | N | |
| Q-8 | H | H | CO$_2$CH$_2$CH$_3$ | — | H | OCH$_3$ | OCH$_3$ | CH | |
| Q-8 | H | H | SCH$_3$ | — | H | CH$_3$ | OCH$_3$ | CH | |
| Q-8 | H | H | SOCH$_3$ | — | H | CH$_3$ | CH$_3$ | CH | |
| Q-8 | H | H | SO$_2$CH$_3$ | — | H | OCH$_3$ | OCH$_3$ | CH | |

TABLE XXI-continued

General Formula XXI

| Q | R | R$_2$ | R$_{14}$ | R$_6$ | X | Y | Z | m.p. °C. |
|---|---|---|---|---|---|---|---|---|
| Q-8 | H | H | SO$_2$N(CH$_3$)$_2$ | — | H | OCH$_3$ | CH$_3$ | CH | |
| Q-8 | H | H | SO$_2$N(CH$_3$)$_2$ | — | H | OCH$_3$ | CH$_3$ | N | |
| Q-8 | H | H | SO$_2$N(CH$_2$CH$_3$)$_2$ | — | H | OCH$_3$ | OCH$_3$ | CH | |
| Q-8 | CH$_3$ | H | Cl | — | H | CH$_3$ | CH$_3$ | CH | |
| Q-8 | H | CH$_3$ | Br | — | H | OCH$_3$ | OCH$_3$ | N | |
| Q-8 | H | Cl | CO$_2$CH$_3$ | — | H | CH$_3$ | OCH$_3$ | CH | |
| Q-9 | H | H | H | H | CH$_3$ | OCH$_3$ | CH | |
| Q-9 | H | H | CH$_3$ | H | CH$_3$ | CH$_3$ | N | |
| Q-9 | H | H | CH$_2$CH$_2$CH$_3$ | H | OCH$_3$ | OCH$_3$ | N | |
| Q-9 | H | H | F | H | OCH$_3$ | OCH$_3$ | CH | |
| Q-9 | H | H | Cl | H | OCH$_3$ | OCH$_3$ | CH | |
| Q-9 | H | H | Cl | H | OCH$_3$ | CH$_3$ | N | |
| Q-9 | H | H | Br | H | CH$_3$ | OCH$_3$ | CH | |
| Q-9 | H | H | NO$_2$ | H | Cl | OCH$_3$ | CH | |
| Q-9 | H | H | SCH$_2$CH$_2$F | H | OCH$_3$ | OCH$_3$ | CH | |
| Q-9 | H | H | CH$_2$—CH=CH$_2$ | H | OCH$_3$ | CH$_3$ | CH | |
| Q-9 | H | H | CH$_2$—C≡CH | H | CH$_3$ | CH$_3$ | CH | |
| Q-9 | H | H | CO$_2$CH$_3$ | H | CH$_3$ | OCH$_3$ | N | |
| Q-9 | H | H | CO$_2$CH$_3$ | H | OCH$_3$ | OCH$_3$ | CH | |
| Q-9 | H | H | CO$_2$CH$_3$ | H | CH$_3$ | OCH$_3$ | CH | |
| Q-9 | H | H | CO$_2$CH$_2$CH$_3$ | H | CH$_3$ | CH$_3$ | CH | |
| Q-9 | H | H | CO$_2$CH$_2$CH$_2$CH$_3$ | H | OCH$_3$ | OCH$_3$ | CH | |
| Q-9 | H | H | SCH$_3$ | H | CH$_3$ | CH$_3$ | N | |
| Q-9 | H | H | SOCH$_3$ | H | CH$_3$ | CH$_3$ | CH | |
| Q-9 | H | H | SO$_2$CH$_3$ | H | OCH$_3$ | OCH$_3$ | CH | |
| Q-9 | H | H | SO$_2$CH$_2$CH$_3$ | H | OCH$_3$ | OCH$_3$ | N | |
| Q-9 | H | H | SO$_2$N(CH$_3$)$_2$ | H | CH$_3$ | OCH$_3$ | CH | |
| Q-9 | H | H | SO$_2$N(CH$_2$CH$_3$)$_2$ | H | OCH$_3$ | OCH$_3$ | CH | |
| Q-9 | CH$_3$ | H | CO$_2$CH$_3$ | H | OCH$_3$ | OCH$_3$ | CH | |
| Q-9 | H | H | Br | H | OCH$_3$ | OCH$_3$ | CH | |
| Q-9 | H | CH$_3$ | Cl | H | OCH$_3$ | OCH$_3$ | N | |
| Q-10 | H | H | H | H | CH$_3$ | OCH$_3$ | CH | |
| Q-10 | H | H | CH$_2$CH$_3$ | H | OCH$_3$ | OCH$_3$ | CH | |
| Q-10 | H | H | F | H | CH$_3$ | CH$_3$ | CH | |
| Q-10 | H | H | Cl | H | OCH$_3$ | OCH$_3$ | CH | |
| Q-10 | H | H | Br | H | OCH$_3$ | CH$_3$ | CH | |
| Q-10 | H | H | NO$_2$ | H | OCH$_3$ | OCH$_3$ | CH | |
| Q-10 | H | H | SCH$_2$F | H | CH$_3$ | OCH$_3$ | CH | |
| Q-10 | H | H | SCH$_2$F | H | OCH$_3$ | OCH$_3$ | CH | |
| Q-10 | H | H | CH$_2$—CH=CH$_2$ | H | Cl | OCH$_3$ | CH | |
| Q-10 | H | H | CH$_2$—C≡CH | H | OCH$_3$ | OCH$_3$ | CH | |
| Q-10 | H | H | CO$_2$CH$_3$ | H | OCH$_3$ | OCH$_3$ | CH | |
| Q-10 | H | H | CO$_2$CH$_3$ | H | OCH$_3$ | CH$_3$ | CH | |
| Q-10 | H | H | CO$_2$CH$_3$ | H | CH$_3$ | CH$_3$ | N | |
| Q-10 | H | H | CO$_2$CH$_2$CH$_3$ | H | OCH$_3$ | OCH$_3$ | CH | |
| Q-10 | H | H | SCH$_3$ | H | CH$_3$ | OCH$_3$ | CH | |
| Q-10 | H | H | SOCH$_3$ | H | CH$_3$ | CH$_3$ | CH | |
| Q-10 | H | H | SO$_2$CH$_3$ | H | OCH$_3$ | OCH$_3$ | CH | |
| Q-10 | H | H | SO$_2$N(CH$_3$)$_2$ | H | OCH$_3$ | CH$_3$ | CH | |
| Q-10 | H | H | SO$_2$N(CH$_3$)$_2$ | H | OCH$_3$ | CH$_3$ | N | |
| Q-10 | H | H | SO$_2$N(CH$_2$CH$_3$)$_2$ | H | OCH$_3$ | OCH$_3$ | CH | |
| Q-10 | CH$_3$ | H | Cl | H | CH$_3$ | CH$_3$ | CH | |
| Q-10 | H | CH$_3$ | Br | H | OCH$_3$ | OCH$_3$ | N | |
| Q-10 | H | Cl | CO$_2$CH$_3$ | H | OCH$_3$ | OCH$_3$ | CH | |
| Q-11 | H | H | H | H | CH$_3$ | OCH$_3$ | CH | |
| Q-11 | H | H | CH$_3$ | H | CH$_3$ | CH$_3$ | N | |
| Q-11 | H | H | CH$_2$CH$_2$CH$_3$ | H | OCH$_3$ | OCH$_3$ | N | |
| Q-11 | H | H | F | H | OCH$_3$ | OCH$_3$ | CH | |
| Q-11 | H | H | Cl | H | OCH$_3$ | OCH$_3$ | CH | |
| Q-11 | H | H | Cl | H | OCH$_3$ | CH$_3$ | N | |
| Q-11 | H | H | Br | H | CH$_3$ | OCH$_3$ | CH | |
| Q-11 | H | H | NO$_2$ | H | Cl | OCH$_3$ | CH | |
| Q-11 | H | H | SCH$_2$CH$_2$F | H | OCH$_3$ | OCH$_3$ | CH | |
| Q-11 | H | H | CH$_2$—CH=CH$_2$ | H | OCH$_3$ | CH$_3$ | CH | |
| Q-11 | H | H | CH$_2$—C≡CH | H | CH$_3$ | CH$_3$ | CH | |
| Q-11 | H | H | CO$_2$CH$_3$ | H | CH$_3$ | OCH$_3$ | N | |
| Q-11 | H | H | CO$_2$CH$_3$ | H | OCH$_3$ | OCH$_3$ | CH | |
| Q-11 | H | H | CO$_2$CH$_3$ | H | CH$_3$ | OCH$_3$ | CH | |
| Q-11 | H | H | CO$_2$CH$_2$CH$_3$ | H | CH$_3$ | CH$_3$ | CH | |
| Q-11 | H | H | CO$_2$CH$_2$CH$_2$CH$_3$ | H | OCH$_3$ | OCH$_3$ | CH | |
| Q-11 | H | H | SCH$_3$ | H | CH$_3$ | CH$_3$ | N | |
| Q-11 | H | H | SOCH$_3$ | H | CH$_3$ | CH$_3$ | CH | |
| Q-11 | H | H | SO$_2$CH$_3$ | H | OCH$_3$ | OCH$_3$ | CH | |
| Q-11 | H | H | SO$_2$CH$_2$CH$_3$ | H | OCH$_3$ | OCH$_3$ | N | |
| Q-11 | H | H | SO$_2$N(CH$_3$)$_2$ | H | CH$_3$ | OCH$_3$ | CH | |
| Q-11 | H | H | SO$_2$N(CH$_2$CH$_3$)$_2$ | H | OCH$_3$ | OCH$_3$ | CH | |
| Q-11 | CH$_3$ | H | CO$_2$CH$_3$ | H | OCH$_3$ | OCH$_3$ | CH | |
| Q-11 | H | H | Br | CH$_3$ | OCH$_3$ | OCH$_3$ | CH | |
| Q-11 | H | CH$_3$ | Cl | H | OCH$_3$ | OCH$_3$ | N | |

TABLE XXI-continued

General Formula XXI

| Q | R | R$_2$ | R$_{14}$ | R$_7$ | R$_6$ | X | Y | Z | m.p. °C. |
|---|---|---|---|---|---|---|---|---|---|
| Q-12 | H | H | H | | H | CH$_3$ | OCH$_3$ | CH | |
| Q-12 | H | H | CH$_2$CH$_3$ | | H | OCH$_3$ | OCH$_3$ | CH | |
| Q-12 | H | H | F | | H | CH$_3$ | CH$_3$ | CH | |
| Q-12 | H | H | Cl | | H | OCH$_3$ | OCH$_3$ | CH | |
| Q-12 | H | H | Br | | H | OCH$_3$ | CH$_3$ | CH | |
| Q-12 | H | H | NO$_2$ | | H | OCH$_3$ | OCH$_3$ | CH | |
| Q-12 | H | H | SCH$_2$F | | H | CH$_3$ | OCH$_3$ | CH | |
| Q-12 | H | H | SCH$_2$F | | H | OCH$_3$ | OCH$_3$ | CH | |
| Q-12 | H | H | CH$_2$—CH=CH$_2$ | | H | Cl | OCH$_3$ | CH | |
| Q-12 | H | H | CH$_2$—C≡CH | | H | OCH$_3$ | OCH$_3$ | CH | |
| Q-12 | H | H | CO$_2$CH$_3$ | | H | OCH$_3$ | OCH$_3$ | CH | |
| Q-12 | H | H | CO$_2$CH$_3$ | | H | OCH$_3$ | CH$_3$ | CH | |
| Q-12 | H | H | CO$_2$CH$_3$ | | H | CH$_3$ | CH$_3$ | N | |
| Q-12 | H | H | CO$_2$CH$_2$CH$_3$ | | H | OCH$_3$ | OCH$_3$ | CH | |
| Q-12 | H | H | SCH$_3$ | | H | CH$_3$ | OCH$_3$ | CH | |
| Q-12 | H | H | SOCH$_3$ | | H | CH$_3$ | CH$_3$ | CH | |
| Q-12 | H | H | SO$_2$CH$_3$ | | H | OCH$_3$ | OCH$_3$ | CH | |
| Q-12 | H | H | SO$_2$N(CH$_3$)$_2$ | | H | OCH$_3$ | CH$_3$ | CH | |
| Q-12 | H | H | SO$_2$N(CH$_3$)$_2$ | | H | OCH$_3$ | CH$_3$ | N | |
| Q-12 | H | H | SO$_2$N(CH$_2$CH$_3$)$_2$ | | H | OCH$_3$ | OCH$_3$ | CH | |
| Q-12 | CH$_3$ | H | Cl | | H | CH$_3$ | CH$_3$ | CH | |
| Q-12 | H | CH$_3$ | Br | | H | OCH$_3$ | OCH$_3$ | N | |
| Q-12 | H | Cl | CO$_2$CH$_3$ | | H | CH$_3$ | OCH$_3$ | CH | |

| Q | R | R$_2$ | R$_{14}$ | R$_7$ | R$_6$ | X | Y | Z | m.p. °C. |
|---|---|---|---|---|---|---|---|---|---|
| Q-13 | H | H | H | — | H | CH$_3$ | OCH$_3$ | CH | |
| Q-13 | H | H | CH$_3$ | — | H | CH$_3$ | CH$_3$ | N | |
| Q-13 | H | H | CH$_2$CH$_2$CH$_3$ | — | H | OCH$_3$ | OCH$_3$ | N | |
| Q-13 | H | H | F | — | H | OCH$_3$ | OCH$_3$ | CH | |
| Q-13 | H | H | Cl | — | H | OCH$_3$ | OCH$_3$ | CH | |
| Q-13 | H | H | Cl | — | H | OCH$_3$ | CH$_3$ | N | |
| Q-13 | H | H | Br | — | H | CH$_3$ | OCH$_3$ | CH | |
| Q-13 | H | H | NO$_2$ | — | H | Cl | OCH$_3$ | CH | |
| Q-13 | H | H | SCH$_2$CH$_2$F | — | H | OCH$_3$ | OCH$_3$ | CH | |
| Q-13 | H | H | CH$_2$—CH=CH$_2$ | — | H | OCH$_3$ | CH$_3$ | CH | |
| Q-13 | H | H | CH$_2$—C≡CH | — | H | CH$_3$ | CH$_3$ | CH | |
| Q-13 | H | H | CO$_2$CH$_3$ | — | H | CH$_3$ | OCH$_3$ | N | |
| Q-13 | H | H | CO$_2$CH$_3$ | — | H | OCH$_3$ | OCH$_3$ | CH | |
| Q-13 | H | H | CO$_2$CH$_3$ | — | H | CH$_3$ | OCH$_3$ | CH | |
| Q-13 | H | H | CO$_2$CH$_2$CH$_3$ | — | H | CH$_3$ | CH$_3$ | CH | |
| Q-13 | H | H | CO$_2$CH$_2$CH$_2$CH$_3$ | — | H | OCH$_3$ | OCH$_3$ | CH | |
| Q-13 | H | H | SCH$_3$ | — | H | CH$_3$ | CH$_3$ | N | |
| Q-13 | H | H | SOCH$_3$ | — | H | CH$_3$ | CH$_3$ | CH | |
| Q-13 | H | H | SO$_2$CH$_3$ | — | H | OCH$_3$ | OCH$_3$ | CH | |
| Q-13 | H | H | SO$_2$CH$_2$CH$_3$ | — | H | OCH$_3$ | OCH$_3$ | N | |
| Q-13 | H | H | SO$_2$N(CH$_3$)$_2$ | — | H | CH$_3$ | OCH$_3$ | CH | |
| Q-13 | H | H | SO$_2$N(CH$_2$CH$_3$)$_2$ | — | H | OCH$_3$ | OCH$_3$ | CH | |
| Q-13 | CH$_3$ | H | CO$_2$CH$_3$ | — | H | OCH$_3$ | OCH$_3$ | CH | |
| Q-13 | H | H | Br | — | CH$_3$ | OCH$_3$ | OCH$_3$ | CH | |
| Q-13 | H | CH$_3$ | Cl | — | H | OCH$_3$ | OCH$_3$ | N | |
| Q-14 | H | H | H | H | H | CH$_3$ | OCH$_3$ | CH | |
| Q-14 | H | H | CH$_2$CH$_3$ | H | H | OCH$_3$ | OCH$_3$ | CH | |
| Q-14 | H | H | F | H | H | CH$_3$ | CH$_3$ | CH | |
| Q-14 | H | H | Cl | H | H | OCH$_3$ | OCH$_3$ | CH | |
| Q-14 | H | H | Br | H | H | OCH$_3$ | OCH$_3$ | CH | |
| Q-14 | H | H | NO$_2$ | H | H | OCH$_3$ | OCH$_3$ | CH | |
| Q-14 | H | H | SCH$_2$F | H | H | CH$_3$ | CH$_3$ | CH | |
| Q-14 | H | H | SCH$_2$F | H | H | OCH$_3$ | OCH$_3$ | CH | |
| Q-14 | H | H | CH$_2$—CH=CH$_2$ | H | H | Cl | OCH$_3$ | CH | |
| Q-14 | H | H | CH$_2$—C≡CH | H | H | OCH$_3$ | OCH$_3$ | CH | |
| Q-14 | H | H | CO$_2$CH$_3$ | H | H | OCH$_3$ | OCH$_3$ | CH | |
| Q-14 | H | H | CO$_2$CH$_3$ | H | H | OCH$_3$ | CH$_3$ | CH | |
| Q-14 | H | H | CO$_2$CH$_3$ | H | H | CH$_3$ | CH$_3$ | N | |
| Q-14 | H | H | CO$_2$CH$_2$CH$_3$ | H | H | CH$_3$ | OCH$_3$ | CH | |
| Q-14 | H | H | SCH$_3$ | H | H | CH$_3$ | OCH$_3$ | CH | |
| Q-14 | H | H | SOCH$_3$ | H | H | CH$_3$ | CH$_3$ | CH | |
| Q-14 | H | H | SO$_2$CH$_3$ | H | H | OCH$_3$ | OCH$_3$ | CH | |
| Q-14 | H | H | SO$_2$N(CH$_3$)$_2$ | H | H | OCH$_3$ | CH$_3$ | CH | |
| Q-14 | H | H | SO$_2$N(CH$_3$)$_2$ | H | H | OCH$_3$ | CH$_3$ | N | |
| Q-14 | H | H | SO$_2$N(CH$_2$CH$_3$)$_2$ | H | H | OCH$_3$ | OCH$_3$ | CH | |
| Q-14 | CH$_3$ | H | Cl | H | H | CH$_3$ | CH$_3$ | CH | |
| Q-14 | H | CH$_3$ | Br | H | H | OCH$_3$ | OCH$_3$ | CH | |
| Q-14 | H | Cl | CO$_2$CH$_3$ | H | H | CH$_3$ | OCH$_3$ | CH | |

| Q | R | R$_2$ | R$_{14}$ | R$_6$ | R$_7$ | X | Y | Z | m.p. °C. |
|---|---|---|---|---|---|---|---|---|---|
| Q-15 | H | H | H | H | H | CH$_3$ | OCH$_3$ | CH | |
| Q-15 | H | H | CH$_3$ | H | H | CH$_3$ | CH$_3$ | N | |
| Q-15 | H | H | CH$_2$CH$_2$CH$_3$ | H | H | OCH$_3$ | OCH$_3$ | N | |
| Q-15 | H | H | F | H | H | OCH$_3$ | OCH$_3$ | CH | |
| Q-15 | H | H | Cl | H | H | OCH$_3$ | OCH$_3$ | CH | |
| Q-15 | H | H | Cl | H | H | OCH$_3$ | CH$_3$ | N | |

TABLE XXI-continued

General Formula XXI

| | | | | | | | | |
|---|---|---|---|---|---|---|---|---|
| Q-15 | H | H | Br | H | H | $CH_3$ | $OCH_3$ | CH |
| Q-15 | H | H | $NO_2$ | H | H | Cl | $OCH_3$ | CH |
| Q-15 | H | H | $SCH_2CH_2F$ | H | H | $OCH_3$ | $OCH_3$ | CH |
| Q-15 | H | H | $CH_2-CH=CH_2$ | H | H | $OCH_3$ | $CH_3$ | CH |
| Q-15 | H | H | $CH_2-C\equiv CH$ | H | H | $CH_3$ | $CH_3$ | CH |
| Q-15 | H | H | $CO_2CH_3$ | H | H | $CH_3$ | $OCH_3$ | N |
| Q-15 | H | H | $CO_2CH_3$ | H | H | $OCH_3$ | $OCH_3$ | CH |
| Q-15 | H | H | $CO_2CH_3$ | H | H | $CH_3$ | $OCH_3$ | CH |
| Q-15 | H | H | $CO_2CH_2CH_3$ | H | H | $CH_3$ | $CH_3$ | CH |
| Q-15 | H | H | $CO_2CH_2CH_2CH_3$ | H | H | $OCH_3$ | $OCH_3$ | CH |
| Q-15 | H | H | $SCH_3$ | H | H | $CH_3$ | $CH_3$ | N |
| Q-15 | H | H | $SOCH_3$ | H | H | $CH_3$ | $CH_3$ | CH |
| Q-15 | H | H | $SO_2CH_3$ | H | H | $OCH_3$ | $OCH_3$ | CH |
| Q-15 | H | H | $SO_2CH_2CH_3$ | H | H | $OCH_3$ | $OCH_3$ | N |
| Q-15 | H | H | $SO_2N(CH_3)_2$ | H | H | $CH_3$ | $OCH_3$ | CH |
| Q-15 | H | H | $SO_2N(CH_2CH_3)_2$ | H | H | $OCH_3$ | $OCH_3$ | CH |
| Q-15 | $CH_3$ | H | $CO_2CH_3$ | H | H | $OCH_3$ | $OCH_3$ | CH |
| Q-15 | H | H | Br | H | $CH_3$ | $OCH_3$ | $OCH_3$ | CH |
| Q-15 | H | $CH_3$ | Cl | H | H | $OCH_3$ | $OCH_3$ | N |
| Q-16 | H | H | H | H | H | $CH_3$ | $OCH_3$ | CH |
| Q-16 | H | H | $CH_2CH_3$ | H | H | $OCH_3$ | $OCH_3$ | CH |
| Q-16 | H | H | F | H | H | $CH_3$ | $CH_3$ | CH |
| Q-16 | H | H | Cl | H | H | $OCH_3$ | $CH_3$ | CH |
| Q-16 | H | H | Br | H | H | $OCH_3$ | $CH_3$ | CH |
| Q-16 | H | H | $NO_2$ | H | H | $OCH_3$ | $OCH_3$ | CH |
| Q-16 | H | H | $SCH_2F$ | H | H | $CH_3$ | $OCH_3$ | CH |
| Q-16 | H | H | $SCH_2F$ | H | H | $OCH_3$ | $OCH_3$ | CH |
| Q-16 | H | H | $CH_2-CH=CH_2$ | H | H | Cl | $OCH_3$ | CH |
| Q-16 | H | H | $CH_2-C\equiv CH$ | H | H | $OCH_3$ | $OCH_3$ | CH |
| Q-16 | H | H | $CO_2CH_3$ | H | H | $OCH_3$ | $OCH_3$ | CH |
| Q-16 | H | H | $CO_2CH_3$ | H | H | $OCH_3$ | $CH_3$ | CH |
| Q-16 | H | H | $CO_2CH_3$ | H | H | $CH_3$ | $CH_3$ | N |
| Q-16 | H | H | $CO_2CH_2CH_3$ | H | H | $OCH_3$ | $OCH_3$ | CH |
| Q-16 | H | H | $SCH_3$ | H | H | $CH_3$ | $OCH_3$ | CH |
| Q-16 | H | H | $SOCH_3$ | H | H | $CH_3$ | $CH_3$ | CH |
| Q-16 | H | H | $SO_2CH_3$ | H | H | $OCH_3$ | $OCH_3$ | CH |
| Q-16 | H | H | $SO_2N(CH_3)_2$ | H | H | $OCH_3$ | $CH_3$ | CH |
| Q-16 | H | H | $SO_2N(CH_3)_2$ | H | H | $OCH_3$ | $CH_3$ | N |
| Q-16 | H | H | $SO_2N(CH_2CH_3)_2$ | H | H | $OCH_3$ | $OCH_3$ | CH |
| Q-16 | $CH_3$ | H | Cl | H | H | $CH_3$ | $CH_3$ | CH |
| Q-16 | H | $CH_3$ | Br | H | H | $OCH_3$ | $OCH_3$ | N |
| Q-16 | H | Cl | $CO_2CH_3$ | H | H | $CH_3$ | $OCH_3$ | CH |
| Q-17 | H | H | H | H | H | $CH_3$ | $OCH_3$ | CH |
| Q-17 | H | H | $CH_3$ | H | H | $CH_3$ | $CH_3$ | N |
| Q-17 | H | H | $CH_2CH_2CH_3$ | H | H | $OCH_3$ | $OCH_3$ | N |
| Q-17 | H | H | F | H | H | $OCH_3$ | $OCH_3$ | CH |
| Q-17 | H | H | Cl | H | H | $OCH_3$ | $OCH_3$ | CH |
| Q-17 | H | H | Cl | H | H | $OCH_3$ | $CH_3$ | N |
| Q-17 | H | H | Br | H | H | $CH_3$ | $OCH_3$ | CH |
| Q-17 | H | H | $NO_2$ | H | H | Cl | $OCH_3$ | CH |
| Q-17 | H | H | $SCH_2CH_2F$ | H | H | $OCH_3$ | $OCH_3$ | CH |
| Q-17 | H | H | $CH_2-CH=CH_2$ | H | H | $OCH_3$ | $CH_3$ | CH |
| Q-17 | H | H | $CH_2-C\equiv CH$ | H | H | $CH_3$ | $CH_3$ | CH |
| Q-17 | H | H | $CO_2CH_3$ | H | H | $CH_3$ | $OCH_3$ | N |
| Q-17 | H | H | $CO_2CH_3$ | H | H | $OCH_3$ | $OCH_3$ | CH |
| Q-17 | H | H | $CO_2CH_3$ | H | H | $CH_3$ | $OCH_3$ | CH |
| Q-17 | H | H | $CO_2CH_2CH_3$ | H | H | $CH_3$ | $CH_3$ | CH |
| Q-17 | H | H | $CO_2CH_2CH_2CH_3$ | H | H | $OCH_3$ | $OCH_3$ | CH |
| Q-17 | H | H | $SCH_3$ | H | H | $CH_3$ | $CH_3$ | N |
| Q-17 | H | H | $SOCH_3$ | H | H | $CH_3$ | $CH_3$ | CH |
| Q-17 | H | H | $SO_2CH_3$ | H | H | $OCH_3$ | $OCH_3$ | CH |
| Q-17 | H | H | $SO_2CH_2CH_3$ | H | H | $OCH_3$ | $OCH_3$ | N |
| Q-17 | H | H | $SO_2N(CH_3)_2$ | H | H | $CH_3$ | $OCH_3$ | CH |
| Q-17 | H | H | $SO_2N(CH_2CH_3)_2$ | H | H | $OCH_3$ | $OCH_3$ | CH |
| Q-17 | $CH_3$ | H | $CO_2CH_3$ | H | H | $OCH_3$ | $OCH_3$ | CH |
| Q-17 | H | H | Br | H | $CH_3$ | $OCH_3$ | $OCH_3$ | CH |
| Q-17 | H | $CH_3$ | Cl | H | H | $OCH_3$ | $OCH_3$ | N |
| Q-18 | H | H | H | H | H | $CH_3$ | $OCH_3$ | CH |
| Q-18 | H | H | $CH_2CH_3$ | H | H | $OCH_3$ | $OCH_3$ | CH |
| Q-18 | H | H | F | H | H | $CH_3$ | $CH_3$ | CH |
| Q-18 | H | H | Cl | H | H | $OCH_3$ | $CH_3$ | CH |
| Q-18 | H | H | Br | H | H | $OCH_3$ | $CH_3$ | CH |
| Q-18 | H | H | $NO_2$ | H | H | $OCH_3$ | $OCH_3$ | CH |
| Q-18 | H | H | $SCH_2F$ | H | H | $CH_3$ | $OCH_3$ | CH |
| Q-18 | H | H | $SCH_2F$ | H | H | $OCH_3$ | $OCH_3$ | CH |
| Q-18 | H | H | $CH_2-CH=CH_2$ | H | H | Cl | $OCH_3$ | CH |
| Q-18 | H | H | $CH_2-C\equiv CH$ | H | H | $OCH_3$ | $OCH_3$ | CH |
| Q-18 | H | H | $CO_2CH_3$ | H | H | $OCH_3$ | $OCH_3$ | CH |
| Q-18 | H | H | $CO_2CH_3$ | H | H | $OCH_3$ | $CH_3$ | CH |
| Q-18 | H | H | $CO_2CH_3$ | H | H | $CH_3$ | $CH_3$ | N |
| Q-18 | H | H | $CO_2CH_2CH_3$ | H | H | $OCH_3$ | $OCH_3$ | CH |

TABLE XXI-continued

General Formula XXI

| Q | R | R$_2$ | R$_{14}$ | R$_6$ | R$_7$ | X | Y | Z |
|---|---|---|---|---|---|---|---|---|
| Q-18 | H | H | SCH$_3$ | H | H | CH$_3$ | OCH$_3$ | CH |
| Q-18 | H | H | SOCH$_3$ | H | H | CH$_3$ | CH$_3$ | CH |
| Q-18 | H | H | SO$_2$CH$_3$ | H | H | OCH$_3$ | OCH$_3$ | CH |
| Q-18 | H | H | SO$_2$N(CH$_3$)$_2$ | H | H | OCH$_3$ | CH$_3$ | CH |
| Q-18 | H | H | SO$_2$N(CH$_3$)$_2$ | H | H | OCH$_3$ | CH$_3$ | N |
| Q-18 | H | H | SO$_2$N(CH$_2$CH$_3$)$_2$ | H | H | OCH$_3$ | OCH$_3$ | CH |
| Q-18 | CH$_3$ | H | Cl | H | H | CH$_3$ | CH$_3$ | CH |
| Q-18 | H | CH$_3$ | Br | H | H | OCH$_3$ | OCH$_3$ | N |
| Q-18 | H | Cl | CO$_2$CH$_3$ | H | H | CH$_3$ | OCH$_3$ | CH |
| Q-19 | H | H | H | H | H | CH$_3$ | OCH$_3$ | CH |
| Q-19 | H | H | CH$_3$ | H | H | CH$_3$ | CH$_3$ | N |
| Q-19 | H | H | CH$_2$CH$_2$CH$_3$ | H | H | OCH$_3$ | OCH$_3$ | N |
| Q-19 | H | H | F | H | H | OCH$_3$ | OCH$_3$ | CH |
| Q-19 | H | H | Cl | H | H | OCH$_3$ | OCH$_3$ | CH |
| Q-19 | H | H | Cl | H | H | OCH$_3$ | CH$_3$ | N |
| Q-19 | H | H | Br | H | H | CH$_3$ | OCH$_3$ | CH |
| Q-19 | H | H | NO$_2$ | H | H | Cl | OCH$_3$ | CH |
| Q-19 | H | H | SCH$_2$CH$_2$F | H | H | OCH$_3$ | OCH$_3$ | CH |
| Q-19 | H | H | CH$_2$—CH=CH$_2$ | H | H | OCH$_3$ | CH$_3$ | CH |
| Q-19 | H | H | CH$_2$—C≡CH | H | H | CH$_3$ | CH$_3$ | CH |
| Q-19 | H | H | CO$_2$CH$_3$ | H | H | CH$_3$ | OCH$_3$ | N |
| Q-19 | H | H | CO$_2$CH$_3$ | H | H | OCH$_3$ | OCH$_3$ | CH |
| Q-19 | H | H | CO$_2$CH$_3$ | H | H | CH$_3$ | OCH$_3$ | CH |
| Q-19 | H | H | CO$_2$CH$_2$CH$_3$ | H | H | CH$_3$ | CH$_3$ | CH |
| Q-19 | H | H | CO$_2$CH$_2$CH$_2$CH$_3$ | H | H | OCH$_3$ | OCH$_3$ | CH |
| Q-19 | H | H | SCH$_3$ | H | H | CH$_3$ | CH$_3$ | N |
| Q-19 | H | H | SOCH$_3$ | H | H | CH$_3$ | CH$_3$ | CH |
| Q-19 | H | H | SO$_2$CH$_3$ | H | H | OCH$_3$ | OCH$_3$ | CH |
| Q-19 | H | H | SO$_2$CH$_2$CH$_3$ | H | H | OCH$_3$ | OCH$_3$ | N |
| Q-19 | H | H | SO$_2$N(CH$_3$)$_2$ | H | H | CH$_3$ | OCH$_3$ | CH |
| Q-19 | H | H | SO$_2$N(CH$_2$CH$_3$)$_2$ | H | H | OCH$_3$ | OCH$_3$ | CH |
| Q-19 | CH$_3$ | H | CO$_2$CH$_3$ | H | H | OCH$_3$ | OCH$_3$ | CH |
| Q-19 | H | H | Br | H | CH$_3$ | OCH$_3$ | OCH$_3$ | CH |
| Q-19 | H | CH$_3$ | Cl | H | H | OCH$_3$ | OCH$_3$ | N |
| Q-20 | H | H | H | H | H | CH$_3$ | OCH$_3$ | CH |
| Q-20 | H | H | CH$_2$CH$_3$ | H | H | OCH$_3$ | OCH$_3$ | CH |
| Q-20 | H | H | F | H | H | CH$_3$ | CH$_3$ | CH |
| Q-20 | H | H | Cl | H | H | OCH$_3$ | OCH$_3$ | CH |
| Q-20 | H | H | Br | H | H | OCH$_3$ | CH$_3$ | CH |
| Q-20 | H | H | NO$_2$ | H | H | OCH$_3$ | OCH$_3$ | CH |
| Q-20 | H | H | SCH$_2$F | H | H | CH$_3$ | OCH$_3$ | CH |
| Q-20 | H | H | SCH$_2$F | H | H | OCH$_3$ | OCH$_3$ | CH |
| Q-20 | H | H | CH$_2$—CH=CH$_2$ | H | H | Cl | OCH$_3$ | CH |
| Q-20 | H | H | CH$_2$—C≡CH | H | H | OCH$_3$ | OCH$_3$ | CH |
| Q-20 | H | H | CO$_2$CH$_3$ | H | H | OCH$_3$ | OCH$_3$ | CH |
| Q-20 | H | H | CO$_2$CH$_3$ | H | H | OCH$_3$ | CH$_3$ | CH |
| Q-20 | H | H | CO$_2$CH$_3$ | H | H | CH$_3$ | CH$_3$ | N |
| Q-20 | H | H | CO$_2$CH$_2$CH$_3$ | H | H | OCH$_3$ | OCH$_3$ | CH |
| Q-20 | H | H | SCH$_3$ | H | H | CH$_3$ | OCH$_3$ | CH |
| Q-20 | H | H | SOCH$_3$ | H | H | CH$_3$ | CH$_3$ | CH |
| Q-20 | H | H | SO$_2$CH$_3$ | H | H | OCH$_3$ | OCH$_3$ | CH |
| Q-20 | H | H | SO$_2$N(CH$_3$)$_2$ | H | H | OCH$_3$ | CH$_3$ | CH |
| Q-20 | H | H | SO$_2$N(CH$_3$)$_2$ | H | H | OCH$_3$ | CH$_3$ | N |
| Q-20 | H | H | SO$_2$N(CH$_2$CH$_3$)$_2$ | H | H | OCH$_3$ | OCH$_3$ | CH |
| Q-20 | CH$_3$ | H | Cl | H | H | CH$_3$ | CH$_3$ | CH |
| Q-20 | H | CH$_3$ | Br | H | H | OCH$_3$ | OCH$_3$ | N |
| Q-20 | H | Cl | CO$_2$CH$_3$ | H | H | CH$_3$ | OCH$_3$ | CH |

| Q | R | R$_2$ | R$_{14}$ | R$_6$ | R$_7$ | X | Y | Z | R$_9$ | m.p. °C. |
|---|---|---|---|---|---|---|---|---|---|---|
| Q-21 | H | H | H | H | H | CH$_3$ | OCH$_3$ | CH | H | |
| Q-21 | H | H | CH$_3$ | H | H | CH$_3$ | CH$_3$ | N | H | |
| Q-21 | H | H | CH$_2$CH$_2$CH$_3$ | H | H | OCH$_3$ | OCH$_3$ | N | H | |
| Q-21 | H | H | F | H | H | OCH$_3$ | OCH$_3$ | CH | H | |
| Q-21 | H | H | Cl | H | H | OCH$_3$ | OCH$_3$ | CH | H | |
| Q-21 | H | H | Cl | H | H | OCH$_3$ | CH$_3$ | N | H | |
| Q-21 | H | H | Br | H | H | CH$_3$ | OCH$_3$ | CH | H | |
| Q-21 | H | H | NO$_2$ | H | H | Cl | OCH$_3$ | CH | H | |
| Q-21 | H | H | SCH$_2$CH$_2$F | H | H | OCH$_3$ | OCH$_3$ | CH | H | |
| Q-21 | H | H | CH$_2$—CH=CH$_2$ | H | H | OCH$_3$ | CH$_3$ | CH | H | |
| Q-21 | H | H | CH$_2$—C≡CH | H | H | CH$_3$ | CH$_3$ | CH | H | |
| Q-21 | H | H | CO$_2$CH$_3$ | H | H | CH$_3$ | OCH$_3$ | N | H | |
| Q-21 | H | H | CO$_2$CH$_3$ | H | H | OCH$_3$ | OCH$_3$ | CH | H | |
| Q-21 | H | H | CO$_2$CH$_3$ | H | H | CH$_3$ | OCH$_3$ | CH | H | |
| Q-21 | H | H | CO$_2$CH$_2$CH$_3$ | H | H | CH$_3$ | CH$_3$ | CH | H | |
| Q-21 | H | H | CO$_2$CH$_2$CH$_2$CH$_3$ | H | H | OCH$_3$ | OCH$_3$ | CH | H | |
| Q-21 | H | H | SCH$_3$ | H | H | CH$_3$ | CH$_3$ | N | H | |
| Q-21 | H | H | SOCH$_3$ | H | H | CH$_3$ | CH$_3$ | CH | H | |
| Q-21 | H | H | SO$_2$CH$_3$ | H | H | OCH$_3$ | OCH$_3$ | CH | H | |
| Q-21 | H | H | SO$_2$CH$_2$CH$_3$ | H | H | OCH$_3$ | OCH$_3$ | N | H | |
| Q-21 | H | H | SO$_2$N(CH$_3$)$_2$ | H | H | CH$_3$ | OCH$_3$ | CH | H | |
| Q-21 | H | H | SO$_2$N(CH$_2$CH$_3$)$_2$ | H | H | OCH$_3$ | OCH$_3$ | CH | H | |

TABLE XXI-continued

General Formula XXI

| | | | | | | | | | |
|---|---|---|---|---|---|---|---|---|---|
| Q-21 | CH$_3$ | H | CO$_2$CH$_3$ | H | H | OCH$_3$ | OCH$_3$ | CH | H |
| Q-21 | H | H | Br | H | CH$_3$ | OCH$_3$ | OCH$_3$ | CH | H |
| Q-21 | H | CH$_3$ | Cl | H | H | OCH$_3$ | OCH$_3$ | N | H |
| Q-22 | H | H | H | H | H | CH$_3$ | OCH$_3$ | CH | H |
| Q-22 | H | H | CH$_2$CH$_3$ | H | H | OCH$_3$ | OCH$_3$ | CH | H |
| Q-22 | H | H | F | H | H | CH$_3$ | CH$_3$ | CH | H |
| Q-22 | H | H | Cl | H | H | OCH$_3$ | OCH$_3$ | CH | H |
| Q-22 | H | H | Br | H | H | OCH$_3$ | CH$_3$ | CH | H |
| Q-22 | H | H | NO$_2$ | H | H | OCH$_3$ | OCH$_3$ | CH | H |
| Q-22 | H | H | SCH$_2$F | H | H | CH$_3$ | OCH$_3$ | CH | H |
| Q-22 | H | H | SCH$_2$F | H | H | OCH$_3$ | OCH$_3$ | CH | H |
| Q-22 | H | H | CH$_2$—CH=CH$_2$ | H | H | Cl | OCH$_3$ | CH | H |
| Q-22 | H | H | CH$_2$—C≡CH | H | H | OCH$_3$ | OCH$_3$ | CH | H |
| Q-22 | H | H | CO$_2$CH$_3$ | H | H | OCH$_3$ | OCH$_3$ | CH | H |
| Q-22 | H | H | CO$_2$CH$_3$ | H | H | OCH$_3$ | CH$_3$ | CH | H |
| Q-22 | H | H | CO$_2$CH$_3$ | H | H | CH$_3$ | CH$_3$ | N | H |
| Q-22 | H | H | CO$_2$CH$_2$CH$_3$ | H | H | OCH$_3$ | OCH$_3$ | CH | H |
| Q-22 | H | H | SCH$_3$ | H | H | CH$_3$ | OCH$_3$ | CH | H |
| Q-22 | H | H | SOCH$_3$ | H | H | CH$_3$ | CH$_3$ | CH | H |
| Q-22 | H | H | SO$_2$CH$_3$ | H | H | OCH$_3$ | OCH$_3$ | CH | H |
| Q-22 | H | H | SO$_2$N(CH$_3$)$_2$ | H | H | OCH$_3$ | CH$_3$ | CH | H |
| Q-22 | H | H | SO$_2$N(CH$_3$)$_2$ | H | H | OCH$_3$ | CH$_3$ | N | H |
| Q-22 | H | H | SO$_2$N(CH$_2$CH$_3$)$_2$ | H | H | OCH$_3$ | OCH$_3$ | CH | H |
| Q-22 | CH$_3$ | H | Cl | H | H | CH$_3$ | CH$_3$ | CH | H |
| Q-22 | H | CH$_3$ | Br | H | H | OCH$_3$ | OCH$_3$ | N | H |
| Q-22 | H | Cl | CO$_2$CH$_3$ | H | H | CH$_3$ | OCH$_3$ | CH | H |
| Q-23 | H | H | H | H | H | CH$_3$ | OCH$_3$ | CH | H |
| Q-23 | H | H | CH$_3$ | H | H | CH$_3$ | CH$_3$ | N | H |
| Q-23 | H | H | CH$_2$CH$_2$CH$_3$ | H | H | OCH$_3$ | OCH$_3$ | N | H |
| Q-23 | H | H | F | H | H | OCH$_3$ | OCH$_3$ | CH | H |
| Q-23 | H | H | Cl | H | H | OCH$_3$ | OCH$_3$ | CH | H |
| Q-23 | H | H | Cl | H | H | OCH$_3$ | CH$_3$ | N | H |
| Q-23 | H | H | Br | H | H | CH$_3$ | OCH$_3$ | CH | H |
| Q-23 | H | H | NO$_2$ | H | H | Cl | OCH$_3$ | CH | H |
| Q-23 | H | H | SCH$_2$CH$_2$F | H | H | OCH$_3$ | OCH$_3$ | CH | H |
| Q-23 | H | H | CH$_2$—CH=CH$_2$ | H | H | OCH$_3$ | CH$_3$ | CH | H |
| Q-23 | H | H | CH$_2$—C≡CH | H | H | CH$_3$ | CH$_3$ | CH | H |
| Q-23 | H | H | CO$_2$CH$_3$ | H | H | CH$_3$ | OCH$_3$ | N | H |
| Q-23 | H | H | CO$_2$CH$_3$ | H | H | OCH$_3$ | OCH$_3$ | CH | H |
| Q-23 | H | H | CO$_2$CH$_3$ | H | H | CH$_3$ | OCH$_3$ | CH | H |
| Q-23 | H | H | CO$_2$CH$_2$CH$_3$ | H | H | CH$_3$ | CH$_3$ | CH | H |
| Q-23 | H | H | CO$_2$CH$_2$CH$_2$CH$_3$ | H | H | OCH$_3$ | OCH$_3$ | CH | H |
| Q-23 | H | H | SCH$_3$ | H | H | CH$_3$ | CH$_3$ | N | H |
| Q-23 | H | H | SOCH$_3$ | H | H | CH$_3$ | CH$_3$ | CH | H |
| Q-23 | H | H | SO$_2$CH$_3$ | H | H | OCH$_3$ | OCH$_3$ | CH | H |
| Q-23 | H | H | SO$_2$CH$_2$CH$_3$ | H | H | OCH$_3$ | OCH$_3$ | N | H |
| Q-23 | H | H | SO$_2$N(CH$_3$)$_2$ | H | H | CH$_3$ | OCH$_3$ | CH | H |
| Q-23 | H | H | SO$_2$N(CH$_2$CH$_3$)$_2$ | H | H | OCH$_3$ | OCH$_3$ | CH | H |
| Q-23 | CH$_3$ | H | CO$_2$CH$_3$ | H | H | OCH$_3$ | OCH$_3$ | CH | H |
| Q-23 | H | H | Br | H | CH$_3$ | OCH$_3$ | OCH$_3$ | CH | H |
| Q-23 | H | CH$_3$ | Cl | H | H | OCH$_3$ | OCH$_3$ | N | H |
| Q-24 | H | H | H | H | H | CH$_3$ | OCH$_3$ | CH | H |
| Q-24 | H | H | CH$_2$CH$_3$ | H | H | OCH$_3$ | OCH$_3$ | CH | H |
| Q-24 | H | H | F | H | H | CH$_3$ | CH$_3$ | CH | H |
| Q-24 | H | H | Cl | H | H | OCH$_3$ | OCH$_3$ | CH | H |
| Q-24 | H | H | Br | H | H | OCH$_3$ | CH$_3$ | CH | H |
| Q-24 | H | H | NO$_2$ | H | H | OCH$_3$ | OCH$_3$ | CH | H |
| Q-24 | H | H | SCH$_2$F | H | H | CH$_3$ | OCH$_3$ | CH | H |
| Q-24 | H | H | SCH$_2$F | H | H | OCH$_3$ | OCH$_3$ | CH | H |
| Q-24 | H | H | CH$_2$—CH=CH$_2$ | H | H | Cl | OCH$_3$ | CH | H |
| Q-24 | H | H | CH$_2$—C≡CH | H | H | OCH$_3$ | OCH$_3$ | CH | H |
| Q-24 | H | H | CO$_2$CH$_3$ | H | H | OCH$_3$ | OCH$_3$ | CH | H |
| Q-24 | H | H | CO$_2$CH$_3$ | H | H | OCH$_3$ | CH$_3$ | CH | H |
| Q-24 | H | H | CO$_2$CH$_3$ | H | H | CH$_3$ | CH$_3$ | N | H |
| Q-24 | H | H | CO$_2$CH$_2$CH$_3$ | H | H | OCH$_3$ | OCH$_3$ | CH | H |
| Q-24 | H | H | SCH$_3$ | H | H | CH$_3$ | OCH$_3$ | CH | H |
| Q-24 | H | H | SOCH$_3$ | H | H | CH$_3$ | CH$_3$ | CH | H |
| Q-24 | H | H | SO$_2$CH$_3$ | H | H | OCH$_3$ | OCH$_3$ | CH | H |
| Q-24 | H | H | SO$_2$N(CH$_3$)$_2$ | H | H | OCH$_3$ | CH$_3$ | CH | H |
| Q-24 | H | H | SO$_2$N(CH$_3$)$_2$ | H | H | OCH$_3$ | CH$_3$ | N | H |
| Q-24 | H | H | SO$_2$N(CH$_2$CH$_3$)$_2$ | H | H | OCH$_3$ | OCH$_3$ | CH | H |
| Q-24 | CH$_3$ | H | Cl | H | H | CH$_3$ | CH$_3$ | CH | H |
| Q-24 | H | CH$_3$ | Br | H | H | OCH$_3$ | OCH$_3$ | N | H |
| Q-24 | H | Cl | CO$_2$CH$_3$ | H | H | CH$_3$ | OCH$_3$ | CH | H |
| Q-25 | H | H | H | H | H | CH$_3$ | OCH$_3$ | CH | H |
| Q-25 | H | H | CH$_3$ | H | H | CH$_3$ | CH$_3$ | N | H |
| Q-25 | H | H | CH$_2$CH$_2$CH$_3$ | H | H | OCH$_3$ | OCH$_3$ | N | H |
| Q-25 | H | H | F | H | H | OCH$_3$ | OCH$_3$ | CH | H |
| Q-25 | H | H | Cl | H | H | OCH$_3$ | OCH$_3$ | CH | H |
| Q-25 | H | H | Cl | H | H | OCH$_3$ | CH$_3$ | N | H |
| Q-25 | H | H | Br | H | H | CH$_3$ | OCH$_3$ | CH | H |

TABLE XXI-continued

General Formula XXI

| | | | | | | | | | |
|---|---|---|---|---|---|---|---|---|---|
| Q-25 | H | H | NO$_2$ | H | H | Cl | OCH$_3$ | CH | H |
| Q-25 | H | H | SCH$_2$CH$_2$F | H | H | OCH$_3$ | OCH$_3$ | CH | H |
| Q-25 | H | H | CH$_2$—CH=CH$_2$ | H | H | OCH$_3$ | CH$_3$ | CH | H |
| Q-25 | H | H | CH$_2$—C≡CH | H | H | CH$_3$ | CH$_3$ | CH | H |
| Q-25 | H | H | CO$_2$CH$_3$ | H | H | CH$_3$ | OCH$_3$ | N | H |
| Q-25 | H | H | CO$_2$CH$_3$ | H | H | OCH$_3$ | OCH$_3$ | CH | H |
| Q-25 | H | H | CO$_2$CH$_3$ | H | H | CH$_3$ | OCH$_3$ | CH | H |
| Q-25 | H | H | CO$_2$CH$_2$CH$_3$ | H | H | CH$_3$ | CH$_3$ | CH | H |
| Q-25 | H | H | CO$_2$CH$_2$CH$_2$CH$_3$ | H | H | OCH$_3$ | OCH$_3$ | CH | H |
| Q-25 | H | H | SCH$_3$ | H | H | CH$_3$ | CH$_3$ | N | H |
| Q-25 | H | H | SOCH$_3$ | H | H | CH$_3$ | CH$_3$ | CH | H |
| Q-25 | H | H | SO$_2$CH$_3$ | H | H | OCH$_3$ | OCH$_3$ | CH | H |
| Q-25 | H | H | SO$_2$CH$_2$CH$_3$ | H | H | OCH$_3$ | OCH$_3$ | N | H |
| Q-25 | H | H | SO$_2$N(CH$_3$)$_2$ | H | H | CH$_3$ | OCH$_3$ | CH | H |
| Q-25 | H | H | SO$_2$N(CH$_2$CH$_3$)$_2$ | H | H | OCH$_3$ | OCH$_3$ | CH | H |
| Q-25 | CH$_3$ | H | CO$_2$CH$_3$ | H | H | OCH$_3$ | OCH$_3$ | CH | H |
| Q-25 | H | H | Br | H | CH$_3$ | OCH$_3$ | OCH$_3$ | CH | H |
| Q-25 | H | CH$_3$ | Cl | H | H | OCH$_3$ | OCH$_3$ | N | H |
| Q-26 | H | H | H | H | H | CH$_3$ | OCH$_3$ | CH | H |
| Q-26 | H | H | CH$_2$CH$_3$ | H | H | OCH$_3$ | OCH$_3$ | CH | H |
| Q-26 | H | H | F | H | H | CH$_3$ | CH$_3$ | CH | H |
| Q-26 | H | H | Cl | H | H | OCH$_3$ | OCH$_3$ | CH | H |
| Q-26 | H | H | Br | H | H | OCH$_3$ | CH$_3$ | CH | H |
| Q-26 | H | H | NO$_2$ | H | H | OCH$_3$ | OCH$_3$ | CH | H |
| Q-26 | H | H | SCH$_2$F | H | H | CH$_3$ | OCH$_3$ | CH | H |
| Q-26 | H | H | SCH$_2$F | H | H | OCH$_3$ | OCH$_3$ | CH | H |
| Q-26 | H | H | CH$_2$—CH=CH$_2$ | H | H | Cl | OCH$_3$ | CH | H |
| Q-26 | H | H | CH$_2$—C≡CH | H | H | OCH$_3$ | OCH$_3$ | CH | H |
| Q-26 | H | H | CO$_2$CH$_3$ | H | H | OCH$_3$ | OCH$_3$ | CH | H |
| Q-26 | H | H | CO$_2$CH$_3$ | H | H | OCH$_3$ | CH$_3$ | CH | H |
| Q-26 | H | H | CO$_2$CH$_3$ | H | H | CH$_3$ | CH$_3$ | N | H |
| Q-26 | H | H | CO$_2$CH$_2$CH$_3$ | H | H | OCH$_3$ | OCH$_3$ | CH | H |
| Q-26 | H | H | SCH$_3$ | H | H | CH$_3$ | OCH$_3$ | CH | H |
| Q-26 | H | H | SOCH$_3$ | H | H | CH$_3$ | CH$_3$ | CH | H |
| Q-26 | H | H | SO$_2$CH$_3$ | H | H | OCH$_3$ | OCH$_3$ | CH | H |
| Q-26 | H | H | SO$_2$N(CH$_3$)$_2$ | H | H | OCH$_3$ | CH$_3$ | CH | H |
| Q-26 | H | H | SO$_2$N(CH$_3$)$_2$ | H | H | OCH$_3$ | CH$_3$ | N | H |
| Q-26 | H | H | SO$_2$N(CH$_2$CH$_3$)$_2$ | H | H | OCH$_3$ | OCH$_3$ | CH | H |
| Q-26 | CH$_3$ | H | Cl | H | H | CH$_3$ | CH$_3$ | CH | H |
| Q-26 | H | CH$_3$ | Br | H | H | OCH$_3$ | OCH$_3$ | N | H |
| Q-26 | H | Cl | CO$_2$CH$_3$ | H | H | CH$_3$ | OCH$_3$ | CH | H |
| Q-27 | H | H | H | H | H | CH$_3$ | CH$_3$ | CH | H |
| Q-27 | H | H | CH$_3$ | H | H | CH$_3$ | CH$_3$ | N | H |
| Q-27 | H | H | CH$_2$CH$_2$CH$_3$ | H | H | OCH$_3$ | OCH$_3$ | N | H |
| Q-27 | H | H | F | H | H | OCH$_3$ | OCH$_3$ | CH | H |
| Q-27 | H | H | Cl | H | H | OCH$_3$ | OCH$_3$ | CH | H |
| Q-27 | H | H | Cl | H | H | OCH$_3$ | CH$_3$ | N | H |
| Q-27 | H | H | Br | H | H | CH$_3$ | OCH$_3$ | CH | H |
| Q-27 | H | H | NO$_2$ | H | H | Cl | OCH$_3$ | CH | H |
| Q-27 | H | H | SCH$_2$CH$_2$F | H | H | OCH$_3$ | OCH$_3$ | CH | H |
| Q-27 | H | H | CH$_2$—CH=CH$_2$ | H | H | OCH$_3$ | CH$_3$ | CH | H |
| Q-27 | H | H | CH$_2$—C≡CH | H | H | CH$_3$ | CH$_3$ | CH | H |
| Q-27 | H | H | CO$_2$CH$_3$ | H | H | CH$_3$ | OCH$_3$ | N | H |
| Q-27 | H | H | CO$_2$CH$_3$ | H | H | OCH$_3$ | OCH$_3$ | CH | H |
| Q-27 | H | H | CO$_2$CH$_3$ | H | H | CH$_3$ | OCH$_3$ | CH | H |
| Q-27 | H | H | CO$_2$CH$_2$CH$_3$ | H | H | CH$_3$ | CH$_3$ | CH | H |
| Q-27 | H | H | CO$_2$CH$_2$CH$_2$CH$_3$ | H | H | OCH$_3$ | OCH$_3$ | CH | H |
| Q-27 | H | H | SCH$_3$ | H | H | CH$_3$ | CH$_3$ | N | H |
| Q-27 | H | H | SOCH$_3$ | H | H | CH$_3$ | CH$_3$ | CH | H |
| Q-27 | H | H | SO$_2$CH$_3$ | H | H | OCH$_3$ | OCH$_3$ | CH | H |
| Q-27 | H | H | SO$_2$CH$_2$CH$_3$ | H | H | OCH$_3$ | OCH$_3$ | N | H |
| Q-27 | H | H | SO$_2$N(CH$_3$)$_2$ | H | H | CH$_3$ | OCH$_3$ | CH | H |
| Q-27 | H | H | SO$_2$N(CH$_2$CH$_3$)$_2$ | H | H | OCH$_3$ | OCH$_3$ | CH | H |
| Q-27 | CH$_3$ | H | CO$_2$CH$_3$ | H | H | OCH$_3$ | OCH$_3$ | CH | H |
| Q-27 | H | H | Br | H | CH$_3$ | OCH$_3$ | OCH$_3$ | CH | H |
| Q-27 | H | CH$_3$ | Cl | H | H | OCH$_3$ | OCH$_3$ | N | H |
| Q-28 | H | H | H | H | H | CH$_3$ | OCH$_3$ | CH | H |
| Q-28 | H | H | CH$_2$CH$_3$ | H | H | OCH$_3$ | OCH$_3$ | CH | H |
| Q-28 | H | H | F | H | H | CH$_3$ | CH$_3$ | CH | H |
| Q-28 | H | H | Cl | H | H | OCH$_3$ | OCH$_3$ | CH | H |
| Q-28 | H | H | Br | H | H | OCH$_3$ | CH$_3$ | CH | H |
| Q-28 | H | H | NO$_2$ | H | H | OCH$_3$ | OCH$_3$ | CH | H |
| Q-28 | H | H | SCH$_2$F | H | H | CH$_3$ | OCH$_3$ | CH | H |
| Q-28 | H | H | SCH$_2$F | H | H | OCH$_3$ | OCH$_3$ | CH | H |
| Q-28 | H | H | CH$_2$—CH=CH$_2$ | H | H | Cl | OCH$_3$ | CH | H |
| Q-28 | H | H | CH$_2$—C≡CH | H | H | OCH$_3$ | CH | H | |
| Q-28 | H | H | CO$_2$CH$_3$ | H | H | OCH$_3$ | OCH$_3$ | CH | H |
| Q-28 | H | H | CO$_2$CH$_3$ | H | H | OCH$_3$ | CH$_3$ | CH | H |
| Q-28 | H | H | CO$_2$CH$_3$ | H | H | CH$_3$ | CH$_3$ | N | H |
| Q-28 | H | H | CO$_2$CH$_2$CH$_3$ | H | H | OCH$_3$ | OCH$_3$ | CH | H |
| Q-28 | H | H | SCH$_3$ | H | H | CH$_3$ | OCH$_3$ | CH | H |

TABLE XXI-continued

General Formula XXI

| Q | R | R₂ | R₁₄ | R₆ | R₇ | X | Y | Z | m.p. °C. |
|---|---|---|---|---|---|---|---|---|---|
| Q-28 | H | H | SOCH₃ | H | H | CH₃ | CH₃ | CH | H |
| Q-28 | H | H | SO₂CH₃ | H | H | OCH₃ | OCH₃ | CH | H |
| Q-28 | H | H | SO₂N(CH₃)₂ | H | H | OCH₃ | CH₃ | CH | H |
| Q-28 | H | H | SO₂N(CH₃)₂ | H | H | OCH₃ | CH₃ | N | H |
| Q-28 | H | H | SO₂N(CH₂CH₃)₂ | H | H | OCH₃ | OCH₃ | CH | H |
| Q-28 | CH₃ | H | Cl | H | H | CH₃ | CH₃ | CH | H |
| Q-28 | H | CH₃ | Br | H | H | OCH₃ | OCH₃ | N | H |
| Q-28 | H | Cl | CO₂CH₃ | H | H | CH₃ | OCH₃ | CH | H |
| Q-29 | H | H | H | H | H | CH₃ | OCH₃ | CH | H |
| Q-29 | H | H | CH₃ | H | H | CH₃ | CH₃ | N | H |
| Q-29 | H | H | CH₂CH₂CH₃ | H | H | OCH₃ | OCH₃ | N | H |
| Q-29 | H | H | F | H | H | OCH₃ | OCH₃ | CH | H |
| Q-29 | H | H | Cl | H | H | OCH₃ | OCH₃ | CH | H |
| Q-29 | H | H | Cl | H | H | OCH₃ | CH₃ | N | H |
| Q-29 | H | H | Br | H | H | CH₃ | OCH₃ | CH | H |
| Q-29 | H | H | NO₂ | H | H | Cl | OCH₃ | CH | H |
| Q-29 | H | H | SCH₂CH₂F | H | H | OCH₃ | OCH₃ | CH | H |
| Q-29 | H | H | CH₂—CH=CH₂ | H | H | OCH₃ | CH₃ | CH | H |
| Q-29 | H | H | CH₂—C≡CH | H | H | CH₃ | CH₃ | CH | H |
| Q-29 | H | H | CO₂CH₃ | H | H | CH₃ | OCH₃ | N | H |
| Q-29 | H | H | CO₂CH₃ | H | H | OCH₃ | OCH₃ | CH | H |
| Q-29 | H | H | CO₂CH₃ | H | H | CH₃ | OCH₃ | CH | H |
| Q-29 | H | H | CO₂CH₂CH₃ | H | H | CH₃ | CH₃ | CH | H |
| Q-29 | H | H | CO₂CH₂CH₂CH₃ | H | H | OCH₃ | OCH₃ | CH | H |
| Q-29 | H | H | SCH₃ | H | H | CH₃ | CH₃ | N | H |
| Q-29 | H | H | SOCH₃ | H | H | CH₃ | CH₃ | CH | H |
| Q-29 | H | H | SO₂CH₃ | H | H | OCH₃ | OCH₃ | CH | H |
| Q-29 | H | H | SO₂CH₂CH₃ | H | H | OCH₃ | OCH₃ | N | H |
| Q-29 | H | H | SO₂N(CH₃)₂ | H | H | CH₃ | OCH₃ | CH | H |
| Q-29 | H | H | SO₂N(CH₂CH₃)₂ | H | H | OCH₃ | OCH₃ | CH | H |
| Q-29 | CH₃ | H | CO₂CH₃ | H | H | OCH₃ | OCH₃ | CH | H |
| Q-29 | H | H | Br | H | CH₃ | OCH₃ | OCH₃ | CH | H |
| Q-29 | H | CH₃ | Cl | H | H | OCH₃ | OCH₃ | N | H |
| Q-30 | H | H | H | H | H | CH₃ | OCH₃ | CH | H |
| Q-30 | H | H | CH₂CH₃ | H | H | OCH₃ | OCH₃ | CH | H |
| Q-30 | H | H | F | H | H | CH₃ | CH₃ | CH | H |
| Q-30 | H | H | Cl | H | H | OCH₃ | OCH₃ | CH | H |
| Q-30 | H | H | Br | H | H | OCH₃ | CH₃ | CH | H |
| Q-30 | H | H | NO₂ | H | H | OCH₃ | OCH₃ | CH | H |
| Q-30 | H | H | SCH₂F | H | H | CH₃ | OCH₃ | CH | H |
| Q-30 | H | H | SCH₂F | H | H | OCH₃ | OCH₃ | CH | H |
| Q-30 | H | H | CH₂—CH=CH₂ | H | H | Cl | OCH₃ | CH | H |
| Q-30 | H | H | CH₂—C≡CH | H | H | OCH₃ | OCH₃ | CH | H |
| Q-30 | H | H | CO₂CH₃ | H | H | OCH₃ | OCH₃ | CH | H |
| Q-30 | H | H | CO₂CH₃ | H | H | OCH₃ | CH₃ | CH | H |
| Q-30 | H | H | CO₂CH₃ | H | H | CH₃ | CH₃ | N | H |
| Q-30 | H | H | CO₂CH₂CH₃ | H | H | OCH₃ | OCH₃ | CH | H |
| Q-30 | H | H | SCH₃ | H | H | CH₃ | OCH₃ | CH | H |
| Q-30 | H | H | SOCH₃ | H | H | CH₃ | CH₃ | CH | H |
| Q-30 | H | H | SO₂CH₃ | H | H | OCH₃ | OCH₃ | CH | H |
| Q-30 | H | H | SO₂N(CH₃)₂ | H | H | OCH₃ | CH₃ | CH | H |
| Q-30 | H | H | SO₂N(CH₃)₂ | H | H | OCH₃ | CH₃ | N | H |
| Q-30 | H | H | SO₂N(CH₂CH₃)₂ | H | H | OCH₃ | OCH₃ | CH | H |
| Q-30 | CH₃ | H | Cl | H | H | CH₃ | CH₃ | CH | H |
| Q-30 | H | CH₃ | Br | H | H | OCH₃ | OCH₃ | N | H |
| Q-30 | H | Cl | CO₂CH₃ | H | H | CH₃ | OCH₃ | CH | H |

| Q | R | R₂ | R₁₄ | R₆ | R₇ | X | Y | Z | m.p. °C. |
|---|---|---|---|---|---|---|---|---|---|
| Q-31 | H | H | H | H | H | CH₃ | OCH₃ | CH | |
| Q-31 | H | H | CH₃ | H | H | CH₃ | CH₃ | N | |
| Q-31 | H | H | CH₂CH₂CH₃ | H | H | OCH₃ | OCH₃ | N | |
| Q-31 | H | H | F | H | H | OCH₃ | OCH₃ | CH | |
| Q-31 | H | H | Cl | H | H | OCH₃ | OCH₃ | CH | |
| Q-31 | H | H | Cl | H | H | OCH₃ | CH₃ | N | |
| Q-31 | H | H | Br | H | H | CH₃ | OCH₃ | CH | |
| Q-31 | H | H | NO₂ | H | H | Cl | OCH₃ | CH | |
| Q-31 | H | H | SCH₂CH₂F | H | H | OCH₃ | OCH₃ | CH | |
| Q-31 | H | H | CH₂—CH=CH₂ | H | H | OCH₃ | CH₃ | CH | |
| Q-31 | H | H | CH₂—C≡CH | H | H | CH₃ | CH₃ | CH | |
| Q-31 | H | CH₃ | CO₂CH₃ | H | H | CH₃ | OCH₃ | N | 185–188 |
| Q-31 | H | CH₃ | CO₂CH₃ | H | H | OCH₃ | OCH₃ | CH | 176–179 |
| Q-31 | H | CH₃ | CO₂CH₃ | H | H | CH₃ | OCH₃ | CH | 151–153 |
| Q-31 | H | H | CO₂CH₃ | H | H | CH₃ | CH₃ | CH | 198–200 |
| Q-31 | H | H | CO₂CH₃ | H | H | OCH₃ | OCH₃ | N | 168–171 |
| Q-31 | H | H | SCH₃ | H | H | CH₃ | CH₃ | N | |
| Q-31 | H | H | SOCH₃ | H | H | CH₃ | CH₃ | CH | |
| Q-31 | H | H | SO₂CH₃ | H | H | OCH₃ | OCH₃ | CH | |
| Q-31 | H | H | SO₂CH₂CH₃ | H | H | OCH₃ | OCH₃ | N | |
| Q-31 | H | H | SO₂N(CH₃)₂ | H | H | CH₃ | OCH₃ | CH | |
| Q-31 | H | H | SO₂N(CH₂CH₃)₂ | H | H | OCH₃ | OCH₃ | CH | |
| Q-31 | H | H | CO₂CH₃ | H | H | Cl | OCH₃ | CH | 178–180 |

TABLE XXI-continued

General Formula XXI

| Q | R | R$_2$ | R$_{14}$ | R$_6$ | X | Y | Z | R$_{10}$ | R$_{11}$ | m.p. °C. |
|---|---|---|---|---|---|---|---|---|---|---|
| Q-31 | H | H | Br | H | CH$_3$ | OCH$_3$ | OCH$_3$ | CH | | |
| Q-31 | H | CH$_3$ | Cl | H | H | OCH$_3$ | OCH$_3$ | N | | |
| Q-32 | H | H | H | H | H | CH$_3$ | OCH$_3$ | CH | | |
| Q-32 | H | H | CH$_2$CH$_3$ | H | H | OCH$_3$ | OCH$_3$ | CH | | |
| Q-32 | H | H | F | H | H | CH$_3$ | CH$_3$ | CH | | |
| Q-32 | H | H | Cl | H | H | OCH$_3$ | OCH$_3$ | CH | | |
| Q-32 | H | H | Br | H | H | OCH$_3$ | CH$_3$ | CH | | |
| Q-32 | H | H | NO$_2$ | H | H | OCH$_3$ | OCH$_3$ | CH | | |
| Q-32 | H | H | SCH$_2$F | H | H | CH$_3$ | OCH$_3$ | CH | | |
| Q-32 | H | H | SCH$_2$F | H | H | OCH$_3$ | OCH$_3$ | CH | | |
| Q-32 | H | H | CH$_2$—CH=CH$_2$ | H | H | Cl | OCH$_3$ | CH | | |
| Q-32 | H | H | CH$_2$—C≡CH | H | H | OCH$_3$ | OCH$_3$ | CH | | |
| Q-32 | H | H | CO$_2$CH$_3$ | H | H | OCH$_3$ | OCH$_3$ | CH | | |
| Q-32 | H | H | CO$_2$CH$_3$ | H | H | OCH$_3$ | CH$_3$ | CH | | |
| Q-32 | H | H | CO$_2$CH$_3$ | H | H | CH$_3$ | CH$_3$ | N | | |
| Q-32 | H | H | CO$_2$CH$_2$CH$_3$ | H | H | OCH$_3$ | OCH$_3$ | CH | | |
| Q-32 | H | H | SCH$_3$ | H | H | CH$_3$ | OCH$_3$ | CH | | |
| Q-32 | H | H | SOCH$_3$ | H | H | CH$_3$ | CH$_3$ | CH | | |
| Q-32 | H | H | SO$_2$CH$_3$ | N | H | OCH$_3$ | OCH$_3$ | CH | | |
| Q-32 | H | H | SO$_2$N(CH$_3$)$_2$ | H | H | OCH$_3$ | CH$_3$ | CH | | |
| Q-32 | H | H | SO$_2$N(CH$_3$)$_2$ | H | H | OCH$_3$ | CH$_3$ | N | | |
| Q-32 | H | H | SO$_2$N(CH$_2$CH$_3$)$_2$ | H | H | OCH$_3$ | OCH$_3$ | CH | | |
| Q-32 | CH$_3$ | H | Cl | H | H | CH$_3$ | CH$_3$ | CH | | |
| Q-32 | H | CH$_3$ | Br | H | H | OCH$_3$ | OCH$_3$ | N | | |
| Q-32 | H | Cl | CO$_2$CH$_3$ | H | H | CH$_3$ | OCH$_3$ | CH | | |
| Q-33 | H | H | H | H | H | CH$_3$ | OCH$_3$ | CH | | |
| Q-33 | H | H | CH$_3$ | H | H | CH$_3$ | CH$_3$ | N | | |
| Q-33 | H | H | CH$_2$CH$_2$CH$_3$ | H | H | OCH$_3$ | OCH$_3$ | N | | |
| Q-33 | H | H | F | H | H | OCH$_3$ | OCH$_3$ | CH | | |
| Q-33 | H | H | Cl | H | H | OCH$_3$ | OCH$_3$ | CH | | |
| Q-33 | H | H | Cl | H | H | OCH$_3$ | CH$_3$ | N | | |
| Q-33 | H | H | Br | H | H | CH$_3$ | OCH$_3$ | CH | | |
| Q-33 | H | H | NO$_2$ | H | H | Cl | OCH$_3$ | CH | | |
| Q-33 | H | H | SCH$_2$CH$_2$F | H | H | OCH$_3$ | OCH$_3$ | CH | | |
| Q-33 | H | H | CH$_2$—CH=CH$_2$ | H | H | OCH$_3$ | CH$_3$ | CH | | |
| Q-33 | H | H | CH$_2$—C≡CH | H | H | CH$_3$ | CH$_3$ | CH | | |
| Q-33 | H | H | CO$_2$CH$_3$ | H | H | CH$_3$ | OCH$_3$ | N | | |
| Q-33 | H | H | CO$_2$CH$_3$ | H | H | OCH$_3$ | OCH$_3$ | CH | | |
| Q-33 | H | H | CO$_2$CH$_3$ | H | H | CH$_3$ | OCH$_3$ | CH | | |
| Q-33 | H | H | CO$_2$CH$_2$CH$_3$ | H | H | CH$_3$ | CH$_3$ | CH | | |
| Q-33 | H | H | CO$_2$CH$_2$CH$_2$CH$_3$ | H | H | OCH$_3$ | OCH$_3$ | CH | | |
| Q-33 | H | H | SCH$_3$ | H | H | CH$_3$ | CH$_3$ | N | | |
| Q-33 | H | H | SOCH$_3$ | H | H | CH$_3$ | CH$_3$ | CH | | |
| Q-33 | H | H | SO$_2$CH$_3$ | H | H | OCH$_3$ | OCH$_3$ | CH | | |
| Q-33 | H | H | SO$_2$CH$_2$CH$_3$ | H | H | OCH$_3$ | OCH$_3$ | N | | |
| Q-33 | H | H | SO$_2$N(CH$_3$)$_2$ | H | H | CH$_3$ | OCH$_3$ | CH | | |
| Q-33 | H | H | SO$_2$N(CH$_2$CH$_3$)$_2$ | H | H | OCH$_3$ | OCH$_3$ | CH | | |
| Q-33 | CH$_3$ | H | CO$_2$CH$_3$ | H | H | OCH$_3$ | OCH$_3$ | CH | | |
| Q-33 | H | H | Br | H | CH$_3$ | OCH$_3$ | OCH$_3$ | CH | | |
| Q-33 | H | CH$_3$ | Cl | H | H | OCH$_3$ | OCH$_3$ | N | | |

| Q | R | R$_2$ | R$_{14}$ | R$_6$ | X | Y | Z | R$_{10}$ | R$_{11}$ | m.p. °C. |
|---|---|---|---|---|---|---|---|---|---|---|
| Q-34 | H | H | H | H | CH$_3$ | OCH$_3$ | CH | H | H | |
| Q-34 | H | H | CH$_2$CH$_3$ | H | OCH$_3$ | OCH$_3$ | CH | H | H | |
| Q-34 | H | H | F | H | CH$_3$ | CH$_3$ | CH | H | H | |
| Q-34 | H | H | Cl | H | OCH$_3$ | OCH$_3$ | CH | H | H | |
| Q-34 | H | H | Br | H | OCH$_3$ | CH$_3$ | CH | H | H | |
| Q-34 | H | H | NO$_2$ | H | OCH$_3$ | OCH$_3$ | CH | H | H | |
| Q-34 | H | H | SCH$_2$F | H | CH$_3$ | OCH$_3$ | CH | H | H | |
| Q-34 | H | H | SCH$_2$F | H | OCH$_3$ | OCH$_3$ | CH | H | H | |
| Q-34 | H | H | CH$_2$—CH=CH$_2$ | H | Cl | OCH$_3$ | CH | H | H | |
| Q-34 | H | H | CH$_2$—C≡CH | H | OCH$_3$ | OCH$_3$ | CH | H | H | |
| Q-34 | H | H | CO$_2$CH$_3$ | H | OCH$_3$ | OCH$_3$ | CH | H | H | |
| Q-34 | H | H | CO$_2$CH$_3$ | H | OCH$_3$ | CH$_3$ | CH | H | H | |
| Q-34 | H | H | CO$_2$CH$_3$ | H | CH$_3$ | CH$_3$ | N | H | H | |
| Q-34 | H | H | CO$_2$CH$_2$CH$_3$ | H | OCH$_3$ | OCH$_3$ | CH | H | H | |
| Q-34 | H | H | SCH$_3$ | H | CH$_3$ | OCH$_3$ | CH | H | H | |
| Q-34 | H | H | SOCH$_3$ | H | CH$_3$ | CH$_3$ | CH | H | H | |
| Q-34 | H | H | SO$_2$CH$_3$ | H | OCH$_3$ | OCH$_3$ | CH | H | H | |
| Q-34 | H | H | SO$_2$N(CH$_3$)$_2$ | H | OCH$_3$ | CH$_3$ | CH | H | H | |
| Q-34 | H | H | SO$_2$N(CH$_3$)$_2$ | H | OCH$_3$ | CH$_3$ | N | H | H | |
| Q-34 | H | H | SO$_2$N(CH$_2$CH$_3$)$_2$ | H | OCH$_3$ | OCH$_3$ | CH | H | H | |
| Q-34 | CH$_3$ | H | Cl | H | CH$_3$ | CH$_3$ | CH | H | H | |
| Q-34 | H | CH$_3$ | Br | H | OCH$_3$ | OCH$_3$ | N | H | H | |
| Q-34 | H | Cl | CO$_2$CH$_3$ | H | CH$_3$ | OCH$_3$ | CH | H | H | |

| Q | R | R$_2$ | R$_{14}$ | R$_{10}$ | R$_{11}$ | X | Y | Z | m.p. °C. |
|---|---|---|---|---|---|---|---|---|---|
| Q-35 | H | H | H | H | H | CH$_3$ | OCH$_3$ | CH | |
| Q-35 | H | H | CH$_3$ | H | H | CH$_3$ | CH$_3$ | N | |
| Q-35 | H | H | CH$_2$CH$_2$CH$_3$ | H | H | OCH$_3$ | OCH$_3$ | N | |
| Q-35 | H | H | F | H | H | OCH$_3$ | OCH$_3$ | CH | |

TABLE XXI-continued

General Formula XXI

| Q | R | R$_2$ | R$_{14}$ | R$_6$ | R$_7$ | X | Y | Z | m.p. °C. |
|---|---|---|---|---|---|---|---|---|---|
| Q-35 | H | H | Cl | H | H | OCH$_3$ | OCH$_3$ | CH | |
| Q-35 | H | H | Cl | H | H | OCH$_3$ | CH$_3$ | N | |
| Q-35 | H | H | Br | H | H | CH$_3$ | OCH$_3$ | CH | |
| Q-35 | H | H | NO$_2$ | H | H | Cl | OCH$_3$ | CH | |
| Q-35 | H | H | SCH$_2$CH$_2$F | H | H | OCH$_3$ | OCH$_3$ | CH | |
| Q-35 | H | H | CH$_2$—CH=CH$_2$ | H | H | OCH$_3$ | CH$_3$ | CH | |
| Q-35 | H | H | CH$_2$—C≡CH | H | H | CH$_3$ | CH$_3$ | CH | |
| Q-35 | H | H | CO$_2$CH$_3$ | H | H | CH$_3$ | OCH$_3$ | N | |
| Q-35 | H | H | CO$_2$CH$_3$ | H | H | OCH$_3$ | OCH$_3$ | CH | |
| Q-35 | H | H | CO$_2$CH$_3$ | H | H | CH$_3$ | OCH$_3$ | CH | |
| Q-35 | H | H | CO$_2$CH$_2$CH$_3$ | H | H | CH$_3$ | CH$_3$ | CH | |
| Q-35 | H | H | CO$_2$CH$_2$CH$_2$CH$_3$ | H | H | OCH$_3$ | OCH$_3$ | CH | |
| Q-35 | H | H | SCH$_3$ | H | H | CH$_3$ | CH$_3$ | N | |
| Q-35 | H | H | SOCH$_3$ | H | H | CH$_3$ | CH$_3$ | CH | |
| Q-35 | H | H | SO$_2$CH$_3$ | H | H | OCH$_3$ | OCH$_3$ | CH | |
| Q-35 | H | H | SO$_2$CH$_2$CH$_3$ | H | H | OCH$_3$ | OCH$_3$ | N | |
| Q-35 | H | H | SO$_2$N(CH$_3$)$_2$ | H | H | CH$_3$ | OCH$_3$ | CH | |
| Q-35 | H | H | SO$_2$N(CH$_2$CH$_3$)$_2$ | H | H | OCH$_3$ | OCH$_3$ | CH | |
| Q-35 | CH$_3$ | H | CO$_2$CH$_3$ | H | H | OCH$_3$ | OCH$_3$ | CH | |
| Q-35 | H | H | Br | H | CH$_3$ | OCH$_3$ | OCH$_3$ | CH | |
| Q-35 | H | CH$_3$ | Cl | H | H | OCH$_3$ | OCH$_3$ | N | |
| Q-36 | H | H | H | H | H | CH$_3$ | OCH$_3$ | CH | |
| Q-36 | H | H | CH$_2$CH$_3$ | H | H | OCH$_3$ | OCH$_3$ | CH | |
| Q-36 | H | H | F | H | H | CH$_3$ | CH$_3$ | CH | |
| Q-36 | H | H | Cl | H | H | OCH$_3$ | OCH$_3$ | CH | |
| Q-36 | H | H | Br | H | H | OCH$_3$ | CH$_3$ | CH | |
| Q-36 | H | H | NO$_2$ | H | H | OCH$_3$ | OCH$_3$ | CH | |
| Q-36 | H | H | SCH$_2$F | H | H | CH$_3$ | OCH$_3$ | CH | |
| Q-36 | H | H | SCH$_2$F | H | H | OCH$_3$ | OCH$_3$ | CH | |
| Q-36 | H | H | CH$_2$—CH=CH$_2$ | H | H | Cl | OCH$_3$ | CH | |
| Q-36 | H | H | CH$_2$—C≡CH | H | H | OCH$_3$ | OCH$_3$ | CH | |
| Q-36 | H | H | CO$_2$CH$_3$ | H | H | OCH$_3$ | OCH$_3$ | CH | |
| Q-36 | H | H | CO$_2$CH$_3$ | H | H | OCH$_3$ | CH$_3$ | CH | |
| Q-36 | H | H | CO$_2$CH$_3$ | H | H | CH$_3$ | CH$_3$ | N | |
| Q-36 | H | H | CO$_2$CH$_2$CH$_3$ | H | H | OCH$_3$ | OCH$_3$ | CH | |
| Q-36 | H | H | SCH$_3$ | H | H | CH$_3$ | OCH$_3$ | CH | |
| Q-36 | H | H | SOCH$_3$ | H | H | CH$_3$ | CH$_3$ | CH | |
| Q-36 | H | H | SO$_2$CH$_3$ | H | H | OCH$_3$ | OCH$_3$ | CH | |
| Q-36 | H | H | SO$_2$N(CH$_3$)$_2$ | H | H | OCH$_3$ | CH$_3$ | CH | |
| Q-36 | H | H | SO$_2$N(CH$_3$)$_2$ | H | H | OCH$_3$ | CH$_3$ | N | |
| Q-36 | H | H | SO$_2$N(CH$_2$CH$_3$)$_2$ | H | H | OCH$_3$ | OCH$_3$ | CH | |
| Q-36 | CH$_3$ | H | Cl | H | H | CH$_3$ | CH$_3$ | CH | |
| Q-36 | H | CH$_3$ | Br | H | H | OCH$_3$ | OCH$_3$ | N | |
| Q-36 | H | Cl | CO$_2$CH$_3$ | H | H | CH$_3$ | OCH$_3$ | CH | |

| Q | R | R$_2$ | R$_{14}$ | R$_6$ | R$_7$ | X | Y | Z | m.p. °C. |
|---|---|---|---|---|---|---|---|---|---|
| Q-37 | H | H | H | H | H | CH$_3$ | OCH$_3$ | CH | |
| Q-37 | H | H | CH$_3$ | H | H | CH$_3$ | CH$_3$ | N | |
| Q-37 | H | H | CH$_2$CH$_2$CH$_3$ | H | H | OCH$_3$ | OCH$_3$ | N | |
| Q-37 | H | H | F | H | H | OCH$_3$ | OCH$_3$ | CH | |
| Q-37 | H | H | Cl | H | H | OCH$_3$ | OCH$_3$ | CH | |
| Q-37 | H | H | Cl | H | H | OCH$_3$ | CH$_3$ | N | |
| Q-37 | H | H | Br | H | H | CH$_3$ | OCH$_3$ | CH | |
| Q-37 | H | H | NO$_2$ | H | H | Cl | OCH$_3$ | CH | |
| Q-37 | H | H | SCH$_2$CH$_2$F | H | H | OCH$_3$ | OCH$_3$ | CH | |
| Q-37 | H | H | CH$_2$—CH=CH$_2$ | H | H | OCH$_3$ | CH$_3$ | CH | |
| Q-37 | H | H | CH$_2$—C≡CH | H | H | CH$_3$ | CH$_3$ | CH | |
| Q-37 | H | H | CO$_2$CH$_3$ | H | H | CH$_3$ | OCH$_3$ | N | |
| Q-37 | H | H | CO$_2$CH$_3$ | H | H | OCH$_3$ | OCH$_3$ | CH | |
| Q-37 | H | H | CO$_2$CH$_3$ | H | H | CH$_3$ | OCH$_3$ | CH | |
| Q-37 | H | H | CO$_2$CH$_2$CH$_3$ | H | H | CH$_3$ | CH$_3$ | CH | |
| Q-37 | H | H | CO$_2$CH$_2$CH$_2$CH$_3$ | H | H | OCH$_3$ | OCH$_3$ | CH | |
| Q-37 | H | H | SCH$_3$ | H | H | CH$_3$ | CH$_3$ | N | |
| Q-37 | H | H | SOCH$_3$ | H | H | CH$_3$ | CH$_3$ | CH | |
| Q-37 | H | H | SO$_2$CH$_3$ | H | H | OCH$_3$ | OCH$_3$ | CH | |
| Q-37 | H | H | SO$_2$CH$_2$CH$_3$ | H | H | OCH$_3$ | OCH$_3$ | N | |
| Q-37 | H | H | SO$_2$N(CH$_3$)$_2$ | H | H | CH$_3$ | OCH$_3$ | CH | |
| Q-37 | H | H | SO$_2$N(CH$_2$CH$_3$)$_2$ | H | H | OCH$_3$ | OCH$_3$ | CH | |
| Q-37 | CH$_3$ | H | CO$_2$CH$_3$ | H | H | OCH$_3$ | OCH$_3$ | CH | |
| Q-37 | H | H | Br | H | CH$_3$ | OCH$_3$ | OCH$_3$ | CH | |
| Q-37 | H | CH$_3$ | Cl | H | H | OCH$_3$ | OCH$_3$ | N | |
| Q-38 | H | H | H | H | H | CH$_3$ | OCH$_3$ | CH | |
| Q-38 | H | H | CH$_2$CH$_3$ | H | H | OCH$_3$ | OCH$_3$ | CH | |
| Q-38 | H | H | F | H | H | CH$_3$ | CH$_3$ | CH | |
| Q-38 | H | H | Cl | H | H | OCH$_3$ | OCH$_3$ | CH | |
| Q-38 | H | H | Br | H | H | OCH$_3$ | CH$_3$ | CH | |
| Q-38 | H | H | NO$_2$ | H | H | OCH$_3$ | OCH$_3$ | CH | |
| Q-38 | H | H | SCH$_2$F | H | H | CH$_3$ | OCH$_3$ | CH | |
| Q-38 | H | H | SCH$_2$F | H | H | OCH$_3$ | OCH$_3$ | CH | |
| Q-38 | H | H | CH$_2$—CH=CH$_2$ | H | H | Cl | OCH$_3$ | CH | |
| Q-38 | H | H | CH$_2$—C≡CH | H | H | OCH$_3$ | OCH$_3$ | CH | |

TABLE XXI-continued

General Formula XXI

| Q | R | R$_2$ | R$_{14}$ | | | X | Y | Z | m.p. °C. |
|---|---|---|---|---|---|---|---|---|---|
| Q-38 | H | H | CO$_2$CH$_3$ | H | H | OCH$_3$ | OCH$_3$ | CH | |
| Q-38 | H | H | CO$_2$CH$_3$ | H | H | OCH$_3$ | CH$_3$ | CH | |
| Q-38 | H | H | CO$_2$CH$_3$ | H | H | CH$_3$ | CH$_3$ | N | |
| Q-38 | H | H | CO$_2$CH$_2$CH$_3$ | H | H | OCH$_3$ | OCH$_3$ | CH | |
| Q-38 | H | H | SCH$_3$ | H | H | CH$_3$ | OCH$_3$ | CH | |
| Q-38 | H | H | SOCH$_3$ | H | H | CH$_3$ | CH$_3$ | CH | |
| Q-38 | H | H | SO$_2$CH$_3$ | H | H | OCH$_3$ | OCH$_3$ | CH | |
| Q-38 | H | H | SO$_2$N(CH$_3$)$_2$ | H | H | OCH$_3$ | CH$_3$ | CH | |
| Q-38 | H | H | SO$_2$N(CH$_3$)$_2$ | H | H | OCH$_3$ | CH$_3$ | N | |
| Q-38 | H | H | SO$_2$N(CH$_2$CH$_3$)$_2$ | H | H | OCH$_3$ | OCH$_3$ | CH | |
| Q-38 | CH$_3$ | H | Cl | H | H | CH$_3$ | CH$_3$ | CH | |
| Q-38 | H | CH$_3$ | Br | H | H | OCH$_3$ | OCH$_3$ | N | |
| Q-38 | H | Cl | CO$_2$CH$_3$ | H | H | CH$_3$ | OCH$_3$ | CH | |

| Q | R | R$_2$ | R$_{14}$ | R$_{12}$ | R$_{13}$ | X | Y | Z | m.p. °C. |
|---|---|---|---|---|---|---|---|---|---|
| Q-39 | H | H | H | H | H | OCH$_3$ | OCH$_3$ | CH | |
| Q-39 | H | H | CH$_3$ | H | H | CH$_3$ | CH$_3$ | N | |
| Q-39 | H | H | CH$_2$CH$_2$CH$_3$ | H | H | OCH$_3$ | OCH$_3$ | N | |
| Q-39 | H | H | F | H | H | OCH$_3$ | OCH$_3$ | CH | |
| Q-39 | H | H | Cl | H | H | OCH$_3$ | OCH$_3$ | CH | |
| Q-39 | H | H | Cl | H | H | OCH$_3$ | CH$_3$ | N | |
| Q-39 | H | H | Br | H | H | CH$_3$ | OCH$_3$ | CH | |
| Q-39 | H | H | NO$_2$ | H | H | Cl | OCH$_3$ | CH | |
| Q-39 | H | H | SCH$_2$CH$_2$F | H | H | OCH$_3$ | OCH$_3$ | CH | |
| Q-39 | H | H | CH$_2$—CH=CH$_2$ | H | H | OCH$_3$ | CH$_3$ | CH | |
| Q-39 | H | H | CH$_2$—C≡CH | H | H | CH$_3$ | CH$_3$ | CH | |
| Q-39 | H | H | CO$_2$CH$_3$ | H | H | CH$_3$ | OCH$_3$ | N | |

| Q | R | R$_2$ | R$_{14}$ | R$_6$ | R$_7$ | X | Y | Z | m.p. °C. |
|---|---|---|---|---|---|---|---|---|---|
| Q-39 | H | H | CO$_2$CH$_3$ | H | H | OCH$_3$ | OCH$_3$ | CH | |
| Q-39 | H | H | CO$_2$CH$_3$ | H | H | CH$_3$ | OCH$_3$ | CH | |
| Q-39 | H | H | CO$_2$CH$_2$CH$_3$ | H | H | CH$_3$ | CH$_3$ | CH | |
| Q-39 | H | H | CO$_2$CH$_2$CH$_2$CH$_3$ | H | H | OCH$_3$ | OCH$_3$ | CH | |
| Q-39 | H | H | SCH$_3$ | H | H | CH$_3$ | CH$_3$ | N | |
| Q-39 | H | H | SOCH$_3$ | H | H | CH$_3$ | CH$_3$ | CH | |
| Q-39 | H | H | SO$_2$CH$_3$ | H | H | OCH$_3$ | OCH$_3$ | CH | |
| Q-39 | H | H | SO$_2$CH$_2$CH$_3$ | H | H | OCH$_3$ | OCH$_3$ | N | |
| Q-39 | H | H | SO$_2$N(CH$_3$)$_2$ | H | H | CH$_3$ | OCH$_3$ | CH | |
| Q-39 | H | H | SO$_2$N(CH$_2$CH$_3$)$_2$ | H | H | OCH$_3$ | OCH$_3$ | CH | |
| Q-39 | CH$_3$ | H | CO$_2$CH$_3$ | H | H | OCH$_3$ | OCH$_3$ | CH | |
| Q-39 | H | H | Br | H | CH$_3$ | OCH$_3$ | OCH$_3$ | CH | |
| Q-39 | H | CH$_3$ | Cl | H | H | OCH$_3$ | OCH$_3$ | N | |
| Q-40 | H | H | H | H | H | CH$_3$ | OCH$_3$ | CH | |
| Q-40 | H | H | CH$_2$CH$_3$ | H | H | OCH$_3$ | OCH$_3$ | CH | |
| Q-40 | H | H | F | H | H | CH$_3$ | CH$_3$ | CH | |
| Q-40 | H | H | Cl | H | H | OCH$_3$ | OCH$_3$ | CH | |
| Q-40 | H | H | Br | H | H | CH$_3$ | OCH$_3$ | CH | |
| Q-40 | H | H | NO$_2$ | H | H | OCH$_3$ | OCH$_3$ | CH | |
| Q-40 | H | H | SCH$_2$F | H | H | CH$_3$ | OCH$_3$ | CH | |
| Q-40 | H | H | SCH$_2$F | H | H | OCH$_3$ | OCH$_3$ | CH | |
| Q-40 | H | H | CH$_2$—CH=CH$_2$ | H | H | Cl | OCH$_3$ | CH | |
| Q-40 | H | H | CH$_2$—C≡CH | H | H | OCH$_3$ | OCH$_3$ | CH | |
| Q-40 | H | H | CO$_2$CH$_3$ | H | H | OCH$_3$ | OCH$_3$ | CH | |
| Q-40 | H | H | CO$_2$CH$_3$ | H | H | OCH$_3$ | CH$_3$ | CH | |
| Q-40 | H | H | CO$_2$CH$_3$ | H | H | CH$_3$ | CH$_3$ | N | |
| Q-40 | H | H | CO$_2$CH$_2$CH$_3$ | H | H | OCH$_3$ | OCH$_3$ | CH | |
| Q-40 | H | H | SCH$_3$ | H | H | CH$_3$ | OCH$_3$ | CH | |
| Q-40 | H | H | SOCH$_3$ | H | H | CH$_3$ | CH$_3$ | CH | |
| Q-40 | H | H | SO$_2$CH$_3$ | H | H | OCH$_3$ | OCH$_3$ | CH | |
| Q-40 | H | H | SO$_2$N(CH$_3$)$_2$ | H | H | OCH$_3$ | CH$_3$ | CH | |
| Q-40 | H | H | SO$_2$N(CH$_3$)$_2$ | H | H | OCH$_3$ | CH$_3$ | N | |
| Q-40 | H | H | SO$_2$N(CH$_2$CH$_3$)$_2$ | H | H | OCH$_3$ | OCH$_3$ | CH | |
| Q-40 | CH$_3$ | H | Cl | H | H | CH$_3$ | CH$_3$ | CH | |
| Q-40 | H | CH$_3$ | Br | H | H | OCH$_3$ | OCH$_3$ | N | |
| Q-40 | H | Cl | CO$_2$CH$_3$ | H | H | CH$_3$ | OCH$_3$ | CH | |

| Q | R | R$_2$ | R$_{14}$ | R$_6$ | X | Y | Z | m.p. °C. |
|---|---|---|---|---|---|---|---|---|
| Q-41 | H | H | H | H | CH$_3$ | OCH$_3$ | CH | |
| Q-41 | H | H | CH$_3$ | H | CH$_3$ | CH$_3$ | N | |
| Q-41 | H | H | CH$_2$CH$_2$CH$_3$ | H | OCH$_3$ | OCH$_3$ | N | |
| Q-41 | H | H | F | H | OCH$_3$ | OCH$_3$ | CH | |
| Q-41 | H | H | Cl | H | OCH$_3$ | OCH$_3$ | CH | |
| Q-41 | H | H | Cl | H | OCH$_3$ | CH$_3$ | N | |
| Q-41 | H | H | Br | H | CH$_3$ | OCH$_3$ | CH | |
| Q-41 | H | H | NO$_2$ | H | Cl | OCH$_3$ | CH | |
| Q-41 | H | H | SCH$_2$CH$_2$F | H | OCH$_3$ | OCH$_3$ | CH | |
| Q-41 | H | H | CH$_2$—CH=CH$_2$ | H | OCH$_3$ | CH$_3$ | CH | |
| Q-41 | H | H | CH$_2$—C≡CH | H | CH$_3$ | CH$_3$ | CH | |
| Q-41 | H | H | CO$_2$CH$_3$ | H | CH$_3$ | OCH$_3$ | N | |
| Q-41 | H | H | CO$_2$CH$_3$ | H | OCH$_3$ | OCH$_3$ | CH | |
| Q-41 | H | H | CO$_2$CH$_3$ | H | CH$_3$ | OCH$_3$ | CH | |

TABLE XXI-continued

General Formula XXI

| | | | | | | | |
|---|---|---|---|---|---|---|---|
| Q-41 | H | H | CO$_2$CH$_2$CH$_3$ | H | CH$_3$ | CH$_3$ | CH |
| Q-41 | H | H | CO$_2$CH$_2$CH$_2$CH$_3$ | H | OCH$_3$ | OCH$_3$ | CH |
| Q-41 | H | H | SCH$_3$ | H | CH$_3$ | CH$_3$ | N |
| Q-41 | H | H | SOCH$_3$ | H | CH$_3$ | CH$_3$ | CH |
| Q-41 | H | H | SO$_2$CH$_3$ | H | OCH$_3$ | OCH$_3$ | CH |
| Q-41 | H | H | SO$_2$CH$_2$CH$_3$ | H | OCH$_3$ | OCH$_3$ | N |
| Q-41 | H | H | SO$_2$N(CH$_3$)$_2$ | H | CH$_3$ | OCH$_3$ | CH |
| Q-41 | H | H | SO$_2$N(CH$_2$CH$_3$)$_2$ | H | OCH$_3$ | OCH$_3$ | CH |
| Q-41 | CH$_3$ | H | CO$_2$CH$_3$ | H | OCH$_3$ | OCH$_3$ | CH |
| Q-41 | H | H | Br | CH$_3$ | OCH$_3$ | OCH$_3$ | CH |
| Q-41 | H | CH$_3$ | Cl | H | OCH$_3$ | OCH$_3$ | N |
| Q-42 | H | H | H | H | CH$_3$ | OCH$_3$ | CH |
| Q-42 | H | H | CH$_2$CH$_3$ | H | OCH$_3$ | OCH$_3$ | CH |
| Q-42 | H | H | F | H | CH$_3$ | CH$_3$ | CH |
| Q-42 | H | H | Cl | H | OCH$_3$ | OCH$_3$ | CH |
| Q-42 | H | H | Br | H | OCH$_3$ | CH$_3$ | CH |
| Q-42 | H | H | NO$_2$ | H | OCH$_3$ | OCH$_3$ | CH |
| Q-42 | H | H | SCH$_2$F | H | CH$_3$ | OCH$_3$ | CH |
| Q-42 | H | H | SCH$_2$F | H | OCH$_3$ | OCH$_3$ | CH |
| Q-42 | H | H | CH$_2$—CH=CH$_2$ | H | Cl | OCH$_3$ | CH |
| Q-42 | H | H | CH$_2$—C≡CH | H | OCH$_3$ | OCH$_3$ | CH |
| Q-42 | H | H | CO$_2$CH$_3$ | H | OCH$_3$ | OCH$_3$ | CH |
| Q-42 | H | H | CO$_2$CH$_3$ | H | OCH$_3$ | CH$_3$ | CH |
| Q-42 | H | H | CO$_2$CH$_3$ | H | CH$_3$ | CH$_3$ | N |
| Q-42 | H | H | CO$_2$CH$_2$CH$_3$ | H | OCH$_3$ | OCH$_3$ | CH |
| Q-42 | H | H | SCH$_3$ | H | CH$_3$ | OCH$_3$ | CH |
| Q-42 | H | H | SOCH$_3$ | H | CH$_3$ | CH$_3$ | CH |
| Q-42 | H | H | SO$_2$CH$_3$ | H | OCH$_3$ | OCH$_3$ | CH |
| Q-42 | H | H | SO$_2$N(CH$_3$)$_2$ | H | OCH$_3$ | CH$_3$ | CH |
| Q-42 | H | H | SO$_2$N(CH$_3$)$_2$ | H | OCH$_3$ | CH$_3$ | N |
| Q-42 | H | H | SO$_2$N(CH$_2$CH$_3$)$_2$ | H | OCH$_3$ | OCH$_3$ | CH |
| Q-42 | CH$_3$ | H | Cl | H | CH$_3$ | CH$_3$ | CH |
| Q-42 | H | CH$_3$ | Br | H | OCH$_3$ | OCH$_3$ | N |
| Q-42 | H | Cl | CO$_2$CH$_3$ | H | CH$_3$ | OCH$_3$ | CH |
| Q-43 | H | H | H | H | CH$_3$ | OCH$_3$ | CH |
| Q-43 | H | H | CH$_3$ | H | CH$_3$ | CH$_3$ | N |
| Q-43 | H | H | CH$_2$CH$_2$CH$_3$ | H | OCH$_3$ | OCH$_3$ | N |
| Q-43 | H | H | F | H | OCH$_3$ | OCH$_3$ | CH |
| Q-43 | H | H | Cl | H | OCH$_3$ | OCH$_3$ | CH |
| Q-43 | H | H | Cl | H | OCH$_3$ | CH$_3$ | N |
| Q-43 | H | H | Br | H | CH$_3$ | OCH$_3$ | CH |
| Q-43 | H | H | NO$_2$ | H | Cl | OCH$_3$ | CH |
| Q-43 | H | H | SCH$_2$CH$_2$F | H | OCH$_3$ | OCH$_3$ | CH |
| Q-43 | H | H | CH$_2$—CH=CH$_2$ | H | OCH$_3$ | CH$_3$ | CH |
| Q-43 | H | H | CH$_2$—C≡CH | H | CH$_3$ | CH$_3$ | CH |
| Q-43 | H | H | CO$_2$CH$_3$ | H | CH$_3$ | OCH$_3$ | N |
| Q-43 | H | H | CO$_2$CH$_3$ | H | OCH$_3$ | OCH$_3$ | CH |
| Q-43 | H | H | CO$_2$CH$_3$ | H | CH$_3$ | CH$_3$ | CH |
| Q-43 | H | H | CO$_2$CH$_2$CH$_3$ | H | CH$_3$ | CH$_3$ | CH |
| Q-43 | H | H | CO$_2$CH$_2$CH$_2$CH$_3$ | H | OCH$_3$ | OCH$_3$ | CH |
| Q-43 | H | H | SCH$_3$ | H | CH$_3$ | CH$_3$ | N |
| Q-43 | H | H | SOCH$_3$ | H | CH$_3$ | CH$_3$ | CH |
| Q-43 | H | H | SO$_2$CH$_3$ | H | OCH$_3$ | OCH$_3$ | CH |
| Q-43 | H | H | SO$_2$CH$_2$CH$_3$ | H | OCH$_3$ | OCH$_3$ | N |
| Q-43 | H | H | SO$_2$N(CH$_3$)$_2$ | H | CH$_3$ | OCH$_3$ | CH |
| Q-43 | H | H | SO$_2$N(CH$_2$CH$_3$)$_2$ | H | OCH$_3$ | OCH$_3$ | CH |
| Q-43 | CH$_3$ | H | CO$_2$CH$_3$ | H | OCH$_3$ | OCH$_3$ | CH |
| Q-43 | H | H | Br | CH$_3$ | OCH$_3$ | OCH$_3$ | CH |
| Q-43 | H | CH$_3$ | Cl | H | OCH$_3$ | OCH$_3$ | N |
| Q-44 | H | H | H | H | CH$_3$ | OCH$_3$ | CH |
| Q-44 | H | H | CH$_2$CH$_3$ | H | OCH$_3$ | OCH$_3$ | CH |
| Q-44 | H | H | F | H | CH$_3$ | CH$_3$ | CH |
| Q-44 | H | H | Cl | H | OCH$_3$ | OCH$_3$ | CH |
| Q-44 | H | H | Br | H | OCH$_3$ | CH$_3$ | CH |
| Q-44 | H | H | NO$_2$ | H | OCH$_3$ | OCH$_3$ | CH |
| Q-44 | H | H | SCH$_2$F | H | CH$_3$ | OCH$_3$ | CH |
| Q-44 | H | H | SCH$_2$F | H | OCH$_3$ | OCH$_3$ | CH |
| Q-44 | H | H | CH$_2$—CH=CH$_2$ | H | Cl | OCH$_3$ | CH |
| Q-44 | H | H | CH$_2$—C≡CH | H | OCH$_3$ | OCH$_3$ | CH |
| Q-44 | H | H | CO$_2$CH$_3$ | H | OCH$_3$ | OCH$_3$ | CH |
| Q-44 | H | H | CO$_2$CH$_3$ | H | OCH$_3$ | CH$_3$ | CH |
| Q-44 | H | H | CO$_2$CH$_3$ | H | CH$_3$ | CH$_3$ | N |
| Q-44 | H | H | CO$_2$CH$_2$CH$_3$ | H | OCH$_3$ | OCH$_3$ | CH |
| Q-44 | H | H | SCH$_3$ | H | CH$_3$ | OCH$_3$ | CH |
| Q-44 | H | H | SOCH$_3$ | H | CH$_3$ | CH$_3$ | CH |
| Q-44 | H | H | SO$_2$CH$_3$ | H | OCH$_3$ | OCH$_3$ | CH |
| Q-44 | H | H | SO$_2$N(CH$_3$)$_2$ | H | OCH$_3$ | CH$_3$ | CH |
| Q-44 | H | H | SO$_2$N(CH$_3$)$_2$ | H | OCH$_3$ | CH$_3$ | N |
| Q-44 | H | H | SO$_2$N(CH$_2$CH$_3$)$_2$ | H | OCH$_3$ | OCH$_3$ | CH |
| Q-44 | CH$_3$ | H | Cl | H | CH$_3$ | CH$_3$ | CH |
| Q-44 | H | CH$_3$ | Br | H | OCH$_3$ | OCH$_3$ | N |

TABLE XXI-continued

General Formula XXI

| Q | R | | | | | | |
|---|---|---|---|---|---|---|---|
| Q-44 | H | Cl | $CO_2CH_3$ | H | $CH_3$ | $OCH_3$ | CH |

TABLE XXII

General Formula XXII

| Q | R | $R_2$ | $R_{14}$ | Z | X | Y | Z | $X_1$ | $Y_1$ | $Y_2$ | m.p. °C. |
|---|---|---|---|---|---|---|---|---|---|---|---|
| Q-1 | H | H | $CO_2CH_3$ | A-1 | $OCH_2F$ | $OCH_3$ | CH | — | — | — | |
| Q-7 | H | H | $CO_2CH_3$ | A-1 | Br | $OCH_3$ | CH | — | — | — | |
| Q-12 | H | H | Br | A-1 | $OCH_2CH_2F$ | $NHCH_3$ | CH | — | — | — | |
| Q-34 | H | H | Cl | A-1 | $CH_2F$ | $OCH_3$ | CH | — | — | — | |
| Q-1 | H | H | $CO_2CH_3$ | A-2 | — | — | — | $OCH_3$ | $CH_2$ | — | |
| Q-29 | H | H | Br | A-3 | — | — | — | $OCH_3$ | — | — | |
| Q-11 | H | H | $CH_2CH_3$ | A-4 | — | — | — | $CH_3$ | — | H | |
| Q-33 | H | H | $CO_2CH_3$ | A-2 | — | — | — | $OCF_2H$ | O | — | |

TABLE XXIII

General Formula XIII

| Q | R | $R_{15}$ | $R_{16}$ | $R_6$ | $R_7$ | X | Y | Z | m.p. °C. |
|---|---|---|---|---|---|---|---|---|---|
| Q-1 | H | H | H | H | H | $CH_3$ | $OCH_3$ | CH | |
| Q-1 | H | H | $CH_3$ | H | H | $CH_3$ | $CH_3$ | N | |
| Q-1 | H | H | $CH_2CH_2CH_3$ | H | H | $OCH_3$ | $OCH_3$ | N | |
| Q-1 | H | H | F | H | H | $OCH_3$ | $OCH_3$ | CH | |
| Q-1 | H | H | Cl | H | H | $OCH_3$ | $OCH_3$ | CH | |
| Q-1 | H | H | Cl | H | H | $OCH_3$ | $CH_3$ | N | |
| Q-1 | H | H | Br | H | H | $CH_3$ | $OCH_3$ | CH | |
| Q-1 | H | H | $NO_2$ | H | H | Cl | $OCH_3$ | CH | |
| Q-1 | H | H | $SCH_2CH_2F$ | H | H | $OCH_3$ | $OCH_3$ | CH | |
| Q-1 | H | H | $CH_2-CH=CH_2$ | H | H | $OCH_3$ | $CH_3$ | CH | |
| Q-1 | H | H | $CH_2-C\equiv CH$ | H | H | $CH_3$ | $CH_3$ | CH | |
| Q-1 | H | H | $CO_2CH_3$ | H | H | $CH_3$ | $OCH_3$ | N | |
| Q-1 | H | H | $CO_2CH_3$ | H | H | $OCH_3$ | $OCH_3$ | CH | |
| Q-1 | H | H | $CO_2CH_3$ | H | H | $CH_3$ | $OCH_3$ | CH | |
| Q-1 | H | H | $CO_2CH_2CH_3$ | H | H | $CH_3$ | $CH_3$ | CH | |
| Q-1 | H | H | $CO_2CH_2CH_2CH_3$ | H | H | $OCH_3$ | $OCH_3$ | CH | |
| Q-1 | H | H | $SCH_3$ | H | H | $CH_3$ | $CH_3$ | N | |
| Q-1 | H | H | $SOCH_3$ | H | H | $CH_3$ | $CH_3$ | CH | |
| Q-1 | H | H | $SO_2CH_3$ | H | H | $OCH_3$ | $OCH_3$ | CH | |
| Q-1 | H | H | $SO_2CH_2CH_3$ | H | H | $OCH_3$ | $CH_3$ | N | |
| Q-1 | H | H | $SO_2N(CH_3)_2$ | H | H | $CH_3$ | $OCH_3$ | CH | |
| Q-1 | H | H | $SO_2N(CH_2CH_3)_2$ | H | H | $OCH_3$ | $OCH_3$ | CH | |
| Q-1 | $CH_3$ | H | $CO_2CH_3$ | H | H | $OCH_3$ | $OCH_3$ | CH | |
| Q-1 | H | H | Br | H | $CH_3$ | $OCH_3$ | $OCH_3$ | CH | |
| Q-1 | H | $CH_3$ | Cl | H | H | $OCH_3$ | $OCH_3$ | N | |
| Q-2 | H | H | H | H | H | $CH_3$ | $OCH_3$ | CH | |
| Q-2 | H | H | $CH_2CH_3$ | H | H | $OCH_3$ | $OCH_3$ | CH | |
| Q-2 | H | H | F | H | H | $CH_3$ | $CH_3$ | CH | |
| Q-2 | H | H | Cl | H | H | $OCH_3$ | $OCH_3$ | CH | |
| Q-2 | H | H | Br | H | H | $OCH_3$ | $CH_3$ | CH | |
| Q-2 | H | H | $NO_2$ | H | H | $OCH_3$ | $OCH_3$ | CH | |
| Q-2 | H | H | $SCH_2F$ | H | H | $CH_3$ | $OCH_3$ | CH | |
| Q-2 | H | H | $SCH_2F$ | H | H | $OCH_3$ | $OCH_3$ | CH | |
| Q-2 | H | H | $CH_2-CH=CH_2$ | H | H | Cl | $OCH_3$ | CH | |
| Q-2 | H | H | $CH_2-C\equiv CH$ | H | H | $OCH_3$ | $OCH_3$ | CH | |
| Q-2 | H | H | $CO_2CH_3$ | H | H | $OCH_3$ | $OCH_3$ | CH | |
| Q-2 | H | H | $CO_2CH_3$ | H | H | $OCH_3$ | $CH_3$ | CH | |
| Q-2 | H | H | $CO_2CH_3$ | H | H | $CH_3$ | $CH_3$ | N | |
| Q-2 | H | H | $CO_2CH_2CH_3$ | H | H | $OCH_3$ | $OCH_3$ | CH | |
| Q-2 | H | H | $SCH_3$ | H | H | $CH_3$ | $OCH_3$ | CH | |
| Q-2 | H | H | $SOCH_3$ | H | H | $CH_3$ | $CH_3$ | CH | |
| Q-2 | H | H | $SO_2CH_3$ | H | H | $OCH_3$ | $OCH_3$ | CH | |
| Q-2 | H | H | $SO_2N(CH_3)_2$ | H | H | $OCH_3$ | $CH_3$ | CH | |
| Q-2 | H | H | $SO_2N(CH_3)_2$ | H | H | $OCH_3$ | $CH_3$ | N | |
| Q-2 | H | H | $SO_2N(CH_2CH_3)_2$ | H | H | $OCH_3$ | $OCH_3$ | CH | |
| Q-2 | $CH_3$ | H | Cl | H | H | $CH_3$ | $CH_3$ | CH | |
| Q-2 | H | $CH_3$ | Br | H | H | $OCH_3$ | $OCH_3$ | N | |
| Q-2 | H | Cl | $CO_2CH_3$ | H | H | $CH_3$ | $OCH_3$ | CH | |
| Q-3 | H | H | H | H | H | $CH_3$ | $OCH_3$ | CH | |
| Q-3 | H | H | $CH_3$ | H | H | $CH_3$ | $CH_3$ | N | |
| Q-3 | H | H | $CH_2CH_2CH_3$ | H | H | $OCH_3$ | $OCH_3$ | N | |
| Q-3 | H | H | F | H | H | $OCH_3$ | $OCH_3$ | CH | |
| Q-3 | H | H | Cl | H | H | $OCH_3$ | $OCH_3$ | CH | |
| Q-3 | H | H | Cl | H | H | $OCH_3$ | $CH_3$ | N | |
| Q-3 | H | H | Br | H | H | $CH_3$ | $OCH_3$ | CH | |
| Q-3 | H | H | $NO_2$ | H | H | Cl | $OCH_3$ | CH | |
| Q-3 | H | H | $SCH_2CH_2F$ | H | H | $OCH_3$ | $OCH_3$ | CH | |
| Q-3 | H | H | $CH_2-CH=CH_2$ | H | H | $OCH_3$ | $CH_3$ | CH | |

TABLE XXIII-continued

General Formula XIII

| | | | | | | | | |
|---|---|---|---|---|---|---|---|---|
| Q-3 | H | H | CH$_2$—C≡CH | H | H | CH$_3$ | CH$_3$ | CH |
| Q-3 | H | H | CO$_2$CH$_3$ | H | H | CH$_3$ | OCH$_3$ | N |
| Q-3 | H | H | CO$_2$CH$_3$ | H | H | OCH$_3$ | OCH$_3$ | CH |
| Q-3 | H | H | CO$_2$CH$_3$ | H | H | CH$_3$ | OCH$_3$ | CH |
| Q-3 | H | H | CO$_2$CH$_2$CH$_3$ | H | H | CH$_3$ | CH$_3$ | CH |
| Q-3 | H | H | CO$_2$CH$_2$CH$_2$CH$_3$ | H | H | OCH$_3$ | OCH$_3$ | CH |
| Q-3 | H | H | SCH$_3$ | H | H | CH$_3$ | CH$_3$ | N |
| Q-3 | H | H | SOCH$_3$ | H | H | CH$_3$ | CH$_3$ | CH |
| Q-3 | H | H | SO$_2$CH$_3$ | H | H | OCH$_3$ | OCH$_3$ | CH |
| Q-3 | H | H | SO$_2$CH$_2$CH$_3$ | H | H | OCH$_3$ | OCH$_3$ | N |
| Q-3 | H | H | SO$_2$N(CH$_3$)$_2$ | H | H | CH$_3$ | OCH$_3$ | CH |
| Q-3 | H | H | SO$_2$N(CH$_2$CH$_3$)$_2$ | H | H | OCH$_3$ | OCH$_3$ | CH |
| Q-3 | CH$_3$ | H | CO$_2$CH$_3$ | H | H | OCH$_3$ | OCH$_3$ | CH |
| Q-3 | H | H | Br | H | CH$_3$ | OCH$_3$ | OCH$_3$ | CH |
| Q-3 | H | CH$_3$ | Cl | H | H | OCH$_3$ | OCH$_3$ | N |
| Q-4 | H | H | H | H | H | CH$_3$ | OCH$_3$ | CH |
| Q-4 | H | H | CH$_2$CH$_3$ | H | H | OCH$_3$ | OCH$_3$ | CH |
| Q-4 | H | H | F | H | H | CH$_3$ | CH$_3$ | CH |
| Q-4 | H | H | Cl | H | H | OCH$_3$ | OCH$_3$ | CH |
| Q-4 | H | H | Br | H | H | OCH$_3$ | CH$_3$ | CH |
| Q-4 | H | H | NO$_2$ | H | H | OCH$_3$ | OCH$_3$ | CH |
| Q-4 | H | H | SCH$_2$F | H | H | CH$_3$ | OCH$_3$ | CH |
| Q-4 | H | H | SCH$_2$F | H | H | OCH$_3$ | OCH$_3$ | CH |
| Q-4 | H | H | CH$_2$—CH=CH$_2$ | H | H | Cl | OCH$_3$ | CH |
| Q-4 | H | H | CH$_2$—C≡CH | H | H | OCH$_3$ | OCH$_3$ | CH |
| Q-4 | H | H | CO$_2$CH$_3$ | H | H | OCH$_3$ | OCH$_3$ | CH |
| Q-4 | H | H | CO$_2$CH$_3$ | H | H | OCH$_3$ | CH$_3$ | CH |
| Q-4 | H | H | CO$_2$CH$_3$ | H | H | CH$_3$ | CH$_3$ | N |
| Q-4 | H | H | CO$_2$CH$_2$CH$_3$ | H | H | OCH$_3$ | OCH$_3$ | CH |
| Q-4 | H | H | SCH$_3$ | H | H | CH$_3$ | OCH$_3$ | CH |
| Q-4 | H | H | SOCH$_3$ | H | H | CH$_3$ | CH$_3$ | CH |
| Q-4 | H | H | SO$_2$CH$_3$ | H | H | OCH$_3$ | CH$_3$ | CH |
| Q-4 | H | H | SO$_2$N(CH$_3$)$_2$ | H | H | OCH$_3$ | CH$_3$ | CH |
| Q-4 | H | H | SO$_2$N(CH$_3$)$_2$ | H | H | OCH$_3$ | CH$_3$ | N |
| Q-4 | H | H | SO$_2$N(CH$_2$CH$_3$)$_2$ | H | H | OCH$_3$ | OCH$_3$ | CH |
| Q-4 | CH$_3$ | H | Cl | H | H | CH$_3$ | CH$_3$ | CH |
| Q-4 | H | CH$_3$ | Br | H | H | OCH$_3$ | OCH$_3$ | N |
| Q-4 | H | Cl | CO$_2$CH$_3$ | H | H | CH$_3$ | OCH$_3$ | CH |
| Q-5 | H | H | H | H | H | CH$_3$ | OCH$_3$ | CH |
| Q-5 | H | H | CH$_3$ | H | H | CH$_3$ | CH$_3$ | N |
| Q-5 | H | H | CH$_2$CH$_2$CH$_3$ | H | H | OCH$_3$ | OCH$_3$ | N |
| Q-5 | H | H | F | H | H | OCH$_3$ | OCH$_3$ | CH |
| Q-5 | H | H | Cl | H | H | OCH$_3$ | OCH$_3$ | CH |
| Q-5 | H | H | Cl | H | H | OCH$_3$ | CH$_3$ | N |
| Q-5 | H | H | Br | H | H | CH$_3$ | OCH$_3$ | CH |
| Q-5 | H | H | NO$_2$ | H | H | Cl | OCH$_3$ | CH |
| Q-5 | H | H | SCH$_2$CH$_2$F | H | H | OCH$_3$ | OCH$_3$ | CH |
| Q-5 | H | H | CH$_2$—CH=CH$_2$ | H | H | OCH$_3$ | CH$_3$ | CH |
| Q-5 | H | H | CH$_2$—C≡CH | H | H | CH$_3$ | CH$_3$ | CH |
| Q-5 | H | H | CO$_2$CH$_3$ | H | H | CH$_3$ | OCH$_3$ | N |
| Q-5 | H | H | CO$_2$CH$_3$ | H | H | OCH$_3$ | OCH$_3$ | CH |
| Q-5 | H | H | CO$_2$CH$_3$ | H | H | OCH$_3$ | OCH$_3$ | CH |
| Q-5 | H | H | CO$_2$CH$_2$CH$_3$ | H | H | CH$_3$ | CH$_3$ | CH |
| Q-5 | H | H | CO$_2$CH$_2$CH$_2$CH$_3$ | H | H | OCH$_3$ | OCH$_3$ | CH |
| Q-5 | H | H | SCH$_3$ | H | H | CH$_3$ | CH$_3$ | N |
| Q-5 | H | H | SOCH$_3$ | H | H | CH$_3$ | CH$_3$ | CH |
| Q-5 | H | H | SO$_2$CH$_3$ | H | H | OCH$_3$ | OCH$_3$ | CH |
| Q-5 | H | H | SO$_2$CH$_2$CH$_3$ | H | H | OCH$_3$ | OCH$_3$ | N |
| Q-5 | H | H | SO$_2$N(CH$_3$)$_2$ | H | H | CH$_3$ | OCH$_3$ | CH |
| Q-5 | H | H | SO$_2$N(CH$_2$CH$_3$)$_2$ | H | H | OCH$_3$ | OCH$_3$ | CH |
| Q-5 | CH$_3$ | H | CO$_2$CH$_3$ | H | H | OCH$_3$ | OCH$_3$ | CH |
| Q-5 | H | H | Br | H | CH$_3$ | OCH$_3$ | OCH$_3$ | CH |
| Q-5 | H | CH$_3$ | Cl | H | H | OCH$_3$ | OCH$_3$ | N |
| Q-6 | H | H | H | H | H | CH$_3$ | OCH$_3$ | CH |
| Q-6 | H | H | CH$_2$CH$_3$ | H | H | OCH$_3$ | OCH$_3$ | CH |
| Q-6 | H | H | F | H | H | CH$_3$ | CH$_3$ | CH |
| Q-6 | H | H | Cl | H | H | OCH$_3$ | OCH$_3$ | CH |
| Q-6 | H | H | Br | H | H | OCH$_3$ | CH$_3$ | CH |
| Q-6 | H | H | NO$_2$ | H | H | OCH$_3$ | OCH$_3$ | CH |
| Q-6 | H | H | SCH$_2$F | H | H | CH$_3$ | OCH$_3$ | CH |
| Q-6 | H | H | SCH$_2$F | H | H | OCH$_3$ | OCH$_3$ | CH |
| Q-6 | H | H | CH$_2$—CH=CH$_2$ | H | H | Cl | OCH$_3$ | CH |
| Q-6 | H | H | CH$_2$—C≡CH | H | H | OCH$_3$ | OCH$_3$ | CH |
| Q-6 | H | H | CO$_2$CH$_3$ | H | H | OCH$_3$ | OCH$_3$ | CH |
| Q-6 | H | H | CO$_2$CH$_3$ | H | H | OCH$_3$ | CH$_3$ | CH |
| Q-6 | H | H | CO$_2$CH$_3$ | H | H | CH$_3$ | CH$_3$ | N |
| Q-6 | H | H | CO$_2$CH$_2$CH$_3$ | H | H | OCH$_3$ | OCH$_3$ | CH |
| Q-6 | H | H | SCH$_3$ | H | H | CH$_3$ | OCH$_3$ | CH |
| Q-6 | H | H | SOCH$_3$ | H | H | CH$_3$ | CH$_3$ | CH |
| Q-6 | H | H | SO$_2$CH$_3$ | H | H | OCH$_3$ | OCH$_3$ | CH |
| Q-6 | H | H | SO$_2$N(CH$_3$)$_2$ | H | H | OCH$_3$ | CH$_3$ | CH |

TABLE XXIII-continued

General Formula XIII

| Q | R | R$_{15}$ | R$_{16}$ | | R$_8$ | R$_6$ | X | Y | Z |
|---|---|---|---|---|---|---|---|---|---|
| Q-6 | H | H | SO$_2$N(CH$_3$)$_2$ | | H | H | OCH$_3$ | CH$_3$ | N |
| Q-6 | H | H | SO$_2$N(CH$_2$CH$_3$)$_2$ | | H | H | OCH$_3$ | OCH$_3$ | CH |
| Q-6 | CH$_3$ | H | Cl | | H | H | CH$_3$ | CH$_3$ | CH |
| Q-6 | H | CH$_3$ | Br | | H | H | OCH$_3$ | OCH$_3$ | N |
| Q-6 | H | Cl | CO$_2$CH$_3$ | | H | H | CH$_3$ | OCH$_3$ | CH |

| Q | R | R$_{15}$ | R$_{16}$ | R$_8$ | R$_6$ | X | Y | Z | m.p. °C. |
|---|---|---|---|---|---|---|---|---|---|
| Q-7 | H | H | H | H | — | CH$_3$ | OCH$_3$ | CH | |
| Q-7 | H | H | CH$_3$ | H | — | CH$_3$ | CH$_3$ | N | |
| Q-7 | H | H | CH$_2$CH$_2$CH$_3$ | H | — | OCH$_3$ | OCH$_3$ | N | |
| Q-7 | H | H | F | H | — | OCH$_3$ | OCH$_3$ | CH | |
| Q-7 | H | H | Cl | H | — | OCH$_3$ | OCH$_3$ | CH | |
| Q-7 | H | H | Cl | H | — | OCH$_3$ | CH$_3$ | N | |
| Q-7 | H | H | Br | H | — | CH$_3$ | OCH$_3$ | CH | |
| Q-7 | H | H | NO$_2$ | H | — | Cl | OCH$_3$ | CH | |
| Q-7 | H | H | SCH$_2$CH$_2$F | H | — | OCH$_3$ | OCH$_3$ | CH | |
| Q-7 | H | H | CH$_2$—CH=CH$_2$ | H | — | OCH$_3$ | CH$_3$ | CH | |
| Q-7 | H | H | CH$_2$—C≡CH | H | — | CH$_3$ | CH$_3$ | CH | |
| Q-7 | H | H | CO$_2$CH$_3$ | H | — | CH$_3$ | OCH$_3$ | N | 0 |
| Q-7 | H | H | CO$_2$CH$_3$ | H | — | OCH$_3$ | OCH$_3$ | CH | |
| Q-7 | H | H | CO$_2$CH$_3$ | H | — | CH$_3$ | OCH$_3$ | CH | |
| Q-7 | H | H | CO$_2$CH$_2$CH$_3$ | H | — | CH$_3$ | CH$_3$ | CH | |
| Q-7 | H | H | CO$_2$CH$_2$CH$_2$CH$_3$ | H | — | OCH$_3$ | OCH$_3$ | CH | |
| Q-7 | H | H | SCH$_3$ | H | — | CH$_3$ | CH$_3$ | N | |
| Q-7 | H | H | SOCH$_3$ | H | — | CH$_3$ | CH$_3$ | CH | |
| Q-7 | H | H | SO$_2$CH$_3$ | H | — | OCH$_3$ | OCH$_3$ | CH | |
| Q-7 | H | H | SO$_2$CH$_2$CH$_3$ | H | — | OCH$_3$ | OCH$_3$ | N | |
| Q-7 | H | H | SO$_2$N(CH$_3$)$_2$ | H | — | CH$_3$ | OCH$_3$ | CH | |
| Q-7 | H | H | SO$_2$N(CH$_2$CH$_3$)$_2$ | H | — | OCH$_3$ | OCH$_3$ | CH | |
| Q-7 | CH$_3$ | H | CO$_2$CH$_3$ | H | — | OCH$_3$ | OCH$_3$ | CH | |
| Q-7 | H | H | Br | H | — | OCH$_3$ | OCH$_3$ | CH | |
| Q-7 | H | CH$_3$ | Cl | H | — | OCH$_3$ | OCH$_3$ | N | |
| Q-8 | H | H | H | — | H | CH$_3$ | OCH$_3$ | CH | |
| Q-8 | H | H | CH$_2$CH$_3$ | — | H | OCH$_3$ | OCH$_3$ | CH | |
| Q-8 | H | H | F | — | H | CH$_3$ | CH$_3$ | CH | |
| Q-8 | H | H | Cl | —H | | OCH$_3$ | OCH$_3$ | CH | |
| Q-8 | H | H | Br | — | H | OCH$_3$ | CH$_3$ | CH | |
| Q-8 | H | H | NO$_2$ | — | H | OCH$_3$ | OCH$_3$ | CH | |
| Q-8 | H | H | SCH$_2$F | — | H | CH$_3$ | OCH$_3$ | CH | |
| Q-8 | H | H | SCH$_2$F | — | H | OCH$_3$ | OCH$_3$ | CH | |
| Q-8 | H | H | CH$_2$—CH=CH$_2$ | — | H | Cl | OCH$_3$ | CH | |
| Q-8 | H | H | CH$_2$—C≡CH | — | H | OCH$_3$ | OCH$_3$ | CH | |
| Q-8 | H | H | CO$_2$CH$_3$ | — | H | OCH$_3$ | OCH$_3$ | CH | |
| Q-8 | H | H | CO$_2$CH$_3$ | — | H | OCH$_3$ | CH$_3$ | CH | |
| Q-8 | H | H | CO$_2$CH$_3$ | — | H | CH$_3$ | CH$_3$ | N | |
| Q-8 | H | H | CO$_2$CH$_2$CH$_3$ | — | H | OCH$_3$ | OCH$_3$ | CH | |
| Q-8 | H | H | SCH$_3$ | — | H | CH$_3$ | OCH$_3$ | CH | |
| Q-8 | H | H | SOCH$_3$ | — | H | CH$_3$ | CH$_3$ | CH | |
| Q-8 | H | H | SO$_2$CH$_3$ | — | H | OCH$_3$ | OCH$_3$ | CH | |
| Q-8 | H | H | SO$_2$N(CH$_3$)$_2$ | — | H | OCH$_3$ | CH$_3$ | CH | |
| Q-8 | H | H | SO$_2$N(CH$_3$)$_2$ | — | H | OCH$_3$ | CH$_3$ | N | |
| Q-8 | H | H | SO$_2$N(CH$_2$CH$_3$)$_2$ | — | H | OCH$_3$ | OCH$_3$ | CH | |
| Q-8 | CH$_3$ | H | Cl | — | H | CH$_3$ | CH$_3$ | CH | |
| Q-8 | H | CH$_3$ | Br | — | H | OCH$_3$ | OCH$_3$ | N | |
| Q-8 | H | Cl | CO$_2$CH$_3$ | — | H | CH$_3$ | OCH$_3$ | CH | |

| Q | R | R$_{15}$ | R$_{16}$ | R$_6$ | X | Y | Z | m.p. °C. |
|---|---|---|---|---|---|---|---|---|
| Q-9 | H | H | H | H | CH$_3$ | OCH$_3$ | CH | |
| Q-9 | H | H | CH$_3$ | H | CH$_3$ | CH$_3$ | N | |
| Q-9 | H | H | CH$_2$CH$_2$CH$_3$ | H | OCH$_3$ | OCH$_3$ | N | |
| Q-9 | H | H | F | H | OCH$_3$ | OCH$_3$ | CH | |
| Q-9 | H | H | Cl | H | OCH$_3$ | OCH$_3$ | CH | |
| Q-9 | H | H | Cl | H | OCH$_3$ | CH$_3$ | N | |
| Q-9 | H | H | Br | H | CH$_3$ | OCH$_3$ | CH | |
| Q-9 | H | H | NO$_2$ | H | Cl | OCH$_3$ | CH | |
| Q-9 | H | H | SCH$_2$CH$_2$F | H | OCH$_3$ | OCH$_3$ | CH | |
| Q-9 | H | H | CH$_2$—CH=CH$_2$ | H | OCH$_3$ | CH$_3$ | CH | |
| Q-9 | H | H | CH$_2$—C≡CH | H | CH$_3$ | CH$_3$ | CH | |
| Q-9 | H | H | CO$_2$CH$_3$ | H | CH$_3$ | OCH$_3$ | N | |
| Q-9 | H | H | CO$_2$CH$_3$ | H | OCH$_3$ | OCH$_3$ | CH | |
| Q-9 | H | H | CO$_2$CH$_3$ | H | CH$_3$ | CH$_3$ | CH | |
| Q-9 | H | H | CO$_2$CH$_2$CH$_3$ | H | CH$_3$ | CH$_3$ | CH | |
| Q-9 | H | H | CO$_2$CH$_2$CH$_2$CH$_3$ | H | OCH$_3$ | OCH$_3$ | CH | |
| Q-9 | H | H | SCH$_3$ | H | CH$_3$ | CH$_3$ | N | |
| Q-9 | H | H | SOCH$_3$ | H | CH$_3$ | CH$_3$ | CH | |
| Q-9 | H | H | SO$_2$CH$_3$ | H | OCH$_3$ | OCH$_3$ | CH | |
| Q-9 | H | H | SO$_2$CH$_2$CH$_3$ | H | OCH$_3$ | OCH$_3$ | N | |
| Q-9 | H | H | SO$_2$N(CH$_3$)$_2$ | H | CH$_3$ | OCH$_3$ | CH | |
| Q-9 | H | H | SO$_2$N(CH$_2$CH$_3$)$_2$ | H | OCH$_3$ | OCH$_3$ | CH | |
| Q-9 | CH$_3$ | H | CO$_2$CH$_3$ | H | OCH$_3$ | OCH$_3$ | CH | |
| Q-9 | H | H | Br | H | OCH$_3$ | OCH$_3$ | CH | |

TABLE XXIII-continued

General Formula XIII

| Q | R | R₁₅ | R₁₆ | R₇ | R₆ | X | Y | Z |
|---|---|---|---|---|---|---|---|---|
| Q-9 | H | CH₃ | Cl | | H | OCH₃ | OCH₃ | N |
| Q-10 | H | H | H | | H | CH₃ | OCH₃ | CH |
| Q-10 | H | H | CH₂CH₃ | | H | OCH₃ | OCH₃ | CH |
| Q-10 | H | H | F | | H | CH₃ | CH₃ | CH |
| Q-10 | H | H | Cl | | H | OCH₃ | OCH₃ | CH |
| Q-10 | H | H | Br | | H | OCH₃ | CH₃ | CH |
| Q-10 | H | H | NO₂ | | H | OCH₃ | OCH₃ | CH |
| Q-10 | H | H | SCH₂F | | H | CH₃ | OCH₃ | CH |
| Q-10 | H | H | SCH₂F | | H | OCH₃ | OCH₃ | CH |
| Q-10 | H | H | CH₂—CH=CH₂ | | H | Cl | OCH₃ | CH |
| Q-10 | H | H | CH₂—C≡CH | | H | OCH₃ | OCH₃ | CH |
| Q-10 | H | H | CO₂CH₃ | | H | OCH₃ | OCH₃ | CH |
| Q-10 | H | H | CO₂CH₃ | | H | OCH₃ | CH₃ | CH |
| Q-10 | H | H | CO₂CH₃ | | H | CH₃ | CH₃ | N |
| Q-10 | H | H | CO₂CH₂CH₃ | | H | OCH₃ | OCH₃ | CH |
| Q-10 | H | H | SCH₃ | | H | CH₃ | OCH₃ | CH |
| Q-10 | H | H | SOCH₃ | | H | CH₃ | CH₃ | CH |
| Q-10 | H | H | SO₂CH₃ | | H | OCH₃ | OCH₃ | CH |
| Q-10 | H | H | SO₂N(CH₃)₂ | | H | OCH₃ | CH₃ | CH |
| Q-10 | H | H | SO₂N(CH₃)₂ | | H | OCH₃ | CH₃ | N |
| Q-10 | H | H | SO₂N(CH₂CH₃)₂ | | H | OCH₃ | OCH₃ | CH |
| Q-10 | CH₃ | H | Cl | | H | CH₃ | CH₃ | CH |
| Q-10 | H | CH₃ | Br | | H | OCH₃ | OCH₃ | N |
| Q-10 | H | Cl | CO₂CH₃ | | H | CH₃ | OCH₃ | CH |
| Q-11 | H | H | H | | H | CH₃ | OCH₃ | CH |
| Q-11 | H | H | CH₃ | | H | CH₃ | CH₃ | N |
| Q-11 | H | H | CH₂CH₂CH₃ | | H | OCH₃ | OCH₃ | N |
| Q-11 | H | H | F | | H | OCH₃ | OCH₃ | CH |
| Q-11 | H | H | Cl | | H | OCH₃ | OCH₃ | CH |
| Q-11 | H | H | Cl | | H | OCH₃ | CH₃ | N |
| Q-11 | H | H | Br | | H | CH₃ | OCH₃ | CH |
| Q-11 | H | H | NO₂ | | H | Cl | OCH₃ | CH |
| Q-11 | H | H | SCH₂CH₂F | | H | OCH₃ | OCH₃ | CH |
| Q-11 | H | H | CH₂—CH=CH₂ | | H | OCH₃ | CH₃ | CH |
| Q-11 | H | H | CH₂—C≡CH | | H | CH₃ | CH₃ | CH |
| Q-11 | H | H | CO₂CH₃ | | H | CH₃ | OCH₃ | N |
| Q-11 | H | H | CO₂CH₃ | | H | OCH₃ | OCH₃ | CH |
| Q-11 | H | H | CO₂CH₃ | | H | CH₃ | OCH₃ | CH |
| Q-11 | H | H | CO₂CH₂CH₃ | | H | CH₃ | CH₃ | CH |
| Q-11 | H | H | CO₂CH₂CH₂CH₃ | | H | OCH₃ | OCH₃ | CH |
| Q-11 | H | H | SCH₃ | | H | CH₃ | CH₃ | N |
| Q-11 | H | H | SOCH₃ | | H | CH₃ | CH₃ | CH |
| Q-11 | H | H | SO₂CH₃ | | H | OCH₃ | OCH₃ | CH |
| Q-11 | H | H | SO₂CH₂CH₃ | | H | OCH₃ | OCH₃ | N |
| Q-11 | H | H | SO₂N(CH₃)₂ | | H | CH₃ | OCH₃ | CH |
| Q-11 | H | H | SO₂N(CH₂CH₃)₂ | | H | OCH₃ | OCH₃ | CH |
| Q-11 | CH₃ | H | CO₂CH₃ | | H | OCH₃ | OCH₃ | CH |
| Q-11 | H | H | Br | | CH₃ | OCH₃ | OCH₃ | CH |
| Q-11 | H | CH₃ | Cl | | H | OCH₃ | OCH₃ | N |
| Q-12 | H | H | H | | H | CH₃ | OCH₃ | CH |
| Q-12 | H | H | CH₂CH₃ | | H | OCH₃ | OCH₃ | CH |
| Q-12 | H | H | F | | H | CH₃ | CH₃ | CH |
| Q-12 | H | H | Cl | | H | OCH₃ | OCH₃ | CH |
| Q-12 | H | H | Br | | H | OCH₃ | CH₃ | CH |
| Q-12 | H | H | NO₂ | | H | OCH₃ | OCH₃ | CH |
| Q-12 | H | H | SCH₂F | | H | CH₃ | OCH₃ | CH |
| Q-12 | H | H | SCH₂F | | H | OCH₃ | OCH₃ | CH |
| Q-12 | H | H | CH₂—CH=CH₂ | | H | Cl | OCH₃ | CH |
| Q-12 | H | H | CH₂—C≡CH | | H | OCH₃ | OCH₃ | CH |
| Q-12 | H | H | CO₂CH₃ | | H | OCH₃ | OCH₃ | CH |
| Q-12 | H | H | CO₂CH₃ | | H | OCH₃ | CH₃ | CH |
| Q-12 | H | H | CO₂CH₃ | | H | CH₃ | CH₃ | N |
| Q-12 | H | H | CO₂CH₂CH₃ | | H | OCH₃ | OCH₃ | CH |
| Q-12 | H | H | SCH₃ | | H | CH₃ | OCH₃ | CH |
| Q-12 | H | H | SOCH₃ | | H | CH₃ | CH₃ | CH |
| Q-12 | H | H | SO₂CH₃ | | H | OCH₃ | OCH₃ | CH |
| Q-12 | H | H | SO₂N(CH₃)₂ | | H | OCH₃ | CH₃ | CH |
| Q-12 | H | H | SO₂N(CH₃)₂ | | H | OCH₃ | CH₃ | N |
| Q-12 | H | H | SO₂N(CH₂CH₃)₂ | | H | OCH₃ | OCH₃ | CH |
| Q-12 | CH₃ | H | Cl | | H | CH₃ | CH₃ | CH |
| Q-12 | H | CH₃ | Br | | H | OCH₃ | OCH₃ | N |
| Q-12 | H | Cl | CO₂CH₃ | | H | CH₃ | OCH₃ | CH |

| Q | R | R₁₅ | R₁₆ | R₇ | R₆ | X | Y | Z | m.p. °C. |
|---|---|---|---|---|---|---|---|---|---|
| Q-13 | H | H | H | — | H | CH₃ | OCH₃ | CH | |
| Q-13 | H | H | CH₃ | — | H | CH₃ | CH₃ | N | |
| Q-13 | H | H | CH₂CH₂CH₃ | — | H | OCH₃ | OCH₃ | N | |
| Q-13 | H | H | F | — | H | OCH₃ | OCH₃ | CH | |
| Q-13 | H | H | Cl | — | H | OCH₃ | OCH₃ | CH | |
| Q-13 | H | H | Cl | — | H | OCH₃ | CH₃ | N | |
| Q-13 | H | H | Br | — | H | CH₃ | OCH₃ | CH | |

TABLE XXIII-continued

General Formula XIII

| Q | R | R₁₅ | R₁₆ | | R₆ | R₇ | X | Y | Z |
|---|---|---|---|---|---|---|---|---|---|
| Q-13 | H | H | NO₂ | — | | H | Cl | OCH₃ | CH |
| Q-13 | H | H | SCH₂CH₂F | — | | H | OCH₃ | OCH₃ | CH |
| Q-13 | H | H | CH₂—CH=CH₂ | — | | H | OCH₃ | CH₃ | CH |
| Q-13 | H | H | CH₂—C≡CH | — | | H | CH₃ | CH₃ | CH |
| Q-13 | H | H | CO₂CH₃ | — | | H | CH₃ | OCH₃ | N |
| Q-13 | H | H | CO₂CH₃ | — | | H | OCH₃ | OCH₃ | CH |
| Q-13 | H | H | CO₂CH₃ | — | | H | CH₃ | OCH₃ | CH |
| Q-13 | H | H | CO₂CH₂CH₃ | — | | H | CH₃ | CH₃ | CH |
| Q-13 | H | H | CO₂CH₂CH₂CH₃ | — | | H | OCH₃ | OCH₃ | CH |
| Q-13 | H | H | SCH₃ | — | | H | CH₃ | CH₃ | N |
| Q-13 | H | H | SOCH₃ | — | | H | CH₃ | CH₃ | CH |
| Q-13 | H | H | SO₂CH₃ | — | | H | OCH₃ | OCH₃ | CH |
| Q-13 | H | H | SO₂CH₂CH₃ | — | | H | OCH₃ | OCH₃ | N |
| Q-13 | H | H | SO₂N(CH₃)₂ | — | | H | CH₃ | OCH₃ | CH |
| Q-13 | H | H | SO₂N(CH₂CH₃)₂ | — | | H | OCH₃ | OCH₃ | CH |
| Q-13 | CH₃ | H | CO₂CH₃ | — | | H | OCH₃ | OCH₃ | CH |
| Q-13 | H | H | Br | — | | CH₃ | OCH₃ | OCH₃ | CH |
| Q-13 | H | CH₃ | Cl | — | | H | OCH₃ | OCH₃ | N |
| Q-14 | H | H | H | H | | H | CH₃ | OCH₃ | CH |
| Q-14 | H | H | CH₂CH₃ | H | | H | OCH₃ | OCH₃ | CH |
| Q-14 | H | H | F | H | | H | CH₃ | CH₃ | CH |
| Q-14 | H | H | Cl | H | | H | OCH₃ | OCH₃ | CH |
| Q-14 | H | H | Br | H | | H | OCH₃ | CH₃ | CH |
| Q-14 | H | H | NO₂ | H | | H | OCH₃ | OCH₃ | CH |
| Q-14 | H | H | SCH₂F | H | | H | CH₃ | OCH₃ | CH |
| Q-14 | H | H | SCH₂F | H | | H | OCH₃ | OCH₃ | CH |
| Q-14 | H | H | CH₂—CH=CH₂ | H | | H | Cl | OCH₃ | CH |
| Q-14 | H | H | CH₂—C≡CH | H | | H | OCH₃ | OCH₃ | CH |
| Q-14 | H | H | CO₂CH₃ | H | | H | OCH₃ | OCH₃ | CH |
| Q-14 | H | H | CO₂CH₃ | H | | H | OCH₃ | CH₃ | CH |
| Q-14 | H | H | CO₂CH₃ | H | | H | CH₃ | CH₃ | N |
| Q-14 | H | H | CO₂CH₂CH₃ | H | | H | OCH₃ | OCH₃ | CH |
| Q-14 | H | H | SCH₃ | H | | H | CH₃ | OCH₃ | CH |
| Q-14 | H | H | SOCH₃ | H | | H | CH₃ | CH₃ | CH |
| Q-14 | H | H | SO₂CH₃ | H | | H | OCH₃ | OCH₃ | CH |
| Q-14 | H | H | SO₂N(CH₃)₂ | H | | H | OCH₃ | CH₃ | CH |
| Q-14 | H | H | SO₂N(CH₃)₂ | H | | H | OCH₃ | CH₃ | N |
| Q-14 | H | H | SO₂N(CH₂CH₃)₂ | H | | H | OCH₃ | OCH₃ | CH |
| Q-14 | CH₃ | H | Cl | H | | H | CH₃ | CH₃ | CH |
| Q-14 | H | CH₃ | Br | H | | H | OCH₃ | OCH₃ | N |
| Q-14 | H | Cl | CO₂CH₃ | H | | H | CH₃ | OCH₃ | CH |

| Q | R | R₁₅ | R₁₆ | R₆ | R₇ | X | Y | Z | m.p. °C. |
|---|---|---|---|---|---|---|---|---|---|
| Q-15 | H | H | H | H | H | CH₃ | OCH₃ | CH | |
| Q-15 | H | H | CH₃ | H | H | CH₃ | CH₃ | N | |
| Q-15 | H | H | CH₂CH₂CH₃ | H | H | OCH₃ | OCH₃ | N | |
| Q-15 | H | H | F | H | H | OCH₃ | OCH₃ | CH | |
| Q-15 | H | H | Cl | H | H | OCH₃ | OCH₃ | CH | |
| Q-15 | H | H | Cl | H | H | OCH₃ | CH₃ | N | |
| Q-15 | H | H | Br | H | H | CH₃ | OCH₃ | CH | |
| Q-15 | H | H | NO₂ | H | H | Cl | OCH₃ | CH | |
| Q-15 | H | H | SCH₂CH₂F | H | H | OCH₃ | OCH₃ | CH | |
| Q-15 | H | H | CH₂—CH=CH₂ | H | H | OCH₃ | CH₃ | CH | |
| Q-15 | H | H | CH₂—C≡CH | H | H | CH₃ | CH₃ | CH | |
| Q-15 | H | H | CO₂CH₃ | H | H | CH₃ | OCH₃ | N | |
| Q-15 | H | H | CO₂CH₃ | H | H | OCH₃ | OCH₃ | CH | |
| Q-15 | H | H | CO₂CH₃ | H | H | CH₃ | OCH₃ | CH | |
| Q-15 | H | H | CO₂CH₂CH₃ | H | H | CH₃ | CH₃ | CH | |
| Q-15 | H | H | CO₂CH₂CH₂CH₃ | H | H | OCH₃ | OCH₃ | CH | |
| Q-15 | H | H | SCH₃ | H | H | CH₃ | CH₃ | N | |
| Q-15 | H | H | SOCH₃ | H | H | CH₃ | CH₃ | CH | |
| Q-15 | H | H | SO₂CH₃ | H | H | OCH₃ | OCH₃ | CH | |
| Q-15 | H | H | SO₂CH₂CH₃ | H | H | OCH₃ | OCH₃ | N | |
| Q-15 | H | H | SO₂N(CH₃)₂ | H | H | CH₃ | OCH₃ | CH | |
| Q-15 | H | H | SO₂N(CH₂CH₃)₂ | H | H | OCH₃ | OCH₃ | CH | |
| Q-15 | CH₃ | H | CO₂CH₃ | H | H | OCH₃ | OCH₃ | CH | |
| Q-15 | H | H | Br | H | CH₃ | OCH₃ | OCH₃ | CH | |
| Q-15 | H | CH₃ | Cl | H | H | OCH₃ | OCH₃ | N | |
| Q-16 | H | H | H | H | H | CH₃ | OCH₃ | CH | |
| Q-16 | H | H | CH₂CH₃ | H | H | OCH₃ | OCH₃ | CH | |
| Q-16 | H | H | F | H | H | CH₃ | CH₃ | CH | |
| Q-16 | H | H | Cl | H | H | OCH₃ | OCH₃ | CH | |
| Q-16 | H | H | Br | H | H | OCH₃ | CH₃ | CH | |
| Q-16 | H | H | NO₂ | H | H | OCH₃ | OCH₃ | CH | |
| Q-16 | H | H | SCH₂F | H | H | CH₃ | OCH₃ | CH | |
| Q-16 | H | H | SCH₂F | H | H | OCH₃ | OCH₃ | CH | |
| Q-16 | H | H | CH₂—CH=CH₂ | H | H | Cl | OCH₃ | CH | |
| Q-16 | H | H | CH₂—C≡CH | H | H | OCH₃ | OCH₃ | CH | |
| Q-16 | H | H | CO₂CH₃ | H | H | OCH₃ | OCH₃ | CH | |
| Q-16 | H | H | CO₂CH₃ | H | H | OCH₃ | CH₃ | CH | |
| Q-16 | H | H | CO₂CH₃ | H | H | CH₃ | CH₃ | N | |

TABLE XXIII-continued

General Formula XIII

| | | | | | | | |
|---|---|---|---|---|---|---|---|
| Q-16 | H | H | CO₂CH₂CH₃ | H | H | OCH₃ | OCH₃ | CH |
| Q-16 | H | H | SCH₃ | H | H | CH₃ | OCH₃ | CH |
| Q-16 | H | H | SOCH₃ | H | H | CH₃ | CH₃ | CH |
| Q-16 | H | H | SO₂CH₃ | H | H | OCH₃ | OCH₃ | CH |
| Q-16 | H | H | SO₂N(CH₃)₂ | H | H | OCH₃ | CH₃ | CH |
| Q-16 | H | H | SO₂N(CH₃)₂ | H | H | OCH₃ | CH₃ | N |
| Q-16 | H | H | SO₂N(CH₂CH₃)₂ | H | H | OCH₃ | OCH₃ | CH |
| Q-16 | CH₃ | H | Cl | H | H | CH₃ | CH₃ | CH |
| Q-16 | H | CH₃ | Br | H | H | OCH₃ | OCH₃ | N |
| Q-16 | H | Cl | CO₂CH₃ | H | H | CH₃ | OCH₃ | CH |
| Q-17 | H | H | H | H | H | CH₃ | OCH₃ | CH |
| Q-17 | H | H | CH₃ | H | H | CH₃ | CH₃ | N |
| Q-17 | H | H | CH₂CH₂CH₃ | H | H | OCH₃ | OCH₃ | N |
| Q-17 | H | H | F | H | H | OCH₃ | OCH₃ | CH |
| Q-17 | H | H | Cl | H | H | OCH₃ | OCH₃ | CH |
| Q-17 | H | H | Cl | H | H | OCH₃ | CH₃ | N |
| Q-17 | H | H | Br | H | H | CH₃ | OCH₃ | CH |
| Q-17 | H | H | NO₂ | H | H | Cl | OCH₃ | CH |
| Q-17 | H | H | SCH₂CH₂F | H | H | OCH₃ | OCH₃ | CH |
| Q-17 | H | H | CH₂—CH=CH₂ | H | H | OCH₃ | CH₃ | CH |
| Q-17 | H | H | CH₂—C≡CH | H | H | CH₃ | CH₃ | CH |
| Q-17 | H | H | CO₂CH₃ | H | H | CH₃ | OCH₃ | N |
| Q-17 | H | H | CO₂CH₃ | H | H | OCH₃ | OCH₃ | CH |
| Q-17 | H | H | CO₂CH₃ | H | H | CH₃ | OCH₃ | CH |
| Q-17 | H | H | CO₂CH₂CH₃ | H | H | CH₃ | CH₃ | CH |
| Q-17 | H | H | CO₂CH₂CH₂CH₃ | H | H | OCH₃ | OCH₃ | CH |
| Q-17 | H | H | SCH₃ | H | H | CH₃ | CH₃ | N |
| Q-17 | H | H | SOCH₃ | H | H | CH₃ | CH₃ | CH |
| Q-17 | H | H | SO₂CH₃ | H | H | OCH₃ | OCH₃ | CH |
| Q-17 | H | H | SO₂CH₂CH₃ | H | H | OCH₃ | OCH₃ | N |
| Q-17 | H | H | SO₂N(CH₃)₂ | H | H | CH₃ | OCH₃ | CH |
| Q-17 | H | H | SO₂N(CH₂CH₃)₂ | H | H | OCH₃ | OCH₃ | CH |
| Q-17 | CH₃ | H | CO₂CH₃ | H | H | OCH₃ | OCH₃ | CH |
| Q-17 | H | H | Br | H | CH₃ | OCH₃ | OCH₃ | CH |
| Q-17 | H | CH₃ | Cl | H | H | OCH₃ | OCH₃ | N |
| Q-18 | H | H | H | H | H | CH₃ | OCH₃ | CH |
| Q-18 | H | H | CH₂CH₃ | H | H | OCH₃ | OCH₃ | CH |
| Q-18 | H | H | F | H | H | CH₃ | CH₃ | CH |
| Q-18 | H | H | Cl | H | H | OCH₃ | OCH₃ | CH |
| Q-18 | H | H | Br | H | H | OCH₃ | CH₃ | CH |
| Q-18 | H | H | NO₂ | H | H | OCH₃ | OCH₃ | CH |
| Q-18 | H | H | SCH₂F | H | H | CH₃ | CH₃ | CH |
| Q-18 | H | H | SCH₂F | H | H | OCH₃ | OCH₃ | CH |
| Q-18 | H | H | CH₂—CH=CH₂ | H | H | Cl | OCH₃ | CH |
| Q-18 | H | H | CH₂—C≡CH | H | H | OCH₃ | OCH₃ | CH |
| Q-18 | H | H | CO₂CH₃ | H | H | OCH₃ | OCH₃ | CH |
| Q-18 | H | H | CO₂CH₃ | H | H | OCH₃ | CH₃ | CH |
| Q-18 | H | H | CO₂CH₃ | H | H | CH₃ | CH₃ | N |
| Q-18 | H | H | CO₂CH₂CH₃ | H | H | OCH₃ | OCH₃ | CH |
| Q-18 | H | H | SCH₃ | H | H | CH₃ | CH₃ | CH |
| Q-18 | H | H | SOCH₃ | H | H | CH₃ | CH₃ | CH |
| Q-18 | H | H | SO₂CH₃ | H | H | OCH₃ | OCH₃ | CH |
| Q-18 | H | H | SO₂N(CH₃)₂ | H | H | OCH₃ | CH₃ | CH |
| Q-18 | H | H | SO₂N(CH₃)₂ | H | H | OCH₃ | CH₃ | N |
| Q-18 | H | H | SO₂N(CH₂CH₃)₂ | H | H | OCH₃ | OCH₃ | CH |
| Q-18 | CH₃ | H | Cl | H | H | CH₃ | CH₃ | CH |
| Q-18 | H | CH₃ | Br | H | H | OCH₃ | OCH₃ | N |
| Q-18 | H | Cl | CO₂CH₃ | H | H | CH₃ | OCH₃ | CH |
| Q-19 | H | H | H | H | H | CH₃ | OCH₃ | CH |
| Q-19 | H | H | CH₃ | H | H | CH₃ | CH₃ | N |
| Q-19 | H | H | CH₂CH₂CH₃ | H | H | OCH₃ | OCH₃ | N |
| Q-19 | H | H | F | H | H | OCH₃ | OCH₃ | CH |
| Q-19 | H | H | Cl | H | H | OCH₃ | OCH₃ | CH |
| Q-19 | H | H | Cl | H | H | OCH₃ | CH₃ | N |
| Q-19 | H | H | Br | H | H | CH₃ | OCH₃ | CH |
| Q-19 | H | H | NO₂ | H | H | Cl | OCH₃ | CH |
| Q-19 | H | H | SCH₂CH₂F | H | H | OCH₃ | OCH₃ | CH |
| Q-19 | H | H | CH₂—CH=CH₂ | H | H | OCH₃ | CH₃ | CH |
| Q-19 | H | H | CH₂—C≡CH | H | H | CH₃ | CH₃ | CH |
| Q-19 | H | H | CO₂CH₃ | H | H | CH₃ | OCH₃ | N |
| Q-19 | H | H | CO₂CH₃ | H | H | OCH₃ | OCH₃ | CH |
| Q-19 | H | H | CO₂CH₃ | H | H | CH₃ | OCH₃ | CH |
| Q-19 | H | H | CO₂CH₂CH₃ | H | H | CH₃ | CH₃ | CH |
| Q-19 | H | H | CO₂CH₂CH₂CH₃ | H | H | OCH₃ | OCH₃ | CH |
| Q-19 | H | H | SCH₃ | H | H | CH₃ | CH₃ | N |
| Q-19 | H | H | SOCH₃ | H | H | CH₃ | CH₃ | CH |
| Q-19 | H | H | SO₂CH₃ | H | H | OCH₃ | OCH₃ | CH |
| Q-19 | H | H | SO₂CH₂CH₃ | H | H | OCH₃ | OCH₃ | N |
| Q-19 | H | H | SO₂N(CH₃)₂ | H | H | CH₃ | OCH₃ | CH |
| Q-19 | H | H | SO₂N(CH₂CH₃)₂ | H | H | OCH₃ | OCH₃ | CH |
| Q-19 | CH₃ | H | CO₂CH₃ | H | H | OCH₃ | OCH₃ | CH |

TABLE XXIII-continued

General Formula XIII

| Q | R | R₁₅ | R₁₆ | R₆ | R₇ | X | Y | Z | R₉ | m.p. °C. |
|---|---|---|---|---|---|---|---|---|---|---|
| Q-19 | H | H | Br | H | CH₃ | OCH₃ | OCH₃ | CH | | |
| Q-19 | H | CH₃ | Cl | H | H | OCH₃ | OCH₃ | N | | |
| Q-20 | H | H | H | H | H | CH₃ | OCH₃ | CH | | |
| Q-20 | H | H | CH₂CH₃ | H | H | OCH₃ | OCH₃ | CH | | |
| Q-20 | H | H | F | H | H | CH₃ | CH₃ | CH | | |
| Q-20 | H | H | Cl | H | H | OCH₃ | OCH₃ | CH | | |
| Q-20 | H | H | Br | H | H | OCH₃ | CH₃ | CH | | |
| Q-20 | H | H | NO₂ | H | H | OCH₃ | OCH₃ | CH | | |
| Q-20 | H | H | SCH₂F | H | H | CH₃ | OCH₃ | CH | | |
| Q-20 | H | H | SCH₂F | H | H | OCH₃ | OCH₃ | CH | | |
| Q-20 | H | H | CH₂—CH=CH₂ | H | H | Cl | OCH₃ | CH | | |
| Q-20 | H | H | CH₂—C≡CH | H | H | OCH₃ | OCH₃ | CH | | |
| Q-20 | H | H | CO₂CH₃ | H | H | OCH₃ | OCH₃ | CH | | |
| Q-20 | H | H | CO₂CH₃ | H | H | OCH₃ | CH₃ | CH | | |
| Q-20 | H | H | CO₂CH₃ | H | H | CH₃ | CH₃ | N | | |
| Q-20 | H | H | CO₂CH₂CH₃ | H | H | OCH₃ | OCH₃ | CH | | |
| Q-20 | H | H | SCH₃ | H | H | CH₃ | OCH₃ | CH | | |
| Q-20 | H | H | SOCH₃ | H | H | CH₃ | CH₃ | CH | | |
| Q-20 | H | H | SO₂CH₃ | H | H | OCH₃ | OCH₃ | CH | | |
| Q-20 | H | H | SO₂N(CH₃)₂ | H | H | OCH₃ | CH₃ | CH | | |
| Q-20 | H | H | SO₂N(CH₃)₂ | H | H | OCH₃ | CH₃ | N | | |
| Q-20 | H | H | SO₂N(CH₂CH₃)₂ | H | H | OCH₃ | OCH₃ | CH | | |
| Q-20 | CH₃ | H | Cl | H | H | CH₃ | CH₃ | CH | | |
| Q-20 | H | CH₃ | Br | H | H | OCH₃ | OCH₃ | N | | |
| Q-20 | H | Cl | CO₂CH₃ | H | H | CH₃ | OCH₃ | CH | | |
| Q-21 | H | H | H | H | H | CH₃ | OCH₃ | CH | H | |
| Q-21 | H | H | CH₃ | H | H | CH₃ | CH₃ | N | H | |
| Q-21 | H | H | CO₂CH₂CH₃ | H | H | OCH₃ | OCH₃ | N | H | |
| Q-21 | H | H | F | H | H | OCH₃ | OCH₃ | CH | H | |
| Q-21 | H | H | Cl | H | H | OCH₃ | OCH₃ | CH | H | |
| Q-21 | H | H | Cl | H | H | OCH₃ | CH₃ | N | H | |
| Q-21 | H | H | Br | H | H | CH₃ | OCH₃ | CH | H | |
| Q-21 | H | H | NO₂ | H | H | Cl | OCH₃ | CH | H | |
| Q-21 | H | H | SCH₂CH₂F | H | H | OCH₃ | OCH₃ | CH | H | |
| Q-21 | H | H | CH₂—CH=CH₂ | H | H | OCH₃ | CH₃ | CH | H | |
| Q-21 | H | H | CH₂—C≡CH | H | H | CH₃ | CH₃ | CH | H | |
| Q-21 | H | H | CO₂CH₃ | H | H | CH₃ | OCH₃ | N | H | |
| Q-21 | H | H | CO₂CH₃ | H | H | OCH₃ | OCH₃ | CH | H | |
| Q-21 | H | H | CO₂CH₃ | H | H | CH₃ | OCH₃ | CH | H | |
| Q-21 | H | H | CO₂CH₂CH₃ | H | H | CH₃ | CH₃ | CH | H | |
| Q-21 | H | H | CO₂CH₂CH₂CH₃ | H | H | OCH₃ | OCH₃ | CH | H | |
| Q-21 | H | H | SCH₃ | H | H | CH₃ | CH₃ | N | H | |
| Q-21 | H | H | SOCH₃ | H | H | CH₃ | CH₃ | CH | H | |
| Q-21 | H | H | SO₂CH₃ | H | H | OCH₃ | OCH₃ | CH | H | |
| Q-21 | H | H | SO₂CH₂CH₃ | H | H | OCH₃ | OCH₃ | N | H | |
| Q-21 | H | H | SO₂N(CH₃)₂ | H | H | CH₃ | OCH₃ | CH | H | |
| Q-21 | H | H | SO₂N(CH₂CH₃)₂ | H | H | OCH₃ | OCH₃ | CH | H | |
| Q-21 | CH₃ | H | CO₂CH₃ | H | H | OCH₃ | OCH₃ | CH | H | |
| Q-21 | H | H | Br | H | CH₃ | OCH₃ | CH | H | | |
| Q-21 | H | CH₃ | Cl | H | H | OCH₃ | OCH₃ | N | H | |
| Q-22 | H | H | H | H | H | CH₃ | OCH₃ | CH | H | |
| Q-22 | H | H | CH₂CH₃ | H | H | OCH₃ | OCH₃ | CH | H | |
| Q-22 | H | H | F | H | H | CH₃ | CH₃ | CH | H | |
| Q-22 | H | H | Cl | H | H | OCH₃ | OCH₃ | CH | H | |
| Q-22 | H | H | Br | H | H | OCH₃ | CH₃ | CH | H | |
| Q-22 | H | H | NO₂ | H | H | OCH₃ | OCH₃ | CH | H | |
| Q-22 | H | H | SCH₂F | H | H | CH₃ | OCH₃ | CH | H | |
| Q-22 | H | H | SCH₂F | H | H | OCH₃ | OCH₃ | CH | H | |
| Q-22 | H | H | CH₂—CH=CH₂ | H | H | Cl | OCH₃ | CH | H | |
| Q-22 | H | H | CH₂—C≡CH | H | H | OCH₃ | OCH₃ | CH | H | |
| Q-22 | H | H | CO₂CH₃ | H | H | OCH₃ | OCH₃ | CH | H | |
| Q-22 | H | H | CO₂CH₃ | H | H | OCH₃ | CH₃ | CH | H | |
| Q-22 | H | H | CO₂CH₃ | H | H | CH₃ | CH₃ | N | H | |
| Q-22 | H | H | CO₂CH₂CH₃ | H | H | OCH₃ | OCH₃ | CH | H | |
| Q-22 | H | H | SCH₃ | H | H | CH₃ | OCH₃ | CH | H | |
| Q-22 | H | H | SOCH₃ | H | H | CH₃ | CH₃ | CH | H | |
| Q-22 | H | H | SO₂CH₃ | H | H | OCH₃ | OCH₃ | CH | H | |
| Q-22 | H | H | SO₂N(CH₃)₂ | H | H | OCH₃ | CH₃ | CH | H | |
| Q-22 | H | H | SO₂N(CH₃)₂ | H | H | OCH₃ | CH₃ | N | H | |
| Q-22 | H | H | SO₂N(CH₂CH₃)₂ | H | H | OCH₃ | OCH₃ | CH | H | |
| Q-22 | CH₃ | H | Cl | H | H | CH₃ | CH₃ | CH | H | |
| Q-22 | H | CH₃ | Br | H | H | OCH₃ | OCH₃ | N | H | |
| Q-22 | H | Cl | CO₂CH₃ | H | H | CH₃ | OCH₃ | CH | H | |
| Q-23 | H | H | H | H | H | CH₃ | OCH₃ | CH | H | |
| Q-23 | H | H | CH₃ | H | H | CH₃ | CH₃ | N | H | |
| Q-23 | H | H | CH₂CH₂CH₃ | H | H | OCH₃ | OCH₃ | N | H | |
| Q-23 | H | H | F | H | H | OCH₃ | OCH₃ | CH | H | |
| Q-23 | H | H | Cl | H | H | OCH₃ | OCH₃ | CH | H | |
| Q-23 | H | H | Cl | H | H | OCH₃ | CH₃ | N | H | |

TABLE XXIII-continued

General Formula XIII

| | | | | | | | | | |
|---|---|---|---|---|---|---|---|---|---|
| Q-23 | H | H | Br | H | H | CH$_3$ | OCH$_3$ | CH | H |
| Q-23 | H | H | NO$_2$ | H | H | Cl | OCH$_3$ | CH | H |
| Q-23 | H | H | SCH$_2$CH$_2$F | H | H | OCH$_3$ | OCH$_3$ | CH | H |
| Q-23 | H | H | CH$_2$—CH=CH$_2$ | H | H | OCH$_3$ | CH$_3$ | CH | H |
| Q-23 | H | H | CH$_2$—C≡CH | H | H | CH$_3$ | CH$_3$ | CH | H |
| Q-23 | H | H | CO$_2$CH$_3$ | H | H | CH$_3$ | OCH$_3$ | N | H |
| Q-23 | H | H | CO$_2$CH$_3$ | H | H | OCH$_3$ | OCH$_3$ | CH | H |
| Q-23 | H | H | CO$_2$CH$_3$ | H | H | CH$_3$ | OCH$_3$ | CH | H |
| Q-23 | H | H | CO$_2$CH$_2$CH$_3$ | H | H | CH$_3$ | CH$_3$ | CH | H |
| Q-23 | H | H | CO$_2$CH$_2$CH$_2$CH$_3$ | H | H | OCH$_3$ | OCH$_3$ | CH | H |
| Q-23 | H | H | SCH$_3$ | H | H | CH$_3$ | CH$_3$ | N | H |
| Q-23 | H | H | SOCH$_3$ | H | H | CH$_3$ | CH$_3$ | CH | H |
| Q-23 | H | H | SO$_2$CH$_3$ | H | H | OCH$_3$ | OCH$_3$ | CH | H |
| Q-23 | H | H | SO$_2$CH$_2$CH$_3$ | H | H | OCH$_3$ | OCH$_3$ | N | H |
| Q-23 | H | H | SO$_2$N(CH$_3$)$_2$ | H | H | CH$_3$ | OCH$_3$ | CH | H |
| Q-23 | H | H | SO$_2$N(CH$_2$CH$_3$)$_2$ | H | H | OCH$_3$ | OCH$_3$ | CH | H |
| Q-23 | CH$_3$ | H | CO$_2$CH$_3$ | H | H | OCH$_3$ | OCH$_3$ | CH | H |
| Q-23 | H | H | Br | H | CH$_3$ | OCH$_3$ | OCH$_3$ | CH | H |
| Q-23 | H | CH$_3$ | Cl | H | H | OCH$_3$ | OCH$_3$ | N | H |
| Q-24 | H | H | H | H | H | CH$_3$ | OCH$_3$ | CH | H |
| Q-24 | H | H | CH$_2$CH$_3$ | H | H | OCH$_3$ | OCH$_3$ | CH | H |
| Q-24 | H | H | F | H | H | CH$_3$ | CH$_3$ | CH | H |
| Q-24 | H | H | Cl | H | H | OCH$_3$ | OCH$_3$ | CH | H |
| Q-24 | H | H | Br | H | H | OCH$_3$ | CH$_3$ | CH | H |
| Q-24 | H | H | NO$_2$ | H | H | OCH$_3$ | OCH$_3$ | CH | H |
| Q-24 | H | H | SCH$_2$F | H | H | CH$_3$ | OCH$_3$ | CH | H |
| Q-24 | H | H | SCH$_2$F | H | H | OCH$_3$ | OCH$_3$ | CH | H |
| Q-24 | H | H | CH$_2$—CH=CH$_2$ | H | H | Cl | OCH$_3$ | CH | H |
| Q-24 | H | H | CH$_2$—C≡CH | H | H | OCH$_3$ | OCH$_3$ | CH | H |
| Q-24 | H | H | CO$_2$CH$_3$ | H | H | OCH$_3$ | OCH$_3$ | CH | H |
| Q-24 | H | H | CO$_2$CH$_3$ | H | H | OCH$_3$ | CH$_3$ | CH | H |
| Q-24 | H | H | CO$_2$CH$_3$ | H | H | CH$_3$ | CH$_3$ | N | H |
| Q-24 | H | H | CO$_2$CH$_2$CH$_3$ | H | H | OCH$_3$ | OCH$_3$ | CH | H |
| Q-24 | H | H | SCH$_3$ | H | H | CH$_3$ | OCH$_3$ | CH | H |
| Q-24 | H | H | SOCH$_3$ | H | H | CH$_3$ | CH$_3$ | CH | H |
| Q-24 | H | H | SO$_2$CH$_3$ | H | H | OCH$_3$ | OCH$_3$ | CH | H |
| Q-24 | H | H | SO$_2$N(CH$_3$)$_2$ | H | H | OCH$_3$ | CH$_3$ | CH | H |
| Q-24 | H | H | SO$_2$N(CH$_3$)$_2$ | H | H | OCH$_3$ | CH$_3$ | N | H |
| Q-24 | H | H | SO$_2$N(CH$_2$CH$_3$)$_2$ | H | H | OCH$_3$ | OCH$_3$ | CH | H |
| Q-24 | CH$_3$ | H | Cl | H | H | CH$_3$ | CH$_3$ | CH | H |
| Q-24 | H | CH$_3$ | Br | H | H | OCH$_3$ | OCH$_3$ | N | H |
| Q-24 | H | Cl | CO$_2$CH$_3$ | H | H | CH$_3$ | OCH$_3$ | CH | H |
| Q-25 | H | H | H | H | H | CH$_3$ | OCH$_3$ | CH | H |
| Q-25 | H | H | CH$_3$ | H | H | CH$_3$ | CH$_3$ | N | H |
| Q-25 | H | H | CH$_2$CH$_2$CH$_3$ | H | H | OCH$_3$ | OCH$_3$ | N | H |
| Q-25 | H | H | F | H | H | OCH$_3$ | OCH$_3$ | CH | H |
| Q-25 | H | H | Cl | H | H | OCH$_3$ | OCH$_3$ | CH | H |
| Q-25 | H | H | Cl | H | H | OCH$_3$ | CH$_3$ | N | H |
| Q-25 | H | H | Br | H | H | CH$_3$ | OCH$_3$ | CH | H |
| Q-25 | H | H | NO$_2$ | H | H | Cl | OCH$_3$ | CH | H |
| Q-25 | H | H | SCH$_2$CH$_2$F | H | H | OCH$_3$ | OCH$_3$ | CH | H |
| Q-25 | H | H | CH$_2$—CH=CH$_2$ | H | H | OCH$_3$ | CH$_3$ | CH | H |
| Q-25 | H | H | CH$_2$—C≡CH | H | H | CH$_3$ | CH$_3$ | CH | H |
| Q-25 | H | H | CO$_2$CH$_3$ | H | H | CH$_3$ | OCH$_3$ | N | H |
| Q-25 | H | H | CO$_2$CH$_3$ | H | H | OCH$_3$ | OCH$_3$ | CH | H |
| Q-25 | H | H | CO$_2$CH$_3$ | H | H | CH$_3$ | OCH$_3$ | CH | H |
| Q-25 | H | H | CO$_2$CH$_2$CH$_3$ | H | H | CH$_3$ | CH$_3$ | CH | H |
| Q-25 | H | H | CO$_2$CH$_2$CH$_2$CH$_3$ | H | H | OCH$_3$ | OCH$_3$ | CH | H |
| Q-25 | H | H | SCH$_3$ | H | H | CH$_3$ | CH$_3$ | N | H |
| Q-25 | H | H | SOCH$_3$ | H | H | CH$_3$ | CH$_3$ | CH | H |
| Q-25 | H | H | SO$_2$CH$_3$ | H | H | OCH$_3$ | OCH$_3$ | CH | H |
| Q-25 | H | H | SO$_2$CH$_2$CH$_3$ | H | H | OCH$_3$ | OCH$_3$ | N | H |
| Q-25 | H | H | SO$_2$N(CH$_3$)$_2$ | H | H | CH$_3$ | OCH$_3$ | CH | H |
| Q-25 | H | H | SO$_2$N(CH$_2$CH$_3$)$_2$ | H | H | OCH$_3$ | OCH$_3$ | CH | H |
| Q-25 | CH$_3$ | H | CO$_2$CH$_3$ | H | H | OCH$_3$ | OCH$_3$ | CH | H |
| Q-25 | H | H | Br | H | CH$_3$ | OCH$_3$ | OCH$_3$ | CH | H |
| Q-25 | H | CH$_3$ | Cl | H | H | OCH$_3$ | OCH$_3$ | N | H |
| Q-26 | H | H | H | H | H | CH$_3$ | OCH$_3$ | CH | H |
| Q-26 | H | H | CH$_2$CH$_3$ | H | H | OCH$_3$ | OCH$_3$ | CH | H |
| Q-26 | H | H | F | H | H | CH$_3$ | CH$_3$ | CH | H |
| Q-26 | H | H | Cl | H | H | OCH$_3$ | OCH$_3$ | CH | H |
| Q-26 | H | H | Br | H | H | OCH$_3$ | CH$_3$ | CH | H |
| Q-26 | H | H | NO$_2$ | H | H | OCH$_3$ | OCH$_3$ | CH | H |
| Q-26 | H | H | SCH$_2$F | H | H | CH$_3$ | OCH$_3$ | CH | H |
| Q-26 | H | H | SCH$_2$F | H | H | OCH$_3$ | OCH$_3$ | CH | H |
| Q-26 | H | H | CH$_2$—CH=CH$_2$ | H | H | Cl | OCH$_3$ | CH | H |
| Q-26 | H | H | CH$_2$—C≡CH | H | H | OCH$_3$ | OCH$_3$ | CH | H |
| Q-26 | H | H | CO$_2$CH$_3$ | H | H | OCH$_3$ | OCH$_3$ | CH | H |
| Q-26 | H | H | CO$_2$CH$_3$ | H | H | OCH$_3$ | CH$_3$ | CH | H |
| Q-26 | H | H | CO$_2$CH$_3$ | H | H | CH$_3$ | CH$_3$ | N | H |
| Q-26 | H | H | CO$_2$CH$_2$CH$_3$ | H | H | OCH$_3$ | OCH$_3$ | CH | H |

TABLE XXIII-continued

General Formula XIII

| | | | | | | | | | |
|---|---|---|---|---|---|---|---|---|---|
| Q-26 | H | H | SCH$_3$ | H | H | CH$_3$ | OCH$_3$ | CH | H |
| Q-26 | H | H | SOCH$_3$ | H | H | CH$_3$ | CH$_3$ | CH | H |
| Q-26 | H | H | SO$_2$CH$_3$ | H | H | OCH$_3$ | OCH$_3$ | CH | H |
| Q-26 | H | H | SO$_2$N(CH$_3$)$_2$ | H | H | OCH$_3$ | CH$_3$ | CH | H |
| Q-26 | H | H | SO$_2$N(CH$_3$)$_2$ | H | H | OCH$_3$ | CH$_3$ | N | H |
| Q-26 | H | H | SO$_2$N(CH$_2$CH$_3$)$_2$ | H | H | OCH$_3$ | OCH$_3$ | CH | H |
| Q-26 | CH$_3$ | H | Cl | H | H | CH$_3$ | CH$_3$ | CH | H |
| Q-26 | H | CH$_3$ | Br | H | H | OCH$_3$ | OCH$_3$ | N | H |
| Q-26 | H | Cl | CO$_2$CH$_3$ | H | H | CH$_3$ | OCH$_3$ | CH | H |
| Q-27 | H | H | H | H | H | CH$_3$ | OCH$_3$ | CH | H |
| Q-27 | H | H | CH$_3$ | H | H | CH$_3$ | CH$_3$ | N | H |
| Q-27 | H | H | CH$_2$CH$_2$CH$_3$ | H | H | OCH$_3$ | OCH$_3$ | N | H |
| Q-27 | H | H | F | H | H | OCH$_3$ | OCH$_3$ | CH | H |
| Q-27 | H | H | Cl | H | H | OCH$_3$ | CH$_3$ | CH | H |
| Q-27 | H | H | Cl | H | H | OCH$_3$ | CH$_3$ | N | H |
| Q-27 | H | H | Br | H | H | CH$_3$ | OCH$_3$ | CH | H |
| Q-27 | H | H | NO$_2$ | H | H | Cl | OCH$_3$ | CH | H |
| Q-27 | H | H | SCH$_2$CH$_2$F | H | H | OCH$_3$ | OCH$_3$ | CH | H |
| Q-27 | H | H | CH$_2$—CH=CH$_2$ | H | H | OCH$_3$ | CH$_3$ | CH | H |
| Q-27 | H | H | CH$_2$—C≡CH | H | H | CH$_3$ | CH$_3$ | CH | H |
| Q-27 | H | H | CO$_2$CH$_3$ | H | H | CH$_3$ | OCH$_3$ | N | H |
| Q-27 | H | H | CO$_2$CH$_3$ | H | H | OCH$_3$ | OCH$_3$ | CH | H |
| Q-27 | H | H | CO$_2$CH$_3$ | H | H | CH$_3$ | OCH$_3$ | CH | H |
| Q-27 | H | H | CO$_2$CH$_2$CH$_3$ | H | H | CH$_3$ | CH$_3$ | CH | H |
| Q-27 | H | H | CO$_2$CH$_2$CH$_2$CH$_3$ | H | H | OCH$_3$ | OCH$_3$ | CH | H |
| Q-27 | H | H | SCH$_3$ | H | H | CH$_3$ | CH$_3$ | N | H |
| Q-27 | H | H | SOCH$_3$ | H | H | CH$_3$ | CH$_3$ | CH | H |
| Q-27 | H | H | SO$_2$CH$_3$ | H | H | OCH$_3$ | OCH$_3$ | CH | H |
| Q-27 | H | H | SO$_2$CH$_2$CH$_3$ | H | H | OCH$_3$ | OCH$_3$ | N | H |
| Q-27 | H | H | SO$_2$N(CH$_3$)$_2$ | H | H | CH$_3$ | OCH$_3$ | CH | H |
| Q-27 | H | H | SO$_2$N(CH$_2$CH$_3$)$_2$ | H | H | OCH$_3$ | OCH$_3$ | CH | H |
| Q-27 | CH$_3$ | H | CO$_2$CH$_3$ | H | H | OCH$_3$ | OCH$_3$ | CH | H |
| Q-27 | H | H | Br | H | CH$_3$ | OCH$_3$ | OCH$_3$ | CH | H |
| Q-27 | H | CH$_3$ | Cl | H | H | OCH$_3$ | OCH$_3$ | N | H |
| Q-28 | H | H | H | H | H | CH$_3$ | OCH$_3$ | CH | H |
| Q-28 | H | H | CH$_2$CH$_3$ | H | H | OCH$_3$ | OCH$_3$ | CH | H |
| Q-28 | H | H | F | H | H | CH$_3$ | CH$_3$ | CH | H |
| Q-28 | H | H | Cl | H | H | OCH$_3$ | OCH$_3$ | CH | H |
| Q-28 | H | H | Br | H | H | OCH$_3$ | CH$_3$ | CH | H |
| Q-28 | H | H | NO$_2$ | H | H | OCH$_3$ | OCH$_3$ | CH | H |
| Q-28 | H | H | SCH$_2$F | H | H | CH$_3$ | OCH$_3$ | CH | H |
| Q-28 | H | H | SCH$_2$F | H | H | OCH$_3$ | OCH$_3$ | CH | H |
| Q-28 | H | H | CH$_2$—CH=CH$_2$ | H | H | Cl | OCH$_3$ | CH | H |
| Q-28 | H | H | CH$_2$—C≡CH | H | H | OCH$_3$ | OCH$_3$ | CH | H |
| Q-28 | H | H | CO$_2$CH$_3$ | H | H | OCH$_3$ | OCH$_3$ | CH | H |
| Q-28 | H | H | CO$_2$CH$_3$ | H | H | OCH$_3$ | CH$_3$ | CH | H |
| Q-28 | H | H | CO$_2$CH$_3$ | H | H | CH$_3$ | CH$_3$ | N | H |
| Q-28 | H | H | CO$_2$CH$_2$CH$_3$ | H | H | OCH$_3$ | OCH$_3$ | CH | H |
| Q-28 | H | H | SCH$_3$ | H | H | CH$_3$ | OCH$_3$ | CH | H |
| Q-28 | H | H | SOCH$_3$ | H | H | CH$_3$ | CH$_3$ | CH | H |
| Q-28 | H | H | SO$_2$CH$_3$ | H | H | OCH$_3$ | OCH$_3$ | CH | H |
| Q-28 | H | H | SO$_2$N(CH$_3$)$_2$ | H | H | OCH$_3$ | CH$_3$ | CH | H |
| Q-28 | H | H | SO$_2$N(CH$_3$)$_2$ | H | H | OCH$_3$ | CH$_3$ | N | H |
| Q-28 | H | H | SO$_2$N(CH$_2$CH$_3$)$_2$ | H | H | OCH$_3$ | OCH$_3$ | CH | H |
| Q-28 | CH$_3$ | H | Cl | H | H | CH$_3$ | CH$_3$ | CH | H |
| Q-28 | H | CH$_3$ | Br | H | H | OCH$_3$ | OCH$_3$ | N | H |
| Q-28 | H | Cl | CO$_2$CH$_3$ | H | H | CH$_3$ | OCH$_3$ | CH | H |
| Q-29 | H | H | H | H | H | CH$_3$ | OCH$_3$ | CH | H |
| Q-29 | H | H | CH$_3$ | H | H | CH$_3$ | CH$_3$ | N | H |
| Q-29 | H | H | CH$_2$CH$_2$CH$_3$ | H | H | OCH$_3$ | OCH$_3$ | N | H |
| Q-29 | H | H | F | H | H | OCH$_3$ | OCH$_3$ | CH | H |
| Q-29 | H | H | Cl | H | H | OCH$_3$ | OCH$_3$ | CH | H |
| Q-29 | H | H | Cl | H | H | OCH$_3$ | CH$_3$ | N | H |
| Q-29 | H | H | Br | H | H | CH$_3$ | OCH$_3$ | CH | H |
| Q-29 | H | H | NO$_2$ | H | H | Cl | OCH$_3$ | CH | H |
| Q-29 | H | H | SCH$_2$F | H | H | OCH$_3$ | OCH$_3$ | CH | H |
| Q-29 | H | H | CH$_2$—CH=CH$_2$ | H | H | OCH$_3$ | CH$_3$ | CH | H |
| Q-29 | H | H | CH$_2$—C≡CH | H | H | CH$_3$ | CH$_3$ | CH | H |
| Q-29 | H | H | CO$_2$CH$_3$ | H | H | CH$_3$ | OCH$_3$ | N | H |
| Q-29 | H | H | CO$_2$CH$_3$ | H | H | OCH$_3$ | OCH$_3$ | CH | H |
| Q-29 | H | H | CO$_2$CH$_3$ | H | H | CH$_3$ | OCH$_3$ | CH | H |
| Q-29 | H | H | CO$_2$CH$_2$CH$_3$ | H | H | CH$_3$ | CH$_3$ | CH | H |
| Q-29 | H | H | CO$_2$CH$_2$CH$_2$CH$_3$ | H | H | OCH$_3$ | OCH$_3$ | CH | H |
| Q-29 | H | H | SCH$_3$ | H | H | CH$_3$ | CH$_3$ | N | H |
| Q-29 | H | H | SOCH$_3$ | H | H | CH$_3$ | CH$_3$ | CH | H |
| Q-29 | H | H | SO$_2$CH$_3$ | H | H | OCH$_3$ | OCH$_3$ | CH | H |
| Q-29 | H | H | SO$_2$CH$_2$CH$_3$ | H | H | OCH$_3$ | OCH$_3$ | N | H |
| Q-29 | H | H | SO$_2$N(CH$_3$)$_2$ | H | H | CH$_3$ | OCH$_3$ | CH | H |
| Q-29 | H | H | SO$_2$N(CH$_2$CH$_3$)$_2$ | H | H | OCH$_3$ | OCH$_3$ | CH | H |
| Q-29 | CH$_3$ | H | CO$_2$CH$_3$ | H | H | OCH$_3$ | OCH$_3$ | CH | H |
| Q-29 | H | H | Br | H | CH$_3$ | OCH$_3$ | OCH$_3$ | CH | H |

TABLE XXIII-continued

General Formula XIII

| Q | R | $R_{15}$ | $R_{16}$ | $R_6$ | $R_7$ | X | Y | Z | |
|---|---|---|---|---|---|---|---|---|---|
| Q-29 | H | $CH_3$ | Cl | H | H | $OCH_3$ | $OCH_3$ | N | H |
| Q-30 | H | H | H | H | H | $CH_3$ | $OCH_3$ | CH | H |
| Q-30 | H | H | $CH_2CH_3$ | H | H | $OCH_3$ | $OCH_3$ | CH | H |
| Q-30 | H | H | F | H | H | $CH_3$ | $CH_3$ | CH | H |
| Q-30 | H | H | Cl | H | H | $OCH_3$ | $OCH_3$ | CH | H |
| Q-30 | H | H | Br | H | H | $OCH_3$ | $CH_3$ | CH | H |
| Q-30 | H | H | $NO_2$ | H | H | $OCH_3$ | $OCH_3$ | CH | H |
| Q-30 | H | H | $SCH_2F$ | H | H | $CH_3$ | $OCH_3$ | CH | H |
| Q-30 | H | H | $SCH_2F$ | H | H | $OCH_3$ | $OCH_3$ | CH | H |
| Q-30 | H | H | $CH_2-CH=CH_2$ | H | H | Cl | $OCH_3$ | CH | H |
| Q-30 | H | H | $CH_2-C\equiv CH$ | H | H | $OCH_3$ | $OCH_3$ | CH | H |
| Q-30 | H | H | $CO_2CH_3$ | H | H | $OCH_3$ | $OCH_3$ | CH | H |
| Q-30 | H | H | $CO_2CH_3$ | H | H | $OCH_3$ | $CH_3$ | CH | H |
| Q-30 | H | H | $CO_2CH_3$ | H | H | $CH_3$ | $CH_3$ | N | H |
| Q-30 | H | H | $CO_2CH_2CH_3$ | H | H | $OCH_3$ | $OCH_3$ | CH | H |
| Q-30 | H | H | $SCH_3$ | H | H | $CH_3$ | $OCH_3$ | CH | H |
| Q-30 | H | H | $SOCH_3$ | H | H | $CH_3$ | $CH_3$ | CH | H |
| Q-30 | H | H | $SO_2CH_3$ | H | H | $OCH_3$ | $OCH_3$ | CH | H |
| Q-30 | H | H | $SO_2N(CH_3)_2$ | H | H | $OCH_3$ | $CH_3$ | CH | H |
| Q-30 | H | H | $SO_2N(CH_3)_2$ | H | H | $OCH_3$ | $CH_3$ | N | H |
| Q-30 | H | H | $SO_2N(CH_2CH_3)_2$ | H | H | $OCH_3$ | $OCH_3$ | CH | H |
| Q-30 | $CH_3$ | H | Cl | H | H | $CH_3$ | $CH_3$ | CH | H |
| Q-30 | H | $CH_3$ | Br | H | H | $OCH_3$ | $OCH_3$ | N | H |
| Q-30 | H | Cl | $CO_2CH_3$ | H | H | $CH_3$ | $OCH_3$ | CH | H |

| Q | R | $R_{15}$ | $R_{16}$ | $R_6$ | $R_7$ | X | Y | Z | m.p. °C. |
|---|---|---|---|---|---|---|---|---|---|
| Q-31 | H | $CH_3$ | $CH_3$ | H | H | $CH_3$ | $OCH_3$ | CH | 172–174 |
| Q-31 | H | $CH_3$ | $CH_3$ | H | H | $CH_3$ | $OCH_3$ | N | 182–183 |
| Q-31 | H | $CH_3$ | $CH_3$ | H | H | $OCH_3$ | $OCH_3$ | N | 183–184 |
| Q-31 | H | H | F | H | H | $OCH_3$ | $OCH_3$ | CH | |
| Q-31 | H | $CH_3$ | $CH_3$ | H | H | Cl | $OCH_3$ | CH | 204–206 |
| Q-31 | H | H | Cl | H | H | $OCH_3$ | $CH_3$ | N | |
| Q-31 | H | H | Br | H | H | $CH_3$ | $OCH_3$ | CH | |
| Q-31 | H | H | $NO_2$ | H | H | Cl | $OCH_3$ | CH | |
| Q-31 | H | H | $SCH_2CH_2F$ | H | H | $OCH_3$ | $OCH_3$ | CH | |
| Q-31 | H | H | $CH_2-CH=CH_2$ | H | H | $OCH_3$ | $CH_3$ | CH | |
| Q-31 | H | H | $CH_2-C\equiv CH$ | H | H | $CH_3$ | $CH_3$ | CH | |
| Q-31 | H | H | $CO_2CH_3$ | H | H | $CH_3$ | $OCH_3$ | N | |
| Q-31 | H | H | $CO_2CH_3$ | H | H | $OCH_3$ | $OCH_3$ | CH | |
| Q-31 | H | H | $CO_2CH_3$ | H | H | $CH_3$ | $OCH_3$ | CH | |
| Q-31 | H | H | $CO_2CH_2CH_3$ | H | H | $CH_3$ | $CH_3$ | CH | |
| Q-31 | H | H | $CO_2CH_2CH_2CH_3$ | H | H | $OCH_3$ | $OCH_3$ | CH | |
| Q-31 | H | $CH_3$ | $CH_3$ | H | H | $CH_3$ | $CH_3$ | CH | 168–172 |
| Q-31 | H | H | $SOCH_3$ | H | H | $CH_3$ | $CH_3$ | CH | |
| Q-31 | H | H | $SO_2CH_3$ | H | H | $OCH_3$ | $OCH_3$ | CH | |
| Q-31 | H | H | $SO_2CH_2CH_3$ | H | H | $OCH_3$ | $OCH_3$ | N | |
| Q-31 | H | H | $SO_2N(CH_3)_2$ | H | H | $CH_3$ | $OCH_3$ | CH | |
| Q-31 | H | H | $SO_2N(CH_2CH_3)_2$ | H | H | $OCH_3$ | $OCH_3$ | CH | |
| Q-31 | $CH_3$ | H | $CO_2CH_3$ | H | H | $OCH_3$ | $OCH_3$ | CH | |
| Q-31 | H | $CH_3$ | $CH_3$ | H | H | $OCH_3$ | $OCH_3$ | CH | |
| Q-31 | H | $CH_3$ | $CH_3$ | H | H | $OCH_3$ | $OCH_3$ | CH | 201–203 |
| Q-32 | H | H | H | H | H | $CH_3$ | $OCH_3$ | CH | |
| Q-32 | H | H | $CH_2CH_3$ | H | H | $OCH_3$ | $OCH_3$ | CH | |
| Q-32 | H | H | F | H | H | $CH_3$ | $CH_3$ | CH | |
| Q-32 | H | H | Cl | H | H | $OCH_3$ | $OCH_3$ | CH | |
| Q-32 | H | H | Br | H | H | $OCH_3$ | $CH_3$ | CH | |
| Q-32 | H | H | $NO_2$ | H | H | $OCH_3$ | $OCH_3$ | CH | |
| Q-32 | H | H | $SCH_2F$ | H | H | $CH_3$ | $OCH_3$ | CH | |
| Q-32 | H | H | $SCH_2F$ | H | H | $OCH_3$ | $OCH_3$ | CH | |
| Q-32 | H | H | $CH_2-CH=CH_2$ | H | H | Cl | $OCH_3$ | CH | |
| Q-32 | H | H | $CH_2-C\equiv CH$ | H | H | $OCH_3$ | $OCH_3$ | CH | |
| Q-32 | H | H | $CO_2CH_3$ | H | H | $OCH_3$ | $OCH_3$ | CH | |
| Q-32 | H | H | $CO_2CH_3$ | H | H | $OCH_3$ | $CH_3$ | CH | |
| Q-32 | H | H | $CO_2CH_3$ | H | H | $CH_3$ | $CH_3$ | N | |
| Q-32 | H | H | $CO_2CH_2CH_3$ | H | H | $OCH_3$ | $OCH_3$ | CH | |
| Q-32 | H | H | $SCH_3$ | H | H | $CH_3$ | $OCH_3$ | CH | |
| Q-32 | H | H | $SOCH_3$ | H | H | $CH_3$ | $CH_3$ | CH | |
| Q-32 | H | H | $SO_2CH_3$ | H | H | $OCH_3$ | $OCH_3$ | CH | |
| Q-32 | H | H | $SO_2N(CH_3)_2$ | H | H | $OCH_3$ | $CH_3$ | CH | |
| Q-32 | H | H | $SO_2N(CH_3)_2$ | H | H | $OCH_3$ | $CH_3$ | N | |
| Q-32 | H | H | $SO_2N(CH_2CH_3)_2$ | H | H | $OCH_3$ | $OCH_3$ | CH | |
| Q-32 | $CH_3$ | H | Cl | H | H | $CH_3$ | $CH_3$ | CH | |
| Q-32 | H | $CH_3$ | Br | H | H | $OCH_3$ | $OCH_3$ | N | |
| Q-32 | H | Cl | $CO_2CH_3$ | H | H | $CH_3$ | $OCH_3$ | CH | |
| Q-33 | H | H | H | H | H | $CH_3$ | $CH_3$ | CH | |
| Q-33 | H | H | $CH_3$ | H | H | $CH_3$ | $CH_3$ | N | |
| Q-33 | H | H | $CH_2CH_2CH_3$ | H | H | $OCH_3$ | $OCH_3$ | N | |
| Q-33 | H | H | F | H | H | $OCH_3$ | $OCH_3$ | CH | |
| Q-33 | H | H | Cl | H | H | $OCH_3$ | $OCH_3$ | CH | |
| Q-33 | H | H | Cl | H | H | $OCH_3$ | $CH_3$ | N | |
| Q-33 | H | H | Br | H | H | $CH_3$ | $OCH_3$ | CH | |

TABLE XXIII-continued
General Formula XIII

| Q | R | R$_{15}$ | R$_{16}$ | R$_6$ | X | Y | Z | |
|---|---|---|---|---|---|---|---|---|
| Q-33 | H | H | NO$_2$ | H | H | Cl | OCH$_3$ | CH |
| Q-33 | H | H | SCH$_2$CH$_2$F | H | H | OCH$_3$ | OCH$_3$ | CH |
| Q-33 | H | H | CH$_2$—CH=CH$_2$ | H | H | OCH$_3$ | CH$_3$ | CH |
| Q-33 | H | H | CH$_2$—C≡CH | H | H | CH$_3$ | CH$_3$ | CH |
| Q-33 | H | H | CO$_2$CH$_3$ | H | H | CH$_3$ | OCH$_3$ | N |
| Q-33 | H | H | CO$_2$CH$_3$ | H | H | OCH$_3$ | OCH$_3$ | CH |
| Q-33 | H | H | CO$_2$CH$_3$ | H | H | CH$_3$ | OCH$_3$ | CH |
| Q-33 | H | H | CO$_2$CH$_2$CH$_3$ | H | H | CH$_3$ | CH$_3$ | CH |
| Q-33 | H | H | CO$_2$CH$_2$CH$_2$CH$_3$ | H | H | OCH$_3$ | OCH$_3$ | CH |
| Q-33 | H | H | SCH$_3$ | H | H | CH$_3$ | CH$_3$ | N |
| Q-33 | H | H | SOCH$_3$ | H | H | CH$_3$ | CH$_3$ | CH |
| Q-33 | H | H | SO$_2$CH$_3$ | H | H | OCH$_3$ | OCH$_3$ | CH |
| Q-33 | H | H | SO$_2$CH$_2$CH$_3$ | H | H | OCH$_3$ | OCH$_3$ | N |
| Q-33 | H | H | SO$_2$N(CH$_3$)$_2$ | H | H | CH$_3$ | OCH$_3$ | CH |
| Q-33 | H | H | SO$_2$N(CH$_2$CH$_3$)$_2$ | H | H | OCH$_3$ | OCH$_3$ | CH |
| Q-33 | CH$_3$ | H | CO$_2$CH$_3$ | H | H | OCH$_3$ | OCH$_3$ | CH |
| Q-33 | H | H | Br | H | CH$_3$ | OCH$_3$ | OCH$_3$ | CH |
| Q-33 | H | CH$_3$ | Cl | H | H | OCH$_3$ | OCH$_3$ | N |

| Q | R | R$_{15}$ | R$_{16}$ | R$_6$ | X | Y | Z | R$_{10}$ | R$_{11}$ | m.p. °C. |
|---|---|---|---|---|---|---|---|---|---|---|
| Q-34 | H | H | H | H | CH$_3$ | OCH$_3$ | CH | H | H | |
| Q-34 | H | H | CH$_2$CH$_3$ | H | OCH$_3$ | OCH$_3$ | CH | H | H | |
| Q-34 | H | H | F | H | CH$_3$ | CH$_3$ | CH | H | H | |
| Q-34 | H | H | Cl | H | OCH$_3$ | OCH$_3$ | CH | H | H | |
| Q-34 | H | H | Br | H | OCH$_3$ | CH$_3$ | CH | H | H | |
| Q-34 | H | H | NO$_2$ | H | OCH$_3$ | OCH$_3$ | CH | H | H | |
| Q-34 | H | H | SCH$_2$F | H | CH$_3$ | OCH$_3$ | CH | H | H | |
| Q-34 | H | H | SCH$_2$F | H | OCH$_3$ | OCH$_3$ | CH | H | H | |
| Q-34 | H | H | CH$_2$—CH=CH$_2$ | H | Cl | OCH$_3$ | CH | H | H | |
| Q-34 | H | H | CH$_2$—C≡CH | H | OCH$_3$ | OCH$_3$ | CH | H | H | |
| Q-34 | H | H | CO$_2$CH$_3$ | H | OCH$_3$ | OCH$_3$ | CH | H | H | |
| Q-34 | H | H | CO$_2$CH$_3$ | H | OCH$_3$ | CH$_3$ | CH | H | H | |
| Q-34 | H | H | CO$_2$CH$_3$ | H | CH$_3$ | CH$_3$ | N | H | H | |
| Q-34 | H | H | CO$_2$CH$_2$CH$_3$ | H | OCH$_3$ | OCH$_3$ | CH | H | H | |
| Q-34 | H | H | SCH$_3$ | H | CH$_3$ | OCH$_3$ | CH | H | H | |
| Q-34 | H | H | SOCH$_3$ | H | CH$_3$ | CH$_3$ | CH | H | H | |
| Q-34 | H | H | SO$_2$CH$_3$ | H | OCH$_3$ | OCH$_3$ | CH | H | H | |
| Q-34 | H | H | SO$_2$N(CH$_3$)$_2$ | H | OCH$_3$ | CH$_3$ | CH | H | H | |
| Q-34 | H | H | SO$_2$N(CH$_3$)$_2$ | H | OCH$_3$ | CH$_3$ | N | H | H | |
| Q-34 | H | H | SO$_2$N(CH$_2$CH$_3$)$_2$ | H | OCH$_3$ | OCH$_3$ | CH | H | H | |
| Q-34 | CH$_3$ | H | Cl | H | CH$_3$ | CH$_3$ | CH | H | H | |
| Q-34 | H | CH$_3$ | Br | H | OCH$_3$ | OCH$_3$ | N | H | H | |
| Q-34 | H | Cl | CO$_2$CH$_3$ | H | CH$_3$ | OCH$_3$ | CH$_3$ | H | H | |

| Q | R | R$_{15}$ | R$_{16}$ | R$_{10}$ | R$_{11}$ | X | Y | Z | m.p. °C. |
|---|---|---|---|---|---|---|---|---|---|
| Q-35 | H | H | H | H | H | CH$_3$ | OCH$_3$ | CH | |
| Q-35 | H | H | CH$_3$ | H | H | CH$_3$ | CH$_3$ | N | |
| Q-35 | H | H | CH$_2$CH$_2$CH$_3$ | H | H | OCH$_3$ | OCH$_3$ | N | |
| Q-35 | H | H | F | H | H | OCH$_3$ | OCH$_3$ | CH | |
| Q-35 | H | H | Cl | H | H | OCH$_3$ | OCH$_3$ | CH | |
| Q-35 | H | H | Cl | H | H | OCH$_3$ | CH$_3$ | N | |
| Q-35 | H | H | Br | H | H | CH$_3$ | OCH$_3$ | CH | |
| Q-35 | H | H | NO$_2$ | H | H | Cl | OCH$_3$ | CH | |
| Q-35 | H | H | SCH$_2$CH$_2$F | H | H | OCH$_3$ | OCH$_3$ | CH | |
| Q-35 | H | H | CH$_2$—CH=CH$_2$ | H | H | OCH$_3$ | CH$_3$ | CH | |
| Q-35 | H | H | CH$_2$—C≡CH | H | H | CH$_3$ | CH$_3$ | CH | |
| Q-35 | H | H | CO$_2$CH$_3$ | H | H | CH$_3$ | OCH$_3$ | N | |
| Q-35 | H | H | CO$_2$CH$_3$ | H | H | OCH$_3$ | OCH$_3$ | CH | |
| Q-35 | H | H | CO$_2$CH$_3$ | H | H | CH$_3$ | OCH$_3$ | CH | |
| Q-35 | H | H | CO$_2$CH$_2$CH$_3$ | H | H | CH$_3$ | CH$_3$ | CH | |
| Q-35 | H | H | CO$_2$CH$_2$CH$_2$CH$_3$ | H | H | OCH$_3$ | OCH$_3$ | CH | |
| Q-35 | H | H | SCH$_3$ | H | H | CH$_3$ | CH$_3$ | N | |
| Q-35 | H | H | SOCH$_3$ | H | H | CH$_3$ | CH$_3$ | CH | |
| Q-35 | H | H | SO$_2$CH$_3$ | H | H | OCH$_3$ | OCH$_3$ | CH | |
| Q-35 | H | H | SO$_2$CH$_2$CH$_3$ | H | H | OCH$_3$ | OCH$_3$ | N | |
| Q-35 | H | H | SO$_2$N(CH$_3$)$_2$ | H | H | CH$_3$ | OCH$_3$ | CH | |
| Q-35 | H | H | SO$_2$N(CH$_2$CH$_3$)$_2$ | H | H | OCH$_3$ | OCH$_3$ | CH | |
| Q-35 | CH$_3$ | H | CO$_2$CH$_3$ | H | H | OCH$_3$ | OCH$_3$ | CH | |
| Q-35 | H | H | Br | H | CH$_3$ | OCH$_3$ | OCH$_3$ | CH | |
| Q-35 | H | CH$_3$ | Cl | H | H | OCH$_3$ | OCH$_3$ | N | |
| Q-36 | H | H | H | H | H | CH$_3$ | OCH$_3$ | CH | |
| Q-36 | H | H | CH$_2$CH$_3$ | H | H | OCH$_3$ | OCH$_3$ | CH | |
| Q-36 | H | H | F | H | H | CH$_3$ | CH$_3$ | CH | |
| Q-36 | H | H | Cl | H | H | OCH$_3$ | OCH$_3$ | CH | |
| Q-36 | H | H | Br | H | H | OCH$_3$ | CH$_3$ | CH | |
| Q-36 | H | H | NO$_2$ | H | H | OCH$_3$ | OCH$_3$ | CH | |
| Q-36 | H | H | SCH$_2$F | H | H | CH$_3$ | OCH$_3$ | CH | |
| Q-36 | H | H | SCH$_2$F | H | H | OCH$_3$ | OCH$_3$ | CH | |
| Q-36 | H | H | CH$_2$—CH=CH$_2$ | H | H | Cl | OCH$_3$ | CH | |
| Q-36 | H | H | CH$_2$—C≡CH | H | H | OCH$_3$ | OCH$_3$ | CH | |
| Q-36 | H | H | CO$_2$CH$_3$ | H | H | OCH$_3$ | OCH$_3$ | CH | |

TABLE XXIII-continued

General Formula XIII

| Q | R | R$_{15}$ | R$_{16}$ | R$_6$ | R$_7$ | X | Y | Z | |
|---|---|---|---|---|---|---|---|---|---|
| Q-36 | H | H | CO$_2$CH$_3$ | H | H | OCH$_3$ | CH$_3$ | CH | |
| Q-36 | H | H | CO$_2$CH$_3$ | H | H | CH$_3$ | CH$_3$ | N | |
| Q-36 | H | H | CO$_2$CH$_2$CH$_3$ | H | H | OCH$_3$ | OCH$_3$ | CH | |
| Q-36 | H | H | SCH$_3$ | H | H | CH$_3$ | OCH$_3$ | CH | |
| Q-36 | H | H | SOCH$_3$ | H | H | CH$_3$ | CH$_3$ | CH | |
| Q-36 | H | H | SO$_2$CH$_3$ | H | H | OCH$_3$ | OCH$_3$ | CH | |
| Q-36 | H | H | SO$_2$N(CH$_3$)$_2$ | H | H | OCH$_3$ | CH$_3$ | CH | |
| Q-36 | H | H | SO$_2$N(CH$_3$)$_2$ | H | H | OCH$_3$ | CH$_3$ | N | |
| Q-36 | H | H | SO$_2$N(CH$_2$CH$_3$)$_2$ | H | H | OCH$_3$ | OCH$_3$ | CH | |
| Q-36 | CH$_3$ | H | Cl | H | H | CH$_3$ | CH$_3$ | CH | |
| Q-36 | H | CH$_3$ | Br | H | H | OCH$_3$ | OCH$_3$ | N | |
| Q-36 | H | Cl | CO$_2$CH$_3$ | H | H | CH$_3$ | OCH$_3$ | CH | |

| Q | R | R$_{15}$ | R$_{16}$ | R$_6$ | R$_7$ | X | Y | Z | m.p. °C. |
|---|---|---|---|---|---|---|---|---|---|
| Q-37 | H | H | H | H | H | CH$_3$ | OCH$_3$ | CH | |
| Q-37 | H | H | CH$_3$ | H | H | CH$_3$ | CH$_3$ | N | |
| Q-37 | H | H | CH$_2$CH$_2$CH$_3$ | H | H | OCH$_3$ | OCH$_3$ | N | |
| Q-37 | H | H | F | H | H | OCH$_3$ | OCH$_3$ | CH | |
| Q-37 | H | H | Cl | H | H | OCH$_3$ | OCH$_3$ | CH | |
| Q-37 | H | H | Cl | H | H | OCH$_3$ | CH$_3$ | N | |
| Q-37 | H | H | Br | H | H | CH$_3$ | OCH$_3$ | CH | |
| Q-37 | H | H | NO$_2$ | H | H | Cl | OCH$_3$ | CH | |
| Q-37 | H | H | SCH$_2$CH$_2$F | H | H | OCH$_3$ | OCH$_3$ | CH | |
| Q-37 | H | H | CH$_2$—CH=CH$_2$ | H | H | OCH$_3$ | CH$_3$ | CH | |
| Q-37 | H | H | CH$_2$—C≡CH | H | H | CH$_3$ | CH$_3$ | CH | |
| Q-37 | H | H | CO$_2$CH$_3$ | H | H | CH$_3$ | OCH$_3$ | N | |
| Q-37 | H | H | CO$_2$CH$_3$ | H | H | OCH$_3$ | OCH$_3$ | CH | |
| Q-37 | H | H | CO$_2$CH$_3$ | H | H | CH$_3$ | OCH$_3$ | CH | |
| Q-37 | H | H | CO$_2$CH$_2$CH$_3$ | H | H | CH$_3$ | CH$_3$ | CH | |
| Q-37 | H | H | CO$_2$CH$_2$CH$_2$CH$_3$ | H | H | OCH$_3$ | OCH$_3$ | CH | |
| Q-37 | H | H | SCH$_3$ | H | H | CH$_3$ | CH$_3$ | N | |
| Q-37 | H | H | SOCH$_3$ | H | H | CH$_3$ | OCH$_3$ | CH | |
| Q-37 | H | H | SO$_2$CH$_3$ | H | H | OCH$_3$ | OCH$_3$ | CH | |
| Q-37 | H | H | SO$_2$CH$_2$CH$_3$ | H | H | OCH$_3$ | OCH$_3$ | N | |
| Q-37 | H | H | SO$_2$N(CH$_3$)$_2$ | H | H | CH$_3$ | OCH$_3$ | CH | |
| Q-37 | H | H | SO$_2$N(CH$_2$CH$_3$)$_2$ | H | H | OCH$_3$ | OCH$_3$ | CH | |
| Q-37 | CH$_3$ | H | CO$_2$CH$_3$ | H | H | OCH$_3$ | OCH$_3$ | CH | |
| Q-37 | H | H | Br | H | CH$_3$ | OCH$_3$ | OCH$_3$ | CH | |
| Q-37 | H | CH$_3$ | Cl | H | H | OCH$_3$ | OCH$_3$ | N | |
| Q-38 | H | H | H | H | H | CH$_3$ | OCH$_3$ | CH | |
| Q-38 | H | H | CH$_2$CH$_3$ | H | H | OCH$_3$ | OCH$_3$ | CH | |
| Q-38 | H | H | F | H | H | CH$_3$ | CH$_3$ | CH | |
| Q-38 | H | H | Cl | H | H | OCH$_3$ | OCH$_3$ | CH | |
| Q-38 | H | H | Br | H | H | OCH$_3$ | CH$_3$ | CH | |
| Q-38 | H | H | NO$_2$ | H | H | OCH$_3$ | OCH$_3$ | CH | |
| Q-38 | H | H | SCH$_2$F | H | H | CH$_3$ | OCH$_3$ | CH | |
| Q-38 | H | H | SCH$_2$F | H | H | OCH$_3$ | OCH$_3$ | CH | |
| Q-38 | H | H | CH$_2$—CH=CH$_2$ | H | H | Cl | OCH$_3$ | CH | |
| Q-38 | H | H | CH$_2$—C≡CH | H | H | OCH$_3$ | OCH$_3$ | CH | |
| Q-38 | H | H | CO$_2$CH$_3$ | H | H | OCH$_3$ | OCH$_3$ | CH | |
| Q-38 | H | H | CO$_2$CH$_3$ | H | H | OCH$_3$ | CH$_3$ | CH | |
| Q-38 | H | H | CO$_2$CH$_3$ | H | H | CH$_3$ | CH$_3$ | N | |
| Q-38 | H | H | CO$_2$CH$_2$CH$_3$ | H | H | OCH$_3$ | OCH$_3$ | CH | |
| Q-38 | H | H | SCH$_3$ | H | H | CH$_3$ | OCH$_3$ | CH | |
| Q-38 | H | H | SOCH$_3$ | H | H | CH$_3$ | CH$_3$ | CH | |
| Q-38 | H | H | SO$_2$CH$_3$ | H | H | OCH$_3$ | OCH$_3$ | CH | |
| Q-38 | H | H | SO$_2$N(CH$_3$)$_2$ | H | H | OCH$_3$ | CH$_3$ | CH | |
| Q-38 | H | H | SO$_2$N(CH$_3$)$_2$ | H | H | OCH$_3$ | CH$_3$ | N | |
| Q-38 | H | H | SO$_2$N(CH$_2$CH$_3$)$_2$ | H | H | OCH$_3$ | OCH$_3$ | CH | |
| Q-38 | CH$_3$ | H | Cl | H | H | CH$_3$ | CH$_3$ | CH | |
| Q-38 | H | CH$_3$ | Br | H | H | OCH$_3$ | OCH$_3$ | N | |
| Q-38 | H | Cl | CO$_2$CH$_3$ | H | H | CH$_3$ | OCH$_3$ | CH | |

| Q | R | R$_{15}$ | R$_{16}$ | R$_{12}$ | R$_{13}$ | X | Y | Z | m.p. °C. |
|---|---|---|---|---|---|---|---|---|---|
| Q-39 | H | H | H | H | H | CH$_3$ | OCH$_3$ | CH | |
| Q-39 | H | H | CH$_3$ | H | H | CH$_3$ | CH$_3$ | N | |
| Q-39 | H | H | CH$_2$CH$_2$CH$_3$ | H | H | OCH$_3$ | OCH$_3$ | N | |
| Q-39 | H | H | F | H | H | OCH$_3$ | OCH$_3$ | CH | |
| Q-39 | H | H | Cl | H | H | OCH$_3$ | OCH$_3$ | CH | |
| Q-39 | H | H | Cl | H | H | OCH$_3$ | CH$_3$ | N | |
| Q-39 | H | H | Br | H | H | CH$_3$ | OCH$_3$ | CH | |
| Q-39 | H | H | NO$_2$ | H | H | Cl | OCH$_3$ | CH | |
| Q-39 | H | H | SCH$_2$CH$_2$F | H | H | OCH$_3$ | OCH$_3$ | CH | |
| Q-39 | H | H | CH$_2$—CH=CH$_2$ | H | H | OCH$_3$ | CH$_3$ | CH | |
| Q-39 | H | H | CH$_2$—C≡CH | H | H | CH$_3$ | CH$_3$ | CH | |
| Q-39 | H | H | CO$_2$CH$_3$ | H | H | CH$_3$ | OCH$_3$ | N | |

| Q | R | R$_{15}$ | R$_{16}$ | R$_6$ | R$_7$ | X | Y | Z | m.p. °C. |
|---|---|---|---|---|---|---|---|---|---|
| Q-39 | H | H | CO$_2$CH$_3$ | H | H | OCH$_3$ | OCH$_3$ | CH | |
| Q-39 | H | H | CO$_2$CH$_3$ | H | H | CH$_3$ | OCH$_3$ | CH | |
| Q-39 | H | H | CO$_2$CH$_2$CH$_3$ | H | H | CH$_3$ | CH$_3$ | CH | |

TABLE XXIII-continued

General Formula XIII

| Q | R | R₁₅ | R₁₆ | R₆ | X | Y | Z | |
|---|---|---|---|---|---|---|---|---|
| Q-39 | H | H | CO₂CH₂CH₂CH₃ | H | H | OCH₃ | OCH₃ | CH |
| Q-39 | H | H | SCH₃ | H | H | CH₃ | CH₃ | N |
| Q-39 | H | H | SOCH₃ | H | H | CH₃ | CH₃ | CH |
| Q-39 | H | H | SO₂CH₃ | H | H | OCH₃ | OCH₃ | CH |
| Q-39 | H | H | SO₂CH₂CH₃ | H | H | OCH₃ | OCH₃ | N |
| Q-39 | H | H | SO₂N(CH₃)₂ | H | H | CH₃ | OCH₃ | CH |
| Q-39 | H | H | SO₂N(CH₂CH₃)₂ | H | H | OCH₃ | OCH₃ | CH |
| Q-39 | CH₃ | H | CO₂CH₃ | H | H | OCH₃ | OCH₃ | CH |
| Q-39 | H | H | Br | H | CH₃ | OCH₃ | OCH₃ | CH |
| Q-39 | H | CH₃ | Cl | H | H | OCH₃ | OCH₃ | N |
| Q-40 | H | H | H | H | H | CH₃ | OCH₃ | CH |
| Q-40 | H | H | CH₂CH₃ | H | H | OCH₃ | OCH₃ | CH |
| Q-40 | H | H | F | H | H | CH₃ | CH₃ | CH |
| Q-40 | H | H | Cl | H | H | OCH₃ | OCH₃ | CH |
| Q-40 | H | H | Br | H | H | OCH₃ | CH₃ | CH |
| Q-40 | H | H | NO₂ | H | H | OCH₃ | OCH₃ | CH |
| Q-40 | H | H | SCH₂F | H | H | CH₃ | OCH₃ | CH |
| Q-40 | H | H | SCH₂F | H | H | OCH₃ | OCH₃ | CH |
| Q-40 | H | H | CH₂—CH=CH₂ | H | H | Cl | OCH₃ | CH |
| Q-40 | H | H | CH₂—C≡CH | H | H | OCH₃ | OCH₃ | CH |
| Q-40 | H | H | CO₂CH₃ | H | H | OCH₃ | OCH₃ | CH |
| Q-40 | H | H | CO₂CH₃ | H | H | OCH₃ | CH₃ | CH |
| Q-40 | H | H | CO₂CH₃ | H | H | CH₃ | CH₃ | N |
| Q-40 | H | H | CO₂CH₂CH₃ | H | H | OCH₃ | OCH₃ | CH |
| Q-40 | H | H | SCH₃ | H | H | CH₃ | OCH₃ | CH |
| Q-40 | H | H | SOCH₃ | H | H | CH₃ | CH₃ | CH |
| Q-40 | H | H | SO₂CH₃ | H | H | OCH₃ | OCH₃ | CH |
| Q-40 | H | H | SO₂N(CH₃)₂ | H | H | OCH₃ | CH₃ | CH |
| Q-40 | H | H | SO₂N(CH₃)₂ | H | H | OCH₃ | CH₃ | N |
| Q-40 | H | H | SO₂N(CH₂CH₃)₂ | H | H | OCH₃ | OCH₃ | CH |
| Q-40 | CH₃ | H | Cl | H | H | CH₃ | CH₃ | CH |
| Q-40 | H | CH₃ | Br | H | H | OCH₃ | OCH₃ | N |
| Q-40 | H | Cl | CO₂CH₃ | H | H | CH₃ | OCH₃ | CH |

| Q | R | R₁₅ | R₁₆ | R₆ | X | Y | Z | m.p. °C. |
|---|---|---|---|---|---|---|---|---|
| Q-41 | H | H | H | H | CH₃ | OCH₃ | CH | |
| Q-41 | H | H | CH₃ | H | CH₃ | CH₃ | N | |
| Q-41 | H | H | CH₂CH₂CH₃ | H | OCH₃ | OCH₃ | N | |
| Q-41 | H | H | F | H | OCH₃ | OCH₃ | CH | |
| Q-41 | H | H | Cl | H | OCH₃ | OCH₃ | CH | |
| Q-41 | H | H | Cl | H | OCH₃ | CH₃ | N | |
| Q-41 | H | H | Br | H | CH₃ | OCH₃ | CH | |
| Q-41 | H | H | NO₂ | H | Cl | OCH₃ | CH | |
| Q-41 | H | H | Sch₂CH₂F | H | OCH₃ | OCH₃ | CH | |
| Q-41 | H | H | CH₂—CH=CH₂ | H | OCH₃ | CH₃ | CH | |
| Q-41 | H | H | CH₂—C≡CH | H | H | CH₃ | CH₃ | CH |
| Q-41 | H | H | CO₂CH₃ | H | CH₃ | OCH₃ | N | |
| Q-41 | H | H | CO₂CH₃ | H | OCH₃ | OCH₃ | CH | |
| Q-41 | H | H | CO₂CH₃ | H | CH₃ | OCH₃ | CH | |
| Q-41 | H | H | CO₂CH₂CH₃ | H | CH₃ | CH₃ | CH | |
| Q-41 | H | H | CO₂CH₂CH₂CH₃ | H | OCH₃ | OCH₃ | CH | |
| Q-41 | H | H | SCH₃ | H | CH₃ | CH₃ | N | |
| Q-41 | H | H | SOCH₃ | H | CH₃ | CH₃ | CH | |
| Q-41 | H | H | SO₂CH₃ | H | OCH₃ | OCH₃ | CH | |
| Q-41 | H | H | SO₂CH₂CH₃ | H | OCH₃ | OCH₃ | N | |
| Q-41 | H | H | SO₂N(CH₃)₂ | H | CH₃ | OCH₃ | CH | |
| Q-41 | H | H | SO₂N(CH₂CH₃)₂ | H | OCH₃ | OCH₃ | CH | |
| Q-41 | CH₃ | H | CO₂CH₃ | H | OCH₃ | OCH₃ | CH | |
| Q-41 | H | H | Br | CH₃ | OCH₃ | OCH₃ | CH | |
| Q-41 | H | CH₃ | Cl | H | OCH₃ | OCH₃ | N | |
| Q-42 | H | H | H | H | CH₃ | OCH₃ | CH | |
| Q-42 | H | H | CH₂CH₃ | H | OCH₃ | OCH₃ | CH | |
| Q-42 | H | H | F | H | CH₃ | CH₃ | CH | |
| Q-42 | H | H | Cl | H | OCH₃ | OCH₃ | CH | |
| Q-42 | H | H | Br | H | OCH₃ | CH₃ | CH | |
| Q-42 | H | H | NO₂ | H | OCH₃ | OCH₃ | CH | |
| Q-42 | H | H | SCH₂F | H | CH₃ | OCH₃ | CH | |
| Q-42 | H | H | SCH₂F | H | OCH₃ | OCH₃ | CH | |
| Q-42 | H | H | CH₂—CH=CH₂ | H | Cl | OCH₃ | CH | |
| Q-42 | H | H | CH₂—C≡CH | H | OCH₃ | OCH₃ | CH | |
| Q-42 | H | H | CO₂CH₃ | H | OCH₃ | OCH₃ | CH | |
| Q-42 | H | H | CO₂CH₃ | H | OCH₃ | CH₃ | CH | |
| Q-42 | H | H | CO₂CH₃ | H | CH₃ | CH₃ | N | |
| Q-42 | H | H | CO₂CH₂CH₃ | H | OCH₃ | OCH₃ | CH | |
| Q-42 | H | H | SCH₃ | H | CH₃ | OCH₃ | CH | |
| Q-42 | H | H | SOCH₃ | H | CH₃ | CH₃ | CH | |
| Q-42 | H | H | SO₂CH₃ | H | OCH₃ | OCH₃ | CH | |
| Q-42 | H | H | SO₂N(CH₃)₂ | H | OCH₃ | CH₃ | CH | |
| Q-42 | H | H | SO₂N(CH₃)₂ | H | OCH₃ | CH₃ | N | |
| Q-42 | H | H | SO₂N(CH₂CH₃)₂ | H | OCH₃ | OCH₃ | CH | |
| Q-42 | CH₃ | H | Cl | H | CH₃ | CH₃ | CH | |

TABLE XXIII-continued

General Formula XIII

| Q | R | R₂ | R₁₄ | R₆ | X | Y | Z |
|---|---|---|---|---|---|---|---|
| Q-42 | H | CH₃ | Br | H | OCH₃ | OCH₃ | N |
| Q-42 | H | Cl | CO₂CH₃ | H | CH₃ | OCH₃ | CH |
| Q-43 | H | H | H | H | CH₃ | OCH₃ | CH |
| Q-43 | H | H | CH₃ | H | CH₃ | CH₃ | N |
| Q-43 | H | H | CH₂CH₂CH₃ | H | OCH₃ | OCH₃ | N |
| Q-43 | H | H | F | H | OCH₃ | OCH₃ | CH |
| Q-43 | H | H | Cl | H | OCH₃ | OCH₃ | CH |
| Q-43 | H | H | Cl | H | OCH₃ | CH₃ | N |
| Q-43 | H | H | Br | H | CH₃ | OCH₃ | CH |
| Q-43 | H | H | NO₂ | H | Cl | OCH₃ | CH |
| Q-43 | H | H | SCH₂CH₂F | H | OCH₃ | OCH₃ | CH |
| Q-43 | H | H | CH₂—CH=CH₂ | H | OCH₃ | CH₃ | CH |
| Q-43 | H | H | CH₂—C≡CH | H | CH₃ | CH₃ | CH |
| Q-43 | H | H | CO₂CH₃ | H | CH₃ | OCH₃ | N |
| Q-43 | H | H | CO₂CH₃ | H | OCH₃ | OCH₃ | CH |
| Q-43 | H | H | CO₂CH₃ | H | CH₃ | CH₃ | CH |
| Q-43 | H | H | CO₂CH₂CH₃ | H | CH₃ | CH₃ | CH |
| Q-43 | H | H | CO₂CH₂CH₂CH₃ | H | OCH₃ | OCH₃ | N |
| Q-43 | H | H | SCH₃ | H | CH₃ | CH₃ | N |
| Q-43 | H | H | SOCH₃ | H | CH₃ | CH₃ | CH |
| Q-43 | H | H | SO₂CH₃ | H | OCH₃ | OCH₃ | CH |
| Q-43 | H | H | SO₂CH₂CH₃ | H | OCH₃ | OCH₃ | N |
| Q-43 | H | H | SO₂N(CH₃)₂ | H | CH₃ | OCH₃ | CH |
| Q-43 | H | H | SO₂N(CH₂CH₃)₂ | H | OCH₃ | OCH₃ | CH |
| Q-43 | CH₃ | H | CO₂CH₃ | H | OCH₃ | OCH₃ | CH |
| Q-43 | H | H | Br | CH₃ | OCH₃ | OCH₃ | CH |
| Q-43 | H | CH₃ | Cl | H | OCH₃ | OCH₃ | N |
| Q-44 | H | H | H | H | CH₃ | OCH₃ | CH |
| Q-44 | H | H | CH₂CH₃ | H | OCH₃ | OCH₃ | CH |
| Q-44 | H | H | F | H | CH₃ | CH₃ | CH |
| Q-44 | H | H | Cl | H | OCH₃ | OCH₃ | CH |
| Q-44 | H | H | Br | H | OCH₃ | CH₃ | CH |
| Q-44 | H | H | NO₂ | H | OCH₃ | OCH₃ | CH |
| Q-44 | H | H | SCH₂F | H | CH₃ | OCH₃ | CH |
| Q-44 | H | H | SCH₂F | H | OCH₃ | OCH₃ | CH |
| Q-44 | H | H | CH₂—CH=CH₂ | H | Cl | OCH₃ | CH |
| Q-44 | H | H | CH₂—C≡CH | H | OCH₃ | OCH₃ | CH |
| Q-44 | H | H | CO₂CH₃ | H | OCH₃ | OCH₃ | CH |
| Q-44 | H | H | CO₂CH₃ | H | OCH₃ | CH₃ | CH |
| Q-44 | H | H | CO₂CH₃ | H | CH₃ | CH₃ | N |
| Q-44 | H | H | CO₂CH₂CH₃ | H | OCH₃ | OCH₃ | CH |
| Q-44 | H | H | SCH₃ | H | CH₃ | CH₃ | CH |
| Q-44 | H | H | SOCH₃ | H | CH₃ | CH₃ | CH |
| Q-44 | H | H | SO₂CH₃ | H | OCH₃ | OCH₃ | CH |
| Q-44 | H | H | SO₂N(CH₃)₂ | H | OCH₃ | CH₃ | CH |
| Q-44 | H | H | SO₂N(CH₃)₂ | H | OCH₃ | CH₃ | N |
| Q-44 | H | H | SO₂N(CH₂CH₃)₂ | H | OCH₃ | OCH₃ | CH |
| Q-44 | CH₃ | H | Cl | H | CH₃ | CH₃ | CH |
| Q-44 | H | CH₃ | Br | H | OCH₃ | OCH₃ | N |
| Q-44 | H | Cl | CO₂CH₃ | H | CH₃ | OCH₃ | CH |

TABLE XXV

General Formula XXV

| Q | R | R₂ | R₁₄ | R₆ | R₇ | X | Y | Z | m.p. °C. |
|---|---|---|---|---|---|---|---|---|---|
| Q-1 | H | H | H | H | H | H | CH₃ | OCH₃ | CH |
| Q-1 | H | H | CH₂CH₂CH₃ H | H | OCH₃ | OCH₃ | N | | |
| Q-1 | H | H | CH₃ | H | H | CH₃ | CH₃ | N | |
| Q-1 | H | H | CH₂CH₂CH₃ | H | H | OCH₃ | OCH₃ | N | |
| Q-1 | H | H | F | H | H | OCH₃ | OCH₃ | CH | |
| Q-1 | H | H | Cl | H | H | OCH₃ | OCH₃ | CH | |
| Q-1 | H | H | Cl | H. | H | OCH₃ | CH₃ | N | |
| Q-1 | H | H | Br | H | H | CH₃ | OCH₃ | CH | |
| Q-1 | H | H | NO₂ | H | H | Cl | OCH₃ | CH | |
| Q-1 | H | H | SCH₂CH₂F | H | H | OCH₃ | OCH₃ | CH | |
| Q-1 | H | H | CH₂—CH=CH₂ | H | H | OCH₃ | CH₃ | CH | |
| Q-1 | H | H | CH₂—C≡CH | H | H | CH₃ | CH₃ | CH | |
| Q-1 | H | H | CO₂CH₃ | H | H | CH₃ | OCH₃ | N | |
| Q-1 | H | H | CO₂CH₃ | H | H | OCH₃ | OCH₃ | CH | |
| Q-1 | H | H | CO₂CH(CH₃)₂ | H | H | CH₃ | OCH₃ | CH | |
| Q-1 | H | H | CO₂CH₂CH₃ | H | H | CH₃ | CH₃ | CH | |
| Q-1 | H | H | CO₂CH₂CH₂CH₃ | H | H | OCH₃ | OCH₃ | CH | |
| Q-1 | H | H | SCH₃ | H | H | CH₃ | CH₃ | N | |
| Q-1 | H | H | SOCH₃ | H | H | CH₃ | CH₃ | CH | |
| Q-1 | H | H | SO₂CH₃ | H | H | OCH₃ | OCH₃ | CH | |
| Q-1 | H | H | SO₂CH₂CH₃ | H | H | OCH₃ | OCH₃ | N | |
| Q-1 | H | H | SO₂N(CH₃)₂ | H | H | CH₃ | OCH₃ | CH | |
| Q-1 | H | H | SO₂N(CH₂CH₃)₂ | H | H | OCH₃ | OCH₃ | CH | |
| Q-1 | CH₃ | H | CO₂CH₂CH=CH₂ | H | H | OCH₃ | OCH₃ | CH | |

TABLE XXV-continued

General Formula XXV

| | | | | | | | | |
|---|---|---|---|---|---|---|---|---|
| Q-1 | H | H | Br | H | CH₃ | OCH₃ | OCH₃ | CH |
| Q-1 | H | CH₃ | Cl | H | H | OCH₃ | OCH₃ | N |
| Q-2 | H | H | H | H | H | CH₃ | OCH₃ | CH |
| Q-2 | H | H | CH₂CH₃ | H | H | OCH₃ | OCH₃ | CH |
| Q-2 | H | H | F | H | H | CH₃ | CH₃ | CH |
| Q-2 | H | H | Cl | H | H | OCH₃ | OCH₃ | CH |
| Q-2 | H | H | Br | H | H | OCH₃ | CH₃ | CH |
| Q-2 | H | H | NO₂ | H | H | OCH₃ | OCH₃ | CH |
| Q-2 | H | H | SCHCF | H | H | CH₃ | OCH₃ | CH |
| Q-2 | H | H | SCH₂F | H | H | OCH₃ | OCH₃ | CH |
| Q-2 | H | H | CH₂—CH=CH₂ | H | H | Cl | OCH₃ | CH |
| Q-2 | H | H | CH₂—C≡CH | H | H | OCH₃ | OCH₃ | CH |
| Q-2 | H | H | CO₂CH₃ | H | H | OCH₃ | OCH₃ | CH |
| Q-2 | H | H | CO₂CH₂C≡CH | H | H | OCH₃ | CH₃ | CH |
| Q-2 | H | H | CO₂CH₃ | H | H | CH₃ | CH₃ | N |
| Q-2 | H | H | CO₂CH₂CH₃ | H | H | OCH₃ | OCH₃ | CH |
| Q-2 | H | H | SCH₃ | H | H | CH₃ | OCH₃ | CH |
| Q-2 | H | H | SOCH₃ | H | H | CH₃ | CH₃ | CH |
| Q-2 | H | H | SO₂CH₃ | H | H | OCH₃ | OCH₃ | CH |
| Q-2 | H | H | SO₂N(CH₃)₂ | H | H | OCH₃ | CH₃ | CH |
| Q-2 | H | H | SO₂N(CH₃)₂ | H | H | OCH₃ | CH₃ | N |
| Q-2 | H | H | SO₂N(CH₂CH₃)₂ | H | H | OCH₃ | OCH₃ | CH |
| Q-2 | CH₃ | H | Cl | H | H | CH₃ | CH₃ | CH |
| Q-2 | H | CH₃ | Br | H | H | OCH₃ | OCH₃ | N |
| Q-2 | H | Cl | CO₂CH₃ | H | H | CH₃ | OCH₃ | CH |
| Q-3 | H | H | H | H | H | CH₃ | OCH₃ | CH |
| Q-3 | H | H | CH₃ | H | H | CH₃ | CH₃ | N |
| Q-3 | H | H | CH₂CH₂CH₃ | H | H | OCH₃ | OCH₃ | N |
| Q-3 | H | H | F | H | H | OCH₃ | OCH₃ | CH |
| Q-3 | H | H | Cl | H | H | OCH₃ | OCH₃ | CH |
| Q-3 | H | H | Cl | H | H | OCH₃ | CH₃ | N |
| Q-3 | H | H | Br | H | H | CH₃ | OCH₃ | CH |
| Q-3 | H | H | NO₂ | H | H | Cl | OCH₃ | CH |
| Q-3 | H | H | SCH₂CH₂F | H | H | OCH₃ | OCH₃ | CH |
| Q-3 | H | H | CH₂—CH=CH₂ | H | H | OCH₃ | CH | |
| Q-3 | H | H | CH₂—C≡CH | H | H | CH₃ | CH₃ | CH |
| Q-3 | H | H | CO₂CH₃ | H | H | CH₃ | OCH₃ | N |
| Q-3 | H | H | CO₂CH₃ | H | H | OCH₃ | OCH₃ | CH |
| Q-3 | H | H | CO₂CH₂CH₂Cl | H | H | CH₃ | CH₃ | CH |
| Q-3 | H | H | CO₂CH₂CH₃ | H | H | CH₃ | CH₃ | CH |
| Q-3 | H | H | CO₂CH₂CH₂CH₃ | H | H | OCH₃ | OCH₃ | CH |
| Q-3 | H | H | SCH₃ | H | H | CH₃ | CH₃ | N |
| Q-3 | H | H | SOCH₃ | H | H | CH₃ | CH₃ | CH |
| Q-3 | H | H | SO₂CH₃ | H | H | OCH₃ | OCH₃ | CH |
| Q-3 | H | H | SO₂CH₂CH₃ | H | H | OCH₃ | OCH₃ | N |
| Q-3 | H | H | SO₂N(CH₃)₂ | H | H | CH₃ | OCH₃ | CH |
| Q-3 | H | H | SO₂N(CH₂CH₃)₂ | H | H | OCH₃ | OCH₃ | CH |
| Q-3 | CH₃ | H | CO₂CH₃ | H | H | OCH₃ | OCH₃ | CH |
| Q-3 | H | H | Br | H | CH₃ | OCH₃ | OCH₃ | CH |
| Q-3 | H | CH₃ | Cl | H | H | OCH₃ | OCH₃ | N |
| Q-4 | H | H | H | H | H | CH₃ | OCH₃ | CH |
| Q-4 | H | H | CH₂CH₃ | H | H | OCH₃ | OCH₃ | CH |
| Q-4 | H | H | F | H | H | CH₃ | CH₃ | CH |
| Q-4 | H | H | Cl | H | H | OCH₃ | OCH₃ | CH |
| Q-4 | H | H | Br | H | H | OCH₃ | CH₃ | CH |
| Q-4 | H | H | NO₂ | H | H | OCH₃ | OCH₃ | CH |
| Q-4 | H | H | SCH₂F | H | H | CH₃ | OCH₃ | CH |
| Q-4 | H | H | SCH₂F | H | H | OCH₃ | OCH₃ | CH |
| Q-4 | H | H | CH₂—CH=CH₂ | H | H | Cl | OCH₃ | CH |
| Q-4 | H | H | CH₂—C≡CH | H | H | OCH₃ | OCH₃ | CH |
| Q-4 | H | H | CO₂CH₃ | H | H | OCH₃ | OCH₃ | CH |
| Q-4 | H | H | C₂CH₃ | H | H | OCH₃ | CH₃ | CH |
| Q-4 | H | H | CO₂CH₂CH₂OCH₃ | H | H | CH₃ | CH₃ | CH |
| Q-4 | H | H | CO₂CH₂CH₃ | H | H | OCH₃ | OCH₃ | CH |
| Q-4 | H | H | SCH₃ | H | H | CH₃ | OCH₃ | CH |
| Q-4 | H | H | SOCH₃ | H | H | CH₃ | CH₃ | CH |
| Q-4 | H | H | SO₂CH₃ | H | H | OCH₃ | OCH₃ | CH |
| Q-4 | H | H | SO₂N(CH₃)₂ | H | H | OCH₃ | CH₃ | CH |
| Q-4 | H | H | SO₂N(CH₃)₂ | H | H | OCH₃ | CH₃ | N |
| Q-4 | H | H | SO₂N(CH₂CH₃)₂ | H | H | OCH₃ | OCH₃ | CH |
| Q-4 | CH₃ | H | Cl | H | H | CH₃ | CH₃ | CH |
| Q-4 | H | CH₃ | Br | H | H | OCH₃ | OCH₃ | N |
| Q-4 | H | Cl | CO₂CH₃ | H | H | CH₃ | OCH₃ | CH |
| Q-5 | H | H | H | H | H | CH₃ | OCH₃ | CH |
| Q-5 | H | H | CH₃ | H | H | CH₃ | CH₃ | N |
| Q-5 | H | H | CH₂CH₂CH₃ | H | H | OCH₃ | OCH₃ | N |
| Q-5 | H | H | F | H | H | OCH₃ | OCH₃ | CH |
| Q-5 | H | H | Cl | H | H | OCH₃ | OCH₃ | CH |
| Q-5 | H | H | Cl | H | H | OCH₃ | CH₃ | N |
| Q-5 | H | H | Br | H | H | CH₃ | OCH₃ | CH |
| Q-5 | H | H | NO₂ | H | H | Cl | OCH₃ | CH |

TABLE XXV-continued

General Formula XXV

| Q- | R | R$_2$ | R$_{14}$ | R$_8$ | R$_6$ | X | Y | Z | m.p. °C. |
|---|---|---|---|---|---|---|---|---|---|
| Q-5 | H | H | SCH$_2$CH$_2$F | H | H | OCH$_3$ | OCH$_3$ | CH | |
| Q-5 | H | H | CH$_2$—CH=CH$_2$ | H | H | OCH$_3$ | OCH$_3$ | CH | |
| Q-5 | H | H | CH$_2$—C≡CH | H | H | CH$_3$ | CH$_3$ | CH | |
| Q-5 | H | H | CO$_2$CH$_3$ | H | H | CH$_3$ | OCH$_3$ | N | |
| Q-5 | H | H | CO$_2$CH$_2$CH=CH$_2$ | H | H | OCH$_3$ | OCH$_3$ | CH | |
| Q-5 | H | H | CO$_2$CH$_2$C≡CH | H | H | CH$_3$ | OCH$_3$ | CH | |
| Q-5 | H | H | CO$_2$CH$_2$CH$_3$ | H | H | CH$_3$ | CH$_3$ | CH | |
| Q-5 | H | H | CO$_2$CH$_2$CH$_2$CH$_3$ | H | H | OCH$_3$ | OCH$_3$ | CH | |
| Q-5 | H | H | SCH$_3$ | H | H | CH$_3$ | CH$_3$ | N | |
| Q-5 | H | H | SOCH$_3$ | H | H | CH$_3$ | CH$_3$ | CH | |
| Q-5 | H | H | SO$_2$CH$_3$ | H | H | OCH$_3$ | OCH$_3$ | CH | |
| Q-5 | H | H | SO$_2$CH$_2$CH$_3$ | H | H | OCH$_3$ | OCH$_3$ | N | |
| Q-5 | H | H | SO$_2$N(CH$_3$)$_2$ | H | H | CH$_3$ | OCH$_3$ | CH | |
| Q-5 | H | H | SO$_2$N(CH$_2$CH$_3$)$_2$ | H | H | OCH$_3$ | OCH$_3$ | CH | |
| Q-5 | CH$_3$ | H | CO$_2$CH$_3$ | H | H | OCH$_3$ | OCH$_3$ | CH | |
| Q-5 | H | H | Br | H | CH$_3$ | OCH$_3$ | OCH$_3$ | CH | |
| Q-5 | H | CH$_3$ | | Cl | H | H | OCH$_3$ | OCH$_3$ | N |
| Q-6 | H | H | H | H | H | CH$_3$ | OCH$_3$ | CH | |
| Q-6 | H | H | CH$_2$CH$_3$ | H | H | OCH$_3$ | OCH$_3$ | CH | |
| Q-6 | H | H | F | H | H | CH$_3$ | CH$_3$ | CH | |
| Q-6 | H | H | Cl | H | H | OCH$_3$ | OCH$_3$ | CH | |
| Q-6 | H | H | Br | H | H | OCH$_3$ | CH$_3$ | CH | |
| Q-6 | H | H | NO$_2$ | H | H | OCH$_3$ | OCH$_3$ | CH | |
| Q-6 | H | H | SCH$_2$F | H | H | CH$_3$ | OCH$_3$ | CH | |
| Q-6 | H | H | SCH$_2$F | H | H | OCH$_3$ | OCH$_3$ | CH | |
| Q-6 | H | H | CH$_2$—CH=CH$_2$ | H | H | Cl | OCH$_3$ | CH | |
| Q-6 | H | H | CH$_2$—C≡CH | H | H | OCH$_3$ | OCH$_3$ | CH | |
| Q-6 | H | H | CO$_2$CH$_3$ | H | H | OCH$_3$ | OCH$_3$ | CH | |
| Q-6 | H | H | CO$_2$CH$_2$CH$_2$Cl | H | H | OCH$_3$ | CH$_3$ | CH | |
| Q-6 | H | H | CO$_2$CH$_3$ | H | H | CH$_3$ | CH$_3$ | N | |
| Q-6 | H | H | CO$_2$CH$_2$CH$_3$ | H | H | OCH$_3$ | OCH$_3$ | CH | |
| Q-6 | H | H | SCH$_3$ | H | H | CH$_3$ | OCH$_3$ | CH | |
| Q-6 | H | H | SOCH$_3$ | H | H | CH$_3$ | CH$_3$ | CH | |
| Q-6 | H | H | SO$_2$CH$_3$ | H | H | OCH$_3$ | OCH$_3$ | CH | |
| Q-6 | H | H | SO$_2$N(CH$_3$)$_2$ | H | H | OCH$_3$ | CH$_3$ | CH | |
| Q-6 | H | H | SO$_2$N(CH$_3$)$_2$ | H | H | OCH$_3$ | CH$_3$ | N | |
| Q-6 | H | H | SO$_2$N(CH$_2$CH$_3$)$_2$ | H | H | OCH$_3$ | OCH$_3$ | CH | |
| Q-6 | CH$_3$ | H | Cl | H | H | CH$_3$ | CH$_3$ | CH | |
| Q-6 | H | CH$_3$ | Br | H | H | OCH$_3$ | OCH$_3$ | N | |
| Q-6 | H | Cl | CO$_2$CH$_3$ | H | H | CH$_3$ | OCH$_3$ | CH | |

| Q- | R | R$_2$ | R$_{14}$ | R$_8$ | R$_6$ | X | Y | Z | m.p. °C. |
|---|---|---|---|---|---|---|---|---|---|
| Q-7 | H | H | H | H | — | CH$_3$ | OCH$_3$ | CH | |
| Q-7 | H | H | CH$_3$ | H | — | CH$_3$ | CH$_3$ | N | |
| Q-7 | H | H | CH$_2$CH$_2$CH$_3$ | H | — | OCH$_3$ | OCH$_3$ | N | |
| Q-7 | H | H | F | H | — | OCH$_3$ | OCH$_3$ | CH | |
| Q-7 | H | H | Cl | H | — | OCH$_3$ | OCH$_3$ | CH | |
| Q-7 | H | H | Cl | H | — | OCH$_3$ | CH$_3$ | N | |
| Q-7 | H | H | Br | H | — | CH$_3$ | OCH$_3$ | CH | |
| Q-7 | H | H | NO$_2$ | H | — | Cl | OCH$_3$ | CH | |
| Q-7 | H | H | SCH$_2$CH$_2$F | H | — | OCH$_3$ | OCH$_3$ | CH | |
| Q-7 | H | H | CH$_2$—CH=CH$_2$ | H | — | OCH$_3$ | CH$_3$ | CH | |
| Q-7 | H | H | CH$_2$—C≡CH | H | — | CH$_3$ | CH$_3$ | CH | |
| Q-7 | H | H | CO$_2$CH$_3$ | H | — | CH$_3$ | OCH$_3$ | N | |
| Q-7 | H | H | CO$_2$CH$_2$CH$_2$OCH$_3$ | H | — | OCH$_3$ | OCH$_3$ | CH | |
| Q-7 | H | H | CO$_2$CH$_3$ | H | — | CH$_3$ | OCH$_3$ | CH | |
| Q-7 | H | H | CO$_2$CH$_2$CH$_3$ | H | — | CH$_3$ | CH$_3$ | CH | |
| Q-7 | H | H | CO$_2$CH$_2$CH$_2$CH$_3$ | H | — | OCH$_3$ | OCH$_3$ | CH | |
| Q-7 | H | H | SCH$_3$ | H | — | CH$_3$ | CH$_3$ | N | |
| Q-7 | H | H | SOCH$_3$ | H | — | CH$_3$ | CH$_3$ | CH | |
| Q-7 | H | H | SO$_2$CH$_3$ | H | — | OCH$_3$ | OCH$_3$ | CH | |
| Q-7 | H | H | SO$_2$CH$_2$CH$_3$ | H | — | OCH$_3$ | | OCH$_3$ | N |
| Q-7 | H | H | SO$_2$N(CH$_3$)$_2$ | H | — | CH$_3$ | OCH$_3$ | CH | |
| Q-7 | H | H | SO$_2$N(CH$_2$CH$_3$)$_2$ | H | — | OCH$_3$ | OCH$_3$ | CH | |
| Q-7 | CH$_3$ | H | CO$_2$CH$_3$ | H | — | OCH$_3$ | OCH$_3$ | CH | |
| Q-7 | H | H | Br | H | — | OCH$_3$ | OCH$_3$ | CH | |
| Q-7 | H | CH$_3$ | Cl | H | — | OCH$_3$ | OCH$_3$ | N | |
| Q-8 | H | H | H | — | H | CH$_3$ | OCH$_3$ | CH | |
| Q-8 | H | H | CH$_2$CH$_3$ | — | H | OCH$_3$ | OCH$_3$ | CH | |
| Q-8 | H | H | F | — | H | CH$_3$ | CH$_3$ | CH | |
| Q-8 | H | H | Cl | — | H | OCH$_3$ | OCH$_3$ | CH | |
| Q-8 | H | H | Br | — | H | OCH$_3$ | CH$_3$ | CH | |
| Q-8 | H | H | NO$_2$ | — | H | OCH$_3$ | OCH$_3$ | CH | |
| Q-8 | H | H | SCH$_2$F | — | H | CH$_3$ | OCH$_3$ | CH | |
| Q-8 | H | H | SCH$_2$F | — | H | OCH$_3$ | OCH$_3$ | CH | |
| Q-8 | H | H | CH$_2$—CH=CH$_2$ | — | H | Cl | OCH$_3$ | CH | |
| Q-8 | H | H | CH$_2$—C≡CH | — | H | OCH$_3$ | OCH$_3$ | CH | |
| Q-8 | H | H | CO$_2$CH$_3$ | — | H | OCH$_3$ | OCH$_3$ | CH | |
| Q-8 | H | H | CO$_2$CH$_2$CH=CH$_2$ | — | H | OCH$_3$ | CH$_3$ | CH | |
| Q-8 | H | H | CO$_2$CH$_3$ | — | H | CH$_3$ | CH$_3$ | N | |
| Q-8 | H | H | CO$_2$CH$_2$CH$_3$ | — | H | OCH$_3$ | OCH$_3$ | CH | |

TABLE XXV-continued

General Formula XXV

| Q | R | R$_2$ | R$_{14}$ | R$_6$ | X | Y | Z | |
|---|---|---|---|---|---|---|---|---|
| Q-8 | H | H | SCH$_3$ | — | H | CH$_3$ | OCH$_3$ | CH |
| Q-8 | H | H | SOCH$_3$ | — | H | CH$_3$ | CH$_3$ | CH |
| Q-8 | H | H | SO$_2$CH$_3$ | — | H | OCH$_3$ | OCH$_3$ | CH |
| Q-8 | H | H | SO$_2$N(CH$_3$)$_2$ | — | H | OCH$_3$ | CH$_3$ | CH |
| Q-8 | H | H | SO$_2$N(CH$_3$)$_2$ | — | H | OCH$_3$ | CH$_3$ | N |
| Q-8 | H | H | SO$_2$N(CH$_2$CH$_3$)$_2$ | — | H | OCH$_3$ | OCH$_3$ | CH |
| Q-8 | CH$_3$ | H | Cl | — | H | CH$_3$ | CH$_3$ | CH |
| Q-8 | H | CH$_3$ | Br | — | H | OCH$_3$ | OCH$_3$ | N |
| Q-8 | H | Cl | CO$_2$CH$_3$ | — | H | CH$_3$ | OCH$_3$ | CH |

| Q | R | R$_2$ | R$_{14}$ | R$_6$ | X | Y | Z | m.p. °C. |
|---|---|---|---|---|---|---|---|---|
| Q-9 | H | H | H | H | CH$_3$ | OCH$_3$ | CH | |
| Q-9 | H | H | CH$_3$ | H | CH$_3$ | CH$_3$ | N | |
| Q-9 | H | H | CH$_2$CH$_2$CH$_3$ | H | OCH$_3$ | OCH$_3$ | N | |
| Q-9 | H | H | F | H | OCH$_3$ | OCH$_3$ | CH | |
| Q-9 | H | H | Cl | H | OCH$_3$ | OCH$_3$ | CH | |
| Q-9 | H | H | Cl | H | OCH$_3$ | CH$_3$ | N | |
| Q-9 | H | H | Br | H | CH$_3$ | OCH$_3$ | CH | |
| Q-9 | H | H | NO$_2$ | H | Cl | OCH$_3$ | CH | |
| O-9 | H | H | SCH$_2$CH$_2$F | H | OCH$_3$ | OCH$_3$ | CH | |
| Q-9 | H | H | CH$_2$—CH=CH$_2$ | H | OCH$_3$ | CH$_3$ | CH | |
| Q-9 | H | H | CH$_2$—C≡CH | H | CH$_3$ | CH$_3$ | CH | |
| Q-9 | H | H | CO$_2$CH$_3$ | H | CH$_3$ | OCH$_3$ | N | |
| Q-9 | H | H | CO$_2$CH$_3$ | H | OCH$_3$ | OCH$_3$ | CH | |
| Q-9 | H | H | CO$_2$CH$_3$ | H | CH$_3$ | OCH$_3$ | CH | |
| Q-9 | H | H | CO$_2$CH$_2$CH$_3$ | H | CH$_3$ | CH$_3$ | CH | |
| Q-9 | H | H | CO$_2$CH$_2$CH$_2$CH$_3$ | H | OCH$_3$ | OCH$_3$ | CH | |
| Q-9 | H | H | SCH$_3$ | H | CH$_3$ | CH$_3$ | N | |
| Q-9 | H | H | SOCH$_3$ | H | CH$_3$ | CH$_3$ | CH | |
| Q-9 | H | H | SO$_2$CH$_3$ | H | OCH$_3$ | OCH$_3$ | CH | |
| Q-9 | H | H | SO$_2$CH$_2$CH$_2$ | H | OCH$_3$ | OCH$_3$ | N | |
| Q-9 | H | H | SO$_2$N(CH$_3$)$_3$ | H | CH$_3$ | OCH$_3$ | CH | |
| Q-9 | H | H | SO$_2$N(CH$_2$CH$_3$)$_2$ | H | OCH$_3$ | OCH$_3$ | CH | |
| Q-9 | CH$_3$ | H | CO$_2$CH$_3$ | H | OCH$_3$ | OCH$_3$ | CH | |
| Q-9 | H | H | Br | H | OCH$_3$ | OCH$_3$ | CH | |
| Q-9 | H | CH$_3$ | Cl | H | OCH$_3$ | OCH$_3$ | N | |
| Q-10 | H | H | H | H | CH$_3$ | OCH$_3$ | CH | |
| Q-10 | H | H | CH$_2$CH$_3$ | H | OCH$_3$ | OCH$_3$ | CH | |
| Q-10 | H | H | F | H | CH$_3$ | CH$_3$ | CH | |
| Q-10 | H | H | Cl | H | OCH$_3$ | OCH$_3$ | CH | |
| Q-10 | H | H | Br | H | OCH$_3$ | CH$_3$ | CH | |
| Q-10 | H | H | NO$_2$ | H | OCH$_3$ | OCH$_3$ | CH | |
| Q-10 | H | H | SCH$_2$F | H | CH$_3$ | OCH$_3$ | CH | |
| Q-10 | H | H | SCH$_2$F | H | OCH$_3$ | OCH$_3$ | CH | |
| Q-10 | H | H | CH$_2$—CH=CH$_2$ | H | Cl | OCH$_3$ | CH | |
| Q-10 | H | H | CH$_2$—C≡CH | H | OCH$_3$ | OCH$_3$ | CH | |
| Q-10 | H | H | CO$_2$CH$_3$ | H | OCH$_3$ | OCH$_3$ | CH | |
| Q-10 | H | H | CO$_2$CH$_3$ | H | OCH$_3$ | CH$_3$ | CH | |
| Q-10 | H | H | CO$_2$CH$_3$ | H | CH$_3$ | CH$_3$ | N | |
| Q-10 | H | H | CO$_2$CH$_2$CH$_3$ | H | OCH$_3$ | OCH$_3$ | CH | |
| Q-10 | H | H | SCH$_3$ | H | CH$_3$ | OCH$_3$ | CH | |
| Q-10 | H | H | SOCH$_3$ | H | CH$_3$ | CH$_3$ | CH | |
| Q-10 | H | H | SO$_2$CH$_3$ | H | OCH$_3$ | OCH$_3$ | CH | |
| Q-10 | H | H | SO$_2$N(CH$_3$)$_2$ | H | OCH$_3$ | CH$_3$ | CH | |
| Q-10 | H | H | SO$_2$N(CH$_3$)$_2$ | H | OCH$_3$ | CH$_3$ | N | |
| Q-10 | H | H | SO$_2$N(CH$_2$CH$_3$)$_2$ | H | OCH$_3$ | OCH$_3$ | CH | |
| Q-10 | CH$_3$ | H | Cl | H | CH$_3$ | CH$_3$ | CH | |
| Q-10 | H | CH$_3$ | Br | H | OCH$_3$ | OCH$_3$ | N | |
| Q-10 | H | Cl | CO$_2$CH$_3$ | H | CH$_3$ | OCH$_3$ | CH | |
| Q-11 | H | H | H | H | CH$_3$ | OCH$_3$ | CH | |
| Q-11 | H | H | CH$_3$ | H | CH$_3$ | CH$_3$ | N | |
| Q-11 | H | H | CH$_2$CH$_2$CH$_3$ | H | OCH$_3$ | OCH$_3$ | N | |
| Q-11 | H | H | F | H | OCH$_3$ | OCH$_3$ | CH | |
| Q-11 | H | H | Cl | H | OCH$_3$ | OCH$_3$ | CH | |
| Q-11 | H | H | Cl | H | OCH$_3$ | CH$_3$ | N | |
| Q-11 | H | H | Br | H | CH$_3$ | OCH$_3$ | CH | |
| Q-11 | H | H | NO$_2$ | H | Cl | OCH$_3$ | CH | |
| Q-11 | H | H | SCH$_2$CH$_2$F | H | OCH$_3$ | OCH$_3$ | CH | |
| Q-11 | H | H | CH$_2$—CH=CH$_2$ | H | OCH$_3$ | CH$_3$ | CH | |
| Q-11 | H | H | CH$_2$—C≡CH | H | CH$_3$ | CH$_3$ | CH | |
| Q-11 | H | H | CO$_2$CH$_3$ | H | CH$_3$ | OCH$_3$ | N | |
| Q-11 | H | H | CO$_2$CH$_3$ | H | OCH$_3$ | OCH$_3$ | CH | |
| Q-11 | H | H | CO$_2$CH$_2$C≡CH | H | CH$_3$ | OCH$_3$ | CH | |
| Q-11 | H | H | CO$_2$CH$_2$CH$_3$ | H | CH$_3$ | CH$_3$ | CH | |
| Q-11 | H | H | CO$_2$CH$_2$CH$_2$CH$_3$ | H | OCH$_3$ | OCH$_3$ | CH | |
| Q-11 | H | H | SCH$_3$ | H | CH$_3$ | CH$_3$ | N | |
| Q-11 | H | H | SOCH$_3$ | H | CH$_3$ | CH$_3$ | CH | |
| Q-11 | H | H | SO$_2$CH$_3$ | H | OCH$_3$ | OCH$_3$ | CH | |
| Q-11 | H | H | SO$_2$CH$_2$CH$_3$ | H | OCH$_3$ | OCH$_3$ | N | |
| Q-11 | H | H | SO$_2$N(CH$_3$)$_2$ | H | CH$_3$ | OCH$_3$ | CH | |
| Q-11 | H | H | SO$_2$N(CH$_2$CH$_3$)$_2$ | H | OCH$_3$ | OCH$_3$ | CH | |

TABLE XXV-continued

General Formula XXV

| Q- | R | R$_2$ | R$_{14}$ | R$_7$ | R$_6$ | X | Y | Z | m.p. °C. |
|---|---|---|---|---|---|---|---|---|---|
| Q-11 | CH$_3$ | H | CO$_2$CH$_3$ | H | OCH$_3$ | OCH$_3$ | CH | | |
| Q-11 | H | H | Br | CH$_3$ | OCH$_3$ | OCH$_3$ | CH | | |
| Q-11 | H | CH$_3$ | Cl | H | OCH$_3$ | OCH$_3$ | N | | |
| Q-12 | H | H | H | H | CH$_3$ | OCH$_3$ | CH | | |
| Q-12 | H | H | CH$_2$CH$_3$ | H | OCH$_3$ | OCH$_3$ | CH | | |
| Q-12 | H | H | F | H | CH$_3$ | CH$_3$ | CH | | |
| Q-12 | H | H | Cl | H | OCH$_3$ | OCH$_3$ | CH | | |
| Q-12 | H | H | Br | H | OCH$_3$ | CH$_3$ | CH | | |
| Q-12 | H | H | NO$_2$ | H | OCH$_3$ | OCH$_3$ | CH | | |
| Q-12 | H | H | SCH$_2$F | H | CH$_3$ | OCH$_3$ | CH | | |
| Q-12 | H | H | SCH$_2$F | H | OCH$_3$ | OCH$_3$ | CH | | |
| Q-12 | H | H | CH$_2$—CH=CH$_2$ | H | Cl | OCH$_3$ | CH | | |
| Q-12 | H | H | CH$_2$—C≡CH | H | OCH$_3$ | OCH$_3$ | CH | | |
| Q-12 | H | H | CO$_2$CH$_3$ | H | OCH$_3$ | OCH$_3$ | CH | | |
| Q-12 | H | H | CO$_2$CH$_3$ | H | OCH$_3$ | CH$_3$ | CH | | |
| Q-12 | H | H | CO$_2$CH$_3$ | H | CH$_3$ | CH$_3$ | N | | |
| Q-12 | H | H | CO$_2$CH$_2$CH$_3$ | H | OCH$_3$ | OCH$_3$ | CH | | |
| Q-12 | H | H | SCH$_3$ | H | CH$_3$ | CH$_3$ | CH | | |
| Q-12 | H | H | SOCH$_3$ | H | CH$_3$ | CH$_3$ | CH | | |
| Q-12 | H | H | SO$_2$CH$_3$ | H | OCH$_3$ | OCH$_3$ | CH | | |
| Q-12 | H | H | SO$_2$N(CH$_3$)$_2$ | H | OCH$_3$ | CH$_3$ | CH | | |
| Q-12 | H | H | SO$_2$N(CH$_3$)$_2$ | H | OCH$_3$ | CH$_3$ | N | | |
| Q-12 | H | H | SO$_2$N(CH$_2$CH$_3$)$_2$ | H | OCH$_3$ | OCH$_3$ | CH | | |
| Q-12 | CH$_3$ | H | Cl | H | CH$_3$ | CH$_3$ | CH | | |
| Q-12 | H | CH$_3$ | Br | H | OCH$_3$ | OCH$_3$ | N | | |
| Q-12 | H | Cl | CO$_2$CH$_3$ | H | CH$_3$ | OCH$_3$ | CH | | |

| Q- | R | R$_2$ | R$_{14}$ | R$_7$ | R$_6$ | X | Y | Z | m.p. °C. |
|---|---|---|---|---|---|---|---|---|---|
| Q-13 | H | H | H | — | H | CH$_3$ | OCH$_3$ | CH | |
| Q-13 | H | H | CH$_3$ | — | H | CH$_3$ | CH$_3$ | N | |
| Q-13 | H | H | CH$_2$CH$_2$CH$_3$ | — | H | OCH$_3$ | OCH$_3$ | N | |
| Q-13 | H | H | F | — | H | OCH$_3$ | OCH$_3$ | CH | |
| Q-13 | H | H | Cl | — | H | OCH$_3$ | OCH$_3$ | CH | |
| Q-13 | H | H | Cl | — | H | OCH$_3$ | CH$_3$ | N | |
| Q-13 | H | H | Br | — | H | CH$_3$ | OCH$_3$ | CH | |
| Q-13 | H | H | NO$_2$ | — | H | Cl | OCH$_3$ | CH | |
| Q-13 | H | H | SCH$_2$CH$_2$F | — | H | OCH$_3$ | OCH$_3$ | CH | |
| Q-13 | H | H | CH$_2$—CH=CH$_2$ | — | H | OCH$_3$ | CH$_3$ | CH | |
| Q-13 | H | H | CH$_2$—C≡CH | — | H | CH$_3$ | CH$_3$ | CH | |
| Q-13 | H | H | CO$_2$CH$_3$ | — | H | CH$_3$ | OCH$_3$ | N | |
| Q-13 | H | H | CO$_2$CH$_3$ | — | H | OCH$_3$ | OCH$_3$ | CH | |
| Q-13 | H | H | CO$_2$CH$_2$CH$_2$Cl | — | H | CH$_3$ | OCH$_3$ | CH | |
| Q-13 | H | H | CO$_2$CH$_2$CH$_3$ | — | H | CH$_3$ | CH$_3$ | CH | |
| Q-13 | H | H | CO$_2$CH$_2$CH$_2$CH$_3$ | — | H | OCH$_3$ | OCH$_3$ | CH | |
| Q-13 | H | H | SCH$_3$ | — | H | CH$_3$ | CH$_3$ | N | |
| Q-13 | H | H | SOCH$_3$ | — | H | CH$_3$ | CH$_3$ | CH | |
| Q-13 | H | H | SO$_2$CH$_3$ | — | H | OCH$_3$ | OCH$_3$ | CH | |
| Q-13 | H | H | SO$_2$CH$_2$CH$_3$ | — | H | OCH$_3$ | OCH$_3$ | N | |
| Q-13 | H | H | SO$_2$N(CH$_3$)$_2$ | — | H | CH$_3$ | OCH$_3$ | CH | |
| Q-13 | H | H | SO$_2$N(CH$_2$CH$_3$)$_2$ | — | H | OCH$_3$ | OCH$_3$ | CH | |
| Q-13 | CH$_3$ | H | CO$_2$CH$_3$ | — | H | OCH$_3$ | OCH$_3$ | CH | |
| Q-13 | H | H | Br | — | CH$_3$ | OCH$_3$ | OCH$_3$ | CH | |
| Q-13 | H | CH$_3$ | Cl | — | H | OCH$_3$ | OCH$_3$ | N | |
| Q-14 | H | H | H | H | H | CH$_3$ | OCH$_3$ | CH | |
| Q-14 | H | H | CH$_2$CH$_3$ | H | H | OCH$_3$ | OCH$_3$ | CH | |
| Q-14 | H | H | F | H | H | CH$_3$ | CH$_3$ | CH | |
| Q-14 | H | H | Cl | H | H | OCH$_3$ | OCH$_3$ | CH | |
| Q-14 | H | H | Br | H | H | OCH$_3$ | CH$_3$ | CH | |
| Q-14 | H | H | NO$_2$ | H | H | OCH$_3$ | OCH$_3$ | CH | |
| Q-14 | H | H | SCH$_2$F | H | H | CH$_3$ | OCH$_3$ | CH | |
| Q-14 | H | H | SCH$_2$F | H | H | OCH$_3$ | OCH$_3$ | CH | |
| Q-14 | H | H | CH$_2$—CH=CH$_2$ | H | H | Cl | OCH$_3$ | CH | |
| Q-14 | H | H | CH$_2$—C≡CH | H | H | OCH$_3$ | OCH$_3$ | CH | |
| Q-14 | H | H | CO$_2$CH$_3$ | H | H | OCH$_3$ | OCH$_3$ | CH | |
| Q-14 | H | H | CO$_2$CH$_3$ | H | H | OCH$_3$ | CH$_3$ | CH | |
| Q-14 | H | H | CO$_2$CH$_2$CH=CH$_2$ | H | H | CH$_3$ | CH$_3$ | N | |
| Q-14 | H | H | CO$_2$CH$_2$CH$_3$ | H | H | OCH$_3$ | OCH$_3$ | CH | |
| Q-14 | H | H | SCH$_3$ | H | H | CH$_3$ | OCH$_3$ | CH | |
| Q-14 | H | H | SOCH$_3$ | H | H | CH$_3$ | CH$_3$ | CH | |
| Q-14 | H | H | SO$_2$CH$_3$ | H | H | OCH$_3$ | OCH$_3$ | CH | |
| Q-14 | H | H | SO$_2$N(CH$_3$)$_2$ | H | H | OCH$_3$ | CH$_3$ | CH | |
| Q-14 | H | H | SO$_2$N(CH$_3$)$_2$ | H | H | OCH$_3$ | CH$_3$ | N | |
| Q-14 | H | H | SO$_2$N(CH$_2$CH$_3$)$_2$ | H | H | OCH$_3$ | OCH$_3$ | CH | |
| Q-14 | CH$_3$ | H | Cl | H | H | CH$_3$ | CH$_3$ | CH | |
| Q-14 | H | CH$_3$ | Br | H | H | OCH$_3$ | OCH$_3$ | N | |
| Q-14 | H | Cl | CO$_2$CH$_3$ | H | H | CH$_3$ | OCH$_3$ | CH | |

| Q | R | R$_2$ | R$_{14}$ | R$_6$ | R$_7$ | X | Y | Z | m.p. °C. |
|---|---|---|---|---|---|---|---|---|---|
| Q-15 | H | H | H | H | H | CH$_3$ | OCH$_3$ | CH | |
| Q-15 | H | H | CH$_3$ | H | H | CH$_3$ | CH$_3$ | N | |
| Q-15 | H | H | CH$_2$CH$_2$CH$_3$ | H | H | OCH$_3$ | OCH$_3$ | N | |

TABLE XXV-continued

General Formula XXV

| | | | | | | | | |
|---|---|---|---|---|---|---|---|---|
| Q-15 | H | H | F | H | H | OCH$_3$ | OCH$_3$ | CH |
| Q-15 | H | H | Cl | H | H | OCH$_3$ | OCH$_3$ | CH |
| Q-15 | H | H | Cl | H | H | OCH$_3$ | CH$_3$ | N |
| Q-15 | H | H | Br | H | H | CH$_3$ | OCH$_3$ | CH |
| Q-15 | H | H | NO$_2$ | H | H | Cl | OCH$_3$ | CH |
| Q-15 | H | H | SCH$_2$CH$_2$F | H | H | OCH$_3$ | OCH$_3$ | CH |
| Q-15 | H | H | CH$_2$—CH=CH$_2$ | H | H | OCH$_3$ | CH$_3$ | CH |
| Q-15 | H | H | CH$_2$—C≡CH | H | H | CH$_3$ | CH$_3$ | CH |
| Q-15 | H | H | CO$_2$CH$_3$ | H | H | CH$_3$ | OCH$_3$ | N |
| Q-15 | H | H | CO$_2$CH$_3$ | H | H | OCH$_3$ | OCH$_3$ | CH |
| Q-15 | H | H | CO$_2$CH$_2$C≡CH | H | H | CH$_3$ | OCH$_3$ | CH |
| Q-15 | H | H | CO$_2$CH$_2$CH$_3$ | H | H | CH$_3$ | CH$_3$ | CH |
| Q-15 | H | H | CO$_2$CH$_2$CH$_2$CH$_3$ | H | H | OCH$_3$ | OCH$_3$ | CH |
| Q-15 | H | H | SCH$_3$ | H | H | CH$_3$ | CH$_3$ | N |
| Q-15 | H | H | SOCH$_3$ | H | H | CH$_3$ | CH$_3$ | CH |
| Q-15 | H | H | SO$_2$CH$_3$ | H | H | OCH$_3$ | OCH$_3$ | CH |
| Q-15 | H | H | SO$_2$CH$_2$CH$_3$ | H | H | OCH$_3$ | OCH$_3$ | N |
| Q-15 | H | H | SO$_2$N(CH$_3$)$_2$ | H | H | CH$_3$ | OCH$_3$ | CH |
| Q-15 | H | H | SO$_2$N(CH$_2$CH$_3$)$_2$ | H | H | OCH$_3$ | OCH$_3$ | CH |
| Q-15 | CH$_3$ | H | CO$_2$CH$_3$ | H | H | OCH$_3$ | OCH$_3$ | CH |
| Q-15 | H | H | Br | H | CH$_3$ | OCH$_3$ | OCH$_3$ | CH |
| Q-15 | H | CH$_3$ | Cl | H | H | OCH$_3$ | OCH$_3$ | N |
| Q-16 | H | H | H | H | H | CH$_3$ | OCH$_3$ | CH |
| Q-16 | H | H | CH$_2$CH$_3$ | H | H | OCH$_3$ | OCH$_3$ | CH |
| Q-16 | H | H | F | H | H | CH$_3$ | CH$_3$ | CH |
| Q-16 | H | H | Cl | H | H | OCH$_3$ | OCH$_3$ | CH |
| Q-16 | H | H | Br | H | H | OCH$_3$ | CH$_3$ | CH |
| Q-16 | H | H | NO$_2$ | H | H | OCH$_3$ | OCH$_3$ | CH |
| Q-16 | H | H | SCH$_2$F | H | H | CH$_3$ | OCH$_3$ | CH |
| Q-16 | H | H | SCH$_2$F | H | H | OCH$_3$ | OCH$_3$ | CH |
| Q-16 | H | H | CH$_2$—CH=CH$_2$ | H | H | Cl | OCH$_3$ | CH |
| Q-16 | H | H | CH$_2$—C≡CH | H | H | OCH$_3$ | OCH$_3$ | CH |
| Q-16 | H | H | CO$_2$CH$_3$ | H | H | OCH$_3$ | OCH$_3$ | CH |
| Q-16 | H | H | CO$_2$CH$_3$ | H | H | OCH$_3$ | CH$_3$ | CH |
| Q-16 | H | H | CO$_2$CH$_2$CH$_2$Cl | H | H | CH$_3$ | CH$_3$ | N |
| Q-16 | H | H | CO$_2$CH$_2$CH$_3$ | H | H | OCH$_3$ | OCH$_3$ | CH |
| Q-16 | H | H | SCH$_3$ | H | H | CH$_3$ | OCH$_3$ | CH |
| Q-16 | H | H | SOCH$_3$ | H | H | CH$_3$ | CH$_3$ | CH |
| Q-16 | H | H | SO$_2$CH$_3$ | H | H | OCH$_3$ | OCH$_3$ | CH |
| Q-16 | H | H | SO$_2$N(CH$_3$)$_2$ | H | H | OCH$_3$ | CH$_3$ | CH |
| Q-16 | H | H | SO$_2$N(CH$_3$)$_2$ | H | H | OCH$_3$ | CH$_3$ | N |
| Q-16 | H | H | SO$_2$N(CH$_2$CH$_3$)$_2$ | H | H | OCH$_3$ | OCH$_3$ | CH |
| Q-16 | CH$_3$ | H | Cl | H | H | CH$_3$ | CH$_3$ | CH |
| Q-16 | H | CH$_3$ | Br | H | H | OCH$_3$ | OCH$_3$ | N |
| Q-16 | H | Cl | CO$_2$CH$_3$ | H | H | CH$_3$ | OCH$_3$ | CH |
| Q-17 | H | H | H | H | H | CH$_3$ | OCH$_3$ | CH |
| Q-17 | H | H | CH$_3$ | H | H | CH$_3$ | CH$_3$ | N |
| Q-17 | H | H | CH$_2$CH$_2$CH$_3$ | H | H | OCH$_3$ | OCH$_3$ | N |
| Q-17 | H | H | F | H | H | OCH$_3$ OCH$_3$ | CH | |
| Q-17 | H | H | Cl | H | H | OCH$_3$ | OCH$_3$ | CH |
| Q-17 | H | H | Cl | H | H | OCH$_3$ | CH$_3$ | N |
| Q-17 | H | H | Br | H | H | CH$_3$ | OCH$_3$ | CH |
| Q-17 | H | H | NO$_2$ | H | H | Cl | OCH$_3$ | CH |
| Q-17 | H | H | SCH$_2$CH$_2$F | H | H | OCH$_3$ | OCH$_3$ | CH |
| Q-17 | H | H | CH$_2$—CH=CH$_2$ | H | H | OCH$_3$ | CH$_3$ | CH |
| Q-17 | H | H | CH$_2$—C≡CH | H | H | CH$_3$ | CH$_3$ | CH |
| Q-17 | H | H | CO$_2$CH$_3$ | H | H | CH$_3$ | OCH$_3$ | N |
| Q-17 | H | H | CO$_2$CH$_3$ | H | H | OCH$_3$ | OCH$_3$ | CH |
| Q-17 | H | H | CO$_2$CH$_3$ | H | H | CH$_3$ | OCH$_3$ | CH |
| Q-17 | H | H | CO$_2$CH$_2$CH$_3$ | H | H | CH$_3$ | CH$_3$ | CH |
| Q-17 | H | H | CO$_2$CH$_2$CH$_2$CH$_3$ | H | H | OCH$_3$ | OCH$_3$ | CH |
| Q-17 | H | H | SCH$_3$ | H | H | CH$_3$ | CH$_3$ | N |
| Q-17 | H | H | SOCH$_3$ | H | H | CH$_3$ | CH$_3$ | CH |
| Q-17 | H | H | SO$_2$CH$_3$ | H | H | OCH$_3$ | OCH$_3$ | CH |
| Q-17 | H | H | SO$_2$CH$_2$CH$_3$ | H | H | OCH$_3$ | OCH$_3$ | N |
| Q-17 | H | H | SO$_2$N(CH$_3$)$_2$ | H | H | CH$_3$ | OCH$_3$ | CH |
| Q-17 | H | H | SO$_2$N(CH$_2$CH$_3$)$_2$ | H | H | OCH$_3$ | OCH$_3$ | CH |
| Q-17 | CH$_3$ | H | CO$_2$CH$_3$ | H | H | OCH$_3$ | OCH$_3$ | CH |
| Q-17 | H | H | Br | H | CH$_3$ | OCH$_3$ | OCH$_3$ | CH |
| Q-17 | H | CH$_3$ | Cl | H | H | OCH$_3$ | OCH$_3$ | N |
| Q-18 | H | H | H | H | H | CH$_3$ | OCH$_3$ | CH |
| Q-18 | H | H | CH$_2$CH$_3$ | H | H | OCH$_3$ | OCH$_3$ | CH |
| Q-18 | H | H | F | H | H | CH$_3$ | CH$_3$ | CH |
| Q-18 | H | H | Cl | H | H | OCH$_3$ | OCH$_3$ | CH |
| Q-18 | H | H | Br | H | H | OCH$_3$ | CH$_3$ | CH |
| Q-18 | H | H | NO$_2$ | H | H | OCH$_3$ | OCH$_3$ | CH |
| Q-18 | H | H | SCH$_2$F | H | H | CH$_3$ | OCH$_3$ | CH |
| Q-18 | H | H | SCH$_2$F | H | H | OCH$_3$ | OCH$_3$ | CH |
| Q-18 | H | H | CH$_2$—CH=CH$_2$ | H | H | Cl | OCH$_3$ | CH |
| Q-18 | H | H | CH$_2$—C≡CH | H | H | OCH$_3$ | OCH$_3$ | CH |

TABLE XXV-continued

General Formula XXV

| Q | R | R$_2$ | R$_{14}$ | R$_6$ | R$_7$ | X | Y | Z |
|---|---|---|---|---|---|---|---|---|
| Q-18 | H | H | CO$_2$CH$_3$ | H | H | OCH$_3$ | OCH$_3$ | CH |
| Q-18 | H | H | CO$_2$CH$_3$ | H | H | OCH$_3$ | CH$_3$ | CH |
| Q-18 | H | H | CO$_2$CH$_2$CH$_2$OCH$_3$ | H | CH$_3$ | CH$_3$ | | |
| Q-18 | H | H | CO$_2$CH$_2$CH$_2$H | H | H | OCH$_3$ | OCH$_3$ | CH |
| Q-18 | H | H | SCH$_3$ | H | H | CH$_3$ | OCH$_3$ | CH |
| Q-18 | H | H | SOCH$_3$ | H | H | CH$_3$ | CH$_3$ | CH |
| Q-18 | H | H | SO$_2$CH$_3$ | H | H | OCH$_3$ | OCH$_3$ | CH |
| Q-18 | H | H | SO$_2$N(CH$_3$)$_2$ | H | H | OCH$_3$ | CH$_3$ | CH |
| Q-18 | H | H | SO$_2$N(CH$_3$)$_2$ | H | H | OCH$_3$ | CH$_3$ | N |
| Q-18 | H | H | SO$_2$N(CH$_2$CH$_3$)$_2$ | H | H | OCH$_3$ | OCH$_3$ | CH |
| Q-18 | CH$_3$ | H | Cl | H | H | CH$_3$ | CH$_3$ | CH |
| Q-18 | H | CH$_3$ | Br | H | H | OCH$_3$ | OCH$_3$ | N |
| Q-18 | H | Cl | CO$_2$CH$_3$ | H | H | CH$_3$ | OCH$_3$ | CH |
| Q-19 | H | H | H | H | H | CH$_3$ | OCH$_3$ | CH |
| Q-19 | H | H | CH$_3$ | H | H | CH$_3$ | CH$_3$ | N |
| Q-19 | H | H | CH$_2$CH$_2$CH$_3$ | H | H | OCH$_3$ | OCH$_3$ | N |
| Q-19 | H | H | F | H | H | OCH$_3$ | OCH$_3$ | CH |
| Q-19 | H | H | Cl | H | H | OCH$_3$ | OCH$_3$ | CH |
| Q-19 | H | H | Cl | H | H | OCH$_3$ | CH$_3$ | N |
| Q-19 | H | H | Br | H | H | CH$_3$ | OCH$_3$ | CH |
| Q-19 | H | H | NO$_2$ | H | H | Cl | OCH$_3$ | CH |
| Q-19 | H | H | SCH$_2$CH$_2$F | H | H | OCH$_3$ | OCH$_3$ | CH |
| Q-19 | H | H | CH$_2$—CH=CH$_2$ | H | H | OCH$_3$ | CH$_3$ | CH |
| Q-19 | H | H | CH$_2$—C≡CH | H | H | CH$_3$ | CH$_3$ | CH |
| Q-19 | H | H | CO$_2$CH$_3$ | H | H | CH$_3$ | OCH$_3$ | N |
| Q-19 | H | H | CO$_2$CH$_3$ | H | H | OCH$_3$ | OCH$_3$ | CH |
| Q-19 | H | H | CO$_2$CH$_3$ | H | H | CH$_3$ | OCH$_3$ | CH |
| Q-19 | H | H | CO$_2$CH$_2$CH$_3$ | H | H | CH$_3$ | CH$_3$ | CH |
| Q-19 | H | H | CO$_2$CH$_2$CH$_2$CH$_3$ | H | H | OCH$_3$ | OCH$_3$ | CH |
| Q-19 | H | H | SCH$_3$ | H | H | CH$_3$ | CH$_3$ | N |
| Q-19 | H | H | SOCH$_3$ | H | H | CH$_3$ | CH$_3$ | CH |
| Q-19 | H | H | SO$_2$CH$_3$ | H | H | OCH$_3$ | OCH$_3$ | CH |
| Q-19 | H | H | SO$_2$CH$_2$CH$_3$ | H | H | OCH$_3$ | OCH$_3$ | N |
| Q-19 | H | H | SO$_2$N(CH$_3$)$_2$ | H | H | CH$_3$ | OCH$_3$ | CH |
| Q-19 | H | H | SO$_2$N(CH$_2$CH$_3$)$_2$ | H | H | OCH$_3$ | OCH$_3$ | CH |
| Q-19 | CH$_3$ | H | CO$_2$CH$_3$ | H | H | OCH$_3$ | OCH$_3$ | CH |
| Q-19 | H | H | Br | H | CH$_3$ | OCH$_3$ | OCH$_3$ | CH |
| Q-19 | H | CH$_3$ | Cl | H | H | OCH$_3$ | OCH$_3$ | N |
| Q-20 | H | H | H | H | H | CH$_3$ | OCH$_3$ | CH |
| Q-20 | H | H | CH$_2$CH$_3$ | H | H | OCH$_3$ | OCH$_3$ | CH |
| Q-20 | H | H | F | H | H | CH$_3$ | CH$_3$ | CH |
| Q-20 | H | H | Cl | H | H | OCH$_3$ | OCH$_3$ | CH |
| Q-20 | H | H | Br | H | H | OCH$_3$ | CH$_3$ | CH |
| Q-20 | H | H | NO$_2$ | H | H | OCH$_3$ | OCH$_3$ | CH |
| Q-20 | H | H | SCH$_2$F | H | H | CH$_3$ | OCH$_3$ | CH |
| Q-20 | H | H | SCH$_2$F | H | H | OCH$_3$ | OCH$_3$ | CH |
| Q-20 | H | H | CH$_2$—CH=CH$_2$ | H | H | Cl | OCH$_3$ | CH |
| Q-20 | H | H | CH$_2$—C≡CH | H | H | OCH$_3$ | OCH$_3$ | CH |
| Q-20 | H | H | CO$_2$CH$_3$ | H | H | OCH$_3$ | OCH$_3$ | CH |
| Q-20 | H | H | CO$_2$CH$_3$ | H | H | OCH$_3$ | CH$_3$ | CH |
| Q-20 | H | H | CO$_2$CH$_2$CH=CH$_2$ | H | H | CH$_3$ | CH$_3$ | N |
| Q-20 | H | H | CO$_2$CH$_2$CH$_3$ | H | H | OCH$_3$ | OCH$_3$ | CH |
| Q-20 | H | H | SCH$_3$ | H | H | CH$_3$ | OCH$_3$ | CH |
| Q-20 | H | H | SOCH$_3$ | H | H | CH$_3$ | CH$_3$ | CH |
| Q-20 | H | H | SO$_2$CH$_3$ | H | H | OCH$_3$ | OCH$_3$ | CH |
| Q-20 | H | H | SO$_2$N(CH$_3$)$_2$ | H | H | OCH$_3$ | CH$_3$ | CH |
| Q-20 | H | H | SO$_2$N(CH$_3$)$_2$ | H | H | OCH$_3$ | CH$_3$ | N |
| Q-20 | H | H | SO$_2$N(CH$_2$CH$_3$)$_2$ | H | H | OCH$_3$ | OCH$_3$ | CH |
| Q-20 | CH$_3$ | H | Cl | H | H | CH$_3$ | CH$_3$ | CH |
| Q-20 | H | CH$_3$ | Br | H | H | OCH$_3$ | CH$_3$ | N |
| Q-20 | H | Cl | CO$_2$CH$_3$ | H | H | CH$_3$ | OCH$_3$ | CH |

| Q | R | R$_2$ | R$_{14}$ | R$_6$ | R$_7$ | X | Y | Z | R$_9$ | m.p. °C. |
|---|---|---|---|---|---|---|---|---|---|---|
| 0-21 | H | H | H | H | H | CH$_3$ | OCH$_3$ | CH | H | |
| Q-21 | H | H | CH$_3$ | H | H | CH$_3$ | CH$_3$ | N | H | |
| Q-21 | H | H | CH$_2$CH$_2$CH$_3$ | H | H | OCH$_3$ | OCH$_3$ | H | | |
| Q-21 | H | H | F | H | H | OCH$_3$ | ·OCH$_3$ | CH | H | |
| Q-21 | H | H | Cl | H | H | OCH$_3$ | OCH$_3$ | CH | H | |
| Q-21 | H | H | Cl | H | H | OCH$_3$ | CH$_3$ | N | H | |
| Q-21 | H | H | Br | H | H | CH$_3$ | OCH$_3$ | CH | H | |
| Q-21 | H | H | NO$_2$ | H | H | Cl | OCH$_3$ | CH | H | |
| Q-21 | H | H | SCH$_2$CH$_2$F | H | H | OCH$_3$ | OCH$_3$ | CH | H | |
| Q-21 | H | H | CH$_2$—CH=CH$_2$ | H | H | OCH$_3$ | CH$_3$ | CH | H | |
| Q-21 | H | H | CH$_2$—C≡CH | H | H | CH$_3$ | CH$_3$ | CH | H | |
| Q-21 | H | H | CO$_2$CH$_3$ | H | H | CH$_3$ | OCH$_3$ | N | H | |
| Q-21 | H | H | CO$_2$CH$_3$ | H | H | OCH$_3$ | OCH$_3$ | CH | H | |
| Q-21 | H | H | CO$_2$CH$_3$ | H | H | CH$_3$ | OCH$_3$ | CH | H | |
| Q-21 | H | H | CO$_2$CH$_2$CH$_3$ | H | H | CH$_3$ | CH$_3$ | CH | H | |
| Q-21 | H | H | CO$_2$CH$_2$CH$_2$CH$_3$ | H | H | OCH$_3$ | OCH$_3$ | CH | H | |
| Q-21 | H | H | SCH$_3$ | H | H | CH$_3$ | CH$_3$ | N | H | |

TABLE XXV-continued

General Formula XXV

| | | | | | | | | |
|---|---|---|---|---|---|---|---|---|
| Q-21 | H | H | SOCH$_3$ | H | H | CH$_3$ | CH$_3$ | CH | H |
| Q-21 | H | H | SO$_2$CH$_3$ | H | H | OCH$_3$ | OCH$_3$ | CH | H |
| Q-21 | H | H | SO$_2$CH$_2$CH$_3$ | H | H | OCH$_3$ | OCH$_3$ | N | H |
| Q-21 | H | H | SO$_2$N(CH$_3$)$_2$ | H | H | CH$_3$ | OCH$_3$ | CH | H |
| Q-21 | H | H | SO$_2$N(CH$_2$CH$_3$)$_2$ | H | H | OCH$_3$ | OCH$_3$ | CH | H |
| Q-21 | CH$_3$ | H | CO$_2$CH$_3$ | H | H | OCH$_3$ | OCH$_3$ | CH | H |
| Q-21 | H | H | Br | H | CH$_3$ | OCH$_3$ | OCH$_3$ | CH | H |
| Q-21 | H | CH$_3$ | Cl | H | H | OCH$_3$ | OCH$_3$ | N | H |
| Q-22 | H | H | H | H | H | CH$_3$ | OCH$_3$ | CH | H |
| Q-22 | H | H | CH$_2$CH$_3$ | H | H | OCH$_3$ | OCH$_3$ | CH | H |
| Q-22 | H | H | F | H | H | CH$_3$ | CH$_3$ | CH | H |
| Q-22 | H | H | Cl | H | H | OCH$_3$ | OCH$_3$ | CH | H |
| Q-22 | H | H | Br | H | H | OCH$_3$ | CH$_3$ | CH | H |
| Q-22 | H | H | NO$_2$ | H | H | OCH$_3$ | OCH$_3$ | CH | H |
| Q-22 | H | H | SCH$_2$F | H | H | CH$_3$ | OCH$_3$ | CH | H |
| Q-22 | H | H | SCH$_2$F | H | H | OCH$_3$ | OCH$_3$ | CH | H |
| Q-22 | H | H | CH$_2$—CH=CH$_2$ | H | H | Cl | OCH$_3$ | CH | H |
| Q-22 | H | H | CH$_2$—C≡CH | H | H | OCH$_3$ | OCH$_3$ | CH | H |
| Q-22 | H | H | CO$_2$CH$_3$ | H | H | OCH$_3$ | OCH$_3$ | CH | H |
| Q-22 | H | H | CO$_2$CH$_3$ | H | H | OCH$_3$ | CH$_3$ | CH | H |
| Q-22 | H | H | CO$_2$CH$_2$C≡CH | H | H | CH$_3$ | CH$_3$ | N | H |
| Q-22 | H | H | CO$_2$CH$_2$CH$_3$ | H | H | OCH$_3$ | OCH$_3$ | CH | H |
| Q-22 | H | H | SCH$_3$ | H | H | CH$_3$ | OCH$_3$ | CH | H |
| Q-22 | H | H | SOCH$_3$ | H | H | CH$_3$ | CH$_3$ | CH | H |
| Q-22 | H | H | SO$_2$CH$_3$ | H | H | OCH$_3$ | OCH$_3$ | CH | H |
| Q-22 | H | H | SO$_2$N(CH$_3$)$_2$ | H | OCH$_3$ | CH$_3$ | CH | H | |
| Q-22 | H | H | SO$_2$N(CH$_3$)$_2$ | H | H | OCH$_3$ | CH$_3$ | N | H |
| Q-22 | H | H | SO$_2$N(CH$_2$CH$_3$)$_2$ | H | H | OCH$_3$ | OCH$_3$ | CH | H |
| Q-22 | CH$_3$ | H | Cl | H | H | CH$_3$ | CH$_3$ | CH | H |
| Q-22 | H | CH$_3$ | Br | H | H | OCH$_3$ | OCH$_3$ | N | H |
| Q-22 | H | Cl | CO$_2$CH$_3$ | H | H | CH$_3$ | OCH$_3$ | CH | H |
| Q-23 | H | H | H | H | H | CH$_3$ | OCH$_3$ | CH | H |
| Q-23 | H | H | CH$_3$ | H | H | CH$_3$ | CH$_3$ | N | H |
| Q-23 | H | H | CH$_2$CH$_2$CH$_3$ | H | H | OCH$_3$ | OCH$_3$ | N | H |
| Q-23 | H | H | F | H | H | OCH$_3$ | OCH$_3$ | CH | H |
| Q-23 | H | H | Cl | H | H | OCH$_3$ | OCH$_3$ | CH | H |
| Q-23 | H | H | Cl | H | H | OCH$_3$ | CH$_3$ | N | H |
| Q-23 | H | H | Br | H | H | CH$_3$ | OCH$_3$ | CH | H |
| Q-23 | H | H | NO$_2$ | H | H | Cl | OCH$_3$ | CH | H |
| Q-23 | H | H | SCH$_2$CH$_2$F | H | H | OCH$_3$ | OCH$_3$ | CH | H |
| Q-23 | H | H | CH$_2$—CH=CH$_2$ | H | H | OCH$_3$ | CH$_3$ | CH | H |
| Q-23 | H | H | CH$_2$—C≡CH | H | H | CH$_3$ | CH$_3$ | CH | H |
| Q-23 | H | H | CO$_2$CH$_3$ | H | H | CH$_3$ | OCH$_3$ | N | H |
| Q-23 | H | H | CO$_2$CH$_3$ | H | H | OCH$_3$ | OCH$_3$ | CH | H |
| Q-23 | H | H | CO$_2$CH$_2$CH$_2$Cl | H | H | CH$_3$ | OCH$_3$ | CH | H |
| Q-23 | H | H | CO$_2$CH$_2$CH$_3$ | H | H | CH$_3$ | CH$_3$ | CH | H |
| Q-23 | H | H | CO$_2$CH$_2$CH$_2$CH$_3$ | H | H | OCH$_3$ | OCH$_3$ | CH | H |
| Q-23 | H | H | SCH$_3$ | H | H | CH$_3$ | CH$_3$ | N | H |
| Q-23 | H | H | SOCH$_3$ | H | H | CH$_3$ | CH$_3$ | CH | H |
| Q-23 | H | H | SO$_2$CH$_3$ | H | H | OCH$_3$ | OCH$_3$ | CH | H |
| Q-23 | H | H | SO$_2$CH$_2$CH$_3$ | H | H | OCH$_3$ | OCH$_3$ | N | H |
| Q-23 | H | H | SO$_2$N(CH$_3$)$_2$ | H | H | CH$_3$ | OCH$_3$ | CH | H |
| Q-23 | H | H | SO$_2$N(CH$_2$CH$_3$)$_2$ | H | H | OCH$_3$ | OCH$_3$ | CH | H |
| Q-23 | CH$_3$ | H | CO$_2$CH$_3$ | H | H | OCH$_3$ | OCH$_3$ | CH | H |
| Q-23 | H | H | Br | H | CH$_3$ | OCH$_3$ | OCH$_3$ | CH | H |
| Q-23 | H | CH$_3$ | Cl | H | H | OCH$_3$ | OCH$_3$ | N | H |
| Q-24 | H | H | H | H | H | CH$_3$ | OCH$_3$ | CH | H |
| Q-24 | H | H | CH$_2$CH$_3$ | H | H | OCH$_3$ | OCH$_3$ | CH | H |
| Q-24 | H | H | F | H | H | CH$_3$ | CH$_3$ | CH | H |
| Q-24 | H | H | Cl | H | H | OCH$_3$ | OCH$_3$ | CH | H |
| Q-24 | H | H | Br | H | H | OCH$_3$ | CH$_3$ | CH | H |
| Q-24 | H | H | NO$_2$ | H | H | OCH$_3$ | OCH$_3$ | CH | H |
| Q-24 | H | H | SCH$_2$F | H | H | CH$_3$ | OCH$_3$ | CH | H |
| Q-24 | H | H | SCH$_2$F | H | H | OCH$_3$ | OCH$_3$ | CH | H |
| Q-24 | H | H | CH$_2$—CH=CH$_2$ | H | H | Cl | OCH$_3$ | CH | H |
| Q-24 | H | H | CH$_2$—C≡CH | H | H | OCH$_3$ | OCH$_3$ | CH | H |
| Q-24 | H | H | CO$_2$CH$_3$ | H | H | OCH$_3$ | OCH$_3$ | CH | H |
| Q-24 | H | H | CO$_2$CH$_3$ | H | H | OCH$_3$ | CH$_3$ | CH | H |
| Q-24 | H | H | CO$_2$CH$_3$ | H | H | CH$_3$ | CH$_3$ | N | H |
| Q-24 | H | H | CO$_2$CH$_2$CH$_3$ | H | H | OCH$_3$ | OCH$_3$ | CH | H |
| Q-24 | H | H | SCH$_3$ | H | H | CH$_3$ | OCH$_3$ | CH | H |
| Q-24 | H | H | SOCH$_3$ | H | H | CH$_3$ | CH$_3$ | CH | H |
| Q-24 | H | H | SO$_2$CH$_3$ | H | H | OCH$_3$ | OCH$_3$ | CH | H |
| Q-24 | H | H | SO$_2$N(CH$_3$)$_2$ | H | H | OCH$_3$ | CH$_3$ | CH | H |
| Q-24 | H | H | SO$_2$N(CH$_3$)$_2$ | H | H | OCH$_3$ | CH$_3$ | N | H |
| Q-24 | H | H | SO$_2$N(CH$_2$CH$_2$)$_2$ | H | H | OCH$_3$ | OCH$_3$ | CH | H |
| Q-24 | CH$_3$ | H | Cl | H | H | CH$_3$ | CH$_3$ | CH | H |
| Q-24 | H | CH$_3$ | Br | H | H | OCH$_3$ | OCH$_3$ | N | H |
| Q-24 | H | Cl | CO$_2$CH$_3$ | H | H | CH$_3$ | OCH$_3$ | CH | H |
| Q-25 | H | H | H | H | H | CH$_3$ | OCH$_3$ | CH | H |
| Q-25 | H | H | CH$_3$ | H | H | CH$_3$ | CH$_3$ | N | H |

TABLE XXV-continued

General Formula XXV

| | | | | | | | | |
|---|---|---|---|---|---|---|---|---|
| Q-25 | H | H | CH₂CH₂CH₃ | H | H | OCH₃ | OCH₃ | N | H |
| Q-25 | H | H | F | H | H | OCH₃ | OCH₃ | CH | H |
| Q-25 | H | H | Cl | H | H | OCH₃ | OCH₃ | CH | H |
| Q-25 | H | H | Cl | H | H | OCH₃ | CH₃ | N | H |
| Q-25 | H | H | Br | H | H | CH₃ | OCH₃ | CH | H |
| Q-25 | H | H | NO₂ | H | H | Cl | OCH₃ | CH | H |
| Q-25 | H | H | SCH₂CH₂F | H | H | OCH₃ | OCH₃ | CH | H |
| Q-25 | H | H | CH₂—CH=CH₂ | H | H | OCH₃ | CH₃ | CH | H |
| Q-25 | H | H | CH₂—C≡CH | H | H | CH₃ | CH₃ | CH | H |
| Q-25 | H | H | CO₂CH₃ | H | H | CH₃ | OCH₃ | N | H |
| Q-25 | H | H | CO₂CH₃ | H | H | OCH₃ | OCH₃ | CH | H |
| Q-25 | H | H | CO₂CH₃ | H | H | CH₃ | OCH₃ | CH | H |
| Q-25 | H | H | CO₂CH₂CH₃ | H | H | CH₃ | CH₃ | CH | H |
| Q-25 | H | H | CO₂CH₂CH₂CH₃ | H | H | OCH₃ | OCH₃ | CH | H |
| Q-25 | H | H | SCH₃ | H | H | CH₃ | CH₃ | N | H |
| Q-25 | H | H | SOCH₃ | H | H | CH₃ | CH₃ | CH | H |
| Q-25 | H | H | SO₂CH₃ | H | H | OCH₃ | OCH₃ | CH | H |
| Q-25 | H | H | SO₂CH₂CH₃ | H | H | OCH₃ | OCH₃ | N | H |
| Q-25 | H | H | SO₂N(CH₃)₂ | H | H | CH₃ | OCH₃ | CH | H |
| Q-25 | H | H | SO₂N(CH₂CH₃)₂ | H | H | OCH₃ | OCH₃ | CH | H |
| Q-25 | CH₃ | H | CO₂CH₃ | H | H | OCH₃ | OCH₃ | CH | H |
| Q-25 | H | H | Br | H | CH₃ | OCH₃ | OCH₃ | CH | H |
| Q-25 | H | CH₃ | Cl | H | H | OCH₃ | OCH₃ | N | H |
| Q-26 | H | H | H | H | H | CH₃ | OCH₃ | CH | H |
| Q-26 | H | H | CH₂CH₃ | H | H | OCH₃ | OCH₃ | CH | H |
| Q-26 | H | H | F | H | H | CH₃ | CH₃ | CH | H |
| Q-26 | H | H | Cl | H | H | OCH₃ | OCH₃ | CH | H |
| Q-26 | H | H | Br | H | H | OCH₃ | CH₃ | CH | H |
| Q-26 | H | H | NO₂ | H | H | OCH₃ | OCH₃ | CH | H |
| Q-26 | H | H | SCH₂F | H | H | CH | OCH₃ | CH | H |
| Q-26 | H | H | SCH₂F | H | H | OCH₃ | OCH₃ | CH | H |
| Q-26 | H | H | CH₂—CH=CH₂ | H | H | Cl | OCH₃ | CH | H |
| Q-26 | H | H | CH₂—C≡CH | H | H | OCH₃ | OCH₃ | CH | H |
| Q-26 | H | H | CO₂CH₃ | H | H | OCH₃ | OCH₃ | CH | H |
| Q-26 | H | H | CO₂CH₃ | H | H | OCH₃ | CH₃ | CH | H |
| Q-26 | H | H | CO₂CH₂CH=CH₂ | H | H | CH₃ | CH₃ | N | H |
| Q-26 | H | H | CO₂CH₂CH₃ | H | H | OCH₃ | OCH₃ | CH | H |
| Q-26 | H | H | SCH₃ | H | H | CH₃ | OCH₃ | CH | H |
| Q-26 | H | H | SOCH₃ | H | H | CH₃ | CH₃ | CH | H |
| Q-26 | H | H | SO₂CH₃ | H | H | OCH₃ | OCH₃ | CH | H |
| Q-26 | H | H | SO₂N(CH₃)₂ | H | H | OCH₃ | CH₃ | CH | H |
| Q-26 | H | H | SO₂N(CH₃)₂ | H | H | OCH₃ | CH₃ | N | H |
| Q-26 | H | H | SO₂N(CH₂CH₃)₂ | H | H | OCH₃ | OCH₃ | CH | H |
| Q-26 | CH₃ | H | Cl | H | H | CH₃ | CH₃ | CH | H |
| Q-26 | H | CH₃ | Br | H | H | OCH₃ | OCH₃ | N | H |
| Q-26 | H | Cl | CO₂CH₃ | H | H | CH₃ | OCH₃ | CH | H |
| Q-27 | H | H | H | H | H | CH₃ | OCH₃ | CH | H |
| Q-27 | H | H | CH₃ | H | H | CH₃ | CH₃ | N | H |
| Q-27 | H | H | CH₂CH₂CH₃ | H | H | OCH₃ | OCH₃ | N | H |
| Q-27 | H | H | F | H | H | OCH₃ | OCH₃ | CH | H |
| Q-27 | H | H | Cl | H | H | OCH₃ | OCH₃ | CH | H |
| Q-27 | H | H | Cl | H | H | OCH₃ | CH₃ | N | H |
| Q-27 | H | H | Br | H | H | CH₃ | OCH₃ | CH | H |
| Q-27 | H | H | NO₂ | H | H | Cl | OCH₃ | CH | H |
| Q-27 | H | H | SCH₂CH₂F | H | H | OCH₃ | OCH₃ | CH | H |
| Q-27 | H | H | CH₂—CH=CH₂ | H | H | OCH₃ | CH₃ | CH | H |
| Q-27 | H | H | CH₂—C≡CH | H | H | CH₃ | CH₃ | CH | H |
| Q-27 | H | H | CO₂CH₃ | H | H | CH₃ | OCH₃ | N | H |
| Q-27 | H | H | CO₂CH₃ | H | H | OCH₃ | OCH₃ | CH | H |
| Q-27 | H | H | CO₂CH₂C≡CH | H | H | CH₃ | OCH₃ | CH | H |
| Q-27 | H | H | CO₂CH₂CH₃ | H | H | CH₃ | CH₃ | CH | H |
| Q-27 | H | H | CO₂CH₂CH₂CH₃ | H | H | OCH₃ | OCH₃ | CH | H |
| Q-27 | H | H | SCH₃ | H | H | CH₃ | CH₃ | N | H |
| Q-27 | H | H | SOCH₃ | H | H | CH₃ | CH₃ | CH | H |
| Q-27 | H | H | SO₂CH₃ | H | H | OCH₃ | OCH₃ | CH | H |
| Q-27 | H | H | SO₂CH₂CH₃ | H | H | OCH₃ | OCH₃ | N | H |
| Q-27 | H | H | SO₂N(CH₃)₂ | H | H | CH₃ | OCH₃ | CH | H |
| Q-27 | H | H | SO₂N(CH₂CH₃)₂ | H | H | OCH₃ | OCH₃ | CH | H |
| Q-27 | CH₃ | H | CO₂CH₃ | H | H | OCH₃ | OCH₃ | CH | H |
| Q-27 | H | H | Br | H | CH₃ | OCH₃ | OCH₃ | CH | H |
| Q-27 | H | CH₃ | Cl | H | H | OCH₃ | OCH₃ | N | H |
| Q-28 | H | H | H | H | H | CH₃ | OCH₃ | CH | H |
| Q-28 | H | H | CH₂CH₃ | H | H | OCH₃ | OCH₃ | CH | H |
| Q-28 | H | H | F | H | H | CH₃ | CH₃ | CH | H |
| Q-28 | H | H | Cl | H | H | OCH₃ | OCH₃ | CH | H |
| Q-28 | H | H | Br | H | H | OCH₃ | CH₃ | CH | H |
| Q-28 | H | H | NO₂ | H | H | OCH₃ | OCH₃ | CH | H |
| Q-28 | H | H | SCH₂F | H | H | CH₃ | OCH₃ | CH | H |
| Q-28 | H | H | SCH₂F | H | H | OCH₃ | OCH₃ | CH | H |
| Q-28 | H | H | CH₂—CH=CH₂ | H | H | Cl | OCH₃ | CH | H |
| Q-28 | H | H | CH₂—C≡CH | H | H | OCH₃ | OCH₃ | CH | H |

TABLE XXV-continued

General Formula XXV

| Q | R | R$_2$ | R$_{14}$ | R$_6$ | R$_7$ | X | Y | X | |
|---|---|---|---|---|---|---|---|---|---|
| Q-28 | H | H | CO$_2$CH$_3$ | H | H | OCH$_3$ | OCH$_3$ | CH | H |
| Q-28 | H | H | CO$_2$CH$_3$ | H | H | OCH$_3$ | CH$_3$ | CH | H |
| Q-28 | H | H | CO$_2$CH$_2$CH$_2$Cl | H | H | CH$_3$ | CH$_3$ | H | |
| Q-28 | H | H | CO$_2$CH$_2$CH$_3$ | H | H | OCH$_3$ | OCH$_3$ | CH | H |
| Q-28 | H | H | SCH$_3$ | H | H | CH$_3$ | OCH$_3$ | CH | H |
| Q-28 | H | H | SOCH$_3$ | H | H | CH$_3$ | CH$_3$ | CH | H |
| Q-28 | H | H | SO$_2$CH$_3$ | H | H | OCH$_3$ | OCH$_3$ | CH | H |
| Q-28 | H | H | SO$_2$N(CH$_3$)$_2$ | H | H | OCH$_3$ | CH$_3$ | CH | H |
| Q-28 | H | H | SO$_2$N(CH$_3$)$_2$ | H | H | OCH$_3$ | CH$_3$ | N | H |
| Q-28 | H | H | SO$_2$N(CH$_2$CH$_3$)$_2$ | H | H | OCH$_3$ | OCH$_3$ | CH | H |
| Q-28 | CH$_3$ | H | Cl | H | H | CH$_3$ | CH$_3$ | CH | H |
| Q-28 | H | CH$_3$ | Br | H | H | OCH$_3$ | OCH$_3$ | N | H |
| Q-28 | H | Cl | CO$_2$CH$_3$ | H | H | CH$_3$ | OCH$_3$ | CH | H |
| Q-29 | H | H | H | H | H | CH$_3$ | OCH$_3$ | CH | H |
| Q-29 | H | H | CH$_3$ | H | H | CH$_3$ | CH$_3$ | N | H |
| Q-29 | H | H | CH$_2$CH$_2$CH$_3$ | H | H | OCH$_3$ | OCH$_3$ | N | H |
| Q-29 | H | H | F | H | H | OCH$_3$ | OCH$_3$ | CH | H |
| Q-29 | H | H | Cl | H | H | OCH$_3$ | OCH$_3$ | CH | H |
| Q-29 | H | H | Cl | H | H | OCH$_3$ | CH$_3$ | N | H |
| Q-29 | H | H | Br | H | H | CH$_3$ | OCH$_3$ | CH | H |
| Q-29 | H | H | NO$_2$ | H | H | Cl | OCH$_3$ | CH | H |
| Q-29 | H | H | SCH$_2$CH$_2$F | H | H | OCH$_3$ | OCH$_3$ | CH | H |
| Q-29 | H | H | CH$_2$—CH=CH$_2$ | H | H | OCH$_3$ | CH$_3$ | CH | H |
| Q-29 | H | H | CH$_2$—C≡CH | H | H | CH$_3$ | CH$_3$ | CH | H |
| Q-29 | H | H | CO$_2$CH$_3$ | H | H | CH$_3$ | OCH$_3$ | N | H |
| Q-29 | H | H | CO$_2$CH$_3$ | H | H | OCH$_3$ | OCH$_3$ | CH | H |
| Q-29 | H | H | CO$_2$CH$_3$ | H | H | CH$_3$ | OCH$_3$ | CH | H |
| Q-29 | H | H | CO$_2$CH$_2$CH$_3$ | H | H | CH$_3$ | CH$_3$ | CH | H |
| Q-29 | H | H | CO$_2$CH$_2$CH$_2$CH$_3$ | H | H | OCH$_3$ | OCH$_3$ | CH | H |
| Q-29 | H | H | SCH$_3$ | H | H | CH$_3$ | CH$_3$ | N | H |
| Q-29 | H | H | SOCH$_3$ | H | H | CH$_3$ | CH$_3$ | CH | H |
| Q-29 | H | H | SO$_2$CH$_3$ | H | H | OCH$_3$ | OCH$_3$ | CH | H |
| Q-29 | H | H | SO$_2$CH$_2$CH$_3$ | H | H | OCH$_3$ | OCH$_3$ | N | H |
| Q-29 | H | H | SO$_2$N(CH$_3$)$_2$ | H | H | CH$_3$ | OCH$_3$ | CH | H |
| Q-29 | H | H | SO$_2$N(CH$_2$CH$_3$)$_2$ | H | H | OCH$_3$ | OCH$_3$ | CH | H |
| Q-29 | CH$_3$ | H | CO$_2$CH$_3$ | H | H | OCH$_3$ | OCH$_3$ | CH | H |
| Q-29 | H | H | Br | H | CH$_3$ | OCH$_3$ | OCH$_3$ | CH | H |
| Q-29 | H | CH$_3$ | Cl | H | H | OCH$_3$ | OCH$_3$ | N | H |
| Q-30 | H | H | H | H | H | CH$_3$ | OCH$_3$ | CH | H |
| Q-30 | H | H | CH$_2$CH$_3$ | H | H | OCH$_3$ | OCH$_3$ | CH | H |
| Q-30 | H | H | F | H | H | CH$_3$ | CH$_3$ | CH | H |
| Q-30 | H | H | Cl | H | H | OCH$_3$ | OCH$_3$ | CH | H |
| Q-30 | H | H | Br | H | H | OCH$_3$ | CH$_3$ | CH | H |
| Q-30 | H | H | NO$_2$ | H | H | OCH$_3$ | OCH$_3$ | CH | H |
| Q-30 | H | H | SCH$_2$F | H | H | CH$_3$ | OCH$_3$ | CH | H |
| Q-30 | H | H | SCH$_2$F | H | H | OCH$_3$ | OCH$_3$ | CH | H |
| Q-30 | H | H | CH$_2$—CH=CH$_2$ | H | H | Cl | OCH$_3$ | CH | H |
| Q-30 | H | H | CH$_2$—C≡CH | H | H | OCH$_3$ | OCH$_3$ | CH | H |
| Q-30 | H | H | CO$_2$CH$_3$ | H | H | OCH$_3$ | OCH$_3$ | CH | H |
| Q-30 | H | H | CO$_2$CH$_3$ | H | H | OCH$_3$ | CH$_3$ | CH | H |
| Q-30 | H | H | CO$_2$CH$_3$ | H | H | CH$_3$ | CH$_3$ | N | H |
| Q-30 | H | H | CO$_2$CH$_3$CH$_3$ | H | H | OCH$_3$ | OCH$_3$ | CH | H |
| Q-30 | H | SCH$_3$ | H | H | CH$_3$ | OCH$_3$ | CH | H | |
| Q-30 | H | H | SOCH$_3$ | H | H | CH$_3$ | CH$_3$ | CH | H |
| Q-30 | H | H | SO$_2$CH$_3$ | H | H | OCH$_3$ | OCH$_3$ | CH | H |
| Q-30 | H | H | SO$_2$N(CH$_3$)$_2$ | H | H | OCH$_3$ | CH$_3$ | CH | H |
| Q-30 | H | H | SO$_2$N(CH$_3$)$_2$ | H | H | OCH$_3$ | CH$_3$ | N | H |
| Q-30 | H | H | SO$_2$N(CH$_2$CH$_3$)$_2$ | H | H | OCH$_3$ | OCH$_3$ | CH | H |
| Q-30 | CH$_3$ | H | Cl | H | H | CH$_3$ | CH$_3$ | CH | H |
| Q-30 | H | CH$_3$ | Br | H | H | OCH$_3$ | OCH$_3$ | N | H |
| Q-30 | H | Cl | CO$_2$CH$_3$ | H | H | CH$_3$ | OCH$_3$ | CH | H |

| Q | R | R$_2$ | R$_{14}$ | R$_6$ | R$_7$ | X | Y | X | m.p. °C. |
|---|---|---|---|---|---|---|---|---|---|
| Q-31 | H | H | H | H | H | CH$_3$ | OCH$_3$ | CH | |
| Q-31 | H | H | CH$_3$ | H | H | CH | CH | | |
| Q-31 | H | H | CH$_2$CH$_2$CH$_3$ | H | H | OCH$_3$ | OCH$_3$ | N | |
| Q-31 | H | H | F | H | H | OCH$_3$ | OCH$_3$ | CH | |
| Q-31 | H | H | Cl | H | H | OCH$_3$ | OCH$_3$ | CH | |
| Q-31 | H | H | Cl | H | H | OCH$_3$ | CH$_3$ | N | |
| Q-31 | H | H | Br | H | H | CH$_3$ | OCH$_3$ | CH | |
| Q-31 | H | H | NO$_2$ | H | H | Cl | OCH$_3$ | CH | |
| Q-31 | H | H | SCH$_2$CH$_2$F | H | H | OCH$_3$ | OCH$_3$ | CH | |
| Q-31 | H | H | CH$_2$—CH=CH$_2$ | H | H | OCH$_3$ | CH$_3$ | CH | |
| Q-31 | H | H | CH$_2$—C≡CH | H | H | CH$_3$ | CH$_3$ | CH | |
| Q-31 | H | H | CO$_2$CH$_3$ | H | H | CH$_3$ | OCH$_3$ | N | |
| Q-31 | H | H | CO$_2$CH$_3$ | H | H | OCH$_3$ | OCH$_3$ | CH | 183–188 |
| Q-31 | H | H | COCH$_2$CH=CH$_2$ | H | H | CH$_3$ | OCH$_3$ | CH | |
| Q-31 | H | H | CO$_2$CH$_2$CH$_3$ | H | H | OCH$_3$ | OCH$_3$ | CH | 158–160.5 |
| Q-31 | H | H | CO$_2$CH$_2$CH$_2$CH$_3$ | H | H | OCH$_3$ | OCH$_3$ | CH | |
| Q-31 | H | H | SCH$_3$ | H | H | CH$_3$ | CH$_3$ | N | |
| Q-31 | H | H | SOCH$_3$ | H | H | CH$_3$ | CH$_3$ | CH | |

TABLE XXV-continued

General Formula XXV

| Q | R | R₂ | R₁₄ | R₆ | X | Y | Z | | |
|---|---|---|---|---|---|---|---|---|---|
| Q-31 | H | H | SO₂CH₃ | H | H | OCH₃ | OCH₃ | CH | |
| Q-31 | H | H | SO₂CH₂CH₃ | H | H | OCH₃ | OCH₃ | N | |
| Q-31 | H | H | SO₂N(CH₃)₂ | H | H | CH₃ | OCH₃ | CH | |
| Q-31 | H | H | SO₂N(CH₂CH₃)₂ | H | H | OCH₃ | OCH₃ | CH | |
| Q-31 | CH₃ | H | CO₂CH₃ | H | H | OCH₃ | OCH₃ | CH | |
| Q-31 | H | H | Br | H | CH₃ | OCH₃ | OCH₃ | CH | |
| Q-31 | H | CH₃ | Cl | H | OCH₃ | OCH₃ | OCH₃ | N | |
| Q-32 | H | H | H | H | H | CH₃ | OCH₃ | CH | |
| Q-32 | H | H | CH₂CH₃ | H | H | OCH₃ | OCH₃ | CH | |
| Q-32 | H | H | F | H | H | CH₃ | CH₃ | CH | |
| Q-32 | H | H | Cl | H | H | OCH₃ | OCH₃ | CH | |
| Q-32 | H | H | Br | H | H | OCH₃ | CH₃ | CH | |
| Q-32 | H | H | NO₂ | H | H | OCH₃ | OCH₃ | CH | |
| Q-32 | H | H | SCH₂F | H | H | CH₃ | OCH₃ | CH | |
| Q-32 | H | H | SCH₂F | H | H | OCH₃ | OCH₃ | CH | |
| Q-32 | H | H | CH₂—CH=CH₂ | H | H | Cl | OCH₃ | CH | |
| Q-32 | H | H | CH₂—C≡CH | H | H | OCH₃ | OCH₃ | CH | |
| Q-32 | H | H | CO₂CH₃ | H | H | OCH₃ | OCH₃ | CH | |
| Q-32 | H | H | CO₂CH₃ | H | H | OCH₃ | CH₃ | CH | |
| Q-32 | H | H | CO₂CH₂C≡CH | H | H | CH₃ | CH₃ | N | |
| Q-32 | H | H | CO₂CH₂CH₃ | H | H | OCH₃ | OCH₃ | CH | |
| Q-32 | H | H | SCH₃ | H | H | CH₃ | OCH₃ | CH | |
| Q-32 | H | H | SOCH₃ | H | H | CH₃ | CH₃ | CH | |
| Q-32 | H | H | SO₂CH₃ | H | H | OCH₃ | OCH₃ | CH | |
| Q-32 | H | H | SO₂N(CH₃)₂ | H | H | OCH₃ | CH₃ | CH | |
| Q-32 | H | H | SO₂N(CH₃)₂ | H | H | OCH₃ | CH₃ | N | |
| Q-32 | H | H | SO₂N(CH₂CH₃)₂ | H | H | OCH₃ | OCH₃ | CH | |
| Q-32 | CH₃ | H | Cl | H | H | CH₃ | CH₃ | CH | |
| Q-32 | H | CH₃ | Br | H | H | OCH₃ | OCH₃ | N | |
| Q-32 | H | Cl | CO₂CH₃ | H | H | CH₃ | OCH₃ | CH | |
| Q-33 | H | H | H | H | H | CH₃ | OCH₃ | CH | |
| Q-33 | H | H | CH₃ | H | H | CH₃ | CH₃ | N | |
| Q-33 | H | H | CH₂CH₂CH₃ | H | H | OCH₃ | OCH₃ | | |
| Q-33 | H | H | F | H | H | OCH₃ | OCH₃ | CH | |
| Q-33 | H | H | Cl | H | H | OCH₃ | OCH₃ | CH | |
| Q-33 | H | H | Cl | H | H | OCH₃ | CH₃ | N | |
| Q-33 | H | H | Br | H | H | CH₃ | OCH₃ | CH | |
| Q-33 | H | H | NO₂ | H | H | Cl | OCH₃ | CH | |
| Q-33 | H | H | SCH₂CH₂F | H | H | OCH₃ | OCH₃ | CH | |
| Q-33 | H | H | CH₂—CH=CH₂ | H | H | OCH₃ | CH₃ | CH | |
| Q-33 | H | H | CH₂—C≡CH | H | H | CH₃ | CH₃ | CH | |
| Q-33 | H | H | CO₂CH₃ | H | H | CH₃ | OCH₃ | N | |
| Q-33 | H | H | CO₂CH₃ | H | H | OCH₃ | OCH₃ | CH | |
| Q-33 | H | H | CO₂CH₃ | H | H | CH₃ | OCH₃ | CH | |
| Q-33 | H | H | CO₂CH₂CH₃ | H | H | CH₃ | CH₃ | CH | |
| Q-33 | H | H | CO₂CH₂CH₂CH₃ | H | H | OCH₃ | OCH₃ | CH | |
| Q-33 | H | H | SCH₃ | H | H | CH₃ | CH₃ | N | |
| Q-33 | H | H | SOCH₃ | H | H | CH₃ | CH₃ | CH | |
| Q-33 | H | H | SO₂CH₃ | H | H | OCH₃ | OCH₃ | CH | |
| Q-33 | H | H | SO₂CH₂CH₃ | H | H | OCH₃ | OCH₃ | N | |
| Q-33 | H | H | SO₂N(CH₃)₂ | H | H | CH₃ | OCH₃ | CH | |
| Q-33 | H | H | SO₂N(CH₂CH₃)₃ | H | H | OCH₃ | OCH₃ | CH | |
| Q-33 | CH₃ | H | CO₂CH₃ | H | H | OCH₃ | OCH₃ | CH | |
| Q-33 | H | H | Br | H | CH₃ | OCH₃ | OCH₃ | CH | |
| Q-33 | H | CH₃ | Cl | H | H | OCH₃ | OCH₃ | N | |

| Q | R | R₂ | R₁₄ | R₆ | X | Y | Z | R₁₀ | R₁₁ | m.p. °C. |
|---|---|---|---|---|---|---|---|---|---|---|
| Q-34 | H | H | H | H | CH₃ | OCH₃ | CH | H | H | |
| Q-34 | H | H | CH₂CH₃ | H | OCH₃ | OCH₃ | CH | H | H | |
| Q-34 | H | H | F | H | CH₃ | CH₃ | CH | H | H | |
| Q-34 | H | H | Cl | H | OCH₃ | OCH₃ | CH | H | H | |
| Q-34 | H | H | Br | H | OCH₃ | CH₃ | CH | H | H | |
| Q-34 | H | H | NO₂ | H | OCH₃ | OCH₃ | CH | H | H | |
| Q-34 | H | H | SCH₂F | H | CH₃ | OCH₃ | CH | H | H | |
| Q-34 | H | H | SCH₂F | H | OCH₃ | OCH₃ | CH | H | H | |
| Q-34 | H | H | CH₂—CH=CH₂ | H | Cl | OCH₃ | CH | H | H | |
| Q-34 | H | H | CH₂—C≡CH | H | OCH₃ | OCH₃ | CH | H | H | |
| Q-34 | H | H | CO₂CH₃ | H | OCH₃ | OCH₃ | CH | H | H | |
| Q-34 | H | H | CO₂CH₃ | H | OCH₃ | CH₃ | CH | H | H | |
| Q-34 | H | H | CO₂CH₃ | H | CH₃ | CH₃ | N | H | H | |
| Q-34 | H | H | CO₂CH₂CH₃ | H | OCH₃ | OCH₃ | CH | H | H | |
| Q-34 | H | H | SCH₃ | H | CH₃ | OCH₃ | CH | H | H | |
| Q-34 | H | H | SOCH₃ | H | CH₃ | CH₃ | CH | H | H | |
| Q-34 | H | H | SO₂CH₃ | H | OCH₃ | OCH₃ | CH | H | H | |
| Q-34 | H | H | SO₂N(CH₃)₂ | H | OCH₃ | CH₃ | CH | H | H | |
| Q-34 | H | H | SO₂N(CH₃)₂ | H | OCH₃ | CH₃ | N | H | H | |
| Q-34 | H | H | SO₂N(CH₂CH₃)₂ | H | OCH₃ | OCH₃ | CH | H | H | |
| Q-34 | CH₃ | H | Cl | H | CH₃ | CH₃ | CH | H | H | |
| Q-34 | H | CH₃ | Br | H | OCH₃ | OCH₃ | N | H | H | |
| Q-34 | H | Cl | CO₂CH₂CH₂OCH₃ | H | CH₃ | OCH₃ | CH | H | H | |

TABLE XXV-continued

General Formula XXV

| Q | R | $R_2$ | $R_{14}$ | $R_{10}$ | $R_{11}$ | X | Y | Z | m.p. °C. |
|---|---|---|---|---|---|---|---|---|---|
| Q-35 | H | H | H | H | H | $CH_3$ | $OCH_3$ | CH | |
| Q-35 | H | H | $CH_3$ | H | H | $CH_3$ | $CH_3$ | N | |
| Q-35 | H | H | $CH_2CH_2CH_3$ | H | H | $OCH_3$ | $OCH_3$ | N | |
| Q-35 | H | H | F | H | H | $OCH_3$ | $OCH_3$ | CH | |
| Q-35 | H | H | Cl | H | H | $OCH_3$ | $OCH_3$ | CH | |
| Q-35 | H | H | Cl | H | H | $OCH_3$ | $CH_3$ | N | |
| Q-35 | H | H | Br | H | H | $CH_3$ | $OCH_3$ | CH | |
| Q-35 | H | H | $NO_2$ | H | H | Cl | $OCH_3$ | CH | |
| Q-35 | H | H | $SCH_2CH_2F$ | H | H | $OCH_3$ | $OCH_3$ | CH | |
| Q-35 | H | H | $CH_2-CH=CH_2$ | H | H | $OCH_3$ | $CH_3$ | CH | |
| Q-35 | H | H | $CH_2-C\equiv CH$ | H | H | $CH_3$ | $CH_3$ | CH | |
| Q-35 | H | H | $CO_2CH_3$ | H | H | $CH_3$ | $OCH_3$ | N | |
| Q-35 | H | H | $CO_2CH_3$ | H | H | $OCH_3$ | $OCH_3$ | CH | |
| Q-35 | H | H | $CO_2CH_3$ | H | H | $CH_3$ | $OCH_3$ | CH | |
| Q-35 | H | H | $CO_2CH_2CH_3$ | H | H | $CH_3$ | $CH_3$ | CH | |
| Q-35 | H | H | $CO_2CH_2CH_2CH_3$ | H | H | $OCH_3$ | $OCH_3$ | CH | |
| Q-35 | H | H | $SCH_3$ | H | H | $CH_3$ | $CH_3$ | N | |
| Q-35 | H | H | $SOCH_3$ | H | H | $CH_3$ | $CH_3$ | CH | |
| Q-35 | H | H | $SO_2CH_3$ | H | H | $OCH_3$ | $OCH_3$ | CH | |
| Q-35 | H | H | $SO_2CH_2CH_3$ | H | H | $OCH_3$ | $OCH_3$ | N | |
| Q-35 | H | H | $SO_2N(CH_3)_2$ | H | H | $CH_3$ | $OCH_3$ | CH | |
| Q-35 | H | H | $SO_2N(CH_2CH_3)_2$ | H | H | $OCH_3$ | $OCH_3$ | CH | |
| Q-35 | $CH_3$ | H | $CO_2CH_3$ | H | H | $OCH_3$ | $OCH_3$ | CH | |
| Q-35 | H | H | Br | H | $CH_3$ | $OCH_3$ | $OCH_3$ | CH | |
| Q-35 | H | $CH_3$ | Cl | H | H | $OCH_3$ | $OCH_3$ | N | |
| Q-36 | H | H | H | H | H | $CH_3$ | $OCH_3$ | CH | |
| Q-36 | H | H | $CH_2CH_3$ | H | H | $OCH_3$ | $OCH_3$ | CH | |
| Q-36 | H | H | F | H | H | $CH_3$ | $CH_3$ | CH | |
| Q-36 | H | H | Cl | H | H | $OCH_3$ | $OCH_3$ | CH | |
| Q-36 | H | H | Br | H | H | $OCH_3$ | $CH_3$ | CH | |
| Q-36 | H | H | $NO_2$ | H | H | $OCH_3$ | $OCH_3$ | CH | |
| Q-36 | H | H | $SCH_2F$ | H | H | $CH_3$ | $OCH_3$ | CH | |
| Q-36 | H | H | $SCH_2F$ | H | H | $OCH_3$ | $OCH_3$ | CH | |
| Q-36 | H | H | $CH_2-CH=CH_2$ | H | H | Cl | $OCH_3$ | CH | |
| Q-36 | H | H | $CH_2-C\equiv CH$ | H | H | $OCH_3$ | $OCH_3$ | CH | |
| Q-36 | H | H | $CO_2CH_3$ | H | H | $OCH_3$ | $OCH_3$ | CH | |
| Q-36 | H | H | $CO_2CH_3$ | H | H | $OCH_3$ | $CH_3$ | CH | |
| Q-36 | H | H | $CO_2CH_2CH=CH_2$ | H | H | $CH_3$ | CH | | |
| Q-36 | H | H | $CO_2CH_2CH_3$ | H | H | $OCH_3$ | $OCH_3$ | CH | |
| Q-36 | H | H | $SCH_3$ | H | H | $CH_3$ | $OCH_3$ | CH | |
| Q-36 | H | H | $SOCH_3$ | H | H | $CH_3$ | $CH_3$ | CH | |
| Q-36 | H | H | $SO_2CH_3$ | H | H | $OCH_3$ | $OCH_3$ | CH | |
| Q-36 | H | H | $SO_2N(CH_3)_2$ | H | H | $OCH_3$ | $CH_3$ | CH | |
| Q-36 | H | H | $SO_2N(CH_3)_2$ | H | H | $OCH_3$ | $CH_3$ | N | |
| Q-36 | H | H | $SO_2N(CH_2CH_3)_2$ | H | H | $OCH_3$ | $OCH_3$ | CH | |
| Q-36 | $CH_3$ | H | Cl | H | H | $CH_3$ | $CH_3$ | CH | |
| Q-36 | H | $CH_3$ | Br | H | H | $OCH_3$ | $OCH_3$ | N | |
| Q-36 | H | Cl | $CO_2CH_3$ | H | H | $CH_3$ | $OCH_3$ | CH | |

| Q | R | $R_2$ | $R_{14}$ | $R_6$ | $R_7$ | X | Y | Z | m.p. °C. |
|---|---|---|---|---|---|---|---|---|---|
| Q-37 | H | H | H | H | H | $CH_3$ | $OCH_3$ | CH | |
| Q-37 | H | H | $CH_3$ | H | H | $CH_3$ | $CH_3$ | | ° |
| Q-37 | H | H | $CH_2CH_2CH_3$ | H | H | $OCH_3$ | $OCH_3$ | N | |
| Q-37 | H | H | F | H | H | $OCH_3$ | $OCH_3$ | CH | |
| Q-37 | H | H | Cl | H | H | $OCH_3$ | $OCH_3$ | CH | |
| Q-37 | H | H | Cl | H | H | $OCH_3$ | $CH_3$ | N | |
| Q-37 | H | H | Br | H | H | $CH_3$ | $OCH_3$ | CH | |
| Q-37 | H | H | $NO_2$ | H | H | Cl | $OCH_3$ | CH | |
| Q-37 | H | H | $SCH_2CH_2F$ | H | H | $OCH_3$ | $OCH_3$ | CH | |
| Q-37 | H | H | $CH_2-CH=CH_2$ | H | H | $OCH_3$ | $CH_3$ | CH | |
| Q-37 | H | H | $CH_2-C\equiv CH$ | H | H | $CH_3$ | $CH_3$ | CH | |
| Q-37 | H | H | $CO_2CH_3$ | H | H | $CH_3$ | $OCH_3$ | N | |
| Q-37 | H | H | $CO_2CH_3$ | H | H | $OCH_3$ | $OCH_3$ | CH | |
| Q-37 | H | H | $CO_2CH_2C\equiv CH$ | H | H | $CH_3$ | $OCH_3$ | CH | |
| Q-37 | H | H | $CO_2CH_2CH_3$ | H | H | $CH_3$ | $CH_3$ | CH | |
| Q-37 | H | H | $CH_2CH_2CH_2CH_3$ | H | H | $OCH_3$ | $OCH_3$ | CH | |
| Q-37 | H | H | $SCH_3$ | H | H | $CH_3$ | $CH_3$ | N | |
| Q-37 | H | H | $SOCH_3$ | H | H | $CH_3$ | $CH_3$ | CH | |
| Q-37 | H | H | $SO_2CH_3$ | H | H | $OCH_3$ | $OCH_3$ | CH | |
| Q-37 | H | H | $SO_2CH_2CH_3$ | H | H | $OCH_3$ | $OCH_3$ | N | |
| Q-37 | H | H | $SO_2N(CH_3)_2$ | H | H | $CH_3$ | $OCH_3$ | CH | |
| Q-37 | H | H | $SO_2N(CH_2CH_3)_2$ | H | H | $OCH_3$ | $OCH_3$ | CH | |
| Q-37 | CH | H | $CO_2CH_3$ | H | H | $OCH_3$ | $OCH_3$ | CH | |
| Q-37 | H | H | Br | H | $CH_3$ | $OCH_3$ | $OCH_3$ | CH | |
| Q-37 | H | $CH_3$ | Cl | H | H | $OCH_3$ | $OCH_3$ | N | |
| Q-38 | H | H | H | H | H | $CH_3$ | $OCH_3$ | CH | |
| Q-38 | H | H | $CH_2CH_3$ | H | H | $OCH_3$ | $OCH_3$ | CH | |
| Q-38 | H | H | F | H | H | $CH_3$ | $CH_3$ | CH | |
| Q-38 | H | H | Cl | H | H | $OCH_3$ | $OCH_3$ | CH | |

TABLE XXV-continued

General Formula XXV

| Q | R | R$_2$ | R$_{14}$ | R$_{12}$ | R$_{13}$ | X | Y | Z | m.p. °C. |
|---|---|---|---|---|---|---|---|---|---|
| Q-38 | H | H | Br | H | H | OCH$_3$ | CH$_3$ | CH | |
| Q-38 | H | H | NO$_2$ | H | H | OCH$_3$ | OCH$_3$ | CH | |
| Q-38 | H | H | SCH$_2$F | H | H | CH$_3$ | OCH$_3$ | CH | |
| Q-38 | H | H | SCH$_2$F | H | H | OCH$_3$ | OCH$_3$ | CH | |
| Q-38 | H | H | CH$_2$—CH=CH$_2$ | H | H | Cl | OCH$_3$ | CH | |
| Q-38 | H | H | CH$_2$—C≡CH | H | H | OCH$_3$ | OCH$_3$ | CH | |
| Q-38 | H | H | CO$_2$CH$_3$ | H | H | OCH$_3$ | OCH$_3$ | CH | |
| Q-38 | H | H | CO$_2$CH$_3$ | H | H | OCH$_3$ | CH$_3$ | CH | |
| Q-38 | H | H | CO$_2$CH$_2$CH$_2$Cl | H | H | CH$_3$ | CH$_3$ | N | |
| Q-38 | H | H | CO$_2$CH$_2$CH$_3$ | H | H | OCH$_3$ | OCH$_3$ | CH | |
| Q-38 | H | H | SCH$_3$ | H | H | CH$_3$ | OCH$_3$ | CH | |
| Q-38 | H | H | SOCH$_3$ | H | H | CH$_3$ | CH$_3$ | CH | |
| Q-38 | H | H | SO$_2$CH$_3$ | H | H | OCH$_3$ | OCH$_3$ | CH | |
| Q-38 | H | H | SO$_2$N(CH$_3$)$_2$ | H | H | OCH$_3$ | CH$_3$ | CH | |
| Q-38 | H | H | SO$_2$N(CH$_3$)$_2$ | H | H | OCH$_3$ | CH$_3$ | N | |
| Q-38 | H | H | SO$_2$N(CH$_2$CH$_3$)$_2$ | H | H | OCH$_3$ | OCH$_3$ | CH | |
| Q-38 | CH$_3$ | H | Cl | H | H | CH$_3$ | CH$_3$ | CH | |
| Q-38 | H | CH$_3$ | Br | H | H | OCH$_3$ | OCH$_3$ | N | |
| Q-38 | H | Cl | CO$_2$CH$_3$ | H | H | CH$_3$ | OCH$_3$ | CH | |

| Q | R | R$_2$ | R$_{14}$ | R$_{12}$ | R$_{13}$ | X | Y | Z | m.p. °C. |
|---|---|---|---|---|---|---|---|---|---|
| Q-39 | H | H | H | H | H | CH$_3$ | OCH$_3$ | CH | |
| Q-39 | H | H | CH$_3$ | H | H | CH$_3$ | CH$_3$ | N | |
| Q-39 | H | H | CH$_2$CH$_2$CH$_3$ | H | H | OCH$_3$ | OCH$_3$ | N | |
| Q-39 | H | H | F | H | H | OCH$_3$ | OCH$_3$ | CH | |
| Q-39 | H | H | Cl | H | H | OCH$_3$ | OCH$_3$ | CH | |
| Q-39 | H | H | Cl | H | H | OCH$_3$ | CH$_3$ | N | |
| Q-39 | H | H | Br | H | H | CH$_3$ | OCH$_3$ | CH | |
| Q-39 | H | H | NO$_2$ | H | H | Cl | OCH$_3$ | CH | |
| Q-39 | H | H | SCH$_2$CH$_2$F | H | H | OCH$_3$ | OCH$_3$ | CH | |
| Q-39 | H | H | CH$_2$—CH=CH$_2$ | H | H | OCH$_3$ | CH$_3$ | CH | |
| Q-39 | H | H | CH$_2$—C≡CH | H | H | CH$_3$ | CH$_3$ | CH | |
| Q-39 | H | H | CO$_2$CH$_3$ | H | H | CH$_3$ | OCH$_3$ | | |

| Q | R | R$_2$ | R$_{14}$ | R$_6$ | R$_7$ | X | Y | Z | m.p. °C. |
|---|---|---|---|---|---|---|---|---|---|
| Q-39 | H | H | CO$_2$CH$_3$ | H | H | OCH$_3$ | OCH$_3$ | CH | |
| Q-39 | H | H | CO$_2$CH$_3$ | H | H | CH$_3$ | OCH$_3$ | CH | |
| Q-39 | H | H | CO$_2$CH$_2$CH$_3$ | H | H | CH$_3$ | CH$_3$ | CH | |
| Q-39 | H | H | CO$_2$CH$_2$CH$_2$CH$_3$ | H | H | OCH$_3$ | OCH$_3$ | CH | |
| Q-39 | H | H | SCH$_3$ | H | H | CH$_3$ | CH$_3$ | N | |
| Q-39 | H | H | SOCH$_3$ | H | H | CH$_3$ | CH$_3$ | CH | |
| Q-39 | H | H | SO$_2$CH$_3$ | H | H | OCH$_3$ | OCH$_3$ | CH | |
| Q-39 | H | H | SO$_2$CH$_2$CH$_3$ | H | H | OCH$_3$ | OCH$_3$ | N | |
| Q-39 | H | H | SO$_2$N(CH$_3$)$_2$ | H | H | CH$_3$ | OCH$_3$ | CH | |
| Q-39 | H | H | SO$_2$N(CH$_2$CH$_3$)$_2$ | H | H | OCH$_3$ | OCH$_3$ | CH | |
| Q-39 | CH$_3$ | H | CO$_2$CH$_3$ | H | H | OCH$_3$ | OCH$_3$ | CH | |
| Q-39 | H | H | Br | H | CH$_3$ | OCH$_3$ | OCH$_3$ | CH | |
| Q-39 | H | CH$_3$ | Cl | H | H | OCH$_3$ | OCH$_3$ | N | |
| Q-40 | H | H | H | H | H | CH$_3$ | OCH$_3$ | CH | |
| Q-40 | H | H | CH$_2$CH$_3$ | H | H | OCH$_3$ | OCH$_3$ | CH | |
| Q-40 | H | H | F | H | H | CH$_3$ | CH$_3$ | CH | |
| Q-40 | H | H | Cl | H | H | OCH$_3$ | OCH$_3$ | CH | |
| Q-40 | H | H | Br | H | H | OCH$_3$ | CH$_3$ | CH | |
| Q-40 | H | H | NO$_2$ | H | H | OCH$_3$ | OCH$_3$ | CH | |
| Q-40 | H | H | SCH$_2$F | H | H | CH$_3$ | OCH$_3$ | CH | |
| Q-40 | H | H | SCH$_2$F | H | H | OCH$_3$ | OCH$_3$ | CH | |
| Q-40 | H | H | CH$_2$—CH=CH$_2$ | H | H | Cl | OCH$_3$ | CH | |
| Q-40 | H | H | CH$_2$—C≡CH | H | H | OCH$_3$ | OCH$_3$ | CH | |
| Q-40 | H | H | CO$_2$CH$_3$ | H | H | OCH$_3$ | OCH$_3$ | CH | |
| Q-40 | H | H | CO$_2$CH$_3$ | H | H | OCH$_3$ | CH$_3$ | CH | |
| Q-40 | H | H | CO$_2$CH$_3$ | H | H | CH$_3$ | CH$_3$ | N | |
| Q-40 | H | H | CO$_2$CH$_2$CH$_3$ | H | H | OCH$_3$ | OCH$_3$ | CH | |
| Q-40 | H | H | SCH$_3$ | H | H | CH$_3$ | OCH$_3$ | CH | |
| Q-40 | H | H | SOCH$_3$ | H | H | CH$_3$ | CH$_3$ | CH | |
| Q-40 | H | H | SO$_2$CH$_3$ | H | H | OCH$_3$ | OCH$_3$ | CH | |
| Q-40 | H | H | SO$_2$N(CH$_3$)$_2$ | H | H | OCH$_3$ | CH$_3$ | CH | |
| Q-40 | H | H | SO$_2$N(CH$_3$)$_2$ | H | H | OCH$_3$ | CH$_3$ | N | |
| Q-40 | H | H | SO$_2$N(CH$_2$CH$_3$)$_2$ | H | H | OCH$_3$ | OCH$_3$ | CH | |
| Q-40 | CH$_3$ | H | Cl | H | H | CH$_3$ | CH$_3$ | CH | |
| Q-40 | H | CH$_3$ | Br | H | H | OCH$_3$ | OCH$_3$ | N | |
| Q-40 | H | Cl | CO$_2$CH$_3$ | H | H | CH$_3$ | OCH$_3$ | CH | |

| Q | R | R$_2$ | R$_{14}$ | R$_6$ | X | Y | Z | m.p. °C. |
|---|---|---|---|---|---|---|---|---|
| Q-41 | H | H | H | H | CH$_3$ | OCH$_3$ | CH | |
| Q-41 | H | H | CH$_3$ | H | CH$_3$ | CH$_3$ | N | |
| Q-41 | H | H | CH$_2$CH$_2$CH$_3$ | H | OCH$_3$ | OCH$_3$ | N | |
| Q-41 | H | H | F | H | OCH$_3$ | OCH$_3$ | CH | |
| Q-41 | H | H | Cl | H | OCH$_3$ | OCH$_3$ | CH | |
| Q-41 | H | H | Cl | H | OCH$_3$ | CH$_3$ | N | |
| Q-41 | H | H | Br | H | CH$_3$ | OCH$_3$ | CH | |

TABLE XXV-continued

General Formula XXV

| | | | | | | | |
|---|---|---|---|---|---|---|---|
| Q-41 | H | H | NO$_2$ | H | Cl | OCH$_3$ | CH |
| Q-41 | H | H | SCH$_2$CH$_2$F | H | OCH$_3$ | OCH$_3$ | CH |
| Q-41 | H | H | CH$_2$—CH=CH$_2$ | H | OCH$_3$ | CH$_3$ | CH |
| Q-41 | H | H | CH$_2$—C≡CH | H | CH$_3$ | CH$_3$ | CH |
| Q-41 | H | H | CO$_2$CH$_3$ | H | CH$_3$ | OCH$_3$ | N |
| Q-41 | H | H | CO$_2$CH$_3$ | H | OCH$_3$ | OCH$_3$ | CH |
| Q-41 | H | H | CO$_2$CH$_2$CH=CH$_2$ | H | CH$_3$ | OCH$_3$ | CH |
| Q-41 | H | H | CO$_2$CH$_2$CH$_3$ | H | CH$_3$ | CH$_3$ | CH |
| Q-41 | H | H | CO$_2$CH$_2$CH$_2$CH$_3$ | H | OCH$_3$ | OCH$_3$ | CH |
| Q-41 | H | H | SCH$_3$ | H | CH$_3$ | CH$_3$ | N |
| Q-41 | H | H | SOCH$_3$ | H | CH$_3$ | CH$_3$ | CH |
| Q-41 | H | H | SO$_2$CH$_3$ | H | OCH$_3$ | OCH$_3$ | CH |
| Q-41 | H | H | SO$_2$CH$_2$CH$_3$ | H | OCH$_3$ | OCH$_3$ | N |
| Q-41 | H | H | SO$_2$N(CH$_3$)$_2$ | H | CH$_3$ | OCH$_3$ | CH |
| Q-41 | H | H | SO$_2$N(CH$_2$CH$_3$)$_2$ | H | OCH$_3$ | OCH$_3$ | CH |
| Q-41 | CH$_3$ | H | CO$_2$CH$_3$ | H | OCH$_3$ | OCH$_3$ | CH |
| Q-41 | H | H | Br | CH$_3$ | OCH$_3$ | OCH$_3$ | CH |
| Q-41 | H | CH$_3$ | Cl | H | OCH$_3$ | OCH$_3$ | N |
| Q-42 | H | H | H | H | CH$_3$ | OCH$_3$ | CH |
| Q-42 | H | H | CH$_2$CH$_3$ | H | OCH$_3$ | OCH$_3$ | CH |
| Q-42 | H | H | F | H | CH$_3$ | CH$_3$ | CH |
| Q-42 | H | H | Cl | H | OCH$_3$ | OCH$_3$ | CH |
| Q-42 | H | H | Br | H | OCH$_3$ | CH$_3$ | CH |
| Q-42 | H | H | NO$_2$ | H | OCH$_3$ | OCH$_3$ | CH |
| Q-42 | H | H | SCH$_2$F | H | CH$_3$ | OCH$_3$ | CH |
| Q-42 | H | H | SCH$_2$F | H | OCH$_3$ | OCH$_3$ | CH |
| Q-42 | H | H | CH$_2$—CH=CH$_2$ | H | Cl | OCH$_3$ | CH |
| Q-42 | H | H | CH$_2$—C≡CH | H | OCH$_3$ | OCH$_3$ | CH |
| Q-42 | H | H | CO$_2$CH$_3$ | H | OCH$_3$ | OCH$_3$ | CH |
| Q-42 | H | H | CO$_2$CH$_3$ | H | OCH$_3$ | CH$_3$ | CH |
| Q-42 | H | H | CO$_2$CH$_3$ | H | CH$_3$ | CH$_3$ | N |
| Q-42 | H | H | CO$_2$CH$_2$CH$_3$ | H | OCH$_3$ | OCH$_3$ | CH |
| Q-42 | H | H | SCH$_3$ | H | CH$_3$ | OCH$_3$ | CH |
| Q-42 | H | H | SOCH$_3$ | H | CH$_3$ | CH$_3$ | CH |
| Q-42 | H | H | SO$_2$CH$_3$ | H | OCH$_3$ | OCH$_3$ | CH |
| Q-42 | H | H | SO$_2$N(CH$_3$)$_2$ | H | OCH$_3$ | CH$_3$ | CH |
| Q-42 | H | H | SO$_2$N(CH$_3$)$_2$ | H | OCH$_3$ | CH$_3$ | N |
| Q-42 | H | H | SO$_2$N(CH$_2$CH$_3$)$_2$ | H | OCH$_3$ | OCH$_3$ | CH |
| Q-42 | CH$_3$ | H | Cl | H | CH$_3$ | CH$_3$ | CH |
| Q-42 | H | CH$_3$ | Br | H | OCH$_3$ | OCH$_3$ | N |
| Q-42 | H | Cl | CO$_2$CH$_3$ | H | CH$_3$ | OCH$_3$ | CH |
| Q-43 | H | H | H | H | CH$_3$ | OCH$_3$ | CH |
| Q-43 | H | H | CH$_3$ | H | CH$_3$ | CH$_3$ | N |
| Q-43 | H | H | CH$_2$CH$_2$CH$_3$ | H | OCH$_3$ | OCH$_3$ | N |
| Q-43 | H | H | F | H | OCH$_3$ | OCH$_3$ | CH |
| Q-43 | H | H | Cl | H | OCH$_3$ | OCH$_3$ | CH |
| Q-43 | H | H | Cl | H | OCH$_3$ | CH$_3$ | N |
| Q-43 | H | H | Br | H | CH$_3$ | OCH$_3$ | CH |
| Q-43 | H | H | NO$_2$ H | Cl | OCH$_3$ | CH | |
| Q-43 | H | H | SCH$_2$CH$_2$F | H | OCH$_3$ | OCH$_3$ | CH |
| Q-43 | H | H | CH$_2$—CH=CH$_2$ | H | OCH$_3$ | CH$_3$ | CH |
| Q-43 | H | H | CH$_2$—C≡CH | H | CH$_3$ | CH$_3$ | CH |
| Q-43 | H | H | CO$_2$CH$_3$ | H | CH$_3$ | OCH$_3$ | N |
| Q-43 | H | H | CO$_2$CH$_3$ | H | OCH$_3$ | OCH$_3$ | CH |
| Q-43 | H | H | CO$_2$CH$_3$ | H | OCH$_3$ | CH$_3$ | CH |
| Q-43 | H | H | CO$_2$CH$_2$CH$_3$ | H | CH$_3$ | CH$_3$ | CH |
| Q-43 | H | H | CO$_2$CH$_2$CH$_2$CH$_3$ | H | OCH$_3$ | OCH$_3$ | CH |
| Q-43 | H | H | SCH$_3$ | H | CH$_3$ | CH$_3$ | N |
| Q-43 | H | H | SOCH$_3$ | H | CH$_3$ | CH$_3$ | CH |
| Q-43 | H | H | SO$_2$CH$_3$ | H | OCH$_3$ | OCH$_3$ | CH |
| Q-43 | H | H | SO$_2$CH$_2$CH$_3$ | H | OCH$_3$ | OCH$_3$ | N |
| Q-43 | H | H | SO$_2$N(CH$_3$)$_2$ | H | CH$_3$ | OCH$_3$ | CH |
| Q-43 | H | H | SO$_2$N(CH$_2$CH$_3$)$_2$ | H | OCH$_3$ | OCH$_3$ | CH |
| Q-43 | CH$_3$ | H | CO$_2$CH$_3$ | H | OCH$_3$ | OCH$_3$ | CH |
| Q-43 | H | H | Br | CH$_3$ | OCH$_3$ | OCH$_3$ | CH |
| Q-43 | H | CH$_3$ | Cl | H | OCH$_3$ | OCH$_3$ | N |
| Q-44 | H | H | H | H | CH$_3$ | OCH$_3$ | CH |
| Q-44 | H | H | CH$_2$CH$_3$ | H | OCH$_3$ | OCH$_3$ | CH |
| Q-44 | H | H | F | H | CH$_3$ | CH$_3$ | CH |
| Q-44 | H | H | Cl | H | OCH$_3$ | OCH$_3$ | CH |
| Q-44 | H | H | Br | H | OCH$_3$ | CH$_3$ | CH |
| Q-44 | H | H | NO$_2$ | H | OCH$_3$ | OCH$_3$ | CH |
| Q-44 | H | H | SCH$_2$F | H | CH$_3$ | OCH$_3$ | CH |
| Q-44 | H | H | SCH$_2$F | H | OCH$_3$ | OCH$_3$ | CH |
| Q-44 | H | H | CH$_2$—CH=CH$_2$ | H | Cl | OCH$_3$ | CH |
| Q-44 | H | H | CH$_2$—C≡CH | H | OCH$_3$ | OCH$_3$ | CH |
| Q-44 | H | H | CO$_2$CH$_3$ | H | OCH$_3$ | OCH$_3$ | CH |
| Q-44 | H | H | CO$_2$CH$_3$ | H | OCH$_3$ | CH$_3$ | CH |
| Q-44 | H | H | CO$_2$CH$_2$CH$_2$Cl | H | CH$_3$ | CH$_3$ | N |
| Q-44 | H | H | CO$_2$CH$_2$CH$_3$ | H | OCH$_3$ | OCH$_3$ | CH |
| Q-44 | H | H | SCH$_3$ | H | CH$_3$ | OCH$_3$ | CH |

TABLE XXV-continued

General Formula XXV

| Q | | | | | | | |
|---|---|---|---|---|---|---|---|
| Q-44 | H | H | SOCH$_3$ | H | CH$_3$ | CH$_3$ | CH |
| Q-44 | H | H | SO$_2$CH$_3$ | H | OCH$_3$ | OCH$_3$ | CH |
| Q-44 | H | H | SO$_2$N(CH$_3$)$_2$ | H | OCH$_3$ | CH$_3$ | CH |
| Q-44 | H | H | SO$_2$N(CH$_3$)$_2$ | H | OCH$_3$ | CH$_3$ | N |
| Q-44 | H | H | SO$_2$N(CH$_2$CH$_3$)$_2$ | H | OCH$_3$ | OCH$_3$ | CH |
| Q-44 | CH$_3$ | H | Cl | H | CH$_3$ | CH$_3$ | CH |
| Q-44 | H | CH$_3$ | Br | H | OCH$_3$ | OCH$_3$ | N |
| Q-44 | H | Cl | CO$_2$CH$_3$ | H | CH$_3$ | OCH$_3$ | CH |

TABLE XXVI

General Formula XXVI
($R_6 = R_7 = R_9 = H$)

| Q | R | R$_2$ | R$_{14}$ | X | Y | Z | X$_1$ | Y$_1$ | Y$_2$ | A | m.p. °C. |
|---|---|---|---|---|---|---|---|---|---|---|---|
| Q-1 | H | H | CO$_2$CH$_3$ | OCF$_2$H | CH$_3$ | CH | — | — | — | A-1 | |
| Q-6 | H | H | Br | CH$_2$F | OCH$_3$ | CH | — | — | — | A-1 | |
| Q-9 | H | H | Cl | Br | OCH$_3$ | CH | — | — | — | A-1 | |
| Q-11 | H | H | CH$_2$CH$_3$ | OCH$_2$CF$_3$ | NHCH$_3$ | CH | — | — | — | A-1 | |
| Q-30 | H | H | SCH$_3$ | CF$_3$ | OCH$_3$ | N | — | — | — | A-1 | |
| Q-32 | H | H | Br | — | — | — | CH$_3$ | O | — | A-2 | |
| Q-37 | H | H | Cl | — | — | — | OCH$_3$ | CH$_2$ | — | A-2 | |
| Q-41 | H | H | CO$_2$CH$_3$ | — | — | — | OCH$_3$ | O | — | A-2 | |
| Q-42 | H | H | CO$_2$CH$_3$ | — | — | — | CH$_3$ | — | — | A-3 | |
| Q-44 | H | H | Cl | — | — | — | OCH$_3$ | — | — | A-3 | |
| Q-4 | H | H | CO$_2$CH$_3$ | — | — | — | OCH$_3$ | — | H | A-4 | |
| Q-8 | H | H | Br | — | — | — | OCF$_2$H | — | CH$_3$ | A-4 | |
| Q-1 | H | H | Cl | — | — | — | OCH$_2$CH$_3$ | — | H | A-4 | |

TABLE XXVII

General Formula XXVII

| Q | | R | R$_2$ | R$_{14}$ | X$_2$ | Y$_3$ | m.p. °C. |
|---|---|---|---|---|---|---|---|
| Q-9 | (R$_6$ = CH$_3$) | H | H | CO$_2$CH$_3$ | CH$_3$ | CH$_3$ | |
| Q-9 | (R$_6$ = CH$_3$) | H | H | Cl | CH$_3$ | CH$_3$ | |
| Q-10 | (R$_6$ = CH$_3$) | H | H | CO$_2$C$_2$H$_5$ | CH$_3$ | CH$_3$ | |
| Q-10 | (R$_6$ = CH$_3$) | H | H | Br | CH$_3$ | CH$_3$ | |
| Q-31 | (R$_6$ = R$_7$ = H) | H | H | NO$_2$ | CH$_3$ | CH$_3$ | |
| Q-31 | (R$_6$ = R$_7$ = H) | H | H | CO$_2$C$_2$H$_5$ | CH$_3$ | CH$_3$ | |
| Q-32 | (R$_6$ = R$_7$ = H) | H | H | Br | CH$_3$ | CH$_3$ | |
| Q-32 | (R$_6$ = R$_7$ = H) | H | H | CO$_2$C$_2$H$_5$ | CH$_3$ | CH$_3$ | |
| Q-33 | (R$_6$ = R$_7$ = H) | H | H | Br | CH$_3$ | CH$_3$ | |
| Q-33 | (R$_6$ = R$_7$ = H) | H | H | CO$_2$C$_2$H$_5$ | CH$_3$ | CH$_3$ | |
| Q-34 | (R$_6$ = R$_{10}$ = R$_{11}$ = H) | H | H | Br | CH$_3$ | CH$_3$ | |
| Q-34 | (R$_6$ = R$_{10}$ = R$_{11}$ = H) | H | H | CO$_2$C$_2$H$_5$ | CH$_3$ | CH$_3$ | |
| Q-37 | (R$_6$ = R$_7$ = H) | H | H | Br | CH$_3$ | CH$_3$ | |
| Q-37 | (R$_6$ = R$_7$ = H) | H | H | CO$_2$C$_2$H$_5$ | CH$_3$ | CH$_3$ | |

TABLE XXVIII

General Formula XXVIII

| Q | | R | R$_2$ | R$_{14}$ | X$_2$ | m.p. °C. |
|---|---|---|---|---|---|---|
| Q-9 | (R$_6$ = CH$_3$) | H | H | CO$_2$CH$_3$ | CH$_3$ | |
| Q-9 | (R$_6$ = CH$_3$) | H | H | Cl | CH$_3$ | |
| Q-10 | (R$_6$ = CH$_3$) | H | H | CO$_2$C$_2$H$_5$ | CH$_3$ | |
| Q-10 | (R$_6$ = CH$_3$) | H | H | Br | CH$_3$ | |
| Q-31 | (R$_6$ = R$_7$ = H) | H | H | NO$_2$ | CH$_3$ | |
| Q-31 | (R$_6$ = R$_7$ = H) | H | H | CO$_2$C$_2$H$_5$ | CH$_3$ | |
| Q-32 | (R$_6$ = R$_7$ = H) | H | H | Br | CH$_3$ | |
| Q-32 | (R$_6$ = R$_7$ = H) | H | H | CO$_2$C$_2$H$_5$ | CH$_3$ | |
| Q-33 | (R$_6$ = R$_7$ = H) | H | H | Br | CH$_3$ | |
| Q-33 | (R$_6$ = R$_7$ = H) | H | H | CO$_2$C$_2$H$_5$ | CH$_3$ | |
| Q-34 | (R$_6$ = R$_{10}$ = R$_{11}$ = H) | H | H | Br | CH$_3$ | |
| Q-34 | (R$_6$ = R$_{10}$ = R$_{11}$ = H) | H | H | CO$_2$C$_2$H$_5$ | CH$_3$ | |
| Q-37 | (R$_6$ = R$_7$ = H) | H | H | Br | CH$_3$ | |
| Q-37 | (R$_6$ = R$_7$ = H) | H | H | CO$_2$C$_2$H$_5$ | CH$_3$ | |

TABLE XXIX

General Formula XXIX

| Q | | R | R$_2$ | R$_{14}$ | X$_4$ | Y$_4$ | Z | m.p. °C |
|---|---|---|---|---|---|---|---|---|
| Q-9 | (R$_6$ = H) | H | H | CO$_2$CH$_3$ | CH$_3$ | CH$_3$ | N | |
| Q-9 | (R$_6$ = H) | H | H | Cl | CH$_3$ | CH$_3$ | CH | |
| Q-10 | (R$_6$ = H) | H | H | CO$_2$C$_2$H$_5$ | CH$_3$ | CH$_3$ | CH | |
| 0-10 | (R$_6$ = H) | H | H | Br | CH$_3$ | CH$_3$ | N | |
| Q-31 | (R$_6$ = R$_7$ = H) | H | H | NO$_2$ | CH$_3$ | CH$_3$ | CH | |
| Q-31 | (R$_6$ = R$_7$ = H) | H | H | CO$_2$C$_2$H$_5$ | CH$_3$ | CH$_3$ | CH | |
| Q-32 | (R$_6$ = R$_7$ = H) | H | H | Br | CH$_3$ | CH$_3$ | CH | |
| Q-32 | (R$_6$ = R$_7$ = H) | H | H | CO$_2$C$_2$H$_5$ | CH$_3$ | CH$_3$ | N | |
| Q-33 | (R$_6$ = R$_7$ = H) | H | H | Br | CH$_3$ | CH$_3$ | CH | |

TABLE XXIX-continued

| Q | | R | $R_2$ | $R_{14}$ | $X_4$ | $Y_4$ | Z | m.p. °C |
|---|---|---|---|---|---|---|---|---|
| Q-33 | ($R_6 = R_7 = H$) | H | H | $CO_2C_2H_5$ | $CH_3$ | $CH_3$ | CH | |
| Q-34 | ($R_6 = R_{10} = R_{11} = H$) | H | H | Br | $CH_3$ | $CH_3$ | CH | |
| Q-34 | ($R_6 = R_{10} = R_{11} = H$) | H | H | $CO_2C_2H_5$ | $CH_3$ | $CH_3$ | CH | |
| Q-37 | ($R_6 = R_7 = H$) | H | H | Br | $CH_3$ | $CH_3$ | N | |
| Q-37 | ($R_6 = R_7 = H$) | H | H | $CO_2C_2H_5$ | $CH_3$ | $CH_3$ | CH | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of a) about 0.1% to 20% surfactant(s) and b) about 5% to 99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 20-90 | 0-74 | 1-10 |
| Oil Suspensions, Emulsions, Solutions (including Emulsifiable Concentrates) | 1-50 | 40-95 | 0-15 |
| Aqueous Suspensions | 5-50 | 40-84 | 1-20 |
| Dusts | 1-25 | 70-99 | 0-5 |
| Granules and Pellets | 1-95 | 5-99 | 0-15 |
| High Strength Compositions | 90-99 | 0-10 | 0-2 |

Lower or higher levels of active ingredient can, of course, be present depending on the intended use and the physical properties of the compound. Higher ratios of surfactant to active ingredient are sometimes desirable, and are achieved by either incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 4th Ed., McGraw-Hill, New York, 1973, pp.8–59ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knüsli, U.S. Pat. No. 2,891,855, June 23, 1959, Col. 3, line 66 through Col. 5, line 17 and Examples 1–4;

G. C. Klingman, "Weed Control as a Science", John Wiley and Sons, Inc., New York, 1961, pp. 81–96;

J. D. Fryer and S. A. Evans, "Weed Control Handbook", 5th Ed., Blackwell Scientific Publications, Oxford, 1968, pp. 101–103;

J. B. Buchanan, U.S. Pat. No. 3,576,834, Apr. 27, 1971, Col. 5, Line 36 through Col. 7, Line 70 and Ex. 1–4, 17, 106 and 123–140;

R. R. Shaffer, U.S. Pat. No. 3,560,616, Feb. 2, 1971, Col. 3, Line 48 through Col. 7, Line 26 and Examples 3–9 and 11–18; and E. Somers, "Formulation", Chapter 6 in Torgeson, "Fungicides", Vol. I, Academic Press, New York, 1967.

In the following examples, all parts are by weight unless otherwise indicated.

EXAMPLE 9

Wettable Powder

| | |
|---|---|
| N—[(4,6-dimethoxypyrimidin-2-yl)aminocarbonyl]-1,5-dimethyl-3-[5-(methylthio)-1,3,4-oxadiazol-2-yl]-1H—pyrazole-4-sulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended and hammer-milled to produce particles of active ingredient essentially all below 20 microns in diameter. The product is reblended before packaging.

EXAMPLE 10

Oil Suspension

| | |
|---|---|
| N—[(4,6-dimethoxypyrimidin-2-yl)amino-carbonyl]-1,3-dimethyl-5-[5-(methylthio)-1,3,4-oxadiazol-2-yl]-1H—pyrazole-4-sulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting suspension may be applied directly, but preferably after being extended with oils or emulsified in water.

EXAMPLE 11

Oil Suspension

| | |
|---|---|
| N—[(4,6-dimethoxypyrimidin-2-yl)amino-carbonyl]-1,5-dimethyl-3-[5-(methylthio)-1,3,4-oxadiazol-2-yl]-1H—pyrazole-4-sulfonamide | 35% |
| blend of polyalcohol carboxylic esters and oil soluble petroleum sulfonates | 6% |
| xylene | 59% |

The ingredients are combined and ground together in a sand mill to produce particles essentially all below 3 microns. The product can be used directly, extended with oils, or emulsified in water.

EXAMPLE 12

Solution

| | |
|---|---|
| N—[(4,6-dimethoxypyrimidin-2-yl)amino-carbonyl]-1,3-dimethyl-5-[5-(methylthio)-1,3,4-oxadiazol-2-yl]-1H—pyrazole-4-sulfonamide | 5% |
| dimethylformamide | 95% |

The ingredients are combined and stirred to produce a solution, which can be used for low volume applications.

EXAMPLE 13

Emulsifiable Concentrate

| | |
|---|---|
| N—[(4,6-dimethoxypyrimidin-2-yl)amino-carbonyl]-1,5-dimethyl-3-[5-(methylthio)-1,3,4-oxadiazol-2-yl]-1H—pyrazole-4-sulfonamide | 5% |
| blend of oil soluble sulfonates and polyoxyethylene ethers | 4% |
| xylene | 91% |

The ingredients are combined and stirred until the active is dissolved. A fine screen filter is included in packaging operation to insure the absence of any extraneous undissolved material in the product.

EXAMPLE 14

Aqueous Suspension

| | |
|---|---|
| N—[(4,6-dimethoxypyrimidin-2-yl)amino-carbonyl]-1,3-dimethyl-5-[5-(methylthio)-1,3,4-oxadiazol-2-yl]-1H—pyrazole-4-sulfonamide | 45% |
| dodecylphenol polyethylene glycol ether | 0.5% |
| calcium ligninsulfonate | 5.0% |
| xanthan gum | 0.2% |
| paraformaldehyde | 0.2% |
| water | 49.1% |

The ingredients are slurried and ground together in a sand, ball or roller mill to produce particles essentially all under five microns in size.

EXAMPLE 15

Dust

| | |
|---|---|
| 3-[[(4,6-dimethoxypyrimidin-2-yl)amino-carbonyl]aminosulfonyl]-1-(2-pyridinyl)-1H—pyrazole-4-carboxylic acid, ethyl ester | 10% |
| attapulgite | 10% |
| talc | 80% |

The active ingredient is blended with attapulgite and then passed through a hammermill to produce particles essentially all below 200 microns. The ground concentrate is then blended with powdered talc until homogeneous.

EXAMPLE 16

Granule

| | |
|---|---|
| Wettable Powder of Example 9 | 94% |
| sugar | 6% |

The ingredients are blended in a rotating or fluid bed mixer and sprayed with water to accomplish granulation. When most of the material has reached the desired range of 1.0 to 0.42 mm (U.S.S. #18 to 40 sieves), the granules are removed, dried, and screened. Oversize material is crushed to produce additional material in the desired range. These granules contain 75.2% active ingredient.

EXAMPLE 17

Granule

| | |
|---|---|
| Wettable Powder of Example 9 | 12.5% |
| attapulgite granules (U.S.S. 20–40 mesh; 0.84–0.42 mm) | 87.5% |

A slurry of wettable powder containing 50% solids is sprayed on the surface of attapulgite granules in a double-cone blender. The granules are dried and packaged.

EXAMPLE 18

Extruded Pellet

| | |
|---|---|
| 3-[[(4,6-dimethoxypyrimidin-2-yl)amino-carbonyl]aminosulfonyl]-1-(2-pyridinyl)-1H—pyrazole-4-carboxylic acid, methyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 19

High Strength Concentrate

| | |
|---|---|
| N—[(4,6-dimethoxypyrimidin-2-yl)amino-carbonyl]-1,3-dimethyl-5-[5-(methylthio)-1,3,4-oxadiazol-2-yl]-1H—pyrazole-4-sulfonamide | 95% |
| synthetic amorphous silica | 5% |

The ingredients are blended and ground in a hammermill to produce a high strength concentrate that essentially all passes through a U.S.S. No. 50 sieve (0.3 mm openings). This material may then be formulated in a variety of ways.

UTILITY

Test results indicate that the compounds of the present invention are active herbicides. They should have utility for broad spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, some of the subject compounds are useful for the selective pre- or post-emergence weed control in crops, such as rice, wheat and barley. Alternatively, the subject compounds are useful to modify plant growth.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.010 to 2 kg/ha, the lower rates being suggested for use on lighter soils and/or those having a low organic matter content, for selective weed control or for situations where only short-term persistence is required.

The compounds of the invention may be used in combination with any other commercial herbicide; examples of which are those of the triazine, triazole, uracil, urea, amide, diphenylether, carbamate, and bipyridylium types.

The herbicidal properties of the subject compounds were discovered in greenhouse tests. The test procedures and results follow:

TEST A

Seeds of crabgrass (Digitaria spp.), barnyardgrass (Echinochloa crusgalli), wild oats (Avena fatua), cheatgrass (Bromus secalinus), velvetleaf (Abutilon theophrasti), morningglory (Ipomoea spp.), cocklebur (Xanthium pensylvanicum), sorghum, corn, soybean, cotton, sugar beet, rice, wheat, and purple nutsedge (Cyperus rotundus) tubers were planted and treated preemergence with the test chemicals dissolved in a nonphytotoxic solvent. At the same time, these crop and weed species were treated with a soil/foliage application. At the time of treatment, the plants ranged in height from 2-18 cm. Treated plants and controls were maintained in a greenhouse for sixteen days, after which all species were compared to controls and visually rated for response to treatment. The ratings are based on a numerical scale extending from 0=no injury, to 10 (or &)=complete control. The accompanying descriptive symbols have the following meanings:

C=chlorosis or necrosis;
B=burn;
D=defoliation;
E=emergence inhibition;
G=growth·retardation;
H=formative effects;
U=unusual pigmentation;
X=axillary stimulation;
S=albinism; and
6Y=abscised buds or flowers.

Compounds

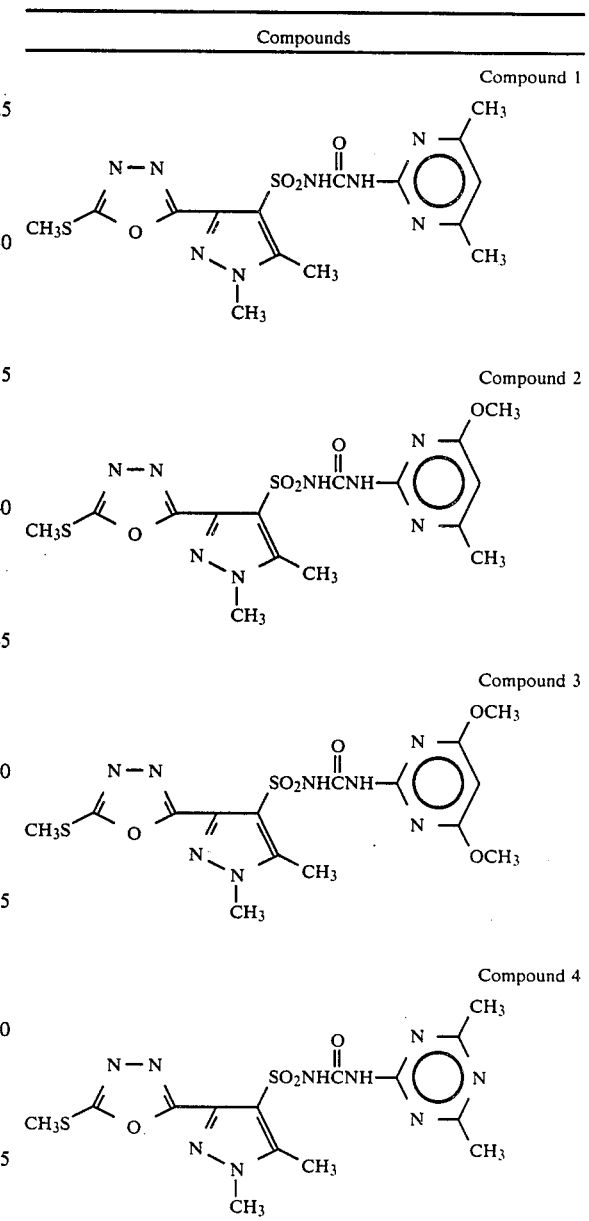

-continued
Compound 5
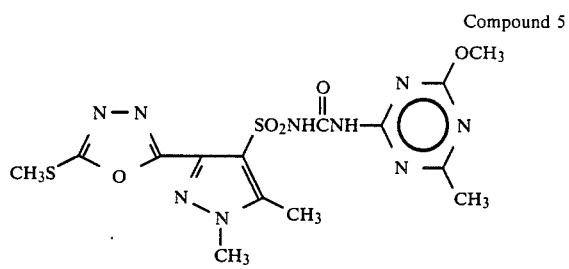
Compound 6
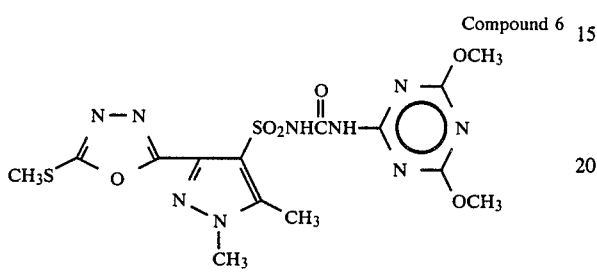
Compound 7
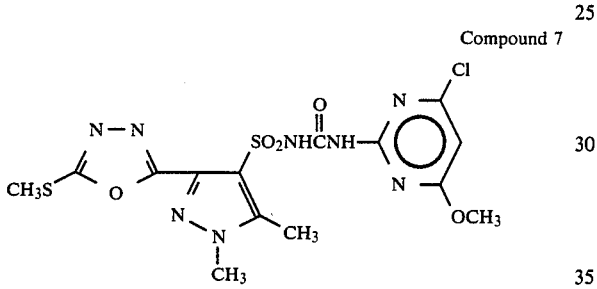
Compound 8
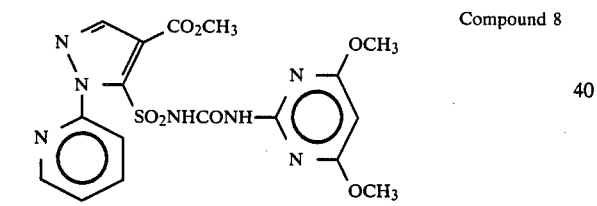
Compound 9
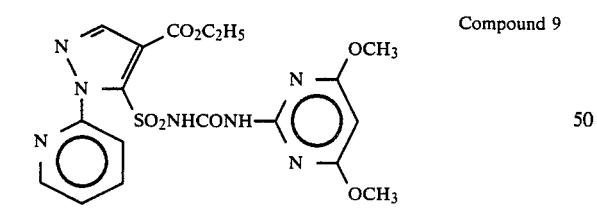
Compound 10
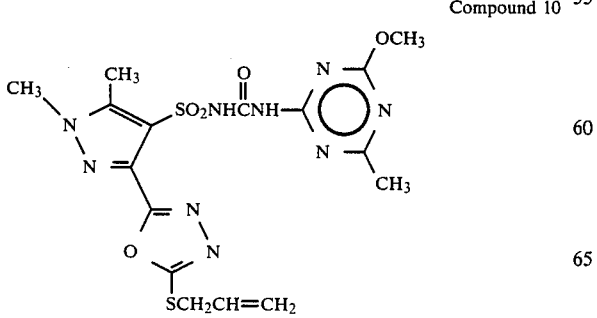
-continued
Compound 11
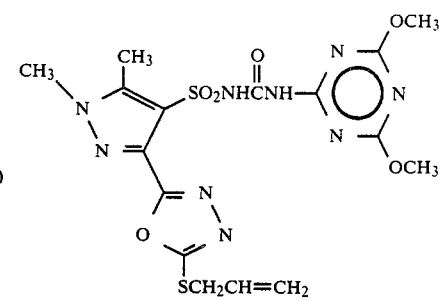
Compound 12
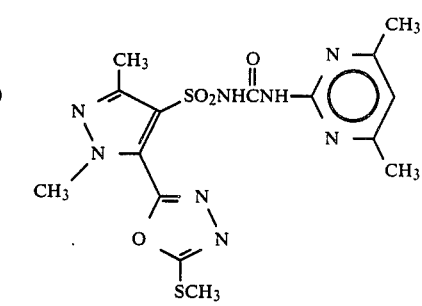
Compound 13
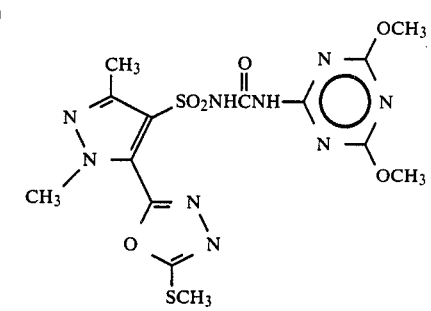
Compound 14
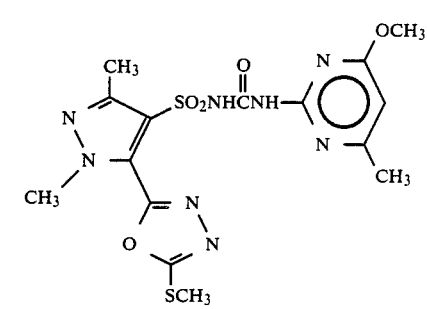
Compound 15
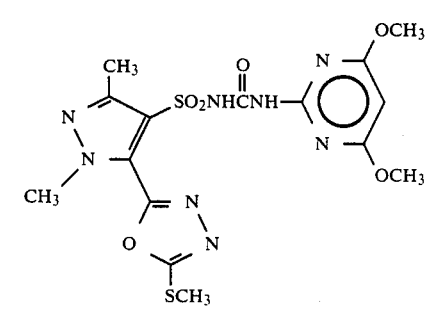

-continued
Compound 16
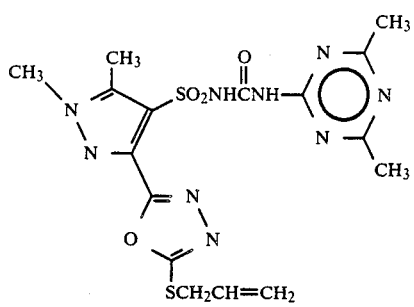
Compound 17
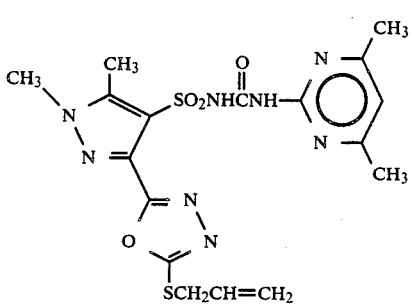
Compound 18
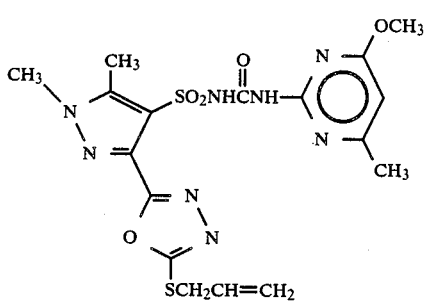
Compound 19
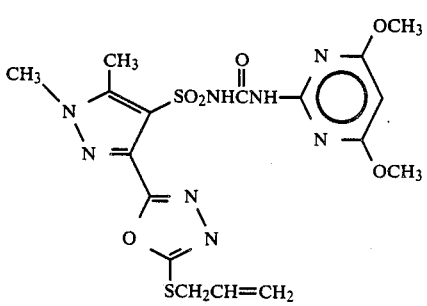
Compound 20
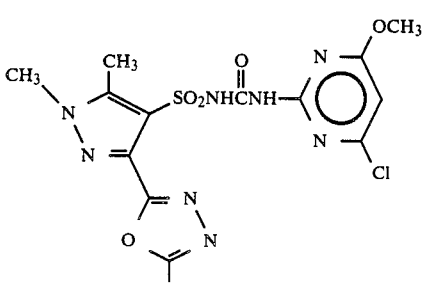
-continued
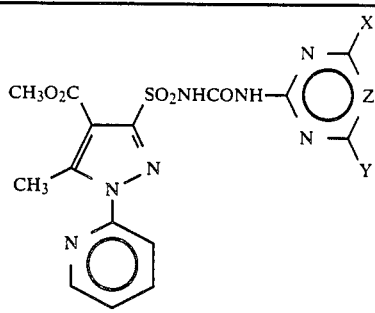
| Compound No. | X | Y | Z |
|---|---|---|---|
| 21 | OCH₃ | OCH₃ | CH |
| 22 | OCH₃ | OCH₃ | N |
| 23 | OCH₃ | CH₃ | CH |
| 24 | CH₃ | CH₃ | CH |
| 25 | Cl | OCH₃ | CH |
| 26 | OCH₃ | CH₃ | N |
Compound 27
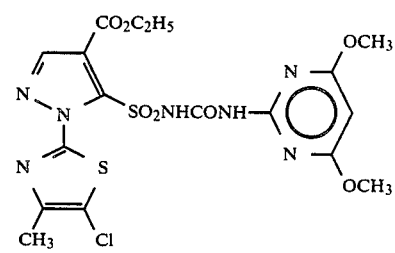
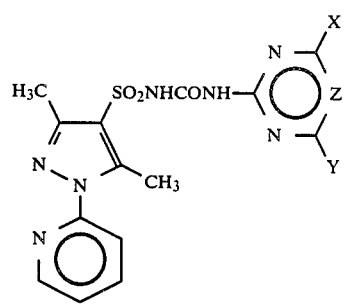
| Compound No. | X | Y | Z |
|---|---|---|---|
| 28 | OCH₃ | OCH₃ | CH |
| 29 | OCH₃ | OCH₃ | N |
| 30 | OCH₃ | CH₃ | CH |
| 31 | CH₃ | CH₃ | CH |
| 32 | Cl | OCH₃ | CH |
| 33 | OCH₃ | CH₃ | N |
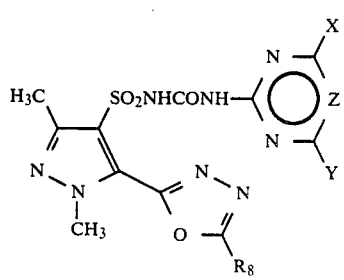
| Compound No. | R₈ | X | Y | Z |
|---|---|---|---|---|
| 34 | SCH₃ | Cl | OCH₃ | CH |
| 35 | SCH₃ | OCH₃ | CH₃ | N |
| 36 | SCH₃ | CH₃ | CH₃ | N |

-continued

| | | | | |
|---|---|---|---|---|
| 37 | SCH$_2$CH=CH$_2$ | CH$_3$ | CH$_3$ | CH |
| 38 | SCH$_2$CH=CH$_2$ | OCH$_3$ | CH$_3$ | CH |
| 39 | SCH$_2$CH=CH$_2$ | OCH$_3$ | OCH$_3$ | CH |
| 40 | SCH$_2$CH=CH$_2$ | Cl | OCH$_3$ | CH |
| 41 | SCH$_2$CH=CH$_2$ | CH$_3$ | CH$_3$ | N |
| 42 | SCH$_2$CH=CH$_2$ | OCH$_3$ | CH$_3$ | N |
| 43 | SCH$_2$CH=CH$_2$ | OCH$_3$ | OCH$_3$ | N |
| 44 | SCH$_2$C(O)CH$_3$ | OCH$_3$ | CH$_3$ | CH |
| 45 | SCH$_2$C(O)CH$_3$ | OCH$_3$ | OCH$_3$ | CH |
| 46 | SCH$_2$C(O)CH$_3$ | Cl | OCH$_3$ | CH |
| 47 | SCH$_2$C(O)CH$_3$ | OCH$_3$ | CH$_3$ | N |
| 48 | SCH$_2$C(O)CH$_3$ | OCH$_3$ | OCH$_3$ | N |
| 49 | SCH$_2$C(O)CH$_3$ | OCH$_3$ | CH$_3$ | CH |
| 50 | SCH(CH$_3$)$_2$ | OCH$_3$ | OCH$_3$ | CH |
| 51 | SCH(CH$_3$)$_2$ | OCH$_3$ | CH$_3$ | N |
| 52 | SCH(CH$_3$)$_2$ | OCH$_3$ | OCH$_3$ | N |
| 53 | SCH$_2$C(Cl)=CH$_2$ | OCH$_3$ | CH$_3$ | CH |
| 54 | SCH$_2$C(Cl)=CH$_2$ | OCH$_3$ | OCH$_3$ | CH |
| 55 | SCH$_2$C(Cl)=CH$_2$ | OCH$_3$ | CH$_3$ | N |
| 56 | SCH$_2$C(Cl)=CH$_2$ | OCH$_3$ | OCH$_3$ | N |
| 57 | SCH$_2$CN | OCH$_3$ | CH$_3$ | CH |
| 58 | SCH$_2$CN | OCH$_3$ | OCH$_3$ | CH |
| 59 | SCH$_2$CN | Cl | OCH$_3$ | CH |
| 60 | SCH$_2$CN | OCH$_3$ | CH$_3$ | N |
| 61 | SCH$_2$CN | OCH$_3$ | OCH$_3$ | N |
| 62 | S(CH$_2$)$_5$CH$_3$ | OCH$_3$ | CH$_3$ | CH |
| 63 | S(CH$_2$)$_5$CH$_3$ | OCH$_3$ | OCH$_3$ | CH |
| 64 | S(CH$_2$)$_5$CH$_3$ | Cl | OCH$_3$ | CH |
| 65 | S(CH$_2$)$_5$CH$_3$ | OCH$_3$ | CH$_3$ | N |
| 66 | S(CH$_2$)$_5$CH$_3$ | OCH$_3$ | OCH$_3$ | N |

| Compound No. | R$_8$ | X | Y | Z |
|---|---|---|---|---|
| 67 | SH | OCH$_3$ | OCH$_3$ | CH |
| 68 | SCH$_3$ | CH$_3$ | CH$_3$ | CH |
| 69 | SCH$_3$ | OCH$_3$ | CH$_3$ | CH |
| 70 | SCH$_3$ | OCH$_3$ | OCH$_3$ | CH |
| 71 | SCH$_3$ | Cl | OCH$_3$ | CH |
| 72 | SCH$_3$ | OCH$_3$ | CH$_3$ | N |
| 73 | SCH$_3$ | OCH$_3$ | OCH$_3$ | N |
| 74 | SCH$_2$C$_6$H$_5$ | CH$_3$ | CH$_3$ | CH |
| 75 | SCH$_2$C$_6$H$_5$ | OCH$_3$ | CH$_3$ | CH |
| 76 | SCH$_2$C$_6$H$_5$ | OCH$_3$ | OCH$_3$ | CH |
| 77 | SCH$_2$C$_6$H$_5$ | Cl | OCH$_3$ | CH |
| 78 | SCH$_2$C$_6$H$_5$ | OCH$_3$ | CH$_3$ | N |
| 79 | SCH$_2$C$_6$H$_5$ | OCH$_3$ | OCH$_3$ | N |

Compound 80

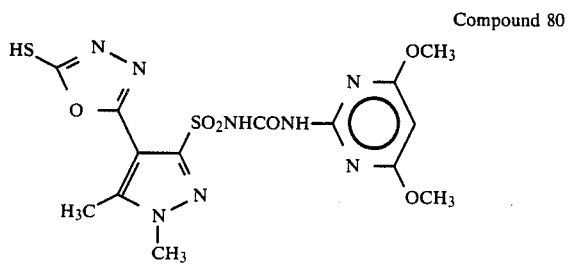

| Compound No. | R$_{18}$ | R$_{19}$ | X | Y | Z |
|---|---|---|---|---|---|
| 81 | SCH$_3$ | CH$_3$ | CH$_3$ | CH$_3$ | CH |
| 82 | SCH$_3$ | CH$_3$ | OCH$_3$ | CH$_3$ | CH |
| 83 | SCH$_3$ | CH$_3$ | OCH$_3$ | OCH$_3$ | CH |
| 84 | SCH$_3$ | CH$_3$ | Cl | OCH$_3$ | CH |
| 85 | SCH$_3$ | CH$_3$ | OCH$_3$ | CH$_3$ | N |
| 86 | SCH$_3$ | CH$_3$ | OCH$_3$ | OCH$_3$ | N |
| 87 | SCH$_3$ | CH$_2$CH=CH$_2$ | OCH$_3$ | OCH$_3$ | CH |
| 88 | SCH$_3$ | CH$_2$CH=CH$_2$ | OCH$_3$ | CH$_3$ | CH |
| 89 | SCH$_2$CH=CH$_2$ | CH$_2$CH=CH$_2$ | OCH$_3$ | OCH$_3$ | CH |
| 90 | SCH$_2$CH=CH$_2$ | CH$_2$CH=CH$_2$ | OCH$_3$ | CH$_3$ | CH |
| 91 | SCH$_2$CH=CH$_2$ | CH$_3$ | OCH$_3$ | OCH$_3$ | CH |
| 92 | SCH$_2$CH=CH$_2$ | CH$_3$ | OCH$_3$ | CH$_3$ | CH |
| 93 | SCH$_3$ | CH$_2$CH=CH$_2$ | CH$_3$ | CH$_3$ | CH |
| 94 | SCH$_3$ | CH$_2$CH=CH$_2$ | Cl | OCH$_3$ | CH |
| 95 | SCH$_3$ | CH$_2$CH=CH$_2$ | OCH$_3$ | CH$_3$ | N |
| 96 | SCH$_3$ | CH$_2$CH=CH$_2$ | OCH$_3$ | OCH$_3$ | N |
| 97 | SCH$_2$CH=CH$_2$ | CH$_2$CH=CH$_2$ | CH$_3$ | CH$_3$ | CH |
| 98 | SCH$_2$CH=CH$_2$ | CH$_2$CH=CH$_2$ | Cl | OCH$_3$ | CH |
| 99 | SCH$_2$CH=CH$_2$ | CH$_2$CH=CH$_2$ | OCH$_3$ | CH$_3$ | N |
| 100 | SCH$_2$CH=CH$_2$ | CH$_2$CH=CH$_2$ | OCH$_3$ | OCH$_3$ | N |
| 101 | SCH$_2$CH=CH$_2$ | CH$_3$ | CH$_3$ | CH$_3$ | CH |
| 102 | SCH$_2$CH=CH$_2$ | CH$_3$ | Cl | OCH$_3$ | CH |
| 103 | SCH$_2$CH=CH$_2$ | CH$_3$ | OCH$_3$ | CH$_3$ | N |
| 104 | SCH$_2$CH=CH$_2$ | CH$_3$ | OCH$_3$ | OCH$_3$ | N |

Compound 105

| Compound No. | R$_8$ | X | Y | Z |
|---|---|---|---|---|
| 106 | SCH$_3$ | CH$_3$ | CH$_3$ | CH |
| 107 | SCH$_3$ | OCH$_3$ | CH$_3$ | CH |
| 108 | SCH$_3$ | OCH$_3$ | OCH$_3$ | CH |
| 109 | SCH$_3$ | Cl | OCH$_3$ | CH |
| 110 | SCH$_3$ | OCH$_3$ | CH$_3$ | N |
| 111 | SCH$_3$ | OCH$_3$ | OCH$_3$ | N |
| 112 | SCH$_2$CH=CH$_2$ | CH$_3$ | CH$_3$ | CH |
| 113 | SCH$_2$CH=CH$_2$ | OCH$_3$ | CH$_3$ | CH |
| 114 | SCH$_2$CH=CH$_2$ | OCH$_3$ | OCH$_3$ | CH |
| 115 | SCH$_2$CH=CH$_2$ | Cl | OCH$_3$ | CH |
| 116 | SCH$_2$CH=CH$_2$ | OCH$_3$ | CH$_3$ | N |
| 117 | SCH$_2$CH=CH$_2$ | OCH$_3$ | OCH$_3$ | N |

-continued
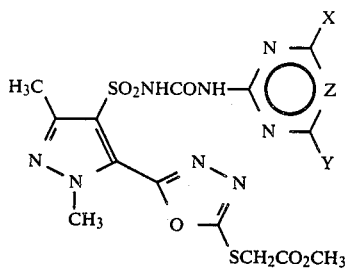
| Compound No. | X | Y | Z |
|---|---|---|---|
| 118 | OCH$_3$ | CH$_3$ | N |
| 119 | OCH$_3$ | CH$_3$ | CH |
| 120 | OCH$_3$ | OCH$_3$ | CH |
-continued
| 121 | Cl | OCH$_3$ | CH |
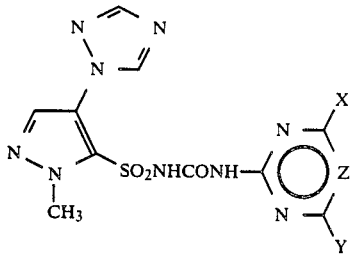
| Compound No. | X | Y | Z |
|---|---|---|---|
| 122 | OCH$_3$ | CH$_3$ | CH |
| 123 | OCH$_3$ | OCH$_3$ | CH |

TABLE A

| Rate | Compound 1 0.05 | Compound 2 0.05 | Compound 3 0.05 | Compound 4 0.05 | Compound 5 0.05 | Compound 6 0.05 | Compound 7 0.05 | Compound 8 0.05 | Compound 9 0.05 | Compound 10 0.05 | Compound 11 0.05 | Compound 12 0.05 |
|---|---|---|---|---|---|---|---|---|---|---|---|---|
| POSTEMERGENCE | | | | | | | | | | | | |
| Morningglory | 1H | 5C,9G | 4C,9G | 0 | 2C,5G | 4H | 7H | 2G | 3G | 0 | 0 | 2C,5G |
| Cocklebur | 2G | 5C,9H | 4C,9H | 1H | 0 | 1H | 7G | 10C | 10C | 0 | 0 | 5C,9G |
| Velvetleaf | 2C,4G | 4C,8H | 9C | 2H | 8G | 2H | 2C,8H | 9C | 9C | 0 | 0 | 6C,9G |
| Nutsedge | 0 | 3C,8G | 2C,9G | 0 | 2C,5G | 0 | 2C | 10C | 10C | 0 | 0 | 3C,8G |
| Crabgrass | 0 | 0 | 2C,5G | 0 | 0 | 0 | 0 | 2G | 2C,5G | 0 | 0 | 3C,6G |
| Barnyardgrass | 0 | 3H | 2C,3H | 0 | 2C,5G | 0 | 0 | 9C | 9C | 0 | 0 | 2C,8H |
| Wild Oats | 0 | 0 | 2G | 0 | 2C,4G | 0 | 0 | 0 | 3C,9G | 0 | 0 | 0 |
| Wheat | 0 | 0 | 3G | 0 | 2C,7G | 0 | 0 | 0 | 3C,9G | 0 | 0 | 2C,8G |
| Corn | 3C,9H | 3C,9H | 4C,9H | 2C,6H | 9G | 4C,9H | 2C,6H | 6C,9G | 5C,9G | 0 | 0 | 1C,3G |
| Soybean | 2C,2H | 4C,8G | 4C,9G,7X | 2C,3G | 2C,2H | 1H | 0 | 2C,9G | 3C,9G | 2C,7H | 0 | 2C,7H |
| Rice | 6G | 8G | 5C,9G | 6G | 4C,9G | 4C,9G | 5G | 3C,9G | 4C,9G | 0 | 0 | 2C,8G |
| Sorghum | 2C,6G | 4C,8H | 9H | 2C,3G | 4C,8H | 2C,8H | 2C,7H | 5C,9H | 9C | 0 | 0 | 3C,9H |
| Cheatgrass | 0 | 2C | 2C,7H | 0 | 2C,8G | 2C | 0 | 3C,8G | 10C | 0 | 0 | 2C,7G |
| Sugar Beets | 0 | 3C,7G | 3C,8G | 0 | 5H | 2C,5H | 0 | 3G | 4G | 3H | 4H | 4C,8H |
| Cotton | 2C,2H | 4C,9H | 4C,9H | 1H | 2C,4H | 2C,4H | 2C,5G | 9C | 4C,9G | 0 | 3G | 4C,9G |
| Sicklepod | | | | | | | | | | | | |
| PREEMERGENCE | | | | | | | | | | | | |
| Morningglory | 0 | 0 | 8H | 2C | 0 | 2C,2H | 1C | 2C,6G | 7G | 0 | 0 | 0 |
| Cocklebur | 0 | 0 | 8H | — | 0 | 0 | — | 9H | 9H | 0 | 2G | 2G |
| Velvetleaf | — | 4C,9G | 4C,9G | 0 | 0 | — | 5G | 3C,9G | 8H | 0 | 0 | 2C,5G |
| Nutsedge | 0 | 0 | 0 | 0 | 0 | 0 | 0 | 10E | 10E | 0 | 0 | 0 |
| Crabgrass | 0 | 0 | 0 | 0 | 0 | 2G | 0 | 0 | 0 | 0 | 4G | 4G |
| Barnyardgrass | 0 | 0 | 2C,7G | 0 | 0 | 2G | 0 | 3C,6H | 3C,8H | 0 | 0 | 0 |
| Wild Oats | 0 | 0 | 2C,6G | 0 | 0 | 2C | 0 | 0 | 0 | 0 | 0 | 0 |
| Wheat | 0 | 0 | 3C,8H | 0 | 0 | 2G | 0 | 0 | 6G | 0 | 4G | 4G |
| Corn | 0 | 0 | 2C | 2G | 0 | 2G | 0 | 4C,9G | 9C | 0 | 2G | 2G |
| Soybean | 0 | 0 | 3C,7H | 0 | 0 | 2G | 0 | 4C,5G | 3C,6G | 0 | 2G | 2G |
| Rice | 0 | 0 | 3C,7H | 0 | 0 | 2G | 0 | 2C,6G | 4C,8H | 0 | 2C,5G | 2C,5G |
| Sorghum | 0 | 0 | 4C,8G | 0 | 0 | 2G | 0 | 3C,9H | 3C,9H | 0 | 3C,6G | 3C,6G |
| Cheatgrass | 0 | 0 | 0 | 0 | 0 | 4G | 0 | 8G | 4C,7G | 0 | 0 | 0 |
| Sugar Beets | 0 | 5G | 5G | 4G | 0 | 3H | 0 | 10E | 8G | 0 | 4H | 4H |
| Cotton | 0 | 5G | 5G | 0 | 0 | 2G | 0 | 9G | 9G | 0 | 3G | 3G |
| Sicklepod | | | | | | | | | | | | |

| Rate | Compound 13 0.05 | Compound 14 0.05 | Compound 15 0.05 | Compound 16 0.05 | Compound 17 0.05 | Compound 18 0.05 | Compound 19 0.05 | Compound 20 0.05 | Compound 21 0.05 | Compound 22 0.05 | Compound 23 0.05 | Compound 24 0.05 |
|---|---|---|---|---|---|---|---|---|---|---|---|---|
| POSTEMERGENCE | | | | | | | | | | | | |
| Morningglory | 10C | 10C | 0 | 0 | 0 | 4C,8H | 0 | 8C | &C | 3C 8H | 4C 9H | 2C 6G |
| Cocklebur | 10C | 10C | 0 | 0 | 0 | 3C,7G | 0 | &C | &C | 2C 5G | 4C 9H | 2C 5G |
| Velvetleaf | 4C,9G | 9C | 0 | 0 | 3C,7H | 5C,9G | 0 | 9C | 9C | 2C 2H | 4C 8H | 2C 5G |
| Nutsedge | 3C,9G | 5C,9G | 0 | 0 | 0 | 3C,8G | 0 | 9G | 9G | 0 | 3C 9G | 0 |
| Crabgrass | 0 | 2G | 0 | 0 | 0 | 2C,7H | 0 | 2C 4G | 2C 4G | 5H | 0 | 2G |
| Barnyardgrass | 4C,9H | 3C,9H | 0 | 0 | 0 | 2C,7H | 0 | 9H | 9H | 5C 9H | 5C 9H | 2C 5H |
| Wild Oats | 2C,9G | 2C,8G | 0 | 0 | 0 | 2H | 0 | 2C 8H | 2C 8H | 0 | 0 | 0 |
| Wheat | 3C,9G | 2C,9G | 0 | 0 | 0 | 2C,6G | 0 | 9G | 9G | 5G | 5G | 0 |
| Corn | 9G | 4C,9H | 0 | 0 | 0 | 3C,9H | 0 | 9C | 9C | 4C 9G | 4C 9G | 4G |
| Soybean | 4C,9G | 5C,9H | 0 | 0 | 0 | 3C,7H | 0 | 5C 9G | 5C 9G | 3C 7H | 5C 9G | 3C 8H |
| Rice | 9C | 5C,9G | 0 | 0 | 2C,5G | 5C,9G | 0 | 9C | 9C | 5C 9G | 9C | 2C 5H |
| Sorghum | 9C | 4C,9G | 0 | 0 | 0 | 4C,8H | 0 | 4C 9H | 4C 9H | 4C 8G | 5C 9H | 4C 8H |

TABLE A-continued

| | Compound 25 | Compound 26 | Compound 27 | Compound 28 | Compound 29 | Compound 30 | Compound 31 | Compound 32 | Compound 33 | Compound 34 | Compound 35 | Compound 36 |
|---|---|---|---|---|---|---|---|---|---|---|---|---|
| Cheatgrass | 5C,9G | 3C,8G | 3C,8G | | | | | | | 2C 8G | 5C 9G | 2C 6G |
| Sugar Beets | 9C | 9C | 9C | | | | | | | 3H | 9C | 3C 7H |
| Cotton | 4C,9G | 9C | 5C,9G | | | 2C,6G | | | | 0 | 4C 9G | 2G |

PREEMERGENCE

| Morningglory | 9C | 9G | 9C | | | | | | | 2C 5H | 8G | 0 |
| Cocklebur | 8H | — | 8H | | | | | | | 0 | 0 | 0 |
| Velvetleaf | 6G | 5C,9G | 4C,9G | | | | | | | 2G | 3C 6H | 0 |
| Nutsedge | 4G | 10E | 10E | | | | | | | 0 | 0 | 0 |
| Crabgrass | 0 | 2C,3G | 0 | | | | | | | 0 | 0 | 0 |
| Barnyardgrass | 2C,3H | 3C,7H | 2C,4G | | | | | | | 0 | 3C 5G | 0 |
| Wild Oats | 2C,5G | 4C,6G | 2C,5G | | | | | | | 0 | 0 | 0 |
| Wheat | 2C,7G | 3C,8G | 6G | | | | | | | 0 | 2C 5G | 2G |
| Corn | 3C,9H | 9H | 9G | | | | | | | 2C 5G | 5C 8H | 2G |
| Soybean | 3C,5H | 2C,6H | 3C,5H | | | 4G | | | | 1C 1H | 4C 6H | 2C |
| Rice | 10E | 10E | 4C,9H | | | | | | | 6G | 4C 9H | 2G |
| Sorghum | 9H | 5C,9H | 2C,9G | | | | | | | 2C 7G | 4C 9H | 2G |
| Cheatgrass | 9G | 10H | 8G | | | | | | | 0 | 7G | 0 |
| Sugar Beets | 5C,9G | 5C,9G | 10E | | | | | | | 0 | 4C 8G | 3G |
| Cotton | 8G | 9G | 8G | | | | | | | 0 | 8G | 0 |
| Sicklepod | | | | | | | | | | | | |

| Rate | 0.05 | 0.05 | 0.05 | 0.05 | 0.05 | 0.05 | 0.05 | 0.05 | 0.05 | 0.05 | 0.05 | 0.05 |

POSTEMERGENCE

| Morningglory | 7G | 2C 2H | | 0 | 3C 9G | 3C 2H | 0 | 2G | 2G | 4C 8G | &C | 4C 8H |
| Cocklebur | 3C 8H | 2G | | 4G | 0 | 3C 9H | 0 | 2C 7G | 2C 7G | &C | &C | 4C 7H |
| Velvetleaf | 1C | 0 | | 0 | 0 | 0 | 0 | 1C | 0 | 9C | 9C | 4C 7G |
| Nutsedge | 6G | 2C 5G | | 2C 6G | 2C 8G | 3C 9G | 0 | 0 | 2C 8G | 2G | 2C 8G | 0 |
| Crabgrass | 0 | 0 | | 3G | 0 | 0 | 0 | 2C 4G | 9H | 9G | 2C 5G | 2C 8G |
| Barnyardgrass | 4C 9H | 2C 5G | | 3C 7G | 2C 5G | 2H | 2H | 4C 9H | 2G | 9C | 9C | 3C 7H |
| Wild Oats | 0 | 0 | | 0 | 8G | 3G | 0 | 3C 8G | 2G | 9G | 9G | 3C 8H |
| Wheat | 0 | 3H | | 3C 7H | 3G | 5G | 0 | 2C 9G | 2G | 9G | 9G | 3G |
| Corn | 4C 9H | 3C 8H | | 2C 7H | 2C | 0 | 4G | 3C 8H | 2C 6G | 2C 6G | 2U 9G | 2H |
| Soybean | 1H | 3C 9G | | 3C 8G | 0 | 2G | 2C 5G | 0 | 2C 8G | 2C 8G | 3C 9G | 2G |
| Rice | 4C 9G | 3C 8H | | 3C 4H | 2C 8G | 3C 8G | 0 | 9G | 4C 9G | 4C 9G | 5C 9G | 4C 9G |
| Sorghum | 4C 8H | 5C 9G | | 2C 5G | 2C 5G | 3C 8G | 0 | 3C 9G | 9H | 9H | 9C | 4C 8H |
| Cheatgrass | 7G | 2C 6G | | 3G | 3G | 3C 3H | 0 | 0 | 6G | 6G | 6C 9G | 6G |
| Sugar Beets | 5G | 2C 6H | | 0 | 0 | 0 | 0 | 9G | 0 | 4C 9G | 4C 9G | 4C 8H |
| Cotton | 4G | 3C 4H | | 0 | 0 | 3C | 0 | 0 | 4C 9G | 4C 9G | 5C 9G | 4C 8H |
| Sicklepod | | | | | | | | | | | | |

PREEMERGENCE

| Morningglory | 2G | | 5G | 8G | 2H | 2C 6H | 0 | 6G | 9G | 9G | 9G | 0 |
| Cocklebur | 0 | | 0 | 6G | 2C | 0 | 0 | 2H | 2H | 9H | 8H | 0 |
| Velvetleaf | 0 | | 0 | 1C | 0 | 2C | 0 | 0 | 9G | 9G | 2C 8G | 0 |
| Nutsedge | 0 | | 0 | 0 | 0 | 0 | 0 | 5G | 9G | 4G | 4G | 0 |
| Crabgrass | 0 | | 0 | 0 | 2C | 0 | 0 | 0 | 2C 5G | 2C 5G | 2G | 0 |
| Barnyardgrass | 0 | | 0 | 3C 8G | 2C | 3C 8G | 0 | 5G | 2H | 2H | 9C | 0 |
| Wild Oats | 0 | | 0 | 2C | 2G | 2C 7G | 0 | 0 | 5G | 0 | 3C 7G | 0 |
| Wheat | 0 | | 0 | 2C | 2G | 0 | 0 | 5G | 0 | 0 | 3C 8G | 0 |
| Corn | 3C 5G | | 5G | 3C 5G | 0 | 2C 2H | 0 | 3G | 2C 9G | 2C 7G | 2C 8G | 0 |
| Soybean | 0 | | 0 | 0 | 0 | 3C | 0 | 1C | 1C | 2C 5G | 4C 9H | 0 |
| Rice | 8H | | 0 | 3C 5G | 0 | | | 6G | | 8H | 7H | 0 |

TABLE A-continued

| | Compound 37 | Compound 38 | Compound 39 | Compound 40 | Compound 41 | Compound 42 | Compound 43 | Compound 44 | Compound 45 | Compound 46 | Compound 47 | Compound 48 |
|---|---|---|---|---|---|---|---|---|---|---|---|---|
| Sorghum | 2C 8H | 2C 7G | 2C 5G | 2C 3G | | 2C | | 2C 5G | 2C 8H | | 3C 9H | |
| Cheatgrass | 0 | 0 | 0 | 0 | | 6G | | 0 | 5G | | 3C 9H | 0 |
| Sugar Beets | 4G | 0 | 0 | 0 | | 3C 7G | | 0 | 4C 9G | | 9C | 0 |
| Cotton | 3G | 0 | 0 | 0 | | 0 | 4G | 0 | 0 | | 9G | 0 |
| Sicklepod | | | | | | | 0 | | | | | |
| Rate | 0.05 | 0.05 | 0.05 | 0.05 | 0.05 | 0.05 | 0.05 | 0.05 | 0.05 | 0.05 | 0.05 | 0.05 |

POSTEMERGENCE

| | Compound 37 | Compound 38 | Compound 39 | Compound 40 | Compound 41 | Compound 42 | Compound 43 | Compound 44 | Compound 45 | Compound 46 | Compound 47 | Compound 48 |
|---|---|---|---|---|---|---|---|---|---|---|---|---|
| Morningglory | 4G | &C | 3C 8G | 2G | 3C 8G | 3C 8H | 4C 9H | 2C 9G | 4C 9H | 1H | 1H | 1H |
| Cocklebur | 8H | &C | 3C 9G | 2C 8H | 3C 9G | 3C 8H | 9C | &C | 4C 9G | 1H | 1H | 1H |
| Velvetleaf | 9C | &C | 5C 9H | 5G | 8H | 3C 8H | 9C | 9C | 4C 8H | 3C 5G | 3C 5G | 0 |
| Nutsedge | 8G | 9C | 4C 9G | 0 | 8G | 5G | 2C 8G | 8G | 8G | 2C | 2C | 3C 5G |
| Crabgrass | 0 | 9C | 3C 7G | 2H | 3C 5G | 3C 8H | 4C 8G | 2C 8G | 2C 8G | 0 | 2C 8G | 4G |
| Barnyardgrass | 4C 8H | 9C | 9H | 0 | 5C 9H | 5G | 4C 9H | 9C | 3C 9H | 2C 8G | 0 | 4H |
| Wild Oats | 2C 8G | 5C 9G | 3C 8G | 2H | 4C 9G | 3C 8H | 4C 9H | 2C 8G | 3C 5G | 0 | 7G | 6G |
| Wheat | 8G | 2C 9G | 7G | 0 | 4C 9G | 2C 8G | 4C 9H | 6G | 1C 4G | 2C 8G | 2C 8H | 4H |
| Corn | 1C 5G | 5C 9G | 9G | 2C 5H | 3H | 3H | 4C 9H | 9C | 4C 9H | 7G | 0 | 1H |
| Soybean | 4C 9G | 5C 9G | 3C 8H | 0 | 5G | 9C | 9C | 6G | 3C 6H 6X | 0 | 5C 9G | 5C 9G |
| Sorghum | 4C 7H | &C | 5C 9G | 5G | 4C 9G | 3C 9H | 9C | 2C 9G | 4C 9G | 5C 9G | 5C 9G | 4C 8H |
| Rice | 2C 8G | 4C 9G | 2C 9G | 2C | 5C 9G | 3C 8G | 4C 9G | 4C 9G | 3C 9G | 3C 8G | 3C 9G | 2C 8G |
| Cheatgrass | 2C 7G | 2C 9G | 8G | 0 | 8G | 3C 8G | 8G | 4C 9G | 9G | 0 | 3C 8G | 2C 8G |
| Sugar Beets | 5C 9G | &C | 9C | 3G | 5C 9G | 3C 7H | 5C 9G | 9C | 2C 8H | 0 | 0 | 2H |
| Cotton | 3C 9H | 9C | 4C 9G | 0 | 5C 9G | 4C 7G | 3C 9H | 2C 9G | 3C 9G | 1H | 1H | 1H |
| Sicklepod | | | | | | | | | | | | |

| | Compound 49 | Compound 50 | Compound 51 | Compound 52 | Compound 53 | Compound 54 | Compound 55 | Compound 56 | Compound 57 | Compound 58 | Compound 59 | Compound 60 |
|---|---|---|---|---|---|---|---|---|---|---|---|---|
| Morningglory | 2H | 9G | 4C 9G | 8G | 3G | 8H | 8H | 3H | 7G | 7H | 0 | 0 |
| Cocklebur | 0 | 8H | 4C 9H | 8H | 3H | 2H | 2H | 0 | 6G | 6G | 0 | 0 |
| Velvetleaf | 3H | 5C 9G | 9C | 9C | 3G | 1H | 1H | 5G | 2C 8G | 2H | 0 | 0 |
| Nutsedge | 0 | 5G | &E | 2C 6H | 0 | 0 | 0 | 0 | 9G | 0 | 0 | 0 |
| Crabgrass | 0 | 2C 5G | 2C 8G | 5G | 0 | 2G | 2G | 3G | 2G | 4G | 4G | 2G |
| Barnyardgrass | 0 | 2C | 9H | 4G | 2H | 1C | 1C | 2G | 3G | 0 | 0 | 0 |
| Wild Oats | 3G | 3C 8G | 9G | 7H | 2C 5G | 2C 4G | 2C 4G | 0 | 2G | 0 | 0 | 0 |
| Wheat | 0 | 9G | 4C 9G | 2C 6G | 3C 8G | 8G | 8G | 3G | 5G | 0 | 4G | 0 |
| Corn | 0 | 2C 8G | 2C 9G | 2C 7G | 3C 7G | 9G | 9G | 4H | 2C 8G | 4C 7G | 0 | 2G |
| Soybean | 0 | 3H 5G | 3C 7H | 9G | 3C | 9G | 9G | 0 | 3G | 2G | 2C 3G | 0 |
| Rice | 0 | 4C 9G | &E | 3C 3H | 8H | 4C 4G | 4C 4G | 3G | 5G | 3C 6H | 2C 3G | 2G |
| Sorghum | 1C | 4C 9G | 5C 9H | 9H | 3C | 9H | 9H | 8H | 5C 9H | 2G | 3C 4G | 0 |
| Cheatgrass | 0 | 2C 7G | 5C 9H | 3C 9G | 8H | 3C 8H | 3C 8H | 3C 6G | 4C 9H | 3C 6H | 3C 4G | 3C 4G |
| Sugar Beets | 5G | 5C 9G | 6C 9G | 8G | 0 | 5G | 5G | 6H | 2C 9H | 2C 8G | 3C 6G | 0 |
| Cotton | 4G | 9G | 9G | 5C 9G | 9G | 3G | 3G | 5C 9G | 0 | 0 | 2G | 0 |
| Sicklepod | 3C 7G | | | 8G | 4C 9G | 0 | 0 | 9G | 4C 8G | 4C 8G | 3H | 0 |
| Rate | 0.05 | 0.05 | 0.05 | 0.05 | 0.05 | 0.05 | 0.05 | 0.05 | 0.05 | 0.05 | 0.05 | 0.05 |

PREEMERGENCE

| | Compound 49 | Compound 50 | Compound 51 | Compound 52 | Compound 53 | Compound 54 | Compound 55 | Compound 56 | Compound 57 | Compound 58 | Compound 59 | Compound 60 |
|---|---|---|---|---|---|---|---|---|---|---|---|---|
| Morningglory | 5C 9G | 9C | 4C 9G | 5C 9G | 2C 8G | 9C | 2C 6G | 3H | 3C 8G | &C | 3C 7G | 2C 3H |
| Cocklebur | 5C 9G | 9C | 4C 9H | 2C 9G | 5C 9G | 9C | 3H | 0 | 5C 9G | &C | 2C 8G | 2G |
| Velvetleaf | 9C | &C | 4C 8H | 2C 8G | &C | 9C | 3C 6G | 5G | &C | &C | 4C 9H | 2C 5G |
| Nutsedge | 9G | 9G | 3G | 2C 9G | 2C 9G | 9C | 0 | 0 | 3C 8G | 3C 9G | 3G | 2C 4G |
| Crabgrass | 3G | 6G | 3G | 3C 8G | 5C 9G | 4C 9G | 2G | 3G | 4C 8G | 4C 9G | 3C 4G | 2C 4G |
| Barnyardgrass | 5C 9G | 9C | 4C 9H | 3C 9G | 5C 9G | 4C 8H | 4C 8H | 4H | 9C | 9C | 9C | 2C 6G |
| Wild Oats | 3C 7G | 0 | 3C 9G | 3C 9G | 4C 9G | 4C 9G | 4C 9G | 3C 7G | 4C 9G | 3C 7G | 3C 7H | 3C 7H |

POSTEMERGENCE

TABLE A-continued

| | Compound 61 | Compound 62 | Compound 63 | Compound 64 | Compound 65 | Compound 66 | Compound 67 | Compound 68 | Compound 69 | Compound 70 | Compound 71 | Compound 72 |
|---|---|---|---|---|---|---|---|---|---|---|---|---|
| Wheat | 2C 8G | 0 | 5G | 5G 3C 8H | 2C 8G | 1C 5G | 2C 7G | 5G | 5G | 5G &C | 3G 9C | 8G 9C |
| Corn | 9G | 4U 9C | 4U 9G | | 2U 9G | 2U 9C | 3C 8G | 6H | | | | 1C 2G |
| Soybean | 4C 9G | 4C 9G | 4C 9G | 5C 9G | 5C 9G | 6C 9G | 3H 5G | 4C 9G | 3C 9G | 5C 9G | 3C 8G | 9C |
| Rice | 6C 9G | 5C 9G | 5C 9G | 3C 9G | 5C 9G | 5C 9G | 9C | 3C 8G | &C | &C | 2C 8G | 4C 9G |
| Sorghum | 2C 9G | 3C 9G | 2C 9H | 3C 8G | 5C 9G | 5C 9G | 2C 9H | 8G | 4C 9G | 4C 9G | &C | 9C |
| Cheatgrass | 4C 9G | 4C 9G | 3C 9G | 2C 8G | 6C 9G | 5C 9G | 2C 9G | 4H | 9C | 9C | 2C 8G | 4C 9G |
| Sugar Beets | 5C 9G | 9C | 3C 8G | 3C 8H | 9C | 9C | 3C 7H | 2G | 4C 9G | 9C | 4C 9H | 4C 9G |
| Cotton | 5C 9G | 4C 9G | 3C 5G | 2C 5G | 6C 9G | 6C 9G | 2C | | 9C | 9C | 5C 9G | 3C 7H |
| Sicklepod | | | | | | | | | &C | | | 3G |
| Morningglory | 9G | 7G | 8G | 8G | 6G | 7G | 5G | 3H | 8G | 8G | 2C 4G | 4H |
| Cocklebur | 8H | 6H | 3H | | 8H | 8H | 5H | | 3C 5H | 8H | 2C 2H | 0 |
| Velvetleaf | 2C 8G | 7G | 5G | 3H | 3C 7G | 3C 8G | 5G | 2H | 3C 5H | 2C 4G | 0 | 0 |
| Nutsedge | 7G | &E | 0 | 3G | 3G | &E | 0 | 0 | 3C 6G | 4G | 0 | 0 |
| Crabgrass | 2G | 2G | 3G | 2G | 2G | 5G | 4C 9H | 0 | 3G | 0 | 0 | 0 |
| Barnyardgrass | 3G | | 5G | 4G | 4G | 4C 9H | 7G | 2C | 3C 3H | 3G | 2G | 2C 3G |
| Wild Oats | 3C 8H | 3C 7H | 2C 8G | 4C 8G | 3C 8G | 7G | 7G | 2G | 3C 5G | 2C 7G | 3C 8G | 0 |
| Wheat | 2C 8G | 8G | 8G | 3C 8G | 3C 8G | 8G | 8G | 2G | 2C 6G | 8G | 3C 3H | 2C 3G |
| Corn | 3C 8G | 8G | 2C 8G | 3C 9G | 3C 9G | 3C | 3C 4G | 3C 4G | 3C 9H | 3C 4G | 3C 7G | 3C |
| Soybean | 2C 9G | 6G | 3C 5H | 2C 5G | 2C 5G | | 0 | 0 | 3C 7G | 3C 4G | 4C 9H | 3C 8H |
| Rice | 3C 3H | 9H | 9H | 5C 9H | 5C 9H | 5H | 8G | 2C 6G | 4C 8H | 4C 9H | 2C 5G | 0 |
| Sorghum | 8H | 2C 9G | 3C 9H | 4C 9H | 4C 9H | 9H | 3C 9G | 3C 8G | 4C 9H | 2C 5G | 2C 8G | 4H |
| Cheatgrass | 3C 9G | 8H | 8H | 5G | 9H | 8G | 3C 9G | 0 | 3C 6G | 5C 9G | 2G | 0 |
| Sugar Beets | 8H | 4C 9G | 3C 8G | 5C 9G | 5C 9G | 5C 9G | 5C 9G | 4G | 5C 9G | 9G | 3C 5H | 4H |
| Cotton | 4C 8G | 8G | 3H 5G | 8G | 7G | 5H | 5H | 0 | 2C 7G | | 2C 6G | 0 |
| Sicklepod | 8G | | | 2G | | 0 | 0 | | | | | |

| Rate | Compound 61 0.05 | Compound 62 0.05 | Compound 63 0.05 | Compound 64 0.05 | Compound 65 0.05 | Compound 66 0.05 | Compound 67 0.05 | Compound 68 0.05 | Compound 69 0.05 | Compound 70 0.05 | Compound 71 0.05 | Compound 72 0.05 |
|---|---|---|---|---|---|---|---|---|---|---|---|---|

POSTEMERGENCE

| | | | | | | | | | | | | |
|---|---|---|---|---|---|---|---|---|---|---|---|---|
| Morningglory | 2C 5G | 2C 4G | &C | 2C 8G | 4G | 9C | 0 | 0 | 2C 5G | 4C 8H | 0 | 0 |
| Cocklebur | 4H | 4C 9G | &C | 5G | 2G | 9C | 0 | 0 | 2C 5G | 5H | 0 | 0 |
| Velvetleaf | 2C 5G | 9C | &C | 9C | 2C 4G | &C | 0 | 0 | 3C 7H | 4C 9H | 0 | 0 |
| Nutsedge | 0 | 8G | 7G | 2C 8G | 3G | 9C | 0 | 0 | 0 | 5G | 0 | 0 |
| Crabgrass | 3G | 5C 8G | 9C | 3C 7G | 3G | 6G | 0 | 0 | 2G | 2H | 0 | 0 |
| Barnyardgrass | 3C 9H | &C | 9C | 9C | 2C 7H | 5C 9H | 0 | 0 | 2H | 0 | 0 | 0 |
| Wild Oats | 3C 8G | 4C 9G | 5G | 2C 7G | 2C | 0 | 0 | 0 | 0 | 7H | 0 | 0 |
| Wheat | 3C 2G | 2C 9G | 5G | 9C | 3C 4H | 3U 9G | 0 | 0 | 2H | 7G | 0 | 0 |
| Corn | 3C 8H | 2U 9G | &C | 2C 9G | 2H | 4C 9G | 0 | 0 | 5H | 3G | 0 | 0 |
| Soybean | 3C 5H | 9C | &C | 5C 9G | 9C | 4C 9G | 0 | 0 | 2G | 3H | 0 | 0 |
| Rice | 9C | 6C 9G | &C | 9C | 3C 8H | 3C 9H | 0 | 0 | 7H | 0 | 0 | 0 |
| Sorghum | 4C 9G | 9C | &C | 4C 9G | 3C 8H | 5C 9G | 0 | 0 | 0 | 3C 7G | 0 | 0 |
| Cheatgrass | 7G | &C | &C | 8G | 8G | 9C | 0 | 4G | 3C 7G | 3C 5G | 0 | 0 |
| Sugar Beets | 3C 6G | &C | &C | 9C | 2C 4G | 6C 9G | 0 | 2C 4G | 3C 5G | | 0 | 0 |
| Cotton | 0 | &C | &C | &C | 2G | | 0 | | | | | |

PREEMERGENCE

| | | | | | | | | | | | | |
|---|---|---|---|---|---|---|---|---|---|---|---|---|
| Morningglory | 2G | 2G | 2H | 2H | 2C 2H | 7H | 0 | 0 | 2G | 3G | 0 | 0 |
| Cocklebur | 1H | 2H | 2C 2H | 0 | 0 | 2H | 0 | 0 | 0 | 0 | 0 | 0 |
| Velvetleaf | 5G | 5G | 2C 9G | 0 | 0 | 4C 7H | 0 | 0 | 3C | 3C | 0 | 0 |
| Nutsedge | 0 | 0 | 5G | 0 | 0 | &E | 0 | 0 | 0 | 0 | 0 | 0 |
| Crabgrass | 0 | 0 | 2G | 2G | 0 | 3G | 0 | 0 | 2G | 0 | 0 | 0 |
| Barnyardgrass | 0 | 0 | 2G | 0 | 0 | 3C 7H | 0 | 0 | 0 | 0 | 0 | 0 |

TABLE A-continued

| | Compound 73 | Compound 74 | Compound 75 | Compound 76 | Compound 77 | Compound 78 | Compound 79 | Compound 80 | Compound 81 | Compound 82 | Compound 83 | Compound 84 |
|---|---|---|---|---|---|---|---|---|---|---|---|---|
| Wild Oats | 0 | 0 | 2G | 0 | 0 | 0 | 0 | 0 | 0 | 0 | 0 | 0 |
| Wheat | 0 | 3C 8H | 2G | 4C 9H | 0 | 0 | 4C 8H | 0 | 0 | 0 | 0 | 0 |
| Corn | 1H | 3C 3H | 7G | 2H | 2C | 1C | 2C | 0 | 0 | 0 | 0 | 0 |
| Soybean | 0 | 2C 4G | 3C 4H | 4C 9H | 1H | 0 | 2G | 0 | 0 | 0 | 0 | 0 |
| Rice | 3C 5G | 3C 6G | 4C 8G | 5G | 2G | 2G | 4C 8G | 0 | 0 | 0 | 0 | 0 |
| Sorghum | 0 | 0 | 2C 5G | 0 | 3C 5G | 3C 7G | 3C 6H | 0 | 7H | 0 | 0 | 0 |
| Cheatgrass | 4H | 4C 8H | 3G | 5H | 5H | 3H | 9C | 0 | 2G | 2G | 0 | 0 |
| Sugar Beets | 5G | 5G | 4C 9G | 2C | 0 | 0 | 5G | 0 | 0 | 0 | 0 | 0 |
| Cotton | | | | | | | | | | | | |
| Sicklepod | | | | | | | | | | | | |

| | Compound 73 | Compound 74 | Compound 75 | Compound 76 | Compound 77 | Compound 78 | Compound 79 | Compound 80 | Compound 81 | Compound 82 | Compound 83 | Compound 84 |
|---|---|---|---|---|---|---|---|---|---|---|---|---|
| Rate | 0.05 | 0.05 | 0.05 | 0.05 | 0.05 | 0.05 | 0.05 | 0.05 | 0.05 | 0.05 | 0.05 | 0.05 |

POSTEMERGENCE

| | Compound 85 | Compound 86 | Compound 87 | Compound 88 | Compound 89 | Compound 90 | Compound 91 | Compound 92 | Compound 93 | Compound 94 | Compound 95 | Compound 96 |
|---|---|---|---|---|---|---|---|---|---|---|---|---|
| Morningglory | 0 | 2G | 4C 5H | 4C 9H | 5H | 2G | 0 | 9C | 2C 3H | 2C 8H | 5H | 3C 8H | 3G |
| Cocklebur | 0 | 0 | 2C | 2H | 0 | 0 | 0 | &C | 2H | 2C 4G | 0 | 3G | 0 |
| Velvetleaf | 2C | 0 | 4C 7H | 4C 9H | 6H | 2G | 0 | 9C | 0 | 3C 6H | 5G | 8H | 0 |
| Nutsedge | 0 | 0 | 5G | 5G | 9G | 0 | 0 | 9C | 0 | 5G | 3H | 4G | 0 |
| Crabgrass | 0 | 0 | 2G | 0 | 5G | 0 | 0 | 4C 8G | 0 | 4G | 0 | 2G | 0 |
| Barnyardgrass | 0 | 0 | 3G | 0 | 5G | 0 | 0 | 5C 9H | 0 | 2C 5H | 0 | 2H | 0 |
| Wild Oats | 0 | 0 | 9H | 8H | 0 | 0 | 0 | 8G | 0 | 2C 7G | 3G | 2C 7G | 0 |
| Wheat | 0 | 0 | 0 | 0 | 0 | 0 | 0 | 7G | 0 | 0 | 3G | 2G | 0 |
| Corn | 0 | 1H | 2H | 3H 8G | 2H | 0 | 0 | 4U 9C | 2C 7H | 2C 7G | 3C 5G | 2C 7H | 0 |
| Soybean | 0 | 0 | 2H 5G | 2G | 1H | 0 | 0 | 9C | 2C 2H | 2C 7G | 0 | 3G | 0 |
| Rice | 0 | 0 | 0 | 2H | 0 | 0 | 0 | 6C 9G | 0 | 4C 8H | 3C 5G | 5C 9G | 0 |
| Sorghum | 0 | 2C | 1H | 5G | 2G | 0 | 0 | 5C 9G | 0 | 4C 9G | 3C 5G | 4C 8G | 0 |
| Cheatgrass | 0 | 0 | 5G | 3C 6H | 3C 6H | 3H 6G | 0 | &E | 0 | 7G | 5G | 8G | 0 |
| Sugar Beets | 0 | 4H | 4C 7G | 0 | 0 | 5H | 0 | 5C 9G | 5G | 3C 6G | 5G | 3C 3H | 0 |
| Cotton | 2G | 0 | 4C 8H | | 5G | 5G | 0 | 8G | 0 | 3C 3H | 0 | 3C 5G | 0 |
| Sicklepod | | | | | | | | | | | | | |

PREEMERGENCE

| | Compound 85 | Compound 86 | Compound 87 | Compound 88 | Compound 89 | Compound 90 | Compound 91 | Compound 92 | Compound 93 | Compound 94 | Compound 95 | Compound 96 |
|---|---|---|---|---|---|---|---|---|---|---|---|---|
| Rate | 0.05 | 0.05 | 0.05 | 0.05 | 0.05 | 0.05 | 0.05 | 0.05 | 0.05 | 0.05 | 0.05 | 0.05 |

POSTEMERGENCE

| | Compound 85 | Compound 86 | Compound 87 | Compound 88 | Compound 89 | Compound 90 |
|---|---|---|---|---|---|---|
| Morningglory | 0 | 0 | 4C 8H | 0 | 0 | 0 |
| Cocklebur | 0 | 0 | 6G | 0 | 0 | 1C 2H |

TABLE A-continued

| | Compound 97 0.05 | Compound 98 0.05 | Compound 99 0.05 | Compound 100 0.05 | Compound 101 0.05 | Compound 102 0.05 | Compound 103 0.05 | Compound 104 0.05 | Compound 105 0.05 | Compound 106 0.05 | Compound 107 0.05 | Compound 108 0.05 | Compound 109 0.05 | Compound 110 0.05 |
|---|---|---|---|---|---|---|---|---|---|---|---|---|---|---|
| Velvetleaf | 0 | 0 | 2C 8G | 0 | 0 | 0 | 1C | 0 | 0 | 0 | 0 | 0 | 0 | 0 |
| Nutsedge | 0 | 0 | 9G | 0 | 0 | 0 | 0 | 0 | 0 | 0 | 0 | 0 | 0 | 0 |
| Crabgrass | 0 | 0 | 3G | 0 | 0 | 0 | 0 | 0 | 0 | 0 | 0 | 0 | 0 | 0 |
| Barnyardgrass | 0 | 0 | 3C 8H | 0 | 0 | 0 | 0 | 0 | 0 | 0 | 0 | 0 | 0 | 0 |
| Wild Oats | 0 | 0 | 3C 8G | 0 | 0 | 0 | 0 | 0 | 0 | 0 | 0 | 0 | 0 | 0 |
| Wheat | 0 | 0 | 2G | 0 | 0 | 0 | 0 | 0 | 0 | 0 | 0 | 0 | 1H | 0 |
| Corn | 0 | 0 | 2C 9G | 0 | 0 | 2H | 0 | 0 | 0 | 0 | 0 | 0 | 0 | 0 |
| Soybean | 0 | 0 | 2C 2G | 0 | 0 | 0 | 0 | 2G | 0 | 0 | 0 | 0 | 0 | 0 |
| Rice | 0 | 0 | 5C 9G | 0 | 0 | 2G | 0 | 5G | 0 | 0 | 0 | 0 | 0 | 0 |
| Sorghum | 0 | 0 | 4C 8H | 0 | 0 | 2H | 0 | 2C 4G | 0 | 0 | 0 | 0 | 0 | 0 |
| Cheatgrass | 0 | 0 | 2C 8G | 0 | 0 | 0 | 0 | 2C 6G | 0 | 0 | 0 | 0 | 0 | 0 |
| Sugar Beets | 0 | 0 | 3C 6G | 0 | 0 | 1H | 0 | 2H | 0 | 0 | 0 | 0 | 0 | 0 |
| Cotton | 0 | 4G | 3C 6G | 0 | 0 | 0 | 2H | 2G | 0 | 0 | 0 | 0 | 0 | 4G |
| Sicklepod | 0 | 0 | 0 | 0 | 0 | 0 | 0 | 0 | 0 | 0 | 0 | 0 | 0 | 0 |

PREEMERGENCE

| | | | | | | | | | | | | | | |
|---|---|---|---|---|---|---|---|---|---|---|---|---|---|---|
| Morningglory | 0 | 0 | 5H | 0 | 0 | 0 | 0 | 1H | 0 | 0 | 0 | 0 | 0 | 0 |
| Cocklebur | 0 | 0 | 0 | 3G | 0 | 0 | 0 | 0 | 0 | 2H | 0 | 0 | 0 | 0 |
| Velvetleaf | 0 | 0 | 3G | 0 | 0 | 0 | 0 | 2G | 0 | 0 | 0 | 0 | 0 | 0 |
| Nutsedge | 0 | 0 | 0 | 0 | 0 | 0 | 0 | 0 | 0 | 0 | 0 | 0 | 0 | 0 |
| Crabgrass | 0 | 0 | 0 | 4C | 0 | 0 | 0 | 2G | 0 | 0 | 0 | 0 | 0 | 0 |
| Barnyardgrass | 0 | 0 | 0 | 0 | 0 | 0 | 0 | 0 | 0 | 0 | 0 | 0 | 0 | 0 |
| Wild Oats | 0 | 0 | 2C 7G | 0 | 0 | 0 | 0 | 0 | 0 | 0 | 0 | 0 | 0 | 0 |
| Corn | 0 | 0 | 3G | 0 | 0 | 0 | 0 | 0 | 0 | 0 | 0 | 0 | 0 | 0 |
| Soybean | 0 | 0 | 3C 7G | 0 | 0 | 0 | 0 | 0 | 0 | 0 | 0 | 0 | 0 | 0 |
| Rice | 0 | 0 | 0 | 0 | 0 | 0 | 0 | 0 | 0 | 0 | 0 | 0 | 0 | 0 |
| Sorghum | 0 | 0 | 3C 7H | 0 | 0 | 0 | 0 | 0 | 0 | 0 | 0 | 0 | 0 | 0 |
| Cheatgrass | 0 | 0 | 3C 6G | 0 | 0 | 0 | 0 | 0 | 0 | 0 | 0 | 0 | 0 | 0 |
| Sugar Beets | 0 | 0 | 2G | 0 | 0 | 0 | 0 | 0 | 0 | 0 | 0 | 0 | 0 | 0 |
| Cotton | 5G | 4G | 3C 5H | 4G | 0 | 0 | 0 | 0 | 0 | 0 | 0 | 0 | 0 | 4G |
| Sicklepod | 0 | 0 | 0 | 0 | 0 | 0 | 0 | 0 | 0 | 0 | 0 | 0 | 0 | 0 |

| Rate | Compound 97 0.05 | Compound 98 0.05 | Compound 99 0.05 | Compound 100 0.05 | Compound 101 0.05 | Compound 102 0.05 | Compound 103 0.05 | Compound 104 0.05 | Compound 105 0.05 | Compound 106 0.05 | Compound 107 0.05 | Compound 108 0.05 | Compound 109 0.05 | Compound 110 0.05 |
|---|---|---|---|---|---|---|---|---|---|---|---|---|---|---|

POSTEMERGENCE

| | | | | | | | | | | | | | | |
|---|---|---|---|---|---|---|---|---|---|---|---|---|---|---|
| Morningglory | 0 | 0 | 0 | 0 | 0 | 0 | 0 | 0 | 0 | 2C 4G | 5C 9G | 8C | 2C 3H | 3C 8H |
| Cocklebur | 0 | 0 | 0 | 0 | 0 | 0 | 0 | 0 | 0 | 2C 9G | 5C 9G | 9C | 2C 3H | 2C 6G |
| Velvetleaf | 0 | 0 | 0 | 0 | 0 | 0 | 0 | 0 | 0 | 3C 8H | 5C 9G | 9C | 2C | 0 |
| Nutsedge | 0 | 0 | 0 | 0 | 0 | 0 | 0 | 0 | 0 | 0 | 2C 8G | 2C 9G | 0 | 0 |
| Crabgrass | 0 | 0 | 0 | 0 | 0 | 0 | 0 | 0 | 0 | 0 | 0 | 5G | 0 | 0 |
| Barnyardgrass | 0 | 0 | 0 | 0 | 0 | 0 | 0 | 0 | 0 | 0 | 3C 8G | 3C 8H | 0 | 2G |
| Wild Oats | 0 | 0 | 0 | 0 | 0 | 0 | 0 | 0 | 0 | 0 | 0 | 0 | 0 | 2C 5G |
| Wheat | 0 | 0 | 0 | 0 | 0 | 0 | 0 | 0 | 0 | 0 | 2G | 2G | 0 | 2G |
| Corn | 0 | 0 | 0 | 0 | 0 | 0 | 0 | 0 | 1C 5G | 0 | 3C 7G | 2C 8H | 0 | 5G |
| Soybean | 0 | 0 | 0 | 0 | 0 | 0 | 0 | 0 | 0 | 0 | 4C 8G | 5C 9G | 0 | 2C 5G |
| Rice | 0 | 0 | 0 | 0 | 0 | 0 | 0 | 0 | 4C 9G | 1C | 5G | 3C 8G | 0 | 2C 5G |
| Sorghum | 0 | 0 | 0 | 0 | 0 | 0 | 0 | 0 | 2C | 3G | 3C 9G | 3C 9H | 0 | 5G |
| Cheatgrass | 0 | 0 | 0 | 0 | 0 | 0 | 0 | 0 | 4G | 1C 3G | 8G | 2C 8G | 2C 4H | 3C 7H |
| Sugar Beets | 0 | 0 | 0 | 0 | 0 | 0 | 0 | 0 | 3H | 2C 5H | 5C 8H | 9C | 0 | 2C 5G |
| Cotton | 0 | 0 | 0 | 0 | 0 | 0 | 0 | 0 | 1C | 5G | 9C | 9C | | |
| Sicklepod | 0 | 0 | 0 | 0 | 0 | 0 | 0 | 0 | | | | | | |

PREEMERGENCE

TABLE A-continued

| | Compound 111 0.05 | Compound 112 0.05 | Compound 113 0.05 | Compound 114 0.05 | Compound 115 0.05 | Compound 116 0.05 | Compound 117 0.05 | Compound 118 0.05 | Compound 119 0.05 | Compound 120 0.05 | Compound 121 0.05 | Compound 122 0.05 | Compound 123 0.05 |
|---|---|---|---|---|---|---|---|---|---|---|---|---|---|
| Morningglory | 0 | 0 | 0 | 0 | 0 | 0 | 0 | 0 | 0 | 0 | 0 | 0 | 2C |
| Cocklebur | 0 | 0 | 0 | 0 | 0 | 0 | 0 | 0 | 0 | 7G | 8G | 0 | 0 |
| Velvetleaf | 0 | 0 | 0 | 0 | 0 | 0 | 0 | 0 | 0 | 8H | 9H | 0 | 0 |
| Nutsedge | 4G | 0 | 0 | 0 | 0 | 0 | 0 | 0 | 0 | 3C 6H | 4C 9G | 0 | 0 |
| Crabgrass | 3G | 0 | 0 | 0 | 0 | 0 | 0 | 0 | 0 | 0 | &E | 5G | 5G |
| Barnyardgrass | 0 | 0 | 0 | 0 | 0 | 0 | 0 | 0 | 0 | 0 | 3G | 0 | 0 |
| Wild Oats | 0 | 0 | 0 | 0 | 0 | 0 | 0 | 0 | 0 | 1H | 5G | 0 | 0 |
| Wheat | 0 | 0 | 0 | 0 | 0 | 0 | 0 | 0 | 0 | 0 | 0 | 0 | 0 |
| Corn | 2C | 0 | 0 | 0 | 0 | 0 | 0 | 0 | 0 | 2C 7G | 3C 8G | 0 | 0 |
| Soybean | 0 | 0 | 0 | 0 | 0 | 0 | 0 | 0 | 0 | 2C | 5G | 0 | 0 |
| Rice | 0 | 0 | 0 | 0 | 0 | 0 | 0 | 0 | 0 | 2C 4G | 5G | 0 | 0 |
| Sorghum | 0 | 0 | 0 | 0 | 0 | 0 | 0 | 0 | 0 | 2C 7G | 2C 6G | 2G | 2G |
| Cheatgrass | 0 | 0 | 0 | 0 | 0 | 0 | 0 | 0 | 0 | 7G | 3C 8H | 0 | 1H |
| Sugar Beets | 0 | 0 | 0 | 0 | 0 | 0 | 0 | 0 | 0 | 8G | 5C 9G | 5G | 0 |
| Cotton | 0 | 0 | 0 | 0 | 0 | 0 | 0 | 0 | 0 | 8G | 8G | 0 | 0 |
| Sicklepod | | | | | | | | | | | | | |

| Rate | Compound 111 0.05 | Compound 112 0.05 | Compound 113 0.05 | Compound 114 0.05 | Compound 115 0.05 | Compound 116 0.05 | Compound 117 0.05 | Compound 118 0.05 | Compound 119 0.05 | Compound 120 0.05 | Compound 121 0.05 | Compound 122 0.05 | Compound 123 0.05 |
|---|---|---|---|---|---|---|---|---|---|---|---|---|---|

POSTEMERGENCE

| Morningglory | 3C 5H | 2G | 3C 9H | 4C 9G | 0 | 2C 3H | 2H | 2G | 1C 5G | 3C 8G | 7G | 2C 6H | 3C 8H |
| Cocklebur | 1C | 1H | 3C 9H | 5C 9G | 1H | 2H | 2H | 1C | 5C 9G | 5C 9G | 5G | 2C 6H | 3C 9H |
| Velvetleaf | 2C | 3C 6H | 9C | &C | 2C 4H | 3H | 2H | 2C | 5C 9H | 5C 9G | 3C 8H | 0 | 2C 2H |
| Nutsedge | 0 | 0 | 9G | 9G | 2C 5G | 0 | 0 | 0 | 2C 9G | 2C 4G | 0 | 0 | 3C 5G |
| Crabgrass | 5G | 0 | 3G | 3C 8G | 0 | 0 | 1H | 3G | 5G | 2C 5G | 0 | 5H | 0 |
| Barnyardgrass | 0 | 0 | 0 | 4C 9H | 2H | 0 | 0 | 3C 7H | 5C 9H | 9C | 2C 8H | 0 | 3C 9H |
| Wild Oats | 0 | 0 | 0 | 2C | 0 | 0 | 0 | 3C 5G | 3C 8G | 2C 7G | 0 | 0 | 0 |
| Wheat | 0 | 0 | 0 | 0 | 0 | 0 | 0 | 4G | 2C 7G | 5G | 0 | 2G | 0 |
| Corn | 1C 1H | 0 | 1H | 4C 9H | 2H | 0 | 0 | 2C 9G | 2C 9G | 9C | 2C 6G | 0 | 3C 9H |
| Soybean | 0 | 0 | 5C 9G | 5C 9G | 0 | 0 | 0 | 5C 9G | 5C 8G | 3C 9G | 3H | 0 | 3C 6G |
| Rice | 2G | 0 | 1C 4G | 4C 9H | 0 | 3G | 0 | 5C 9G | 5C 9G | 5C 9G | 5G | 3G | 8G |
| Sorghum | 2C 3G | 0 | 3C 5G | 5C 9G | 3C 6G | 2G | 0 | 4C 9H | 4C 9G | 6C 9G | 2C 7H | 4G | 3G |
| Cheatgrass | 0 | 2C 4H | 2C 8G | 2C 9G | 2C 4H | 1H | 0 | 7G | 2C 9G | 2C 8G | 0 | 3C 6G | 2C 5G |
| Sugar Beets | 3C 5H | 4C 5G | 5C 8H | 9C | 4C 8H | 2G | 0 | 2C | 9G | 9C | 5G | 2C | 3C 8G |
| Cotton | 0 | 0 | 9H | 4C 9G | 0 | 0 | 1H | 2C | 4C 9H | 3C 8G | 3C &G | 0 | 4C 8H |
| Sicklepod | | | | | | | | | | | | | |

PREEMERGENCE

| Morningglory | 1C | 1C | 6G | 9G | 1C | 0 | 0 | 0 | 3H | 3G | 0 | 0 | 1C |
| Cocklebur | 0 | 0 | 7G | 9H | 2H | 0 | 0 | 0 | 3G | 4G | | 0 | 0 |
| Velvetleaf | 4G | 0 | 3C 5H | 8H | 2G | 0 | 0 | 0 | 3H | 3G | | 0 | 0 |
| Nutsedge | 0 | 0 | 0 | 5G | 0 | 0 | 0 | 0 | 0 | 0 | | 0 | 0 |
| Crabgrass | 0 | 0 | 0 | 4G | 8G | 0 | 0 | 0 | 0 | 0 | | 0 | 0 |
| Barnyardgrass | 0 | 0 | 1C | 3C 8G | 0 | 0 | 0 | 0 | 2C | 3G | | 0 | 0 |
| Wild Oats | 0 | 0 | 0 | 2C 3G | 0 | 0 | 0 | 0 | 3G | 3G | | 0 | 0 |
| Wheat | 0 | 0 | 0 | 3G | 0 | 0 | 0 | 0 | 3G | 3G | | 0 | 0 |
| Corn | 2G | 0 | 3C 4G | 8G | 2G | 0 | 2C | 2G | 2C 9G | 2C 7G | 2C | 3C 6G | 3C 6G |
| Soybean | 2G | 0 | 1H | 2C 6G | 0 | 0 | 0 | 0 | 2C 8H | 1H | 0 | 1H | 3C 6G |
| Rice | 2G | 0 | 0 | 3C 8H | 4G | 0 | 0 | 2G | 8H | 5G | 3C 6G | 2C | 8G |
| Sorghum | 2G | 4G | 2C 3G | 3C 9H | 2C 5G | 0 | 0 | 2G | 3C 7H | 0 | 3C 6G | 0 | 3C 6G |
| Cheatgrass | 0 | 0 | 3C 6G | 2C 9G | 0 | 0 | 0 | 2C 3G | 3G | 3C 7G | 3C 6G | 2H | 3C 8G |
| Sugar Beets | 2G | 0 | 0 | 4C 8G | 0 | 0 | 0 | 0 | 7G | 3C 8G | 3C 6G | 3G | 4C 6G |
| Cotton | 0 | 0 | 3C 6G | 3C 9G | 0 | 0 | 0 | 0 | 7G | 2G | 2G | | 0 |
| Sicklepod | | | | | | | | | | | | | |

What is claimed is:
1. A compound of the formula:

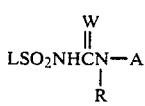

wherein
L is

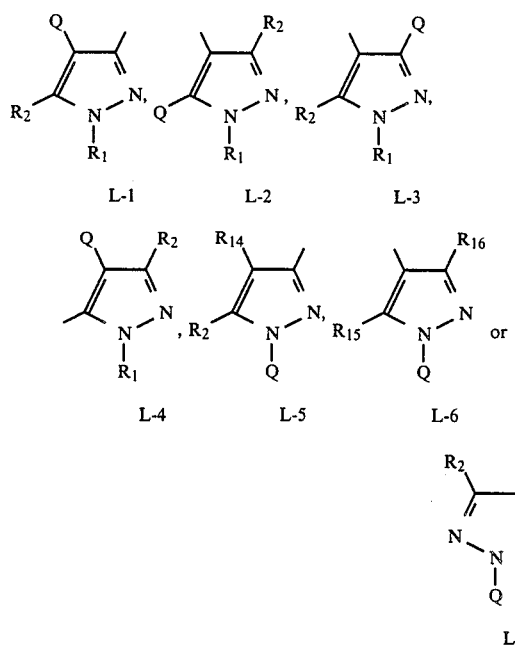

Q is selected from a saturated 5- or 6-membered ring containing one S or O heteroatom, and an unsaturated 5- or 6-membered ring containing 1-3 heteroatoms selected from one S, and one O, 1-3N and combinations thereof and Q may optionally be substituted by one or more groups selected from $C_1$-$C_4$ alkyl, $C_1$-$C_4$ haloalkyl, mercapto, benzylthio, halogen, $C_1$-$C_4$ alkoxy, $C_1$-$C_6$ alkylthio, $C_3$-$C_4$ alkenyl, $C_3$-$C_4$ alkenylthio, $C_3$-$C_4$ alkynylthio, $C_3$-$C_4$ haloalkenylthio, $C_3$-$C_4$ alkenyloxy, $C_1$-$C_2$ haloalkoxy, $C_1$-$C_2$ haloalkylthio, $C_2$-$C_4$ cyanoalkylthio, $C_3$-$C_6$ alkoxycarbonylalkylthio, $C_2$-$C_5$ alkoxyalkylthio or $C_3$-$C_5$ acetylalkylthio:

W is O;
R is H or $CH_3$;
$R_1$ is H, $C_1$-$C_3$ alkyl, $C_1$-$C_3$ haloalkyl or phenyl optionally substituted by Cl, $NO_2$, $CH_3$ or $OCH_3$;
$R_2$ is H, Cl or $CH_3$;
$R_{14}$ is H, $C_1$-$C_4$ alkyl, F, Cl, Br, $NO_2$, $C_1$-$C_3$ haloalkylthio, $C_3$-$C_4$ alkenyl, $C_3$-$C_4$ alkynyl, $CO_2R_{17}$, $C_1$-$C_3$ alkylthio, $C_1$-$C_3$ alkylsulfinyl, $C_1$-$C_3$ alkylsulfonyl or $SO_2NR^IR^{II}$;
$R_{15}$ and $R_{16}$ are independently H, $C_1$-$C_4$ alkyl, $C_2$-$C_4$ alkoxyalkyl, $C_1$-$C_3$ haloalkylthio, $C_1$-$C_3$ haloalkoxy, $C_1$-$C_3$ alkoxy, $C_1$-$C_3$ alkylthio, $C_1$-$C_3$ alkylsulfonyl, F, Cl, Br, $CO_2R_{17}$ or $SO_2NR^IR^{II}$;
$R^I$ and $R^{II}$ are independently $C_1$-$C_3$ alkyl;
$R_{17}$ is $C_1$-$C_3$ alkyl, $CH_2CH$=$CH_2$, $CH_2C$≡$CH$, $CH_2CH_2Cl$ or $CH_2CH_2OCH_3$;
A is

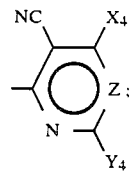

Z is CH;
$X_4$ is $CH_3$, $OCH_3$, $OC_2H_5$, $CH_2OCH_3$ or Cl; and
$Y_4$ is $CH_3$, $OCH_3$ or $OC_2H_5$;

and their agriculturally suitable salts; provided that when L is L-5, L-6 or L-7, then Q must be bonded to the pyrazole ring nitrogen through a carbon atom.

2. The compounds of claim 1 where Q is

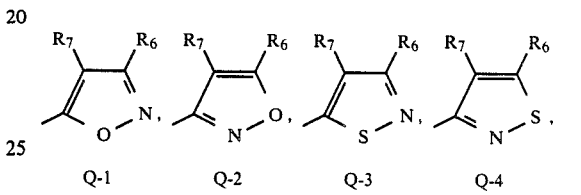

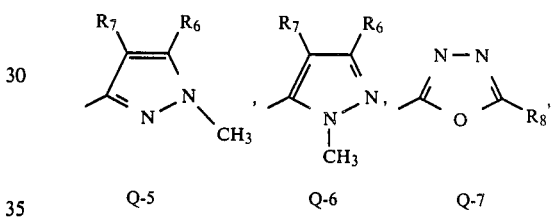

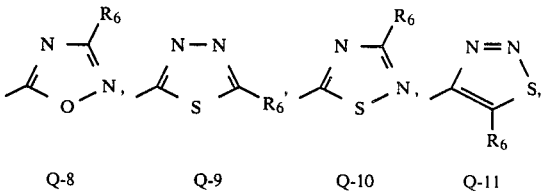

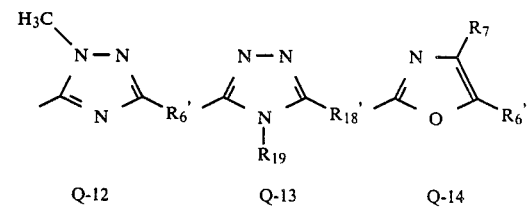

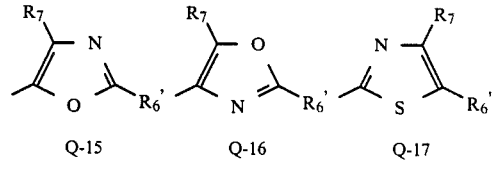

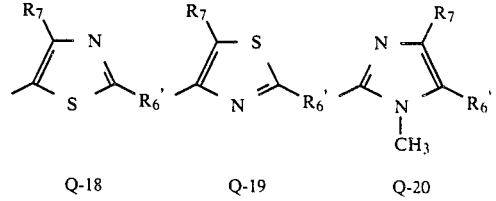

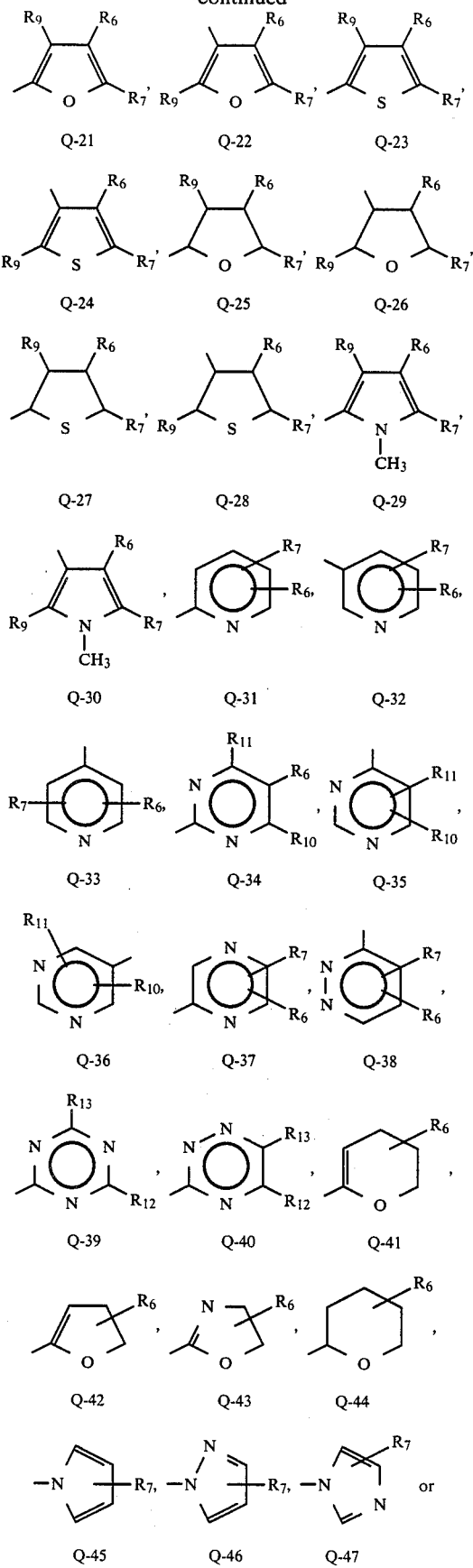

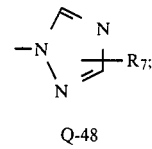

$R_6$ and $R_9$ are independently H or $CH_3$;
$R_7$ is H, $CH_3$ or Cl;
$R_8$ is H, SH, $CH_3$, $CH_2CH_3$, $S(C_1$-$C_4$ alkyl), $S(C_3$-$C_4$ alkenyl) optionally substituted with 1 or 2 halogen atoms, $S(C_3$-$C_4$ alkynyl), $OCH_3$, $OCH_2CH_3$, $SCF_2H$, $CF_3$, or $S(C_1$-$C_3$ alkyl) substituted with CN, $CO_2R_4$, $OR_4$ or $C(O)CH_3$;
$R_{10}$ and $R_{11}$ are independently H, $CH_3$ or $OCH_3$;
$R_{12}$ and $R_{13}$ are independently $CH_3$ or $OCH_3$;
$R_{18}$ is H, $C_1$-$C_3$ alkyl or $C_1$-$C_3$ alkylthio; and
$R_{19}$ is $C_1$-$C_3$ alkyl or $CH_2CH=CH_2$;
provided that when L is L-5, L-6 or L-7, then Q is not Q-25, Q-26, Q-27, Q-28, Q-41, Q-42, Q-43 or Q-44.

3. The compounds of claim 2 where R is H.

4. The compounds of claim 3 where $R_1$ is $C_1$-$C_3$ alkyl, $R_8$ is H, SH, $CH_3$, $SCH_3$ or $OCH_3$, $R_{14}$ is H, $CH_3$, $C_2H_5$, $CO_2CH_3$, $CO_2C_2H_5$, F, Cl, Br, $SO_2CH_3$, $SO_2C_2H_5$, $OCF_2H$ or $SO_2N(CH_3)_2$, and $R_{15}$ and $R_{16}$ are independently H, $CH_3$, $C_2H_5$, $CO_2CH_3$, $CO_2C_2H_5$, F, Cl, Br, $SO_2CH_3$, $SO_2C_2H_5$, $OCF_2H$, or $SO_2N(CH_3)_2$.

5. The compounds of claim 4 where L is L-1 and Q is selected from Q-7, Q-13, Q-15, Q-17, Q-18, Q-24, Q-31, Q-32, Q-33, Q-37, Q-45, Q-46, Q-47 and Q-48.

6. The compounds of claim 4 where L is L-2 and Q is selected from Q-7, Q-13, Q-15, Q-17, Q-18, Q-24, Q-31, Q-32, Q-33, Q-37, Q-45, Q-46, Q-47 and Q-48.

7. The compounds of claim 4 where L is L-7 and Q is Q-31.

8. An agriculturally suitable composition suitable for controlling the growth of undesired vegetation comprising an effective amount of a compound of claim 1 and at least one of the following: surfactant, solid or liquid diluent.

9. An agriculturally suitable composition suitable for controlling the growth of undesired vegetation comprising an effective amount of a compound of claim 2 and at least one of the following: surfactant, solid or liquid diluent.

10. An agriculturally suitable composition suitable for controlling the growth of undesired vegetation comprising an effective amount of a compound of claim 3 and at least one of the following: surfactant, solid or liquid diluent.

11. An agriculturally suitable composition suitable for controlling the growth of undesired vegetation comprising an effective amount of a compound of claim 4 and at least one of the following: surfactant, solid or liquid diluent.

12. An agriculturally suitable composition suitable for controlling the growth of undesired vegetation comprising an effective amount of a compound of claim 5 and at least one of the following: surfactant, solid or liquid diluent.

13. An agriculturally suitable composition suitable for controlling the growth of undesired vegetation comprising an effective amount of a compound of claim 6 and at least one of the following: surfactant, solid or liquid diluent.

14. An agriculturally suitable composition suitable for controlling the growth of undesired vegetation comprising an effective amount of a compound of claim 7 and at least one of the following: surfactant, solid or liquid diluent.

15. A method for controlling the growth of undesired vegetation which comprises applying to the locus to be protected an effective amount of a compound of claim 1.

16. A method for controlling the growth of undesired vegetation which comprises applying to the locus to be protected an effective amount of a compound of claim 2.

17. A method for controlling the growth of undesired vegetation which comprises applying to the locus to be protected an effective amount of a compound of claim 3.

18. A method for controlling the growth of undesired vegetation which comprises applying to the locus to be protected an effective amount of a compound of claim 4.

19. A method for controlling the growth of undesired vegetation which comprises applying to the locus to be protected an effective amount of a compound of claim 5.

20. A method for controlling the growth of undesired vegetation which comprises applying to the locus to be protected an effective amount of the compound of claim 6.

21. A method for controlling the growth of undesired vegetation which comprises applying to the locus to be protected an effective amount of a compound of claim 7.

* * * * *